US011028380B2

(12) United States Patent
Wolfe et al.

(10) Patent No.: US 11,028,380 B2
(45) Date of Patent: Jun. 8, 2021

(54) CAS9-CAS9 FUSION PROTEINS

(71) Applicant: University of Massachusetts, Boston, MA (US)

(72) Inventors: Scot Andrew Wolfe, Winchester, MA (US); Mehmet Fatih Bolukbasi, Worcester, MA (US); Ankit Gupta, Worcester, MA (US); Erik J Sontheimer, Auburndale, MA (US); Nadia Amrani, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/226,202

(22) Filed: Dec. 19, 2018

(65) Prior Publication Data

US 2019/0276810 A1    Sep. 12, 2019

Related U.S. Application Data

(63) Continuation of application No. 14/976,196, filed on Dec. 21, 2015, now Pat. No. 10,190,106.

(60) Provisional application No. 62/095,399, filed on Dec. 22, 2014.

(51) Int. Cl.
*C12N 9/22*    (2006.01)

(52) U.S. Cl.
CPC ............ *C12N 9/22* (2013.01); *C07K 2319/80* (2013.01); *C12Y 301/00* (2013.01)

(58) Field of Classification Search
None
See application file for complete search history.

(56) References Cited

U.S. PATENT DOCUMENTS

| 2005/0064474 | A1 | 3/2005 | Urnov et al. ................. 435/6.18 |
| 2014/0273226 | A1 | 9/2014 | Wu ................................ 435/455 |
| 2014/0273231 | A1 | 9/2014 | Cong et al. | |
| 2014/0295556 | A1 | 10/2014 | Joung et al. ................... 435/440 |
| 2014/0295557 | A1 | 10/2014 | Joung et al. ................... 435/455 |
| 2015/0252358 | A1* | 9/2015 | Maeder .................... C12N 9/22 424/93.2 |
| 2015/0353917 | A1 | 12/2015 | Miller ............................. 435/441 |

FOREIGN PATENT DOCUMENTS

| WO | WO/2014/059244 | 4/2014 |
| WO | WO 2016/057961 | 4/2016 |
| WO | WO 2016/141224 | 9/2016 |

OTHER PUBLICATIONS

Anders, C. et al. (2014) "Structural basis of PAM-dependent target DNA recognition by the Cas9 endonuclease," *Nature* 513(7519), 569-573.

Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.

Atkinson, H. et al. (2010) "Delivering the goods: viral and non-viral gene therapy systems and the inherent limits on cargo DNA and internal sequences," *Genetica* 138(5), 485-498.

Barrangou, R. et al. (2014) "CRISPR-Cas systems: Prokaryotes upgrade to adaptive immunity," *Molecular Cell* 54(2), 234-244.

Benjamini, Y. et al. (1995) "Controlling the false discovery rate: a practical and powerful approach to multiple testing," *Journal of the Royal Statistical Society* 57(1), 289-300.

Bhakta, M. S. et al. (2013) "Highly active zinc-finger nucleases by extended modular assembly," *Genome Research* 23(3), 530-538.

Boissel, S. et al. (2014) "megaTALs: a rare-cleaving nuclease architecture for therapeutic genome engineering," *Nucleic Acids Research* 42(4), 2591-2601.

Briggs, A. W. et al. (2012) "Iterative capped assembly: rapid and scalable synthesis of repeat-module DNA such as TAL effectors from individual monomers," *Nucleic Acids Research* 40(15), e117-e117.

Brunet, E. et al. (2009) "Chromosomal translocations induced at specified loci in human stem cells," *Proceedings of the National Academy of Sciences of the United States of America* 106(26), 10620-10625.

Carroll, D. et al. (2006) "Design, construction and in vitro testing of zinc finger nucleases," *Nature Protocols* 1(3), 1329-1341.

Cencic, R. et al. (2014) "Protospacer Adjacent Motif (PAM)-Distal Sequences Engage CRISPR Cas9 DNA Target Cleavage," *PLoS ONE* 9(10), e109213.

Cho, S. W. et al. (2014) "Analysis of off-target effects of CRISPR/Cas-derived RNA-guided endonucleases and nickases," *Genome Research* 24(1), 132-141.

Chu, S. W. et al. (2012) "Exploring the DNA-recognition potential of homeodomains," *Genome Research* 22(10), 1889-1898.

(Continued)

*Primary Examiner* — Rebecca E Prouty
(74) *Attorney, Agent, or Firm* — Medlen & Carroll, LLP

(57) ABSTRACT

The present invention provides a Cas9 platform to facilitate single-site nuclease gene editing precision within a human genome. For example, a Cas9 nuclease/DNA-targeting unit (Cas9-DTU) fusion protein precisely delivers a Cas9/sgRNA complex to a specific target site within the genome for subsequent sgRNA-dependent cleavage of an adjacent target sequence. Alternatively, attenuating Cas9 binding using mutations to the a protospacer adjacent motif (PAM) recognition domain makes Cas9 target site recognition dependent on the associated DTU, all while retaining Cas9's sgRNA-mediated DNA cleavage fidelity. Cas9-DTU fusion proteins have improved target site binding precision, greater nuclease activity, and a broader sequence targeting range than standard Cas9 systems. Existing Cas9 or sgRNA variants (e.g., truncated sgRNAs (tru-gRNAs), nickases and FokI fusions) are compatible with these improvements to further reduce off-target cleavage. A robust, broadly applicable strategy is disclosed to impart Cas9 genome-editing systems with the single-genomic-site accuracy needed for safe, effective clinical application.

13 Claims, 148 Drawing Sheets
Specification includes a Sequence Listing.

(56) References Cited

OTHER PUBLICATIONS

Chylinski, K. et al. (2014) "Classification and evolution of type 11 CRISPR-Cas systems," *Nucleic Acids Research* 42(10), 6091-6105.
Cong, L. et al. (2013) "Multiplex genome engineering using CRISPR/Cas systems," *Science* 339(6121), 819-823.
Davis, K. M. et al. (2015) "Small Molecule-Triggered Cas9 Protein with Improved Genome-Editing Specificity," *Nature Chemical Biology* 11(5), 316-318.
Daya, S. et al. (2008) "Gene Therapy Using Adeno-Associated Virus Vectors," *Clinical Microbiology Reviews* 21(4), 583-593.
Deng, D. et al. (2012) "Structural Basis for Sequence-Specific Recognition of DNA by TAL Effectors," *Science* 335(6069), 720-723.
Doudna, J. A. et al. (2014) "Genome editing. The new frontier of genome engineering with CRISPR-Cas9," *Science* 346(6213), 1258096.
Doyle, E. L. et al. (2012) "TAL Effector-Nucleotide Targeter (TALE-NT) 2.0: tools for TAL effector design and target prediction," *Nucleic Acids Research* 40(Web Server issue), W117-W122.
Doyon, Y. et al. (2008) "Heritable targeted gene disruption in zebrafish using designed zinc-finger nucleases," *Nature Biotechnology* 26(6), 702-708.
Dreier, B. et al. (2001) "Development of Zinc Finger Domains for Recognition of the 5'-ANN-3' Family of DNA Sequences and Their Use in the Construction of Artificial Transcription Factors," *Journal of Biological Chemistry* 276(31), 29466-29478.
Dreier, B. et al. (2000) "Insights into the molecular recognition of the 5'-GNN-3' family of DNA sequences by zinc finger domains," *Journal of Molecular Biology* 303(4), 489-502.
Enuameh, M. S. et al. (2013) "Global analysis of Drosophila Cys2-His2 zinc finger proteins reveals a multitude of novel recognition motifs and binding determinants," *Genome Research* 23(6), 928-940.
Fonfara, I. et al. (2014) "Phylogeny of Cas9 determines functional exchangeability of dual-RNA and Cas9 among orthologous type II CRISPR-Cas systems," *Nucleic Acids Research* 42(4), 2577-2590.
Forbes, S. A. et al. (2011) "COSMIC: mining complete cancer genomes in the Catalogue of Somatic Mutations in Cancer," *Nucleic Acids Research* 39(Database issue), D945-D950.
Frock, R. L. et al. (2015) "Genome-wide detection of DNA double-stranded breaks induced by engineered nucleases," *Nature Biotechnology* 33(2), 179-186.
Fu, Y. et al. (2013) "High-frequency off-target mutagenesis induced by CRISPR-Cas nucleases in human cells," *Nature Biotechnology* 31(9), 822-826.
Fu, Y. et al. (2014) "Improving CRISPR-Cas nuclease specificity using truncated guide RNAs," *Nature Biotechnology* 32(3), 279-284.
Greisman, H. A. et al. (1997) "A general strategy for selecting high-affinity zinc finger proteins for diverse DNA target sites," *Science* 275(5300), 657-661.
Guilinger, J. P. et al. (2014) "Fusion of catalytically inactive Cas9 to FokI nuclease improves the specificity of genome modification," *Nature Biotechnology* 32(6), 577-582.
Gupta, A. et al. (2014) "An improved predictive recognition model for Cys(2)-His(2) zinc finger proteins," *Nucleic Acids Research* 42(8), 4800-4812.
Gupta, A. et al. (2012) "An optimized two-finger archive for ZFN-mediated gene targeting," *Nature Methods* 9(6), 588-590.
Gupta, A. et al. (2013) "Targeted chromosomal deletions and inversions in zebrafish," *Genome Research* 23(6),1008-1017.
Gupta, A. et al. (2011) "Zinc finger protein-dependent and -independent contributions to the in vivo off-target activity of zinc finger nucleases," *Nucleic Acids Research* 39(1), 381-392.
Gupta, R. M. et al. (2014) "Expanding the genetic editing tool kit: ZFNs, TALENs, and CRISPR-Cas9," *Journal of Clinical Investigation* 124(10), 4154-4161.
Hathaway, N. A. et al. (2012) "Dynamics and Memory of Heterochromatin in Living Cells," *Cell* 1447-1460.
Ho, S. N. et al. (1996) "Dimeric ligands defuse a role for transcriptional activation domains in reinitiation," *Nature*382(6594), 822-826.
Hou, Z. et al. (2013) "Efficient genome engineering in human pluripotent stem cells using Cas9 from Neisseria meningitidis," *Proceedings of the National Academy of Sciences* 110(39), 15644-15649.
Hsu, P. D. et al. (2014) "Development and applications of CRISPR-Cas9 for genome engineering," *Cell* 157(6), 1262-1278.
Hsu, P. D. et al. (2013) "DNA targeting specificity of RNA-guided Cas9 nucleases," *Nature Biotechnology* 31(9), 827-832.
Hu, J. et al. (2014) "Direct activation of human and mouse Oct4 genes using engineered TALE and Cas9 transcription factors," *Nucleic Acids Research* 42(7), 4375-4390.
Hu, W. et al. (2014) "RNA-directed gene editing specifically eradicates latent and prevents new HIV-1 infection," *Proceedings of the National Academy of Sciences of the United States of America* 111(31), 11461-11466.
Jiang. F. et al. (2015) "Structural Biology. A Cas9-guide RNA complex preorganized for target DNA recognition," *Science* 348(6242), 1477-1481.
Jiang, W. et al. (2013) "CRISPR-assisted editing of bacterial genomes," *Nature Biotechnology* 31(3), 233-239.
Jinek, M. et al. (2012) "A programmable dual-RNA-guided DNA endonuclease in adaptive bacterial immunity," *Science* 337(6096), 816-821.
Jinek, M. et al. (2014) "Structures of Cas9 Endonucleases Reveal RNA-Mediated Conformational Activation," *Science* 343(6176).
Joung, J. K. et al. (2013) "TALENs: a widely applicable technology for targeted genome editing," *Nature Reviews Molecular Cell Biology* 14(1), 49-55.
Kearns, N. A. et al. (2014) "Cas9 effector-mediated regulation of transcription and differentiation in human pluripotent stem cells," *Development* 141(1), 219-223.
Khalil. A. S. et al. (2012) "A Synthetic Biology Framework for Programming Eukaryotic Transcription Functions," *Cell* 150(3), 647-658.
Kim, H. J. et al. (2009) "Targeted genome editing in human cells with zinc finger nucleases constructed via modular assembly," *Genome Research* 19(7), 1279-1288.
Kim, S. et al. (2014) "Highly efficient RNA-guided genome editing in human cells via delivery of purified Cas9 ribonucleoproteins," *Genome Research* 24(6), 1012-1019.
Kleinstiver, B. P. et al. (2015) "Engineered CRISPR-Cas9 nucleases with altered PAM specificities," *Nature* 523(7561), 481-485.
Klemm, J. D. et al. (1996) "Oct-1 POU domain-DNA interactions: cooperative binding of isolated subdomains and effects of covalent linkage," *Genes & Development* 10(1), 27-36.
Konermann, S. et al. (2013) "Optical control of mammalian endogenous transcription and epigenetic states," *Nature* 500(7463), 472-476.
Lamb, B. M. et al. (2013) "Directed evolution of the TALE N-terminal domain for recognition of all 5' bases," *Nucleic Acids Research* 41(21), 9779-9785.
Larson, M. H. et al. (2013) "CRISPR interference (CRISPRi) for sequence-specific control of gene expression," *Nature Protocols* 8(11), 2180-2196.
Ledford, H. (2015) "CRISPR, the disruptor," *Nature* 522(7554), 20-24.
Lee, H. J. et al. (2010) "Targeted chromosomal deletions in human cells using zinc finger nucleases," *Genome Research* 20(1), 81-89.
Li, H. et al. (2011) "In vivo genome editing restores hemostasis in a mouse model of hemophilia," *Nature* 475(7355), 217-221.
Liang, F.-S. et al. (2011) "Engineering the ABA Plant Stress Pathway for Regulation of Induced Proximity," *Science Signaling* 4(164), rs2-rs2.
Lin, Y. et al. (2014) "CRISPR/Cas9 systems have off-target activity with insertions or deletions between target DNA and guide RNA sequences," *Nucleic Acids Research* 42(11), 7473-7485.
Liu, J. et al. (1994) "Evidence for a non-alpha-helical DNA-binding motif in the Rel homology region," *Proceedings of the National Academy of Sciences of the United States of America* 91(3), 908-912.

(56) References Cited

OTHER PUBLICATIONS

Lu, X.-J. et al. (2008) "3DNA: a versatile, integrated software system for the analysis, rebuilding, and visualization of three-dimensional nucleic-acid structures," *Nature Protocols* 3(7), 1213-1227.

Luscombe, N. M. et al. (2001) "Amino acid-base interactions: a three-dimensional analysis of protein-DNA interactions at an atomic level," *Nucleic Acids Research* 29(13), 2860-2874.

Lutz, R. el al. (1997) "Independent and tight regulation of transcriptional units in *Escherichia coli* via the LacR/O, the TetR/O and AraC/II-I2 regulatory elements," *Nucleic Acids Research* 25(6), 1203-1210.

Maeder, M. L. et al. (2008) "Rapid "open-source" engineering of customized zinc-finger nucleases for highly efficient gene modification," *Molecular Cell* 31(2), 294-301.

Maeder, M. L. et al. (2009) "Oligomerized Pool ENgineering (OPEN): An "Open-Source" Protocol for Making Customized Zinc Finger Arrays," *Nature Protocols* 4(10), 1471-1501.

Mahiny, A. J. et al. (2015) "In vivo genome editing using nuclease-encoding mRNA corrects SP-B deficiency," *Nature Biotechnology* 33(6), 584-586.

Mak, A. N.-S. et al. (2012) "The crystal structure of TAL effector PthXol bound to its DNA target," *Science* 335(6069), 716-719.

Mali, P. et al. (2013) "RNA-guided human genome engineering via Cas9," *Science* 339(6121), 823-826.

Mandell, J. G. et al. (2006) "Zinc Finger Tools: custom DNA-binding domains for transcription factors and nucleases," *Nucleic Acids Research* 34(suppl 2), W516-W523.

Meckler, J. F. et al. (2013) "Quantitative analysis of TALE-DNA interactions suggests polarity effects," *Nucleic Acids Research* 41(7), 4118-4128.

Meng, X. et al. (2005) "A bacterial one-hybrid system for determining the DNA-binding specificity of transcription factors," *Nature Biotechnology* 23(8), 988-994.

Meng, X. et al. (2008) "Targeted gene inactivation in zebrafish using engineered zinc finger nucleases," *Nature Biotechnology* 26(6), 695-701.

Moffat, J. et al. (2006) "A Lentiviral RNAi Library for Human and Mouse Genes Applied to an Arrayed Viral High-Content Screen," *Cell* 124(6), 1283-1298.

Noyes, M. B. et al. (2008) "Analysis of homeodomain specificities allows the family-wide prediction of preferred recognition sites," *Cell* 133(7), 1277-1289.

Pavletich, N. P. et al. (1991) "Zinc finger-DNA recognition: crystal structure of a Zif268-DNA complex at 2.1 A," *Science* 252(5007), 809-817.

Persikov, A. V. et al. (2015) "A systematic survey of the Cys(2)His(2) zinc finger DNA-binding landscape," *Nucleic Acids Research* 43(3), 1965-1984.

Pfister, E. L. et al. (2009) "Five siRNAs targeting three SNPs in Huntingtin may provide therapy for three-quarters of Huntington's disease patients," *Current Biology* 19(9), 774-778.

Qi, L. S. et al. (2013) "Repurposing CRISPR as an RNA-guided platform for sequence-specific control of gene expression," *Cell* 152(5), 1173-1183.

Ramakrishna, S. et al. (2014) "Gene disruption by cell-penetrating peptide-mediated delivery of Cas9 protein and guide RNA," *Genome Research* 24(6), 1020-1027.

Ran, F. A. et al. (2015) "In vivo genome editing using *Staphylococcus aureus* Cas9," *Nature* 520(7546), 186-191.

Ran, F. A. et al. (2013) "Double Nicking by RNA-Guided CRISPR Cas9 for Enhanced Genome Editing Specificity," *Cell* 154(6), 1380-1389.

Reyon, D. et al. (2012) "FLASH Assembly of TALENs Enables High-Throughput Genome Editing," *Nature Biotechnology* 30(5), 460-465.

Root, D. E. et al. (2006) "Genome-scale loss-of-function screening with a lentiviral RNAi library," *Nature Methods* 3(9), 715-719.

Sander, J. D. et al. (2011) "Selection-Free Zinc-Finger Nuclease Engineering by Context-Dependent Assembly (CoDA)," *Nature Methods* 8(1), 67-69.

Sander, J. D. et al. (2014) "CRISPR-Cas systems for genome editing, regulation and targeting," *Nature Biotechnology* 32(4), 347-355.

Sander, J. D. et al. (2010) "ZiFiT (Zinc Finger Targeter): an updated zinc finger engineering tool," *Nucleic Acids Research* 38(Web Server issue), W462-W468.

Schneider, C. A. et al. (2012) "NIH Image to ImageJ: 25 years of image analysis," *Nature Methods* 9(7), 671-675.

Segal, D. J. et al. (1999) "Toward controlling gene expression at will: Selection and design of zinc finger domains recognizing each of the 5'-GNN-3' DNA target sequences," *Proceedings of the National Academy of Sciences of the United States of America* 96(6), 2758-2763.

Shroyer, M. J. et al. (1999) "Mutation of an active site residue in *Escherichia coli* uracil-DNA glycosylase: effect on DNA binding, uracil inhibition and catalysis," *Biochemistry* 38(15), 4834-4845.

Sims, D. et al. (2011) "High-throughput RNA interference screening using pooled shRNA libraries and next generation sequencing," *Genome Biology* 12(10), R104.

Spencer, D. M. et al. (1993) "Controlling signal transduction with synthetic ligands," *Science* 262(5136), 1019-1024.

Stankunas, K. et al. (2007) "Rescue of Degradation-Prone Mutants of the FK506-Rapamycin Binding (FRB) Protein with Chemical Ligands," *ChemBioChem* 8(10), 1162-1169.

Sternberg, S. H. et al. (2014) "DNA interrogation by the CRISPR RNA-guided endonuclease Cas9," *Nature* 507(7490), 62-67.

Stewart, S. A. et al. (2003) "Lentivirus-delivered stable gene silencing by RNAi in primary cells," *RNA* 9(4), 493-501.

Szczelkun, M. D. el al. (2014) "Direct observation of R-loop formation by single RNA-guided Cas9 and Cascade effector complexes," *Proceedings of the National Academy of Sciences of the United States of America* 111(27), 9798-9803.

Tsai, Shengdar Q. et al. (2014) "What's Changed with Genome Editing?," *Cell Stem Cell* 15(1), 3-4.

Tsai, S. Q. et al. (2014) "Dimeric CRISPR RNA-guided FokI nucleases for highly specific genome editing," *Nature Biotechnology* 32(6), 569-576.

Tsai, S. Q. et al. (2015) "GUIDE-Seq enables genome-wide profiling of off-target cleavage by CRISPR-Cas nucleases," *Nature Biotechnology* 33(2), 187-197.

Villefranc, J. A. et al. (2007) "Gateway Compatible Vectors for Analysis of Gene Function in the Zebrafish," *Developmental Dynamics* 236(11), 3077-3087.

Wang, H. et al. (2013) "One-step generation of in ice carrying imitations in multiple genes by CRISPR/Cas-mediated genome engineering," *Cell* 153(4), 910-918.

Wilson, K. A. et al. (2013) "Design and Development of Artificial Zinc Finger Transcription Factors and Zinc Finger Nucleases to the hTERT Locus," *Molecular Therapy—Nucleic Acids* 2(4), e87.

Wolfe, S. A. et al. (1997) "Unusual Rel-like architecture in the DNA-binding domain of the transcription factor NFATc,"*Nature* 385(6612), 172-176.

Wright, A. V. et al. (2015) "Rational design of a split-Cas9 enzyme complex," *Proceedings of the National Academy of Sciences of the United States of America* 112(10), 2984-2989.

Wu, X. et al. (2014) "Genome-wide binding of the CRISPR endonuclease Cas9 in mammalian cells," *Nature Biotechnology* 32(7), 670-676.

Yin, H. et al. (2014) "Genome editing with Cas9 in adult mice corrects a disease mutation and phenotype," *Nature Biotechnology* 32(6), 551-553.

Yoshimi, K. et al. (2014) "Allele-specific genome editing and correction of disease-associated phenotypes in rats using the CRISPR-Cas platform," *Nature Communications* 5, 4240.

Yusa, K. et al. (2011) "Targeted gene correction of α(1)-antitrypsin deficiency in induced pluripotent stem cells," *Nature* 478(7369), 391-394.

Zetche, B. et al. (2015) "A Split Cas9 Architecture for Inducible Genome Editing and Transcription Modulation," *Nature Biotechnology* 33(2), 139-142.

(56) References Cited

OTHER PUBLICATIONS

Zetsche, B. et al. (2015) "Cpf1 Is a Single RNA-Guided Endonuclease of a Class 2 CRISPR-Cas System," *Cell* 163(3), 759-771.

Zhang, Y. et al. (2014) "Comparison of non-canonical PAMs for CRISPR/Cas9-mediated DNA cleavage in human cells," *Scientific Reports* 4, 5405.

Zhang, Y. et al. (2013) "Processing-Independent CRISPR RNAs Limit Natural Transformation in Neisseria meningitidis,"*Molecular Cell* 50(4), 488-503.

Zhu, C. et al. (2013) "Using defined finger—finger interfaces as units of assembly for constructing zinc-finger nucleases," *Nucleic Acids Research* 41(4), 2455-2465.

Zhu, L. J. et al. (2010) "ChIPpeakAnno: a Bioconductor package to annotate ChIP-seq and ChIP-chip data," *BMC Bioinformatics* 11, 237-237.

Zhu, L. J. et al. (2014) "CRISPRseek: A Bioconductor Package to Identify Target-Specific Guide RNAs for CRISPR-Cas9 Genome-Editing Systems," *PLoS ONE* 9(9), e108424.

Christy and Nathans, "DNA Binding Site of the Growth Factor-Inducible Protein Zif268", PNAS 86:8737-8741. 1989.

Bolukbasi, et al. "DNA-binding-domain fusions enhance the targeting range and precision of Cas9." Nature Methods ePub 19 vol. 12 No. 12. pp. 1150-1156. 2015with Extended Data.

Anders, C. et al., (2014) "Structural basis of PAM-dependent target DNA recognition by the Cas9 endonuclease," *Nature* 513(7519), 569-573 with Extended Data.

Kleinstiver, B. P. et al., (2015) "Engineered CRISPR-Cas9 nucleases with altered PAM specificities," *Nature* 523(7561), 481-485 with Extended Data.

\* cited by examiner

Figure 2A
N-Cas9-DBD-C
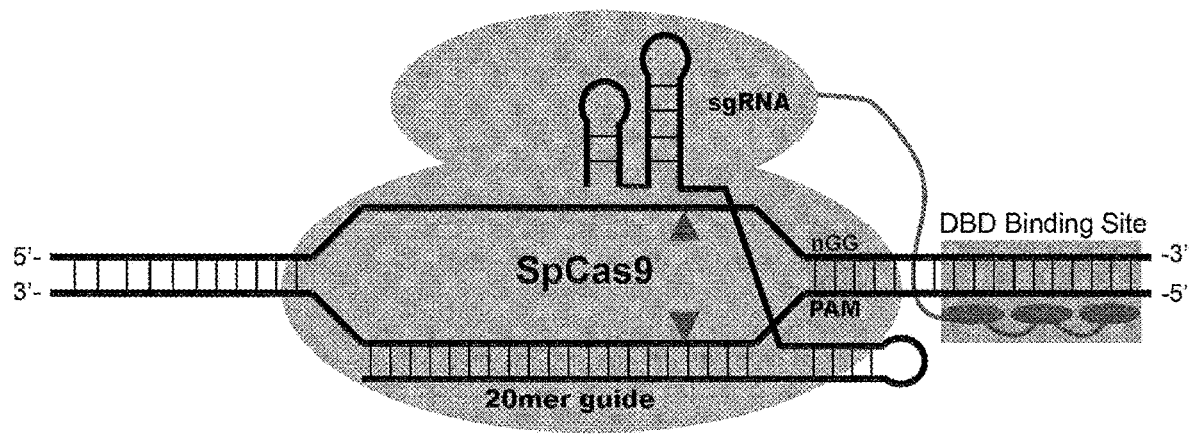
N-DBD-Cas9-C
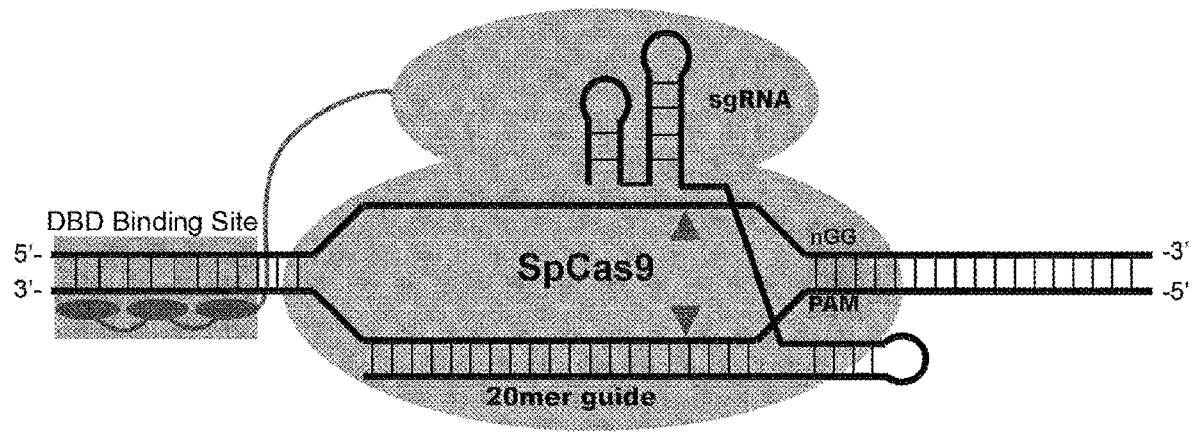
Figure 2B
Figure 2

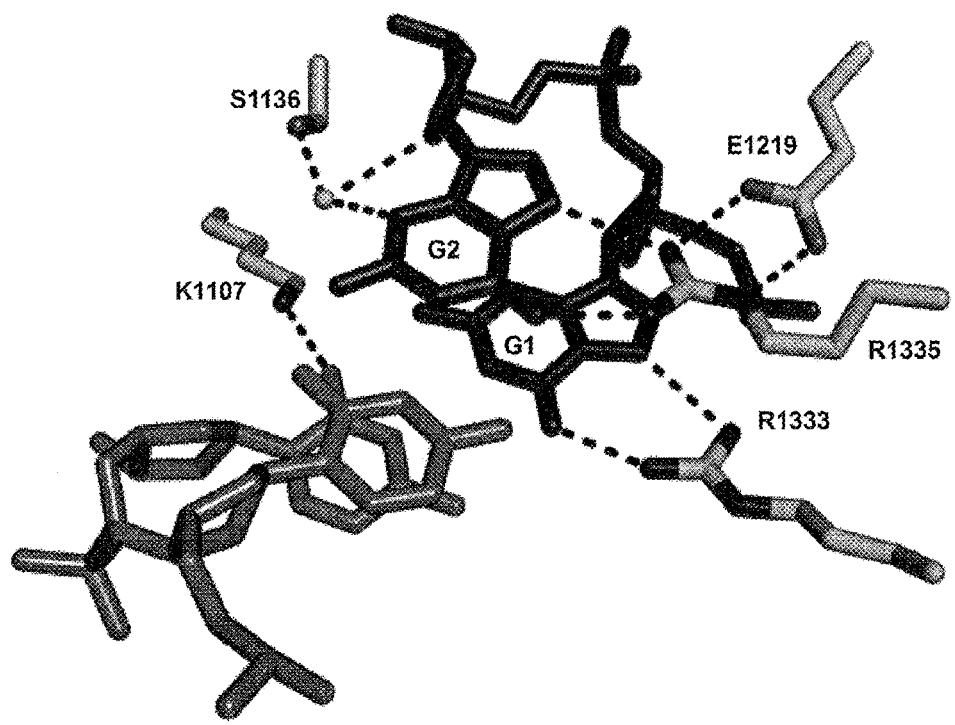
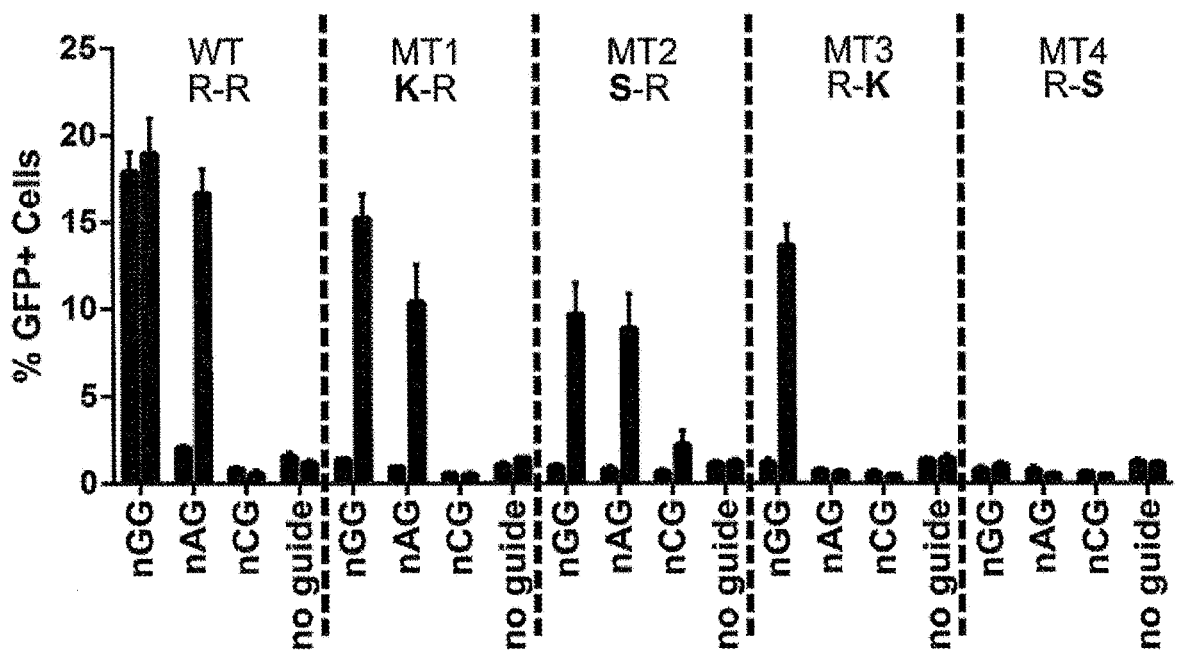
Figure 9

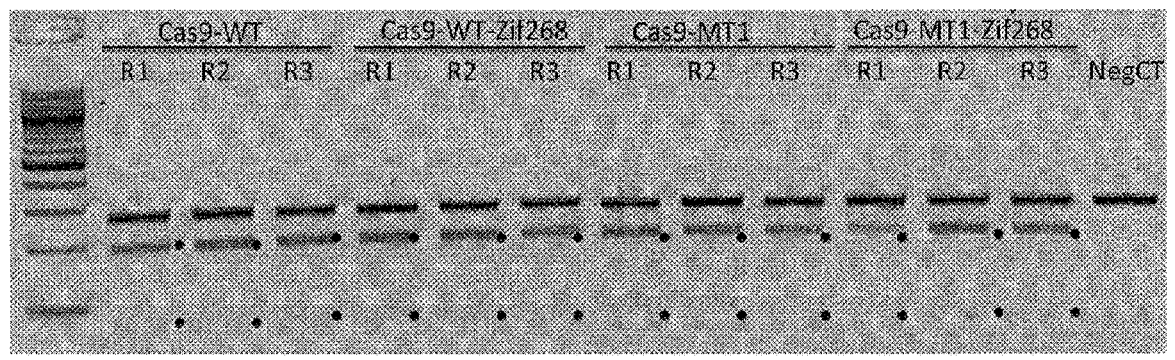
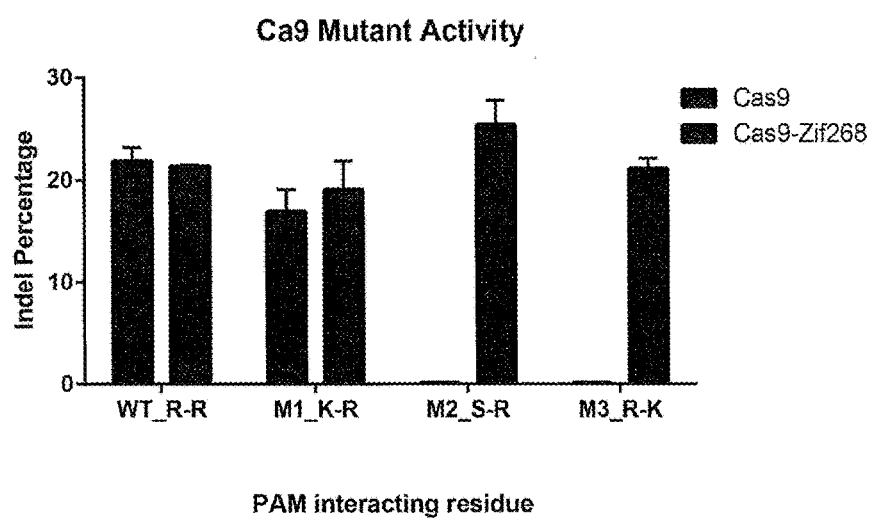
Figure 10

GTGGGTGAGTGAGTGTGTGCGTGTGGGGTTGAGGGCGTTGGAGCGGGG
VEGFA Cas9 TS3                    ZFP target site
SEQ ID NO: 49
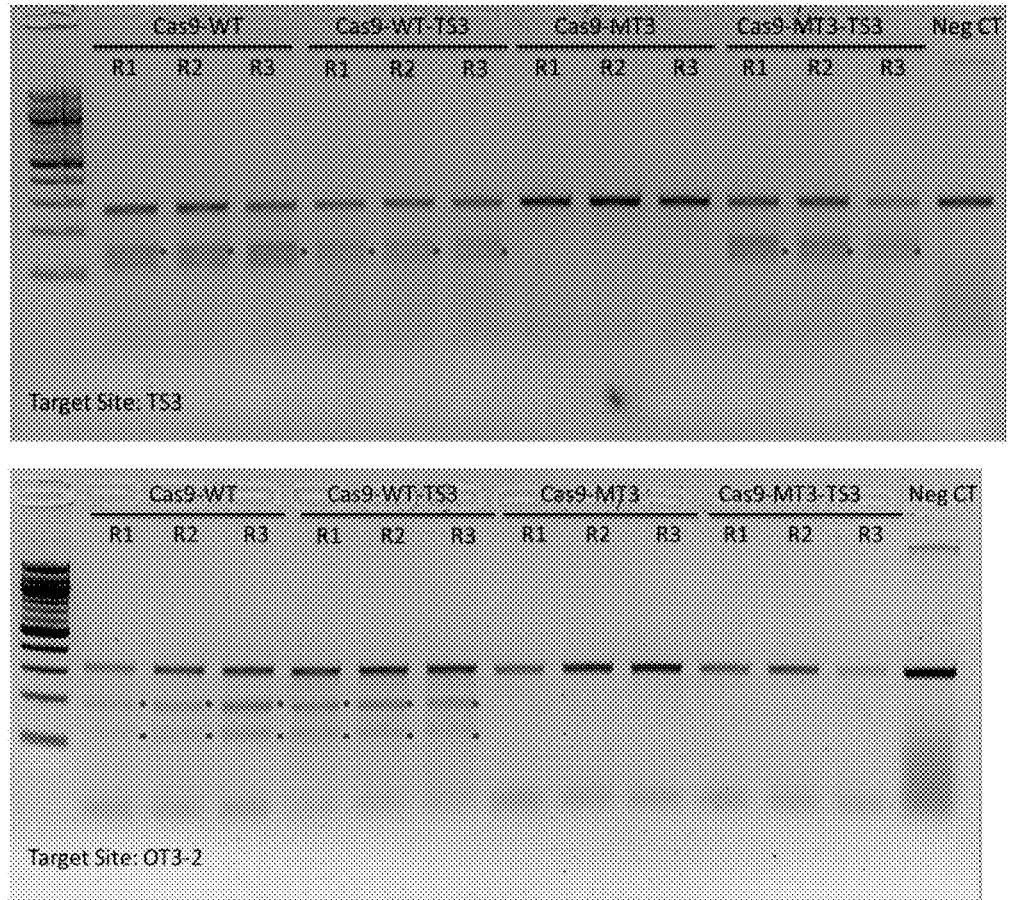
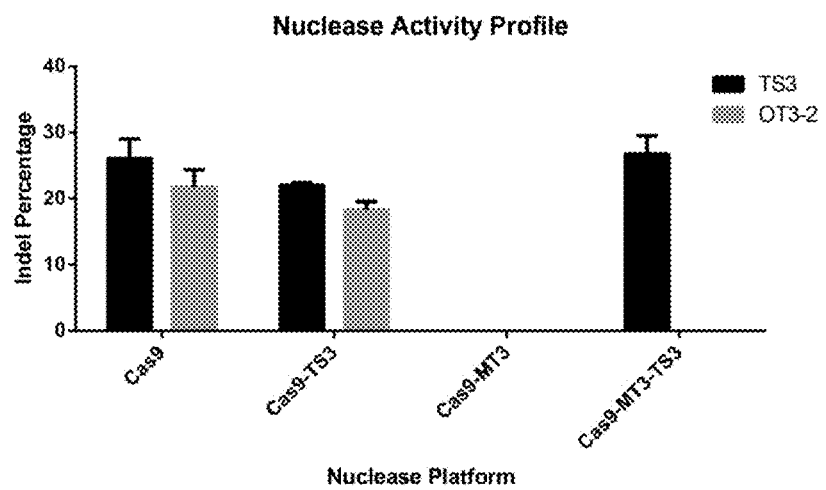
FIGURE 12

CCT<u>GAGTCCGAGCAGAAGAAGA</u>AGGGCTCCCAT<u>CACATCAACCGGTGG</u>
<u>EMX1 Cas9 TS4</u>                    <u>ZFP target site</u>

SEQ ID NO: 51

SpCas9MT-DBD with truncated sgRNA
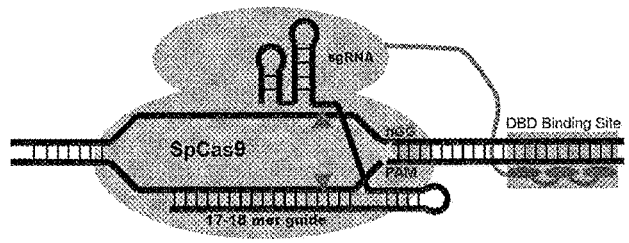
SpCas9MT-DBD as dual nickases
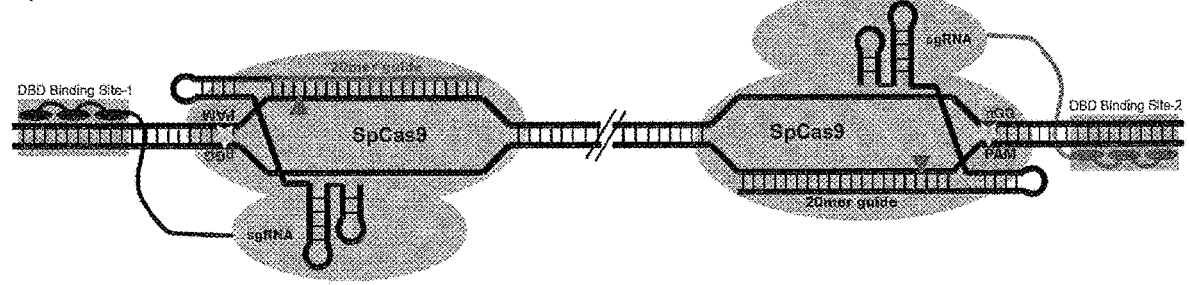
FokI-SpdCas9MT-DBD
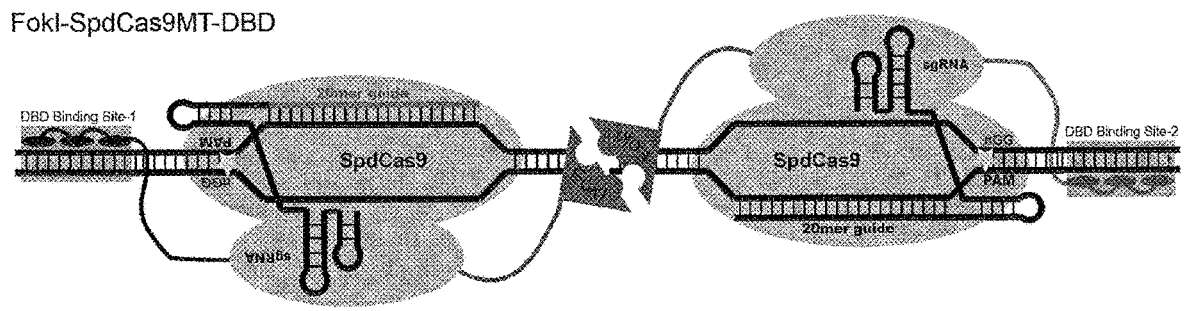
Figure 22

SEQ ID NOS: 62, 63, 64, 65, 66

```
WT-RKR    GGCGCGCCTGCAGCCTTCAAGTACTTCGACACCACCATAGAC▓▓▓▓TACACCTCT 60
MT1-KKR   GGCGCGCCTGCAGCCTTCAAGTACTTCGACACCACCATAGACAAA▓▓▓TACACCTCT 60
MT2-SKR   GGCGCGCCTGCAGCCTTCAAGTACTTCGACACCACCATAGACAGC▓▓▓TACACCTCT 60
MT3-RKK   GGCGCGCCTGCAGCCTTCAAGTACTTCGACACCACCATAGAC▓▓▓AAGTACACCTCT 60
MT4-RKS   GGCGCGCCTGCAGCCTTCAAGTACTTCGACACCACCATAGAC▓▓▓AGCTACACCTCT 60
          ******************************************    ***  ********

WT-RKR    ACAAAGGAGGTCCTGGACGCCACACTGATTCATCAGTCAATTACGGGGCTCTATGAAACA 120
MT1-KKR   ACAAAGGAGGTCCTGGACGCCACACTGATTCATCAGTCAATTACGGGGCTCTATGAAACA 120
MT2-SKR   ACAAAGGAGGTCCTGGACGCCACACTGATTCATCAGTCAATTACGGGGCTCTATGAAACA 120
MT3-RKK   ACAAAGGAGGTCCTGGACGCCACACTGATTCATCAGTCAATTACGGGGCTCTATGAAACA 120
MT4-RKS   ACAAAGGAGGTCCTGGACGCCACACTGATTCATCAGTCAATTACGGGGCTCTATGAAACA 120
          ************************************************************

WT-RKR    AGAATCGACCTCTCTCAGCTCGGTGGAGACGGCACCGGCG 160
MT1-KKR   AGAATCGACCTCTCTCAGCTCGGTGGAGACGGCACCGGCG 160
MT2-SKR   AGAATCGACCTCTCTCAGCTCGGTGGAGACGGCACCGGCG 160
MT3-RKK   AGAATCGACCTCTCTCAGCTCGGTGGAGACGGCACCGGCG 160
MT4-RKS   AGAATCGACCTCTCTCAGCTCGGTGGAGACGGCACCGGCG 160
          ****************************************
```

Figure 26

SEQ ID NO: 67

>pCS-Dest_Cas9-Zif268

ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAAGGGAATACTGCAGACCGTTAAGGTCGTGGATGAACTCGTC
AAAGTAATGGGAAGGCATAAGCCCGAGAATATCGTTATCGAGATGGCCCGAGAGAACCAAACTACCCAGAAGGGACA

Figure 27

```
GAAGAACAGTAGGGAAAGGATGAAGAGGATTGAAGAGGGTATAAAAGAACTGGGGTCCCAAATCCTTAAGGAACACC
CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC████████TACACCTCTA
CAAAGGAGGTCCTGGACGCCACACTGATTCATCAGTCAATTACGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAGAAACTGGATTTCGAATCCGGA████████████████████████████████████████████
████████████████████████████████████████████████████████████████████████████
████████████████████████████████████████████████████████████TAAGCGGCCGCC
TCGAGATATCTAGACCCAGCTTTCTTGTACAAAGTGGTTGATCCTCTCGAGCCTCTAGAACTATAGTGAGTCGTATT
ACGTAGATCCAGACATGATAAGATACATTGATGAGTTTGGACAAACCACAACTAGAATGCAGTGAAAAAAATGCTTT
ATTTGTGAAATTTGTGATGCTATTGCTTTATTTGTAACCATTATAAGCTGCAATAAACAAGTTAACAACAACAATTG
CATTCATTTTATGTTTCAGGTTCAGGGGGAGGTGTGGGAGGTTTTTTAATTCGCGGCCGCGGCGCCAATGCATTGGG
CCCGGTACCCAGCTTTTGTTCCCTTTAGTGAGGGTTAATTGCGCGCTTGGCGTAATCATGGTCATAGCTGTTTCCTG
TGTGAAATTGTTATCCGCTCACAATTCCACACAACATACGAGCCGGAAGCATAAAGTGTAAAGCCTGGGGTGCCTAA
```

Figure 27 CONT

```
TGAGTGAGCTAACTCACATTAATTGCGTTGCGCTCACTGCCCGCTTTCCAGTCGGGAAACCTGTCGTGCCAGCTGCA
TTAATGAATCGGCCAACGCGCGGGGAGAGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAGCAGAGCGAGGTAT
GTAGGCGGTGCTACAGAGTTCTTGAAGTGGTGGCCTAACTACGGCTACACTAGAAGGACAGTATTTGGTATCTGCGC
TCTGCTGAAGCCAGTTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGATCTTTTCTACGGGG
TCTGACGCTCAGTGGAACGAAAACTCACGTTAAGGGATTTTGGTCATGAGATTATCAAAAAGGATCTTCACCTAGAT
CCTTTTAAATTAAAAATGAAGTTTTAAATCAATCTAAAGTATATATGAGTAAACTTGGTCTGACAGTTACCAATGCT
TAATCAGTGAGGCACCTATCTCAGCGATCTGTCTATTTCGTTCATCCATAGTTGCCTGACTCCCCGTCGTGTAGATA
ACTACGATACGGGAGGGCTTACCATCTGGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTCCTGCAACTTTATCCGCCTCCATCCAGT
CTATTAATTGTTGCCGGGAAGCTAGAGTAAGTAGTTCGCCAGTTAATAGTTTGCGCAACGTTGTTGCCATTGCTACA
GGCATCGTGGTGTCACGCTCGTCGTTTGGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGCGTCAATACGGGATAA
TACCGCGCCACATAGCAGAACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTAAATTGTAAGCGTTAATATTT
TGTTAAAATTCGCGTTAAATTTTGTTAAATCAGCTCATTTTTAACCAATAGGCCGAAATCGGCAAAATCCCTTAT
AAATCAAAAGAATAGACCGAGATAGGGTTGAGTGTTGTTCCAGTTTGGAACAAGAGTCCACTATTAAAGAACGTGGA
CTCCAACGTCAAAGGGCGAAAAACCGTCTATCAGGGCGATGGCCCACTACGTGAACCATCACCCTAATCAAGTTTTT
TGGGGTCGAGGTGCCGTAAAGCACTAAATCGGAACCCTAAAGGGAGCCCCGATTTAGAGCTTGACGGGGAAAGCCG
GCGAACGTGGCGAGAAAGGAAGGGAAGAAAGCGAAAGGAGCGGGCGCTAGGGCGCTGGCAAGTGTAGCGGTCACGCT
GCGCGTAACCACCACACCCGCCGCGCTTAATGCGCCGCTACAGGGCGCGTCCCATTCGCCATTCAGGCTGCGCAACT
GTTGGGAAGGGCGATCGGTGCGGGCCTCTTCGCTATTACGCCAGTCGACCATAGCCAATTCAATATGGCGTATATGG
ACTCATGCCAATTCAATATGGTGGATCTGGACCTGTGCCAATTCAATATGGCGTATATGGACTCGTGCCAATTCAAT
```

Figure 27 CONT

ATGGTGGATCTGGACCCCAGCCAATTCAATATGGCGGACTTGGCACCATGCCAATTCAATATGGCGGACTTGGCACT
GTGCCAACTGGGGAGGGGTCTACTTGGCACGGTGCCAAGTTTGAGGAGGGGTCTTGGCCCTGTGCCAAGTCCGCCAT
ATTGAATTGGCATGGTGCCAATAATGGCGGCCATATTGGCTATATGCCAGGATCAATATATAGGCAATATCCAATAT
GGCCCTATGCCAATATGGCTATTGGCCAGGTTCAATACTATGTATTGGCCCTATGCCATATAGTATTCCATATATGG
GTTTTCCTATTGACGTAGATAGCCCCTCCCAATGGGCGGTCCCATATACCATATATGGGGCTTCCTAATACCGCCCA
TAGCCACTCCCCCATTGACGTCAATGGTCTCTATATATGGTCTTTCCTATTGACGTCATATGGGCGGTCCTATTGAC
GTATATGGCGCCTCCCCCATTGACGTCAATTACGGTAAATGGCCCGCCTGGCTCAATGCCCATTGACGTCAATAGGA
CCACCCACCATTGACGTCAATGGGATGGCTCATTGCCCATTCATATCCGTTCTCACGCCCCTATTGACGTCAATGA
CGGTAAATGGCCCACTTGGCAGTACATCAATATCTATTAATAGTAACTTGGCAAGTACATTACTATTGGAAGGACGC
CAGGGTACATTGGCAGTACTCCCATTGACGTCAATGGCGGTAAATGGCCCGCGATGGCTGCCAAGTACATCCCCATT
GACGTCAATGGGGAGGGGCAATGACGCAAATGGGCGTTCCATTGACGTAAATGGGCGGTAGGCGTGCCTAATGGGAG
GTCTATATAAGCAATGCTCGTTTAGGGA

Figure 27 CONT

SEQ ID NO: 68

> pCS-Dest_Zif268_Cas9

ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACcatgGGtagAGC
CGCGCCGGCAGCTAAGAAAAAGAAACTGGATCaattG
CccggGT
CTGGAGGTAGCGGCTCAAGTGGCCGTACGGCAGCTCCTGCGGCAAAAAGAAAAAGTTGGACTCTGAATTCGGAAGC
GAcaagaagtactccattgggctcgatatcGgtacCAACAGCGTCGGCTGGGCCGTCATTACGGACGAGTACAAGGT
GCCGAGCAAAAAATTCAAAGTTCTGGGCAATACCGATCGCCACAGCATAAAGAAGAACCTCATTGGAGCCCTCCTGT
TCGACTCCGGGGAGACGGCCGAAGCCACGCGGCTCAAAAGAACAGCACGGCGCAGATATACCCGCAGAAAGAATCGG
ATCTGCTACCTGCAGGAGATCTTTAGTAATGAGATGGCTAAGGTGGATGACTCTTTCTTCCATAGGCTGGAGGAGTC
CTTTTTGGTGGAGGAGGATAAAAAGCACGAGCGCCACCCAATCTTTGGCAATATCGTGGACGAGGTGGCGTACCATG
AAAAGTACCCAACCATATATCATCTGAGGAAGAAGCTGGTAGACAGTACTGATAAGGCTGACTTGCGGTTGATCTAT
CTCGCGCTGGCGCACATGATCAAATTCGGGGACACTTCCTCATCGAGGGGGACCTGAACCCAGACAACAGCGATGT
CGACAAACTCTTTATCCAACTGGTTCAGACTTACAATCAGCTTTTCGAGGAGAACCCGATCAACGCATCCGGCGTTG
ACGCCAAAGCAATCCTGAGCGCTAGGCTGTCCAAATCCCGGCGGCTCGAAAACCTCATCGCACAGCTCCCTGGGGAG
AAGAAGAACGGCCTGTTTGGTAATCTTATCGCCCTGTCACTCGGGCTGACCCCCAACTTTAAATCTAACTTCGACCT
GGCCGAAGATGCCAAGCTGCAACTGAGCAAAGACACCTACGATGATGATCTCGACAATCTGCTGGCCCAGATCGGCG
ACCAGTACGCAGACCTTTTTTTGGCGGCAAAGAACCTGTCAGACGCCATTCTGCTGAGTGATATTCTGCGAGTGAAC
ACGGAGATCACCAAAGCTCCGCTGAGCGCTAGTATGATCAAGCGCTATGATGAGCACCACCAAGACTTGACTTTGCT
GAAGGCCCTTGTCAGACAGCAACTGCCTGAGAAGTACAAGGAAATTTTCTTCGATCAGTCTAAAAATGGCTACGCCG
GATACATTGACGGCGGAGCAAGCCAGGAGGAATTTACAAATTTATTAAGCCCATCTTGGAAAAAATGGACGGCACC
GAGGAGCTGCTGGTAAAGCTGAACAGAGAAGATCTGTTGCGCAAACAGCGCACTTTCGACAATGGAAGCATCCCCCA
CCAGATTCACCTGGGCGAACTGCACGCTATCCTCAGGCGGCAAGAGGATTTCTACCCCTTTTTGAAAGATAACAGGG
AAAAGATTGAGAAAATCCTCACATTTCGGATACCCTACTATGTAGGCCCCCTCGCTCGGGGAAATTCCAGATTCGCG
TGGATGACTCGCAAATCAGAAGAGACCATCACTCCCTGGAACTTCGAGGAAGTCGTGGATAAGGGGCCTCTGCCCA
GTCCTTCATCGAAAGGATGACTAACTTTGATAAAAATCTGCCTAACGAAAAGGTGCTTCCTAAACACTCTCTGCTGT
ACGAGTACTTCACAGTTTATAACGAGCTCACCAAGGTCAAATACGTCACAGAAGGGATGAGAAAGCCAGCATTCCTG
TCTGGAGAGCAGAAGAAAGCTATCGTGGACCTCCTCTTCAAGACGAACCGGAAAGTTACCGTGAAACAGCTCAAAGA
AGACTATTTCAAAAGATTGAATGTTTCGACTCTGTTGAAATCAGCGGAGTGGAGGATCGCTTCAACGCATCCCTGG
GAACGTATCACGATCTCCTGAAAATCATTAAAGACAAGGACTTCCTGGACAATGAGGAGAACGAGGACATTCTTGAG
GACATTGTCCTCACCCTTACGTTGTTTGAAGATAGGGAGATGATTGAAGAACGCTTGAAAACTTACGCTCATCTCTT
CGACGACAAAGTCATGAAACAGCTCAAGAGACGCCGATATACAGGATGGGGGCGGCTGTCAAGAAAACTGATCAATG
GCATCCGAGACAAGCAGAGTGGAAAGACAATCCTGGATTTTCTTAAGTCCGATGGATTTGCCAACCGGAACTTCATG

Figure 28

```
CAGTTGATCCATGATGACTCTCTCACCTTTAAGGAGGACATCCAGAAAGCACAAGTTTCTGGCCAGGGGGACAGTCT
TCACGAGCACATCGCTAATCTTGCAGGTAGCCCAGCTATCAAAAAGGGAATACTGCAGACCGTTAAGGTCGTGGATG
AACTCGTCAAAGTAATGGGAAGGCATAAGCCCGAGAATATCGTTATCGAGATGGCCCGAGAGAACCAAACTACCCAG
AAGGGACAGAAGAACAGTAGGGAAAGGATGAAGAGGATTGAAGAGGGTATAAAAGAACTGGGGTCCCAAATCCTTAA
GGAACACCCAGTTGAAAACACCCAGCTTCAGAATGAGAAGCTCTACCTGTACTACCTGCAGAACGGCAGGGACATGT
ACGTGGATCAGGAACTGGACATCAACCGGTTGTCCGACTACGACGTGGATCATATCGTGCCCCAAAGCTTTCTCAAA
GATGATTCTATTGATAATAAAGTGTTGACAAGATCCGATAAAAATAGAGGGAAGAGTGATAACGTCCCCTCAGAAGA
AGTTGTCAAGAAAATGAAAAATTATTGGCGGCAGCTGCTGAACGCCAAACTGATCACACAACGGAAGTTCGATAATC
TGACTAAGGCTGAACGAGGTGGCCTGTCTGAGTTGGATAAAGCCGGCTTCATCAAAAGGCAGCTTGTTGAGACACGC
CAGATCACCAAGCACGTGGCCCAAATTCTCGATTCACGCATGAACACCAAGTACGATGAAAATGACAAACTGATTCG
AGAGGTGAAAGTTATTACTCTGAAGTCTAAGCTGGTCTCAGATTTCAGAAAGGACTTTCAGTTTTATAAGGTGAGAG
AGATCAACAATTACCACCATGCGCATGATGCCTACCTGAATGCAGTGGTAGGCACTGCACTTATCAAAAAATATCCC
AAGCTGGAATCTGAATTTGTTTACGGAGACTATAAAGTGTACGATGTTAGGAAAATGATCGCAAAGTCTGAGCAGGA
AATAGGCAAGGCCACCGCTAAGTACTTCTTTTACAGCAATATTATGAATTTTTTCAAGACCGAGATTACACTGGCCA
ATGGAGAGATTCGGAAGCGACCACTTATCGAAACAAACGGAGAAACAGGAGAAATCGTGTGGGACAAGGGTAGGGAT
TTCGCGACAGTCCGCAAGGTCCTGTCCATGCCGCAGGTGAACATCGTTAAAAAGACCGAAGTACAGACCGGAGGCTT
CTCCAAGGAAAGTATCCTCCCGAAAAGGAACAGCGACAAGCTGATCGCACGCAAAAAGATTGGGACCCCAAGAAAT
ACGGCGGATTCGATTCTCCTACAGTCGCTTACAGTGTACTGGTTGTGGCCAAAGTGGAGAAAGGGAAGTCTAAAAAA
CTCAAAAGCGTCAAGGAACTGCTGGGCATCACAATCATGGAGCGATCCAGCTTCGAGAAAAACCCCATCGACTTTCT
CGAAGCGAAAGGATATAAAGAGGTCAAAAAAGACCTCATCATTAAGCTGCCCAAGTACTCTCTCTTTGAGCTTGAAA
ACGGCCGGAAACGAATGCTCGCTAGTGCGGGCGAGCTGCAGAAAGGTAACGAGCTGGCACTGCCCTCTAAATACGTT
AATTTCTTGTATCTGGCCAGCCACTATGAAAAGCTCAAAGGGTCTCCCGAAGATAATGAGCAGAAGCAGCTGTTCGT
GGAACAACACAAACACTACCTTGATGAGATCATCGAGCAAATAAGCGAGTTCTCCAAAAGAGTGATCCTCGCCGACG
CTAACCTCGATAAGGTGCTTTCTGCTTACAATAAGCACAGGGATAAGCCCATCAGGGAGCAGGCAGAAAACATTATC
CACTTGTTTACTCTGACCAACTTGGGCGCGCCTGCAGCCTTCAAGTACTTCGACACCACCATAGAC░░░░░░░░TA
CACCTCTACAAAGGAGGTCCTGGACGCCACACTGATTCATCAGTCAATTACGGGGCTCTATGAAACAAGAATCGACC
TCTCTCAGCTCGGTGGAGACGGCACCGGCGGGCCCAAGAAGAAGAGGAAGGTATACCCATACGATGTTCCTGACTAT
GCGGGCTATCCCTATGACGTCCCGGACTATGCAGGATCGTATCCTTATGACGTTCCAGATTACGCTGGATCCTAATG
ATTCGAATCCGGATAAGCGGCCGCCTCGAGATATCTAGACCCAGCTTTCTTGTACAAAGTGGTTGATCCTCTCGAGC
CTCTAGAACTATAGTGAGTCGTATTACGTAGATCCAGACATGATAAGATACATTGATGAGTTTGGACAAACCACAAC
TAGAATGCAGTGAAAAAAATGCTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGAGGTGTGGGAGGTTTTTTAATTC
GCGGCCGCGGCGCCAATGCATTGGGCCCGGTACCCAGCTTTTGTTCCCTTTAGTGAGGGTTAATTGCGCGCTTGGCG
TAATCATGGTCATAGCTGTTTCCTGTGTGAAATTGTTATCCGCTCACAATTCCACACAACATACGAGCCGGAAGCAT
AAAGTGTAAAGCCTGGGGTGCCTAATGAGTGAGCTAACTCACATTAATTGCGTTGCGCTCACTGCCCGCTTTCCAGT
CGGGAAACCTGTCGTGCCAGCTGCATTAATGAATCGGCCAACGCGCGGGGAGAGGCGGTTTGCGTATTGGGCGCTCT
```

Figure 28 CONT

```
TCCGCTTCCTCGCTCACTGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAATCGACGCTCAAGT
CAGAGGTGGCGAAACCCGACAGGACTATAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAATCTAAAGTATATATGAGTAA
ACTTGGTCTGACAGTTACCAATGCTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTGGCCCCAGTGCTGCAATGATACCGC
GAGACCCACGCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGTTAATAGTTT
GCGCAACGTTGTTGCCATTGCTACAGGCATCGTGGTGTCACGCTCGTCGTTTGGTATGGCTTCATTCAGCTCCGGTT
CCCAACGATCAAGGCGAGTTACATGATCCCCCATGTTGTGCAAAAAAGCGGTTAGCTCCTTCGGTCCTCCGATCGTT
GTCAGAAGTAAGTTGGCCGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTATGCGGCGACCGAGTTGCT
CTTGCCCGGCGTCAATACGGGATAATACCGCGCCACATAGCAGAACTTTAAAAGTGCTCATCATTGGAAAACGTTCT
TCGGGGCGAAAACTCTCAAGGATCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCATTTATCAGGGTTATTGTCTC
ATGAGCGGATACATATTTGAATGTATTTAGAAAAATAAACAAATAGGGGTTCCGCGCACATTTCCCCGAAAAGTGCC
ACCTAAATTGTAAGCGTTAATATTTTGTTAAAATTCGCGTTAAATTTTTGTTAAATCAGCTCATTTTTTAACCAATA
GGCCGAAATCGGCAAAATCCCTTATAAATCAAAAGAATAGACCGAGATAGGGTTGAGTGTTGTTCCAGTTGGAACA
AGAGTCCACTATTAAAGAACGTGGACTCCAACGTCAAAGGGCGAAAAACCGTCTATCAGGGCGATGGCCCACTACGT
GAACCATCACCCTAATCAAGTTTTTTGGGGTCGAGGTGCCGTAAAGCACTAAATCGGAACCCTAAAGGGAGCCCCCG
ATTTAGAGCTTGACGGGGAAAGCCGGCGAACGTGGCGAGAAAGGAAGGGAAGAAAGCGAAAGGAGCGGGCGCTAGGG
CGCTGGCAAGTGTAGCGGTCACGCTGCGCGTAACCACCACACCCGCCGCGCTTAATGCGCCGCTACAGGGCGCGTCC
CATTCGCCATTCAGGCTGCGCAACTGTTGGGAAGGGCGATCGGTGCGGGCCTCTTCGCTATTACGCCAGTCGACCAT
AGCCAATTCAATATGGCGTATATGGACTCATGCCAATTCAATATGGTGGATCTGGACCTGTGCCAATTCAATATGGC
GTATATGGACTCGTGCCAATTCAATATGGTGGATCTGGACCCCAGCCAATTCAATATGGCGGACTTGGCACCATGCC
AATTCAATATGGCGGACTTGGCACTGTGCCAACTGGGGAGGGGTCTACTTGGCACGGTGCCAAGTTTGAGGAGGGGT
CTTGGCCCTGTGCCAAGTCCGCCATATTGAATTGGCATGGTGCCAATAATGGCGGCCATATTGGCTATATGCCAGGA
```

Figure 28 CONT

TCAATATATAGGCAATATCCAATATGGCCCTATGCCAATATGGCTATTGGCCAGGTTCAATACTATGTATTGGCCCT
ATGCCATATAGTATTCCATATATGGGTTTTCCTATTGACGTAGATAGCCCCTCCCAATGGGCGGTCCCATATACCAT
ATATGGGGCTTCCTAATACCGCCCATAGCCACTCCCCCATTGACGTCAATGGTCTCTATATATGGTCTTTCCTATTG
ACGTCATATGGGCGGTCCTATTGACGTATATGGCGCCTCCCCCATTGACGTCAATTACGGTAAATGGCCCGCCTGGC
TCAATGCCCATTGACGTCAATAGGACCACCCACCATTGACGTCAATGGGATGGCTCATTGCCCATTCATATCCGTTC
TCACGCCCCTATTGACGTCAATGACGGTAAATGGCCCACTTGGCAGTACATCAATATCTATTAATAGTAACTTGGC
AAGTACATTACTATTGGAAGGACGCCAGGGTACATTGGCAGTACTCCCATTGACGTCAATGGCGGTAAATGGCCCGC
GATGGCTGCCAAGTACATCCCCATTGACGTCAATGGGGAGGGGCAATGACGCAAATGGGCGTTCCATTGACGTAAAT
GGGCGGTAGGCGTGCCTAATGGGAGGTCTATATAAGCAATGCTCGTTTAGGGA

Figure 28 CONT

SEQ ID NO: 69

> pCS-Dest_Cas9_TAL268

```
ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAAGGGAATACTGCAGACCGTTAAGGTCGTGGATGAACTCGTC
AAAGTAATGGGAAGGCATAAGCCCGAGAATATCGTTATCGAGATGGCCCGAGAGAACCAAACTACCCAGAAGGGACA
GAAGAACAGTAGGGAAAGGATGAAGAGGATTGAAGAGGGTATAAAAGAACTGGGGTCCCAAATCCTTAAGGAACACC
```

Figure 29

CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC▓▓▓▓▓▓▓TACACCTCTA
CAAAGGAGGTCCTGGACGCCACACTGATTCATCAGTCAATTACGGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAAGAAACTGGATTTCGAATCCGGAGTACCTATGGTGGACTTGAGGACACTCGGTTATTCGCAACAGCAA
CAGGAGAAAATCAAGCCTAAGGTCAGGAGCACCGTCGCGCAACACCACGAGGCGCTTGTGGGGCATGGCTTCACTCA
TGCGCATATTGTCGCGCTTTCACAGCACCCTGCGGCGCTTGGGACGGTGGCTGTCAAATACCAAGATATGATTGCGG
CCCTGCCCGAAGCCACGCACGAGGCAATTGTAGGGGTCGGTAAACAGTGGTCGGGAGCGCGAGCACTTGAGGCGCTG
CTGACTGTGGCGGGTGAGCTTAGGGGGCCTCCGCTCCAGCTCGACACCGGGCAGCTGCTGAAGATCGCGAAGAGAGG
GGGAGTAACAGCGGTAGAGGCAGTGCACGCCTGGCGCAATGCGCTCACCGGGGCCCCCTTGCCCCTGAACCTGACCC
CGGACCAAGTGGTGGCTATCGCCAGCAACAATGGCGGCAAGCAAGCGCTCGAAACGGTGCAGCGGCTGTTGCCGGTG
CTGTGCCAGGACCATGGCCTGACTCCGGACCAAGTGGTGGCTATCGCCAGCCACGATGGCGGCAAGCAAGCGCTCGA
AACGGTGCAGCGGCTGTTGCCGGTGCTGTGCCAGGACCATGGCCTGACCCCGGACCAAGTGGTGGCTATCGCCAGCA
ACAATGGCGGCAAGCAAGCGCTCGAAACGGTGCAGCGGCTGTTGCCGGTGCTGTGCCAGGACCATGGCCTGACCCCG
GACCAAGTGGTGGCTATCGCCAGCAACGGTGGCGGCAAGCAAGCGCTCGAAACGGTGCAGCGGCTGTTGCCGGTGCT
GTGCCAGGACCATGGCCTGACCCCGGACCAAGTGGTGGCTATCGCCAGCAACAATGGCGGCAAGCAAGCGCTCGAAA

Figure 29 CONT

```
CGGTGCAGCGGCTGTTGCCGGTGCTGTGCCAGGACCATGGCCTGACCCCGGACCAAGTGGTGGCTATCGCCAGCAAC
AATGGCGGCAAGCAAGCGCTCGAAACGGTGCAGCGGCTGTTGCCGGTGCTGTGCCAGGACCATGGCCTGACCCCGGA
CCAAGTGGTGGCTATCGCCAGCAACAATGGCGGCAAGCAAGCGCTCGAAACGGTGCAGCGGCTGTTGCCGGTGCTGT
GCCAGGACCATGGCCTGACTCCGGACCAAGTGGTGGCTATCGCCAGCCACGATGGCGGCAAGCAAGCGCTCGAAACG
GTGCAGCGGCTGTTGCCGGTGCTGTGCCAGGACCATGGCCTGACCCCGGACCAAGTGGTGGCTATCGCCAGCAACAA
TGGCGGCAAGCAAGCGCTCGAAACGGTGCAGCGGCTGTTGCCGGTGCTGTGCCAGGACCATGGCCTGACCCCGGACC
AAGTGGTGGCTATCGCTAATAATAACGGAGGACGGCCAGCCTTGGAGTCCATCGTAGCCCAATTGTCCAGCGCCGAT
CCCGCGTTGGCTGCGTTAACGAATGACCATCTGGTGGCGTTGGCATGTCTTGGTGGACGACCCGCGCTCGATGCAGT
CAAAAAGGGTCTGCCTCATGCTCCCGCATTGATCAAAAGAACCAACCGGCGGATTCCCGAGAGAACTTCCCATCGAG
TCGCGGGATCtTAAGCGGCCGCCTCGAGATATCTAGACCCAGCTTTCTTGTACAAAGTGGTTGATCCTCTCGAGCCT
CTAGAACTATAGTGAGTCGTATTACGTAGATCCAGACATGATAAGATACATTGATGAGTTTGGACAAACCACAACTA
GAATGCAGTGAAAAAAATGCTTTATTTGTGAAATTTGTGATGCTATTGCTTTATTTGTAACCATTATAAGCTGCAAT
AAACAAGTTAACAACAACAATTGCATTCATTTTATGTTTCAGGTTCAGGGGGAGGTGTGGGAGGTTTTTTAATTCGC
GGCCGCGGCGCCAATGCATTGGGCCCGGTACCCAGCTTTTGTTCCCTTTAGTGAGGGTTAATTGCGCGCTTGGCGTA
ATCATGGTCATAGCTGTTTCCTGTGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGCGCTCACTGCCCGCTTTCCAGTCG
GGAAACCTGTCGTGCCAGCTGCATTAATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGGCCTAACTACGGCTACACTAGA
AGGACAGTATTTGGTATCTGCGCTCTGCTGAAGCCAGTTACCTTCGGAAAAAGAGTTGGTAGCTCTTGATCCGGCAA
ACAAACCACCGCTGGTAGCGGTGGTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCATGAGATTA
TCAAAAAGGATCTTCACCTAGATCCTTTTAAATTAAAAATGAAGTTTTAAATCAATCTAAAGTATATATGAGTAAAC
TTGGTCTGACAGTTACCAATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAGTGCTGCAATGATACCGCGA
GACCCACGCTCACCGGCTCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTTGGTATGGCTTCATTCAGCTCCGGTTCC
```

Figure 29 CONT

```
CAACGATCAAGGCGAGTTACATGATCCCCCATGTTGTGCAAAAAGCGGTTAGCTCCTTCGGTCCTCCGATCGTTGT
CAGAAGTAAGTTGGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGACCGAGTTGCTCT
TGCCCGGCGTCAATACGGGATAATACCGCGCCACATAGCAGAACTTTAAAAGTGCTCATCATTGGAAAACGTTCTTC
GGGGCGAAAACTCTCAAGGATCTTACCGCTGTTGAGATCCAGTTCGATGTAACCCACTCGTGCACCCAACTGATCTT
CAGCATCTTTTACTTTCACCAGCGTTTCTGGGTGAGCAAAAACAGGAAGGCAAATGCCGCAAAAAAGGGAATAAGG
GCGACACGGAAATGTTGAATACTCATACTCTTCCTTTTTCAATATTATTGAAGCATTTATCAGGGTTATTGTCTCAT
GAGCGGATACATATTTGAATGTATTTAGAAAAATAAACAAATAGGGGTTCCGCGCACATTTCCCCGAAAAGTGCCAC
CTAAATTGTAAGCGTTAATATTTTGTTAAAATTCGCGTTAAATTTTGTTAAATCAGCTCATTTTTTAACCAATAGG
CCGAAATCGGCAAAATCCCTTATAAATCAAAAGAATAGACCGAGATAGGGTTGAGTGTTGTTCCAGTTTGGAACAAG
AGTCCACTATTAAAGAACGTGGACTCCAACGTCAAAGGGCGAAAAACCGTCTATCAGGGCGATGGCCCACTACGTGA
ACCATCACCCTAATCAAGTTTTTTGGGGTCGAGGTGCCGTAAAGCACTAAATCGGAACCCTAAAGGGAGCCCCCGAT
TTAGAGCTTGACGGGGAAAGCCGGCGAACGTGGCGAGAAAGGAAGGGAAGAAAGCGAAAGGAGCGGGCGCTAGGGCG
CTGGCAAGTGTAGCGGTCACGCTGCGCGTAACCACCACACCCGCCGCGCTTAATGCGCCGCTACAGGGCGCGTCCCA
TTCGCCATTCAGGCTGCGCAACTGTTGGGAAGGGCGATCGGTGCGGGCCTCTTCGCTATTACGCCAGTCGACCATAG
CCAATTCAATATGGCGTATATGGACTCATGCCAATTCAATATGGTGGATCTGGACCTGTGCCAATTCAATATGGCGT
ATATGGACTCGTGCCAATTCAATATGGTGGATCTGGACCCCAGCCAATTCAATATGGCGGACTTGGCACCATGCCAA
TTCAATATGGCGGACTTGGCACTGTGCCAACTGGGGAGGGGTCTACTTGGCACGGTGCCAAGTTTGAGGAGGGGTCT
TGGCCCTGTGCCAAGTCCGCCATATTGAATTGGCATGGTGCCAATAATGGCGGCCATATTGGCTATATGCCAGGATC
AATATATAGGCAATATCCAATATGGCCCTATGCCAATATGGCTATTGGCCAGGTTCAATACTATGTATTGGCCCTAT
GCCATATAGTATTCCATATATGGGTTTTCCTATTGACGTAGATAGCCCCTCCCAATGGGCGGTCCCATATACCATAT
ATGGGGCTTCCTAATACCGCCCATAGCCACTCCCCATTGACGTCAATGGTCTCTATATATGGTCTTTCCTATTGAC
GTCATATGGGCGGTCCTATTGACGTATATGGCGCCTCCCCATTGACGTCAATTACGGTAAATGGCCCGCCTGGCTC
AATGCCCATTGACGTCAATAGGACCACCCACCATTGACGTCAATGGGATGGCTCATTGCCCATTCATATCCGTTCTC
ACGCCCCTATTGACGTCAATGACGGTAAATGGCCCACTTGGCAGTACATCAATATCTATTAATAGTAACTTGGCAA
GTACATTACTATTGGAAGGACGCCAGGGTACATTGGCAGTACTCCCATTGACGTCAATGGCGGTAAATGGCCCGCGA
TGGCTGCCAAGTACATCCCCATTGACGTCAATGGGGAGGGGCAATGACGCAAATGGGCGTTCCATTGACGTAAATGG
GCGGTAGGCGTGCCTAATGGGAGGTCTATATAAGCAATGCTCGTTTAGGGA
```

Figure 29 CONT

SEQ ID NO: 70

> pCS-Dest_TAL268_Cas9

ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACcatgGGtagAGC
CGCGCCGGCAGCTAAGAAAAAGAAACTGGATCaattGGTACCTATGGTGGACTTGAGGACACTCGGTTATTCGCAAC
AGCAACAGGAGAAAATCAAGCCTAAGGTCAGGAGCACCGTCGCGCAACACCACGAGGCGCTTGTGGGCATGGCTTC
ACTCATGCGCATATTGTCGCGCTTTCACAGCACCCTGCGGCGCTTGGGACGGTGGCTGTCAAATACCAAGATATGAT
TGCGGCCCTGCCCGAAGCCACGCACGAGGCAATTGTAGGGGTCGGTAAACAGTGGTCGGGAGCGCGAGCACTTGAGG
CGCTGCTGACTGTGGCGGGTGAGCTTAGGGGGCCTCCGCTCCAGCTCGACACCGGGCAGCTGCTGAAGATCGCGAAG
AGAGGGGGAGTAACAGCGGTAGAGGCAGTGCACGCCTGGCGCAATGCGCTCACCGGGGCCCCCTTGCCCCTGAACCT
GACCCCGGACCAAGTGGTGGCTATCGCCAGCAACAATGGCGGCAAGCAAGCGCTCGAAACGGTGCAGCGGCTGTTGC
CGGTGCTGTGCCAGGACCATGGCCTGACTCCGGACCAAGTGGTGGCTATCGCCAGCCACGATGGCGGCAAGCAAGCG
CTCGAAACGGTGCAGCGGCTGTTGCCGGTGCTGTGCCAGGACCATGGCCTGACCCCGGACCAAGTGGTGGCTATCGC
CAGCAACAATGGCGGCAAGCAAGCGCTCGAAACGGTGCAGCGGCTGTTGCCGGTGCTGTGCCAGGACCATGGCCTGA
CCCCGGACCAAGTGGTGGCTATCGCCAGCAACGGTGGCGGCAAGCAAGCGCTCGAAACGGTGCAGCGGCTGTTGCCG
GTGCTGTGCCAGGACCATGGCCTGACCCCGGACCAAGTGGTGGCTATCGCCAGCAACAATGGCGGCAAGCAAGCGCT
CGAAACGGTGCAGCGGCTGTTGCCGGTGCTGTGCCAGGACCATGGCCTGACCCCGGACCAAGTGGTGGCTATCGCCA
GCAACAATGGCGGCAAGCAAGCGCTCGAAACGGTGCAGCGGCTGTTGCCGGTGCTGTGCCAGGACCATGGCCTGACC
CCGGACCAAGTGGTGGCTATCGCCAGCAACAATGGCGGCAAGCAAGCGCTCGAAACGGTGCAGCGGCTGTTGCCGGT
GCTGTGCCAGGACCATGGCCTGACTCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACCCCGGACCAAGTGGTGGCTATCGCCAGC
AACAATGGCGGCAAGCAAGCGCTCGAAACGGTGCAGCGGCTGTTGCCGGTGCTGTGCCAGGACCATGGCCTGACCCC
GGACCAAGTGGTGGCTATCGCTAATAATAACGGAGGACGGCCAGCCTTGGAGTCCATCGTAGCCCAATTGTCCAGGC
CCGATCCCGCGTTGGCTGCGTTAACGAATGACCATCTGGTGGCGTTGGCATGTCTTGGTGGACGACCCGCGCTCGAT
GCAGTCAAAAAGGGTCTGCCTCATGCTCCCGCATTGATCAAAAGAACCAACCGGCGGATTCCCGAGAGAACTTCCCA
TCGAGTCGCGGGATCtcccggGTCTGGAGGTAGCGGCTCAAGTGGCCGTACGGCAGCTCCTGCGGCAAAAAGAAAA
AGTTGGACTCTGAATTCGGAAGCGAcaagaagtactccattgggctcgatatcGgtacCAACAGCGTCGGCTGGGCC
GTCATTACGGACGAGTACAAGGTGCCGAGCAAAAAATTCAAAGTTCTGGGCAATACCGATCGCCACAGCATAAAGAA
GAACCTCATTGGAGCCCTCCTGTTCGACTCCGGGGAGACGGCCGAAGCCACGCGGCTCAAAAGAACAGCACGGCGCA
GATATACCCGCAGAAAGAATCGGATCTGCTACCTGCAGGAGATCTTTAGTAATGAGATGGCTAAGGTGGATGACTCT
TTCTTCCATAGGCTGGAGGAGTCCTTTTTGGTGGAGGAGGATAAAAAGCACGAGCGCCACCCAATCTTTGCAATAT
CGTGGACGAGGTGGCGTACCATGAAAAGTACCCAACCATATATCATCTGAGGAAGAAGCTGGTAGACAGTACTGATA
AGGCTGACTTGCGGTTGATCTATCTCGCGCTGGCGCACATGATCAAATTTCGGGGACACTTCCTCATCGAGGGGGAC

Figure 30

```
CTGAACCCAGACAACAGCGATGTCGACAAACTCTTTATCCAACTGGTTCAGACTTACAATCAGCTTTTCGAGGAGAA
CCCGATCAACGCATCCGGCGTTGACGCCAAAGCAATCCTGAGCGCTAGGCTGTCCAAATCCCGGCGGCTCGAAAACC
TCATCGCACAGCTCCCTGGGGAGAAGAAGAACGGCCTGTTTGGTAATCTTATCGCCCTGTCACTCGGGCTGACCCCC
AACTTTAAATCTAACTTCGACCTGGCCGAAGATGCCAAGCTGCAACTGAGCAAAGACACCTACGATGATGATCTCGA
CAATCTGCTGGCCCAGATCGGCGACCAGTACGCAGACCTTTTTTTGGCGGCAAAGAACCTGTCAGACGCCATTCTGC
TGAGTGATATTCTGCGAGTGAACACGGAGATCACCAAAGCTCCGCTGAGCGCTAGTATGATCAAGCGCTATGATGAG
CACCACCAAGACTTGACTTTGCTGAAGGCCCTTGTCAGACAGCAACTGCCTGAGAAGTACAAGGAAATTTTCTTCGA
TCAGTCTAAAAATGGCTACGCCGGATACATTGACGGCGGAGCAAGCCAGGAGGAATTTTACAAATTTATTAAGCCCA
TCTTGGAAAAAATGGACGGCACCGAGGAGCTGCTGGTAAAGCTGAACAGAGAAGATCTGTTGCGCAAACAGCGCACT
TTCGACAATGGAAGCATCCCCCACCAGATTCACCTGGGCGAACTGCACGCTATCCTCAGGCGGCAAGAGGATTCTA
CCCCTTTTTGAAAGATAACAGGGAAAAGATTGAGAAAATCCTCACATTTCGGATACCCTACTATGTAGGCCCCCTCG
CTCGGGGAAATTCCAGATTCGCGTGGATGACTCGCAAATCAGAAGAGACCATCACTCCCTGGAACTTCGAGGAAGTC
GTGGATAAGGGGGCCTCTGCCCAGTCCTTCATCGAAAGGATGACTAACTTTGATAAAAATCTGCCTAACGAAAAGGT
GCTTCCTAAACACTCTCTGCTGTACGAGTACTTCACAGTTTATAACGAGCTCACCAAGGTCAAATACGTCACAGAAG
GGATGAGAAAGCCAGCATTCCTGTCTGGAGAGCAGAAGAAAGCTATCGTGGACCTCCTCTTCAAGACGAACCGGAAA
GTTACCGTGAAACAGCTCAAAGAAGACTATTTCAAAAAGATTGAATGTTTCGACTCTGTTGAAATCAGCGGAGTGGA
GGATCGCTTCAACGCATCCCTGGGAACGTATCACGATCTCCTGAAAATCATTAAAGACAAGGACTTCCTGGACAATG
AGGAGAACGAGGACATTCTTGAGGACATTGTCCTCACCCTTACGTTGTTTGAAGATAGGGAGATGATTGAAGAACGC
TTGAAAACTTACGCTCATCTCTTCGACGACAAAGTCATGAAACAGCTCAAGAGACGCCGATATACAGGATGGGGCG
GCTGTCAAGAAAACTGATCAATGGCATCCGAGACAAGCAGAGTGGAAAGACAATCCTGGATTTTCTTAAGTCCGATG
GATTTGCCAACCGGAACTTCATGCAGTTGATCCATGATGACTCTCTCACCTTTAAGGAGGACATCCAGAAAGCACAA
GTTTCTGGCCAGGGGACAGTCTTCACGAGCACATCGCTAATCTTGCAGGTAGCCCAGCTATCAAAAAGGGAATACT
GCAGACCGTTAAGGTCGTGGATGAACTCGTCAAAGTAATGGGAAGGCATAAGCCCGAGAATATCGTTATCGAGATGG
CCCGAGAGAACCAAACTACCCAGAAGGGACAGAAGAACAGTAGGGAAAGGATGAAGAGGATTGAAGAGGGTATAAAA
GAACTGGGGTCCCAAATCCTTAAGGAACACCCAGTTGAAAACACCCAGCTTCAGAATGAGAAGCTCTACCTGTACTA
CCTGCAGAACGGCAGGGACATGTACGTGGATCAGGAACTGGACATCAACCGGTTGTCCGACTACGACGTGGATCATA
TCGTGCCCCAAAGCTTTCTCAAAGATGATTCTATTGATAATAAAGTGTTGACAAGATCCGATAAAAATAGAGGGAAG
AGTGATAACGTCCCCTCAGAAGAAGTTGTCAAGAAAATGAAAAATTATTGGCGGCAGCTGCTGAACGCCAAACTGAT
CACACAACGGAAGTTCGATAATCTGACTAAGGCTGAACGAGGTGGCCTGTCTGAGTTGGATAAAGCCGGCTTCATCA
AAAGGCAGCTTGTTGAGACACGCCAGATCACCAAGCACGTGGCCCAAATTCTCGATTCACGCATGAACACCAAGTAC
GATGAAAATGACAAACTGATTCGAGAGGTGAAAGTTATTACTCTGAAGTCTAAGCTGGTCTCAGATTTCAGAAAGGA
CTTTCAGTTTTATAAGGTGAGAGAGATCAACAATTACCACCATGCGCATGATGCCTACCTGAATGCAGTGGTAGGCA
CTGCACTTATCAAAAAATATCCCAAGCTGGAATCTGAATTTGTTTACGGAGACTATAAAGTGTACGATGTTAGGAAA
ATGATCGCAAAGTCTGAGCAGGAAATAGGCAAGGCCACCGCTAAGTACTTCTTTTACAGCAATATTATGAATTTTTT
CAAGACCGAGATTACACTGGCCAATGGAGAGATTCGGAAGCGACCACTTATCGAAACAAACGGAGAAACAGGAGAAA
TCGTGTGGGACAAGGGTAGGGATTTCGCGACAGTCCGCAAGGTCCTGTCCATGCCGCAGGTGAACATCGTTAAAAAG
```

Figure 30 CONT

```
ACCGAAGTACAGACCGGAGGCTTCTCCAAGGAAAGTATCCTCCCGAAAAGGAACAGCGACAAGCTGATCGCACGCAA
AAAAGATTGGGACCCCAAGAAATACGGCGGATTCGATTCTCCTACAGTCGCTTACAGTGTACTGGTTGTGGCCAAAG
TGGAGAAAGGGAAGTCTAAAAAACTCAAAAGCGTCAAGGAACTGCTGGGCATCACAATCATGGAGCGATCCAGCTTC
GAGAAAAACCCCATCGACTTTCTCGAAGCGAAAGGATATAAAGAGGTCAAAAAAGACCTCATCATTAAGCTGCCCAA
GTACTCTCTCTTTGAGCTTGAAAACGGCCGGAAACGAATGCTCGCTAGTGCGGGCGAGCTGCAGAAAGGTAACGAGC
TGGCACTGCCCTCTAAATACGTTAATTTCTTGTATCTGGCCAGCCACTATGAAAAGCTCAAAGGGTCTCCCGAAGAT
AATGAGCAGAAGCAGCTGTTCGTGGAACAACACAAACACTACCTTGATGAGATCATCGAGCAAATAAGCGAGTTCTC
CAAAAGAGTGATCCTCGCCGACGCTAACCTCGATAAGGTGCTTTCTGCTTACAATAAGCACAGGGATAAGCCCATCA
GGGAGCAGGCAGAAAACATTATCCACTTGTTTACTCTGACCAACTTGGGCGCGCCTGCAGCCTTCAAGTACTTCGAC
ACCACCATAGAC▓▓▓▓▓▓▓TACACCTCTACAAAGGAGGTCCTGGACGCCACACTGATTCATCAGTCAATTACGGG
GCTCTATGAAACAAGAATCGACCTCTCTCAGCTCGGTGGAGACGGCACCGGCGGGCCCAAGAAGAAGAGGAAGGTAT
ACCCATACGATGTTCCTGACTATGCGGGCTATCCCTATGACGTCCCGGACTATGCAGGATCGTATCCTTATGACGTT
CCAGATTACGCTGGATCCTAATGATTCGAATCCGGATAAGCGGCCGCCTCGAGATATCTAGACCCAGCTTTCTTGTA
CAAAGTGGTTGATCCTCTCGAGCCTCTAGAACTATAGTGAGTCGTATTACGTAGATCCAGACATGATAAGATACATT
GATGAGTTTGGACAAACCACAACTAGAATGCAGTGAAAAAAATGCTTTATTTGTGAAATTTGTGATGCTATTGCTTT
ATTTGTAACCATTATAAGCTGCAATAAACAAGTTAACAACAACAATTGCATTCATTTTATGTTTCAGGTTCAGGGGG
AGGTGTGGGAGGTTTTTTAATTCGCGGCCGCGGCGCCAATGCATTGGGCCCGGTACCCAGCTTTTGTTCCCTTTAGT
GAGGGTTAATTGCGCGCTTGGCGTAATCATGGTCATAGCTGTTTCCTGTGTGAAATTGTTATCCGCTCACAATTCCA
CACAACATACGAGCCGGAAGCATAAAGTGTAAAGCCTGGGGTGCCTAATGAGTGAGCTAACTCACATTAATTGCGTT
GCGCTCACTGCCCGCTTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCGTTCGCTCCAAGCTGGGCTGTGTGCACG
AACCCCCCGTTCAGCCCGACCGCTGCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAGGCGGTGCTACAGAGTTCTTGAAGTG
GTGGCCTAACTACGGCTACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAGATTACG
CGCAGAAAAAAGGATCTCAAGAAGATCCTTTGATCTTTTCTACGGGGTCTGACGCTCAGTGGAACGAAAACTCACG
TTAAGGGATTTTGGTCATGAGATTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTGAGGCACCTATCTCAGCGATC
TGTCTATTTCGTTCATCCATAGTTGCCTGACTCCCCGTCGTGTAGATAACTACGATACGGGAGGGCTTACCATCTGG
CCCCAGTGCTGCAATGATACCGCGAGACCCACGCTCACCGGCTCCAGATTTATCAGCAATAAACCAGCCAGCCGGAA
GGGCCGAGCGCAGAAGTGGTCCTGCAACTTTATCCGCCTCCATCCAGTCTATTAATTGTTGCCGGGAAGCTAGAGTA
```

Figure 30 CONT

```
AGTAGTTCGCCAGTTAATAGTTTGCGCAACGTTGTTGCCATTGCTACAGGCATCGTGGTGTCACGCTCGTCGTTTGG
TATGGCTTCATTCAGCTCCGGTTCCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACTCATGGTTATGGCAGCACTGCAT
AATTCTCTTACTGTCATGCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACATAGCAGAACTTTAAAAG
TGCTCATCATTGGAAAACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGCAAAAACAGGAAGGCA
AAATGCCGCAAAAAAGGGAATAAGGGCGACACGGAAATGTTGAATACTCATACTCTTCCTTTTTCAATATTATTGAA
GCATTTATCAGGGTTATTGTCTCATGAGCGGATACATATTTGAATGTATTTAGAAAAATAAACAAATAGGGGTTCCG
CGCACATTTCCCCGAAAAGTGCCACCTAAATTGTAAGCGTTAATATTTTGTTAAAATTCGCGTTAAATTTTGTTAA
ATCAGCTCATTTTTTAACCAATAGGCCGAAATCGGCAAAATCCCTTATAAATCAAAAGAATAGACCGAGATAGGGTT
GAGTGTTGTTCCAGTTTGGAACAAGAGTCCACTATTAAAGAACGTGGACTCCAACGTCAAAGGGCGAAAAACCGTCT
ATCAGGGCGATGGCCCACTACGTGAACCATCACCCTAATCAAGTTTTTTGGGGTCGAGGTGCCGTAAAGCACTAAAT
CGGAACCCTAAAGGGAGCCCCCGATTTAGAGCTTGACGGGGAAAGCCGGCGAACGTGGCGAGAAAGGAAGGGAAGAA
AGCGAAAGGAGCGGGCGCTAGGGCGCTGGCAAGTGTAGCGGTCACGCTGCGCGTAACCACCACACCCGCCGCGCTTA
ATGCGCCGCTACAGGGCGCGTCCCATTCGCCATTCAGGCTGCGCAACTGTTGGGAAGGGCGATCGGTGCGGGCCTCT
TCGCTATTACGCCAGTCGACCATAGCCAATTCAATATGGCGTATATGGACTCATGCCAATTCAATATGGTGGATCTG
GACCTGTGCCAATTCAATATGGCGTATATGGACTCGTGCCAATTCAATATGGTGGATCTGGACCCCAGCCAATTCAA
TATGGCGGACTTGGCACCATGCCAATTCAATATGGCGGACTTGGCACTGTGCCAACTGGGGAGGGTCTACTTGGCA
CGGTGCCAAGTTTGAGGAGGGGTCTTGGCCCTGTGCCAAGTCCGCCATATTGAATTGGCATGGTGCCAATAATGGCG
GCCATATTGGCTATATGCCAGGATCAATATATAGGCAATATCCAATATGGCCCTATGCCAATATGGCTATTGGCCAG
GTTCAATACTATGTATTGGCCCTATGCCATATAGTATTCCATATATGGGTTTTCCTATTGACGTAGATAGCCCCTCC
CAATGGGCGGTCCCATATACCATATATGGGGCTTCCTAATACCGCCCATAGCCACTCCCCCATTGACGTCAATGGTC
TCTATATATGGTCTTTCCTATTGACGTCATATGGGCGGTCCTATTGACGTATATGGCGCCTCCCCCATTGACGTCAA
TTACGGTAAATGGCCCGCCTGGCTCAATGCCCATTGACGTCAATAGGACCACCCACCATTGACGTCAATGGGATGGC
TCATTGCCCATTCATATCCGTTCTCACGCCCCCTATTGACGTCAATGACGGTAAATGGCCCACTTGGCAGTACATCA
ATATCTATTAATAGTAACTTGGCAAGTACATTACTATTGGAAGGACGCCAGGGTACATTGGCAGTACTCCCATTGAC
GTCAATGGCGGTAAATGGCCCGCGATGGCTGCCAAGTACATCCCCATTGACGTCAATGGGGAGGGGCAATGACGCAA
ATGGGCGTTCCATTGACGTAAATGGGCGGTAGGCGTGCCTAATGGGAGGTCTATATAAGCAATGCTCGTTTAGGGA
```

Figure 30 CONT

SEQ ID NO: 71

> pCS-Dest_Cas9_ZFTS2

ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAAGGGAATACTGCAGACCGTTAAGGTCGTGGATGAACTCGTC
AAAGTAATGGGAAGGCATAAGCCCGAGAATATCGTTATCGAGATGGCCCGAGAGAACCAAACTACCCAGAAGGGACA
GAAGAACAGTAGGGAAAGGATGAAGAGGATTGAAGAGGGTATAAAAGAACTGGGGTCCCAAATCCTTAAGGAACACC

Figure 31

```
CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC███████TACACCTCTA
CAAAGGAGGTCCTGGACGCCACACTGATTCATCAGTCAATTACGGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAGAAACTGGATTTCGAATccggAAAGCCCTATAAATGTCCTGAATGTGGCAAGTCCTTCTCGGAGAAG
AGCCACCTGACACGGCACCAACGCACGCACACTGGTGAGAAGCCATACGCGTGTCCTGTCGAGTCCTGTGACCGGCCG
CTTCAGTCGGAGCGACCACCTGACACAGCACATCCGCATTCACACAGGGCAAAAACCGTTTCAATGCCGCATCTGCA
TGAGGAACTTCAGCGACAAGGGCCACCTGACCCGGCACATCCGCACCCACACAGGAGAAAAGCCCTTCGCCTGTGAC
ATCTGCGGCAGGAAGTTCGCGCGGAGCGACGACCTGACACGGCACACCAAGATCCACCTCCGTCAGAAAGACCccgg
GTAATGACtcgaGCCTCTAGAACTATAGTGAGTCGTATTACGTAGATCCAGACATGATAAGATACATTGATGAGTTT
GGACAAACCACAACTAGAATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGGTTCAGGGGGAGGTGTGGG
AGGTTTTTTAATTCGCGGCCGCGGCGCCAATGCATTGGGCCCGGTACCCAGCTTTTGTTCCCTTTAGTGAGGGTTAA
TTGCGCGCTTGGCGTAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGGGAGAGGCGGTTTGC
```

Figure 31 CONT

```
GTATTGGGCGCTCTTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGGAT
TTTGGTCATGAGATTATCAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGTTCCGCGCACATTT
CCCCGAAAAGTGCCACCTAAATTGTAAGCGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAAAACCGTCTATCAGGGCG
ATGGCCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGGTGCGGGCCTCTTCGCTATTA
CGCCAGTCGACCATAGCCAATTCAATATGGCGTATATGGACTCATGCCAATTCAATATGGTGGATCTGGACCTGTGC
CAATTCAATATGGCGTATATGGACTCGTGCCAATTCAATATGGTGGATCTGGACCCCAGCCAATTCAATATGGCGGA
CTTGGCACCATGCCAATTCAATATGGCGGACTTGGCACTGTGCCAACTGGGGAGGGTCTACTTGGCACGGTGCCAA
GTTTGAGGAGGGGTCTTGGCCCTGTGCCAAGTCCGCCATATTGAATTGGCATGGTGCCAATAATGGCGGCCATATTG
```

Figure 31 CONT

```
GCTATATGCCAGGATCAATATATAGGCAATATCCAATATGGCCCTATGCCAATATGGCTATTGGCCAGGTTCAATAC
TATGTATTGGCCCTATGCCATATAGTATTCCATATATGGGTTTTCCTATTGACGTAGATAGCCCCTCCCAATGGGCG
GTCCCATATACCATATATGGGGCTTCCTAATACCGCCCATAGCCACTCCCCCATTGACGTCAATGGTCTCTATATAT
GGTCTTTCCTATTGACGTCATATGGGCGGTCCTATTGACGTATATGGCGCCTCCCCCATTGACGTCAATTACGGTAA
ATGGCCCGCCTGGCTCAATGCCCATTGACGTCAATAGGACCACCCACCATTGACGTCAATGGGATGGCTCATTGCCC
ATTCATATCCGTTCTCACGCCCCCTATTGACGTCAATGACGGTAAATGGCCCACTTGGCAGTACATCAATATCTATT
AATAGTAACTTGGCAAGTACATTACTATTGGAAGGACGCCAGGGTACATTGGCAGTACTCCCATTGACGTCAATGGC
GGTAAATGGCCCGCGATGGCTGCCAAGTACATCCCCATTGACGTCAATGGGGAGGGGCAATGACGCAAATGGGCGTT
CCATTGACGTAAATGGGCGGTAGGCGTGCCTAATGGGAGGTCTATATAAGCAATGCTCGTTTAGGGA
```

Figure 31 CONT

SEQ ID NO: 72

> pCS-Dest_Cas9$^{MT3}$_ZFTS2

ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAGGGAATACTGCAGACCGTTAAGGTCGTGGATGAACTCGTC
AAAGTAATGGGAAGGCATAAGCCCGAGAATATCGTTATCGAGATGGCCCGAGAGAACCAAACTACCCAGAAGGGACA
GAAGAACAGTAGGGAAAGGATGAAGAGGATTGAAGAGGGTATAAAAGAACTGGGGTCCCAAATCCTTAAGGAACACC

Figure 32

```
CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC████TACACCTCTA
CAAAGGAGGTCCTGGACGCCACACTGATTCATCAGTCAATTACGGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAAGAAACTGGATTTCGAATccggAAAGCCCTATAAATGTCCTGAATGTGGCAAGTCCTTCTCGGAGAAG
AGCCACCTGACACGGCACCAACGCACGCACACTGGTGAGAAGCCATACGCGTGTCCTGTCGAGTCCTGTGACCGCCG
CTTCAGTCGGAGCGACCACCTGACACAGCACATCCGCATTCACACAGGGCAAAAACCGTTTCAATGCCGCATCTGCA
TGAGGAACTTCAGCGACAAGGGCCACCTGACCCGGCACATCCGCACCCACACAGGAGAAAAGCCCTTCGCCTGTGAC
ATCTGCGGCAGGAAGTTCGCGCGGAGCGACGACCTGACACGGCACACCAAGATCCACCTCCGTCAGAAAGACCccgg
GTAATGActcgaGCCTCTAGAACTATAGTGAGTCGTATTACGTAGATCCAGACATGATAAGATACATTGATGAGTTT
GGACAAACCACAACTAGAATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGGTTCAGGGGGAGGTGTGGG
AGGTTTTTTAATTCGCGGCCGCGGCGCCAATGCATTGGGCCCGGTACCCAGCTTTTGTTCCCTTTAGTGAGGGTTAA
TTGCGCGCTTGGCGTAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGGAGAGGCGGTTTGC
```

```
GTATTGGGCGCTCTTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGGAT
TTTGGTCATGAGATTATCAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGTTCCGCGCACATTT
CCCCGAAAAGTGCCACCTAAATTGTAAGCGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAAAACCGTCTATCAGGGCG
ATGGCCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGGTGCGGGCCTCTTCGCTATTA
CGCCAGTCGACCATAGCCAATTCAATATGGCGTATATGGACTCATGCCAATTCAATATGGTGGATCTGGACCTGTGC
CAATTCAATATGGCGTATATGGACTCGTGCCAATTCAATATGGTGGATCTGGACCCCAGCCAATTCAATATGGCGGA
CTTGGCACCATGCCAATTCAATATGGCGGACTTGGCACTGTGCCAACTGGGGAGGGTCTACTTGGCACGGTGCCAA
GTTTGAGGAGGGGTCTTGGCCCTGTGCCAAGTCCGCCATATTGAATTGGCATGGTGCCAATAATGGCGGCCATATTG
```

Figure 32 CONT

```
GCTATATGCCAGGATCAATATATAGGCAATATCCAATATGGCCCTATGCCAATATGGCTATTGGCCAGGTTCAATAC
TATGTATTGGCCCTATGCCATATAGTATTCCATATATGGGTTTTCCTATTGACGTAGATAGCCCCTCCCAATGGGCG
GTCCCATATACCATATATGGGGCTTCCTAATACCGCCCATAGCCACTCCCCCATTGACGTCAATGGTCTCTATATAT
GGTCTTTCCTATTGACGTCATATGGGCGGTCCTATTGACGTATATGGCGCCTCCCCCATTGACGTCAATTACGGTAA
ATGGCCCGCCTGGCTCAATGCCCATTGACGTCAATAGGACCACCCACCATTGACGTCAATGGGATGGCTCATTGCCC
ATTCATATCCGTTCTCACGCCCCCTATTGACGTCAATGACGGTAAATGGCCCACTTGGCAGTACATCAATATCTATT
AATAGTAACTTGGCAAGTACATTACTATTGGAAGGACGCCAGGGTACATTGGCAGTACTCCCATTGACGTCAATGGC
GGTAAATGGCCCGCGATGGCTGCCAAGTACATCCCCATTGACGTCAATGGGGAGGGGCAATGACGCAAATGGGCGTT
CCATTGACGTAAATGGGCGGTAGGCGTGCCTAATGGGAGGTCTATATAAGCAATGCTCGTTTAGGGA
```

Figure 32 CONT

SEQ ID NO: 73

> pCS-Dest_Cas9_ZFTS3

```
ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAGGGAATACTGCAGACCGTTAAGGTCGTGGATGAACTCGTC
AAAGTAATGGGAAGGCATAAGCCCGAGAATATCGTTATCGAGATGGCCCGAGAGAACCAAACTACCCAGAAGGGACA
GAAGAACAGTAGGGAAAGGATGAAGAGGATTGAAGAGGGTATAAAAGAACTGGGGTCCCAAATCCTTAAGGAACACC
```

Figure 33

CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC░░░░░░░TACACCTCTA
CAAAGGAGGTCCTGGACGCCACACTGATTCATCAGTCAATTACGGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAGAAACTGGATTTCGAATccggA░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░
░░░░░░░░CtcgaGCCTCTAGAACTATAGTGAGTCGTATTACGTAGATCCAGACATGATAAGATACATTGATGAGTTT
GGACAAACCACAACTAGAATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGGTTCAGGGGGAGGTGTGGG
AGGTTTTTTAATTCGCGGCCGCGGCGCCAATGCATTGGGCCCGGTACCCAGCTTTTGTTCCCTTTAGTGAGGGTTAA
TTGCGCGCTTGGCGTAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGGGAGAGGCGGTTTGC

Figure 33 CONT

```
GTATTGGGCGCTCTTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGTTCCGCGCACATTT
CCCCGAAAAGTGCCACCTAAATTGTAAGCGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAAAACCGTCTATCAGGGCG
ATGGCCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGGTGCGGGCCTCTTCGCTATTA
CGCCAGTCGACCATAGCCAATTCAATATGGCGTATATGGACTCATGCCAATTCAATATGGTGGATCTGGACCTGTGC
CAATTCAATATGGCGTATATGGACTCGTGCCAATTCAATATGGTGGATCTGGACCCCAGCCAATTCAATATGGCGGA
CTTGGCACCATGCCAATTCAATATGGCGGACTTGGCACTGTGCCAACTGGGGAGGGTCTACTTGGCACGGTGCCAA
GTTTGAGGAGGGGTCTTGGCCCTGTGCCAAGTCCGCCATATTGAATTGGCATGGTGCCAATAATGGCGGCCATATTG
```

Figure 33 CONT

```
GCTATATGCCAGGATCAATATATAGGCAATATCCAATATGGCCCTATGCCAATATGGCTATTGGCCAGGTTCAATAC
TATGTATTGGCCCTATGCCATATAGTATTCCATATATGGGTTTTCCTATTGACGTAGATAGCCCCTCCCAATGGGCG
GTCCCATATACCATATATGGGGCTTCCTAATACCGCCCATAGCCACTCCCCCATTGACGTCAATGGTCTCTATATAT
GGTCTTTCCTATTGACGTCATATGGGCGGTCCTATTGACGTATATGGCGCCTCCCCCATTGACGTCAATTACGGTAA
ATGGCCCGCCTGGCTCAATGCCCATTGACGTCAATAGGACCACCCACCATTGACGTCAATGGGATGGCTCATTGCCC
ATTCATATCCGTTCTCACGCCCCCTATTGACGTCAATGACGGTAAATGGCCCACTTGGCAGTACATCAATATCTATT
AATAGTAACTTGGCAAGTACATTACTATTGGAAGGACGCCAGGGTACATTGGCAGTACTCCCATTGACGTCAATGGC
GGTAAATGGCCCGCGATGGCTGCCAAGTACATCCCCATTGACGTCAATGGGGAGGGGCAATGACGCAAATGGGCGTT
CCATTGACGTAAATGGGCGGTAGGCGTGCCTAATGGGAGGTCTATATAAGCAATGCTCGTTTAGGGA
```

Figure 33 CONT

SEQ ID NO: 74

> pCS-Dest_Cas9$^{MT3}$_ZFTS3

ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAAGGGAATACTGCAGACCGTTAAGGTCGTGGATGAACTCGTC

Figure 34

```
AAAGTAATGGGAAGGCATAAGCCCGAGAATATCGTTATCGAGATGGCCCGAGAGAACCAAACTACCCAGAAGGGACA
GAAGAACAGTAGGGAAAGGATGAAGAGGATTGAAGAGGGTATAAAAGAACTGGGGTCCCAAATCCTTAAGGAACACC
CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC████████TACACCTCTA
CAAAGGAGGTCCTGGACGCCACACTGATTCATCAGTCAATTACGGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAGAAACTGGATTTCGAATccggA████████████████████████████████████████████
████████████████████████████████████████████████████████████████████████████
████████████████████████████████████████████████████████████████████████████
████████████████████████████████████████████████████████████████████████████
████████CtcgaGCCTCTAGAACTATAGTGAGTCGTATTACGTAGATCCAGACATGATAAGATACATTGATGAGTTT
GGACAAACCACAACTAGAATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGGTTCAGGGGGAGGTGTGGG
AGGTTTTTTAATTCGCGGCCGCGGCGCCAATGCATTGGGCCCGGTACCCAGCTTTTGTTCCCTTTAGTGAGGGTTAA
TTGCGCGCTTGGCGTAATCATGGTCATAGCTGTTTCCTGTGTGAAATTGTTATCCGCTCACAATTCCACACAACATA
```

Figure 34 CONT

```
CGAGCCGGAAGCATAAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGGGAGAGGCGGTTTGC
GTATTGGGCGCTCTTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAAGCGGTTAGCTCCTTCG
GTCCTCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGTTCCGCGCACATTT
CCCCGAAAAGTGCCACCTAAATTGTAAGCGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAAAACCGTCTATCAGGGCG
ATGGCCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGGTGCGGGCCTCTTCGCTATTA
CGCCAGTCGACCATAGCCAATTCAATATGGCGTATATGGACTCATGCCAATTCAATATGGTGGATCTGGACCTGTGC
CAATTCAATATGGCGTATATGGACTCGTGCCAATTCAATATGGTGGATCTGGACCCCAGCCAATTCAATATGGCGGA
```

Figure 34 CONT

```
CTTGGCACCATGCCAATTCAATATGGCGGACTTGGCACTGTGCCAACTGGGGAGGGGTCTACTTGGCACGGTGCCAA
GTTTGAGGAGGGGTCTTGGCCCTGTGCCAAGTCCGCCATATTGAATTGGCATGGTGCCAATAATGGCGGCCATATTG
GCTATATGCCAGGATCAATATATAGGCAATATCCAATATGGCCCTATGCCAATATGGCTATTGGCCAGGTTCAATAC
TATGTATTGGCCCTATGCCATATAGTATTCCATATATGGGTTTTCCTATTGACGTAGATAGCCCCTCCCAATGGGCG
GTCCCATATACCATATATGGGGCTTCCTAATACCGCCCATAGCCACTCCCCATTGACGTCAATGGTCTCTATATAT
GGTCTTTCCTATTGACGTCATATGGGCGGTCCTATTGACGTATATGGCGCCTCCCCCATTGACGTCAATTACGGTAA
ATGGCCCGCCTGGCTCAATGCCCATTGACGTCAATAGGACCACCCACCATTGACGTCAATGGGATGGCTCATTGCCC
ATTCATATCCGTTCTCACGCCCCCTATTGACGTCAATGACGGTAAATGGCCCACTTGGCAGTACATCAATATCTATT
AATAGTAACTTGGCAAGTACATTACTATTGGAAGGACGCCAGGGTACATTGGCAGTACTCCCATTGACGTCAATGGC
GGTAAATGGCCCGCGATGGCTGCCAAGTACATCCCCATTGACGTCAATGGGAGGGGCAATGACGCAAATGGGCGTT
CCATTGACGTAAATGGGCGGTAGGCGTGCCTAATGGGAGGTCTATATAAGCAATGCTCGTTTAGGGA
```

Figure 34 CONT

SEQ ID NO: 75

> pCS-Dest_Cas9_ZFTS4

```
ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAAGGGAATACTGCAGACCGTTAAGGTCGTGGATGAACTCGTC
AAAGTAATGGGAAGGCATAAGCCCGAGAATATCGTTATCGAGATGGCCCGAGAGAACCAAACTACCCAGAAGGGACA
GAAGAACAGTAGGGAAAGGATGAAGAGGATTGAAGAGGGTATAAAAGAACTGGGGTCCCAAATCCTTAAGGAACACC
```

Figure 35

CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC░░░░░░░TACACCTCTA
CAAAGGAGGTCCTGGACGCCACACTGATTCATCAGTCAATTACGGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAGAAACTGGATTTCGAATccggA░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░
░░░░░░CtcgaGCCTCTAGAACTATAGTGAGTCGTATTACGTAGATCCAGACATGATAAGATACATTGATGAGTTT
GGACAAACCACAACTAGAATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGGTTCAGGGGGAGGTGTGGG
AGGTTTTTTAATTCGCGGCCGCGGCGCCAATGCATTGGGCCCGGTACCCAGCTTTTGTTCCCTTTAGTGAGGGTTAA
TTGCGCGCTTGGCGTAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGGAGAGGCGGTTTGC

Figure 35 CONT

```
GTATTGGGCGCTCTTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGGAT
TTTGGTCATGAGATTATCAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGTTCCGCGCACATTT
CCCCGAAAAGTGCCACCTAAATTGTAAGCGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAAAACCGTCTATCAGGGCG
ATGGCCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGGTGCGGGCCTCTTCGCTATTA
CGCCAGTCGACCATAGCCAATTCAATATGGCGTATATGGACTCATGCCAATTCAATATGGTGGATCTGGACCTGTGC
CAATTCAATATGGCGTATATGGACTCGTGCCAATTCAATATGGTGGATCTGGACCCCAGCCAATTCAATATGGCGGA
CTTGGCACCATGCCAATTCAATATGGCGGACTTGGCACTGTGCCAACTGGGGAGGGTCTACTTGGCACGGTGCCAA
GTTTGAGGAGGGGTCTTGGCCCTGTGCCAAGTCCGCCATATTGAATTGGCATGGTGCCAATAATGGCGGCCATATTG
```

Figure 35 CONT

GCTATATGCCAGGATCAATATATAGGCAATATCCAATATGGCCCTATGCCAATATGGCTATTGGCCAGGTTCAATAC
TATGTATTGGCCCTATGCCATATAGTATTCCATATATGGGTTTTCCTATTGACGTAGATAGCCCCTCCCAATGGGCG
GTCCCATATACCATATATGGGGCTTCCTAATACCGCCCATAGCCACTCCCCCATTGACGTCAATGGTCTCTATATAT
GGTCTTTCCTATTGACGTCATATGGGCGGTCCTATTGACGTATATGGCGCCTCCCCCATTGACGTCAATTACGGTAA
ATGGCCCGCCTGGCTCAATGCCCATTGACGTCAATAGGACCACCCACCATTGACGTCAATGGGATGGCTCATTGCCC
ATTCATATCCGTTCTCACGCCCCTATTGACGTCAATGACGGTAAATGGCCCACTTGGCAGTACATCAATATCTATT
AATAGTAACTTGGCAAGTACATTACTATTGGAAGGACGCCAGGGTACATTGGCAGTACTCCCATTGACGTCAATGGC
GGTAAATGGCCCGCGATGGCTGCCAAGTACATCCCCATTGACGTCAATGGGGAGGGGCAATGACGCAAATGGGCGTT
CCATTGACGTAAATGGGCGGTAGGCGTGCCTAATGGGAGGTCTATATAAGCAATGCTCGTTTAGGGA

Figure 35 CONT

SEQ ID NO: 76

> pCS-Dest_Cas9<sup>MT3</sup>_ZFTS4

```
ACCGCCATTCTGCCTGGGGACGTCGGAGCAAGCTTGATTTAGGTGACACTATAGAATACAAGCTACTTGTTCTTTTT
GCAGGATCCCATCGATTCGAATTCAAGGATCAACAAGTTTGTACAAAAAAGCAGGCTGGCGCCACCATGGACAAGAA
GTACTCCATTGGGCTCGATATCGGTACCAACAGCGTCGGCTGGGCCGTCATTACGGACGAGTACAAGGTGCCGAGCA
AAAAATTCAAAGTTCTGGGCAATACCGATCGCCACAGCATAAAGAAGAACCTCATTGGAGCCCTCCTGTTCGACTCC
GGGGAGACGGCCGAAGCCACGCGGCTCAAAAGAACAGCACGGCGCAGATATACCCGCAGAAAGAATCGGATCTGCTA
CCTGCAGGAGATCTTTAGTAATGAGATGGCTAAGGTGGATGACTCTTTCTTCCATAGGCTGGAGGAGTCCTTTTTGG
TGGAGGAGGATAAAAAGCACGAGCGCCACCCAATCTTTGGCAATATCGTGGACGAGGTGGCGTACCATGAAAAGTAC
CCAACCATATATCATCTGAGGAAGAAGCTGGTAGACAGTACTGATAAGGCTGACTTGCGGTTGATCTATCTCGCGCT
GGCGCACATGATCAAATTTCGGGGACACTTCCTCATCGAGGGGACCTGAACCCAGACAACAGCGATGTCGACAAAC
TCTTTATCCAACTGGTTCAGACTTACAATCAGCTTTTCGAGGAGAACCCGATCAACGCATCCGGCGTTGACGCCAAA
GCAATCCTGAGCGCTAGGCTGTCCAAATCCCGGCGGCTCGAAAACCTCATCGCACAGCTCCCTGGGGAGAAGAAGAA
CGGCCTGTTTGGTAATCTTATCGCCCTGTCACTCGGGCTGACCCCCAACTTTAAATCTAACTTCGACCTGGCCGAAG
ATGCCAAGCTGCAACTGAGCAAAGACACCTACGATGATGATCTCGACAATCTGCTGGCCCAGATCGGCGACCAGTAC
GCAGACCTTTTTTTGGCGGCAAAGAACCTGTCAGACGCCATTCTGCTGAGTGATATTCTGCGAGTGAACACGGAGAT
CACCAAAGCTCCGCTGAGCGCTAGTATGATCAAGCGCTATGATGAGCACCACCAAGACTTGACTTTGCTGAAGGCCC
TTGTCAGACAGCAACTGCCTGAGAAGTACAAGGAAATTTTCTTCGATCAGTCTAAAAATGGCTACGCCGGATACATT
GACGGCGGAGCAAGCCAGGAGGAATTTTACAAATTTATTAAGCCCATCTTGGAAAAAATGGACGGCACCGAGGAGCT
GCTGGTAAAGCTGAACAGAGAAGATCTGTTGCGCAAACAGCGCACTTTCGACAATGGAAGCATCCCCACCAGATTC
ACCTGGGCGAACTGCACGCTATCCTCAGGCGGCAAGAGGATTTCTACCCCTTTTTGAAAGATAACAGGGAAAAGATT
GAGAAAATCCTCACATTTCGGATACCCTACTATGTAGGCCCCCTCGCTCGGGGAAATTCCAGATTCGCGTGGATGAC
TCGCAAATCAGAAGAGACCATCACTCCCTGGAACTTCGAGGAAGTCGTGGATAAGGGGGCCTCTGCCCAGTCCTTCA
TCGAAAGGATGACTAACTTTGATAAAAATCTGCCTAACGAAAAGGTGCTTCCTAAACACTCTCTGCTGTACGAGTAC
TTCACAGTTTATAACGAGCTCACCAAGGTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTACCGTGAAACAGCTCAAAGAAGACTATT
TCAAAAAGATTGAATGTTTCGACTCTGTTGAAATCAGCGGAGTGGAGGATCGCTTCAACGCATCCCTGGGAACGTAT
CACGATCTCCTGAAAATCATTAAAGACAAGGACTTCCTGGACAATGAGGAGAACGAGGACATTCTTGAGGACATTGT
CCTCACCCTTACGTTGTTTGAAGATAGGGAGATGATTGAAGAACGCTTGAAAACTTACGCTCATCTCTTCGACGACA
AAGTCATGAAACAGCTCAAGAGACGCCGATATACAGGATGGGGCGGCTGTCAAGAAAACTGATCAATGGCATCCGA
GACAAGCAGAGTGGAAAGACAATCCTGGATTTTCTTAAGTCCGATGGATTTGCCAACCGGAACTTCATGCAGTTGAT
CCATGATGACTCTCTCACCTTTAAGGAGGACATCCAGAAAGCACAAGTTTCTGGCCAGGGGACAGTCTTCACGAGC
ACATCGCTAATCTTGCAGGTAGCCCAGCTATCAAAAGGGAATACTGCAGACCGTTAAGGTCGTGGATGAACTCGTC
AAAGTAATGGGAAGGCATAAGCCCGAGAATATCGTTATCGAGATGGCCCGAGAGAACCAAACTACCCAGAAGGGACA
GAAGAACAGTAGGGAAAGGATGAAGAGGATTGAAGAGGGTATAAAAGAACTGGGGTCCCAAATCCTTAAGGAACACC
```

Figure 36

```
CAGTTGAAAACACCCAGCTTCAGAATGAGAAGCTCTACCTGTACTACCTGCAGAACGGCAGGGACATGTACGTGGAT
CAGGAACTGGACATCAACCGGTTGTCCGACTACGACGTGGATCATATCGTGCCCCAAAGCTTTCTCAAAGATGATTC
TATTGATAATAAAGTGTTGACAAGATCCGATAAAAATAGAGGGAAGAGTGATAACGTCCCCTCAGAAGAAGTTGTCA
AGAAAATGAAAATTATTGGCGGCAGCTGCTGAACGCCAAACTGATCACACAACGGAAGTTCGATAATCTGACTAAG
GCTGAACGAGGTGGCCTGTCTGAGTTGGATAAAGCCGGCTTCATCAAAAGGCAGCTTGTTGAGACACGCCAGATCAC
CAAGCACGTGGCCCAAATTCTCGATTCACGCATGAACACCAAGTACGATGAAAATGACAAACTGATTCGAGAGGTGA
AAGTTATTACTCTGAAGTCTAAGCTGGTCTCAGATTTCAGAAAGGACTTTCAGTTTTATAAGGTGAGAGAGATCAAC
AATTACCACCATGCGCATGATGCCTACCTGAATGCAGTGGTAGGCACTGCACTTATCAAAAAATATCCCAAGCTGGA
ATCTGAATTTGTTTACGGAGACTATAAAGTGTACGATGTTAGGAAAATGATCGCAAAGTCTGAGCAGGAAATAGGCA
AGGCCACCGCTAAGTACTTCTTTTACAGCAATATTATGAATTTTTTCAAGACCGAGATTACACTGGCCAATGGAGAG
ATTCGGAAGCGACCACTTATCGAAACAAACGGAGAAACAGGAGAAATCGTGTGGGACAAGGGTAGGGATTTCGCGAC
AGTCCGCAAGGTCCTGTCCATGCCGCAGGTGAACATCGTTAAAAAGACCGAAGTACAGACCGGAGGCTTCTCCAAGG
AAAGTATCCTCCCGAAAAGGAACAGCGACAAGCTGATCGCACGCAAAAAGATTGGGACCCCAAGAAATACGGCGGA
TTCGATTCTCCTACAGTCGCTTACAGTGTACTGGTTGTGGCCAAAGTGGAGAAAGGGAAGTCTAAAAAACTCAAAAG
CGTCAAGGAACTGCTGGGCATCACAATCATGGAGCGATCCAGCTTCGAGAAAAACCCCATCGACTTTCTCGAAGCGA
AAGGATATAAAGAGGTCAAAAAAGACCTCATCATTAAGCTGCCCAAGTACTCTCTCTTTGAGCTTGAAAACGGCCGG
AAACGAATGCTCGCTAGTGCGGGCGAGCTGCAGAAAGGTAACGAGCTGGCACTGCCCTCTAAATACGTTAATTTCTT
GTATCTGGCCAGCCACTATGAAAAGCTCAAAGGGTCTCCCGAAGATAATGAGCAGAAGCAGCTGTTCGTGGAACAAC
ACAAACACTACCTTGATGAGATCATCGAGCAAATAAGCGAGTTCTCCAAAAGAGTGATCCTCGCCGACGCTAACCTC
GATAAGGTGCTTTCTGCTTACAATAAGCACAGGGATAAGCCCATCAGGGAGCAGGCAGAAAACATTATCCACTTGTT
TACTCTGACCAACTTGGGCGCGCCTGCAGCCTTCAAGTACTTCGACACCACCATAGAC░░░░░TACACCTCTA
CAAAGGAGGTCCTGGACGCCACACTGATTCATCAGTCAATTACGGGGCTCTATGAAACAAGAATCGACCTCTCTCAG
CTCGGTGGAGACGGCACCGGCGGGCCCAAGAAGAAGAGGAAGGTATACCCATACGATGTTCCTGACTATGCGGGCTA
TCCCTATGACGTCCCGGACTATGCAGGATCGTATCCTTATGACGTTCCAGATTACGCTGGATCCGCCGCTCCGGCAG
CTAAGAAAAGAAACTGGATTTCGAATccggA░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░
░░░░░░░░░░░░░░░░░░░░░░░░░░░░░░░░░░░░░░░░░░░░░░░░░░░░░░░░░░░░░░░░░░░░░░░░░░░░░
░░░░░CtcgaGCCTCTAGAACTATAGTGAGTCGTATTACGTAGATCCAGACATGATAAGATACATTGATGAGTTT
GGACAAACCACAACTAGAATGCAGTGAAAAAAATGCTTTATTTGTGAAATTTGTGATGCTATTGCTTTATTTGTAAC
CATTATAAGCTGCAATAAACAAGTTAACAACAACAATTGCATTCATTTTATGTTTCAGGTTCAGGGGGAGGTGTGGG
AGGTTTTTTAATTCGCGGCCGCGGCGCCAATGCATTGGGCCCGGTACCCAGCTTTTGTTCCCTTTAGTGAGGGTTAA
TTGCGCGCTTGGCGTAATCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTAATTGCGTTGCGCTCACT
GCCCGCTTTCCAGTCGGGAAACCTGTCGTGCCAGCTGCATTAATGAATCGGCCAACGCGCGGGAGAGGCGGTTTGC
```

Figure 36 CONT

```
GTATTGGGCGCTCTTCCGCTTCCTCGCTCACTGACTCGCTGCGCTCGGTCGTTCGGCTGCGGCGAGCGGTATCAGCT
CACTCAAAGGCGGTAATACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCCTGACGAGCATCACAAAA
ATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAGCACTGCATAATTCTCTT
ACTGTCATGCCATCCGTAAGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGTTCCGCGCACATTT
CCCCGAAAAGTGCCACCTAAATTGTAAGCGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAAAACCGTCTATCAGGGCG
ATGGCCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGGTGCGGGCCTCTTCGCTATTA
CGCCAGTCGACCATAGCCAATTCAATATGGCGTATATGGACTCATGCCAATTCAATATGGTGGATCTGGACCTGTGC
CAATTCAATATGGCGTATATGGACTCGTGCCAATTCAATATGGTGGATCTGGACCCCAGCCAATTCAATATGGCGGA
CTTGGCACCATGCCAATTCAATATGGCGGACTTGGCACTGTGCCAACTGGGGAGGGTCTACTTGGCACGGTGCCAA
GTTTGAGGAGGGGTCTTGGCCCTGTGCCAAGTCCGCCATATTGAATTGGCATGGTGCCAATAATGGCGGCCATATTG
```

Figure 36 CONT

```
GCTATATGCCAGGATCAATATATAGGCAATATCCAATATGGCCCTATGCCAATATGGCTATTGGCCAGGTTCAATAC
TATGTATTGGCCCTATGCCATATAGTATTCCATATATGGGTTTTCCTATTGACGTAGATAGCCCCTCCCAATGGGCG
GTCCCATATACCATATATGGGGCTTCCTAATACCGCCCATAGCCACTCCCCCATTGACGTCAATGGTCTCTATATAT
GGTCTTTCCTATTGACGTCATATGGGCGGTCCTATTGACGTATATGGCGCCTCCCCCATTGACGTCAATTACGGTAA
ATGGCCCGCCTGGCTCAATGCCCATTGACGTCAATAGGACCACCCACCATTGACGTCAATGGGATGGCTCATTGCCC
ATTCATATCCGTTCTCACGCCCCCTATTGACGTCAATGACGGTAAATGGCCCACTTGGCAGTACATCAATATCTATT
AATAGTAACTTGGCAAGTACATTACTATTGGAAGGACGCCAGGGTACATTGGCAGTACTCCCATTGACGTCAATGGC
GGTAAATGGCCCGCGATGGCTGCCAAGTACATCCCCATTGACGTCAATGGGGAGGGGCAATGACGCAAATGGGCGTT
CCATTGACGTAAATGGGCGGTAGGCGTGCCTAATGGGAGGTCTATATAAGCAATGCTCGTTTAGGGA
```

Figure 36 CONT

SEQ ID NO: 77

Legend: SpCas9 NLS HA tag pDBD

>Protein sequence of SpCas9-Zif268
MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSREPMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGDGTGGPKKKRKV GSGSGS
GS GGSGGSGSAAPAAKKKKLDPESGRPYACPVESCDRRFSRSDELTRHIRIHTGQRPFQCRI
CMRNFSRSDHLTTHIRTHTGEKPFACDICGRKFARSDERRRHTKIHLRQKD*

FIGURE 37

SEQ ID NO: 78

>Protein_sequence_N-Zif268_Cas9

MGRAAPAAKKKKLDQLRPYACPVESCDRRFSRSDELTRHIRIHTGQKPFQCRICMRNFSRSDHLTTHIRTHTGEKPF
ACDICGRKFARSDERKRHTKIHLRQKDPGSGGSGSSGRTAAPAAKKKKLDSEFGSDKKYSIGLDIGTNSVGWAVITD
EYKVPSKKFKVLGNTDRHSIKKNLIGALLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKADLRLIYLALAHMIKFRGHFLIEGDLNPD
NSDVDKLFIQLVQTYNQLFEENPINASGVDAKAILSARLSKSRRLENLIAQLPGEKKNGLFGNLIALSLGLTPNFKS
NFDLAEDAKLQLSKDTYDDDLDNLLAQIGDQYADLFLAAKNLSDAILLSDILRVNTEITKAPLSASMIKRYDEHHQD
LTLLKALVRQQLPEKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEETITPWNFEEVVDKG
ASAQSFIERMTNFDKNLPNEKVLPKHSLLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEENEDILEDIVLTLTLFEDREMIEERLKTY
AHLFDDKVMKQLKRRRYTGWGRLSRKLINGIRDKQSGKTILDFLKSDGFANRNFMQLIHDDSLTFKEDIQKAQVSGQ
GDSLHEHIANLAGSPAIKKGILQTVKVVDELVKVMGRHKPENIVIEMARENQTTQKGQKNSRERMKRIEEGIKELGS
QILKEHPVENTQLQNEKLYLYYLQNGRDMYVDQELDINRLSDYDVDHIVPQSFLKDDSIDNKVLTRSDKNRGKSDNV
PSEEVVKKMKNYWRQLLNAKLITQRKFDNLTKAERGGLSELDKAGFIKRQLVETRQITKHVAQILDSRMNTKYDEND
KLIREVKVITLKSKLVSDFRKDFQFYKVREINNYHHAHDAYLNAVVGTALIKKYPKLESEFVYGDYKVYDVRKMIAK
SEQEIGKATAKYFFYSNIMNFFKTEITLANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEKGKSKKLKSVKELLGITIMERSSFEKNP
IDFLEAKGYKEVKKDLIIKLPKYSLFELENGRKRMLASAGELQKGNELALPSKYVNFLYLASHYEKLKGSPEDNEQK
QLFVEQHKHYLDEIIEQISEFSKRVILADANLDKVLSAYNKHRDKPIREQAENIIHLFTLTNLGAPAAFKYFDTTID
RKRYTSTKEVLDATLIHQSITGLYETRIDLSQLGGDGTGGPKKKRKVYPYDVPDYAGYPYDVPDYAGSYPYDVPDYA
GS*

FIGURE 38

SEQ ID NO: 79

>Protein sequence of SpCas9-TAL268
MGRAAPAAKKKKLDQLGASGSPGSGGSGSSGRTAAPAAKKKKLDSEFGSGSDKKYSIGLDIGTNSVGWAVITDEYKV
PSKKFKVLGNTDRHSIKKNLIGALLFDSGETAEATRLKRTARRRYTRRKNRICYLQEIFSNEMAKVDDSFFHRLEES
FLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDL
AEDAKLQLSKDTYDDDLDNLLAQIGDQYADLFLAAKNLSDAILLSDILRVNTEITKAPLSASMIKRYDEHHQDLTLL
KALVRQQLPEKYKEIFFDQSKNGYAGYIDGGASQEEFYKFIKPILEKMDGTEELLVKLNREDLLRKQRTFDNGSIPH
QIHLGELHAILRRQEDFYPFLKDNREKIEKILTFRIPYYVGPLARGNSRFAWMTRKSEETITPWNFEEVVDKGASAQ
SFIERMTNFDKNLPNEKVLPKHSLLYEYFTVYNELTKVKYVTEGMRKPAFLSGEQKKAIVDLLFKTNRKVTVKQLKE
DYFKKIECFDSVEISGVEDRFNASLGTYHDLLKIIKDKDFLDNEENEDILEDIVLTLTLFEDREMIEERLKTYAHLF
DDKVMKQLKRRRYTGWGRLSRKLINGIRDKQSGKTILDFLKSDGFANRNFMQLIHDDSLTFKEDIQKAQVSGQGDSL
HEHIANLAGSPAIKKGILQTVKVVDELVKVMGRHKPENIVIEMARENQTTQKGQKNSRERMKRIEEGIKELGSQILK
EHPVENTQLQNEKLYLYYLQNGRDMYVDQELDINRLSDYDVDHIVPQSFLKDDSIDNKVLTRSDKNRGKSDNVPSEE
VVKKMKNYWRQLLNAKLITQRKFDNLTKAERGGLSELDKAGFIKRQLVETRQITKHVAQILDSRMNTKYDENDKLIR
EVKVITLKSKLVSDFRKDFQFYKVREINNYHHAHDAYLNAVVGTALIKKYPKLESEFVYGDYKVYDVRKMIAKSEQE
IGKATAKYFFYSNIMNFFKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLGITIMERSSFEKNPIDFL
EAKGYKEVKKDLIIKLPKYSLFELENGRKRMLASAGELQKGNELALPSKYVNFLYLASHYEKLKGSPEDNEQKQLFV
EQHKHYLDEIIEQISEFSKRVILADANLDKVLSAYNKHRDKPIREQAENIIHLFTLTNLGAPAAFKYFDTTIDRKRY
TSTKEVLDATLIHQSITGLYETRIDLSQLGGDGTGGPKKKRKV[highlighted]GSAA
PAAKKKKLDFESGVPMVDLRTLGYSQQQEKIKPKVRSTVAQHHEALVGHGFTHAHIVALSQHPAALGTVAVKYQDM
IAALPEATHEAIVGVGKQWSGARALEALLTVAGELRGPPLQLDTGQLLKIAKRGGVTAVEAVHAWRNALTGAPLPLN
LTPDQVVAIASNNGGKQALETVQRLLPVLCQDHGLTPDQVVAIASHDGGKQALETVQRLLPVLCQDHGLTPDQVVAI
ASNNGGKQALETVQRLLPVLCQDHGLTPDQVVAIASNGGGKQALETVQRLLPVLCQDHGLTPDQVVAIASNNGGKQA
LETVQRLLPVLCQDHGLTPDQVVAIASNNGGKQALETVQRLLPVLCQDHGLTPDQVVAIASNNGGKQALETVQRLLP
VLCQDHGLTPDQVVAIASHDGGKQALETVQRLLPVLCQDHGLTPDQVVAIASNNGGKQALETVQRLLPVLCQDHGLT
PDQVVAIANNNGGRPALESIVAQLSRPDPALAALTNDHLVALACLGGRPALDAVKKGLPHAPALIKRTNRRIPERTS
HRVAGS*

FIGURE 39

SEQ ID NO: 80

>Protein sequence N-TAL268-Cas9

```
MGRAAPAAKKKKLDQLVPMVDLRTLGYSQQQQEKIKPKVRSTVAQHHEALVGHGFTHAHIVALSQHPAALGTVAVKY
QDMIAALPEATHEAIVGVGKQWSGARALEALLTVAGELRGPPLQLDTGQLLKIAKRGGVTAVEAVHAWRNALTGAPL
PLNLTPDQVVAIASNNGGKQALETVQRLLPVLCQDHGLTPDQVVAIASHDGGKQALETVQRLLPVLCQDHGLTPDQV
VAIASNNGGKQALETVQRLLPVLCQDHGLTPDQVVAIASNGGGKQALETVQRLLPVLCQDHGLTPDQVVAIASNNGG
KQALETVQRLLPVLCQDHGLTPDQVVAIASNNGGKQALETVQRLLPVLCQDHGLTPDQVVAIASNNGGKQALETVQR
LLPVLCQDHGLTPDQVVAIASHDGGKQALETVQRLLPVLCQDHGLTPDQVVAIASNNGGKQALETVQRLLPVLCQDH
GLTPDQVVAIANNNGGRPALESIVAQLSRPDPALAALTNDHLVALACLGGRPALDAVKKGLPHAPALIKRTNRRIPE
RTSHRVAGSPGSGGSGSSGRTAAPAAKKKKLDSEFGSDKKYSIGLDIGTNSVGWAVITDEYKVPSKKFKVLGNTDRH
SIKKNLIGALLFDSGETAEATRLKRTARRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHFLIEGDLNPDNSDVDKLFIQLVQTYNQL
FEENPINASGVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLLKALVRQQLPEKYKE
IFFDQSKNGYAGYIDGGASQEEFYKFIKPILEKMDGTEELLVKLNREDLLRKQRTFDNGSIPHQIHLGELHAILRRQ
EDFYPFLKDNREKIEKILTFRIPYYVGPLARGNSRFAWMTRKSEETITPWNFEEVVDKGASAQSFIERMTNFDKNLP
NEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYT
GWGRLSRKLINGIRDKQSGKTILDFLKSDGFANRNFMQLIHDDSLTFKEDIQKAQVSGQGDSLHEHIANLAGSPAIK
KGILQTVKVVDELVKVMGRHKPENIVIEMARENQTTQKGQKNSRERMKRIEEGIKELGSQILKEHPVENTQLQNEKL
YLYYLQNGRDMYVDQELDINRLSDYDVDHIVPQSFLKDDSIDNKVLTRSDKNRGKSDNVPSEEVVKKMKNYWRQLLN
AKLITQRKFDNLTKAERGGLSELDKAGFIKRQLVETRQITKHVAQILDSRMNTKYDENDKLIREVKVITLKSKLVSD
FRKDFQFYKVREINNYHHAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTGGFSKESILPKRNSDKL
IARKKDWDPKKYGGFDSPTVAYSVLVVAKVEKGKSKKLKSVKELLGITIMERSSFEKNPIDFLEAKGYKEVKKDLII
KLPKYSLFELENGRKRMLASAGELQKGNELALPSKYVNFLYLASHYEKLKGSPEDNEQKQLFVEQHKHYLDEIIEQI
SEFSKRVILADANLDKVLSAYNKHRDKPIREQAENIIHLFTLTNLGAPAAFKYFDTTIDRKRYTSTKEVLDATLIHQ
SITGLYETRIDLSQLGGDTGGPKKKRKVYPYDVPDYAGYPYDVPDYAGSYPYDVPDYAGS*
```

FIGURE 40

SEQ ID NO: 81

>Protein sequence of SpCas9-ZFP^TS4
MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSREMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGDGGGPKKKRKV░░░░░░░░
░░░░░░░░░░░GSAAPAAKKKKLDFESGKPYKCPECGKSFSQSGDLTRHQRTHTGEKPYACPVES
CDRRFSEKSHLTRHIRIHTGQRPFQCRICMRNFSCAHHLTRHIRTHTGEKPFACDICGRKFADRSTLTQHTKIHLRQ
KDPG*

FIGURE 41

SEQ ID NO: 82

>Protein sequence of SpCas9-ZFP$^{TS2*}$
MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGDGTGGPKKKRKV░░░░░
░░G░░░░░░GS░░░░░░GSAAPAAKKKKLDFESGKPYKCPECGKSFSQKGHLTRHQRTHTGEKPYACPVES
CDRRFSDRSDLTRHIRIHTGQKPFQCRICMRNFSRSDHLTRHIRTHTGEKPFACDICGRKFAQSGDLTRHTKIHLRQ
KDPG*

FIGURE 42

SEQ ID NO: 83

>Protein sequence of SpCas9-ZFP^TS3
MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGD*GTGGPKKKRKV▓▓▓▓▓▓
▓▓▓▓▓▓▓▓▓▓GS▓▓▓▓▓▓GSAAPAAKKKKLDFES*GKPYKCPECGKSFSRSDDLTRHQRTHTGEKPYACPVES*
CDRRFSQKGHLTRHIRIHTGQKPFQCRICMRNFSIRSSLTRHIRTHTGEKPFACDICGRKFALSHHLTRHTKIHLRQ*
KDPG*

FIGURE 43

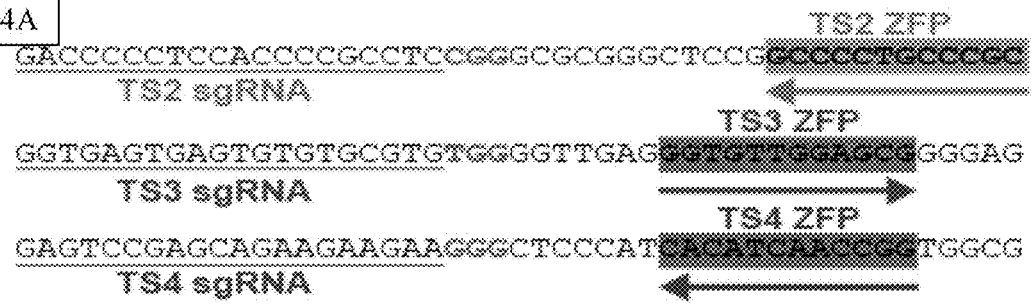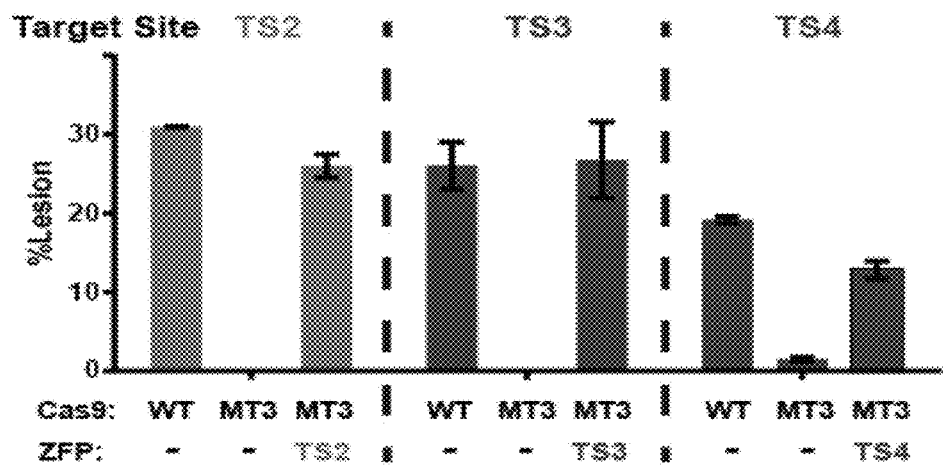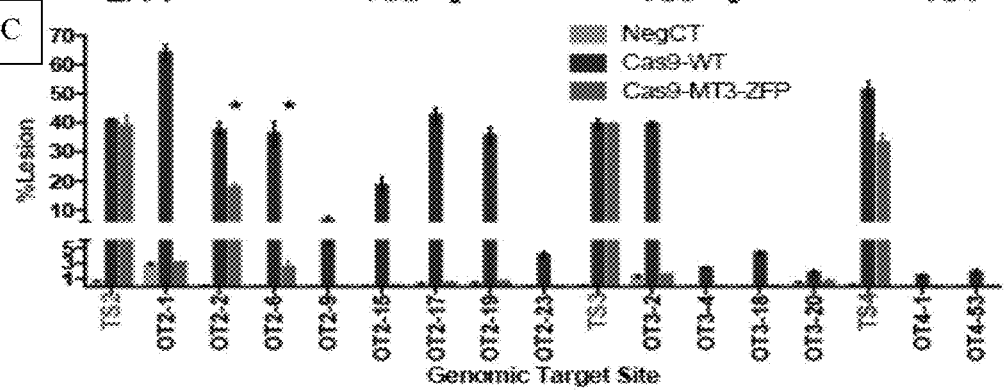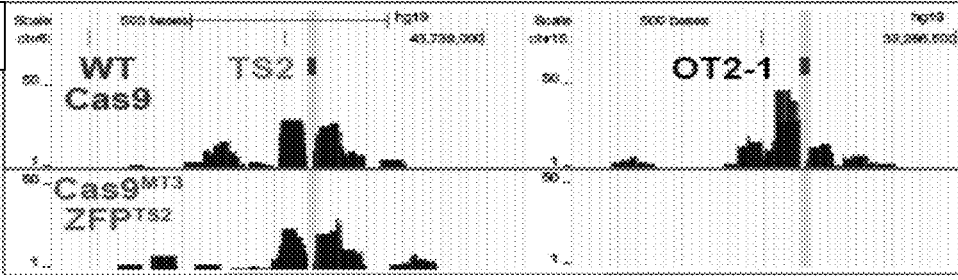
FIGURE 44

Off-target score for top 10 sites

FIG.53A Exons

FIG.53B Promoters

Fraction of the best guides that have bulged off-target sites

FIG.53C Exons

FIG.53D Promoters

Figure 56A
SEQ ID NO: 93
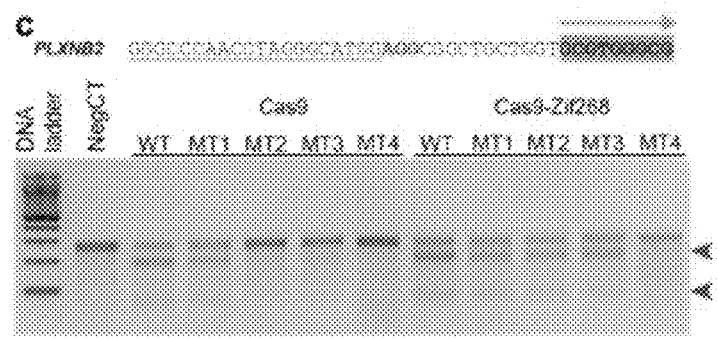
Figure 56B
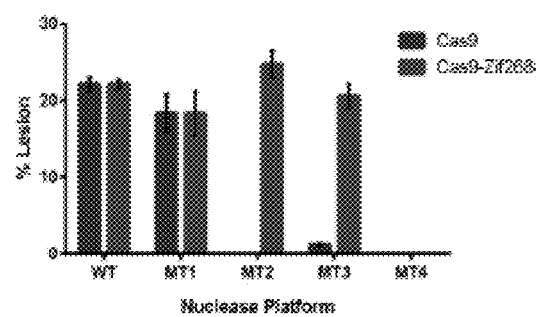
FIGURES 56A – 56B

SEQ ID NO: 95, 96
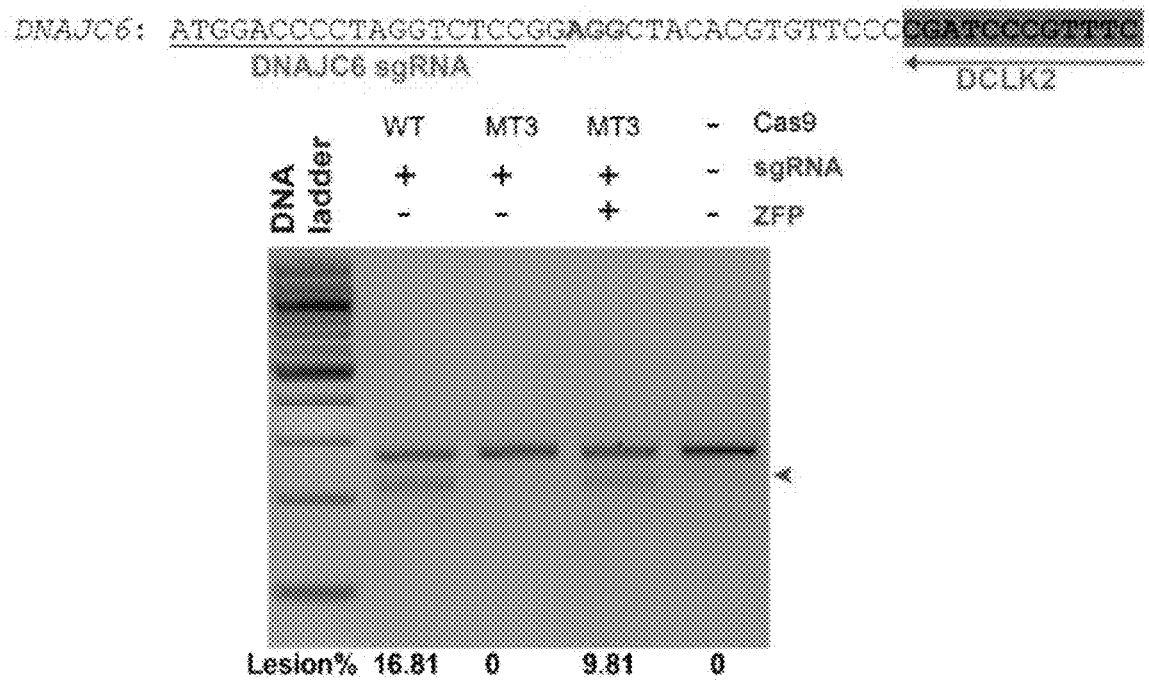
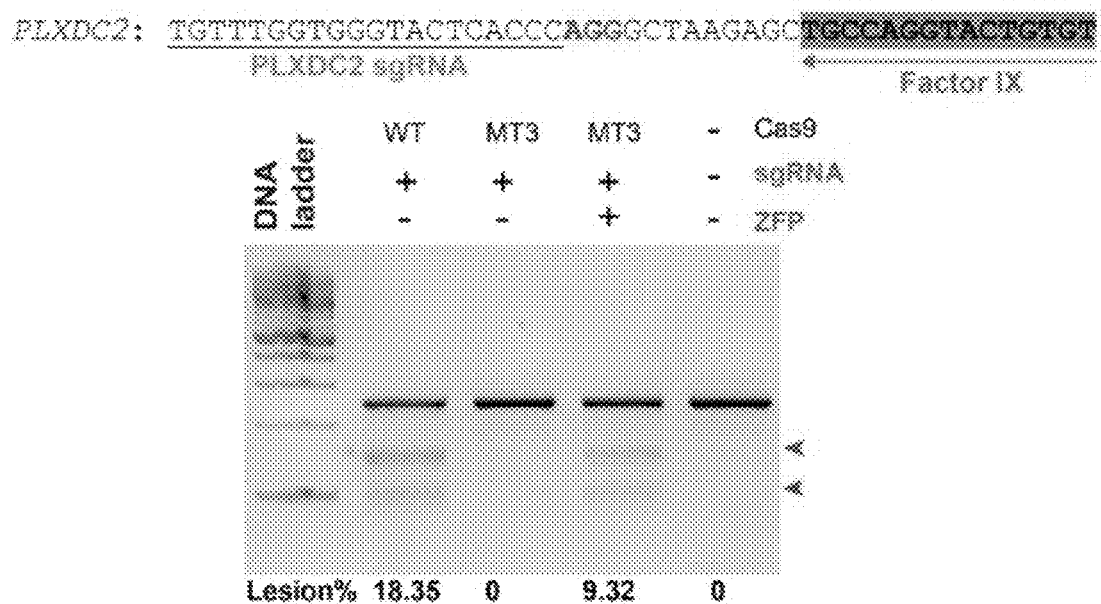
FIGURE 59

SEQ ID NO: 101, 102
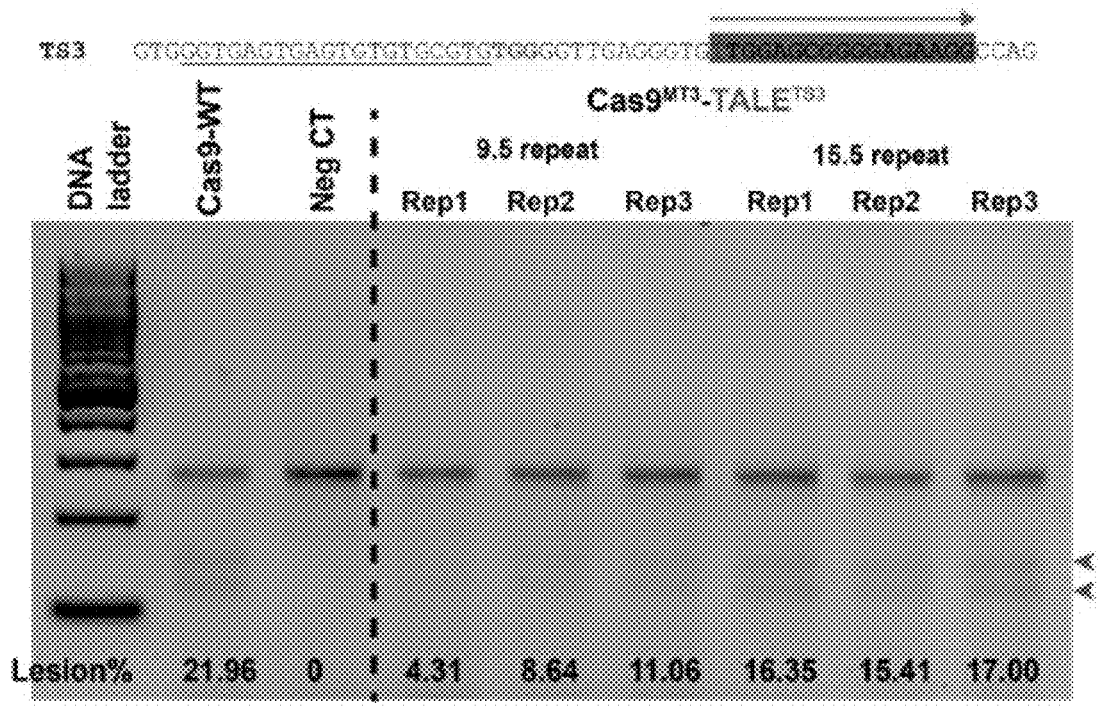
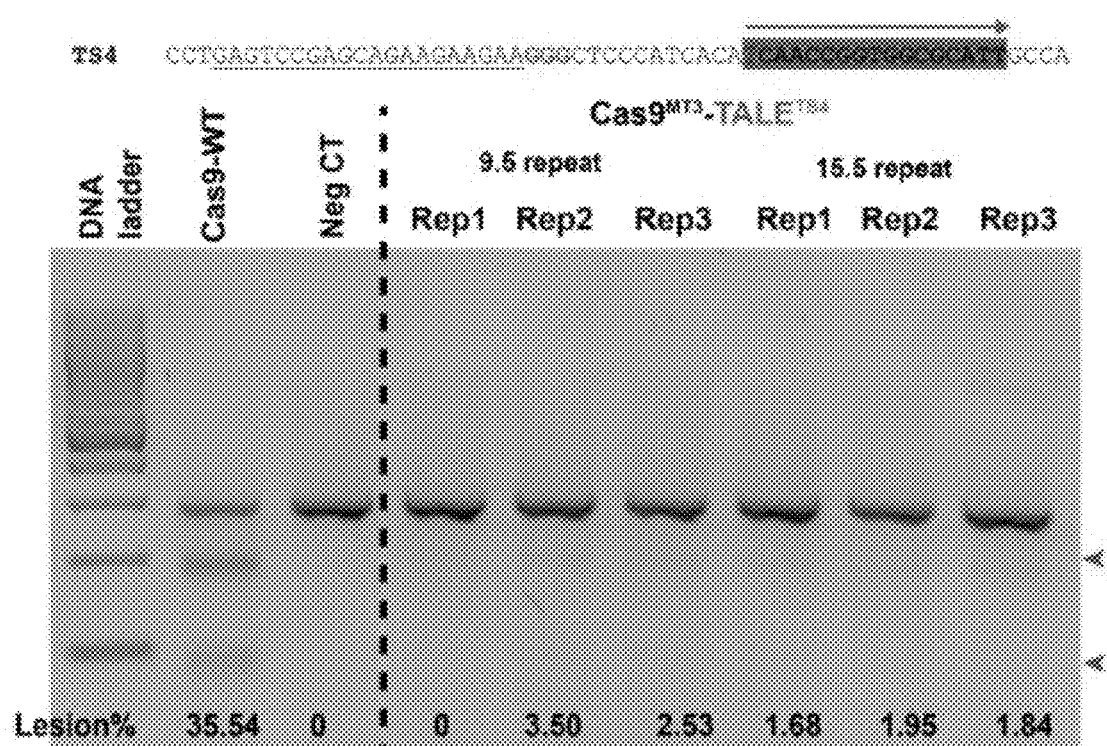
FIGURE 62

SEQ ID NO: 103, 104, 105, 106
FIG.63A
FIG.63B
FIG.63C
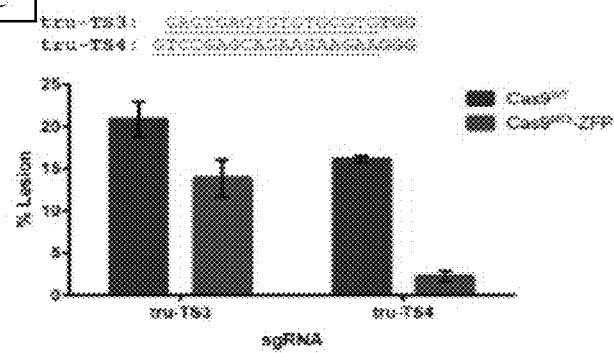
FIGURES 63A – 63C

SEQ ID NO: 107, 108
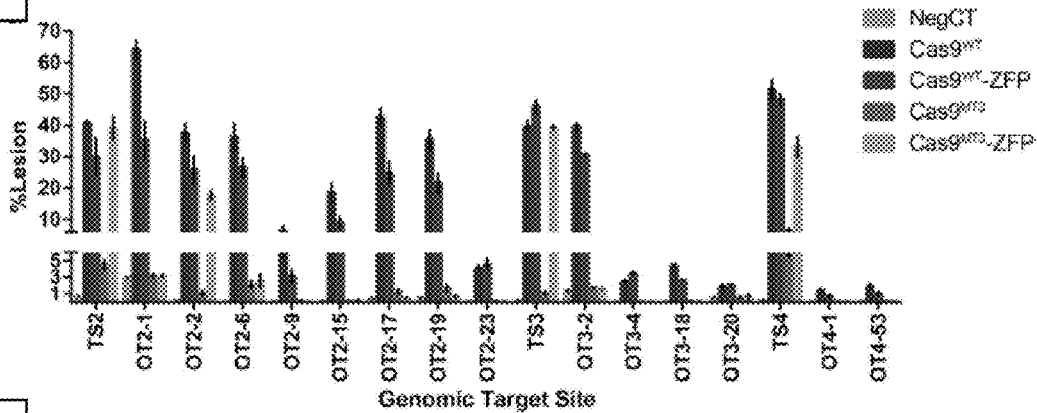
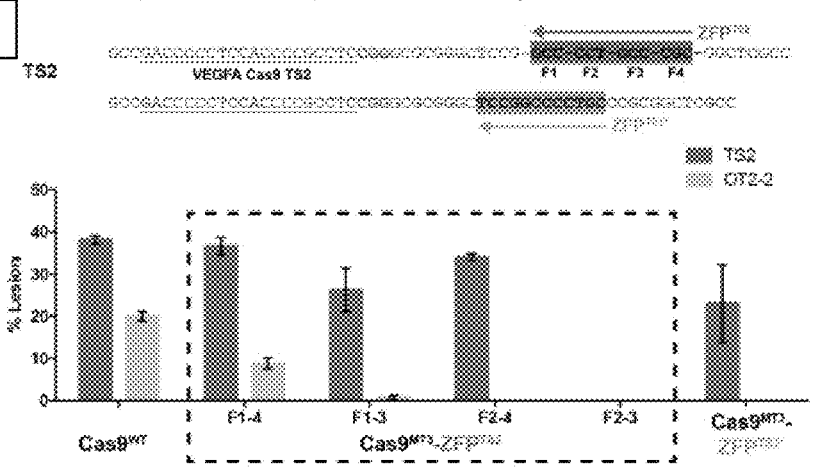
FIGURES 64A-64C

SEQ ID NO: 111, 112, 113

Effect of DBD spacing on the suppression of NmCas9 PIM mutations in the presence of Zif268 binding site and GATT PAM
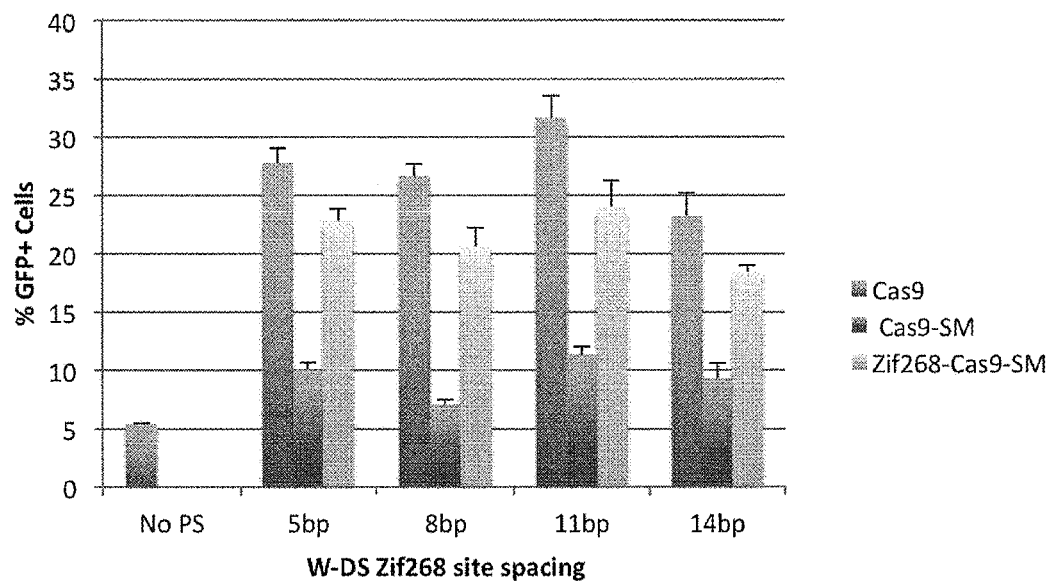
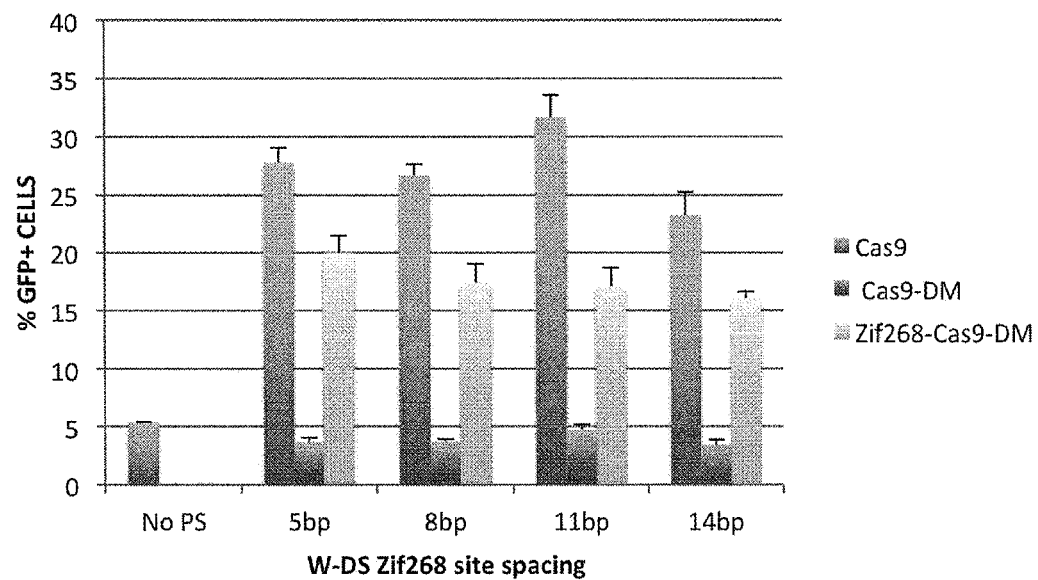
Figure 72

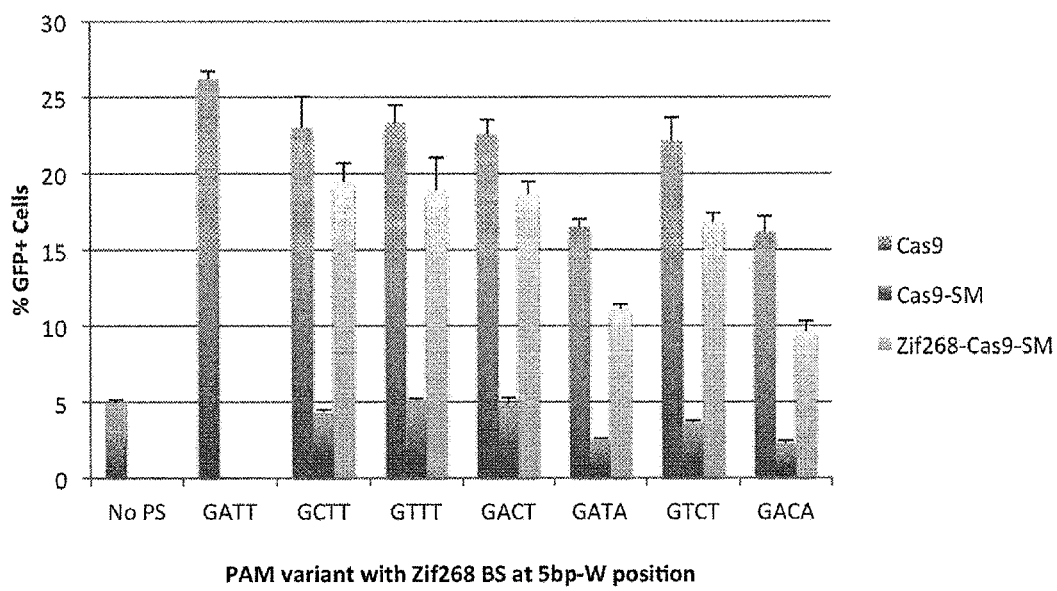
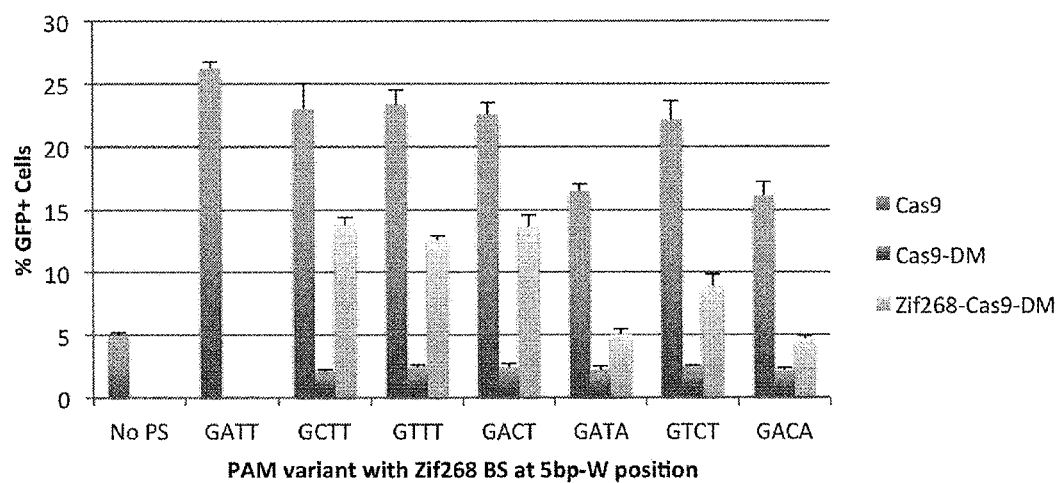
Figure 79

SEQ ID NO: 114

NmCas9 amino acid sequence:

Grey: SV40 NLS

Brown letters: NmeCas9

Red: HA tag

Light green: Synthetic NLS

MVPKKKRKVAAFKPNSINYILGLDIGIASVGWAMVEIDEEENPIRLIDLGVRVFERAE
VPKTGDSLAMARRLARSVRRLTRRRAHRLLRTRRLLKREGVLQAANFDENGLIKS
LPNTPWQLRAAALDRKLTPLEWSAVLLHLIKHRGYLSQRKNEGETADKELGALLK
GVAGNAHALQTGDFRTPAELALNKFEKESGHIRNQRSDYSHTFSRKDLQAELILLF
EKQKEFGNPHVSGGLKEGIETLLMTQRPALSGDAVQKMLGHCTFEPAEPKAAKNT
YTAERFIWLTKLNNLRILEQGSERPLTDTERATLMDEPYRKSKLTYAQARKLLGLE
DTAFFKGLRYGKDNAEASTLMEMKAYHAISRALEKEGLKDKKSPLNLSPELQDEI
GTAFSLFKTDEDITGRLKDRIQPEILEALLKHISFDKFVQISLKALRRIVPLMEQGKR
YDEACAEIYGDHYGKKNTEEKIYLPPIPADEIRNPVVLRALSQARKVINGVVRRYGS
PARIHIETAREVGKSFKDRKEIEKRQEENRKDREKAAAKFREYFPNFVGEPKSKDIL
KLRLYEQQHGKCLYSGKEINLGRLNEKGYVEIDHALPFSRTWDDSFNNKVLVLGS
ENQNKGNQTPYEYFNGKDNSREWQEFKARVETSRFPRSKKQRILLQKFDEDGFKE
RNLNDTRYVNRFLCQFVADRMRLTGKGKKRVFASNGQITNLLRGFWGLRKVRAE
NDRHHALDAVVVACSTVAMQQKITRFVRYKEMNAFDGKTIDKETGEVLHQKTHF
PQPWEFFAQEVMIRVFGKPDGKPEFEEADTLEKLRTLLAEKLSSRPEAVHEYVTPL
FVSRAPNRKMSGQGHMETVKSAKRLDEGVSVLRVPLTQLKLKDLEKMVNREREP
KLYEALKARLEAHKDDPAKAFAEPFYKYDKAGNRTQQVKAVRVEQVQKTGVWV
RNHNGIADNATMVRVDVFEKGDKYYLVPIYSWQVAKGILPDRAVVQGKDEEDWQ
LIDDSFNFKFSLHPNDLVEVITKDARMFGYFASCHRGTGNINIRIHDLDHKIGKNGIL
EGIGVKTALSFQKYQIDELGKEIRPCRLKKRPPVR████████AAPAAKKKKLD*

Figure 84

SEQ ID NO: 115

Single Mutant-NmCas9 amino acid sequence:

Grey: SV40 NLS

Brown letters: NmeCas9

Red: HA tag

Light green: Synthetic NLS

MVPKKKRKVAAFKPNSINYILGLDIGIASVGWAMVEIDEEENPIRLIDLGVRVFERAE
VPKTGDSLAMARRLARSVRRLTRRRAHRLLRTRRLLKREGVLQAANFDENGLIKS
LPNTPWQLRAAALDRKLTPLEWSAVLLHLIKHRGYLSQRKNEGETADKELGALLK
GVAGNAHALQTGDFRTPAELALNKFEKESGHIRNQRSDYSHTFSRKDLQAELILLF
EKQKEFGNPHVSGGLKEGIETLLMTQRPALSGDAVQKMLGHCTFEPAEPKAAKNT
YTAERFIWLTKLNNLRILEQGSERPLTDTERATLMDEPYRKSKLTYAQARKLLGLE
DTAFFKGLRYGKDNAEASTLMEMKAYHAISRALEKEGLKDKKSPLNLSPELQDEI
GTAFSLFKTDEDITGRLKDRIQPEILEALLKHISFDKFVQISLKALRRIVPLMEQGKR
YDEACAEIYGDHYGKKNTEEKIYLPPIPADEIRNPVVLRALSQARKVINGVVRRYGS
PARIHIETAREVGKSFKDRKEIEKRQEENRKDREKAAAKFREYFPNFVGEPKSKDIL
KLRLYEQQHGKCLYSGKEINLGRLNEKGYVEIDHALPFSRTWDDSFNNKVLVLGS
ENQNKGNQTPYEYFNGKDNSREWQEFKARVETSRFPRSKKQRILLQKFDEDGFKE
RNLNDTRYVNRFLCQFVADRMRLTGKGKKRVFASNGQITNLLRGFWGLRKVRAE
NDRHHALDAVVVACSTVAMQQKITRFVRYKEMNAFDGKTIDKETGEVLHQKTHF
PQPWEFFAQEVMIRVFGKPDGKPEFEEADTLEKLRTLLAEKLSSRPEAVHEYVTPL
FVSRAPNRKMSGQGHMETVKSAKRLDEGVSVLRVPLTQLKLKDLEKMVNREREP
KLYEALKARLEAHKDDPAKAFAEPFYKYDKAGNRTQQVKAVRVEQVQKTGVWV
RNHNGIADNATMVRVDVFEKGDKYYLVPIYSWQVAKGILPDRAVVQGKDEEDWQ
LIDDSFNFKFSLHPNDLVEVITKQARMFGYFASCHQGTGNINIRIHDLDHKIGKNGIL
EGIGVKTALSFQKYQIDELGKEIRPCRLKKRPPVR[YPYDVPDYA]AAPAAKKKKLD*

Figure 85

SEQ ID NO: 116

Double Mutant-NmCas9 amino acid sequence:

Grey: SV40 NLS

Brown letters: NmeCas9

Red: HA tag

Light green: Synthetic NLS

MVPKKKRKVAAFKPNSINYILGLDIGIASVGWAMVEIDEEENPIRLIDLGVRVFERAE
VPKTGDSLAMARRLARSVRRLTRRRAHRLLRTRRLLKREGVLQAANFDENGLIKS
LPNTPWQLRAAALDRKLTPLEWSAVLLHLIKHRGYLSQRKNEGETADKELGALLK
GVAGNAHALQTGDFRTPAELALNKFEKESGHIRNQRSDYSHTFSRKDLQAELILLF
EKQKEFGNPHVSGGLKEGIETLLMTQRPALSGDAVQKMLGHCTFEPAEPKAAKNT
YTAERFIWLTKLNNLRILEQGSERPLTDTERATLMDEPYRKSKLTYAQARKLLGLE
DTAFFKGLRYGKDNAEASTLMEMKAYHAISRALEKEGLKDKKSPLNLSPELQDEI
GTAFSLFKTDEDITGRLKDRIQPEILEALLKHISFDKFVQISLKALRRIVPLMEQGKR
YDEACAEIYGDHYGKKNTEEKIYLPPIPADEIRNPVVLRALSQARKVINGVVRRYGS
PARIHIETAREVGKSFKDRKEIEKRQEENRKDREKAAAKFREYFPNFVGEPKSKDIL
KLRLYEQQHGKCLYSGKEINLGRLNEKGYVEIDHALPFSRTWDDSFNNKVLVLGS
ENQNKGNQTPYEYFNGKDNSREWQEFKARVETSRFPRSKKQRILLQKFDEDGFKE
RNLNDTRYVNRFLCQFVADRMRLTGKGKKRVFASNGQITNLLRGFWGLRKVRAE
NDRHHALDAVVVACSTVAMQQKITRFVRYKEMNAFDGKTIDKETGEVLHQKTHF
PQPWEFFAQEVMIRVFGKPDGKPEFEEADTLEKLRTLLAEKLSSRPEAVHEYVTPL
FVSRAPNRKMSGQGHMETVKSAKRLDEGVSVLRVPLTQLKLKDLEKMVNREREP
KLYEALKARLEAHKDDPAKAFAEPFYKYDKAGNRTQQVKAVRVEQVQKTGVWV
RNHNGIADNATMVRVDVFEKGDKYYLVPIYSWQVAKGILPDRAVVQGKDEEDWQ
LIDDSFNFKFSLHPNDLVEVITKYARMFGYFASCHRGTGNINIRIHDLDHKIGKNGIL
EGIGVKTALSFQKYQIDELGKEIRPCRLKKRPPVRKAAPAAKKKKLD*

SEQ ID NO: 117

Zif268-NmCas9 amino acid sequence:

Magenta: cMyc NLS

Yellow: Zif268

Dark green: GS linker

Grey: SV40 NLS

Brown letters: NmeCas9

Red: HA tag

Light green: Synthetic NLS

MGR░░░░░░░░░░░░QLRPYACPVESCDRRFSRSDELTRHIRIHTGQKPFQCRICMRNFSRSDHLT
THIRTHTGEKPFACDICGRKFARSDERKRHTKIHLRQKDP░░░░░░░RT░░░░░░░░IRK
LVPKKKRKVAAFKPNSINYILGLDIGIASVGWAMVEIDEEENPIRLIDLGVRVFERAEVPKTG
DSLAMARRLARSVRRLTRRRAHRLLRTRRLLKREGVLQAANFDENGLIKSLPNTPWQLRA
AALDRKLTPLEWSAVLLHLIKHRGYLSQRKNEGETADKELGALLKGVAGNAHALQTGDF
RTPAELALNKFEKESGHIRNQRSDYSHTFSRKDLQAELILLFEKQKEFGNPHVSGGLKEGIE
TLLMTQRPALSGDAVQKMLGHCTFEPAEPKAAKNTYTAERFIWLTKLNNLRILEQGSERP
LTDTERATLMDEPYRKSKLTYAQARKLLGLEDTAFFKGLRYGKDNAEASTLMEMKAYHA
ISRALEKEGLKDKKSPLNLSPELQDEIGTAFSLFKTDEDITGRLKDRIQPEILEALLKHISFDK
FVQISLKALRRIVPLMEQGKRYDEACAEIYGDHYGKKNTEEKIYLPPIPADEIRNPVVLRAL
SQARKVINGVVRRYGSPARIHIETAREVGKSFKDRKEIEKRQEENRKDREKAAAKFREYFP
NFVGEPKSKDILKLRLYEQQHGKCLYSGKEINLGRLNEKGYVEIDHALPFSRTWDDSFNNK
VLVLGSENQNKGNQTPYEYFNGKDNSREWQEFKARVETSRFPRSKKQRILLQKFDEDGFK
ERNLNDTRYVNRFLCQFVADRMRLTGKGKKRVFASNGQITNLLRGFWGLRKVRAENDRH
HALDAVVVACSTVAMQQKITRFVRYKEMNAFDGKTIDKETGEVLHQKTHFPQPWEFFAQ
EVMIRVFGKPDGKPEFEEADTLEKLRTLLAEKLSSRPEAVHEYVTPLFVSRAPNRKMSGQG
HMETVKSAKRLDEGVSVLRVPLTQLKLKDLEKMVNREREPKLYEALKARLEAHKDDPAK
AFAEPFYKYDKAGNRTQQVKAVRVEQVQKTGVWVRNHNGIADNATMVRVDVFEKGDKY
YLVPIYSWQVAKGILPDRAVVQGKDEEDWQLIDDSFNFKFSLHPNDLVEVITK░ARMFGYF
ASCH░GTGNINIRIHDLDHKIGKNGILEGIGVKTALSFQKYQIDELGKEIRPCRLKKRPPVR
░░░░░░░░░░░AAPAAKKKKLD*

Figure 87

SEQ ID NO: 118

NmCas9-Zif268 amino acid sequence:

Magenta: cMyc NLS

Yellow: Zif268

Grey: SV40 NLS

Brown letters: NmeCas9

Red: HA tag

Light green: Synthetic NLS

MVPKKKRKVAAFKPNSINYILGLDIGIASVGWAMVEIDEEENPIRLIDLGVRVFERAEVPKTG
DSLAMARRLARSVRRLTRRRAHRLLRTRRLLKREGVLQAANFDENGLIKSLPNTPWQLRA
AALDRKLTPLEWSAVLLHLIKHRGYLSQRKNEGETADKELGALLKGVAGNAHALQTGDF
RTPAELALNKFEKESGHIRNQRSDYSHTFSRKDLQAELILLFEKQKEFGNPHVSGGLKEGIE
TLLMTQRPALSGDAVQKMLGHCTFEPAEPKAAKNTYTAERFIWLTKLNNLRILEQGSERP
LTDTERATLMDEPYRKSKLTYAQARKLLGLEDTAFFKGLRYGKDNAEASTLMEMKAYHA
ISRALEKEGLKDKKSPLNLSPELQDEIGTAFSLFKTDEDITGRLKDRIQPEILEALLKHISFDK
FVQISLKALRRIVPLMEQGKRYDEACAEIYGDHYGKKNTEEKIYLPPIPADEIRNPVVLRAL
SQARKVINGVVRRYGSPARIHIETAREVGKSFKDRKEIEKRQEENRKDREKAAAKFREYFP
NFVGEPKSKDILKLRLYEQQHGKCLYSGKEINLGRLNEKGYVEIDHALPFSRTWDDSFNNK
VLVLGSENQNKGNQTPYEYFNGKDNSREWQEFKARVETSRFPRSKKQRILLQKFDEDGFK
ERNLNDTRYVNRFLCQFVADRMRLTGKGKKRVFASNGQITNLLRGFWGLRKVRAENDRH
HALDAVVVACSTVAMQQKITRFVRYKEMNAFDGKTIDKETGEVLHQKTHFPQPWEFFAQ
EVMIRVFGKPDGKPEFEEADTLEKLRTLLAEKLSSRPEAVHEYVTPLFVSRAPNRKMSGQG
HMETVKSAKRLDEGVSVLRVPLTQLKLKDLEKMVNREREPKLYEALKARLEAHKDDPAK
AFAEPFYKYDKAGNRTQQVKAVRVEQVQKTGVWVRNHNGIADNATMVRVDVFEKGDKY
YLVPIYSWQVAKGILPDRAVVQGKDEEDWQLIDDSFNFKFSLHPNDLVEVITKKARMFGYF
ASCHKGTGNINIRIHDLDHKIGKNGILEGIGVKTALSFQKYQIDELGKEIRPCRLKKRPPVR
AGTGGPKKKRKVGSFESGRPYACPVESCDRRFSRSDELTRHIRIHTGQKPFQCRICMRNFSRSDHLTTHIRTHTGEKP
FACDICGRKFARSDERKRHTKIHLRQKD\*

Figure 88

SEQ ID NO: 119

Single Mutant-Zif268-NmCas9 amino acid sequence:

Magenta: cMyc NLS

Yellow: Zif268

Dark green: GS linker

Grey: SV40 NLS

Brown letters: NmeCas9

Red: HA tag

Light green: Synthetic NLS

MGR████████████QLRPYACPVESCDRRFSRSDELTRHIRIHTGQKPFQCRICMRNFSRSDHL T
THIRTHTGEKPFACDICGRKFARSDERKRHTKIHLRQKDP████████RT████████IRK
LV██████AAFKPNSINYILGLDIGIASVGWAMVEIDEEENPIRLIDLGVRVFERAEVPKTG
DSLAMARRLARSVRRLTRRRAHRLLRTRRLLKREGVLQAANFDENGLIKSLPNTPWQLRA
AALDRKLTPLEWSAVLLHLIKHRGYLSQRKNEGETADKELGALLKGVAGNAHALQTGDF
RTPAELALNKFEKESGHIRNQRSDYSHTFSRKDLQAELILLFEKQKEFGNPHVSGGLKEGIE
TLLMTQRPALSGDAVQKMLGHCTFEPAEPKAAKNTYTAERFIWLTKLNNLRILEQGSERP
LTDTERATLMDEPYRKSKLTYAQARKLLGLEDTAFFKGLRYGKDNAEASTLMEMKAYHA
ISRALEKEGLKDKKSPLNLSPELQDEIGTAFSLFKTDEDITGRLKDRIQPEILEALLKHISFDK
FVQISLKALRRIVPLMEQGKRYDEACAEIYGDHYGKKNTEEKIYLPPIPADEIRNPVVLRAL
SQARKVINGVVRRYGSPARIHIETAREVGKSFKDRKEIEKRQEENRKDREKAAAKFREYFP
NFVGEPKSKDILKLRLYEQQHGKCLYSGKEINLGRLNEKGYVEIDHALPFSRTWDDSFNNK
VLVLGSENQNKGNQTPYEYFNGKDNSREWQEFKARVETSRFPRSKKQRILLQKFDEDGFK
ERNLNDTRYVNRFLCQFVADRMRLTGKGKKRVFASNGQITNLLRGFWGLRKVRAENDRH
HALDAVVVACSTVAMQQKITRFVRYKEMNAFDGKTIDKETGEVLHQKTHFPQPWEFFAQ
EVMIRVFGKPDGKPEFEEADTLEKLRTLLAEKLSSRPEAVHEYVTPLFVSRAPNRKMSGQG
HMETVKSAKRLDEGVSVLRVPLTQLKLKDLEKMVNREREPKLYEALKARLEAHKDDPAK
AFAEPFYKYDKAGNRTQQVKAVRVEQVQKTGVWVRNHNGIADNATMVRVDVFEKGDKY
YLVPIYSWQVAKGILPDRAVVQGKDEEDWQLIDDSFNFKFSLHPNDLVEVITK█ARMFGYF
ASCH█GTGNINIRIHDLDHKIGKNGILEGIGVKTALSFQKYQIDELGKEIRPCRLKKRPPVR
████████AAPA█KKKKL█*

Figure 89

SEQ ID NO: 120

Single Mutant-NmCas9- Zif268 amino acid sequence:

Magenta: cMyc NLS

Yellow: Zif268

Grey: SV40 NLS

Brown letters: NmeCas9

Red: HA tag

Light green: Synthetic NLS

MVPKKKRKVAAFKPNSINYILGLDIGIASVGWAMVEIDEEENPIRLIDLGVRVFERAEVPKTG
DSLAMARRLARSVRRLTRRRAHRLLRTRRLLKREGVLQAANFDENGLIKSLPNTPWQLRA
AALDRKLTPLEWSAVLLHLIKHRGYLSQRKNEGETADKELGALLKGVAGNAHALQTGDF
RTPAELALNKFEKESGHIRNQRSDYSHTFSRKDLQAELILLFEKQKEFGNPHVSGGLKEGIE
TLLMTQRPALSGDAVQKMLGHCTFEPAEPKAAKNTYTAERFIWLTKLNNRILEQGSERP
LTDTERATLMDEPYRKSKLTYAQARKLLGLEDTAFFKGLRYGKDNAEASTLMEMKAYHA
ISRALEKEGLKDKKSPLNLSPELQDEIGTAFSLFKTDEDITGRLKDRIQPEILEALLKHISFDK
FVQISLKALRRIVPLMEQGKRYDEACAEIYGDHYGKKNTEEKIYLPPIPADEIRNPVVLRAL
SQARKVINGVVRRYGSPARIHIETAREVGKSFKDRKEIEKRQEENRKDREKAAAKFREYFP
NFVGEPKSKDILKLRLYEQQHGKCLYSGKEINLGRLNEKGYVEIDHALPFSRTWDDSFNNK
VLVLGSENQNKGNQTPYEYFNGKDNSREWQEFKARVETSRFPRSKKQRILLQKFDEDGFK
ERNLNDTRYVNRFLCQFVADRMRLTGKGKKRVFASNGQITNLLRGFWGLRKVRAENDRH
HALDAVVVACSTVAMQQKITRFVRYKEMNAFDGKTIDKETGEVLHQKTHFPQPWEFFAQ
EVMIRVFGKPDGKPEFEEADTLEKLRTLLAEKLSSRPEAVHEYVTPLFVSRAPNRKMSGQG
HMETVKSAKRLDEGVSVLRVPLTQLKLKDLEKMVNREREPKLYEALKARLEAHKDDPAK
AFAEPFYKYDKAGNRTQQVKAVRVEQVQKTGVWVRNHNGIADNATMVRVDVFEKGDKY
YLVPIYSWQVAKGILPDRAVVQGKDEEDWQLIDDSFNFKFSLHPNDLVEVITKARMFGYF
ASCHGTGNINIRIHDLDHKIGKNGILEGIGVKTALSFQKYQIDELGKEIRPCRLKKRPPVR
AGTGGPKKKRKV GS
FESGRPYACPVESCDRRFSRSDELTRHIRIHTGQKPFQCRICMRNFSRSDHLTTHIRTHTGEKP
FACDICGRKFARSDERKRHTKIHLRQKD*

Figure 90

SEQ ID NO: 121

Double Mutant-Zif268-NmCas9 amino acid sequence:

Magenta: cMyc NLS

Yellow: Zif268

Dark green: GS linker

Grey: SV40 NLS

Brown letters: NmeCas9

Red: HA tag

Light green: Synthetic NLS

MGR███████████QLRPYACPVESCDRRFSRSDELTRHIRIHTGQKPFQCRICMRNFSRSDHLT
THIRTHTGEKPFACDICGRKFARSDERKRHTKIHLRQKDP██████RT██████IRK
LV██████AAFKPNSINYILGLDIGIASVGWAMVEIDEEENPIRLIDLGVRVFERAEVPKTG
DSLAMARRLARSVRRLTRRRAHRLLRTRRLLKREGVLQAANFDENGLIKSLPNTPWQLRA
AALDRKLTPLEWSAVLLHLIKHRGYLSQRKNEGETADKELGALLKGVAGNAHALQTGDF
RTPAELALNKFEKESGHIRNQRSDYSHTFSRKDLQAELILLFEKQKEFGNPHVSGGLKEGIE
TLLMTQRPALSGDAVQKMLGHCTFEPAEPKAAKNTYTAERFIWLTKLNNLRILEQGSERP
LTDTERATLMDEPYRKSKLTYAQARKLLGLEDTAFFKGLRYGKDNAEASTLMEMKAYHA
ISRALEKEGLKDKKSPLNLSPELQDEIGTAFSLFKTDEDITGRLKDRIQPEILEALLKHISFDK
FVQISLKALRRIVPLMEQGKRYDEACAEIYGDHYGKKNTEEKIYLPPIPADEIRNPVVLRAL
SQARKVINGVVRRYGSPARIHIETAREVGKSFKDRKEIEKRQEENRKDREKAAAKFREYFP
NFVGEPKSKDILKLRLYEQQHGKCLYSGKEINLGRLNEKGYVEIDHALPFSRTWDDSFNNK
VLVLGSENQNKGNQTPYEYFNGKDNSREWQEFKARVETSRFPRSKKQRILLQKFDEDGFK
ERNLNDTRYVNRFLCQFVADRMRLTGKGKKRVFASNGQITNLLRGFWGLRKVRAENDRH
HALDAVVVACSTVAMQQKITRFVRYKEMNAFDGKTIDKETGEVLHQKTHFPQPWEFFAQ
EVMIRVFGKPDGKPEFEEADTLEKLRTLLAEKLSSRPEAVHEYVTPLFVSRAPNRKMSGQG
HMETVKSAKRLDEGVSVLRVPLTQLKLKDLEKMVNREREPKLYEALKARLEAHKDDPAK
AFAEPFYKYDKAGNRTQQVKAVRVEQVQKTGVWVRNHNGIADNATMVRVDVFEKGDKY
YLVPIYSWQVAKGILPDRAVVQGKDEEDWQLIDDSFNFKFSLHPNDLVEVITK█ARMFGYF
ASCH█GTGNINIRIHDLDHKIGKNGILEGIGVKTALSFQKYQIDELGKEIRPCRLKKRPPVR
████████AAPAAKKKKLD*

Figure 91

SEQ ID NO: 122

Double Mutant-NmCas9- Zif268 amino acid sequence:

Magenta: cMyc NLS

Yellow: Zif268

Grey: SV40 NLS

Brown letters: NmeCas9

Red: HA tag

Light green: Synthetic NLS

MVPKKKRKVAAFKPNSINYILGLDIGIASVGWAMVEIDEEENPIRLIDLGVRVFERAEVPKTG
DSLAMARRLARSVRRLTRRRAHRLLRTRRLLKREGVLQAANFDENGLIKSLPNTPWQLRA
AALDRKLTPLEWSAVLLHLIKHRGYLSQRKNEGETADKELGALLKGVAGNAHALQTGDF
RTPAELALNKFEKESGHIRNQRSDYSHTFSRKDLQAELILLFEKQKEFGNPHVSGGLKEGIE
TLLMTQRPALSGDAVQKMLGHCTFEPAEPKAAKNTYTAERFIWLTKLNNRILEQGSERP
LTDTERATLMDEPYRKSKLTYAQARKLLGLEDTAFFKGLRYGKDNAEASTLMEMKAYHA
ISRALEKEGLKDKKSPLNLSPELQDEIGTAFSLFKTDEDITGRLKDRIQPEILEALLKHISFDK
FVQISLKALRRIVPLMEQGKRYDEACAEIYGDHYGKKNTEEKIYLPPIPADEIRNPVVLRAL
SQARKVINGVVRRYGSPARIHIETAREVGKSFKDRKEIEKRQEENRKDREKAAAKFREYFP
NFVGEPKSKDILKLRLYEQQHGKCLYSGKEINLGRLNEKGYVEIDHALPFSRTWDDSFNNK
VLVLGSENQNKGNQTPYEYFNGKDNSREWQEFKARVETSRFPRSKKQRILLQKFDEDGFK
ERNLNDTRYVNRFLCQFVADRMRLTGKGKKRVFASNGQITNLLRGFWGLRKVRAENDRH
HALDAVVVACSTVAMQQKITRFVRYKEMNAFDGKTIDKETGEVLHQKTHFPQPWEFFAQ
EVMIRVFGKPDGKPEFEEADTLEKLRTLLAEKLSSRPEAVHEYVTPLFVSRAPNRKMSGQG
HMETVKSAKRLDEGVSVLRVPLTQLKLKDLEKMVNREREPKLYEALKARLEAHKDDPAK
AFAEPFYKYDKAGNRTQQVKAVRVEQVQKTGVWVRNHNGIADNATMVRVDVFEKGDKY
YLVPIYSWQVAKGILPDRAVVQGKDEEDWQLIDDSFNFKFSLHPNDLVEVITKHARMFGYF
ASCHHGTGNINIRIHDLDHKIGKNGILEGIGVKTALSFQKYQIDELGKEIRPCRLKKRPPVR
AGTGGPKKKRKV GS
FESGRPYACPVESCDRRFSRSDELTRHIRIHTGQKPFQCRICMRNFSRSDHLTTHIRTHTGEKP
FACDICGRKFARSDERKRHTKIHLRQKD*

SEQ ID NO: 123

Direction-1 (D1) sp==> PAM XXX PAM <==nm
TCCCCGGCATCCTAGCGCGCTGGgctagcAATCGCCTCCGCGTCCCTTCCAACAGTACC

SEQ ID NO: 124

Direction-2 (D2) sp==> PAM XXX nm==> PAM
TCCCCGGCATCCTAGCGCGCTGGgctagcGGTACTGTTGGAAGGGACGCGGAGGCGATT

SEQ ID NO: 125

Direction-3 (D3) nm==> PAM XXX sp==>PAM
GGTACTGTTGGAAGGGACGCGGAGGCGATTgctagcTCCCCGGCATCCTAGCGCGCTGG

SEQ ID NO: 126

Direction-4 (D4) PAM <==nm XXX sp==> PAM
AATCGCCTCCGCGTCCCTTCCAACAGTACCgctagcTCCCCGGCATCCTAGCGCGCTGG

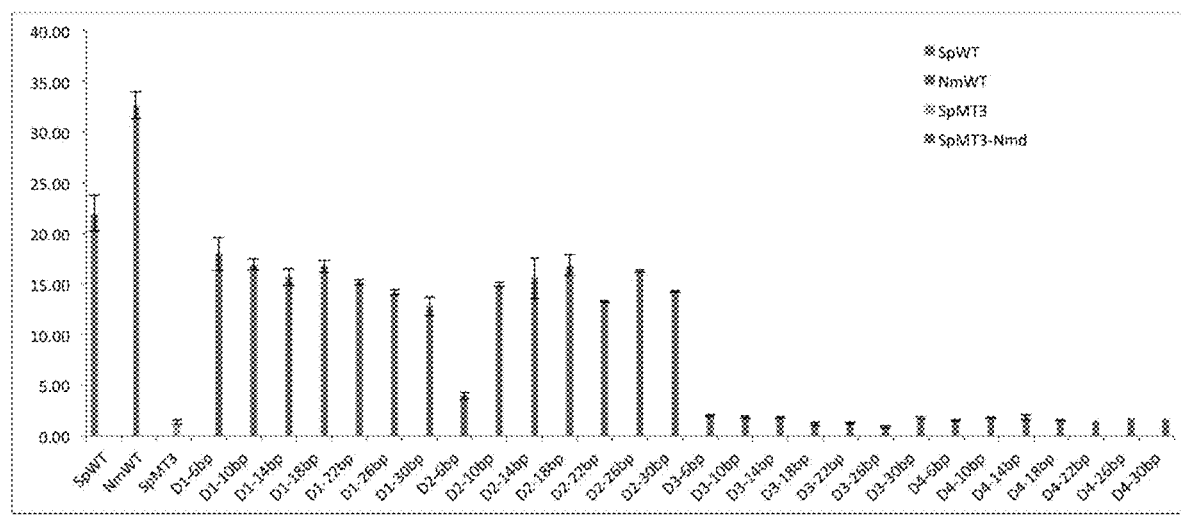

Figure 93

SEQ ID NO: 127

Direction-1 (D1) sp==> PAM XXX PAM <==nm
TCCCCGGCATCCTAGCGCGCTGGgctagcAATCGCCTCCGCGTCCCTTCCAACAGTACC

SEQ ID NO: 128

Direction-2 (D2) sp==> PAM XXX nm==> PAM
TCCCCGGCATCCTAGCGCGCTGGgctagcGGTACTGTTGGAAGGGACGCGGAGGCGATT

SEQ ID NO: 129

Direction-3 (D3) nm==> PAM XXX sp==>PAM
GGTACTGTTGGAAGGGACGCGGAGGCGATTgctagcTCCCCGGCATCCTAGCGCGCTGG

SEQ ID NO: 130

Direction-4 (D4) PAM <==nm XXX sp==> PAM
AATCGCCTCCGCGTCCCTTCCAACAGTACCgctagcTCCCCGGCATCCTAGCGCGCTGG

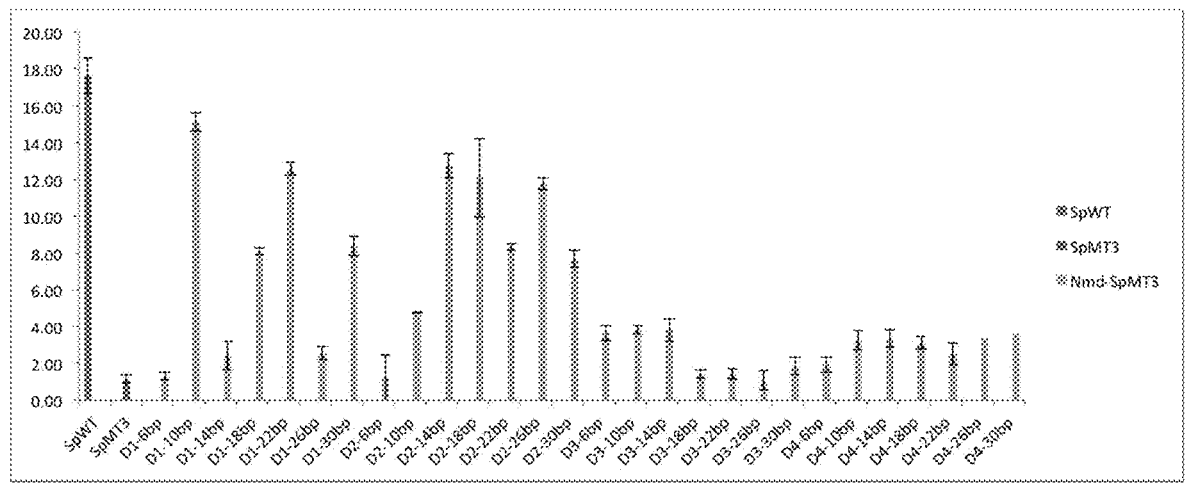

Figure 94

SEQ ID NO: 131

TS3

GGTGAGTGAGTGTGTGCGTG TGGGGTTGAGGGCGTTGGAGC GGGGAGAAGGCCAGGGGTCACT CCAGGATT

SEQ ID NO: 132, 133

>TS2      GACCCCCTCCACCCCGCCTCCGG
>OTG2-1   CTGCCCCCCACCCCGCCACTGG

SEQ ID NO: 134

2xNLS-Cas9$^{MT3}$-NLS-FKBP

MGRAAPAAKKKKLDQLGASGSPGSGGSGSSGRTAAPAAKKKKLDSEFGSGSDKKYSIGLD
IGTNSVGWAVITDEYKVPSKKFKVLGNTDRHSIKKNLIGALLFDSGETAEATRLKRTARR
RYTRRKNRICYLQEIFSNEMAKVDDSFFHRLEESFLVEEDKKHERHPIFGNIVDEVAYHE
KYPTIYHLRKKLVDSTDKADLRLIYLALAHMIKFRGHFLIEGDLNPDNSDVDKLFIQLVQ
TYNQLFEENPINASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAILLSDILRVNT
EITKAPLSASMIKRYDEHHQDLTLLKALVRQQLPEKYKEIFFDQSKNGYAGYIDGGASQE
EFYKFIKPILEKMDGTEELLVKLNREDLLRKQRTFDNGSIPHQIHLGELHAILRRQEDFY
PFLKDNREKIEKILTFRIPYYVGPLARGNSRFAWMTRKSEETITPWNFEEVVDKGASAQS
FIERMTNFDKNLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKIIKDKDFLDNE
ENEDILEDIVLTLTLFEDREMIEERLKTYAHLFDDKVMKQLKRRRYTGWGRLSRKLINGI
RDKQSGKTILDFLKSDGFANRNFMQLIHDDSLTFKEDIQKAQVSGQGDSLHEHIANLAGS
PAIKKGILQTVKVVDELVKVMGRHKPENIVIEMARENQTTQKGQKNSRERMKRIEEGIKE
LGSQILKEHPVENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNLTKAERGGLSELDK
AGFIKRQLVETRQITKHVAQILDSRMNTKYDENDKLIREVKVITLKSKLVSDFRKDF
QFYKVREINNYHHAHDAYLNAVVGTALIKKYPKLESEFVYGDYKVYDVRKMIAKSEQEIG
KATAKYFFYSNIMNFFKTEITLANGEIRKRPLIETNGETGEIVWDKGRDFATVRKVLSMP
QVNIVKKTEVQTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPKYSLFELENGR
KRMLASAGELQKGNELALPSKYVNFLYLASHYEKLKGSPEDNEQKQLFVEQHKHYLDEII
EQISEFSKRVILADANLDKVLSAYNKHRDKPIREQAENIIHLFTLTNLGAPAAFKYFDTT
IDRKKYTSTKEVLDATLIHQSITGLYETRIDLSQLGGDGTGGPKKKRKVIGSSGMGVQVE
TISPGDGRTFPKRGQTCVVHYTGMLEDGKKFDSSRDRNKPFKFMLGKQEVIRGWEEGVAQMSV
GQRAKLTISPDYAYGATGHPGIIPPHATLVFDVELLKLE*

Figure 103

SEQ ID NO: 135

2xNLS-3xFlag-2xNES-TS2$^{ZF}$-FRB*

MGRGSLQAAPAAKKKKLDQLASGGGGSGAAPKKKRKVSELGGGGSDYKDHDGDYKDHDIDY
KDDDDKLEGGGGSGLDLASLILGNPGSLDLASLILPRGGGGSGAGGGVPSGKPYKCPEC
GKSFSEKSHLTRHQRTHTGEKPYACPVESCDRRFSRSDHLTQHIRIHTGQKPFQCRICMR
NFSDKGHLTRHIRTHTGEKPFACDICGRKFARSDDLTRHTKIHLRQKDPGGSGSGGGGSG
GGGSRTILWHEMWHEGLEEASRLYFGERNVKGMFEVLEPLHAMMERGPQTLKETSFNQAYGR
DLMEAQEWCRKYMKSGNVPDLLQAFDLYYHVFRRISKEF*

Figure 104

SEQ ID NO: 136

NLS-Split-NCas9-NLS-FRB

MGRAAPAAKKKKLDQLGASGSPGSDKKYSIGLDIGTNSVGWAVITDEYKVPSKKFKVLGN
TDRHSIKKNLIGALLFDSGETAEATRLKRTARRRYTRRKNRICYLQEIFSNEMAKVDDSF
FHRLEESFLVEEDKKHERHPIFGNIVDEVAYHEKYPTIYHLRKKLVDSTDKADLRLIYLA
LAHMIKFRGHFLIEGDLNPDNSDVDKLFIQLVQTYNQLFEENPINASGVDAKAILSARLS
KSRRLENLIAQLPGEKKNGLFGNLIALSLGLTPNFKSNFDLAEDAKLQLSKDTYDDDLDN
LLAQIGDQYADLFLAAKNLSDAILLSDILRVNTEITKAPLSASMIKRYDEHHQDLTLLKA
LVRQQLPEKYKEIFFDQSKNGYAGYIDGGASQEEFYKFIKPILEKMDGTEELLVKLNRED
LLRKQRTFDNGSIPHQIHLGELHAILRRQEDFYPFLKDNREKIEKILTFRIPYYVGPLAR
GNSRFAWMTRKSEETITPWNFEEVVDKGASAQSFIERMTNFDKNLPNEKVLPKHSLLYEYFTVY
NELTKVKYVTEGMRKPAFLSGEQKKAIVDLLFKTNRKVTVKQLKEDYFKKIEGTGGPKKKRKVI
GSSGILWHEMWHEGLEEASRLYFGERNVKGMFEVLEPLHAMMERGPQTLKETSFNQAYGRDL
MEAQEWCRKYMKSGNVKDLTQAWDLYYHVFRRISKLE*

Figure 105

SEQ ID NO: 137

FKBP-Split-CCas9<sup>MT3</sup>-NLS-3xHA-NLS-TS2<sup>ZF</sup>-3XFLAG-2XNLS

MGVQVETISPGDGRTFPKRGQTCVVHYTGMLEDGKKFDSSRDRNKPFKFMLGKQEVIRGWEEG
VAQMSVGQRAKLTISPDYAYGATGHPGIIPPHATLVFDVELLKLEGAGGCFDSVEIS
GVEDRFNASLGTYHDLLKIIKDKDFLDNEENEDILEDIVLTLTLFEDREMIEERLKTYAH
LFDDKVMKQLKRRRYTGWGRLSRKLINGIRDKQSGKTILDFLKSDGFANRNFMQLIHDDS
LTFKEDIQKAQVSGQGDSLHEHIANLAGSPAIKKGILQTVKVVDELVKVMGRHKPENIVI
EMARENQTTQKGQKNSRERMKRIEEGIKELGSQILKEHPVENTQLQNEKLYLYYLQNGRD
MYVDQELDINRLSDYDVDHIVPQSFLKDDSIDNKVLTRSDKNRGKSDNVPSEEVVKKMKN
YWRQLLNAKLITQRKFDNLTKAERGGLSELDKAGFIKRQLVETRQITKHVAQILDSRMNT
KYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRP
LIETNGETGEIVWDKGRDFATVRKVLSMPQVNIVKKTEVQTGGFSKESILPKRNSDKLIA
RKKDWDPKKYGGFDSPTVAYSVLVVAKVEKGKSKKLKSVKELLGITIMERSSFEKNPIDF
LEAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKP
IREQAENIIHLFTLTNLGAPAAFKYFDTTIDRKRYTSTKEVLDATLIHQSITGLYETRID
LSQLGGDGTGGPKKKRKVYPYDVPDYAGYPYDVPDYAGSYPYDVPDYAGSAAPAAKKKKL
DFESGKPYKCPECGKSFSRSDDLTRHQRTHTGEKPYACPVESCDRRFSQKGHLTRHIRIH
TGQKPFQCRICMRNFSIRSSLTRHIRTHTGEKPFACDICGRKFALSHHLTRHTKIHLRQK
DPGGSGSLEGDYKDHDGDYKDHDIDYKDDDDKQGSELGSGRAAPAAKKKKLDQLGASGSSGG
SSGAAPKKKRKVSEF*

Figure 106

SEQ ID NOS: 138, 139, 140

T5 target site: GGGAGCTCTCTGGCTAACTAGGGAACCCACTGCTTAAGCCTC

T6 target site: CCTCCCTGGAAAGTCCCCAGCGGAAAGTCCCTTGTAGAAAGCTCGA

Z1 target site: CCGCTGGGGACTTTCCAGGGAGGTGTGGCCTGGGCGGGACTGGGGAG

Cas9$^{MT3}$-NLS-3xHA-NLS-ZFP$^{T5}$
MDKKYSIGLDIGTNSVGWAVITDEYKVPSKKFKVLGNTDRHSIKKNLIGALLFDSGETAE
ATRLKRTARRRYTRRKNRICYLQEIFSNEMAKVDDSFFHRLEESFLVEEDKKHERHPIFG
NIVDEVAYHEKYPTIYHLRKKLVDSTDKADLRLIYLALAHMIKFRGHFLIEGDLNPDNSD
VDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDQSKNGYA
GYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPAFL
SGEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRRYTGWG
RLSRKLINGIRDKQSGKTILDFLKSDGFANRNFMQLIHDDSLTFKEDIQKAQVSGQGDSL
HEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDH
IVPQSFLKDDSIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDPKKYGGFDSPTVA
YSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGA
PAAFKYFDTTIDRKKYTSTKEVLDATLIHQSITGLYETRIDLSQLGGDGTGGPKKKRKVY
PYDVPDYAGYPYDVPDYAGSYPYDVPDYAGSAAPAAKKKKLDFESGRPFACDICGKKFAR
SDHLTTHTKIHTGQKPFQCRICMRNFSRSDNLKQHIRTHTGEKPFACDICGKKFARNSNL
TQHTKIHTHPRAPIPKPFQCRICMRNFSQSSDLTRHIRTHTGEKPFACDICGRKFARSDN
LTRHTKIHLRDKQPG*

Figure 109

SEQ ID NO: 142

Cas9$^{MT3}$-NLS-3xHA-NLS-ZFP$^{T6}$

MDKKYSIGLDIGTNSVGWAVITDEYKVPSKKFKVLGNTDRHSIKKNLIGALLFDSGETAE
ATRLKRTARRRYTRRKNRICYLQEIFSNEMAKVDDSFFHRLEESFLVEEDKKHERHPIFG
NIVDEVAYHEKYPTIYHLRKKLVDSTDKADLRLIYLALAHMIKFRGHFLIEGDLNPDNSD
VDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDQSKNGYA
GYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPAFL
SGEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRRYTGWG
RLSRKLINGIRDKQSGKTILDFLKSDGFANRNFMQLIHDDSLTFKEDIQKAQVSGQGDSL
HEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDH
IVPQSFLKDDSIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDPKKYGGFDSPTVA
YSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGA
PAAFKYFDTTIDRKKYTSTKEVLDATLIHQSITGLYETRIDLSQLGGDGTGGPKKKRKVY
PYDVPDYAGYPYDVPDYAGSYPYDVPDYAGSAAPAAKKKKLDFESGRPFQCRICMRNFSQ
SGHLKSHIRTHTGEKPFACDICGKKFAQSSDLTRHTKIHTHPRAPIPKPFQCRICMRNFS
QSGNLTRHIRTHTGEKPFACDICGRKFAQSGALTRHTKIHLRDKQPG*

Figure 110

SEQ ID NO: 143

Cas9$^{MT3}$-NLS-3xHA-NLS-ZFP$^{Z1}$

MDKKYSIGLDIGTNSVGWAVITDEYKVPSKKFKVLGNTDRHSIKKNLIGALLFDSGETAE
ATRLKRTARRRYTRRKNRICYLQEIFSNEMAKVDDSFFHRLEESFLVEEDKKHERHPIFG
NIVDEVAYHEKYPTIYHLRKKLVDSTDKADLRLIYLALAHMIKFRGHFLIEGDLNPDNSD
VDKLFIQLVQTYNQLFEENPINASGVDAKAILSARLSKSRRLENLIAQLPGEKKNGLFGN
LIALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDQSKNGYA
GYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPAFL
SGEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRRYTGWG
RLSRKLINGIRDKQSGKTILDFLKSDGFANRNFMQLIHDDSLTFKEDIQKAQVSGQGDSL
HEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDH
IVPQSFLKDDSIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLIREVKVITLKS
KLVSDFRKDFQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDPKKYGGFDSPTVA
YSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGA
PAAFKYFDTTIDRKKYTSTKEVLDATLIHQSITGLYETRIDLSQLGGD**GTGGPKKKRKVY
PYDVPDYAGYPYDVPDYAGSYPYDVPDYAGSAAPAAKKKKLDFESGRPFQCRICMRNFSR
SDNLTRHIRTHTGEKPFACDICGKKFARSDHLTRHTKIHTHPRAPIPKPFQCRICMRNFS
LKGNLTRHIRTHTGEKPFACDICGRKFARSDHLSDHTKIHLRDKQPG***

SEQ ID NO: 144

SpCas9 TS2 sgRNA:

GACCCCCTCCACCCCGCCTCGTTTTAGAGCTAGAAATAGCAAGTTAAAATAAGGCTA
GTCCGTTATCAACTTGAAAAAGTGGCACCGAGTCGGTGCTTTTTT

SEQ ID NO 145

SpCas9 TS3 sgRNA:
GGTGAGTGAGTGTGTGCGTGGTTTTAGAGCTAGAAATAGCAAGTTAAAATAAGGCT
AGTCCGTTATCAACTTGAAAAAGTGGCACCGAGTCGGTGCTTTTTT

SEQ ID NO: 146

SpCas9 TS4 sgRNA:
GAGTCCGAGCAGAAGAAGAAGTTTTAGAGCTAGAAATAGCAAGTTAAAATAAGGCT
AGTCCGTTATCAACTTGAAAAAGTGGCACCGAGTCGGTGCTTTTTT

SEQ ID NO: 147

SpCas9 Pmpca sgRNA:
TACTTCCGGGCACAGTCCACGTTTTAGAGCTAGAAATAGCAAGTTAAAATAAGGCTA
GTCCGTTATCAACTTGAAAAAGTGGCACCGAGTCGGTGCTTTTTT

SEQ ID NO: 148

NmCas9 TS3 sgRNA:
GGGGAGAAGGCCAGGGGTCACTGTTGTAGCTCCCTTTCTCATTTCGGAAACGAAATG
AGAACCGTTGCTACAATAAGGCCGTCTGAAAAGATGTGCCGCAACGCTCTGCCCCTT
AAAGCTTCTGCTTTAAGGGGCATCGTTTATTTTTTT

Figure 112

SEQ ID NO: 149

>Protein sequence of NmdCas9-SpCas9<sup>MT3</sup>

Legend: NLS *NmdCas9* NLS Flag tag NLS SpCas9 NLS

MPKKKRKV<u>AAFKPNFINYILGLAIGIASVGWAMVEIDEDENPICLIDLGVRVFERAEVPKTGDSLAMARRLARSVRR</u>
<u>LTRRRAHRLLRARRLLKREGVLQAADFDENGLIKSLPNTPWQLRAAALDRKLTPLEWSAVLLHLIKHRGYLSQRKNE</u>
<u>GETADKELGALLKGVADNAHALQTGDFRTPAELALNKFEKESGHIRNQRGDYSHTFSRKDLQAELILLFEKQKEFGN</u>
<u>PHVSGGLKEGIETLLMTQRPALSGDAVQKMLGHCTFEPAEPKAAKNTYTAERFIWLTKLNNLRILEQGSERPLTDTE</u>
<u>RATLMDEPYRKSKLTYAQARKLLGLEDTAFFKGLRYGKDNAEASTLMEMKAYHAISRALEKEGLKDKKSPLNLSPEL</u>
<u>QDEIGTAFSLFKTDEDITGRLKDRIQPEILEALLKHISFDKFVQISLKALRRIVPLMEQGKRYDEACAEIYGDHYGK</u>
<u>KNTEEKIYLPPIPADEIRNPVVLRALSQARKVINGVVRRYGSPARIHIETAREVGKSFKDRKEIEKRQEENRKDREK</u>
<u>AAAKFREYFPNFVGEPKSKDILKLRLYEQQHGKCLYSGKEINLGRLNEKGYVEIAAALPFSRTWDDSFNNKVLVLGS</u>
<u>EAQNKGNQTPYEYFNGKDNSREWQEFKARVETSRFPRSKKQRILLQKFDEDGFKERNLNDTRYVNRFLCQFVADRMR</u>
<u>LTGKGKKRVFASNGQITNLLRGFWGLRKVRAENDRHHALDAVVVACSTVAMQQKITRFVRYKEMNAFDGKTIDKETG</u>
<u>EVLHQKTHFPQPWEFFAQEVMIRVFGKPDGKPEFEEADTPEKLRTLLAEKLSSRPEAVHEYVTPLFVSRAPNRKMSG</u>
<u>QGHMETVKSAKRLDEGVSVLRVPLTQLKLKDLEKMVNREREPKLYEALKARLEAHKDDPAKAFAEPFYKYDKAGNRT</u>
<u>QQVKAVREQVQKTGVWVRNHNGIADNATMVRVDVFEKGDKYYLVPIYSWQVAKGILPDRAVVQGKDEEDWQLIDDS</u>
<u>FNFKFSLHPNDLVEVITKKARMFGYFASCHRGTGNINIRIHDLDHKIGKNGILEGIGVKTALSFQKYQIDELGKEIR</u>
<u>PCRLKKRPPVRS</u>PADPKKKRKVEAS████G████I████KTSGGGSGGGSRTAAPAAKKKKLDSEFGSGS
DKKYSIGLDIGTNSVGWAVITDEYKVPSKKFKVLGNTDRHSIKKNLIGALLFDSGETAEATRLKRTARRRYTRRKNR
ICYLQEIFSNEMAKVDDSFFHRLEESFLVEEDKKHERHPIFGNIVDEVAYHEKYPTIYHLRKKLVDSTDKADLRLIY
LALAHMIKFRGHFLIEGDLNPDNSDVDKLFIQLVQTYNQLFEENPINASGVDAKAILSARLSKSRRLENLIAQLPGE
KKNGLFGNLIALSLGLTPNFKSNFDLAEDAKLQLSKDTYDDDLDNLLAQIGDQYADLFLAAKNLSDAILLSDILRVN
TEITKAPLSASMIKRYDEHHQDLTLLKALVRQQLPEKYKEIFFDQSKNGYAGYIDGGASQEEFYKFIKPILEKMDGT
EELLVKLNREDLLRKQRTFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTVYNELTKVKYVTEGMRKPAFL
SGEQKKAIVDLLFKTNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKTILDFLKSDGFANRNFM
QLIHDDSLTFKEDIQKAQVSGQGDSLHEHIANLAGSPAIKKGILQTVKVVDELVKVMGRHKPENIVIEMARENQTTQ
KGQKNSRERMKRIEEGIKELGSQILKEHPVENTQLQNEKLYLYYLQNGRDMYVDQELDINRLSDYDVDHIVPQSFLK
DDSIDNKVLTRSDKNRGKSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHDAYLNAVVGTALIKKYP
KLESEFVYGDYKVYDVRKMIAKSEQEIGKATAKYFFYSNIMNFFKTEITLANGEIRKRPLIETNGETGEIVWDKGRD
FATVRKVLSMPQVNIVKKTEVQTGGFSKESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFELENGRKRMLASAGELQKGNELALPSKYV
NFLYLASHYEKLKGSPEDNEQKQLFVEQHKHYLDEIIEQISEFSKRVILADANLDKVLSAYNKHRDKPIREQAENII
HLFTLTNLGAPAAFKYFDTTIDRKKYTSTKEVLDATLIHQSITGLYETRIDLSQLGGDGTGGPKKKRKVIGSSGSGG
SGSLE*

Figure 113

SEQ ID NO: 150

>Protein sequence of SpCas9^MT3-NmdCas9

Legend: SpCas9 NLS HA tag NmdCas9 Flag tag

MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKKYTSTKEVLDATLIHQSITGLYETRIDLSQLGGDGTGGPKKKRKV
GS GSAAPAAKKKKLDFESGMPKKKRKV*AAFKPNPINYILGL*IGIASVGWAMVEID
EDENPICLIDLGVRVFERAEVPKTGDSLAMARRLARSVRRLTRRRAHRLLRARRLLKREGVLQAADFDENGLIKSLP
NTPWQLRAAALDRKLTPLEWSAVLLHLIKHRGYLSQRKNEGETADKELGALLKGVADNAHALQTGDFRTPAELALNK
FEKESGHIRNQRGDYSHTFSRKDLQAELILLFEKQKEFGNPHVSGGLKEGIETLLMTQRPALSGDAVQKMLGHCTFE
PAEPKAAKNTYTAERFIWLTKLNNLRILEQGSERPLTDTERATLMDEPYRKSKLTYAQARKLLGLEDTAFFKGLRYG
KDNAEASTLMEMKAYHAISRALEKEGLKDKKSPLNLSPELQDEIGTAFSLFKTDEDITGRLKDRIQPEILEALLKHI
SFDKFVQISLKALRRIVPLMEQGKRYDEACAEIYGDHYGKKNTEEKIYLPPIPADEIRNPVVLRALSQARKVINGVV
RRYGSPARIHIETAREVGKSFKDRKEIEKRQEENRKDREKAAAKFREYFPNFVGEPKSKDILKLRLYEQQHGKCLYS
GKEINLGRLNEKGYVEI ALPFSRTWDDSFNNKVLVLGSE QNKGNQTPYEYFNGKDNSREWQEFKARVETSRFPR
SKKQRILLQKFDEDGFKERNLNDTRYVNRFLCQFVADRMRLTGKGKKRVFASNGQITNLLRGFWGLRKVRAENDRHH
ALDAVVVACSTVAMQQKITRFVRYKEMNAFDGKTIDKETGEVLHQKTHFPQPWEFFAQEVMIRVFGKPDGKPEFEEA
DTPEKLRTLLAEKLSSRPEAVHEYVTPLFVSRAPNRKMSGQGHMETVKSAKRLDEGVSVLRVPLTQLKLKDLEKMVN
REREPKLYEALKARLEAHKDDPAKAFAEPFYKYDKAGNRTQQVKAVRVEQVQKTGVWVRNHNGIADNATMVRVDVFE
KGDKYYLVPIYSWQVAKGILPDRAVVQGKDEEDWQLIDDSFNFKFSLHPNDLVEVITKKARMFGYFASCHRGTGNIN
IRIHDLDHKIGKNGILEGIGVKTALSFQKYQIDELGKEIRPCRLKKRPPVRSRADPKKKRKVEAS G
I K*

Figure 114

SEQ ID NO: 151

>Protein sequence of SpCas9$^{MT3}$-NmCas9n$^{RuvC}$

MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKKYTSTKEVLDATLIHQSITGLYETRIDLSQLGGDTGGPKKKRKV
GPKKKRKVGSPKKKRKVGSAAPAAKKKKLDFESGMPKKKRKVAAFKPNPINYILGIDIGIASVGWAMVEID
EDENPICLIDLGVRVFERAEVPKTGDSLAMARRLARSVRRLTRRRAHRLLRARRLLKREGVLQAADFDENGLIKSLP
NTPWQLRAAALDRKLTPLEWSAVLLHLIKHRGYLSQRKNEGETADKELGALLKGVADNAHALQTGDFRTPAELALNK
FEKESGHIRNQRGDYSHTFSRKDLQAELILLFEKQKEFGNPHVSGGLKEGIETLLMTQRPALSGDAVQKMLGHCTFE
PAEPKAAKNTYTAERFIWLTKLNNLRILEQGSERPLTDTERATLMDEPYRKSKLTYAQARKLLGLEDTAFFKGLRYG
KDNAEASTLMEMKAYHAISRALEKEGLKDKKSPLNLSPELQDEIGTAFSLFKTDEDITGRLKDRIQPEILEALLKHI
SFDKFVQISLKALRRIVPLMEQGKRYDEACAEIYGDHYGKKNTEEKIYLPPIPADEIRNPVVLRALSQARKVINGVV
RRYGSPARIHIETAREVGKSFKDRKEIEKRQEENRKDREKAAAKFREYFPNFVGEPKSKDILKLRLYEQQHGKCLYS
GKEINLGRLNEKGYVEIDALPFSRTWDDSFNNKVLVLGSEQNKGNQTPYEYFNGKDNSREWQEFKARVETSRFPR
SKKQRILLQKFDEDGFKERNLNDTRYVNRFLCQFVADRMRLTGKGKKRVFASNGQITNLLRGFWGLRKVRAENDRHH
ALDAVVVACSTVAMQQKITRFVRYKEMNAFDGKTIDKETGEVLHQKTHFPQPWEFFAQEVMIRVFGKPDGKPEFEEA
DTPEKLRTLLAEKLSSRPEAVHEYVTPLFVSRAPNRKMSGQGHMETVKSAKRLDEGVSVLRVPLTQLKLKDLEKMVN
REREPKLYEALKARLEAHKDDPAKAFAEPFYKYDKAGNRTQQVKAVRVEQVQKTGVWVRNHNGIADNATMVRVDVFE
KGDKYYLVPIYSWQVAKGILPDRAVVQGKDEEDWQLIDDSFNFKFSLHPNDLVEVITKKARMFGYFASCHRGTGNIN
IRIHDLDHKIGKNGILEGIGVKTALSFQKYQIDELGKEIRPCRLKKRPPVVRSRADPKKKRKVEASG
IK*

Figure 115

SEQ ID NO: 152

>Protein sequence of SpCas9$^{MT3}$-NmCas9n$^{HNH}$

MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKKYTSTKEVLDATLIHQSITGLYETRIDLSQLGGDTGGPKKKRKV░░░░░░
░░G░░░░░░GS░░░░░░GSAAPAAKKKKLDFESGMPKKKRKV_AAFKPNPINYILGI_░_IGIASVGWAMVEID_
_EDENPICLIDLGVRVFERAEVPKTGDSLAMARRLARSVRRLTRRRAHRLLRARRLLKREGVLQAADFDENGLIKSLP_
_NTPWQLRAAALDRKLTPLEWSAVLLHLIKHRGYLSQRKNEGETADKELGALLKGVADNAHALQTGDFRTPAELALNK_
_FEKESGHIRNQRGDYSHTFSRKDLQAELILLFEKQKEFGNPHVSGGLKEGIETLLMTQRPALSGDAVQKMLGHCTFE_
_PAEPKAAKNTYTAERFIWLTKLNNLRILEQGSERPLTDTERATLMDEPYRKSKLTYAQARKLLGLEDTAFFKGLRYG_
_KDNAEASTLMEMKAYHAISRALEKEGLKDKKSPLNLSPELQDEIGTAFSLFKTDEDITGRLKDRIQPEILEALLKHI_
_SFDKFVQISLKALRRIVPLMEQGKRYDEACAEIYGDHYGKKNTEEKIYLPPIPADEIRNPVVLRALSQARKVINGVV_
_RRYGSPARIHIETAREVGKSFKDRKEIEKRQEENRKDREKAAAKFREYFPNFVGEPKSKDILKLRLYEQQHGKCLYS_
_GKEINLGRLNEKGYVEI_░_ALPFSRTWDDSFNNKVLVLGSE_░_QNKGNQTPYEYFNGKDNSREWQEFKARVETSRFPR_
_SKKQRILLQKFDEDGFKERNLNDTRYVNRFLCQFVADRMRLTGKGKKRVFASNGQITNLLRGFWGLRKVRAENDRHH_
_ALDAVVVACSTVAMQQKITRFVRYKEMNAFDKTIDKETGEVLHQKTHFPQPWEFFAQEVMIRVFGKPDGKPEFEEA_
_DTPEKLRTLLAEKLSSRPEAVHEYVTPLFVSRAPNRKMSGQGHMETVKSAKRLDEGVSVLRVPLTQLKLKDLEKMVN_
_REREPKLYEALKARLEAHKDDPAKAFAEPFYKYDKAGNRTQQVKAVRVEQVQKTGVWVRNHNGIADNATMVRVDVFE_
_KGDKYYLVPIYSWQVAKGILPDRAVVQGKDEEDWQLIDDSFNFKFSLHPNDLVEVITKKARMFGYFASCHRGTGNIN_
_IRIHDLDHKIGKNGILEGIGVKTALSFQKYQIDELGKEIRPCRLKKRPPVR_SRADPKKKRKVEAS░░░░░░G░░░░░░
░I░░░░░░K*

Figure 116

SEQ ID NO: 153

>Protein sequence of SpCas9<sup>MT3</sup>-NmCas9<sup>WT</sup>

MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNF
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKKYTSTKEVLDATLIHQSITGLYETRIDLSQLGGDTGGPKKKRKV░░░░░░░
░G░░░░░░GS░░░░░░GSAAPAAKKKKLDFESGMPKKKRKVAAFKPNPINYILGI░IGIASVGWAMVEID
EDENPICLIDLGVRVFERAEVPKTGDSLAMARRLARSVRRLTRRRAHRLLRARRLLKREGVLQAADFDENGLIKSLP
NTPWQLRAAALDRKLTPLEWSAVLLHLIKHRGYLSQRKNEGETADKELGALLKGVADNAHALQTGDFRTPAELALNK
FEKESGHIRNQRGDYSHTFSRKDLQAELILLFEKQKEFGNPHVSGGLKEGIETLLMTQRPALSGDAVQKMLGHCTFE
PAEPKAAKNTYTAERFIWLTKLNNLRILEQGSERPLTDTERATLMDEPYRKSKLTYAQARKLLGLEDTAFFKGLRYG
KDNAEASTLMEMKAYHAISRALEKEGLKDKKSPLNLSPELQDEIGTAFSLFKTDEDITGRLKDRIQPEILEALLKHI
SFDKFVQISLKALRRIVPLMEQGKRYDEACAEIYGDHYGKKNTEEKIYLPPIPADEIRNPVVLRALSQARKVINGVV
RRYGSPARIHIETAREVGKSFKDRKEIEKRQEENRKDREKAAAKFREYFPNFVGEPKSKDILKLRLYEQQHGKCLYS
GKEINLGRLNEKGYVEI░ALPFSRTWDDSFNNKVLVLGSE░QNKGNQTPYEYFNGKDNSREWQEFKARVETSRFPR
SKKQRILLQKFDEDGFKERNLNDTRYVNRFLCQFVADRMRLTGKGKKRVFASNGQITNLLRGFWGLRKVRAENDRHH
ALDAVVVACSTVAMQQKITRFVRYKEMNAFDGKTIDKETGEVLHQKTHFPQPWEFFAQEVMIRVFGKPDGKPEFEEA
DTPEKLRTLLAEKLSSRPEAVHEYVTPLFVSRAPNRKMSGQGHMETVKSAKRLDEGVSVLRVPLTQLKLKDLEKMVN
REREPKLYEALKARLEAHKDDPAKAFAEPFYKYDKAGNRTQQVKAVRVEQVQKTGVWVRNHNGIADNATMVRVDVFE
KGDKYYLVPIYSWQVAKGILPDRAVVQGKDEEDWQLIDDSFNFKFSLHPNDLVEVITKKARMFGYFASCHRGTGNIN
IRIHDLDHKIGKNGILEGIGVKTALSFQKYQIDELGKEIRPCRLKKRPPVRSRADPKKKRKVEAS░░░░░░G░░░░░░
░I░░░░░░K*

Figure 117

CAS9-CAS9 FUSION PROTEINS

GOVERNMENT SUPPORT

This invention was made with government support under Grant nos. AI117839 and HL093766 awarded by National Institutes of Health. The Government has certain rights in the invention.

FIELD OF THE INVENTION

The present invention may be related to the field of genetic engineering. In particular, specific genes or sequences within a genome can be deleted or modified in a directed manner with improved precision when a Cas9 nuclease may be coupled to an independent DNA targeting unit: for example, a programmable DNA-binding domain (pDBD) and/or to an alternate Cas9 isoform. An improvement in the precision of cleavage from this Cas9 nuclease-DNA targeting unit chimera may be realized by attenuating the DNA-binding affinity of the conventional Cas9 nuclease via specific mutations, such that an association of a Cas9 nuclease with its target site may be dependent on the specificity of the associated targeting unit (e.g., for example, either a programmable DNA-binding domain or to an alternate Cas9 isoform). These modifications have an added advantage of increasing the diversity of sequences that can be utilized as a target site, allowing breaks to be positioned more precisely near a specific target of interest. The association of Cas9 and the DNA targeting unit need not be covalent, but can be mediated through drug-dependent dimerization, which affords temporal control over the activity of this chimeric nuclease complex. This chimeric nuclease can be used in conjunction with other variants of Cas9 (e.g., for example, truncated guide RNAs, nickases or FokI fusions) that improve precision to further reduce the chance of cleaving unwanted sites within the treated genome.

BACKGROUND

Cas9 (clustered regularly interspaced short palindromic repeats; CRISPR-associated system) may be part of a bacterial immune response to foreign nucleic acid introduction. The development of Type II CRISPR/Cas9 systems as programmable nucleases for genome engineering has been beneficial in the biomedical sciences. For example, a Cas9 platform has enabled gene editing in a large variety of biological systems, where both gene knockouts and tailor-made alterations are possible within complex genomes. The CRISPR/Cas9 system has the potential for application to gene therapy approaches for disease treatment, whether for the creation of custom, genome-edited cell-based therapies or for direct correction or ablation of aberrant genomic loci within patients.

The safe application of Cas9 in gene therapy requires exceptionally high precision to ensure that undesired collateral damage to the treated genome may be minimized or, ideally, eliminated. Numerous studies have outlined features of Cas9 that can drive editing promiscuity, and a number of strategies (e.g. truncated single-guide RNAs (sgRNAs), nickases and FokI fusions) have been developed that improve the precision of this system. However all of these systems still suffer from a degree of imprecision (cleavage resulting in lesions at unintended target sites within the genome).

However, what may be needed in the art are further improvements in editing precision to facilitate reliable clinical applications that require simultaneous efficient and accurate editing of multigigabase genomes in billions to trillions of cells, depending on the scope of genetic repair that may be needed for therapeutic efficacy.

SUMMARY OF THE INVENTION

The present invention may be related to the field of genetic engineering. In particular, specific genes or sequences within a genome can be deleted or modified in a directed manner with improved precision when a Cas9 nuclease may be coupled to an independent DNA targeting unit: for example, a programmable DNA-binding domain and/or to an alternate Cas9 isoform. An improvement in the precision of cleavage from this Cas9 nuclease-DNA targeting unit chimera may be realized by attenuating the DNA-binding affinity of the conventional Cas9 nuclease via specific mutations, such that an association of a Cas9 nuclease with its target site may be dependent on the specificity of the associated targeting unit (e.g., for example, either a programmable DNA-binding domain or to an alternate Cas9 isoform). These modifications have an added advantage of increasing the diversity of sequences that can be utilized as a target site, allowing breaks to be positioned more precisely near a specific target of interest. In addition, the fusion of a DNA targeting unit to Cas9 can also increase its activity relative to wild-type Cas9. The association of Cas9 and the DNA targeting unit need not be covalent, but can be mediated through drug-dependent or light-dependent dimerization, which afford temporal control over the activity of this chimeric nuclease complex. This chimeric nuclease can be used in conjunction with other variants of Cas9 (e.g., for example, truncated guide RNAs, nickases for FokI fusions) that improve precision to further reduce the chance of cleaving unwanted sites within the treated genome.

In one embodiment, the present invention contemplates a fusion protein comprising a Cas9 nuclease, said nuclease comprising a mutated protospacer adjacent motif recognition domain and a peptide linker, wherein said peptide linker is attached to a DNA binding domain (DBD) protein. In one embodiment, said Cas9 nuclease is selected from the group consisting of SpCas9, SaCas9, NmCas9 and AnCas9. In one embodiment, said mutated protospacer adjacent motif recognition domain is selected from the group consisting of $Cas9^{MT1}$, $Cas9^{MT2}$, $Cas9^{MT3}$, $NmCas9^{SM}$ and $NmCas9^{DM}$. In one embodiment, said DBD protein is selected from the group consisting of $DBD^{268}$, $DBD^{TS1}$, $DBD^{TS2}$, $DBD^{TS3}$ and $DBD^{TS4}$. In one embodiment, said DBD protein is selected from the group consisting of a zinc finger protein and a transcription activator-like effector protein. In one embodiment, said fusion protein further comprises a guide RNA which is attached to a guide sequence element. In one embodiment, said mutated protospacer adjacent motif recognition domain comprises mutated DNA phosphodiester recognition amino acid residues. In one embodiment, said guide RNA is selected from the group consisting of an sgRNA sequence, a crRNA sequence and a tracrRNA sequence. In one embodiment, said guide sequence element is truncated. In one embodiment, said truncated guide sequence element is less than twenty nucleotides.

In one embodiment, the present invention contemplates a fusion protein comprising a Cas9 nuclease, said nuclease comprising a protospacer adjacent motif recognition domain and a truncated peptide linker, wherein said truncated peptide linker is attached to a DNA binding domain (DBD) protein. In one embodiment, said truncated peptide linker is between two and sixty amino acids. In one embodiment, said truncated peptide linker is between twenty-five and sixty amino acids. In one embodiment, said Cas9 nuclease is selected from the group consisting of SpCas9, SaCas9, NmCas9 and AnCas9. In one embodiment, said DBD protein is selected from the group consisting of $DBD^{268}$, $DBD^{TS1}$, $DBD^{TS2}$, $DBD^{TS3}$ and $DBD^{TS4}$. In one embodiment, said DBD protein is selected from the group consisting of a zinc finger protein and a transcription activator-like effector protein. In one embodiment, said fusion protein further comprises a guide RNA, which contains a guide sequence element. In one embodiment, said guide RNA is selected from the group consisting of an sgRNA sequence, a crRNA sequence and a tracrRNA sequence. In one embodiment, said guide sequence element is truncated. In one embodiment, said truncated guide sequence element is less than twenty nucleotides.

In one embodiment, the present invention contemplates a fusion protein comprising a Cas9 nuclease, said nuclease comprising a mutated protospacer adjacent motif recognition domain and a truncated peptide linker, wherein said truncated peptide linker is attached to a DNA binding domain (DBD) protein. In one embodiment, said truncated peptide linker is between two and sixty amino acids. In one embodiment, said truncated peptide linker is between twenty-five and sixty amino acids. In one embodiment, said mutated protospacer adjacent motif recognition domain is selected from the group consisting of $Cas9^{MT1}$, $Cas9^{MT2}$, $Cas9^{MT3}$, $NmCas9^{SM}$ and $NmCas9^{DM}$. In one embodiment, mutated protospacer adjacent motif recognition domain comprises mutated DNA phosphodiester recognition amino acid residues. In one embodiment, said Cas9 nuclease is selected from the group consisting of SpCas9, SaCas9, NmCas9 and AnCas9. In one embodiment, said DBD protein is selected from the group consisting of $DBD^{268}$, $DBD^{TS1}$, $DBD^{TS2}$, $DBD^{TS3}$ and $DBD^{TS4}$. In one embodiment, said DBD protein is selected from the group consisting of a zinc finger protein and a transcription activator-like effector protein. In one embodiment, said fusion protein further comprises a guide RNA which contains a guide sequence element. In one embodiment, said guide RNA is selected from the group consisting of an sgRNA sequence, a crRNA sequence and a tracrRNA sequence. In one embodiment, said guide sequence element is truncated. In one embodiment, truncated guide sequence element is less than twenty nucleotides.

In one embodiment, the present invention contemplates a DNA/protein complex comprising a Cas9 nuclease, said nuclease comprises a mutated protospacer adjacent motif recognition domain and a peptide linker, wherein said peptide linker is attached to a DNA binding domain (DBD) protein, wherein said mutated protospacer adjacent motif recognition domain at least partially binds to a DNA protospacer adjacent motif sequence and said DBD protein binds to a DNA target site, where target site cleavage precision has a specificity ratio greater than a $Cas9^{WT}$ nuclease. In one embodiment, the DNA target site is a neighboring DNA target site. In one embodiment, said specificity ratio ranges between a two-fold to a one-hundred and fifty six fold greater than said $Cas9^{WT}$ nuclease. In one embodiment, said Cas9 nuclease is selected from the group consisting of SpCas9, SaCas9, NmCas9 and AnCas9. In one embodiment, the mutated protospacer adjacent motif recognition domain renders target recognition dependent on the DNA-binding domain. In one embodiment, said mutated protospacer adjacent motif recognition domain is selected from the group consisting of $Cas9^{MT1}$, $Cas9^{MT2}$, $Cas9^{MT3}$, $NmCas9^{SM}$ and $NmCas9^{DM}$. In one embodiment, said DBD protein is selected from the group consisting of $DBD^{268}$, $DBD^{TS1}$, $DBD^{TS2}$, $DBD^{TS3}$ and $DBD^{TS4}$. In one embodiment, said DNA target site is selected from the group consisting of a Zif268 site, a TS1 site, a TS2 site, a TS3 site and a TS4 site. In one embodiment, said DBD protein is selected from the group consisting of a zinc finger protein and a transcription activator-like effector protein. In one embodiment, said complex further comprises a guide RNA attached to a guide sequence element that is complementary to a region of the DNA target site. In one embodiment, said Cas9 nuclease comprises mutated DNA phosphodiester recognition amino acid residues. In one embodiment, said guide RNA is selected from the group consisting of an sgRNA sequence, a crRNA sequence and a tracrRNA sequence. In one embodiment, said guide sequence element is truncated. In one embodiment, said truncated guide sequence element is less than twenty nucleotides.

In one embodiment, the present invention contemplates a DNA/protein complex comprising a Cas9 nuclease, said nuclease comprises a protospacer adjacent motif recognition domain and a truncated peptide linker, wherein said truncated peptide linker is attached to a DNA binding domain (DBD) protein, wherein said protospacer adjacent motif recognition domain binds to a DNA protospacer adjacent motif sequence, and said DBD protein binds to a DNA target site, where target site cleavage precision has a specificity ratio greater than a $Cas9^{WT}$ nuclease. In one embodiment, the DNA target site is a neighboring DNA target site. In one embodiment, said truncated peptide linker is between two and sixty amino acids. In one embodiment, said peptide linker comprises between twenty-five and sixty amino acids. In one embodiment, said specificity ratio ranges between a two-fold to a one-hundred and fifty six fold greater than said $Cas9^{WT}$ nuclease. In one embodiment, said Cas9 nuclease is selected from the group consisting of SpCas9, SaCas9, NmCas9 and AnCas9. In one embodiment, said DNA target site is selected from the group consisting of a Zif268 site, a TS1 site, a TS2 site, a TS3 site and a TS4 site. In one embodiment, said DBD protein is selected from the group consisting of $DBD^{268}$, $DBD^{TS1}$, $DBD^{TS2}$, $DBD^{TS3}$ and $DBD^{TS4}$. In one embodiment, said DBD protein is selected from the group consisting of a zinc finger protein and a transcription activator-like effector protein. In one embodiment, said complex further comprises a guide RNA attached to a guide sequence element that is complementary to a region of the DNA target site. In one embodiment, said guide RNA is selected from the group consisting of an sgRNA sequence, a crRNA sequence and a tracrRNA sequence. In one embodiment, said guide sequence element is truncated. In one embodiment, said truncated guide sequence element is less than twenty nucleotides.

In one embodiment, the present invention contemplates, a DNA/protein complex comprising a Cas9 nuclease, said nuclease comprises a mutated protospacer adjacent motif recognition domain and a truncated peptide linker, wherein said truncated peptide linker is attached to a DNA binding domain (DBD) protein, wherein said mutated protospacer adjacent motif recognition domain at least partially binds to a DNA protospacer adjacent motif sequence, and said DBD protein binds to a DNA target site, where target site cleavage has a specificity ratio greater than a $Cas9^{WT}$ nuclease. In one embodiment, the DNA target site is a neighboring DNA target site. In one embodiment, said truncated peptide linker comprises between two and sixty amino acids. In one embodiment, said truncated peptide linker comprises between twenty-five and sixty amino acids. In one embodiment, said specificity ratio ranges between a two-fold to a one-hundred and fifty six fold greater than said $Cas9^{WT}$ nuclease. In one embodiment, the mutated protospacer adjacent motif recognition domain renders target recognition dependent on the DNA-binding domain. In one embodiment, said mutated protospacer adjacent motif recognition domain is selected from the group consisting of $Cas9^{MT1}$, $Cas9^{MT2}$, $Cas9^{MT3}$, $NmCas9^{SM}$ and $NmCas9^{DM}$. In one embodiment, said mutated protospacer adjacent motif recognition domain comprises mutated DNA phosphodiester recognition amino acid residues. In one embodiment, said DNA target site is selected from the group consisting of a Zif268 site, a TS1 site, a TS2 site, a TS3 site and a TS4 site. In one embodiment, said DBD protein is selected from the group consisting of $DBD^{268}$, $DBD^{TS1}$, $DBD^{TS2}$, $DBD^{TS3}$ and $DBD^{TS4}$. In one embodiment, said DBD protein is selected from the group consisting of a zinc linger protein and a transcription activator-like effector protein. In one embodiment, said fusion protein further comprises a guide RNA attached to a guide sequence element that is complementary to a region of the DNA target site. In one embodiment, said guide RNA is selected from the group consisting of an sgRNA sequence, a crRNA sequence and a tracrRNA sequence. In one embodiment, said guide sequence element is truncated. In one embodiment, said truncated guide sequence element is less than twenty nucleotides.

In one embodiment, the present invention contemplates a method for genome editing of DNA, comprising: a) providing: i) a DNA sequence comprising a target site sequence, and a protospacer adjacent motif sequence; and ii) a fusion protein comprising a Cas9 nuclease, said nuclease comprising a mutated protospacer adjacent motif recognition domain and a peptide linker, wherein said peptide linker is attached to a DNA targeting unit (DTU) protein; b) contacting said fusion protein with said target site sequence such that said DTU binds to said target site sequence and said mutated protospacer adjacent motif recognition domain at least partially binds to said protospacer adjacent motif sequence; and c) cleaving said target site with said Cas9 nuclease. In one embodiment, said cleaving is at a single nucleotide target site. In one embodiment, the cleaving performs gene editing. In one embodiment, said DNA sequence is within a cell. In one embodiment, said target site further comprises a sequence complementary to the guide sequence element, a protospacer adjacent motif sequence and a recognition sequence for the DNA targeting unit In one embodiment, said Cas9 nuclease cleaves said target site with a precision that has a specificity ratio between two and one-hundred and fifty six fold greater than a $Cas9^{WT}$ nuclease. In one embodiment, said Cas9 nuclease is selected from the group consisting of SpCas9, SaCas9, NmCas9 and AnCas9. In one embodiment, the mutated protospacer adjacent motif recognition domain renders target recognition dependent on the DNA-binding domain. In one embodiment, said mutated protospacer adjacent motif recognition domain is selected from the group consisting of $Cas9^{MT1}$, $Cas9^{MT2}$, $Cas9^{MT3}$, $NmCas9^{SM}$ and $NmCas9^{DM}$. In one embodiment, said DNA target site is selected from the group consisting of a Zif268 site, a TS1 site, a TS2 site, a TS3 site and a TS4 site. In one embodiment, said DTU is selected from the group consisting of $DBD^{268}$, $DBD^{TS1}$, $DBD^{TS2}$, $DBD^{TS3}$, $DBD^{TS4}$ and nuclease-dead NmCas9 (NmdCas9). In one embodiment, said DTU is selected from the group consisting of a zinc finger protein, a transcription activator-like effector protein and an alternate Cas9 isoform. In one embodiment, said fusion protein further comprises one guide RNA for each Cas9 isoform incorporated, which contains a guide sequence element that is complementary to a region of the target site sequence. In one embodiment, said mutated protospacer adjacent motif recognition domain comprises mutated DNA phosphodiester recognition amino acid residues. In one embodiment, said guide RNA is selected from the group consisting of an sgRNA sequence, a crRNA sequence and a tracrRNA sequence. In one embodiment, said guide sequence element is truncated. In one embodiment, said truncated guide sequence element is less than twenty nucleotides.

In one embodiment, a method for genome editing of DNA within a cell, comprising: a) providing: i) a DNA sequence comprising a target site sequence, and a protospacer adjacent motif sequence; and ii) a fusion protein comprising a Cas9 nuclease, said nuclease comprising a protospacer adjacent motif recognition domain and a truncated peptide linker, wherein said truncated peptide linker is attached to a DNA targeting unit (DTU); b) contacting said fusion protein with said DNA sequence such that said DTU binds to said target site sequence and said protospacer adjacent motif recognition domain binds to said protospacer adjacent motif sequence; and c) cleaving said target sequence with said Cas9 nuclease. In one embodiment, the cleaving is a single nucleotide target site. In one embodiment, the cleaving performs gene editing. In one embodiment, said target site comprises a sequence complementary to the guide sequence element, a protospacer adjacent motif sequence and a recognition sequence for the DNA targeting unit. In one embodiment, said Cas9 fusion protein cleaves said target site with a precision that has a specificity ratio between two and one-hundred and fifty six fold greater than a $Cas9^{WT}$ nuclease. In one embodiment, said truncated peptide linker is between two and sixty amino acids. In one embodiment, said truncated peptide linker is between twenty-five and sixty amino acids. In one embodiment, said Cas9 nuclease is selected from the group consisting of SpCas9, SaCas9, NmCas9 and AnCas9. In one embodiment, said DNA target site is selected from the group consisting of a Zif268 site, a TS1 site, a TS2 site, a TS3 site and a TS4 site. In one embodiment, said DTU is selected from the group consisting of $DBD^{268}$, $DBD^{TS1}$, $DBD^{TS2}$, $DBD^{TS3}$, $DBD^{TS4}$ and nuclease-dead NmCas9 (NmdCas9). In one embodiment, said DTU is selected from the group consisting of a zinc finger protein, a transcription activator-like effector protein and an alternate Cas9 isoform. In one embodiment, said fusion protein further comprises one guide RNA for each Cas9 isoform incorporated, which contains a guide sequence element that is complementary to a region of the target site sequence. In one embodiment, said guide RNA sequence is selected from the group consisting of an sgRNA sequence, a crRNA sequence and a tracrRNA sequence. In one embodiment, said guide sequence element is truncated. In one embodiment, said truncated guide sequence element is less than twenty nucleotides.

In one embodiment, genome editing of DNA within a cell, comprising: a) providing: i) a DNA sequence comprising a target site sequence, and a protospacer adjacent motif sequence; and ii) a fusion protein comprising a Cas9 nuclease, said nuclease comprising a mutated protospacer adjacent motif recognition domain and a truncated peptide linker, wherein said truncated peptide linker is attached to a DNA targeting unit (DTU); b) contacting said fusion protein with said DNA sequence such that said DTU protein binds within said target site sequence and said protospacer adjacent motif recognition domain binds to said protospacer adjacent motif sequence; and c) cleaving the target site with said Cas9 nuclease. In one embodiment, said target site comprises a sequence complementary to the guide sequence element, a protospacer adjacent motif sequence and a recognition sequence for the DNA targeting unit. In one embodiment, the cleaving is performed at a single nucleotide target site. In one embodiment, the cleaving performs gene editing. In one embodiment, said Cas9 fusion protein cleaves said target site with a precision that has a specificity ratio between two and one-hundred and fifty six fold greater than a Cas9$^{WT}$ nuclease. In one embodiment, said truncated peptide linker is between two and sixty amino acids. In one embodiment, said truncated peptide linker is between twenty-five and sixty amino acids. In one embodiment, the mutated protospacer adjacent motif recognition domain renders target recognition dependent on the DNA-binding domain. In one embodiment, said mutated protospacer adjacent motif recognition domain is selected from the group consisting of Cas9$^{MT1}$, Cas9$^{MT2}$, Cas9$^{MT3}$, NmCas9$^{SM}$ and NmCas9$^{DM}$. In one embodiment, said the mutated protospacer adjacent motif recognition domain comprises mutated DNA phosphodiester recognition amino acid residues. In one embodiment, said Cas9 nuclease is selected from the group consisting of SpCas9, SaCas9, NmCas9 and AnCas9. In one embodiment, said DNA target site is selected from the group consisting of a Zif268 site, a TS1 site, a TS2 site, a TS3 site and a TS4 site. In one embodiment, said DTU is selected from the group consisting of DBD$^{268}$, DBD$^{TS1}$, DBD$^{TS2}$, DBD$^{TS3}$, DBD$^{TS4}$ and nuclease-dead NmCas9 (NmdCas9). In one embodiment, said DTU is selected from the group consisting of a zinc finger protein, a transcription activator-like effector protein and an alternate Cas9 isoform. In one embodiment, said fusion protein further comprises one guide RNA for each Cas9 isoform incorporated, which contains a guide sequence element that is complementary to a region of the target site sequence. In one embodiment, said guide RNA is selected from the group consisting of an sgRNA sequence, a crRNA sequence and a tracrRNA sequence. In one embodiment, said guide sequence element is truncated. In one embodiment, said trucated guide sequence element is less than twenty nucleotides.

In one embodiment, the present invention contemplates a method of treatment, comprising: a) providing: i) a patient exhibiting at least one symptom of a genetic disease and comprising a cell with a DNA target site, said DNA target site comprising a gene mutation responsible for said genetic disease; ii) a delivery vehicle comprising a Cas9-DNA targeting unit (DTU) fusion protein capable of genome editing selected from the group consisting of: A) a Cas9 nuclease, said nuclease comprising a mutated protospacer adjacent motif recognition domain and a peptide linker, wherein said peptide linker is attached to a DNA targeting unit (DTU); B) a Cas9 nuclease, said nuclease comprising a protospacer adjacent motif recognition domain and a truncated peptide linker, wherein said truncated peptide linker is attached to a DNA targeting unit (DTU); and C) a Cas9 nuclease, said nuclease comprising a mutated protospacer adjacent motif recognition domain and a truncated peptide linker, wherein said truncated peptide linker is attached to a targeting unit (DTU); b) administering said plasmid to said patient such that said plasmid transfects said cell; c) expressing said plasmid within said cell such that said expressed Cas9-DBD fusion protein contacts said DNA target site; d) editing said DNA target site with said Cas9 nuclease; and e) reducing said at least one symptom of said genetic disease in said patient. In one embodiment, said Cas9 fusion protein cleaves said target site with a precision that has a specificity ratio between two and one-hundred and fifty six fold greater than a Cas9$^{WT}$ nuclease. In one embodiment, the delivery vehicle includes, but is not limited to, a plasmid, a vector, a virus or an mRNA. In one embodiment, said truncated peptide linker is between two and sixty amino acids. In one embodiment, said truncated peptide linker is between twenty-five and sixty amino acids. In one embodiment, the mutated protospacer adjacent motif recognition domain renders target recognition dependent on the DNA-binding domain. In one embodiment, said mutated protospacer adjacent motif recognition domain is selected from the group consisting of Cas9$^{MT1}$, Cas9$^{MT2}$, Cas9$^{MT3}$, NmCas9$^{SM}$ and NmCas9$^{DM}$. In one embodiment, said mutated protospacer adjacent motif recognition domain comprises mutated DNA phosphodiester recognition amino acid residues. In one embodiment, said Cas9 nuclease is selected from the group consisting of SpCas9, SaCas9, NmCas9 and AnCas9. In one embodiment, said DNA target site is selected from the group consisting of a Zif268 site, a TS1 site, a TS2 site, a TS3 site and a TS4 site. In one embodiment, said DTU is selected from the group consisting of DBD$^{268}$, DBD$^{TS1}$, DBD$^{TS2}$, DBD$^{TS3}$, DBD$^{TS4}$ and nuclease-dead NmCas9 (NmdCas9). In one embodiment, said DTU is selected from the group consisting of a zinc finger protein, a transcription activator-like effector protein and an alternate Cas9 isoform. In one embodiment, said fusion protein further comprises one guide RNA for each Cas9 isoform incorporated, which contains a guide sequence element that is complementary to a region of the target site sequence. In one embodiment, said guide RNA is selected from the group consisting of an sgRNA sequence, a crRNA sequence and a tracrRNA sequence. In one embodiment, said guide sequence element is truncated. In one embodiment, said truncated guide sequence element is less than twenty nucleotides. In one embodiment, said genetic disease is selected from the group consisting of chronic granulomatous disease, Huntington's disease, myotonic dystrophy, and HIV.

In one embodiment, the present invention contemplates a method of prevention, comprising: a) providing: i) a patient comprising a cell with a DNA target site, said DNA target site comprising a gene mutation responsible for a genetic disease; ii) a plasmid comprising a Cas9-DNA targeting unit (DTU) fusion protein capable of genome editing selected from the group consisting of: A) a Cas9 nuclease, said nuclease comprising a mutated protospacer adjacent motif recognition domain and a peptide linker, wherein said peptide linker is attached to a DNA targeting unit (DTU); B) a Cas9 nuclease, said nuclease comprising a protospacer adjacent motif recognition domain and a truncated peptide linker, wherein said truncated peptide linker is attached to a DNA targeting unit (DTU); and C) a Cas9 nuclease, said nuclease comprising a mutated protospacer adjacent motif recognition domain and a truncated peptide linker, wherein said truncated peptide linker is attached to a DNA targeting unit (DTU); b) administering said plasmid to said patient such that said plasmid transfects said cell; c) expressing said plasmid within said cell such that said expressed Cas9-DTU fusion protein contacts said DNA target site; d) editing said DNA target site with said Cas9 nuclease; and e) preventing the development of said genetic disease in said patient. In one embodiment, said Cas9 fusion protein cleaves said target site with a precision that has a specificity ratio between two and one-hundred and fifty six fold greater than a Cas9$^{WT}$ nuclease. In one embodiment, said truncated peptide linker is between two and sixty amino acids. In one embodiment, said truncated peptide linker is between twenty-five and sixty amino acids. In one embodiment, the mutated protospacer adjacent motif recognition domain renders target recognition dependent on the DNA-binding domain. In one embodiment, said mutated protospacer adjacent motif recognition domain is selected from the group consisting of Cas9$^{MT1}$, Cas9$^{MT2}$, Cas9$^{MT3}$, NmCas9$^{SM}$ and NmCas9$^{DM}$. In one embodiment, said mutated protospacer adjacent motif recognition domain comprises mutated DNA phosphodiester recognition amino acid residues. In one embodiment, said Cas9 nuclease is selected from the group consisting of SpCas9, SaCas9, NmCas9 and AnCas9. In one embodiment, said DNA target site is selected from the group consisting of a Zif268 site, a TS1 site, a TS2 site, a TS3 site and a TS4 site. In one embodiment, said DTU is selected from the group consisting of DBD$^{268}$, DBD$^{TS1}$, DBD$^{TS2}$, DBD$^{TS3}$, DBD$^{TS4}$ and nuclease-dead NmCas9 (NmdCas9). In one embodiment, said DTU is selected from the group consisting of a Zinc finger protein, a transcription activator-like effector protein and an alternate Cas9 isoform. In one embodiment, said fusion protein further comprises one guide RNA for each Cas9 isoform incorporated, which contains a guide sequence element that is complementary to a region of the DNA target site. In one embodiment, said guide RNA is selected from the group consisting of an sgRNA sequence, a crRNA, sequence and a tracrRNA sequence. In one embodiment, said guide sequence element is truncated. In one embodiment, said trucated guide sequence element is less than twenty nucleotides. In one embodiment, said genetic disease is selected from the group consisting of Chronic granulomatous disease, Huntington's disease, myotonic dystrophy and HIV.

In one embodiment, the present invention contemplates a kit, comprising: a) a first container comprising a Cas9-DTU fusion protein selected from the group consisting of: A) a Cas9 nuclease, said nuclease comprising a mutated protospacer adjacent motif recognition domain and a peptide linker, wherein said peptide linker is attached to a DNA targeting unit (DTU); B) a Cas9 nuclease, said nuclease comprising a protospacer adjacent motif recognition domain and a truncated peptide linker, wherein said truncated peptide linker is attached to a DNA targeting unit (DTU); and C) a Cas9 nuclease, said nuclease comprising a mutated protospacer adjacent motif recognition domain and a truncated peptide linker, wherein said truncated peptide linker is attached to a DNA targeting unit (DTU); b) a second container comprising a single guide RNA complementary to a specific genomic target sequence for each Cas9 isoform present; and c) a set of instructions for genome editing of said specific genomic target. In one embodiment, said Cas9-DTU fusion protein is encoded by a plasmid. In one embodiment, said Cas9 fusion protein cleaves said target site with a precision that has a specificity ratio between two and one-hundred and fifty six fold greater than a Cas9$^{WT}$ nuclease. In one embodiment, said truncated peptide linker is between two and sixty amino acids. In one embodiment, said truncated peptide linker is between twenty-five and sixty amino acids. In one embodiment, the mutated protospacer adjacent motif recognition domain renders target recognition dependent on the DNA-binding domain. In one embodiment, said mutated protospacer adjacent motif recognition domain is selected from the group consisting of Cas9$^{MT1}$, Cas9$^{MT2}$, Cas9$^{MT3}$, NmCas9$^{SM}$ and NmCas9$^{DM}$. In one embodiment, said mutated protospacer adjacent motif recognition domain comprises mutated DNA phosphodiester recognition amino acid residues. In one embodiment, said Cas9 nuclease is selected from the group consisting of SpCas9, SaCas9, NmCas9 and AnCas9. In one embodiment, said DNA target site is selected from the group consisting of a Zif268 site, a TS1 site, a TS2 site, a TS3 site and a TS4 site. In one embodiment, said DTU is selected from the group consisting of DBD$^{268}$, DBD$^{TS1}$, DBD$^{TS2}$, DBD$^{TS3}$, DBD$^{TS4}$ and nuclease-dead NmCas9 (NmdCas9). In one embodiment, said DBD protein is selected from the group consisting of a zinc finger protein, a transcription activator-like effector protein and an alternate Cas9 isoform. In one embodiment, said fusion protein further comprises one guide RNA for each Cas9 isoform incorporated, which contains a guide sequence element that is complementary to a region of the DNA target site. In one embodiment, said guide RNA is selected from the group consisting of an sgRNA sequence, a crRNA sequence and a tracrRNA sequence. In one embodiment, said guide sequence element is truncated. In one embodiment, said trucated guide sequence element is less than twenty nucleotides. In one embodiment, said kit further comprises instructions for treating a genetic disease. In one embodiment, said genetic disease is selected from the group consisting of chronic granulomatous disease, Huntington's disease, myotonic dystrophy and HIV.

In one embodiment, the present invention contemplates a composition comprising a Cas9 nuclease-DNA targeting unit fusion protein. In one embodiment, the DNA targeting unit may be a programmable DNA binding domain such as a zinc finger protein. In one embodiment, the DNA targeting unit may be a programmable DNA binding domain such as a transcription activator-like effector protein. In one embodiment, the DNA targeting unit may be a programmable DNA binding domain such as a homeodomain protein. In one embodiment, the DNA targeting unit may be a different Cas9 isoform that can be independently programmed with a single guide RNA to a neighboring target site. In one embodiment, the Cas9 nuclease comprises a mutated protospacer adjacent motif recognition sequence. In one embodiment, the Cas9 nuclease comprises mutated residues that bind the phosphodiester backbone of the DNA or RNA. In one embodiment, the composition further comprises a single guide RNA which contains a guide sequence element that is complementary to a region of the DNA target site. In one embodiment, the single guide RNA may be truncated. In one embodiment, the composition further comprises a two orthogonal single guide RNAs. In one embodiment, both single guide RNAs are truncated. In one embodiment, the truncated single guide sequence element contains a guide segments that may be less than twenty nucleotides. In one embodiment, the mutated protospacer adjacent motif recognition sequence comprises at least one mutation.

In one embodiment, the present invention contemplates a composition comprising a Cas9 nuclease and a DNA targeting unit. In one embodiment, the DNA targeting unit comprises at least one dimerization domain. In one embodiment, the Cas9 nuclease and said DNA targeting unit are fused at said dimerization domain. In one embodiment, the DNA targeting unit may be a programmable DNA binding domain such as a zinc finger protein. In one embodiment, the DNA targeting unit may be a programmable DNA binding domain such as a transcription activator-like effector protein. In one embodiment, the DNA targeting unit may be a programmable DNA binding domain such as a homeodomain protein. In one embodiment, the DNA targeting unit may be a different Cas9 isoform that can be independently programmed with a single guide RNA to a neighboring target site. In one embodiment, the Cas9 nuclease comprises a mutated protospacer adjacent motif recognition sequence. In one embodiment, the Cas9 nuclease comprises mutated residues that bind the phosphodiester backbone of the DNA or RNA. In one embodiment, the composition further comprises a single guide RNA which contains a guide sequence element that is complementary to a region of the DNA target site. In one embodiment, the single guide RNA may be truncated. In one embodiment, the composition further comprises a two orthogonal single guide RNAs. In one embodiment, both single guide RNAs are truncated within the region complementary to the target site. In one embodiment, the at least one dimerization domain may be heterotypic. In one embodiment, at least one dimerization domain may be fused to an RNA binding protein that recognizes a sequence within the sgRNA. In one embodiment, a complementary RNA binding domain may be fused to a DNA targeting unit (DTU). In one embodiment, at least one dimerization domain may be complementary an RNA segment fused to the sgRNA of an orthogonal Cas9/sgRNA isoform. In one embodiment, the truncated single guide RNA contains a guide segment that may be less than twenty nucleotides. In one embodiment, the mutated protospacer adjacent motif recognition sequence comprises at least one mutation.

In one embodiment, the present invention contemplates a method, comprising: a) providing: i) a cell comprising a specific genomic target, wherein said specific genomic target comprises an on-target binding sequence; ii) a first vector encoding a Cas9 nuclease-DNA targeting unit fusion protein; iii) a second vector comprising a single guide RNA gene capable of expressing a single guide RNA (sgRNA) having complete complementarity to said specific genomic target; and b) expressing said first and second vectors in said cell, wherein a Cas9-DNA targeting unit fusion protein/sgRNA complex may be created; c) binding said Cas9-DNA targeting fusion protein/sgRNA complex to said on-target binding sequence, under conditions such that said specific genomic target may be cleaved. In one embodiment, the Cas9-DNA targeting unit fusion protein further comprises a mutated protospacer adjacent motif recognition sequence. In one embodiment, the mutated protospacer adjacent motif recognition sequence prevents independent binding of the Cas9 to DNA without the prior binding of the DNA-targeting unit. In one embodiment, the mutated protospacer adjacent motif comprises at least one mutation. In one embodiment, the DNA targeting unit may be a programmable DNA binding domain selected from a zinc finger protein, a transcription activator-like effector protein and a homeodomain protein. In one embodiment, the DNA targeting unit may be an alternate Cas9 isoform that may be programmed with an orthogonal sgRNA to the sgRNA that may be used to program the Cas9 nuclease. In one embodiment, the sgRNA sequence may be truncated. In one embodiment, the truncated sgRNA may be complementary to said target site at less than nucleotides. In one embodiment, the specific genomic target may be a gene of interest. In one embodiment, the specific genomic target may be a single allele.

In one embodiment, the present invention contemplates a kit, comprising: a) a first container comprising a Cas9 nuclease-DNA targeting unit fusion protein capable of binding to a specific genomic target; b) a second container comprising a single guide RNA complementary to said specific genomic target or a pair of orthogonal single guide RNAs if the DNA targeting unit may be an alternate Cas9 isoform, and c) a set of instructions for employing these reagents to cleave said specific genomic target. In one embodiment, the DNA targeting unit may be a programmable DNA binding domain selected from the group consisting of a zinc finger protein, a transcription activator-like effector protein and a homeodomain protein. In one embodiment, the Cas9 fusion protein comprises a mutated protospacer adjacent motif recognition sequence. In one embodiment, the single guide RNA may be truncated. In one embodiment, the truncated guide sequence element may be less than twenty nucleotides. In one embodiment, the mutated protospacer adjacent motif recognition sequence comprises at least one mutation.

In one embodiment, the present invention contemplates a kit, comprising: a) a first container comprising a Cas9 nuclease fused to a dimerization domain; b) a second container comprising a DNA targeting unit fused to a complementary dimerization domain capable of binding to a specific sequence neighboring the genomic target site or being programmed to recognize this sequence with an appropriate guide RNA; c) a third container comprising a single guide RNA complementary to said specific genomic target or a pair of orthogonal single guide RNAs if the DNA targeting unit may be an alternate Cas9 isoform, where the second guide RNA recognizes a binding site neighboring the target site, and d) a set of instructions for employing these reagents to cleave said specific genomic target. In one embodiment, the DNA targeting unit may be a programmable DNA binding domain selected from the group consisting of a zinc finger protein, a transcription activator-like effector protein and a homeodomain protein. In one embodiment, the Cas9 fusion protein comprises a mutated protospacer adjacent motif recognition sequence. In one embodiment, the single guide RNA may be truncated. In one embodiment, the truncated guide sequence element may be less than twenty nucleotides. In one embodiment, the mutated protospacer adjacent motif recognition sequence comprises at least one mutation.

In one embodiment, the present invention contemplates a kit, comprising: a) a first container comprising a first vector encoding a Cas9-programmable DNA binding domain fusion protein capable of binding to a specific genomic target; b) a second container comprising a second vector comprising a single guide RNA gene encoding a guide sequence element complementary to said specific genomic target, and c) a set of instructions for deleting said specific genomic target. In one embodiment, the programmable DNA binding domain may be selected from the group consisting of a zinc finger protein and a transcription activator-like effector protein. In one embodiment, the DNA targeting unit may be an alternate Cas9 isoform that may be programmed with an orthogonal sgRNA to the sgRNA that may be used to program the Cas9 nuclease. In one embodiment, the Cas9 fusion protein comprises a mutated protospacer adjacent motif recognition domain sequence. In one embodiment, the Cas9 nuclease comprises mutated residues that bind the phosphodiester backbone of the DNA or RNA. In one embodiment, the guide sequence element may be truncated. In one embodiment, the truncated guide sequence element may be less than twenty nucleotides. In one embodiment, the mutated protospacer adjacent motif recognition domain comprises at least one mutation.

In one embodiment, the present invention contemplates a fusion protein comprising a Cas9 nuclease, said nuclease comprising a mutated protospacer adjacent motif recognition domain and a peptide linker, wherein said peptide linker is attached to a DNA targeting unit (DTU) comprising a second Cas9 nuclease. In one embodiment, the Cas9 nucleases are selected from the group consisting of SpCas9, SaCas9, NmCas9 and AnCas9. In one embodiment, the mutated protospacer adjacent motif recognition domain comprises mutated DNA phosphodiester recognition amino acid residues. In one embodiment, the mutated protospacer adjacent motif recognition domain is selected from the group consisting of SpCas9$^{MT1}$, SpCas9$^{MT2}$, SpCas9$^{MT3}$, NmCas9$^{SM}$ and NmCas9$^{DM}$. In one embodiment, the DTU includes, but is not limited to, a Cas9 nuclease, a Cas9 nickase or a nuclease-dead Cas9 (dCas9). In one embodiment, the DTU is selected from the group consisting of nuclease-dead NmCas9 (NmdCas9), NmCas9 nuclease, NmCas9 nickase (HNH), and NmCas9 nickase (RuvC). In one embodiment, each Cas9 within the fusion protein has guide RNA attached to a guide sequence element. In one embodiment, said guide RNAs are selected from the group consisting of an sgRNA sequence, a crRNA sequence and a tracrRNA sequence. In one embodiment, the guide sequence element is truncated. In one embodiment, the truncated guide sequence element is less than twenty nucleotides.

In one embodiment, the present invention contemplates a two component Cas9 nuclease DNA targeting unit (DTU) system, wherein said system is inactive until assembled via drug-dependent or light-dependent dimerization thereby improving nuclease precision and activity, said system comprising: a) a fusion protein comprising: i) a Cas9 nuclease, said nuclease comprising a mutated protospacer adjacent motif recognition domain and a first peptide linker, wherein said peptide linker is attached to a first drug-dependent or light-dependent dimerization domain (Cas9 nuclease component); and ii) a DNA targeting unit (DTU) and a second peptide linker, wherein said second peptide linker is attached to a second drug-dependent or light-dependent dimerization domain (DTU component); and b) a DNA target site. In one embodiment, the Cas9 nuclease is selected from the group consisting of SpCas9, SaCas9, NmCas9 and AnCas9. In one embodiment, the mutated protospacer adjacent motif recognition domain renders recognition of said DNA target site by the Cas9 nuclease component dependent on the DTU. In one embodiment, the mutated protospacer adjacent motif recognition domain comprises mutated DNA phosphodiester recognition amino acid residues. In one embodiment, the mutated protospacer adjacent motif recognition domain is selected from the group consisting of SpCas9$^{MT1}$, SpCas9$^{MT2}$, SpCas9$^{MT3}$, NmCas9$^{SM}$ and NmCas9$^{DM}$. In one embodiment, the DTU can be a zinc finger protein, a transcription activator-like effector protein, a Cas9 nuclease, a Cas9 nickase or a nuclease-dead Cas9 (dCas9). In one embodiment, the DTU is selected from the group consisting of nuclease-dead NmCas9 (NmdCas9), NmCas9 nuclease, NmCas9 nickase (HNH), and NmCas9 nickase (RuvC). In one embodiment, the DTU is selected from the group consisting of DBD$^{268}$, DBD$^{TS1}$, DBD$^{TS2}$, DBD$^{TS3}$, DBD$^{TS4}$ and nuclease-dead NmCas9 (NmdCas9). In one embodiment, the two component Cas9 nuclease DNA targeting unit (DTU) system comprises one guide RNA for each Cas9 protein present, wherein each of said Cas9 proteins contain a guide sequence element that is complementary to a region of the DNA target site. In one embodiment, the guide RNAs are selected from the group consisting of an sgRNA sequence, a crRNA sequence and a tracrRNA sequence. In one embodiment, the guide sequence element is truncated. In one embodiment, the truncated guide sequence element is less than twenty nucleotides. In one embodiment, the drug-dependent dimerization domains within the Cas9 nuclease component are selected from the group consisting of FRB, FRB*, FKBP, ABI and PYL. In one embodiment, the drug-dependent dimerization domains within the DTU component are selected from the group consisting of FRB, FRB*, FKBP, ABI and PYL. In one embodiment, the light-dependent dimerization domains within the DTU component are selected from the group consisting of pMag, nMag, CRY2 and CIB1. In one embodiment, the light-dependent dimerization domains within DTU component are selected from the group consisting of pMag, nMag, CRY2 and CIB1. In one embodiment, the first linker joining the Cas9 nuclease and the drug-dependent or light-dependent dimerization domain is between two and sixty amino acids. In one embodiment, the second linker joining the DTU and the drug-dependent or light-dependent dimerization domain is between two and sixty amino acids. In one embodiment, the two component Cas9 nuclease DNA targeting unit (DTU) system upon addition of the stimulus (drug or light) has improved cleavage activity at the target site relative to the same wild-type Cas9 isoform. In one embodiment, the two component Cas9 nuclease DNA targeting unit (DTU) system upon addition of the stimulus (drug or light) has improved cleavage activity at a target site with suboptimal PAMs relative to the same wild-type Cas9 isoform. In one embodiment, the two component SpCas9 nuclease DNA targeting unit (DTU) system upon addition of the stimulus (drug or light) has improved cleavage activity at a target site with suboptimal PAMs (NAG, NGA or NGC) relative to wild-type SpCas9. In one embodiment, the two component Cas9 nuclease DNA targeting unit (DTU) system upon addition of the stimulus (drug or light) has improved cleavage precision at the target site relative to the same wild-type Cas9 isoform. In one embodiment, the two component SpCas9 nuclease DNA targeting unit (DTU) system upon addition of the stimulus (drug or light) cleaves said target site with a precision that has a specificity ratio between two and one-hundred and fifty six fold greater than a SpCas9$^{WT}$ nuclease.

In one embodiment, the present invention contemplates a two component Split-Cas9 nuclease DNA targeting unit (DTU) system, wherein said system is inactive until assembled via drug-dependent or light-dependent dimerization thereby improving nuclease precision and activity, said system comprising: a) a fusion protein comprising; i) a N-terminal fragment of Cas9 nuclease, said nuclease fragment comprising a first peptide linker, wherein said first peptide linker is attached to a drug-dependent or light-dependent dimerization domain (N-terminal nuclease component); and ii) a C-terminal fragment of Cas9 nuclease, said nuclease fragment comprising a mutated protospacer adjacent motif recognition domain a second peptide linker and a third peptide linker, wherein said second peptide linker is attached to a drug-dependent or light-dependent dimerization domain and said third peptide linker is attached to DNA targeting unit (DTU) (DTU component); and b) a DNA target site. In one embodiment, the Cas9 nuclease are selected from the group consisting of SpCas9, SaCas9, NmCas9 and AnCas9. In one embodiment, the mutated protospacer adjacent motif recognition domain renders target recognition by the Cas9 nuclease dependent on the DTU. In one embodiment, the mutated protospacer adjacent motif recognition domain comprises mutated DNA phosphodiester recognition amino acid residues. In one embodiment, the mutated protospacer adjacent motif recognition domain is selected from the group consisting of SpCas9$^{MT1}$, SpCas9$^{MT2}$, SpCas9$^{MT3}$, NmCas9$^{SM}$ and NmCas9$^{DM}$. In one embodiment, the DTU can be a zinc finger protein, a transcription activator-like effector protein, a Cas9 nuclease, a Cas9 nickase or a nuclease-dead Cas9 (dCas9). In one embodiment, the DTU is selected from the group consisting of nuclease-dead NmCas9 (NmdCas9), NmCas9 nuclease, NmCas9 nickase (HNH), and NmCas9 nickase (RuvC). In one embodiment, the DTU is selected from the group consisting of DBD$^{268}$, DBD$^{TS1}$, DBD$^{TS2}$, DBD$^{TS3}$, DBD$^{TS4}$ and nuclease-dead NmCas9 (NmdCas9). In one embodiment, the fusion protein further comprises one guide RNA for each Cas9 present each guide RNA contains a guide sequence element that is complementary to a region of the DNA target site. In one embodiment, the guide RNAs are selected from the group consisting of an sgRNA sequence, a crRNA sequence and a tracrRNA sequence. In one embodiment, the guide sequence element is truncated. In one embodiment, the truncated guide sequence element is less than twenty nucleotides. In one embodiment, the drug-dependent dimerization domain fused to the N-terminal nuclease component are selected from the group consisting of FRB, FRB*, FKBP, ABI and PYL. In one embodiment, the drug-dependent dimerization domain fused to the DTU component are selected from the group consisting of FRB, FRB*, FKBP, ABI and PYL. In one embodiment, the light-dependent dimerization domain fused to the N-terminal nuclease component are selected from the group consisting of pMag, nMag, CRY2 and CIB1. In one embodiment, the light-dependent dimerization domain fused to the DTU component are selected from the group consisting of pMag, nMag, CRY2 and CIB1. In one embodiment, the linker joining the N-terminal Cas9 fragment and the drug-dependent or light-dependent dimerization domain is between two and sixty amino acids. In one embodiment, the linker joining the C-terminal Cas9 fragment and the drug-dependent or light-dependent dimerization domain is between two and sixty amino acids. In one embodiment, the linker joining the C-terminal Cas9 fragment and DTU is between two and sixty amino acids. In one embodiment, the N-terminal Cas9 fragment is composed of residues 2-573 of SpCas9. In one embodiment, the C-terminal Cas9 fragment is composed of residues 574-1368 of SpCas9. In one embodiment, the two component Split-Cas9 nuclease DNA targeting unit (DTU) system upon addition of the stimulus (drug or light) has improved cleavage activity at the target site relative to the same wild-type Cas9 isoform. In one embodiment, the two component Split-Cas9 nuclease DNA targeting unit (DTU) system upon addition of the stimulus (drug or light) has improved cleavage activity at a target site with suboptimal PAMs relative to the same wild-type Cas9 isoform. In one embodiment, the two component Split-SpCas9 nuclease DNA targeting unit (DTU) system upon addition of the stimulus (drug or light) has improved cleavage activity at a target site with suboptimal PAMs (NAG, NGA or NGC) relative to wild-type SpCas9. In one embodiment, the two component Split-Cas9 nuclease DNA targeting unit (DTU) system upon addition of the stimulus (drug or light) has improved cleavage precision at the target site relative to the same wild-type Cas9 isoform. In one embodiment, the two component Split-Cas9 nuclease DNA targeting unit (DTU) system upon addition of the stimulus (drug or light) the resulting nuclease cleaves said target site with a precision that has a specificity ratio between two and one-hundred and fifty six fold greater than a $Cas9^{WT}$ nuclease.

In one embodiment, the present invention contemplates a fusion protein comprising a Cas9 nuclease, said nuclease comprising a peptide linker, wherein said peptide linker is attached to a DNA targeting unit (DTU). In one embodiment, the Cas9 nuclease is selected from the group consisting of SpCas9, SaCas9, NmCas9 and AnCas9. In one embodiment, the DTU can be a zinc finger protein, a transcription activator-like effector protein, a Cas9 nuclease, a Cas9 nickase or a nuclease-dead Cas9 (dCas9). In one embodiment, the DTU is selected from the group consisting of nuclease-dead NmCas9 (NmdCas9), NmCas9 nuclease, NmCas9 nickase (HNH), and NmCas9 nickase (RuvC). In one embodiment, the DTU is selected from the group consisting of $DBD^{268}$, $DBD^{TS1}$, $DBD^{TS2}$, $DBD^{TS3}$, $DBD^{TS4}$ and nuclease-dead NmCas9 (NmdCas9). In one embodiment, the fusion protein further comprises a guide RNA for each Cas9 module attached to a guide sequence element. In one embodiment, the guide RNA is selected from the group consisting of an sgRNA sequence, a crRNA sequence and a tracrRNA sequence. In one embodiment, the guide sequence element is truncated. In one embodiment, the truncated guide sequence element is less than twenty nucleotides. In one embodiment, the resulting nuclease has improved cleavage activity at the target site relative to the same wild-type. Cas9 isoform. In one embodiment, the resulting nuclease has improved cleavage activity at a target site with suboptimal PAMs relative to the same wild-type Cas9 isoform. In one embodiment, the fusion protein comprising SpCas9 as the nuclease has improved cleavage activity at a target site with suboptimal PAMs (NAG, NGA or NGC) relative to wild-type SpCas9.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein may be used to describe specific embodiments of the invention, but their usage does not delimit the invention, except as outlined in the claims.

The term "about" as used herein, in the context of any of any assay measurements refers to +/−5% of a given measurement.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by 30 or so base pairs known as "spacer DNA". The spacers are short segments of DNA from a virus and may serve as a 'memory' of past exposures to facilitate an adaptive defense against future invasions (PMID 25430774).

As used herein, the term "Cas" or "CRISPR-associated (cas)" refers to genes often associated with CRISPR repeat-spacer arrays (PMID 25430774).

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence (PMID 22745249).

As used herein, the term "nuclease deficient Cas9", "nuclease dead Cas9" or "dCas9" refers to a modified Cas9 nuclease wherein the nuclease activity has been disabled by mutating residues in the RuvC and HNH catalytic domains. Disabling of both cleavage domains can convert Gas9 from a RNA-programmable nuclease into an RNA-programmable DNA recognition complex to deliver effector domains to specific target sequences (Qi, et al, 2013 (PMID 23452360) and Gilbert, et al, 2013 PMID 23849981) or to deliver an independent nuclease domain such as FokI. A nuclease dead Cas9 can bind to DNA via its PAM recognition sequence and guide RNA, but will not cleave the DNA.

The term "nuclease dead Cas9 FokI fusion" or "FokI-dCas9" as used herein, refers to a nuclease dead Cas9 that may be fused to the cleavage domain of FokI, such that DNA recognition may be mediated by dCas9 and the incorporated guide RNA, but that DNA cleavage may be mediated by the FokI domain (Tsai, et al. 2014 (PMID 24770325) and Guilinger, et al. (PMID 24770324). FokI normally requires dimerization in order to cleave the DNA, and as a consequence two FokI-dCas9 complexes must bind in proximity in order to cleave the DNA. FokI can be engineer such that it functions as an obligate heterodimer.

As used herein, the term "catalytically active Cas9" refers to an unmodified Cas9 nuclease comprising full nuclease activity.

The term "nickase" as used herein, refers to a nuclease that cleaves only a single DNA strand, either due to its natural function or because it has been engineered to cleave only a single DNA strand. Cas9 nickase variants that have either the RuvC or the HNH domain mutated provide control over which DNA strand is cleaved and which remains intact (Jinek, et al. 2012 (PMID 22745249) and Cong, et al. 2013 (PMID 23287718)).

The term "DNA targeting unit", "DTU" as used herein, refers to any type of system that can be programmed to recognize a specific DNA sequence of interest. Such DNA targeting units can include, but are not limited to a "programmable DNA binding domain" (either called a pDBD or simply a DBD), as defined below, and/or a CRISPR/Cas9 or CRISPR/CpfI system that may be programmed by a RNA guide (either a single guide RNA or a crRNA and tracrRNA combination) to recognize a particular target site.

The term, "trans-activating crRNA", "tracrRNA" as used herein, refers to a small trans-encoded RNA. For example, CRISPR/Cas (clustered, regularly interspaced short palindromic repeats/CRISPR-associated proteins) constitutes an RNA-mediated defense system, which protects against viruses and plasmids. This defensive pathway has three steps. First a copy of the invading nucleic acid is integrated into the CRISPR locus. Next, CRISPR RNAs (crRNAs) are transcribed from this CRISPR locus. The crRNAs are then incorporated into effector complexes, where the crRNA guides the complex to the invading nucleic acid and the Cas proteins degrade this nucleic acid. There are several pathways of CRISPR activation, one of which requires a tracrRNA, which plays a role in the maturation of crRNA. TracrRNA is complementary to base pairs with a pre-crRNA forming an RNA duplex. This is cleaved by RNase III, an RNA-specific ribonuclease, to form a crRNA/tracrRNA hybrid. This hybrid acts as a guide for the endonuclease Cas9, which cleaves the invading nucleic acid.

The term "programmable DNA binding domain" as used herein, refers to any protein comprising a pre-determined sequence of amino acids that bind to a specific nucleotide sequence. Such binding domains can include, but are not limited to, a zinc finger protein, a homeodomain and/or a transcription activator-like effector protein.

The term "protospacer adjacent motif" (or PAM) as used herein, refers to a DNA sequence that may be required for a Cas9/sgRNA to form an R-loop to interrogate a specific DNA sequence through Watson-Crick pairing of its guide RNA with the genome. The PAM specificity may be a function of the DNA-binding specificity of the Cas9 protein (e.g., a "protospacer adjacent motif recognition domain" at the C-terminus of Cas9).

As used herein, the term "sgRNA" refers to single guide RNA used in conjunction with CRISPR associated systems (Cas). sgRNAs are a fusion of crRNA and tracrRNA and contain nucleotides of sequence complementary to the desired target site (Jinek, et al. 2012 (PMID 22745249)). Watson-Crick pairing of the sgRNA with the target site permits R-loop formation, which in conjunction with a functional PAM permits DNA cleavage or in the case of nuclease-deficient Cas9 allows binds to the DNA at that locus.

As used herein, the term "orthogonal" refers targets that are non-overlapping, uncorrelated, or independent. For example, if two orthogonal Cas9 isoforms were utilized, they would employ orthogonal sgRNAs that only program one of the Cas9 isoforms for DNA recognition and cleavage (Esvelt, et al. 2013 (PMID 24076762)). For example, this would allow one Cas9 isoform (e.g. *S. pyogenes* Cas9 or spCas9) to function as a nuclease programmed by a sgRNA that may be specific to it, and another Cas9 isoform (e.g. *N. meningitidis* Cas9 or nmCas9) to operate as a nuclease dead Cas9 that provides DNA targeting to a binding site through its PAM specificity and orthogonal sgRNA. Other Cas9s include *S. aureus* Cas9 or SaCas9 and *A. naeslundii* Cas9 or AnCas9.

The term "truncated" as used herein, when used in reference to either a polynucleotide sequence or an amino acid sequence means that at least a portion of the wild type sequence may be absent. In some cases truncated guide sequences within the sgRNA or crRNA may improve the editing precision of Cas9 (Fu, et al. 2014 (PMID 24463574)).

The term "dimerization domain" as used herein, refers to a domain, either protein, polynucleotide that allows the associate of two different molecules. A dimerization domain can allow homotypic and/or heterotypic interactions. Dimerization domains can also be drug-dependent (i.e. depending on the presence of a small molecule in order to function) (Liang, et al. (PMID 21406691) and Ho, et al. 1996 (PMID 87522781).

The term "base pairs" as used herein, refer to specific nucleobases (also termed nitrogenous bases), that are the building blocks of nucleotide sequences that form a primary structure of both DNA and RNA. Double stranded DNA may be characterized by specific hydrogen bonding patterns, base pairs may include, but are not limited to, guanine-cytosine and adenine-thymine) base pairs.

The term "specific genomic target" as used herein, refers to any pre-determined nucleotide sequence capable of binding to a Cas9 protein contemplated herein. The target may include, but may be not limited to, a nucleotide sequence complementary to a programmable DNA binding domain or an orthogonal Cas9 protein programmed with its own guide RNA, a nucleotide sequence complementary to a single guide RNA, a protospacer adjacent motif recognition sequence, an on-target binding sequence and an off-target binding sequence.

The term "on-target binding sequence" as used herein, refers to a subsequence of a specific genomic target that may be completely complementary to a programmable DNA binding domain and/or a single guide RNA sequence.

The term "off-target binding sequence" as used herein, refers to a subsequence of a specific genomic target that may be partially complementary to a programmable DNA binding domain and/or a single guide RNA sequence.

The term "fails to bind" as used herein, refers to any nucleotide-nucleotide interaction or a nucleotide-amino acid interaction that exhibits partial complementarity, but has insufficient complementarity for recognition to trigger the cleavage of the target site by the Cas9 nuclease. Such binding failure may result in weak or partial binding of two molecules such that an expected biological function (e.g., nuclease activity) fails.

The term "cleavage" as used herein, may be defined as the generation of a break in the DNA. This could be either a single-stranded break or a double-stranded break depending on the type of nuclease that may be employed.

As used herein, the term "edit" "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target or the specific inclusion of new sequence through the use of an exogenously supplied DNA template. Such a specific genomic target includes, but may be not limited to, a chromosomal region, mitochondrial DNA, a gene, a promoter, an open reading frame or any nucleic acid sequence.

The term "delete", "deleted", "deleting" or "deletion" as used herein, may be defined as a change in either nucleotide or amino acid sequence in which one or more nucleotides or amino acid residues, respectively, are, or become, absent.

As used herein, the terms "complementary" or "complementarity" are used in reference to "polynucleotides" and "oligonucleotides" (which are interchangeable terms that refer to a sequence of nucleotide) related by the base-pairing rules. For example, the sequence "C-A-G-T," may be complementary to the sequence "A-C-T-G." Complementarity can be "partial" or "total." "Partial" complementarity may be where one or more nucleic acid bases may be not matched according to the base pairing rules. "Total" or "complete" complementarity between nucleic acids may be where each and every nucleic acid base may be matched with another base under the base pairing rules. The degree of complementarity between nucleic acid strands has significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which may be partially complementary, i.e., "substantially homologous," to a nucleic acid sequence may be one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This may be not to say that conditions of low stringency are such that non-specific binding may be permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be detected in a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which may be a "homolog" may be defined herein as an oligonucleotide sequence which exhibits greater than or equal to 50% identity to a sequence, when sequences having a length of 100 bp or larger are compared.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "gene of interest" as used herein, refers to any pre-determined gene for which deletion may be desired.

The term "allele" as used herein, refers to any one of a number of alternative forms of the same gene or same genetic locus.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and may be, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the term "hybridization" may be used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) may be impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" may be used in reference to the "melting temperature." The melting temperature may be the temperature at which a population of double-stranded nucleic acid molecules becomes half dissociated into single strands. As indicated by standard references, a simple estimate of the $T_m$ value may be calculated by the equation: $T_m=81.5+0.41$(% G+C), when a nucleic acid may be in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" may be used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences may be usually low between such organisms).

As used herein, the term "amplifiable nucleic acid" may be used in reference to nucleic acids which may be amplified by any amplification method. It may be contemplated that "amplifiable nucleic acid" will usually comprise "sample template."

As used herein, the term "sample template" refers to nucleic acid originating from a sample which may be analyzed for the presence of a target sequence of interest. In contrast, "background template" may be used in reference to nucleic acid other than sample template which may or may not be present in a sample. Background template may be most often inadvertent. It may be the result of carryover, or it may be due to the presence of nucleic acid contaminants sought to be purified away from the sample. For example, nucleic acids from organisms other than those to be detected may be present as background in a test sample.

"Amplification" may be defined as the production of additional copies of a nucleic acid sequence and may be generally carried out using polymerase chain reaction. Dieffenbach C. W. and G. S. Dveksler (1995) In: *PCR Primer, a Laboratory Manual*, Cold Spring Harbor Press, Plainview, N.Y.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring may be attached to the 3' oxygen of its neighbor in one direction via a phosphodiester linkage. Therefore, an end of an oligonucleotide may be referred to as the "5' end" if its 5' phosphate may be not linked to the 3' oxygen of a mononucleotide pentose ring. An end of an oligonucleotide may be referred to as the "3' end" if its 3' oxygen may be not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "bind", "binding", or "bound" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That may be typical when the binding component may be an enzyme and the analyte may be a substrate for the enzyme. Reactions resulting from contact between the binding agent and the analyte are also within the definition of binding for the purposes of the present invention.

BRIEF DESCRIPTION OF THE FIGURES

FIGS. 2A and 2B present schematic overviews of an exemplary CRISPR/Cas9 system fused to a DNA-targeting unit (in this case a programmable DNA-binding domain; DBD). For example, Cas9 recognizes a target sequence through Watson-Crick pairing of approximately 20 bases of an sgRNA (purple sequence) with one strand of the target DNA sequence and recognition of the neighboring PAM sequence (NGG—magenta letters) by the PAM-Interacting domain of the protein. Upon binding a target sequence, Cas9 generates a double stranded break (DSB) by cleaving each strand (blue arrowheads). The DBD (orange) can be fused to the N- or C-terminus (or perhaps both, where "N-" and "-C" indicate the N-terminus and C-terminus, respectively) with a linker molecule (orange) and programmed to recognize a neighboring sequence (pDBD binding site) to enhance specificity or increase the range of target sequences that can be cleaved by Cas9.

FIG. 9 illustrates one embodiment of PAM-interacting amino acid residues neighboring a NGG PAM (magenta) in the structure of SpCas9 (PMID 25079318; Top panel). The bottom panel presents an activity profile of SpCas9 (Blue) or SpCas9-Zif268 (red) bearing mutations at positions 1333 or 1335 in the PAM recognition sequence in comparison to wild-type (WT) SpCas9. SpCas9 bearing these mutations may be inactive on its own, but when fused to Zif268 (also referred to as DBD$^{268}$), activity may be restored due to a nearby a Zif268 binding site (Watson-5 bp). MT3 (R1335K) appears to have more stringent specificity (NAG PAM may be not functional). Data are from three independent biological replicates performed on different days, where HEK293T cells transfected with 50 ng Cas9$^{MT}$/Cas9$^{MT}$-Zif268 plasmid, 50 ng sgRNA plasmid, 150 ng GFP reporter with target site and 100 ng mCherry control plasmid.

FIG. 10 presents one embodiment of a T7EI assay on PCR products spanning a genomic target site with an NGG PAM and neighboring Zif268 site (Watson-11 bp) for various SpCas9 SpCas9-Zif268 mutants (MT #). For SpCas9$^{MT2}$ & SpCas9$^{MT3}$, strong activity may be observed when Zif268 is fused. Top Panel: Agarose gel images used showing three independent replicates (R1, R2, R3) for each nuclease platform. Cleaved bands indicating nuclease activity at each locus are indicated by red dots. Bottom Panel: The quantification of lesion frequencies data from three independent biological replicates performed on different days, where HEK293T cells transfected with 50 ng Cas9/Cas9-Zif268 plasmid, 50 ng sgRNA plasmid, and 100 ng mCherry control plasmid.

FIG. 11A: Local sequences of the PAM interacting domain mutants at positions 1333 or 1335 of SpCas9.

FIG. 11B: Analysis of SpCas9 mutant activity on different nGn or nnG PAM-containing target sites in the GFP reporter assay. Mutations that alter the interaction of R1333 with its guanine contact (nGn, green) reveal modest activity at nnG PAMs. Correspondingly, mutations that alter the interaction of R1335 with its guanine contact (nnG, magenta) reveal modest activity at nGn PAMs. Data are from three independent biological replicates performed on different days in HEK293T cells. Residues above each panel are positions 1333 through 1335 in SpCas9. Data are from three independent biological replicates performed on different days, where HEK293T cells transfected with 50 ng Cas9$^{MT}$/Cas9$^{MT}$-Zif268 plasmid, 50 ng sgRNA plasmid, 150 ng GFP reporter with target site and 100 ng mCherry control plasmid. Error bars indicate standard error of the mean.

FIG. 12 presents exemplary data of T7EI assays on PCR products spanning target site TS3 or off-target site 2 (OT3-2) in nuclease treated (or control) HEK293T cells (PMID 24463574). An sgRNA for TS3 (sgRNA-TS3) was used to program cleavage of SpCas9$^{WT}$, SpCas9-ZFP$^{TS3}$, SpCas9$^{MT3}$ or SpCas9$^{MT3}$-ZFP$^{TS3}$, where the ZFP was assembled from an archive of zinc fingers of defined specificity. Zhu et al., Using defined finger-finger interfaces as units of assembly for constructing zinc-finger nucleases. Nucleic Acids Research. 2013 Feb. 1; 41(4):4455-65; and Gupta et al., An optimized two-finger archive for ZFN-mediated gene targeting. Nature Methods. 2012 Apr. 29; 9(6):588-90. Top Panel: An exemplary agarose gel image displaying DNA lesion profile after T7EI treatment. Cleaved bands indicating nuclease activity at each locus are indicated by red dots. SpCas9$^{MT3}$-ZFP$^{TS3}$ shows no apparent activity at OT3-2, whereas it cleaves the target site efficiently. Bottom Panel: Quantification of lesion frequencies data from three independent biological replicates, where HEK293T cells transfected with 50 ng Cas9/Cas9$^{MT3}$/Cas9-ZFP$^{TS3}$/Cas9$^{MT3}$-ZFP$^{TS3}$ plasmid, 50 ng sgRNA plasmid, and 100 ng mCherry control plasmid.

FIG. 22 illustrates a schematic of chimeric SpCas9-DTU in the context of existing SpCas9 variants (e.g., for example, truncated sgRNAs, nickases, and FokI-dCas9). These platforms can be combined with a Cas9 nuclease-DTU to use mutant versions of Cas9 that are attentuated (yellow star) to maintain activity dependence on the DTU.

FIG. 23A: a schematic overview of a B2H system where interaction domains on RNA polymerase and dSpCas9-DBD facilitate recruitment of polymerase and promoter activation upon target site recognition within a reporter vector. The selection of an optimal linker from a randomized library that promotes efficient binding by dSpCas9-DBD should be possible in this framework;
and FIG. 23B: an initial test of a dSpCas9 system on an NGG PAM target site (e.g., no DBD). Right: a 10× dilution series on non-selective media; Left: the same series but on selective media with 2 mM 3-AT and no histidine. The dCas9/sgRNA-programmed cells with a complementary target site in the reporter survive the selection. Further optimization of the expression construct may yield cells that grow at a rate even closer to that of the positive control.

FIG. 26 presents a DNA sequence alignment of a short region nearby PAM interacting residues (Red highlight residues 1333 to 1335) of wild type SpCas9 and mutants described here.

FIG. 27 presents one embodiment of a plasmid expressing SpCas9-Zif268 fusion protein. SpCas9 sequence may be underlined where PAM interacting residues are highlighted in red and Zif268 may be highlighted in green.

FIG. 28 presents one embodiment of a plasmid expressing Zif268-SpCas9 fusion protein. SpCas9 sequence may be underlined where PAM interacting residues are highlighted in red and Zif268 may be highlighted in green.

FIG. 29 presents one embodiment of a plasmid expressing SpCas9-TAL268 fusion protein. SpCas9 sequence may be underlined where PAM interacting residues are highlighted in red and TAL268 may be highlighted in blue.

FIG. 30 presents one embodiment of a plasmid expressing TAL268-SpCas9 fusion protein. SpCas9 sequence may be underlined where PAM interacting residues are highlighted in red and TAL268 may be highlighted in blue.

FIG. 31 presents one embodiment of a plasmid expressing SpCas9-ZFP$^{TS2}$ fusion protein. SpCas9 sequence may be underlined where PAM interacting residues are highlighted in red and ZFP$^{TS2}$ may be highlighted in yellow.

FIG. 32 presents one embodiment of a plasmid expressing SpCas9$^{MT3}$-ZFP$^{TS2}$ fusion protein. SpCas9 sequence may be underlined where PAM interacting residues are highlighted in red/gray and ZFP$^{TS2}$ may be highlighted in yellow.

FIG. 33 presents one embodiment of a plasmid expressing SpCas9-ZF$^{TS3}$ fusion protein. SpCas9 sequence may be underlined where PAM interacting residues are highlighted in red and ZFP$^{TS3}$ may be highlighted in magenta.

FIG. 34 presents one embodiment of a plasmid expressing SpCas9-ZFP$^{TS3}$ fusion protein. SpCas9 sequence may be underlined where PAM interacting residues are highlighted in red/gray and ZFP$^{TS3}$ may be highlighted in magenta.

FIG. 35 presents one embodiment of a plasmid expressing SpCas9-ZFP$^{TS4}$ fusion protein. SpCas9 sequence may be underlined where PAM interacting residues are highlighted in red and ZFP$^{TS4}$ may be highlighted in cyan.

FIG. 36 presents one embodiment of a plasmid expressing SpCas9$^{MT3}$-ZFP$^{TS4}$ fusion protein. SpCas9 sequence may be underlined where PAM interacting residues are highlighted in red/gray and ZFP$^{TS4}$ may be highlighted in cyan.

FIG. 37 presents one embodiment of a sequence of Cas9-Zif268 (also referred to as DBD$^{268}$) fusion protein.

FIG. 38 presents one embodiment of a sequence of Zif268-Cas9 fusion protein.

FIG. 39 presents one embodiment of a sequence of Cas9-TAL268 fusion protein.

FIG. 40 presents one embodiment of a sequence of TAL268-Cas9 fusion protein.

FIG. 41 presents one embodiment of a sequence of Cas9-ZFP$^{TS4}$ fusion protein.

FIG. 42 presents one embodiment of a sequence of Cas9-ZFP$^{TS2*}$ fusion protein.

FIG. 43 presents one embodiment of a sequence of Cas9-ZFP$^{TS3}$ fusion protein.

FIG. 44A-D presents exemplary data showing that SpCas9$^{MT}$-ZFP chimeras have improved precision.

FIG. 44A: Sequences of Target Site 2 (TS2), TS3 and TS4$^{20,26}$ with the 12 bp ZFP binding sites highlighted in green, red and blue, respectively, with the arrow indicating the bound DNA strand.

FIG. 44B: Lesion rates determined by T7EI assay$^{77,78}$ for SpCas9, SpCas9$^{MT3}$ and SpCas9$^{MT3}$-ZFP at TS2, TS3 and TS4. Data are from three independent biological replicates performed in HEK293T cells. Error bars indicate s.e.m.

FIG. 44C: Deep sequencing analysis of SpCas9$^{MT3}$-ZFP precision. Lesion rates for target sites and off-target sites with significant activity assayed by sequencing PCR products spanning each genomic locus for SpCas9 (blue), SpCas9$^{MT3}$-ZFP (red) and Neg control (green). Error bars indicate s.e.m. Asterisks indicate OT sites where the cleavage rate for SpCas9$^{MT3}$-ZFP is significantly above the NegCT.

FIG. 44D: Example GUIDE-seq peaks for Cas9$^{WT}$ (top) and SpCas9$^{MT3}$-ZFP$^{TS2}$ (bottom). Both have strong peaks at TS2 target site, but only Cas9$^{WT}$ has signal at OT2-1. The position of each site is indicated above the peak.

FIG. 49A: Activity profile of NmCas9 and Zif268-NmCas9 on a common target site with different PAM sequences and a neighboring Zif268 site.

FIG. 49B: Activity profile of NmCas9, NmCas9$^{DM}$ (attenuated by K1013A and R1025A), and Zif268-NmCas9$^{DM}$ on a common target site, with different spacings between the GATT PAM and a Zif268 site.

FIG. 52A: Schematic of the SpCas9/sgRNA system and the two sequential stages of licensing required for cleavage: Stage 1—PAM recognition (nGG is highly preferred) and Stage 2—complementary R-loop formation between the 20 nucleotide guide RNA and the interrogated DNA sequence.

FIG. 52B: Genome-wide analysis using CRISPRseek[21] of the potential off target sites for a representative set of 124,793 guide RNAs targeting human exons sequences. Guides were binned based on the predicted off-target site with the smallest number of mismatches to the guide sequence. A perfect match indicates the presence of an off-target site with a perfect guide match (red wedge). Only 1.6% of these guide sequences do not have an off-target site with 3 or fewer mismatches to the guide sequence (green wedge). This subset would be the best candidates for precise genome editing. The vast majority of guides typically have many potential off-target sequences with 3 or fewer mismatches.

FIG. 52C: Genome-wide analysis of the minimum number of mismatches in off-target sites for a representative set of 55,687 guide RNAs targeting human promoter regions (binned as describe above). Only 1% of these guide sequences do not have an off-target site with 3 or fewer mismatches to the guide sequence (green wedge).

FIG. 53A: Genome-wide analysis of the sum of off-target scores determined by CRISPRseek[28] for the top 10 off-target sites for a representative set of 124,793 guide RNAs targeting gene exons. These were binned into five different categories where a lower score is better. An off-target site is scored as 100 if it is a perfect match to the guide sequence.

FIG. 53B: Genome-wide analysis of the sum of the off-target scores determined by CRISPRseek[28] for the top 10 off-target sites for a representative set of 55,687 guide RNAs targeting gene promoter regions.

FIG. 53C: Guide RNAs targeting gene exons with no predicted off-targets with <=3 mismatches (green wedge) are analyzed for off-target sites with potential bulges in the sgRNA:DNA heteroduplex[29]. Red wedges indicate the fraction of guides that have one or more off-target sites that have perfect complementarity with the exception of a single bulge.

FIG. 53D: Guide RNAs targeting gene promoters with no predicted off-targets with <=3 mismatches (green wedge) are analyzed for off-target sites with potential bulges in the sgRNA:DNA duplex. Red wedges indicate the fraction of guides that have one or more off-target sites that have perfect complementarity with the exception of a single bulge.

FIG. 56A presents exemplary data showing T7 Endonuclease I (T7EI) assays on PCR products spanning a genomic target site (underlined) with an NGG PAM (magenta) and neighboring Zif268 site (orange) for SpCas9 or SpCas9 mutants with or without a Zif268 fusion. For SpCas9$^{MT2}$ & SpCas9$^{MT3}$, robust nuclease activity is only observed when Zif268 is fused to the C-terminus. The gel image is representative of T7EI assays at this genomic target site, where cleaved products are noted by magenta arrowheads.

FIG. 56B presents exemplary data showing quantification of average T7EI-based lesion rates at the PLXNB2 locus from three independent biological replicates performed on different days in HEK293T cells. Error bars indicate standard error of the mean.

FIG. 59 presents exemplary data of an analysis of a genomic activity profile of SpCas9$^{MT3}$-ZFP$^{DCLK2}$ and SpCas9$^{MT3}$-ZFP$^{F9}$ at DNAJC6 and PLXDC2 sites respectively. These sequences have compatible binding sites for the DCLK2[7] and Factor IX[1] ZFPs. T7 EI assay data from PCR products spanning the target site from single experiment done in HEK293T cells. Cleaved products are indicated by magenta arrowheads. Similar analysis of SpCas9$^{MT3}$-ZFP$^{HEBP2}$ (targeting a compatible binding site for the HEBP2 ZFP6) at GPRC5B did not detect any lesions for this SpCas9$^{MT3}$-ZFP fusion (data not shown).

FIG. 60A: Sequences of Target Site 2 (TS2), Target Site 3 (TS3) and Target Site 4 (TS4) for the SpCas9/sgRNAs described by Joung and colleagues[14,25]. The 12 bp ZFP binding sites for TS2, TS3 and TS4 are highlighted in green, red and blue, respectively, with the arrow indicating the strand that is bound.

FIG. 60B: Lesion rates determined by T7EI assay for SpCas9, SpCas9$^{MT3}$ and SpCas9$^{MT3}$-ZFP at TS2, TS3 and TS4. Data are from three independent biological replicates performed on different days in HEK293T cells. Error bars indicate standard error of the mean.

FIG. 60C: Representative T7EI assay comparing lesion rates at TS3 and off-target site 2 (OT3-2)[25] for various SpCas9-chimera/sgRNA combinations. The activity at the target site for SpCas9$^{MT3}$-ZFP is dependent on the cognate sgRNA and ZFP, where SpCas9$^{MT3}$-ZFP$^{TS3}$ can discriminate between TS3 and OT3-2.

FIG. 60D: Genomic target site cleavage activity by SpCas9, SpCas9$^{WT}$-ZFP$^{TS3}$ and SpCas9$^{MT3}$-ZFP$^{TS3}$ in response to dinucleotide mismatches placed at different positions within the guide sequence targeting the TS3 site. (Top Panel) T7EI assay data from PCR products spanning TS3 site in three independent biological replicates performed on different days in HEK293T cells. Error bars indicate standard error of the mean. (Bottom Panel) Schematic indicating the position of the dinucleotide mismatches across the guide sequence. SpCas9$^{MT3}$-ZFP$^{TS3}$ displays superior discrimination to SpCas9 for dinucleotide mismatches in the sgRNA recognition sequence.

FIG. 62 presents exemplary data showing an analysis of a genomic activity profile of SpCas9$^{MT3}$-TALE$^{TS3}$ and SpCas9$^{MT3}$-TALE$^{TS4}$ at the TS3 and TS4 sites, respectively. An arrow indicates the strand (Watson) of the highlighted sequence that is bound by the TALE. Two different TALE repeat lengths (9.5 and 15.5) were examined at each target site. T7EI assay data from PCR products spanning the target site in three independent biological replicates (Rep1, Rep2, Rep3) performed on different days in HEK293T cells. Cleaved products are indicated by magenta arrowheads.

FIG. 63A-C presents exemplary data showing an activity profile of SpCas9$^{MT3}$-ZFP$^{TS3/TS4}$ with truncated sgRNAs (tru-gRNA)[34].

FIG. 63A: Nuclease activity based on T7EI assay for SpCas9$^{WT}$ and SpCas9$^{MT1}$-ZFP$^{TS3}$ with a 17 nucleotide truncated guide at the TS3 target site.

FIG. 63B: Nuclease activity based on T7EI assay for SpCas9$^{WT}$ and SpCas9$^{MT3}$-ZFP$^{TS4}$ with an 18 nucleotide truncated guide at the TS4 target site. Cleaved products are indicated by magenta arrowheads.

FIG. 63C: Target sites for the TS3 and TS4 tru-gRNAs and graph showing the average activity at each target site in three independent biological replicates performed on different days in HEK293T cells. Error bars indicate standard error of the mean. For both TS3 and TS4, the SpCas9$^{MT3}$-ZFP chimera is more sensitive to the truncation of the guide sequence, which is consistent with the greater sensitivity of this system to guide mismatches.

FIG. 64A-C presents exemplary data showing a deep sequencing analysis of SpCas9$^{MT3}$-ZFP chimera precision.

FIG. 64A: Lesion rates for target sites and off-target sites with significant activity assayed by deep sequencing PCR products spanning each genomic locus for SpCas9 (blue). SpCas9$^{MT3}$ (light blue), SpCas9$^{WT}$-ZFP (red) and SpCas9$^{MT3}$-ZFP (pink) and untreated (NegCT, green). Error bars indicate standard error of the mean.

FIG. 64B: Improvement in precision of SpCas9$^{MT3}$-ZFP relative to SpCas9$^{WT}$ as measured by the relative Specificity Ratio of target site lesion rate relative to each off-target lesion rate (Specificity Ratio=Target site lesion rate/Off-target lesion rate).

FIG. 64C: Comparison of average lesion rates at TS2 and OT2-2 determined by T7EI assay for SpCas9$^{WT}$ and SpCas9$^{MT3}$-ZFP$^{TS3}$ variants that alter the number of zinc fingers or change them completely (TS2*). The binding site for the ZFP$^{TS2*}$ is indicated in blue. Removing finger 1 (F2-4) or finger 4 (F1-3) from the four finger TS2 ZFP array (F1-4) at most modestly impacts target site activity, but it dramatically improves precision. Data are from three independent biological replicates performed on different days in HEK293T cells. Error bars indicate standard error of the mean.

FIG. 66A: Both Cas9$^{WT}$ and SpCas9$^{MT3}$-ZFP$^{TS2}$ with four fingers (F1-4) result in efficient cleavage at the TS2 target site (magenta arrowheads indicate cleaved products). Removing a single finger from either end of the zinc finger array (F1-3 or F2-4) at most modestly reduces activity of the SpCas9$^{MT3}$-ZFP chimera. Removing a both terminal fingers from the zinc finger array (F2-3) dramatically reduces activity of the SpCas9$^{MT3}$-ZFP chimera. Construction of an alternate ZFP (TS2*) that recognizes an overlapping target site can also promote target cleavage.

FIG. 66B Both Cas9$^{WT}$ and SpCas9$^{MT3}$-ZFP$^{TS2}$ with four fingers (F1-4) result in efficient cleavage at the OT2-2 off-target site (magenta arrowheads indicate cleaved products). Removing a single finger from either end of the zinc finger array (F1-3 or F2-4) dramatically reduces activity of the SpCas9$^{MT3}$-ZFP chimera. As does the utilization of an alternate ZFP (TS2*) that recognizes a different target site. Data from three independent biological replicates (Rep1, Rep2, Rep3) performed on different days in HEK293T cells.

FIG. 67A: Number of off-target sites with nuclease activity detected for SpCas9$^{WT}$ (blue) and SpCas9$^{MT3}$-ZFP (red) with TS2, TS3 and TS4 guides.

FIGS. 77B-67D: Number of unique reads captured by GUIDE-seq for nuclease active sites within the genome (TS2/TS3/TS4 target site [bold] and off-target sites). Previously defined off-target sites are colored black[14,17] and potential new off-target sites that were identified in this analysis are colored green for SpCas9$^{WT}$ or orange for SpCas9$^{MT3}$-ZFP. Some sites (e.g. OGT2-10 & OGT2-20) contain only reads from a single library for SpCas9MT3-ZFP and are not binned as off-target sites.

FIG. 72, presents exemplary data examining the impact of spacing of a downstream Zif268 binding site relative to the PAM on the activity of NmCas9$^{SM}$ or NmCas9$^{DM}$ fused to Zif268 in the split-GFP reporter assay. The spacing between the PAM and the downstream Zif268 binding site (W orientation) was varied as indicated. In addition, only the fusion with Zif268 at the N-terminus of NmeCas9 was used, and NmeCas9 included the 1025A single mutation alone (top) or the K1013A/R1025A double mutation (bottom).

FIG. 79 presents exemplary data demonstrating that a ZFP fusion can restore activity of the single or double NmCas9 mutants at a number of alternate PAMs in the split-GFP reporter assay. These reporters include a Zif268 binding site (Watson orientation), 5 base pairs downstream of the PAM. The PAM was either wild-type (GATT), or mutated as indicated. The NmCas9-expressing plasmid encoded either WT NmeCas9, the R1025A single-mutant NmCas9 (SM, top panel), or the K1013A/R1025A double-mutant NmCas9 (DM, lower panel). In addition, NmCas9 was fused to no additional domains [blue bars, wild-type NmCas9; red bars, SM NmCas9 (top panel) or DM NmCas9 (bottom panel)], or to N-terminal Zif268 (green bars). HEK293 cells in 24-well plates were transfected with 100 ng split-GFP reporter. Also included in the transfections were 10 ng of an mCherry-expressing plasmid (as a transfection marker), and 290 ng of the plasmid expressing NmCas9 and the spacer 9-containing sgRNA. Three identical transfections were done on different days. In each case, after 48 hours post-transfection, cells were harvested and analyzed by flow cytometry to identify the fraction of mCherry-positive cells that were also GFP-positive.

FIG. 84 presents one embodiment of a sequence of NmCas9.

FIG. 85 presents one embodiment of a sequence of NmCas9 R1025A (also referred to as NmCas9$^{SM}$) fusion protein.

FIG. 86 presents one embodiment of a sequence of NmCas9 K1013A/R1025A (also referred to as NmCas9$^{DM}$) fusion protein.

FIG. 87 presents one embodiment of a sequence of Zif268-NmCas9 fusion protein.

FIG. 88 presents one embodiment of a sequence of NmCas9-Zif268 fusion protein.

FIG. 89 presents one embodiment of a sequence of Zif268-NmCas9$^{SM}$ fusion protein.

FIG. 90 presents one embodiment of a sequence of NmCas9$^{SM}$-Zif268 fusion protein.

FIG. 91 presents one embodiment of a sequence of Zif268-NmCas9$^{DM}$ fusion protein.

FIG. 92 presents one embodiment of a sequence of NmCas9$^{DM}$-Zif268 fusion protein.

FIG. 93 presents exemplary data demonstrating that SpCas9$^{MT3}$-NmdCas9 nucleases programmed with orthogonal guides for neighboring target sites can function as a cohesive unit to cleave DNA. Four different combinations (D1 through D4) of SpCas9 (underlined target sequence neighboring Red TGG PAM) and NmCas9 (underlined target sequence neighboring Blue GATT or AATC PAM depending on DNA strand that is bound). These different target site orientations are separated by 6 to 30 bp of DNA (6 bp "gctagc" spacer shown in each sequence) in the Split-GFP reporter assay. The bar graph represents the mean activities of SpCas9 (SpWT—blue bar), NmCas9 (NmWT—red bar), SpCas9$^{MT3}$ (SpMT3—green bar) or SpCas9$^{MT3}$-NmdCas9 (SpMT3-Nmd—purple bars) for biological triplicate experiments. Error bars represent standard error of the mean. SpCas9$^{MT3}$-NmdCas9 displays good activity on D1 and D2 oriented sites at most spacings. Note—SpCas9$^{MT3}$ has only background activity on site D1-6 bp (green bar).

FIG. 94 presents exemplary data demonstrating that NmdCas9-SpCas9$^{MT3}$ nucleases programmed with orthogonal guides for neighboring target sites can function as a cohesive unit to cleave DNA. Four different combinations (D1 through D4) of SpCas9 (underlined target sequence neighboring Red TGG PAM) and NmCas9 (underlined target sequence neighboring Blue GATT or AATC PAM (SEQ ID NO:2) depending on DNA strand that is bound). These different target site orientations are separated by 6 to 30 bp of DNA (6 bp "gctagc" spacer shown in each sequence) in the Split-GFP reporter assay. The bar graph represents the mean activities of SpCas9 (SpWT—blue bar), SpCas9$^{MT3}$ (SpMT3—red bar) or NmdCas9-SpCas9$^{MT3}$ (Nmd-SpMT3—green bars) for biological triplicate experiments. Error bars represent standard error of the mean. NmdCas9-SpCas9$^{MT3}$ displays good activity on some D1 and D2 oriented sites depending on the spacing between the domains. Note—SpCas9$^{MT3}$ has only background activity on site D1-6 bp (red bar).

Figure 95:
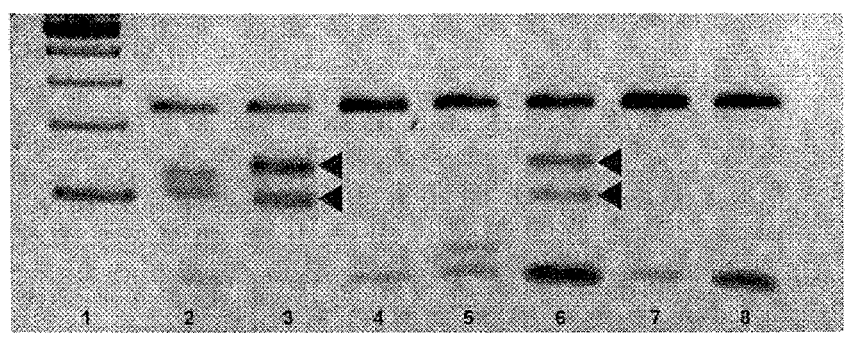

FIG. 95 presents exemplary data demonstrating that the SpCas9$^{MT3}$-NmdCas9 nucleases programmed with orthogonal guides for neighboring target sites can target genomic sequences. T7 Endonuclease I (T7EI) assay showing cleavage activity of SpCas9$^{MT3}$-dNmCas9 fusions at a genomic target site. (Top) Organization of the target site where the binding sites of SpCas9$^{MT3}$ and dNmCas9 are oriented with the PAMs between the protospacers. (SpCas9 NGG PAM on Watson strand and dNmCas9 NNNNGATT PAM (SEQ ID NO:1) on the Crick Strand, where 20 and 24 bp represent the sgRNA complementary regions for SpCas9 and NmCas9, respectively.) (Bottom) T7EI nuclease assay on PCR products of genomic regions spanning the SpCas9$^{MT3}$-dNmCas9 target site. Different combinations of fused or unfused SpCas9 and NmCas9 or SpCas9$^{MT3}$-dNmCas9 are examined with different combinations of sgRNAs. Both the wildtype (WT) SpCas9 (magenta arrowheads, lane 3) and NmCas9 nuclease can cleave their respective target sites. However, SpCas9$^{MT3}$ is ineffective, but can be rescued by dNmCas9 fused to the C-terminus, which substitutes as the DTU (lane 6).

Figure 96:
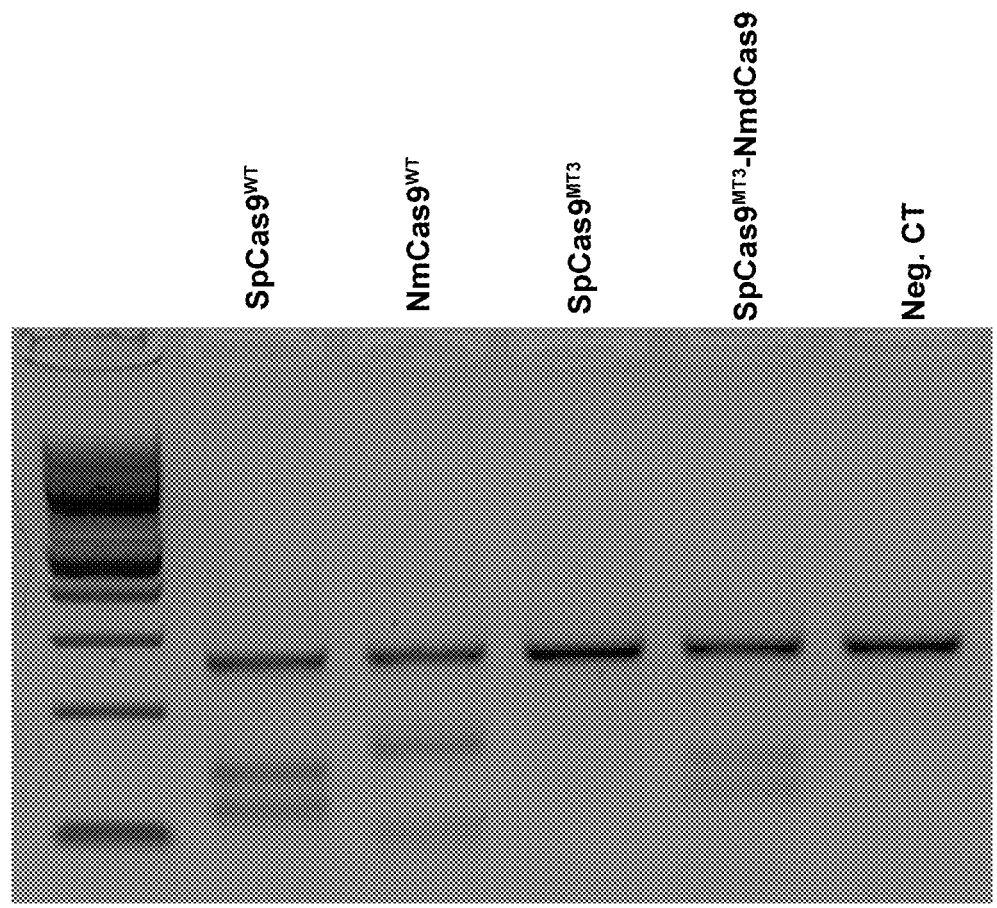

FIG. 96 presents exemplary data demonstrating that the SpCas9$^{MT3}$-NmdCas9 nucleases programmed with orthogonal guides for neighboring target sites can efficiently cleave the TS3 target site. (Top) Organization of the target site where the binding sites of SpCas9$^{MT3}$ and dNmCas9 are oriented with the PAMs on the same strand. (SpCas9 NGG PAM—red and dNmCas9 NNNNGATT PAM (SEQ ID NO:1)—blue, where underlined 20 and 24 bp represent the sgRNA complementary regions for SpCas9 and NmCas9, respectively). (Bottom) T7EI nuclease assay on PCR products of genomic regions spanning the SpCas9$^{MT3}$-NmdCas9 target site (TS3). Wild-type SpCas9 (SpCas9$^{WT}$) and wild-type NmCas9 (NmCas9$^{WT}$) programmed with their sgRNAs can cleave the target site. Attenuated SpCas9 (SpCas9$^{MT3}$) cannot cleave the target unless tethered to NmdCas9 (SpCas9$^{MT3}$-NmdCas9).

Figure 97:
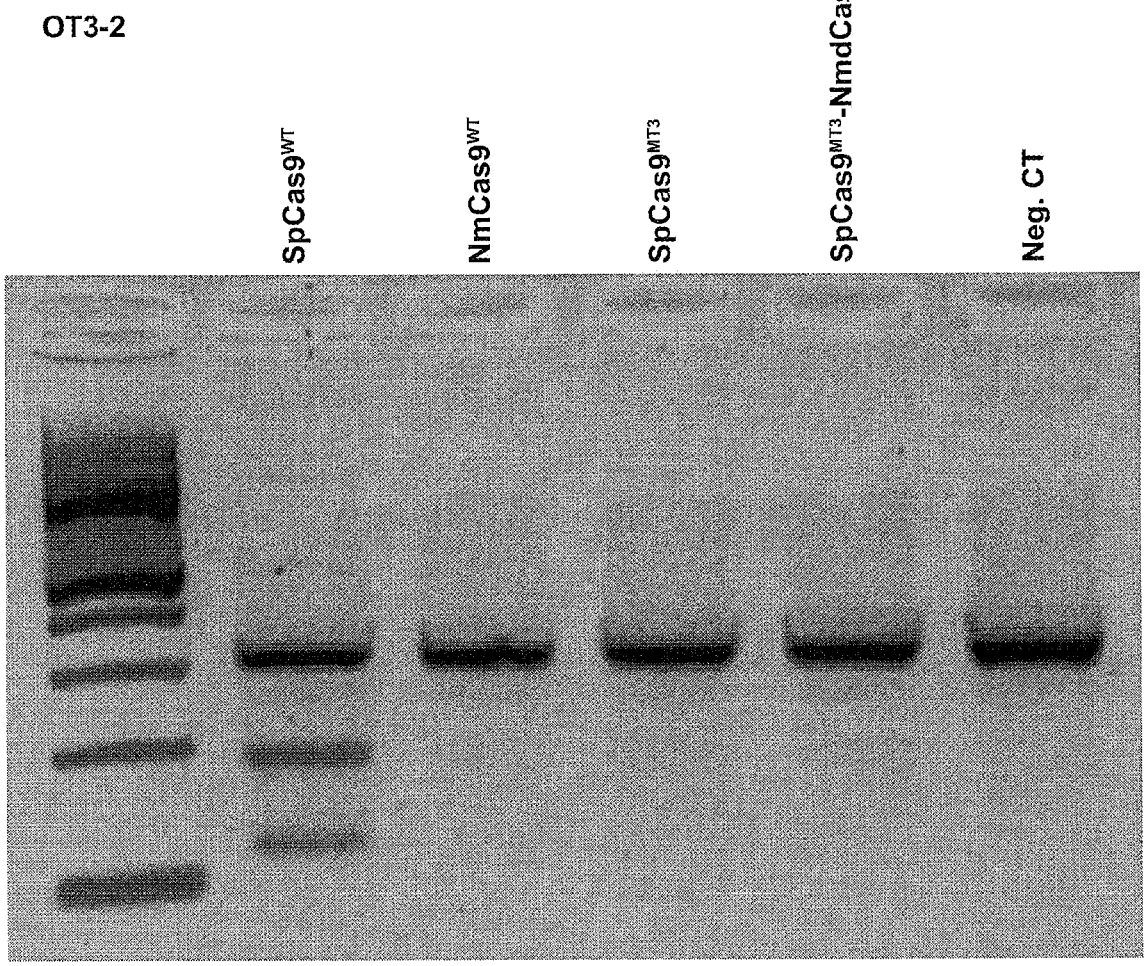

FIG. 97 presents exemplary data demonstrating that the SpCas9$^{MT3}$-NmdCas9 nucleases programmed with orthogonal guides for neighboring target sites have greatly improved precision relative to wild-type SpCas9 (SpCas9$^{WT}$). Genomic DNA treated with the constructs from FIG. 95 (i.e. programmed to target the TS3 genomic site) were analyzed to examine the off-target activity at site OT3-2, which is the most active off-target site for wild-type SpCas9. T7EI nuclease assay on PCR products of genomic regions spanning the OT3-2 off-target site for cells treated with each nuclease programmed with sgRNAs for the TS3 locus. Wild-type SpCas9 efficiently cleaves this off-target site whereas SpCas9$^{MT3}$-NmdCas9 displays no activity. This demonstrates a dramatic improvement in the precision of our attenuated dual Cas9 fusion protein.

Figure 98:
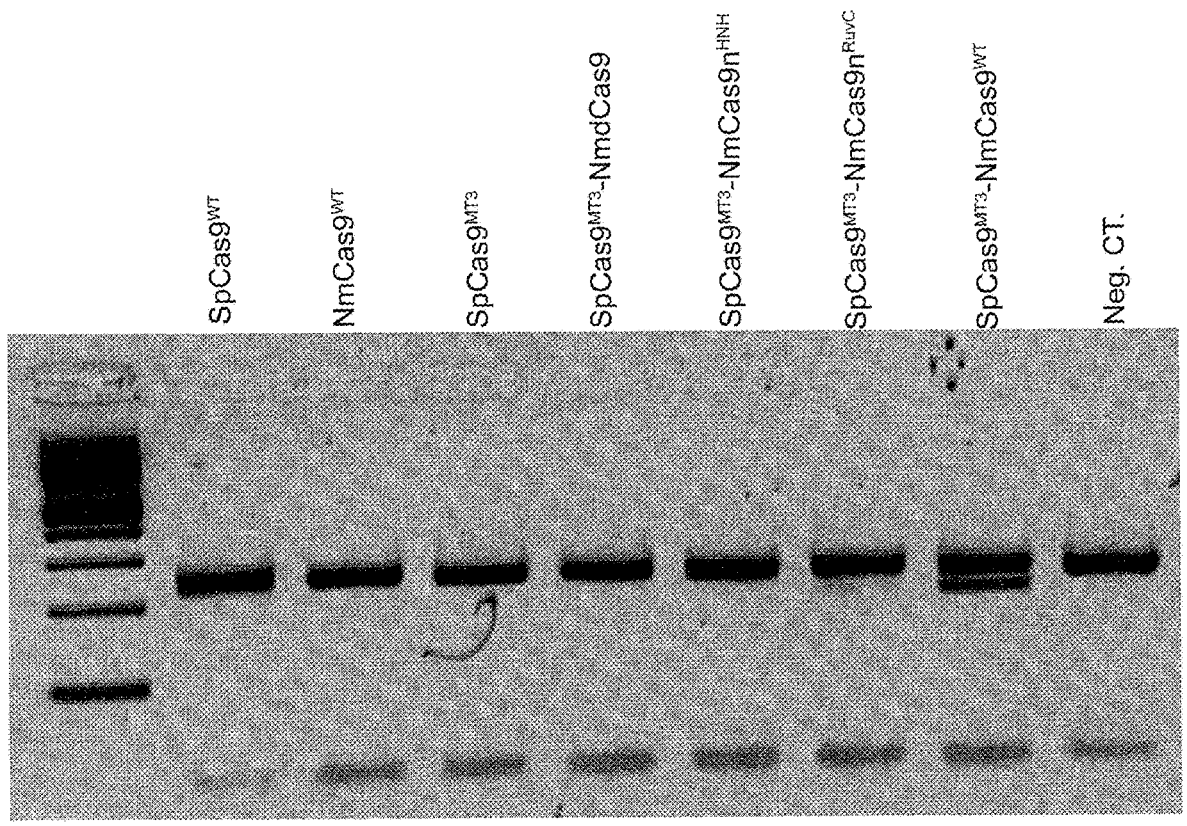

FIG. 98 presents exemplary data demonstrating that SpCas9$^{MT3}$-NmCas9 fusions can generate local deletions within the genome. Cells were treated with the corresponding nuclease and their complementary sgRNAs. The local genomic sequence was PCR amplified from the genomic DNA of treated cells and run on an agarose gel. There is evidence of a deletion (smaller amplified product) at the genomic locus in the SpCas9$^{MT3}$-NmCas9 dual nuclease treated cells.

Figure 99:
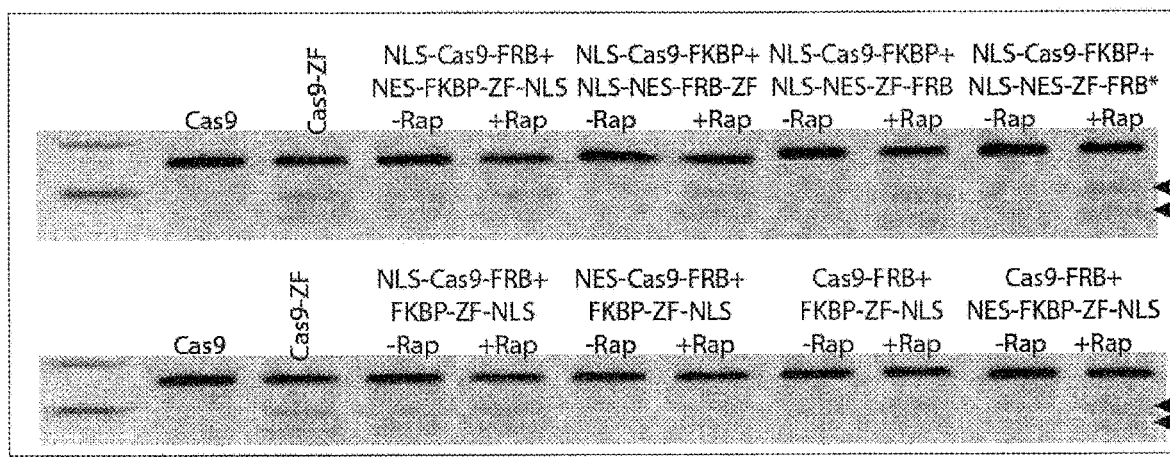

FIG. 99 presents exemplary data demonstrating that the fusion partners of the FRB and FKBP domains influences activity of the nuclease and that the incorporation of a Nuclear localization sequence (NLS) and nuclear export sequence (NES) on different components are critical for improving activity and reducing the background cleavage rate in the absence of the dimerizing drug (Rapamycin). Improvements in the substituents and the order of the localization and dimerization domains on the SpCas9 and pDBD scaffold plays an important role in improving function. Top: Fusion of Cas9 to FKBP and a C-terminal fusion of destabilized FRB (FRB*) to ZF was found to be superior for achieving maximum activity in presence of drug (Rapamycin: Rap) and lowest background in absence of drug. (Magenta arrowheads denote bands indicating nuclease activity) Bottom: Removing NLS from Cas9 and adding 2×NES and 2×NLS to the DBD component reduces background and increases drug-dependent activity at the target site.

Figure 100:
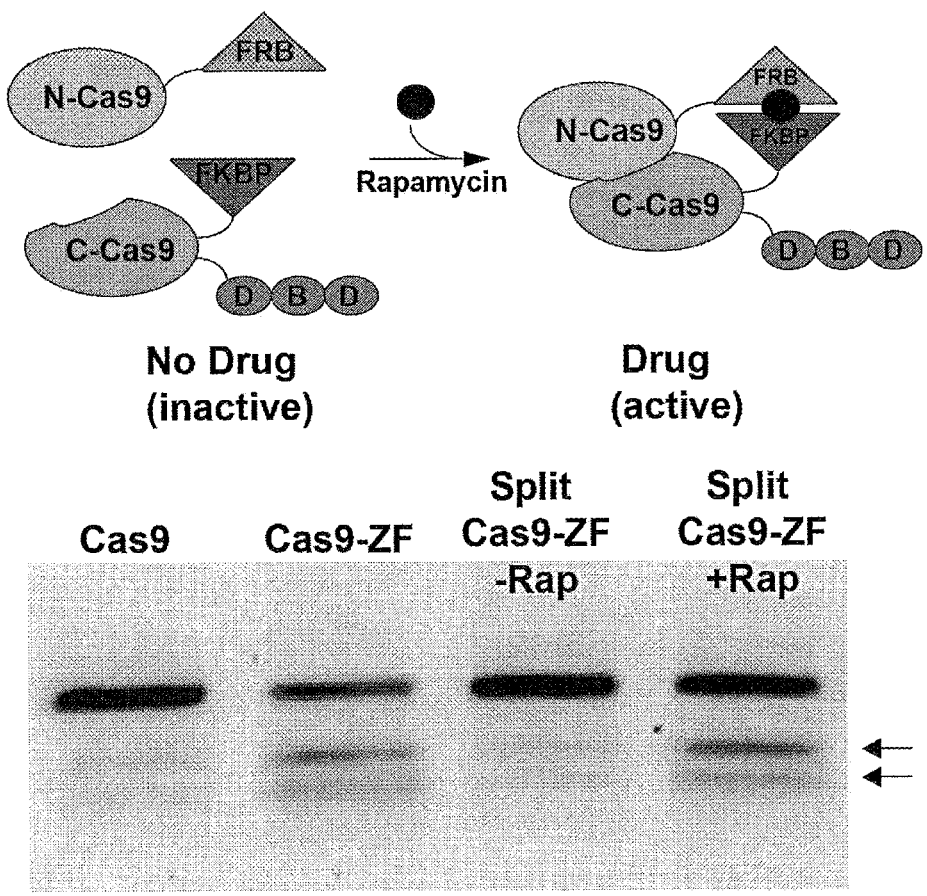

FIG. 100 presents exemplary data demonstrating that fusion of Zif268 to Split-SpCas9 broadens the targeting range of this system. Top: schematic of drug-inducible split-cas9-DBD fusion. Bottom: Fusion of DBD of the C-terminal component of drug-inducible split Cas9 results in high activity at the target site containing a suboptimal NAG PAM and a neighboring zinc finger binding site only in the presence of the drug (Rapamycin). Lesions in the genomic DNA are detected by T7EI assay, where the bands indicative of nuclease modification of the genome are indicated by arrows.

Figure 101:
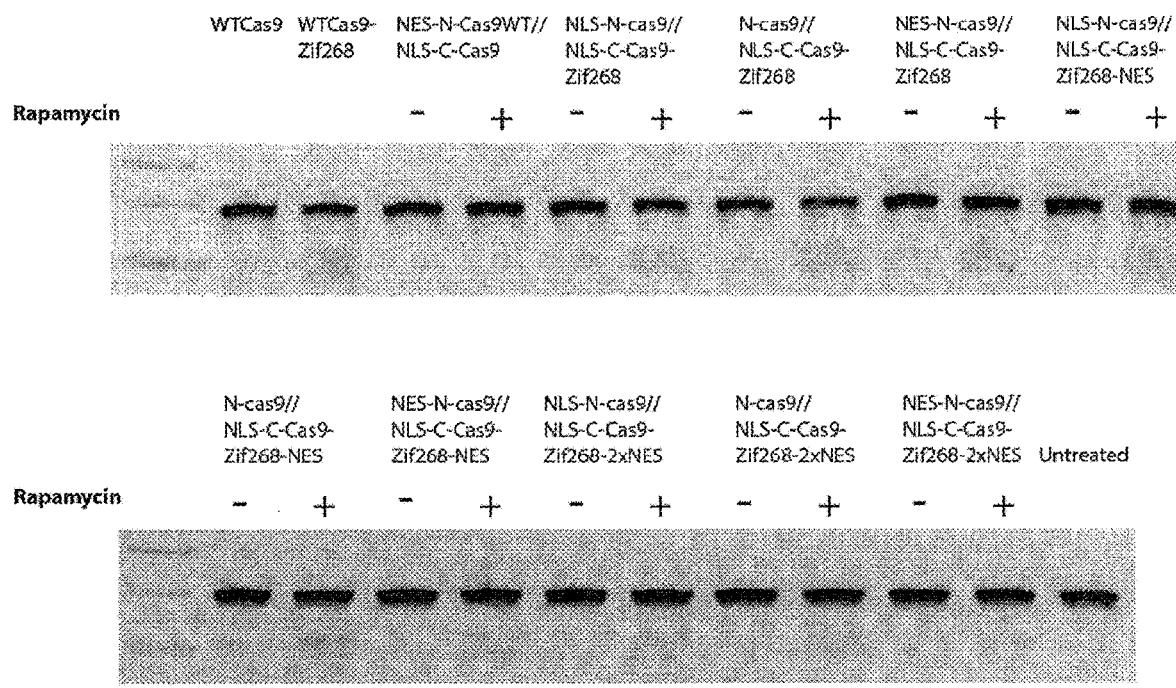

FIG. 101 presents exemplary data demonstrating the analysis of various combinations of NES and NLS sequences on Split-Cas9 and Split-Cas9-ZFP activity at a target site containing and AG PAM at the Pmpca locus. The N-terminal domain of the Split-Cas9 (blue) contains FKBP and the C-terminal domain (red) contains FRB. Activity should be realized by the presence of Rapamycin, where this is assessed via a T7EI assay. Modulating the presence and number of the NLS and NES domains on each component can dramatically change the drug-dependent activity and background cleavage rates.

Figure 102:
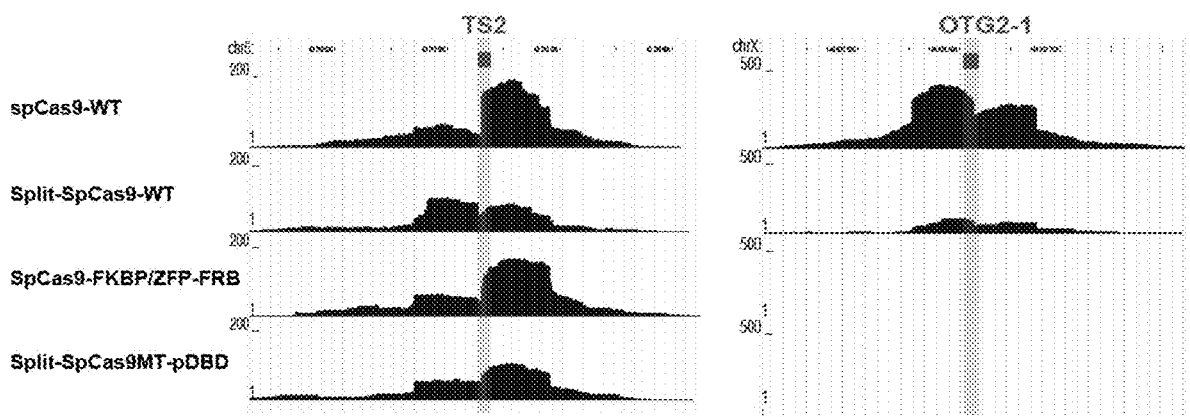

FIG. 102 presents exemplary data demonstrating the improved specificity of out engineered drug dependent systems programmed with the sgRNA and ZFP targeting the TS2 target site based on GUIDE-seq. (Top) comparison of the sequence of the TS2 target site and a highly active off-target site (OTG2-1), where the PAM is bold and the non-canonical bases in OTG2-1 are in red. The figure shows a pileup of sequence reads around each locus for wild-type SpCas9 (spCas9-WT), Split-SpCas9 from the Zhang lab (Split-SpCas9), our drug-dependent SpCas9-FKBP/ZFP-FRB and our drug-dependent Split-SpCas9$^{MT3}$-pDBD, where the latter three are all in the presence of rapamycin. All constructs have high activity at the target site, but off-target activity is limited to the spCas9-WT and Split-SpCas9 from the Zhang lab.

FIG. 103 presents one embodiment of a sequence of the 2×NLS-Cas9$^{MT3}$-NLS-FKBP fusion protein. NLS (magenta), SpCas9$^{MT3}$ (blue), FKBP (orange).

FIG. 104 presents one embodiment of a sequence of the 2×NLS-3×Flag-2×NES-TS2$^{ZF}$-FRB* fusion protein. NLS (magenta), NES (cyan), ZFP$^{TS2}$ (green), FRB* (red).

FIG. 105 presents one embodiment of a sequence of the NLS-Split-NCas9-NLS-FRB fusion protein. NLS (magenta), N-terminal SpCas9 fragment (blue), FRB (red).

FIG. 106 presents one embodiment of a sequence of the FKBP-Split-CCas9$^{MT3}$-NLS-3×HA-NLS-TS2$^{ZF}$-3×FLAG-2×NLS fusion protein. FKBP (orange), NLS (magenta), C-terminal SpCas9$^{MT3}$ (blue, mutant R1335K bold), ZFP$^{TS2}$ (green).

Figure 107:
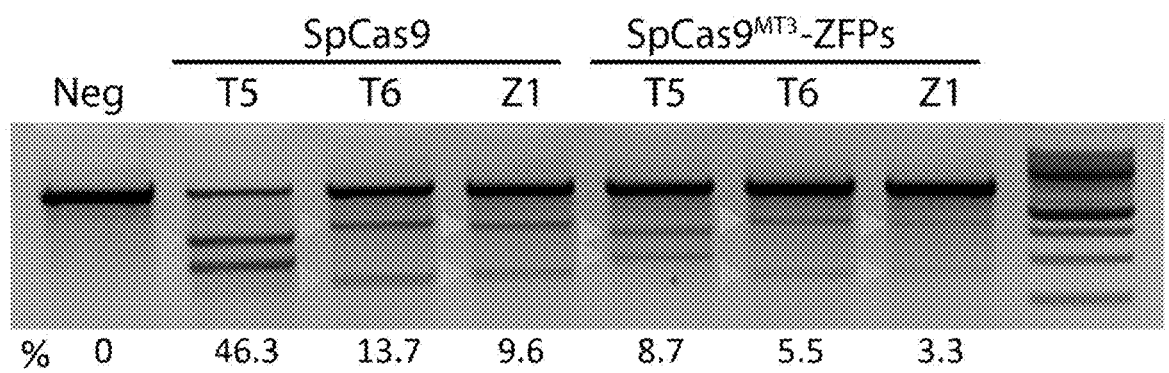

FIG. 107 presents exemplary data comparing the lesion rates at target sites T5, T6 & Z1 for SpCas9 and three different SpCas9$^{MT3}$-ZFPs by T7EI assay. Nuclease constructs and sgRNA expression vectors were transfected into a Jurkat cell line with an integrated HIV provirus (J-Lat line) and after 72 hours the lesion rates within the 5' LTR of HIV were analyzed by T7EI assay. The T5 nuclease in particular displays good activity (cyan arrowheads indicate the bands indicative of target site lesions and the values below each column indicate the calculated lesion rate). Each target site is listed above the gel where the sgRNA target site is underlined, the NGG PAM is in Red and the ZFP binding site is in yellow.

Figure 108:
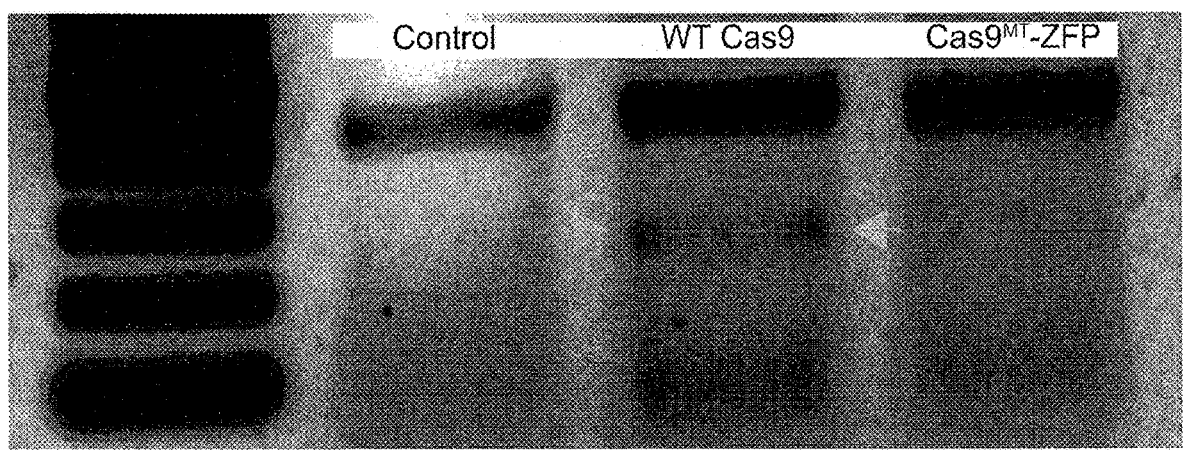

FIG. 108 presents exemplary data comparing the off-target lesion rates for SpCas9 and three different SpCas9$^{MT3}$-ZFP$^{T5}$ programmed with the T5 sgRNA by T7EI assay. Nuclease constructs and sgRNA expression vectors were transfected into a Jurkat cell line with an integrated HIV provirus (J-Lat line) and after 72 hours the lesion rates were analyzed by T7EI assay. Comparison of lesion rates at one computationally predicted off-target sites for the T5 sgRNAs with either wild-type SpCas9 or SpCas9$^{MT3}$-ZFP$^{T5}$ by T7EI assay. Lesions are evident for SpCas9 at this off-target site (cyan arrowheads) but these are absent for SpCas9$^{MT3}$-ZFP$^{T5}$.

FIG. 109 presents one embodiment of a sequence of the Cas9$^{MT3}$-NLS-3×HA-NLS-ZFP$^{T5}$ that targets the T5 site in the HIV LTR.

FIG. 110 presents one embodiment of a sequence of the Cas9$^{MT3}$-NLS-3×HA-NLS-ZFP$^{T6}$ that targets the T6 site in the HIV LTR.

FIG. 111 presents one embodiment of a sequence of the Cas9$^{MT3}$-NLS-3×HA-NLS-ZFP$^{Z1}$ that targets the Z1 site in the HIV LTR.

FIG. 112 representative sgRNA sequences for various loci for SpCas9 and NmCas9. The guide sequence element is indicated in red.

FIG. 113 presents one embodiment of a sequence of the NmdCas9-SpCas9$^{MT3}$, where NmCas9 is nuclease dead.

FIG. 114 presents one embodiment of a sequence of the SpCas9$^{MT3}$-NmdCas9, where NmCas9 is nuclease dead.

FIG. 115 presents one embodiment of a sequence of the SpCas9$^{MT3}$-NmCas9n$^{RuvC}$, where NmCas9 is a nickase via inactivation of the HNH domain.

FIG. 116 presents one embodiment of a sequence of the SpCas9$^{MT3}$-NmCas9n$^{HNH}$, where NmCas9 is a nickase via inactivation of the RuvC domain.

FIG. 117 presents one embodiment of a sequence of the SpCas9$^{MT3}$-NmCas9$^{WT}$ dual nuclease system.

DETAILED DESCRIPTION OF THE INVENTION

The present invention may be related to the field of genetic engineering. In particular, specific genes can be cleaved, edited or deleted using Cas9 nucleases with improved precision when coupled to DNA targeting units, which can be either programmable DNA-binding domains or an alternate isoform of Cas9 that are programmed to recognize a site neighboring the sequence targeted by the Cas9 nuclease.

The CRISPR/Cas9 system is commonly employed in biomedical research; however, the precision of Cas9 is sub-optimal for gene therapy applications that involve editing a large population of cells. Variations on a standard Cas9 system have yielded improvements in the precision of targeted DNA cleavage, but often restrict the range of targetable sequences. It remains unclear whether these variations can limit lesions to a single site within the human genome over a large cohort of treated cells. In some embodiments, the present invention contemplates that fusing a programmable DNA-binding domain (pDBD) to Cas9 combined with an attenuation of Cas9's inherent DNA binding affinity produces a Cas9-pDBD chimera with dramatically improved precision and increased targeting range. Because the specificity and affinity of this framework is easily tuned, Cas9-pDBDs provide a flexible system that can be tailored to achieve extremely precise genome editing at nearly any genomic locus—characteristics that are ideal for gene therapy applications.

Conventional CRISPR technology has been used to effect genome editing with Cas9 nuclease activity in combination with specific guide RNAs (sgRNAs) to place the enzyme on specific genomic DNA sequence where a double-stranded break is generated. Target location by Cas9 nuclease is typically a two step process. First, the PAM specificity of Cas9 acts as a first sieve by defining a subset of sequences that are bound for a sufficient length of time to be interrogated by the incorporate guide RNA. This step may be a kinetic selection for functional target sequences. Sequences with sufficient homology to a PAM specificity of the Cas9 nuclease are interrogated by the incorporate guide RNA through R-loop formation that allows Watson-Crick pairing between the guide RNA and the bound DNA target site. If there may be sufficient complementarity in this interaction the nuclease domains within Cas9 (the RuvC and HNH domains) will generate a double-stranded break in the DNA. Szczelkun et al., Direct observation of R-loop formation by single RNA-guided Cas9 and Cascade effector complexes. Prop Natl Acad Sci USA. 2014 Jul. 8; 111(27):9798-803.

The precision of a Cas9 nuclease—DNA targeting unit chimera may be improved by attenuating an independent recognition of target sites by a Cas9 nuclease, which can be achieved by altering its PAM recognition sequence and/or its affinity for a phosphodiester backbone by mutating residues that are involved in contacting the RNA or DNA. Further attenuation can be achieved by using a truncated single guide RNA to program a Cas9 nuclease. By attenuating the affinity of Cas9 for the DNA, the ability of a Cas9 nuclease to achieve a kinetic selection of a target sequence may be abrogated. Consequently, a Cas9 nuclease may be completely dependent on a coupled DNA targeting unit to achieve sufficient residence time on the DNA to allow R-loop formation with the incorporated guide RNA. Complementarity between a PAM specificity of a Cas9 nuclease and a target site may be still required for R-loop formation, but it may be no longer sufficient for initiating this event. This creates a system where the cleavage of a target site may be dependent on at least three features of the Cas9 nuclease—DNA targeting unit chimera: 1) recognition of the sequence by the DNA-targeting unit, 2) complementarity between the Cas9 nuclease PAM specificity and the sequence, and 3) complementarity between the guide RNA and the target site. An added advantage of the Cas9 nuclease—DNA targeting unit fusion may be that it expands the targeting range of the Cas9 nuclease by allowing a broader range of PAM sequences to be utilized, as normally low affinity PAM sequences can be utilized.

Figure 65:
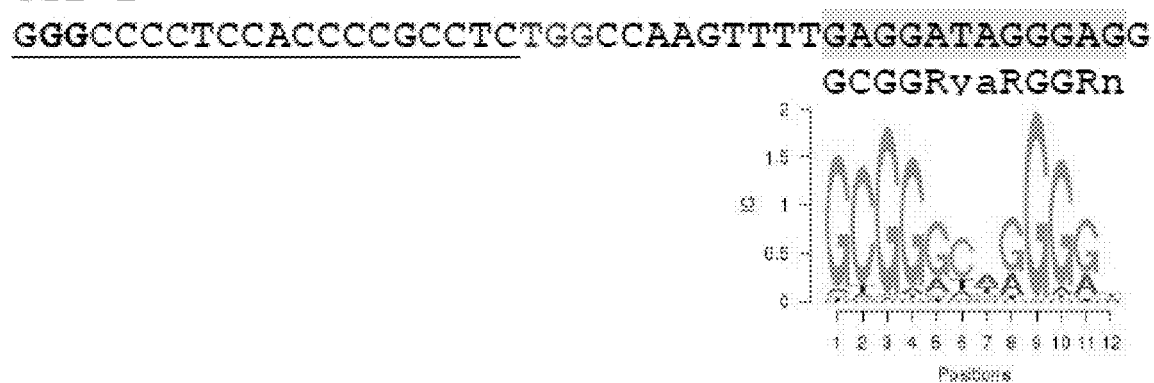
FIG. 65 presents an exemplary OT2-2 genomic sequence. The sequence complementary to the guide is underlined with the two mismatched positions in bold. The nGG PAM is red and the potential ZFP$^{TS2}$ binding site highlighted in yellow. Below the genomic sequence is predicted consensus recognition motif and sequence logo for ZFP$^{TS2}$ based on a Random Forest model of ZFP recognition[35]. The predicted recognition motif only differs substantially at one position in the finger 4 binding site (C versus A).
Figure 66A:
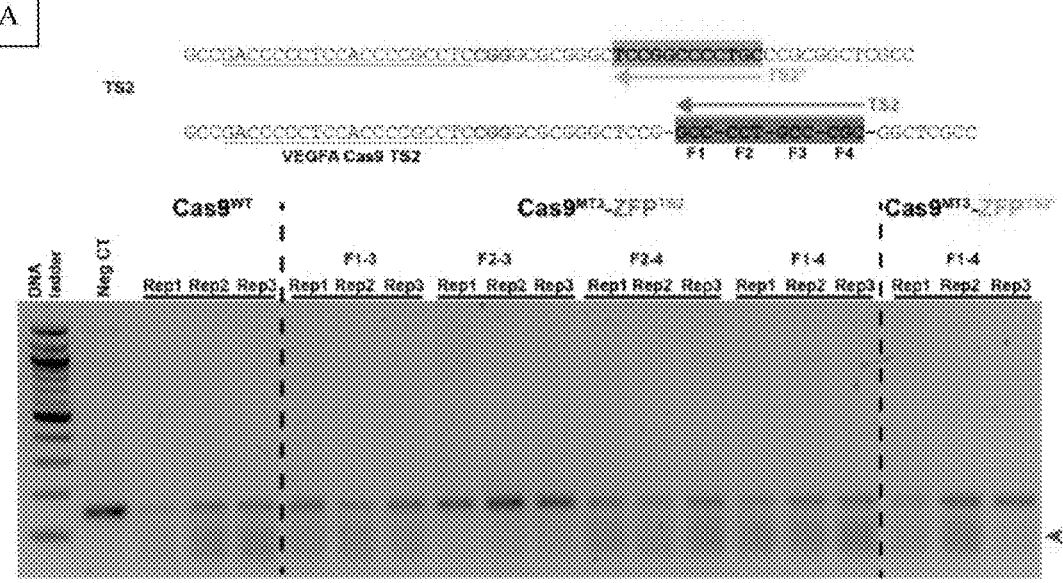
FIG. 66A-B presents exemplary data showing a T7EI activity profile of SpCas9$^{MT3}$-ZFP$^{TS2}$ at the TS2 genomic locus and OT2-2 as a function of the number of incorporated fingers.
Figure 66B:
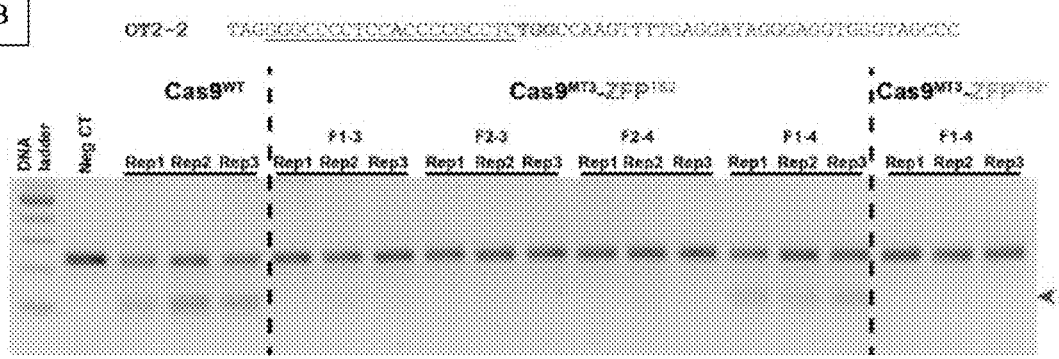

One potential advantage of a SpCas9-pDBD system over other Cas9 platforms is an ability to rapidly tune affinity and specificity of an attached pDBD to further improve its precision. Consequently, improved precision of SpCas9$^{MT3}$-ZFP$^{TS2}$ was obtained by truncating a zinc finger protein commonly abbreviated as ZFP, ZnF or ZF) to reduce its affinity for target site OT2-2. Constructs with a truncation of any of the terminal zinc fingers may display high activity at a target site. However, these truncations also reduced or eliminated off-target activity sat OT2-2, reflecting a profound improvement in the precision of SpCas9$^{MT3}$-ZFP$^{TS2}$. FIG. 64C and FIG. 65.

Figure 6:
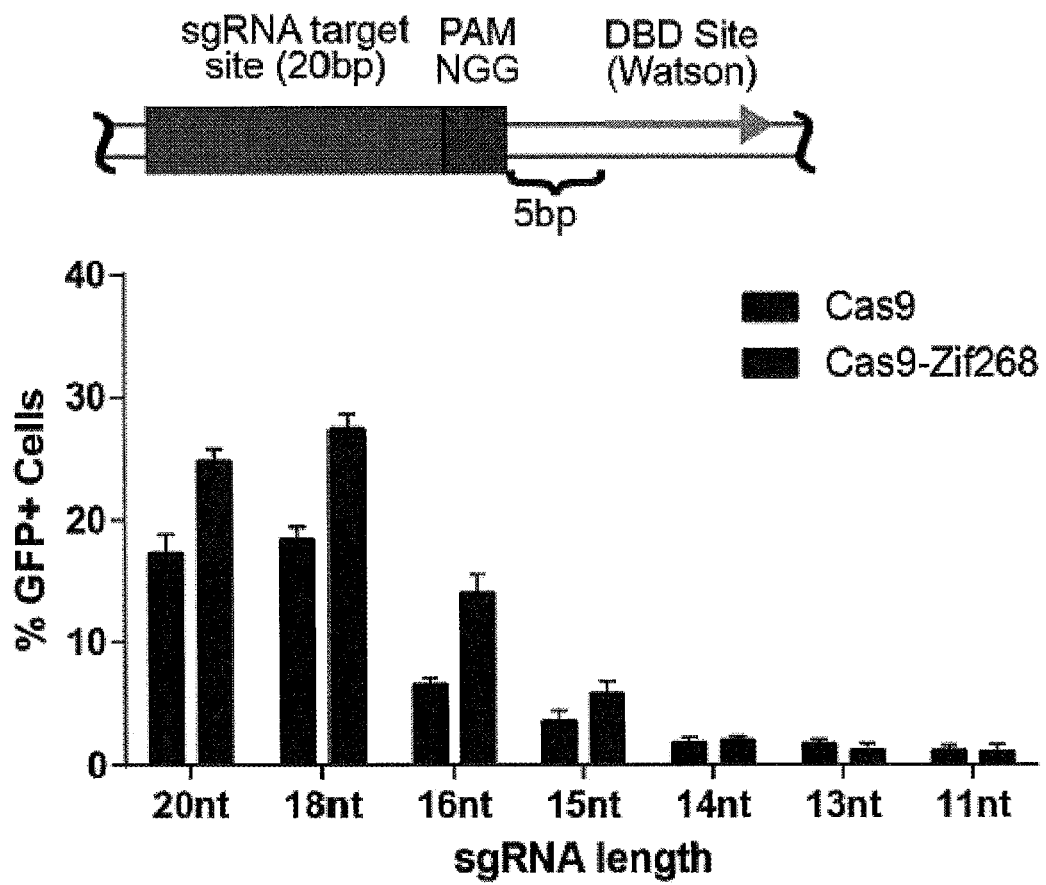
FIG. 6 presents exemplary data showing an activity profile of SpCas9 (blue) or SpCas9-Zif268 (also referred to as SpCas9-DBD$^{268}$) (red) with sgRNAs of different length (truncated) on a common target site with a NGG PAM sequences and a neighboring Zif268 site 5 base pairs away in Watson orientation. Cas9-Zif268 display higher activity between 15 and 20 nt of length in the guide sequence. Data are from three independent biological replicates performed on different days, where HEK293T cells transfected with 50 ng Cas9/Cas9-Zif268 plasmid, 50 ng sgRNA plasmid, 150 ng GFP reporter with target site and 100 ng mCherry control plasmid.

Similarly, utilization of a ZFP (e.g., TS2*) that recognizes an alternate sequence neighboring an TS2 guide target site also abolishes off-target activity at OT2-2, confirming that cleavage by SpCas9$^{MT3}$-ZFP$^{TS2}$ at this off-target site is dependent on an ZFP. FIG. 64C & FIG. 6. Given the improvements in precision realized by these simple adjustments in the composition of a ZFP, it should be possible to achieve even greater enhancements in precision via more focused modification of a ZFP composition and a linker connecting a ZFP to a SpCas9 protein.

GUIDE-seq[17] was employed to provide an unbiased assessment of the propensity for SpCas9$^{MT3}$-ZFP chimeras to cleave at alternate off-target sites within a genome. Using a modified protocol with a customized bioinformatics analysis of peaks within a genome, genome-wide DSB induction by SpCas9 and SpCas9$^{MT3}$-ZFP$^{TS2/TS3/TS4}$ were assessed.

Figures 67A, 67B, 67C, 67D:
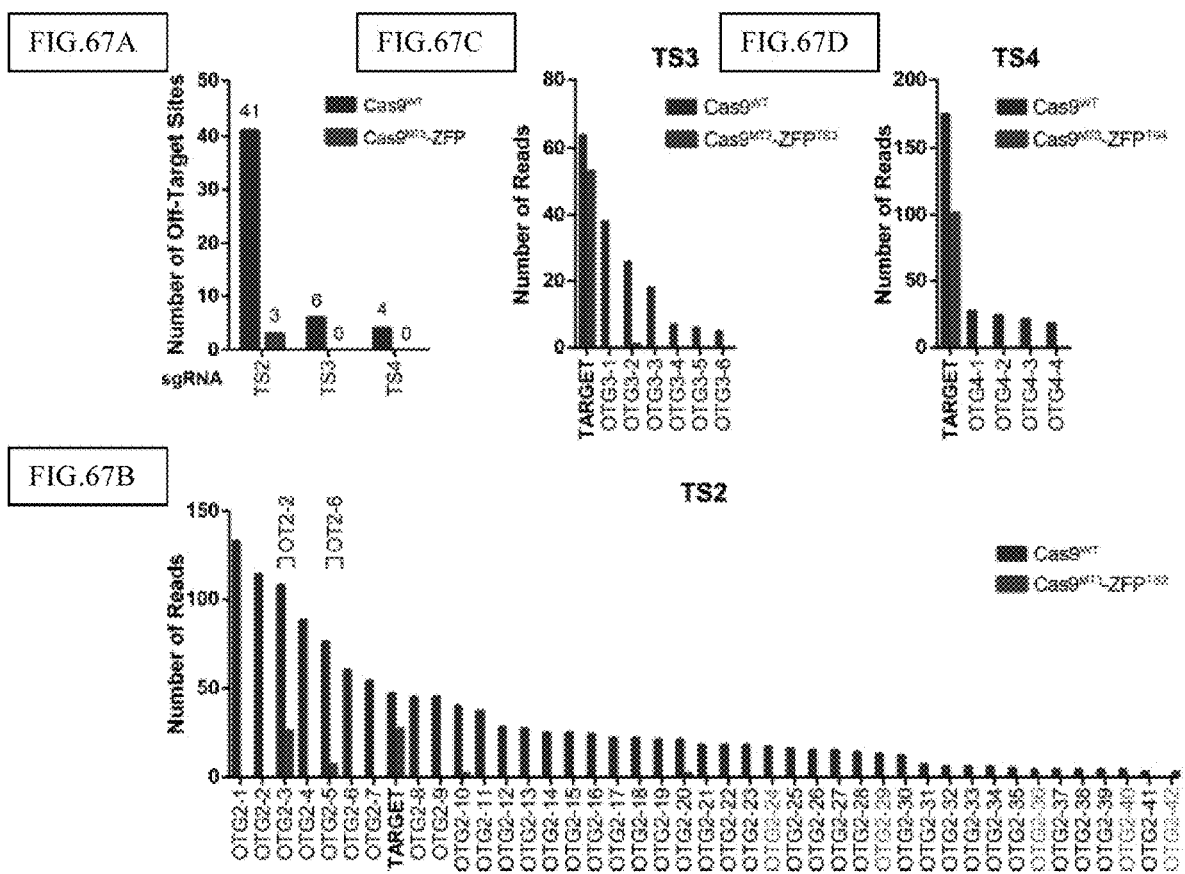
FIG. 67A-D presents exemplary data for as genome-wide off-target analysis of SpCas9$^{MT3}$-ZFPs by GUIDE-seq[17].

This analysis reveals a dramatic enhancement of the precision of the SpCas9$^{MT3}$-ZFPs at all three of the target sites. FIG. 67. For SpCas9$^{MT3}$-ZFP$^{TS3}$ and SpCas9$^{MT3}$-ZFP$^{TS4}$ nuclease dependent-oligonucleotide capture did not detect at any cleavage site besides the target site. For SpCas9$^{MT3}$-ZFP$^{TS2}$, which retains three active off-target sites that overlap with SpCas9, there is a dramatic reduction in cleavage activity at all of these alternate sequences. In addition, there is one new weak off-target site (OTG2-42) for SpCas9MT3-ZFP$^{TS2}$. Thus, these data demonstrate that the presence of the ZFP fusion does not generate a new category of ZFP-mediated highly active off-target sequences for SpCas9$^{MT3}$.

In some embodiments, the present invention contemplates compositions and methods that improve Cas9 effector systems. In some embodiments, Cas9 fusion proteins are contemplated comprising a DNA targeting unit that may be a DNA binding domain (DBD). In some embodiments, Cas9 fusion proteins are contemplated comprising a DNA targeting unit that may be another Cas9 isoform (e.g. SpCas9-NmCas9) programmed with an orthogonal sgRNA. In some embodiments a Cas9 nuclease would be directly fused to the DNA-targeting unit. In some embodiments, a Cas9 nuclease would be associated with the DNA-targeting unit via a dimerization domain. In some embodiments, the dimerization domain would be a heterotypic dimerization domain, which would allow control over component association. In some embodiments, the dimerization domain would be drug-dependent, which would provide temporal control over the activity of the nuclease based on the presence of the small molecule dimerizer within the cell.

Improvements in targeting precision have been achieved through the use of truncated sgRNAs (e.g., for example, less than 20 complementary bases). Fu et al., Improving CRISPR-Cas nuclease specificity using truncated guide RNAs. Nature Biotechnology (2014). Previous studies on truncated sgRNA have suggested that sgRNAs for spCas9 with less than 17 base pairs of complementarity to the target sequence have not been shown to be active in a genomic context. Improvements in precision have also been achieved by using pairs of Cas9 nickases to generate a double strand break. Mali et al., CAS9 transcriptional activators for target specificity screening and paired nickases for cooperative genome engineering. Nature Biotechnology 31, 833-838 (2013); and Cho et al., Analysis of off-target effects of CRISPR/Cas-derived RNA-guided endonucleases and nickases. Genome Research 24, 132-141 (2014). In addition, nuclease dead Cas9 (dCas9) variants have been fused to the FokI nuclease domain to generate programmable nucleases where dCas9 serves as the DNA-targeting unit and FokI may be the cleavage domain. Tsai et al., Dimeric CRISPR RNA-guided FokI nucleases for highly specific genome editing. Nature Biotechnology, 2014 June; 32(6):569-76; and Guilinger et al., Fusion of catalytically inactive Cas9 to FokI nuclease improves the specificity of genome modification. Nature Biotechnology, 2014 June; 32(6):577-82.

The proposed strategies described herein provide improved and more efficient Cas9-pDBD platforms that facilitate the construction of compact Cas9 orthologs. These compact orthologs permit alternate delivery methods (e.g. adeno-associated virus or AAV) broadening the clinical therapeutic modalities available for diseases including, but not limited to CGD. These strategies are also applicable to the treatment of a wide range of other monogenic disorders.

I. Conventional Cas9 Protein Modifications

Recently, an RNA-guided adaptive immune system that may be widespread in bacteria and archaea has been adapted for achieving targeted DNA cleavage or gene regulation in prokaryotic and eukaryotic genomes. Clustered Regularly Interspaced Short Palindromic Repeat (CRISPR) RNA sequences and CRISPR-associated (Cas) genes form catalytic protein-RNA complexes that utilize the incorporated RNA to generate sequence-specific double strand breaks at a complementary DNA sequence. This nuclease platform has displayed remarkable robustness for targeted gene inactivation or tailor-made genome editing. Sander et al., CRISPR-Cas systems for editing, regulating and targeting genomes. Nature Biotechnology 32, 347-355 (2014); Mali et al. RNA-guided human genome engineering via Cas9. Science 339, 823-826 (2013); Ran et al. Double Nicking by RNA-Guided CRISPR Cas9 for Enhanced Genome Editing Specificity. Cell 154, 1380-1389 (2013); Fu et al., Improving CRISPR-Cas nuclease specificity using truncated guide RNAs. Nature Biotechnology 32, 279-284 (2014); and Wang et al. One-step generation of mice carrying mutations in multiple genes by CRISPR/Cas-mediated genome engineering. Cell 153, 910-918 (201).

Figure 1:
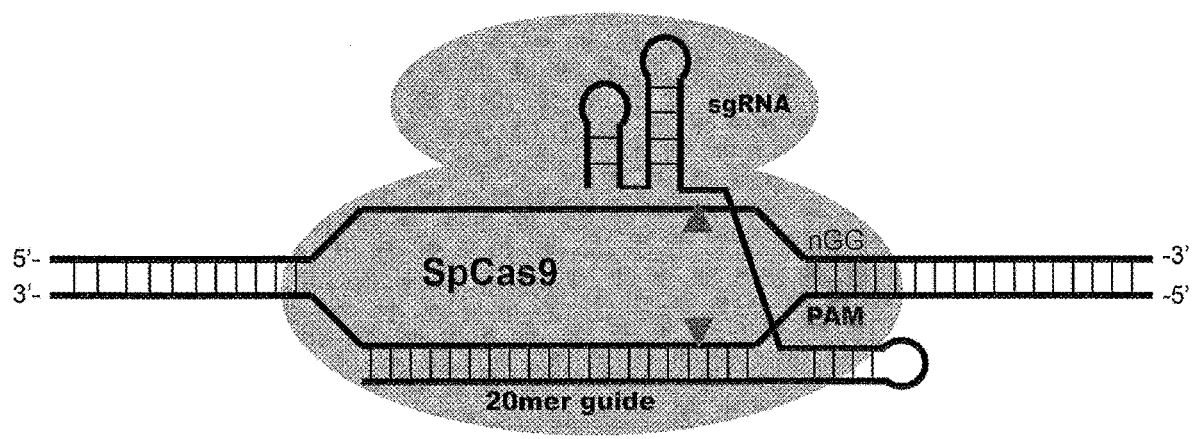
FIG. 1 presents a schematic overview of an exemplary CRISPR/Cas9 system. For example, SpCas9 (gray) may recognize a target sequence through Watson-Crick pairing of approximately 20 bases of the sgRNA and recognition of a neighboring PAM sequence (e.g., for example, NGG). Upon binding to its target, Cas9 generates a double stranded break (DSB) via cleavage of each strand (blue arrowheads).

The CRISPR/Cas9 genome engineering system is revolutionizing biological sciences due to its simplicity and efficacy[1-3]. The most commonly studied Cas9 nuclease originates from *Streptococcus pyogenes* (SpCas9)[4]. SpCas9 and its associated guide RNA license a DNA sequence for cleavage based on at least two stages of sequence interrogation[4-8]: i) compatibility of a PAM element with the specificity of the PAM-interacting domain, and ii) complementarity of a guide RNA sequence with the target site. Because it is straightforward to program Cas9 to cleave a desired target site through incorporation of a complementary single guide RNA (sgRNA)[4], a primary constraint on Cas9 targeting is the presence of a compatible PAM element[4,9,10]. For example, a PAM-interacting domain of wild-type SpCas9 (SpCas9$^{WT}$) preferentially recognizes a nGG element[4], although it can inefficiently utilize other PAM sequences (e.g. nAG, nGA)[9,11]. The simplicity of a SpCas9/sgRNA system allows facile editing of genomes in a variety of organisms and cell lines[1-3]. Target specificity may be a function of recognition by both the guide RNA (through Watson-Crick base pairing) and an inherent specificity of Cas9 through recognition of a neighboring motif (e.g., for example, a protospacer adjacent motif (PAM)). FIG. 1.

Figures 52A, 52B, 52C:
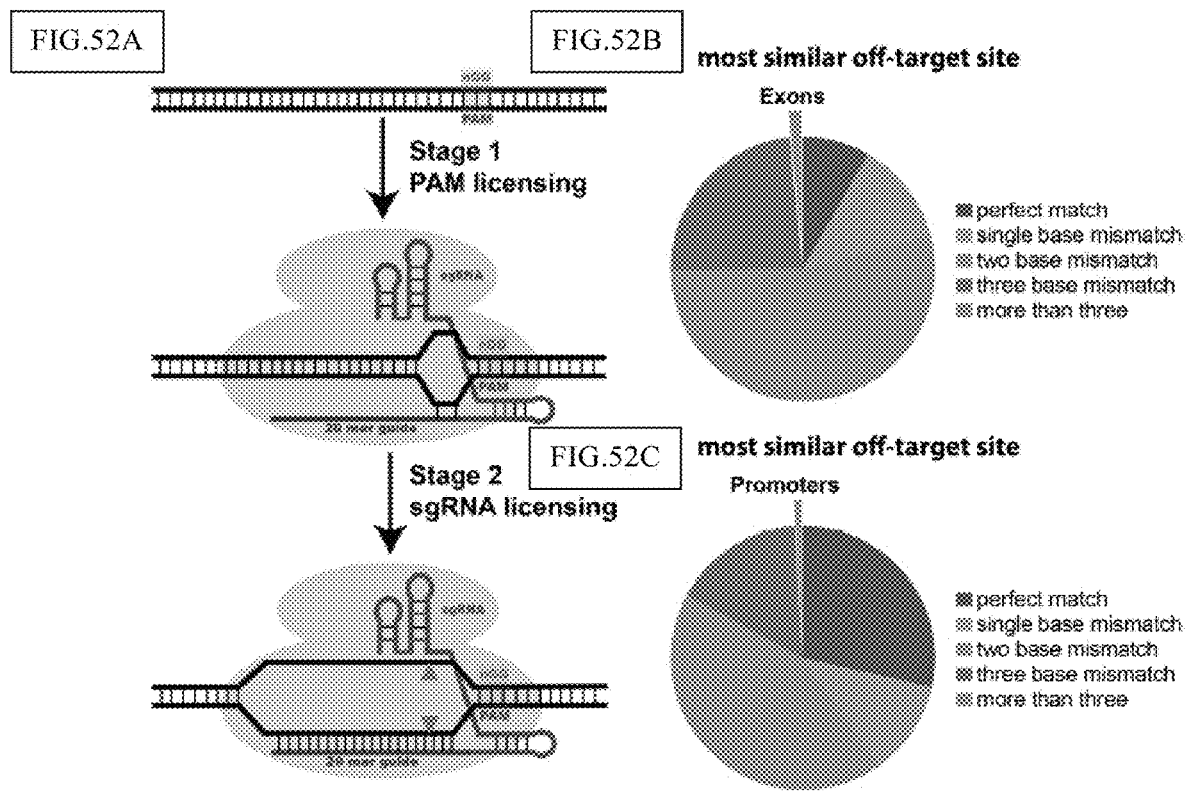
FIG. 52A-C presents an illustrative overview of the distribution of potential SpCas9 off-target it within the human genome.
Figure 53A:
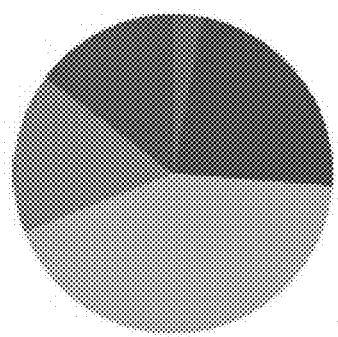
FIG. 53A-D presents an illustrative overview of the distribution of potential SpCas9 off target sites within a human genome.
Figure 53B:
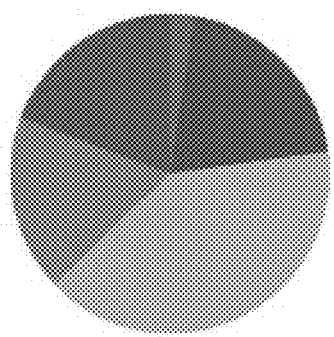
Figure 53C:
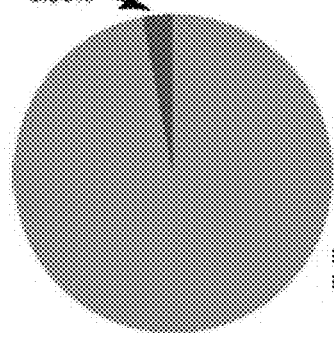
Figure 53D:
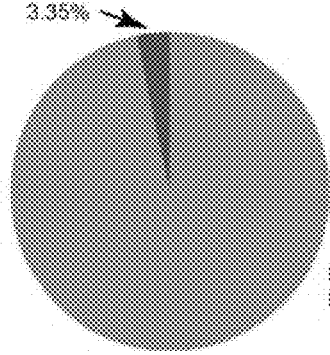

SpCas9 targeting precision is sub-optimal for most gene therapy applications involving editing of a large population of cells[12,13]. Numerous studies have demonstrated that SpCas9 can cleave a genome at unintended sites[9,14-20], with some guides acting at more than 100 off-target sites[17]. Recent genome-wide analyses of SpCas9 precision indicate that a majority of genomic loci that differ from a guide RNA sequence at 2 nucleotides, and a subset of genomic loci that differ at 3 nucleotides are cleaved with moderate activity[17-20]. For some guides, off-target sites that differ by up to 6 nucleotides can be inefficiently cleaved[17-20]. In addition, at some off-target sites bulges can be accommodated within the sgRNA:DNA heteroduplex to allow cleavage[15]. In this light, a global analysis was performed of potential SpCas9 target sites in exons or promoter regions using CRISPRseek[21,22] to assess the general frequency of potential off-target sites with three or fewer mismatches for guide RNAs filling in two categories of sequence elements: exon regions or promoter regions. A vast majority of guides (~98% in exons and ~99% in promoters) was found to have one or more off-target sites with 3 or fewer mismatches and thus are likely to have some level of off-target activity. FIGS. 52 and 53. Because off-target breaks have the potential to cause both local mutagenesis and genomic rearrangements (e.g., segmental deletions, inversions and translocations)[17,18,23,24], the resulting collateral damage for SpCas9 could have adverse consequences in therapeutic applications.

Reduced off-target cleavage rates have been reported with several modifications to the structure or delivery of a CRISPR/Cas9 system. Examples include, but are not limited to: changing guide sequence length and composition[25,26]; employing pairs of Cas9 nickases[26-28]; dimeric FokI-dCas9 nucleases[10,29]; inducible assembly of split Cas9[30-33]; Cas9 PAM variants with enhanced specificity[34]; and delivery of Cas9/sgRNA ribonucleoprotein complexes[35-37]. However, it remains uncertain whether these variations can restrict cleavage to a single site within the human genome over a large cohort of treated cells[12,38]. In addition, some of the most promising approaches (e.g., paired nickases or dimeric FokI-dCas9) restrict a targetable sequence space by requiring the proximity of two sequences compatible with Cas9 recognition.

Cas9 isoforms derived from different species can display different PAM specificities. Esvelt et al., Orthogonal Cas9 proteins for RNA-guided gene regulation and editing. Nature Methods 10, 1116-1121 (2013); Zhang et al., Processing-independent CRISPR RNAs limit natural transformation in *Neisseria meningitidis*. Molecular Cell 50, 488-503 (2013); Hou et al., Efficient genome engineering in human pluripotent stem cells using Cas9 from *Neisseria meningitides* (NmCas9). Proceedings of the National Academy of Sciences (2013); and Fonfara et al., Phylogeny of Cas9 determines functional exchangeability of dual-RNA and Cas9 among orthologous type II CRISPR-Cas systems. Nucleic Acids Research 43, 2577-2590 (2014). The Cas9 nuclease from *Streptococcus pyogenes* (hereafter, Cas9, or SpCas9 or catalytically active Cas9) can be guided to specific sites in a genome through base-pair complementation between a 20 nucleotide guide region of an engineered RNA (sgRNA) and a genomic target sequence. Cho et al., Targeted genome engineering in human cells with the Cas9 RNA-guided endonuclease. Nature Biotechnology 31, 230-233 (2013); Cong et al., Multiplex genome engineering using CRISPR/Cas systems. Science 339, 819-823 (2013); Jinek et al., RNA-programmed genome editing in human cells. eLife 2, e00471 (2013); and Sternberg et al., DNA interrogation by the CRISPR RNA-guided endonuclease Cas9. Nature 507, 7490 (2014).

Structural information may be also available on Cas9 and Cas9-sgRNA-DNA complexes. Jinek et al., Structures of Cas9 Endonucleases Reveal RNA-Mediated Conformational Activation. Science (2014); Nishimasu et al., Crystal Structure of Cas9 in Complex with Guide RNA and Target DNA. Cell 1-23 (2014); and Anders et al., Structural basis of PAM-dependent target DNA recognition by the Cas9 endonuclease. Nature, 2014 Sep. 25; 513(7519):569-73. Various other studies have reported on Cas9 precision (e.g., activity at its target site relative to off-target sequences) within a genome. Studies on Cas9 nuclease have demonstrated that off-target cleavage can occur at both NGG and NAG PAMs, where there can be up to 5 mismatches within the guide recognition sequence. Fu et al., High-frequency off-target mutagenesis induced by CRISPR-Cas nucleases in human cells. Nature Biotechnology 31, 822-826 (2013); Pattanayak et al., High-throughput profiling of off-target DNA cleavage reveals RNA-programmed Cas9 nuclease specificity. Nature Biotechnology 31, 839-843 (2013); and Hsu et al., DNA targeting specificity of RNA-guided Cas9 nucleases. Nature Biotechnology 31, 827-832 (2013).

Other Cas9 variants for improving specificity have also been investigated. For example, double-strand breaks may be generated through the nicks generated in each strand by RuvC and HNH nuclease domains of Cas9. Jinek et al., A programmable dual-RNA-guided DNA endonuclease in adaptive bacterial immunity. Science 337, 816-821 (2012); and FIG. 22. Inactivation of one of the two nuclease sites within Cas9 (e.g., for example, a D10A mutation in the RuvC domain) generates a nickase that cleaves only a single strand. Alternatively, a pair of nickases that cut opposite strands in close proximity can generate a double-strand break and thereby improve precision since cleavage by a single nickase at a target site should not be as mutagenic as a double strand break. Mali et al., CAS9 transcriptional activators for target specificity screening and paired nickases for cooperative genome engineering. Nature Biotechnology 31, 833-838 (2013); and Cho et al., Analysis of off-target effects of CRISPR/Cas-derived RNA-guided endonucleases and nickases. Genome Research 24, 132-141 (2014).

However, it has recently been shown that single nickases can be mutagenic with lesion rates >1% depending on the target site. Tsai et al., Dimeric CRISPR RNA-guided FokI nucleases for highly specific genome editing. Nature Biotechnology (2014); and Guilinger et al., Fusion of catalytically inactive Cas9 to FokI nuclease improves the specificity of genome modification. Nature Biotechnology 32, 577-582 (2014). Alternately, a catalytically-inactive, programmable, RNA-dependent DNA-binding protein (dCas9) can be generated by mutating both endonuclease domains within Cas9. Larson et al., CRISPR interference (CRISPRi) for sequence-specific control of gene expression. Nat Protoc 8, 2180-2196 (2013); and Qi et al., Repurposing CRISPR as an RNA-guided platform for sequence-specific control of gene expression. Cell. 2013 Feb. 28; 152(5):1173-83. When fused to a FokI endonuclease domain this construct can be used like zinc fingers or TALE domains to create the above dimeric nucleases, which display improved precision over a standard Cas9. FIG. 22. However, recently reported ChIP-seq datasets on dCas-sgRNA complexes reveal much more permissive binding (e.g., off-target binding) than cleavage, such that many sites are bound by Cas9 but not cut. Kuscu et al., Genome-wide analysis reveals characteristics of off-target sites bound by the Cas9 endonuclease. Nature Biotechnology 32, 677-683 (2014). This type of permissive binding may be a problem for FokI-dCas9 nucleases, leading to a greater number of off-target sites that are cleaved. Thus, there may be a need for an improved Cas9 platform having greater binding precision that may provide a platform for future gene therapy applications.

Type II CRISPR/Cas9 systems have been used for targeted genome editing in complex genomes, Barrangou et al., CRISPR-Cas systems: Prokaryotes upgrade to adaptive immunity. Molecular Cell. 2014 Apr. 24; 54(2):234-44; Hsu et al., Development and Applications of CRISPR-Cas9 for Genome Engineering. Cell. 2014 Jun. 5; 157(6):1262-78; and Sander et al., CRISPR-Cas systems for editing, regulating and targeting genomes. Nature Biotechnology. 2014 April; 32(4):347-55. Editing sites can be selected based primarily on two features: complementarity to a single-guide RNA (sgRNA), and proximity to a short (2-5 base pair) sequence called a protospacer adjacent motif (PAM). Subsequent DNA cleavage and repair enables gene inactivation by non-homologous end joining (NHEJ), or sequence correction and/or insertion by homology-directed repair (HDR). This technology has relevance to the construction of animal and cell models and gene therapy. Hu et al., RNA-directed gene editing specifically eradicates latent and prevents new HIV-1 infection. Proceedings of the National Academy of Sciences. 2014 Aug. 5; 111(31):11461-6; and Yin et al., Genome editing with Cas9 in adult mice corrects a disease mutation and phenotype. Nature Biotechnology. 2014 June; 32(6):551-3.

Despite these advantages, clinical genome editing may require even greater precision. Numerous reports have described promiscuity of standard Cas9, which leads to collateral damage at unintended sites. Fu et al., High-frequency off-target mutagenesis induced by CRISPR-Cas nucleases in human cells. Nature Biotechnology, 2013 September; 31(9):822-6; Pattanayak et al., High-throughput profiling of off-target DNA cleavage reveals RNA-programmed Cas9 nuclease specificity. Nature Biotechnology. 2013 September; 31(9):839-43; Hsu et al., DNA targeting specificity of RNA-guided Cas9 nucleases. Nature Biotechnology. 2013 September; 31(9):827-32; and Lin et al., CRISPR/Cas9 systems have off-target activity with insertions or deletions between target DNA and guide RNA sequences. Nucleic Acids Research. 2014; 42(11):7473-85.

Cas9/sgRNA variations that can improve precision but do not eliminate off-target activity include, but are not limited to: i) dual nickases (Mali et al., CAS9 transcriptional activators for target specificity screening and paired nickases for cooperative genome engineering. Nature Biotechnology. 2013 September; 31(9):833-8; and Ran et al., Double Nicking by RNA-Guided CRISPR Cas9 for Enhanced Genome Editing Specificity. Cell. 2013 Sep. 12; 154(6):1380-9); ii) truncated sgRNAs (tru-sgRNAs; FIG. 22; Fu et al., Improving CRISPR-Cas nuclease specificity using truncated guide RNAs. Nature Biotechnology. 2014 March; 32(3):279-84); and iii) FokI fusions to dCas9 (Tsai et al., Dimeric CRISPR RNA-guided FokI nucleases for highly specific genome editing. Nature Biotechnology, 2014 June; 32(6):569-76; and Guilinger et al., Fusion of catalytically inactive Cas9 to FokI nuclease improves the specificity of genome modification. Nature Biotechnology. 2014 June; 32(6):577-82). Consequently, there may be an unmet need for a Cas9-based system that can be cut at only a single site within a genome.

The PAM interaction residues for SpCas9 have been described (Anders et al., (2014) Structural Basis of PAM-Dependent Target DNA Recognition by the Cas9 Endonuclease, Nature 513(7519), 569-571), but this study does not provide information on how to generate an improved Cas9 fusion protein with a DNA targeting unit or truncated sgRNA sequences.

It has been reported that PAM recognition sequences may play a role to efficiently engage Cas9 nucleolytic activity, thereby providing an explanation for low off-target editing rates. While describing Cas9 modification of DNA, this reference does not describe fusion proteins combining the elements, nor does it discuss modification of the Cas9 PAM site or other modifications beyond the targeting RNA. Cencic et al., (2014) Protospacer Adjacent Motif (PAM)-Distal Sequences Engage CRISPR Cas9 DNA Target Cleavage, PLoS. ONE 9(10), e109213.

An X-ray crystal structural analysis of Cas9 in a complex with guide RNA and target DNA has been reported. Nishimasu et al., (2014) Crystal Structure of Cas9 in Complex with Guide RNA and Target DNA, Cell 156(5), 935-949. E-published Feb. 13, 2014. This structural analysis provides insight into the identity of a Cas9 protospacer adjacent motif recognition domain and other sequence recognition features. While describing the orientation and features of the Cas9 in complex with and sgRNA and DNA, this reference does not describe the type of Cas9 modifications, fusion proteins, or mutations needed to make an attenuated Cas9.

A fusion protein using catalytically inactive Cas9 and FokI nuclease (FokI-dCas9) has been reported. Guilinger et al. (2014) Fusion of Catalytically Inactive Cas9 to FokI Nuclease Improves the Specificity of Genome Modification, Nat Biotech 32(6), 577-582. Cleavage of the sequence requires the combination of two of these FokI-dCas9 monomers where the targeting was greater than 140 fold higher specificity than wild type Cas9 with the same efficiency. While describing a Cas9 fusion protein complex that increases targeting, this reference does not describe a fusion protein with specific DNA binding proteins, modification of the PAM site, or truncated targeting sequences.

The fusion of both zinc fingers and TAL effectors as programmable DNA binding protein with non-Cas9 proteins has been reported to produce various effects upon targeted DNA sequences. Strauβ et al., (2013) Zinc Fingers, Tal Effectors, or Cas9-Based DNA Binding Proteins: What's Best for Targeting Desired Genome Loci?, Mol. Plant 6(5), 1384-1387. While describing zinc fingers, TAL effectors, and Cas9, this reference does not describe fusion proteins combining these elements, nor does it discuss any modification of the Cas9 protein (e.g., for example, specific mutations), beyond the targeting RNA.

dCas9 or TALE proteins have been fused with effector constructs (e.g., activation or repression domains) to modulate the expression of the Oct4 genes. Hu et al., (2014) Direct Activation of Human and Mouse Oct4 Genes Using Engineered TALE and Cas9 Transcription Factors, Nucleic Acids Res. 42(7), 4375-4390. While describing zinc fingers, TAL effectors, and Cas9, this reference does not describe fusion proteins combining these elements, nor does it discuss modification of the Cas9 (e.g., for example, specific mutations), beyond the targeting RNA.

CRISPR/Cas systems has been reported to be generally useful for genomic modification and gene modulation. Wu, F. "CRISPR/Cas Systems for Genomic Modification and Gene Modulation," United States Patent Application Publication Number US 2014-0273226 (herein incorporated by reference). While describing Cas9 modification of DNA, this reference does not describe fusion proteins combining these elements, nor does it discuss modification of the Cas9 (e.g., for example, specific mutations), beyond the targeting RNA.

A single Cas enzyme has been programmed by a short RNA molecule to recognize a specific DNA target, in other words, the reported Cas enzyme can be recruited to a specific DNA target using said short RNA molecule. Cong et al., "CRISPR-Cas Component Systems, Methods and Compositions for Sequence Manipulation," United States Patent Application Publication Number US 2014/0273231 (herein incorporated by reference). The reference describes a vector system that delivers the elements of the Cas system to affect changes to the DNA target. The reference also describes the importance of the PAM sequences into target DNA. While describing Gas9 modification of DNA, this reference does not describe fusion proteins combining these elements, nor does it discuss modification of the Cas9 PAM recognition domain (e.g., for example, specific mutations) or other modifications beyond the targeting RNA.

Non-Cas9/TALE fusion proteins have been reported where the TALEs are engineered, programmable DNA-binding domains which bind specifically to a preselected target sequence. Joung et al., "Transcription Activator-Like Effector (TALE)—Lysine-Specific Demethylase I (Lsd1) Fusion Proteins," WO/2014/059255. This reference does not describe a fusion protein with Cas9 systems, nor does it discuss modification of the Cas9 PAM recognition domain (e.g., for example, specific mutations) or other modifications.

It has been reported that a mutation within an active site of an enzyme results in a change in DNA binding affinity. Shroyer et al., (1999) Mutation of an Active Site Residue in *Escherichia coli* Uracil-DNA Glycosylase: Effect on DNA Binding, Uracil Inhibition and Catalysis, Biochemistry 38(15), 4834-4845. This reference does not describe Cas9 fusion proteins, nor does it discuss modification of the Cas9 PAM recognition domain (e.g., for example, specific mutations) or other modifications beyond the targeting RNA.

II. Cas9 Nuclease-DNA Targeting Unit Fusion Proteins

In some embodiments, the present invention contemplates a Cas9 nuclease-DNA Targeting Unit (Cas9-DTU) fusion protein that cleaves a single site within a genome. In one embodiment, the Cas9-DTU fusion protein may be compatible with previously reported specificity-enhancing variations of Cas9. In some embodiments, the present invention contemplates Cas9-DTU fusion proteins using a wide variety of Cas9 orthologs including, but not limited to, SpCas9 (e.g., Type II-A) and NmCas9 (e.g., Type II-C), both of which are validated as genome-editing platforms. Jinek et al., A programmable dual-RNA-guided DNA endonuclease in adaptive bacterial immunity. Science 2012 Aug. 7; 337 (6096):816-21; Hou et al., Efficient genome engineering in human pluripotent stem cells using Cas9 from *Neisseria meningitidis*. Proceedings of the National Academy of Sciences. 2013 Sep. 24; 110(39):15644-9; Jinek et al., RNA-programmed genome editing in human cells. eLife. 2013; 2:e00471; Mali et al., RNA-guided human genome engineering via Cas9. Science, 2013 Feb. 15; 339(6121):823-6; and Cong et al., Multiplex genome engineering using CRISPR/Cas systems. Science. 2013 Feb. 15; 339(6121): 819-23. Because >90% of known Cas9 orthologs are either Type II-A or Type II-C (Fonfara I, Le Rhun A, Chylinski K, Makarova K S, Lécrivain A-L, Bzdrenga J, Koonin E V, Charpentier E. Phylogeny of Cas9 determines functional exchangeability of dual-RNA and Cas9 among orthologous type II CRISPR-Cas systems. Nucleic Acids Research. 2014 Feb. 1; 42(4):2577-90. PMCID: PMC3936727), the present invention facilitates embodiments to nearly any desired Type II Cas9 system.

Figure 4:
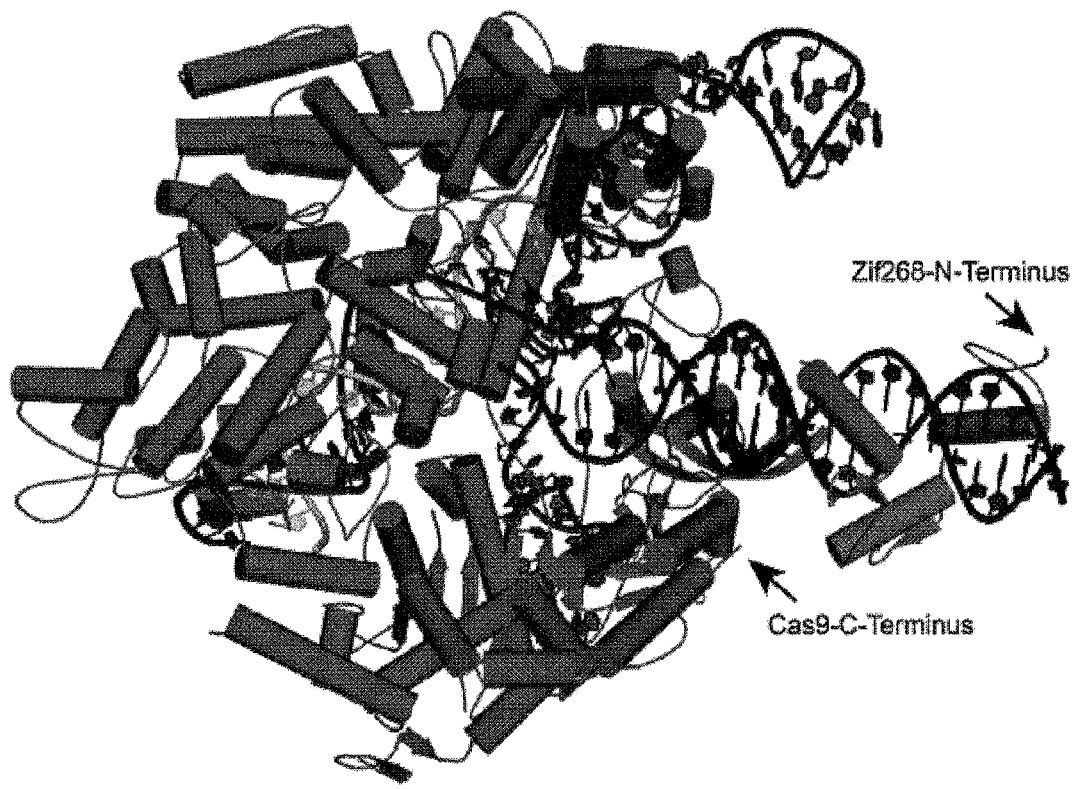
FIG. 4 presents one embodiment of a structural model for SpCas9-Zif$^{268}$ (also referred as SpCas9-DBD$^{268}$). A B-DNA model containing Zif268 binding site (Watson-11 bp) may be constructed using 3DNA (PMID 1860022) and appended 3' to the PAM (magenta) in the SpCas9 structure (grey). In parallel with the spacing parameters in accordance with FIG. 3, a W-11 bp configuration Zif268 (green) does not generate steric clashes within the model to SpCas9.

In one embodiment, the present invention contemplates an improved Cas9 platform, where target recognition precision is improved by incorporation of a programmable DNA-binding domain (pDBD), such as Cys2-His2 zinc finger protein (ZFPs)[39] or transcription-activator like effectors (TALEs)[40]. FIGS. 2A and 4. Both of these pDBD platforms can be programmed to recognize nearly any sequence within the genome[39-42]. Indeed, pDBDs have been employed with great success as targeting domains for programmable nucleases by incorporating non-specific FokI nuclease domain (ZFNs[39] and TALENs[40]) or sequence-specific nuclease domains (e.g. megaTAL[43]).

One favorable characteristic of the presently disclosed pDBDs is their inherent modularity whereby specificity and affinity can be rationally tuned by adjusting the number and composition of incorporated modules and the linkage between modules[44,45]. In one embodiment, the present invention contemplates that a fusion of a pDBD to a mutant SpCas9 with an attenuated DNA-binding affinity generates a chimeric nuclease fusion protein comprising a broad sequence targeting range and dramatically improved precision (a compared to conventional Cas9 platforms). Although it is not necessary to understand the mechanism of an invention, it is believed that the present disclosed SpCas9-pDBD platforms have favorable properties for genome engineering applications. In addition, it is shown herein that these SpCas9-pDBD chimeras provide new insights into the barriers involved in licensing target site cleavage by a SpCas9/sgRNA complex.

Innovations to achieve an ultimate goal of precisely editing a single site within a genome comprise two general strategies that have applicability to all Cas9 systems. First, a DTU could be a programmable DBD fusion protein comprising either a ZFP (Umov et al., Genome editing with engineered zinc finger nucleases. Nat Rev Genet. 2010 Sep. 1; 11(9):636-46) or a TALE protein (Joung J K, Sander J D. TALENs: a widely applicable technology for targeted genome editing. Nat. Rev. Mol. Cell Biol. 2013 January; 14(1):49-55). These DTU fusion proteins can precisely deliver a Cas9/sgRNA complex to a specific site within a genome and thereby facilitate sgRNA-dependent cleavage of an adjacent target sequence. Alternately, a DTU could be an orthogonal Cas9 isoform (e.g. nmCas9) that through the use of an orthogonal sgRNA targets the Cas9 nuclease to a specific site in the genome. In some embodiments, an orthogonal Cas9 DTU would be a nuclease-dead Cas9, so that it merely functions as a DNA recognition domain. In some embodiments, an orthogonal Cas9 DTU would be an active nuclease (either a nickase or nuclease), so that it can also break the DNA. In some embodiments, an orthogonal Cas9 DTU could also have attenuated DNA-binding affinity (NmCas9$^{DM}$, FIG. 49), such that both attenuated Cas9s bind cooperatively. Second, attenuation of an initial binding of a Cas9 nuclease to a PAM or to DNA in general though mutations in contact to the phosphodiester backbone makes target site acquisition reliant on an accessory DTU, all the while retaining Cas9's RNA-guided cleavage fidelity.

In one embodiment, the present invention contemplates a coupled DNA cleavage system including at least three levels of licensing: 1) recognition of a neighboring site by an attached DTU, 2) PAM recognition, and 3) sgRNA complementarity. The data presented herein indicate that PAM specificity of a Cas9 can be tuned, which provides an opportunity to alter and/or refine the sequence preference of Cas9 to a high levels of precision, and may also allow allele-specific targeting using SNPs as discriminators—e.g., for inactivation of dominant disease alleles. In some embodiments, a combined DTU fusion protein and altered PAM recognition strategy may be also compatible with all prior variants of Cas9 (e.g., dual nickases, tru-sgRNAs, or FokI fusions) further extending the precision of these constructs. In some embodiments, a Cas nuclease-DTU will extend the number of target sites that are functional sequences, allowing the efficient discrimination of alleles based on SNPs that distinguish these alleles, where these SNPs if present in the PAM recognition sequence would be the discriminators between active and inactive target sites. Although it may be not necessary to understand the mechanism of an invention, it is believed that the presently disclosed Cas9-DTU fusion proteins yield constructs that provide a single site precision sufficient for targeted genome editing, thereby facilitating gene therapy applications.

In one embodiment, the present invention contemplates a flexible, highly precise Cas9-based nuclease platform that cleaves only a single site within a multigigabase genome. This level of precision facilitates Cas9-based in vivo gene corrections, which may require precise genome editing of billions to trillions of cells. Currently achievable levels of genome editing specificity with conventional platforms must be increased to circumvent the hazards of unintended, difficult-to-predict off-target mutations. Although it may be not necessary to understand the mechanism of an invention, it is believed that the specificity and activity of Cas9 gene editing can be dramatically improved through an incorporation of an appended, programmable DNA-binding domain (pDBD). It is also believed that such improvements in editing specificity may result from a Cas9 platform that comprises: i) PAM recognition by Cas9; ii) DNA recognition by an sgRNA; and iii) flanking sequence recognition by a DBD. The data herein demonstrate the improvement in precision with SpCas9 systems (Type II-A) and functionality with NmCas9 systems (Type II-C), but one of skill in the art would appreciate that the disclosed strategy is applicable to all Cas9 based systems, such as *Staphylococcus aureus* (SaCas9) systems (Type II-A). Ran, F. A. et al. In vivo genome editing using *Staphylococcus aureus* Cas9. *Nature* 520, 186-191 (2015).

The development of Cas9-DBDs in the context of these two most prevalent subtypes (with their distinct domain arrangements) facilitates application of the present invention to nearly any Cas9-based genome editing system. Jinek et al., Structures of Cas9 endonucleases reveal RNA mediated conformational activation. Science. 2014 Mar. 14; 343 (6176):1247997. In addition, the presently disclosed Cas9-DBD framework should also be compatible with existing variants (e.g. dual nickases, tru-sgRNAs and/or FokI fusions) that have been reported to increase nuclease precision thereby enhancing precision. Fu et al., improving CRISPR-Cas nuclease specificity using truncated guide RNAs. Nature Biotechnology. 2014 March; 32(3):279-84; Tsai et al., Dimeric CRISPR RNA-guided FokI nucleases for highly specific genome editing. Nature Biotechnology, 2014 June; 32(6):569-76; and Guilinger et al., Fusion of catalytically inactive Cas9 to FokI nuclease improves the specificity of genome modification. Nature Biotechnology. 2014 June; 32(6):577-82.

In some embodiments, the present invention contemplates a method for improving precision in genome editing using a Cas9-DBD fusion protein by engineering two representative Cas9 orthologs: *S. pyogenes* Cas9 (SpCas9; Type IIA) and *N. meningitidis* Cas9 (NmCas9; Type II-C, almost 300 aa smaller than SpCas9). These orthologs are validated genome-editing platforms, and the Type II-A and II-C families together encompass >90% of all Cas9 sequences. Modifications are presented that permit fused DBDs to increase precision and activity of both of these Cas9 orthologs as well as refine their inherent targeting range. One of skill in the art recognizes that the embodiments presented herein may be extended to other Cas9 systems or related CRISPR nuclease effectors (e.g. CpfI; Zetsche, B, et al. CpfI is a Single RNA-Guided Endonuclease of a Class 2 CRISPR-Cas System. *Cell* (2015), doi:10.1016/j.cell.2015.09.038), since it may be possible that alternative Cas9 variants within these classes or other CRISPR nuclease effectors may have equivalent or superior properties for clinical applications.

Based on reported structures of Cas9, some embodiments of the present invention contemplate fusions between any Cas9 protein and programmable DNA-binding domains (e.g., for example, Cys2His2 zinc fingers (ZFP), homeodomains or TALE domains). Both ZFPs, homeodomains and TALEs can be easily programmed to recognize a variety of DNA sequences, and have been employed with FokI nuclease to generate dimeric nucleases. Umov et al., Genome editing with engineered zinc finger nucleases. Nat Rev Genet 11, 636-646 (2010); and Joung et al., TALENs: a widely applicable technology for targeted genome editing. Nat. Rev. Mol. Cell Biol. 14, 49-55 (2013); PMID 22539651. Although it may not be necessary to understand the mechanism of an invention, it is believed that by fusing a Cas9 to a DNA-binding domain (DBD), a hybrid nuclease may be created where the activity of the Cas9 component may be defined, in part, by an associated DNA-binding domain. FIGS. 2A and 2B.

Figures 2, 2C:
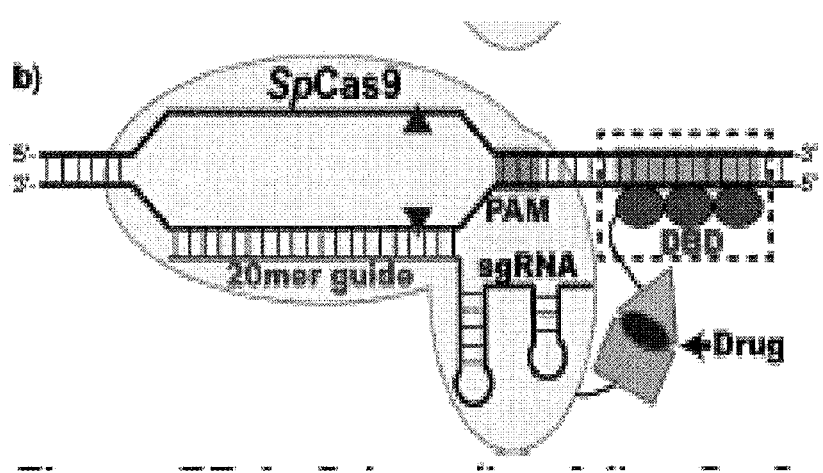
FIG. 2C presents a schematic showing that a Cas9-pDBD can be conferred with drug-dependent activity by inserting drug-dependent dimerization domains into a linker.

The genome editing precision of available nuclease platforms may be improved to circumvent the hazards of unintended, difficult-to-predict off-target mutations[1], which can alter gene function through direct mutagenesis or translocations. Although it is not necessary to understand the mechanism of an invention, it is believed that the present method improves the specificity of Cas9 through an attachment of a pDBD to Cas9 with attenuated DNA-binding affinity, thereby establishing a system where Cas9 target site cleavage is dependent on sequence recognition by a pDBD. In addition, the present invention contemplates regulatable Cas9-pDBD prototypes where, for example, drug-dependent dimerization domains control the association of Cas9 and a pDBD. FIG. 2C.

In some embodiment of the present invention an association of a Cas9-nuclease and the DTU may be mediated by dimerization domains. These dimerization domains could be, but are not limited to homotypic dimerization domains, heterotypic dimerization domains, light mediated dimerization domains and/or drug-dependent dimerization domains. These dimerization domains could be, but are not limited to protein or RNA.

In one embodiment, the present invention contemplates a Cas9-pDBDs chimeric protein for target recognition and cleavage purposes by using a variety of Cas9 orthologs. In one embodiment, the method optimizes a SpCas9-pDBD system. In one embodiment, the method extends an approach to NmCas9 (Type II-C) and SaCas9[16], which are more amenable to viral delivery. Although it is not necessary to understand the mechanism of an invention, it is believed that the development of Cas9-pDBDs in the context of the two most prevalent subtypes facilitates application of some of the present embodiments into future Cas9-based genome editing system. In one embodiment, the present invention provides a Cas9 editing platform that establishes efficient and precise gene correction. For example, by applying this approach in HSPCs an avenue for the ex vivo generation of a cell-based therapy can be established. Once established, this approach should be applicable to other HSPC-based monogenic disorders.

Preliminary data were collected using a Cas9-ZFP fusion protein (e.g., Zif268), where a ZFP was bound to both a Cas9 N-terminus (Zif268-Cas9) and/or a Cas9 C-terminus (Cas9-Zif268) via a long linker to provide flexibility in binding. The Zif268 sequence recognizes a nucleic acid target sequence of 5'-GCGTGGGCG-3' (SEQ ID NO:3). C-terminal Cas9-ZFP/sgRNA complex activity was demonstrated using a GFP reporter assay, where the reporter construct may be inactive until a double-strand break was created within a target sequence (e.g., demonstrating a gain of function readout). The data demonstrated that both N-terminal Zif268-Cas9 and C-terminal Cas9-Zif268 were active, but that C-terminal Cas9-Zif268 showed the greatest activity.

A. Development and Validation

Based on SpCas9 structures, a fusion protein was designed between SpCas9 and a programmable DBD, wherein a DBD comprised either ZFP or TALE domains (e.g. FIG. 4). Umov et al. Genome editing with engineered zinc finger nucleases. Nat Rev Genet. 2010 Sep. 1; 11(9): 636-46; Joung et al., TALENs: a widely applicable technology for targeted genome editing. Nat. Rev. Mol. Cell Biol. 2013 January; 14(1):49-55; Jinek et al., Structures of Cas9 endonucleases reveal RNA mediated conformational activation. Science. 2014 Mar. 14; 343(6176):1247997; and Nishimasu et al., Crystal structure of Cas9 in complex with guide RNA and target DNA. Cell. 2014 Feb. 27; 156(5):935-49.

Both ZFPs and TALEs can be programmed to recognize nearly any sequence within a genome, where their affinities and specificities can be tuned based on the number of modules incorporated. Rebar et al., Heritable targeted gene disruption in zebrafish using designed zinc-finger nucleases. Nature Biotechnology. 2008 Jun. 25; 26(6):702-8; Bhakta et al., Highly active zinc-finger nucleases by extended modular assembly. Genome Research. 2013 March; 23(3):530-8; Zhu et al., Using defined finger-finger interfaces as units of assembly for constructing zinc-finger nucleases. Nucleic Acids Research. 2013 Feb. 1; 41(4):2455-65; Kim et al., Preassembled zinc-finger arrays for rapid construction of ZFNs. Nature Methods. 2011; 8(1):7; Meckler et al., Quantitative analysis of TALE-DNA interactions suggests polarity effects. Nucleic Acids Research, 2013 April; 41(7):4118-28; and Reyon et al., FLASH assembly of TALENs for high-throughput genome editing. Nature Biotechnology. 2012 May; 30(5):460-5. Preliminary experiments discussed herein resulted in the fusion of Cas9 with Zif268 or a TALE domain programmed to recognize the same sequence (TAL268), to the N-terminus (e.g. Zif268-SpCas9) or C-terminus (e.g. SpCas9-Zif268) of SpCas9 via a long linker. Cermak et al., Efficient design and assembly of custom TALEN and other TAL effector-based constructs for DNA targeting. Nucleic Acids Research. 2011 July; 39(12):e82-2; and Meng et al., Counter-selectable marker for bacterial-based interaction trap systems. Biotechniques. 2006 February; 40(2):179-84. Although it may be not necessary to understand the mechanism of an invention, it is believed that a DBD, by recruiting Cas9 to a target site, would allow suboptimal PAM sequences to be cleaved efficiently, since there may be a kinetic barrier to R-loop formation by Cas9 at suboptimal PAM sequences. Szczelkun et al., Direct Observation of R-loop formation by single RNA-guided Cas9 and Cascade effector complexes. Proc Natl Acad Sci USA. 2014 May 27.

SpCas9 may be believed to have a strong sequence preference for NGG over NAG and NGA PAMs and may be essentially inactive at other NXX PAM trinucleotides. Hsu et al., DNA targeting specificity of RNA-guided Cas9 nucleases. Nature Biotechnology. 2013 September; 31(9):827-32; Jiang et al., RNA-guided editing of bacterial genomes using CRISPR-Cas systems. Nature Biotechnology. 2013 March; 31(3):233-9; and Zhang et al., Comparison of non-canonical PAMs for CRISPR/Cas9-mediated DNA cleavage in human cells. Sci Rep. 2014; 4:5405. It has been reported that an SpCas9 target site with an NAG PAM shows increased activity mediated by an appended DBD. A co-transfected plasmid GFP reporter system assay in Human Embryonic Kidney (HEK 293T) cells may be used to measure targeted DSB activity. Wilson et al., Expanding the Repertoire of Target Sites for Zinc Finger Nuclease-mediated Genome Modification. Mol Ther Nucleic Acids. 2013 April; 2(4):e88.

Figure 3:
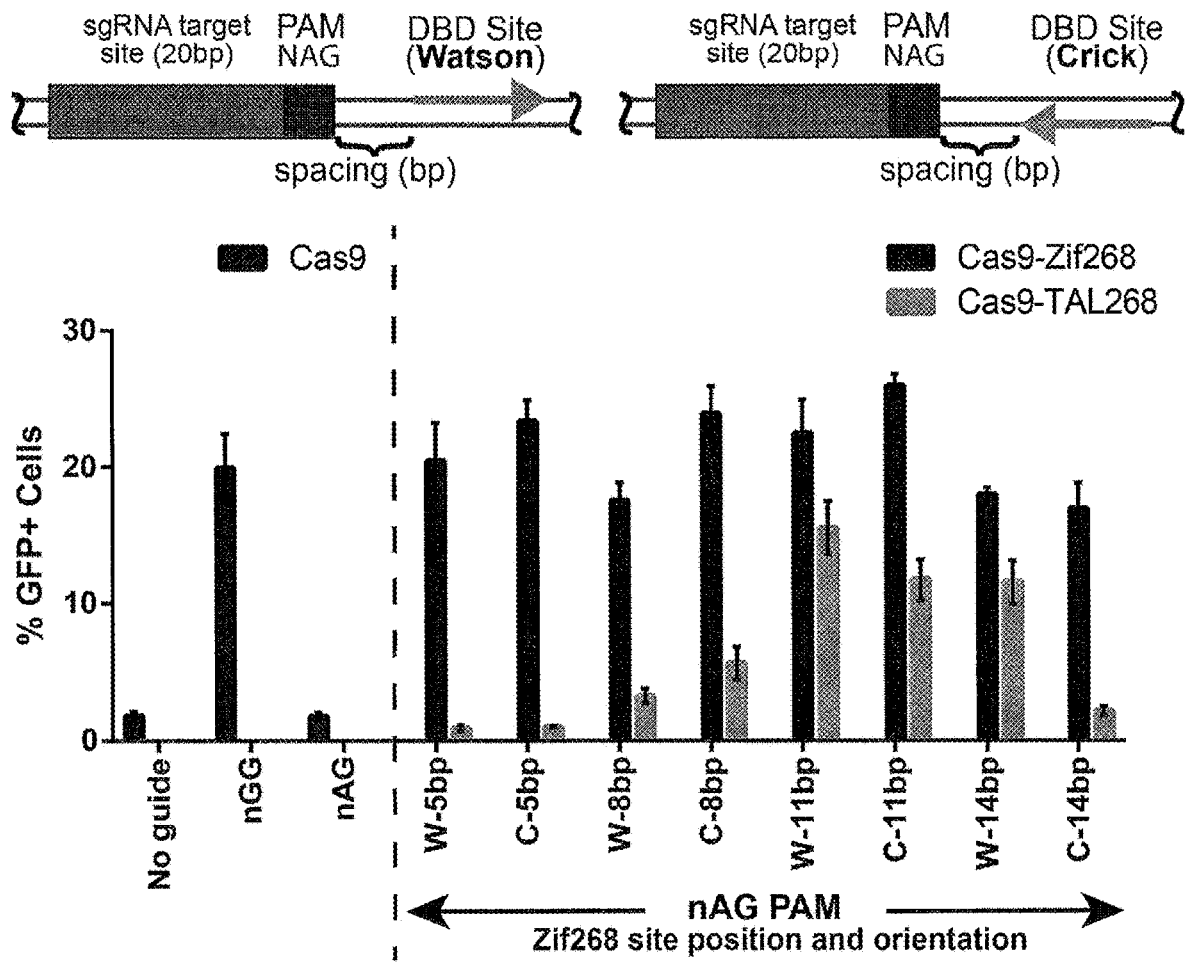
FIG. 3 the top panel presents an illustrative schematic of orientation and spacing parameters for the presently disclosed chimeric Cas9-pDBD constructs. The position and 5' to 3' orientation of the DBD binding site may be represented by an orange arrow relative to the PAM element of the Cas9 binding site. The bottom panel displays the activity profile of Cas9 (blue, on an NGG or NAG PAM), Cas9-Zif268 (also referred to as Cas9-DBD$^{268}$) (red, NAG PAM) or Cas9-TAL268 (green, NAG PAM) on a common sgRNA target site. DBD site orientation may be either Watson (W) or Crick (C), and spacing may be 5, 8, 11 or 14 bp from the PAM (see schematic). While no activity for Cas9 was detected above background on an AG PAM (relative to the no guide control), on an NAG PAM, Cas9-Zif268 displayed activity on all AG PAM target sites. A TALE domain programmed to recognize the same target site (TAL268) may be also functional on a subset of spacings and orientations of the DBD binding site. Data are from three independent biological replicates performed on different days, where HEK293T cells transfected with 50 ng Cas9/Cas9-Zif268/Cas9-TAL268 plasmid, 50 ng sgRNA plasmid, 150 ng GFP reporter with target site and 100 ng mCherry control plasmid. Error bars indicate standard error of the mean.
Figure 17:
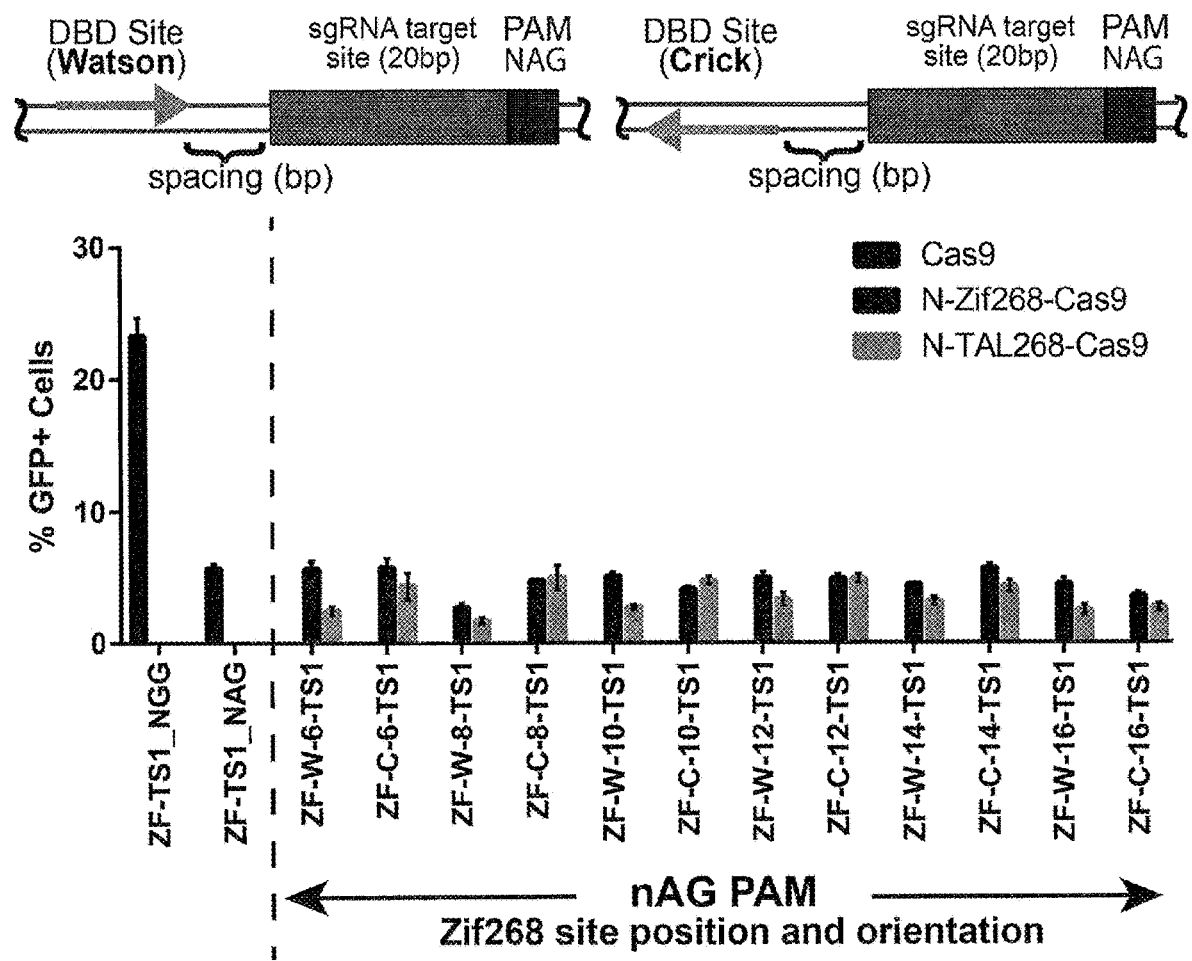
FIG. 17 presents a schematic of the orientation and spacing parameters examined in these assays (Top Panel). The position and 5' to 3' orientation of the DTU binding site may be represented by an orange arrow relative to the position of 5' nucleotide of the sgRNA of the Cas9 binding site. The bottom panel displays the activity profile of Cas9 (blue, on an NGG or NAG PAM), N-Zif268-Cas9 (red, NAG PAM) or N-TAL268-Cas9 (green, NAG PAM) on a common sgRNA target site. DTU site orientation may be either Watson (W) or Crick (C), and spacing may be 6, 8, 10, 12, 14 or 16 bp from the 5' of sgRNA (see schematic). Enhanced nuclease activity was not detected for either Cas9 or N-Zif268-Cas9 nor N-TAL268-Cas9 above the background on an AG PAM. Data are from three independent biological replicates on performed on different days, where HEK293T cells transfected with 50 ng Cas9/N-Zif268-Cas9/N-TAL268-Cas9 plasmid, 50 ng sgRNA plasmid, 150 ng GFP reporter with target site and 100 ng mCherry control plasmid.
Figure 18:
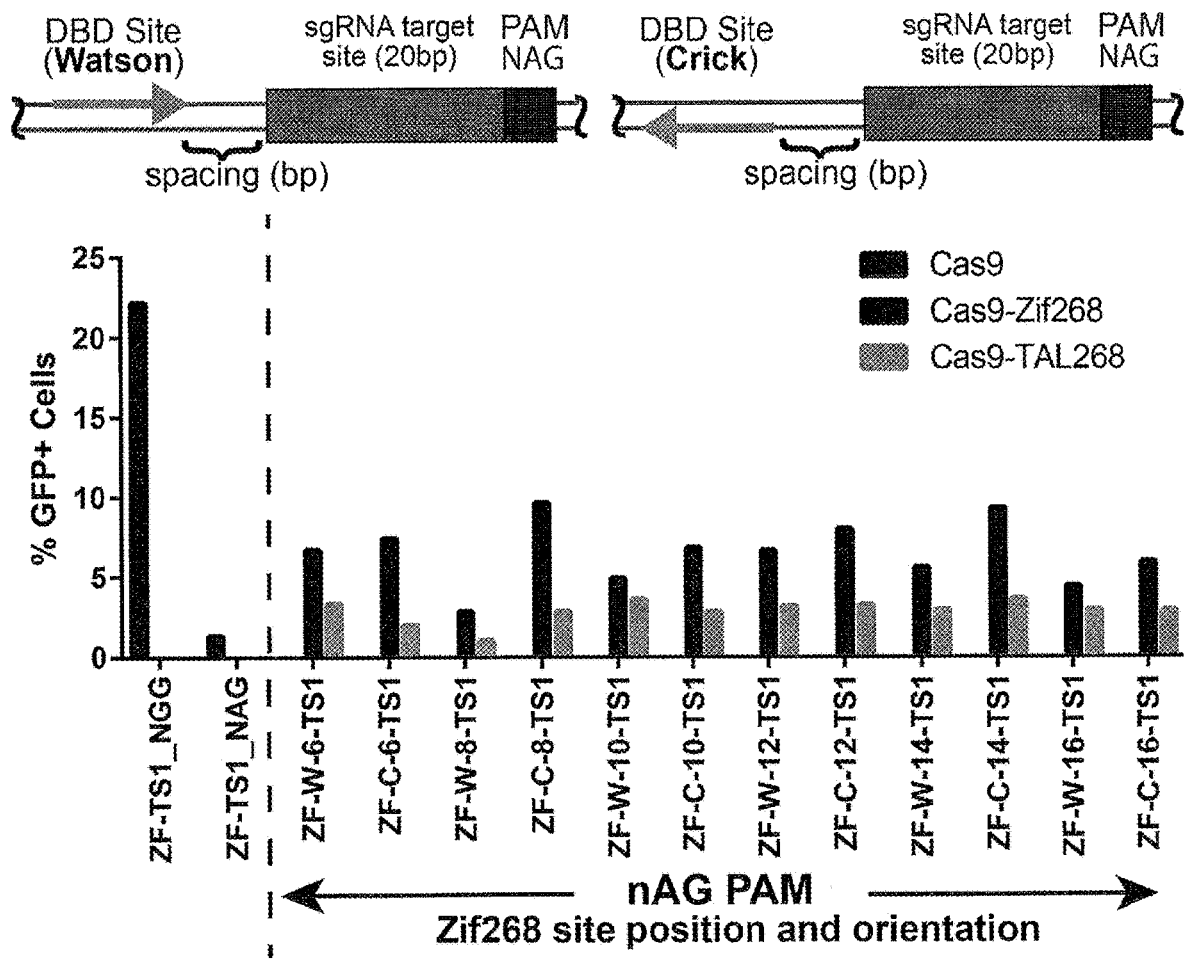
FIG. 18 presents a schematic of the orientation and spacing parameters examined in these assays (top panel). The position and 5' to 3' orientation of the DTU binding site may be represented by an orange arrow relative to the position of 5' nucleotide of the sgRNA of the Cas9 binding site. The bottom panel displays the activity profile of Cas9 (blue, on an NGG or NAG PAM), Cas9-Zif268 (red, NAG PAM) or Cas9-TAL268 (green, NAG PAM) on a common sgRNA target site. DTU site orientation may be either Watson (W) or Crick (C), and spacing may be 6, 8, 10, 12, 14 or 16 bp from the 5' of sgRNA (see schematic). While no activity was detected for Cas9 and for Cas9-TAL268 above background on an NAG PAM, Cas9-Zif268 displayed modest activity on most of the NAG PAM target sites above the background on an NAG PAM. Datum may be from single replicates, where HEK293T cells transfected with 50 ng Cas9/Cas9-Zif268/Cas9-TAL268 plasmid, 50 ng sgRNA plasmid, 150 ng GFP reporter with target site and 100 ng mCherry control plasmid.
Figure 19:
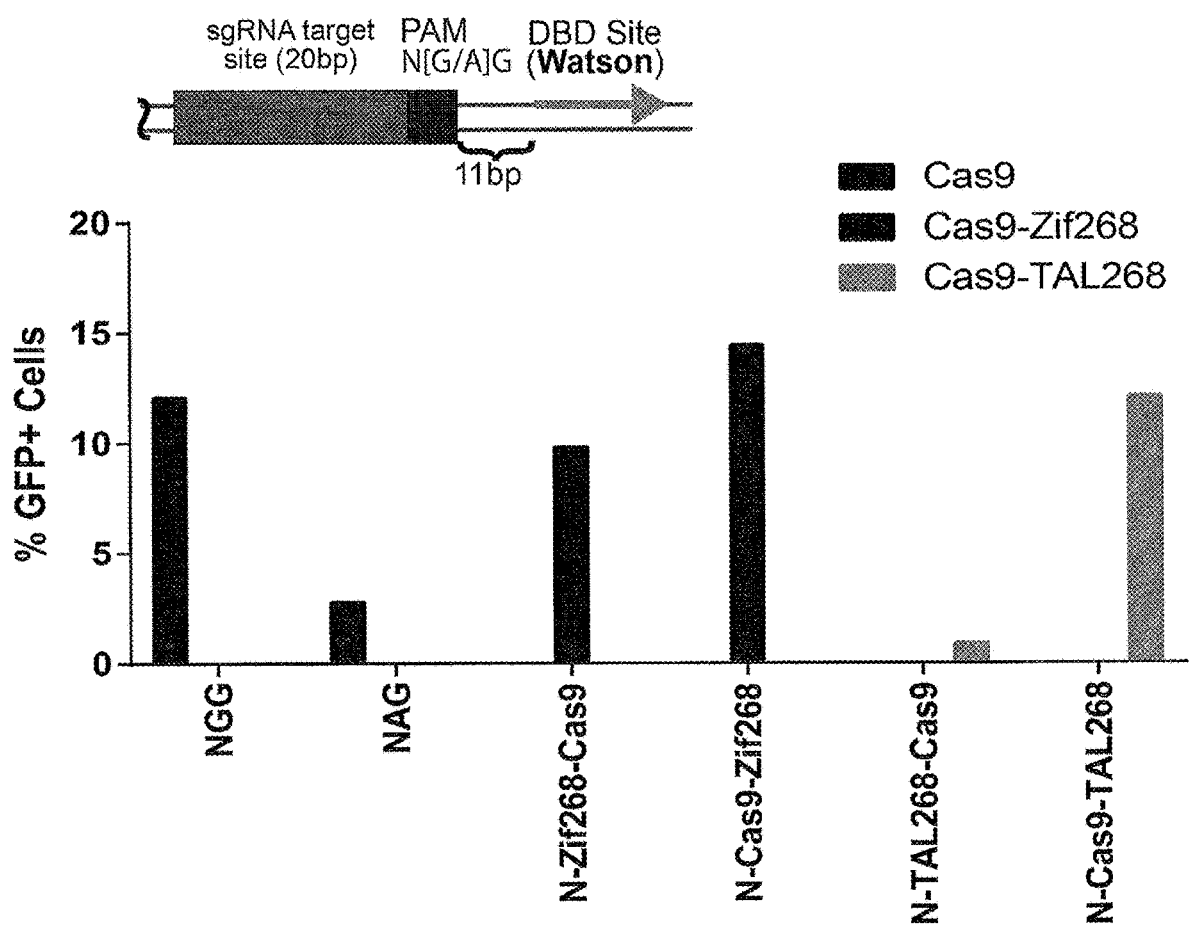
FIG. 19 presents a schematic of the orientation and spacing parameters examined in these assays (top panel). The position and 5' to 3' orientation of the DTU binding site may be represented by an orange arrow relative to the PAM element of the Cas9 binding site (Watson 11 bp). No activity was detected for Cas9 and for N-TAL$^{268}$-Cas9 above background on an NAG PAM. However, Cas9-Zif268, N-Zif268-Cas9, and Cas9-TAL$^{268}$ all displayed activity on this NAG PAM target site above the background on an NAG PAM. Datum may be from single replicates, where HEK293T cells transfected with 50 ng Cas9/N-Zif268-Cas9/Cas9-Zif268/N-TAL$^{268}$-Cas9/Cas9-TAL$^{268}$ plasmid, 50 ng sgRNA plasmid, 150 ng GFP reporter with target site and 100 ng mCherry control plasmid.

It was observed that C-terminal DBD fusions (e.g., SpCas9-Zif268) display superior activity N-terminal fusions (FIG. 17, 18, 19). Consequently, the activity of Cas9-Zif268 and SpCas9-TAL268 were further examined on a number of different arrangements of their binding sites to define optimal spacing and orientation for DBD recognition sites relative to a Cas9 target sequence for cleavage. A pDBD fusion (ZFP or TALE) to an SpCas9 may enhance nuclease activity when a pDBD binding sites are located at different positions and orientations relative to the Cas9 target site. FIG. 3. In preliminary experiments, the most robust activity was observed when using a C-terminal fusion of a ZFP or a TALE to SpCas9 and the pDBD binding sites were positioned 3' to the PAM element (data not shown).

Figure 5:
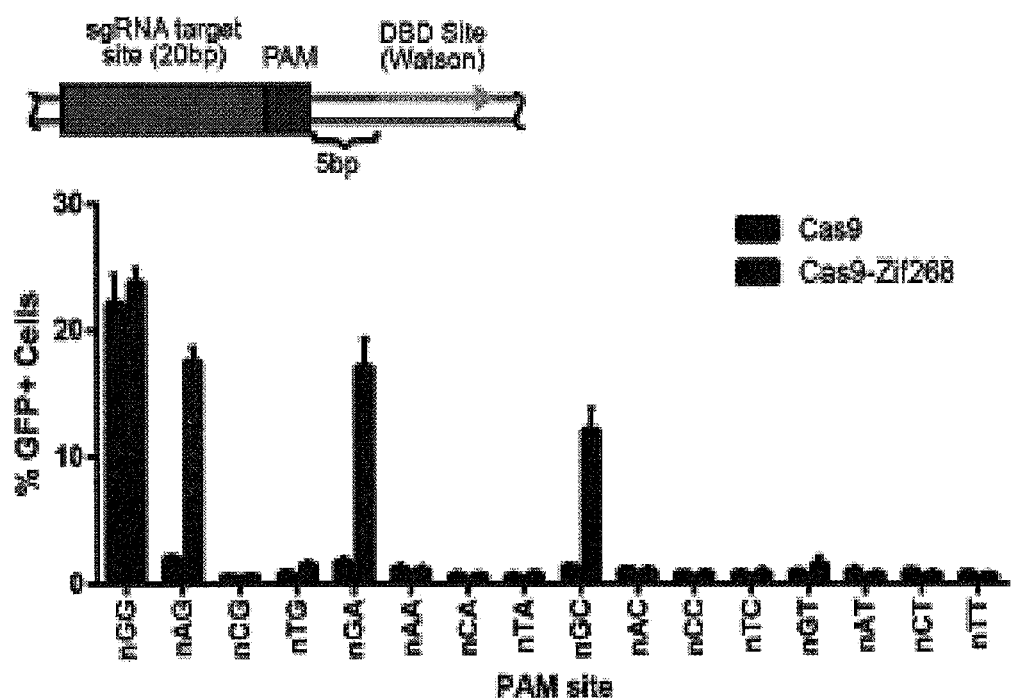
FIG. 5 presents exemplary data showing an activity profile of SpCas9 (blue) or SpCas9-Zif268 (red) on a common target site with different PAM sequences and a neighboring Zif268 site (Watson-5 bp). SpCas9 may be active only on the NGG PAM, whereas SpCas9-Zif268 may be active on NGG, NAG, NGA and NGC PAMs. Data are from three independent biological replicates performed on different days, where HEK293T cells transfected with 50 ng Cas9/Cas9-Zif268 plasmid, 50 ng sgRNA plasmid, 150 ng GFP reporter with target site and 100 ng mCherry control plasmid.
Figure 7:
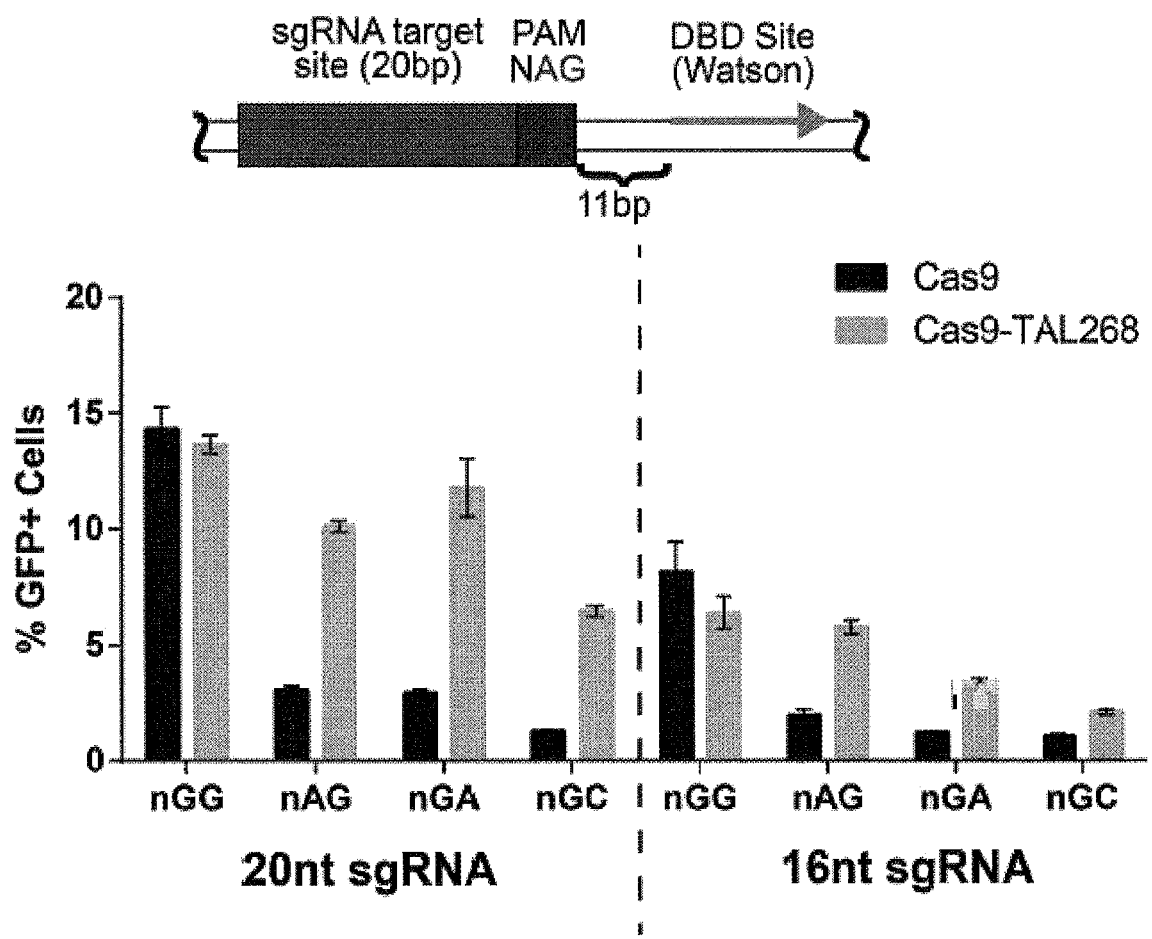
FIG. 7 presents exemplary data showing an activity profile of SpCas9 (blue) and SpCas9-TAL268 (green) in the GFP reporter assay with sgRNAs of 20 nt vs 16 nt lengths on NGG, NAG, NGA, NGC PAM target sites with a neighboring Zif268 site (Watson-5 bp). SpCas9 displays robust activity only on the NGG PAM, whereas SpCas9-TAL268 may be active on NGG, NAG, NGA and NGC PAMs. Data are from three independent biological replicates performed on different days, where HEK293T cells transfected with 50 ng Cas9/Cas9-TAL268 plasmid, 50 ng sgRNA plasmid, 150 ng GFP reporter with target site and 100 ng mCherry control plasmid.
Figure 8:
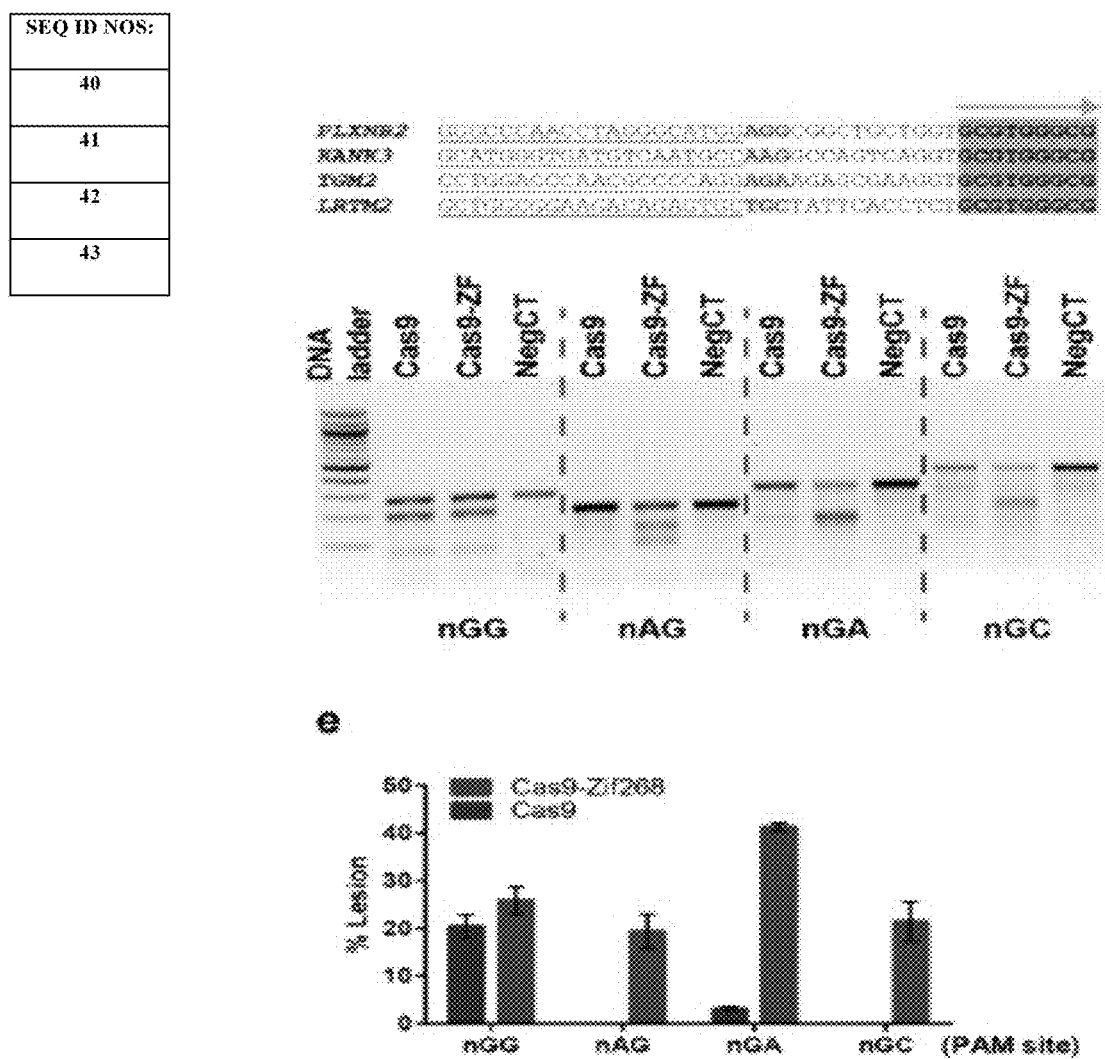
FIG. 8 presents exemplary data showing a quantification of lesion frequencies from three independent biological replicates performed on different days in HEK293T cells. Error bars indicate standard error of the mean. Genomic activity profiles of SpCas9 and SpCas9-Zif268 programmed independently with 4 different sgRNAs targeting 4 different genomic sites with neighboring Zif$^{268}$ binding sites (Watson-11 bp). SpCas9 cuts efficiently only the GG PAM, but SpCas9-Zif$^{268}$ also cuts efficiently at AG, GA or GC PAMs. Genomic regions were PCR-amplified, and lesions (i.e., for example, cleavages and mutagenic NHEJ's) were detected by T7 Endonuclease I (T7EI) assay. Top panel may be the exemplary agarose gel image displaying DNA lesion profile after T7EI treatment. The bottom panel may be the quantification of lesion frequencies data from three independent biological replicates performed on different days, where HEK293T cells transfected with 50 ng Cas9/Cas9-Zif268 plasmid, 50 ng sgRNA plasmid, and 100 ng mCherry control plasmid.
Figure 54:
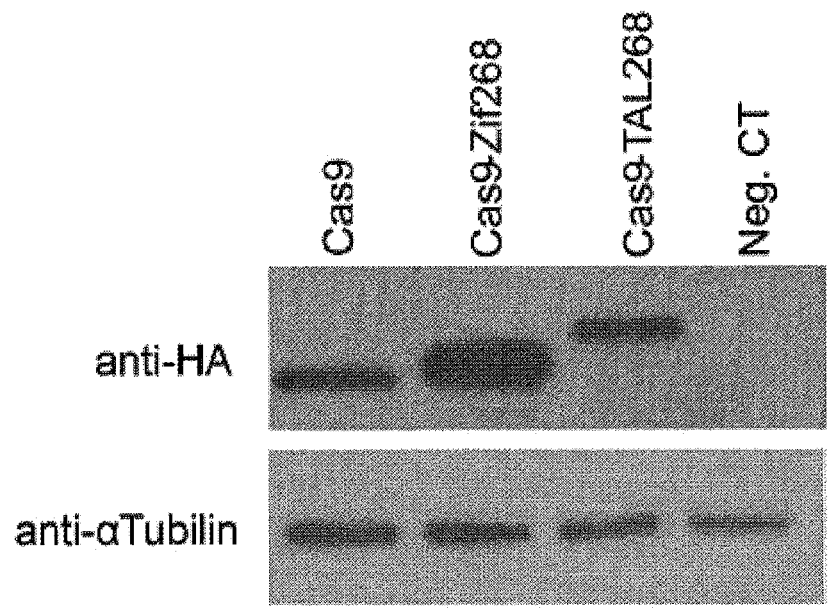
FIG. 54 presents exemplary data showing a protein expression analysis of SpCas9 and SpCas9-Zif268 and SpCas9-TAL268 platforms. HEK293T cells are transfected with the indicated Cas9 plasmid which has triple HA-tag. Top Panel: Full length protein is probed with anti-HA antibody. Bottom Panel: Alpha-tubulin is used as loading control.
Figure 55:
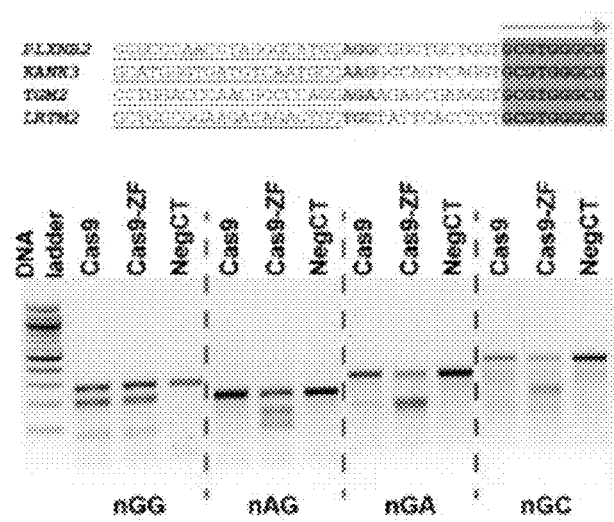
FIG. 55 presents exemplary data showing SpCas9 or SpCas9-Zif268 programmed independently with four different sgRNAs targeting four different genomic sites with neighboring Zif268 binding sites (highlighted in orange) (Top Panel), and that SpCas9 cuts efficiently only at the target site with a nGG PAM, but SpCas9-Zif$^{268}$ cuts efficiently at additional target sites with nAG, nGA or nGC PAMs (Bottom Panel). Genomic regions were PCR-amplified, and lesions (e.g., insertions or deletions within a local sequence) were detected by T7 Endonuclease I (T7EI) assay.

Both SpCas9-ZFP and SpCas9-TALE proteins can dramatically enhance nuclease activity on a nAG PAM target to a level comparable to wild-type SpCas9 (SpCas9$^{WT}$) activity on a nGG PAM while being expressed at similar levels. FIG. 54. SpCas9-pDBD nuclease activity remains dependent on the length of the guide sequence, confirming that a chimera retains a guide-dependent licensing stage for sequence cleavage. FIG. 6. To define the functional PAM elements utilized by a SpCas9-pDBD, activity at each of the 16 possible sequence combinations was examined. In contrast to wild type SpCas9, SpCas9-pDBD displayed high activity for nAG, nGA, nGC as well as the standard nGG PAM. FIG. 5 and FIG. 7. Importantly, a more flexible PAM recognition of SpCas9-pDBDs was also observed at genomic target sites. FIG. 55 and FIG. 8. Accounting for reverse complements of the functional PAM elements, SpCas9-pDBD chimeras can recognize 7 of the 16 possible dinucleotide sequence combinations, which markedly increases the number of accessible target sites. Because of a smaller size of SpCas9-ZFPs relative to SpCas9-TALEs, ZFP chimeras have advantages for delivery by certain viral delivery systems[47]. Consequently SpCas9-ZFP are preferred chimeras for many embodiments disclosed herein.

Figure 16:
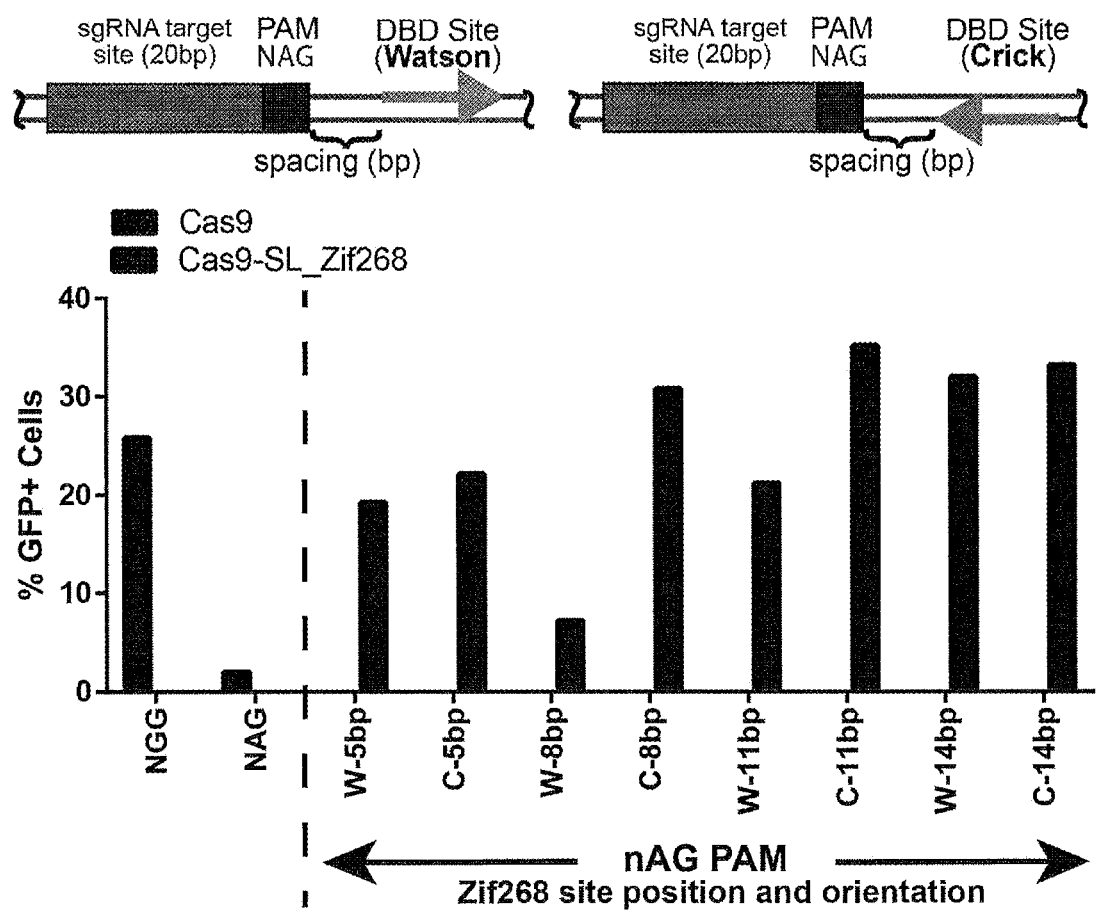
FIG. 16 presents illustrative schematic of the orientation and spacing parameters examined in these assays. Top Panel: Position and 5' to 3' orientation of the DTU binding site may be represented by an orange arrow relative to the PAM element of the Cas9 binding site. Bottom Panel: Displays an exemplary activity profile of Cas9 (blue, on an NGG or NAG PAM) or Cas9-SL_Zif268 (also referred to as Cas9$^{SL}$-ZFP268) (red, NAG PAM), where SL stands for shortened peptide linker between Cas9 and the DTU, on a common sgRNA target site. DTU site orientation may be either Watson (W) or Crick (C), and spacing may be 5, 8, 11 or 14 bp from the PAM (see schematic). No activity was detected for Cas9 above background on an NAG PAM, a Cas9-SL_Zif268 construct displayed activity on all AG PAM target sites in various levels. These data suggest that the linker length can be utilized as a parameter to adjust increased specificity on a desired target. Datum may be from single replicate, where HEK293T cells transfected with 50 ng Cas9/Cas9-Zif268/Cas9-TAL268 plasmid, 50 ng sgRNA plasmid, 150 ng GFP reporter with target site and 100 ng mCherry Control plasmid.

In one embodiment, a linker between a Cas9 nuclease and a DBD contains a plurality of amino acids (e.g., for example, approximately fifty-eight (58) amino acids) thereby providing good flexibility between the nuclease and the DBD. The data show that a standard SpCas9/sgRNA may be only functional with an NGG PAM, but not on an NAG PAM (blue bars). SpCas9-Zif268 (red bars) may be active on all spacings and orientations of the tested binding sites. SpCas9-TAL268 (green bars) has a much more restricted spacing and orientation, but strong activity can nonetheless be observed. Shorter linkers (e.g., for example, approximately twenty-five (25) amino acids) between a Cas9 nuclease and Zif268 have also been evaluated which provide a more restricted spacing between the nuclease and the DBD (FIG. 16). When fused to a DTU (e.g., for example, Zif268) Cas9 nuclease activity may be still dependent on the sgRNA, as demonstrated by determining Cas9 activity in a GFP reporter assay using truncated sgRNAs (FIG. 6). The activity profile of Cas9 and Cas9-Zif268 on a target site with a neighboring Zif268 binding site and an NGG PAM may be similar. Interestingly, Cas9-DTU fusions may be able to tolerate truncations of the sgRNA to 16 nucleotides within the guide segment, which has not been demonstrated previously. This may allow further improvements in precision with a truncated guide RNAs. Fu et al., Improving CRISPR-Cas nuclease specificity using truncated guide RNAs. Nat Biotechnol. 2014 March; 32(3):279-84.

SpCas9 and SpCas9-Zif268 were tested on all sixteen (16) possible NXX PAM combinations to define the breadth of sequences that can be targeted. It was found that NGG, NGA, NAG, and NGC PAMs have very similar activity for SpCas9-Zif268 in the presence of a neighboring Zif268 target site, whereas SpCas9 only cleaved NGG PAM efficiently. FIG. 5. This extension in the activity of alternate PAM specificities was also observed for SpCas9-TAL268 (FIG. 7). This extended activity profile was recapitulated for endogenous (i.e., not reporter) genomic target sites with suboptimal PAMs. FIG. 8. These data demonstrate that SpCas9-DBD fusions have increased activity and broader targeting range than a standard Cas9 system. Given that Cas9 fusion proteins contemplated by the present invention can target 7 of the 16 potential NXX or XXN permutations (e.g., CCN, TCN & CTN by targeting the opposite strand), and that TALEs can be programmed to recognize any sequence, SpCas9-TALEs can be programmed for cleavage of sites that occur roughly every other base pair within the genome. Lamb et al., Directed evolution of the TALE N-terminal domain for recognition of all 5' bases. Nucleic Acids Research. 2013 November; 41(21):9779-85.

B. Attenuated Cas9 Platforms

In one embodiment, the present invention contemplates an attenuated SpCas9 comprising a mutated PAM recognition sequence, wherein an SpCas9 has a reduced affinity for a specific target sequence ($Cas9^{MT}$ protein). Based on the structure of a SpCas9/sgRNA/target complex and conservation in phylogenetically neighboring Cas9 orthologs, two arginines involved in PAM recognition ($R^{1333}$ and $R^{1335}$) were identified as mutation targets (FIG. 9). Nishimasu et al., Crystal structure of Cas9 in complex with guide RNA and target DNA. Cell. 2014 Feb. 27; 156(5):935-49; and Anders et al., Structural basis of RAM-dependent target DNA recognition by the Cas9 endonuclease. Nature. 2014 Sep. 25; 513(7519):569-73. The impact of two different mutations at each site (R mutated to K or S) was examined using an SpCas9 and SpCas9-DBD GFP reporter activity assay. The data show that each mutation dramatically attenuates SpCas9 activity. Surprisingly, however, three of the four mutations regained functionality when incorporated into a SpCas9-DBD fusion protein. FIG. 9. On endogenous targets in HEK293T cells, two of these mutations appear to drastically inactivate SpCas9, whereas they remain fully functional as SpCas9-Zif268 fusion proteins (FIG. 10). Notably, mutations to SpCas9 PAM recognition residues can also yield $SpCas9^{MT}$-DBD nucleases with altered PAM preferences. The R1335K mutant (MT3) displays a strong preference for GG over AG at this target, unlike the original SpCas9 (FIG. 11). These results suggest that SpCas9 PAM specificity can be refined or potentially even altered, but that a fused DBD may be necessary to unmask this behavior.

Figures 11A, 11B:
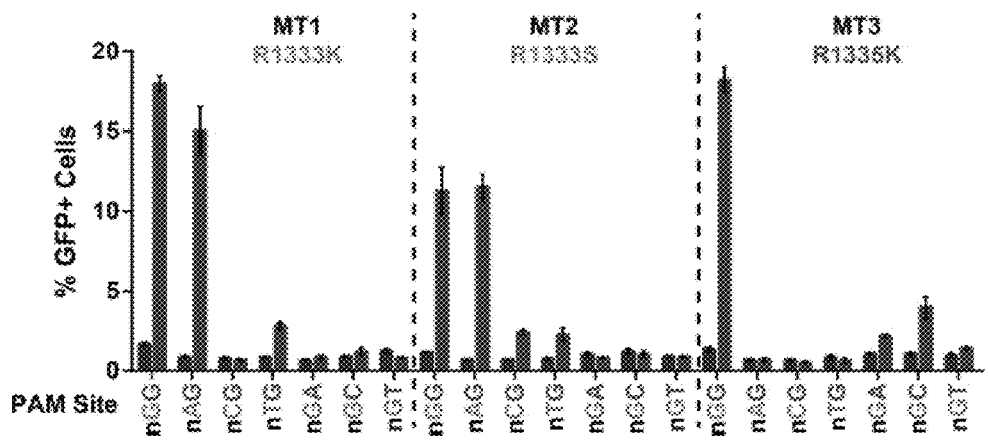
FIG. 11A-B presents exemplary data of an analysis of the activity of SpCas9 mutants (e.g., MT1, MT2 & MT3) on different PAM-containing target sites with a neighboring Zif268 site (Watson-5 bp) in a GFP reporter assay.
Figure 57:
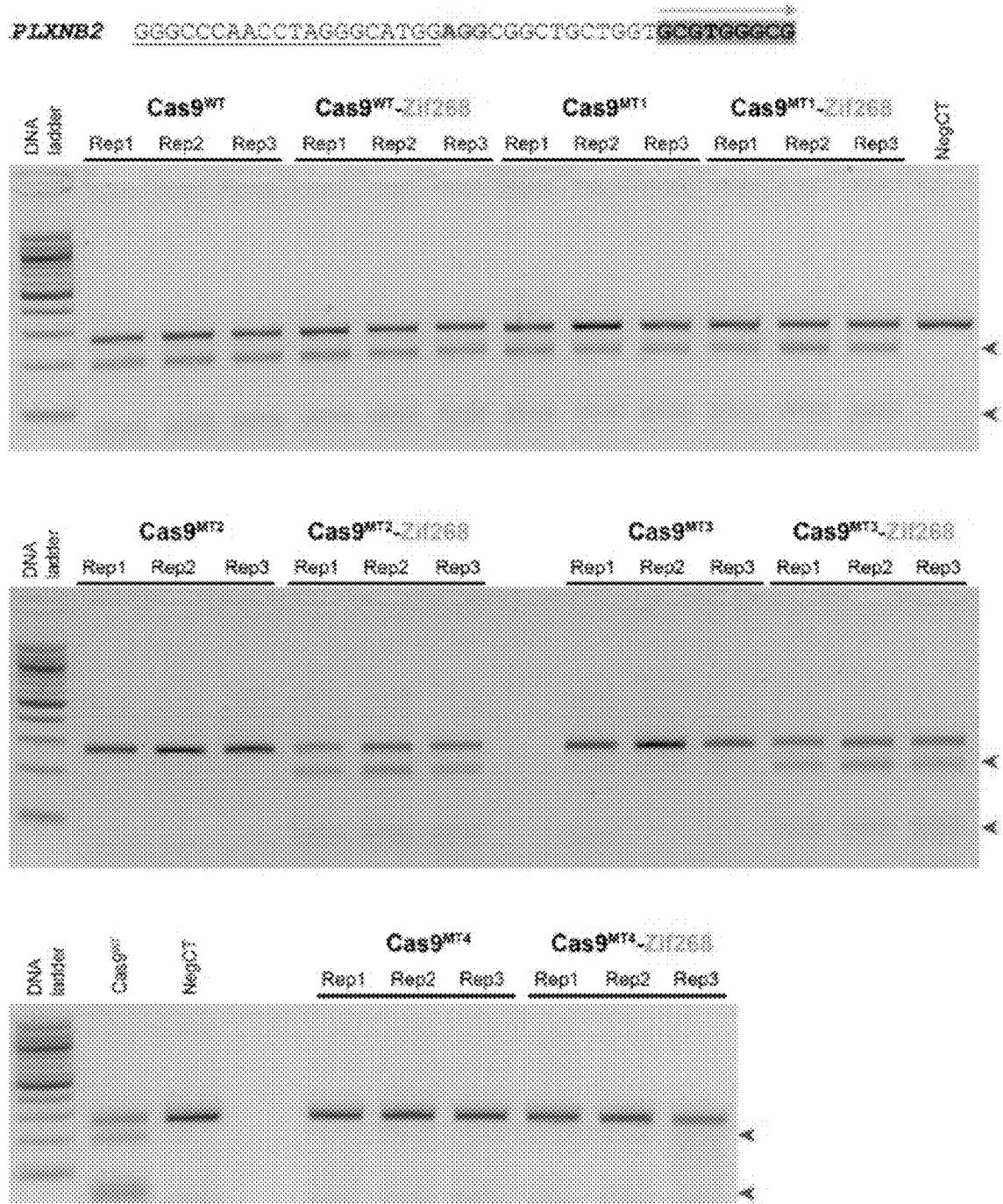
FIG. 57 presents exemplary data showing an analysis of the genomic activity profile of SpCas9 mutants (MT1, MT2, MT3 & MT4) independently and as SpCas9-Zif268 fusions at the PLXNB2 locus at a target site with an nGG PAM and a Zif268 binding site 11 bp away on the Watson strand. T7EI assay data from PCR products spanning the target site in three independent biological replicates (Rep1, Rep2, Rep3) performed on different days in HEK293T cells. Cleaved products are indicated by magenta arrowheads.
Figure 58:
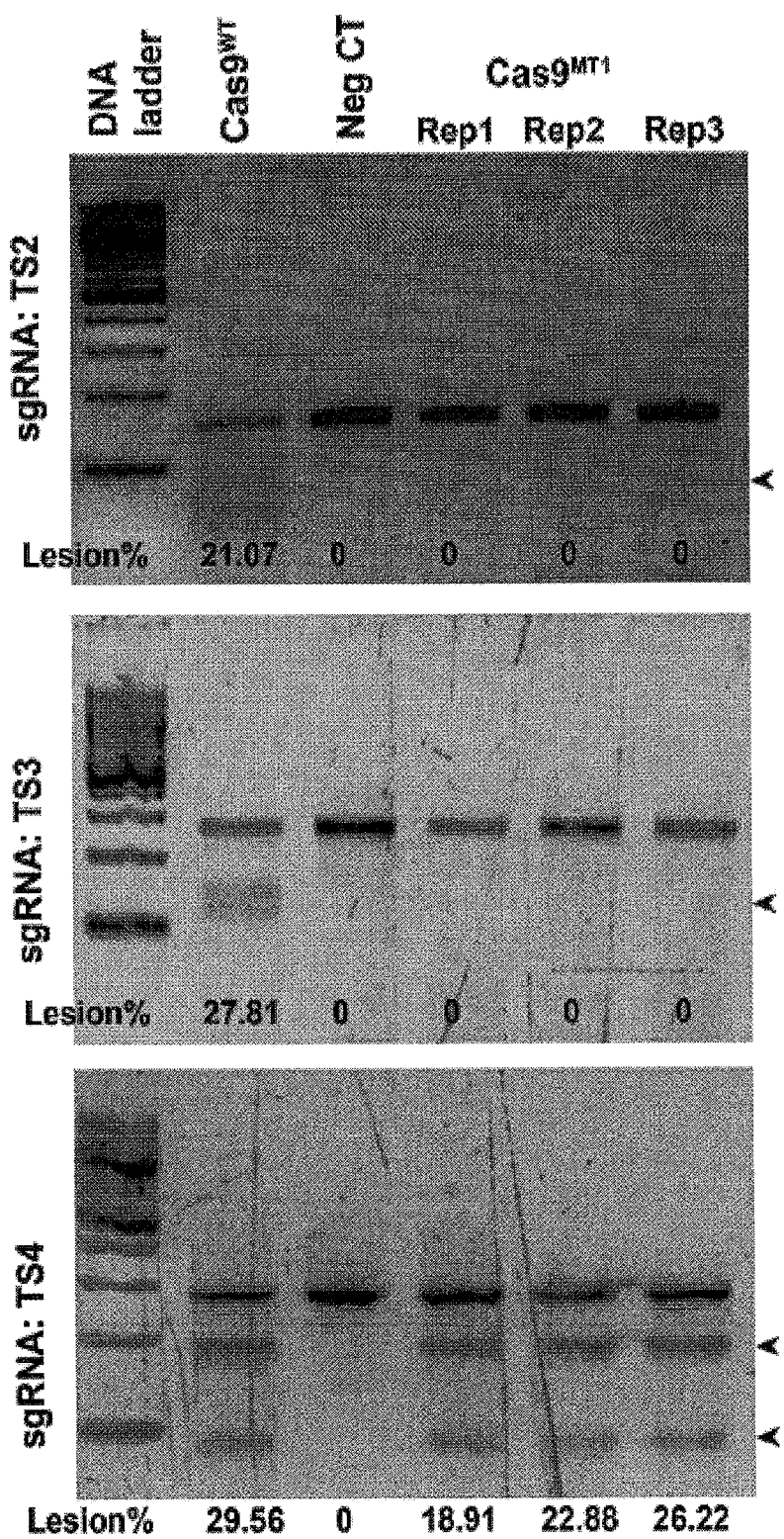
FIG. 58 presents exemplary data showing an analysis of the genomic activity profile of SpCas9$^{MT1}$ at TS2, TS3 and TS4 sites. T7EI assay data from PCR products spanning the target site in three independent biological replicates (Rep1, Rep2, Rep3) performed on different days in HEK293T cells. Cleaved products are indicated by magenta arrowheads.

The fusion of a pDBD to SpCas9 should increase nuclease precision if target cleavage is dependent on DNA recognition by the pDBD. To achieve this, DNA-binding affinity of SpCas9 was attenuated by independently mutating the key PAM recognition residues (Arg1333 and Arg1335)[7] to either Lysine or Serine. FIG. 9A and FIG. 11A. In as plasmid reporter assay, all four of these mutations reduced the nuclease activity of wild type SpCas9 to background levels; a fused ZFP domain and complementary target site restored nuclease activity in all mutants except R1335S ($SpCas9^{MT4}$). FIG. 9B. It was found that R1335K ($SpCas9^{MT3}$) was not functional with the nAG PAM even as a SpCas9-ZFP fusion. A broader evaluation of PAM specificity of the three active SpCas9-ZFP mutants determined a weak activity at alternate PAMs that retained an unaltered arginine—guanine interaction[7] (i.e. R1333 mutants prefer nnG PAMs, whereas the R1335K mutant prefers nGn PAMs). FIG. 11B. Activity of each SpCas9 mutant was also determined independently, or as a ZFP fusion, on a compatible genomic target site with an nGG PAM. FIGS. 56A&B, FIG. 57 and FIG. 58.

R1333K ($SpCas9^{MT1}$) retained independent activity on a subset of target sequences, whereas R1333S ($SpCas9^{MT2}$) and R1335K ($SpCas9^{MT3}$) display only background activity, which could be restored to wild type levels in the presence of a ZFP fusion. To confirm that the ZFP-dependent restoration of activity is general, the nuclease activity of three additional $SpCas9^{MT3}$-ZFP fusions were assessed, two of which restore nuclease function. FIG. 59 and Table 1.

TABLE 1

Summary of $SpCas9^{MT3}$-pDBD nuclease activities (T7EI)

| SEQ ID NO: | pDBD Name | Type | Target Sequence | sgRNA | Activity (%Lesion) |
|---|---|---|---|---|---|
| 4 | $ZFP^{TS2}$ | 4 Finger ZFP | GCGGGCAGGGGC | TS2 | 36.64 |
| 5 | $ZFP^{TS2}$ | 4 Finger ZFP | GCAGGGGCCGGA | TS2 | 23.04 |
| 6 | $ZFP^{TS3}$ | 4 Finger ZFP | GGCGTTGGAGCG | TS3 | 26.75 |
| 7 | $ZFP^{TS4}$ | 4 Finger ZFP | CCGGTTGATGTG | TS4 | 12.86 |
| 8 | Zif268 | 3 Finger ZFP | GCGTGGGCG | PLXNB2 | 25.81 |
| 9 | $ZFP^{DCLK2}$ | 4 Finger ZFP | GAAACGGGATCG | DNAJC6 | 9.32 |
| 10 | $ZFP^{FactorIX}$ | 5 Finger ZFP | ACACAGTACCTGGCA | PLXDC2 | 9.90 |
| 11 | $ZFP^{HEBP2}$ | 4 Finger ZFP | GAAAAGTATCAA | GPRC5B | N.D |
| 12 | TAL268 | 8.5 Module TALE | TGCGTGGGCG | PLXNB2 | N.D |
| 13 | $TALE^{TS3-S}$ | 9.5 Module TALE | TTGGAGCGGGG | TS3 | 8.00 |
| 14 | $TALE^{TS3-L}$ | 15.5 Module TALE | TTGGAGCGGGGAGAAGG | TS3 | 16.26 |
| 15 | $TALE^{TS4-S}$ | 9.5 Module TALE | TCAACCGGTGG | TS4 | 2.01** |
| 16 | $TALE^{TS4-L}$ | 15.5 Module TALE | TCAACCGGTGGCGCATT | TS4 | 1.82** |

N.D: Not Detected
**: Not above background independent activity for $SpCas9^{MT3}$.

Thus, altering an affinity of Cas9 PAM recognition domains through mutation generates SpCas9 variants that are dependent on an attached pDBD for efficient function. This dependence on an attached pDBD establishes a third stage of target site licensing for the presently disclosed SpCas9MT3-pDBDs, which are observed to increase their precision.

To evaluate precision of an SpCas9$^{MT}$-DBD fusion protein, validated SpCas9 target sites were tested (e.g., TS2, TS3 & TS4; all with NGG PAMs). Fu et al., Improving CRISPR-Cas nuclease specificity using truncated guide RNAs. Nature Biotechnology, 2014 March; 32(3):279-84; Fu, Y., Foden, J. A., Khayter, C., Maeder, M. L., Reyon, D., Joung, J. K., & Sander, J. D. (2013). High-frequency off-target mutagenesis induced by CRISPR-Cas nucleases in human cells. *Nature Biotechnology*, 31(9), 822-826, doi: 10.1038/nbt.2623. SgRNAs that recognize these sites have well-defined on- and off-target activities, and thus provide a benchmark to rapidly assess improvements in precision by evaluating activity at high-efficiency off-target sites.

Figure 13:
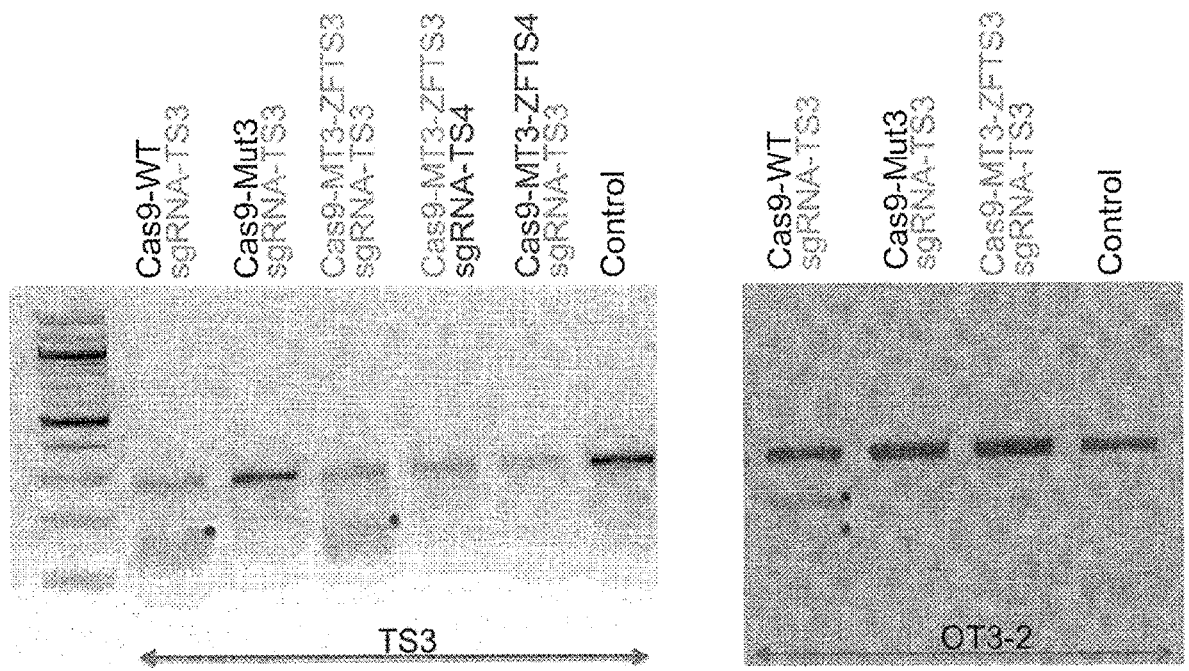
FIG. 13 presents exemplary data of T7EI assays on PCR products spanning TS3 or off-site 2 (OT3-2) in nuclease treated (or control) HEK293T cells. An sgRNA for TS3 (sgRNA-TS3) was used to program cleavage of SpCas9$^{WT}$, SpCas9$^{MT3}$ or SpCas9$^{MT3}$-ZFP$^{TS3}$, where the ZFP was assembled from an archive of zinc fingers of defined specificity. Zhu et al., Using defined finger-finger interfaces as units of assembly for constructing zinc-finger nucleases. Nucleic Acids Research. 2013 Feb. 1; 41(4):2455-65; and Gupta et al., An optimized two-finger archive for ZFN-mediated gene targeting. Nature Methods. 2012 Apr. 29; 9(6):588-90. Cleaved bands indicating nuclease activity at each locus are indicated by red dots. SpCas9$^{MT3}$-ZFP$^{TS3}$ may be programmed with a non-cognate sgRNA-TS4, or SpCas9$^{MT3}$ may be fused to a ZFP recognizing a different binding site (SpCas9$^{MT3}$-ZFP$^{TS4}$) such that no activity may be observed at TS3.
Figure 14:
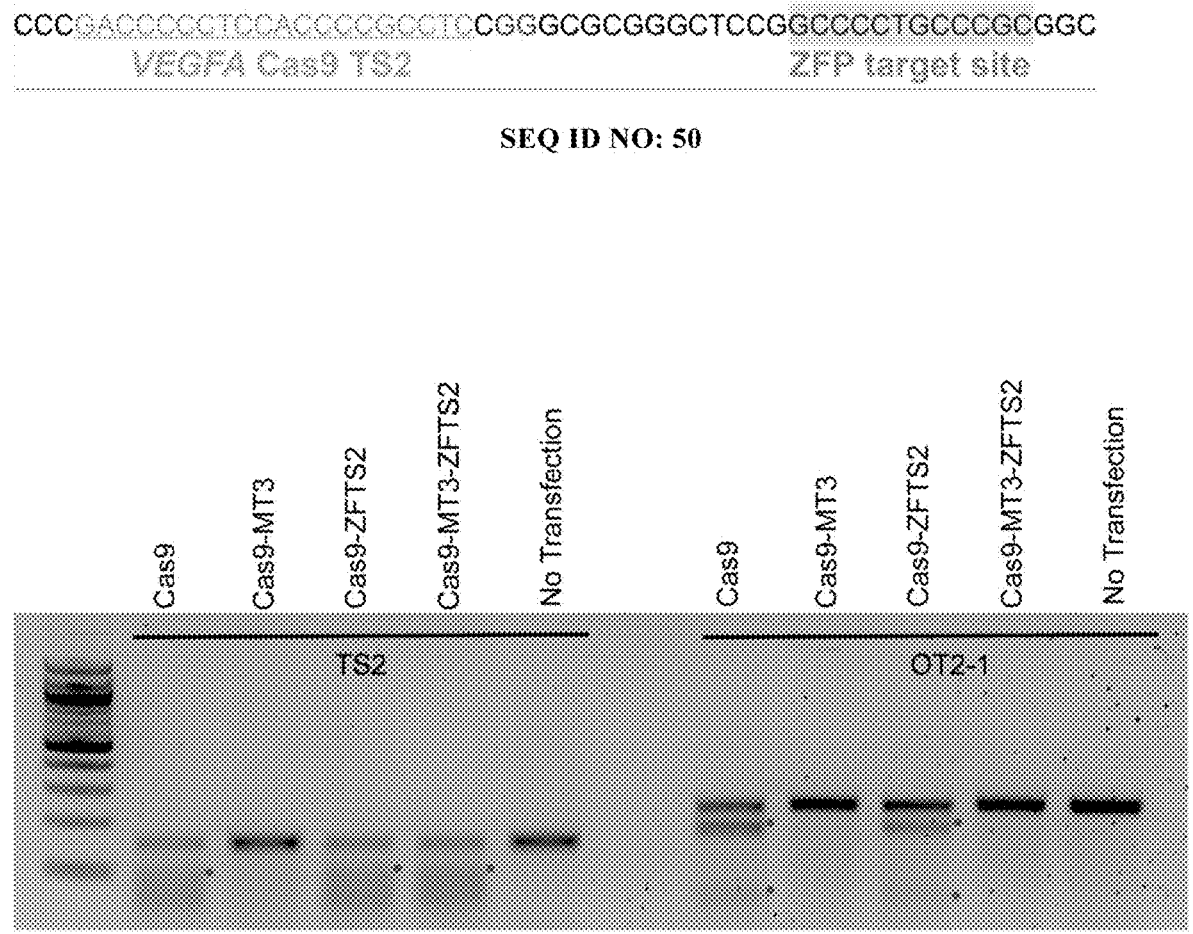
FIG. 14 presents exemplary data of T7EI assays on PCR products spanning TS2 or off-target site 2 (OT2-1) in nuclease treated (or control) HEK293T cells (PMID 24463574). An sgRNA for TS2 (sgRNA-TS2) was used to program cleavage of SpCas9$^{WT}$, SpCas9-ZFP$^{TS2}$, SpCas9$^{MT3}$ or SpCas9$^{MT3}$-ZFP$^{TS2}$, where the ZFP was assembled from an archive of zinc fingers of defined specificity, Zhu et al., Using defined finger-finger interfaces as units of assembly for constructing zinc-finger nucleases. Nucleic Acids Research. 2013 Feb. 1; 41(4):2455-65; and Gupta et al., An optimized two-finger archive for ZFN-mediated gene targeting. Nature Methods. 2012 Apr. 29; 9(6):588-90. Cleaved bands indicating nuclease activity at each locus are indicated by magenta dots. SpCas9$^{MT3}$-ZFP$^{TS2}$ shows no apparent activity at OT2-1, whereas it cleaves the target site efficiently.
Figure 15:
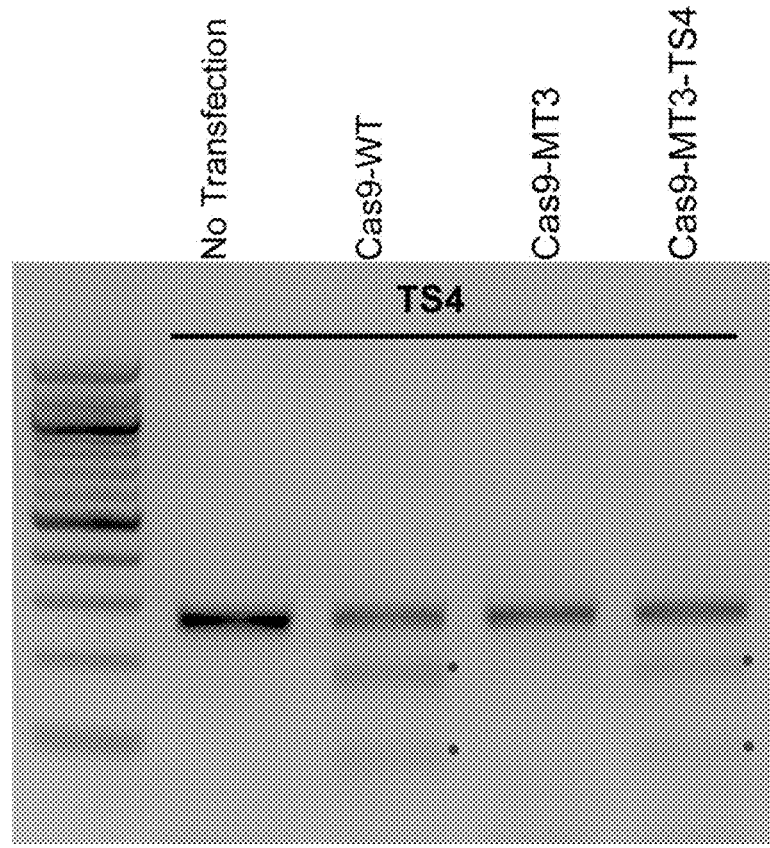
FIG. 15 presents exemplary data of T7EI assays on PCR products spanning TS4 in nuclease treated (or control) HEK293T cells (PMID 24463574). An sgRNA for TS4 (sgRNA-TS4) was used to program cleavage of SpCas9$^{WT}$, SpCas9$^{MT3}$ or SpCas9$^{MT3}$-ZFP$^{TS4}$, where the ZFP was assembled from an archive of zinc fingers of defined specificity. Zhu et al., Using defined finger-finger interfaces as units of assembly for constructing zinc-finger nucleases. Nucleic Acids Research, 2013 Feb. 1; 41(4):2455-65; and Gupta et al., An optimized two-finger archive for ZFN-mediated gene targeting. Nature Methods. 2012 Apr. 29; 9(6):588-90. Cleaved hands indicating nuclease activity at each locus are indicated by red dots.

A ZFP DBD (i.e., for example, ZFP$^{TS3}$) was designed to recognize a sequence near a TS3 target site (FIG. 12) and the editing activities were compared of TS3 sgRNA-programmed SpCas9, SpCas9$^{MT3}$ and SpCas9$^{MT3}$-ZFP$^{TS3}$ at the target site and a highly active off-target site (OT3-2). FIG. 10. The data confirms that a standard SpCas9 was highly active at both sites, and that SpCas9$^{MT3}$ was inactive at both sites. Remarkably, SpCas9$^{MT3}$-ZFP$^{TS3}$ displays high activity only at the target site (TS3), and appears inactive at OT3-2. Cleavage of a target site may be still sgRNA-dependent, as a non-cognate guide (sgRNA-TS4) fails to drive TS3 cleavage (FIG. 13). Likewise, a non-cognate ZFP (i.e., for example, ZFP$^{TS4}$) fails to target TS3 when fused to SpCas9$^{MT3}$ loaded with a TS3-targeting sgRNA (FIG. 13). These data are in comparison with other data showing OT3-2 cleavage with standard SpCas9 even with a specificity-enhancing tru-sgRNA. Fu et al., Improving CRISPR-Cas nuclease specificity using truncated guide RNAs. Nature Biotechnology. 2014 March; 32(3):279-84. Thus, SpCas9$^{MT}$ editing activity may be abrogated, but can be regained in a highly specificity-enhanced fashion when constructed as a fusion protein with a programmable DBD, as contemplated by the invention herein. Similar ability to selectively target Cas9$^{MT3}$ to function at TS2 (FIG. 14) and TS4 (FIG. 15) using an attached zinc finger protein has been achieved.

Sequences of a number of the Cas9-DTU fusions used in these preliminary studies are presented in FIGS. 27-36. Number of amino acid sequences of Cas9-DTU fusions used in these studies are presented in FIGS. 37-43

C. NmCas9 Gene Editing Platform

Cas9 is believed to be a Type II CRISPR/Cas system and may be further subdivided into three subtypes: i) II-A (including the 1368-aa SpCas9); ii) II-B; and iii) II-C. Barrangou et al., CRISPR-Cas systems: Prokaryotes upgrade to adaptive immunity. Molecular Cell. 2014 Apr. 24; 54(2):234-44. Type II-C Cas9s are believed to be compact and more prevalent than the other two subtypes; (e.g., for example, ~55% II-C; ~38% (II-A); ~7% (II-B)). Further, Type II-C Cas9s may serve to extend the potential targeting specificity via their range of PAM recognition requirements. Fonfara et al., Phylogeny of Cas9 determines functional exchangeability of dual-RNA and Cas9 among orthologous type II CRISPR-Cas systems. Nucleic Acids Research, 2014 Feb. 1; 42(4):2577-90. The shorter length of some Type II-C Cas9s (as small as ~970-1100 aa) may facilitate delivery, as viral payload limitations make the larger SpCas9 suboptimal for some clinical applications (e.g., adeno-associated viruses). Daya et al., Gene therapy using adeno-associated virus vectors. Clin. Microbiol. Rev. 2008 October; 21(4): 583-93.

An in-depth analysis of as *Neisseria meningitidis* Type II-C system (NmCas9), including a definition of its apparent PAM (5'-NNNNGATT-3') (SEQ ID NO: 1), has been reported. Zhang et al., Processing-independent CRISPR RNAs limit natural transformation in *Neisseria meningitidis*. Molecular Cell. 2013 May 23; 50(4):488-503. Further, a 1082-aa NmCas9 has been validated as an efficient genome-editing platform in human cells. Hou et al., Efficient genome engineering in human pluripotent stem cells using Cas9 from *Neisseria meningitidis*. Proceedings of the National Academy of Sciences. 2013 Sep. 24; 110(39):15644-9; and Esvelt et al., Orthogonal Cas9 proteins for RNA guided gene regulation and editing. Nature Methods. 2013 November; 10(11):1116-21. The structure of a different Type II-C Cas9 from *Actinomyces naeslundii* (AnCas9) may be known, revealing a distinct arrangement of peripheral domains (in comparison with SpCas9) around a similarly structured nuclease core, though AnCas9's PAM specificity and genome editing efficacy have not been reported. Jinek et al., Structures of Cas9 endonucleases reveal RNA-mediated conformational activation. Science. 2014 Mar. 14; 343 (6176):1247997.

Figure 75:
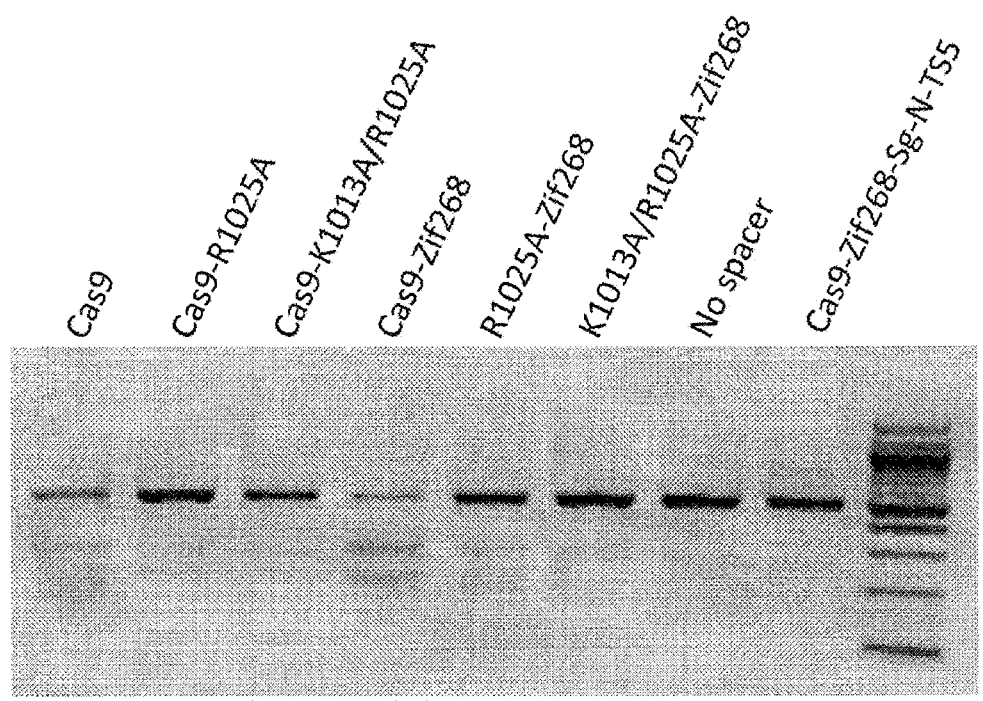
FIG. 75 presents exemplary data demonstrating that a ZFP fusion can restore activity of the single NmCas9 mutant at a chromosomal target site that has a GATT PAM with an 11 bp spacing and Crick (C) orientation of the ZFP binding site. Experiment performed as in FIG. 73, except that a different chromosomal target (N-TS9) site was tested. There is weak background T7EI cleavage activity in all of the lanes including the controls.
Figure 76:
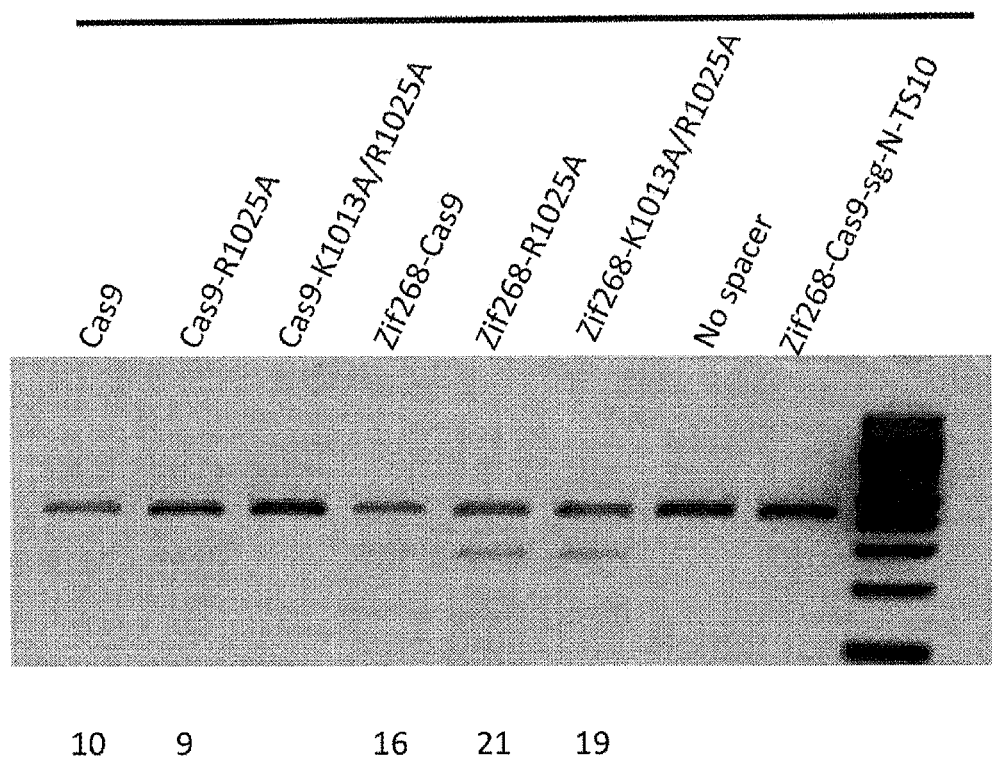
FIG. 76 presents exemplary data demonstrating that a ZFP fusion can restore activity of the double NmCas9 mutant at a chromosomal target site that has a GATT PAM with an 9 bp spacing and Watson (W) orientation of the ZFP binding site. Experiment performed as in FIG. 73, except that a different chromosomal target (N-TS8) site was tested.
Figure 77:
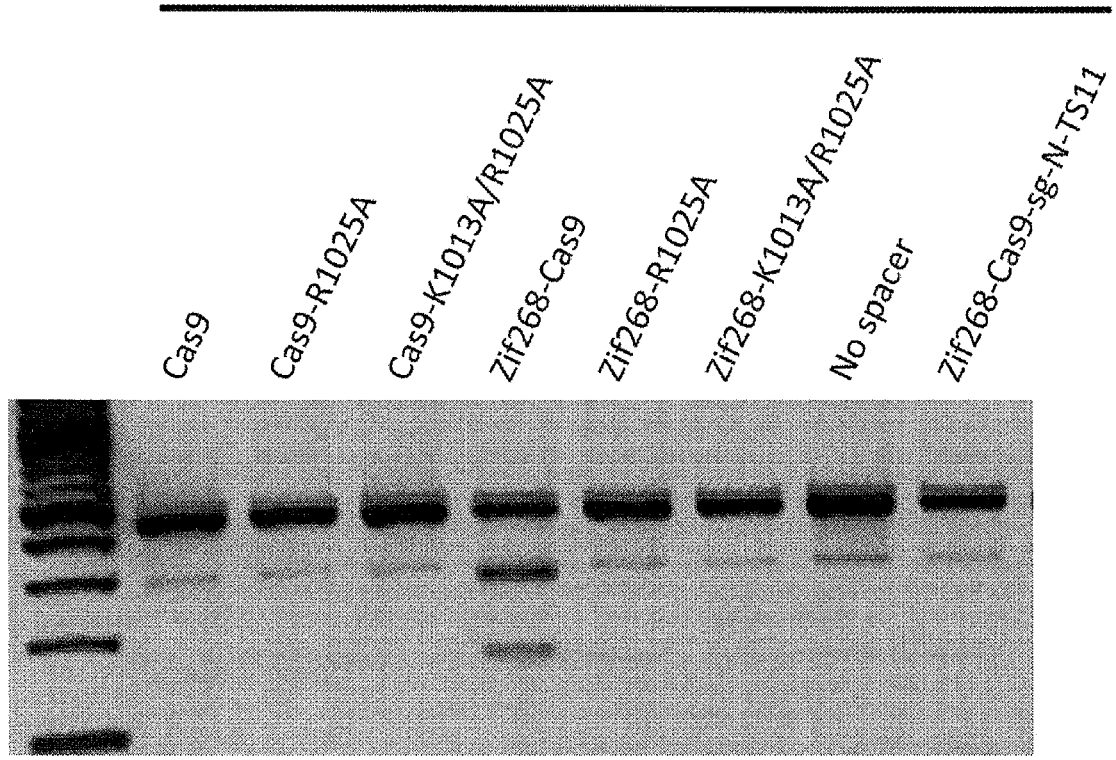
FIG. 77 presents exemplary data demonstrating that a ZFP fusion can enhance activity of NmCas9 at a chromosomal target site that has a GATT PAM with an 12 bp spacing and Watson (W) orientation of the ZFP binding site. Experiment performed as in FIG. 73, except that a different chromosomal target (N-TS10) site was tested. There is weak background T7EI cleavage activity in all of the lanes including the controls.
Figure 78:
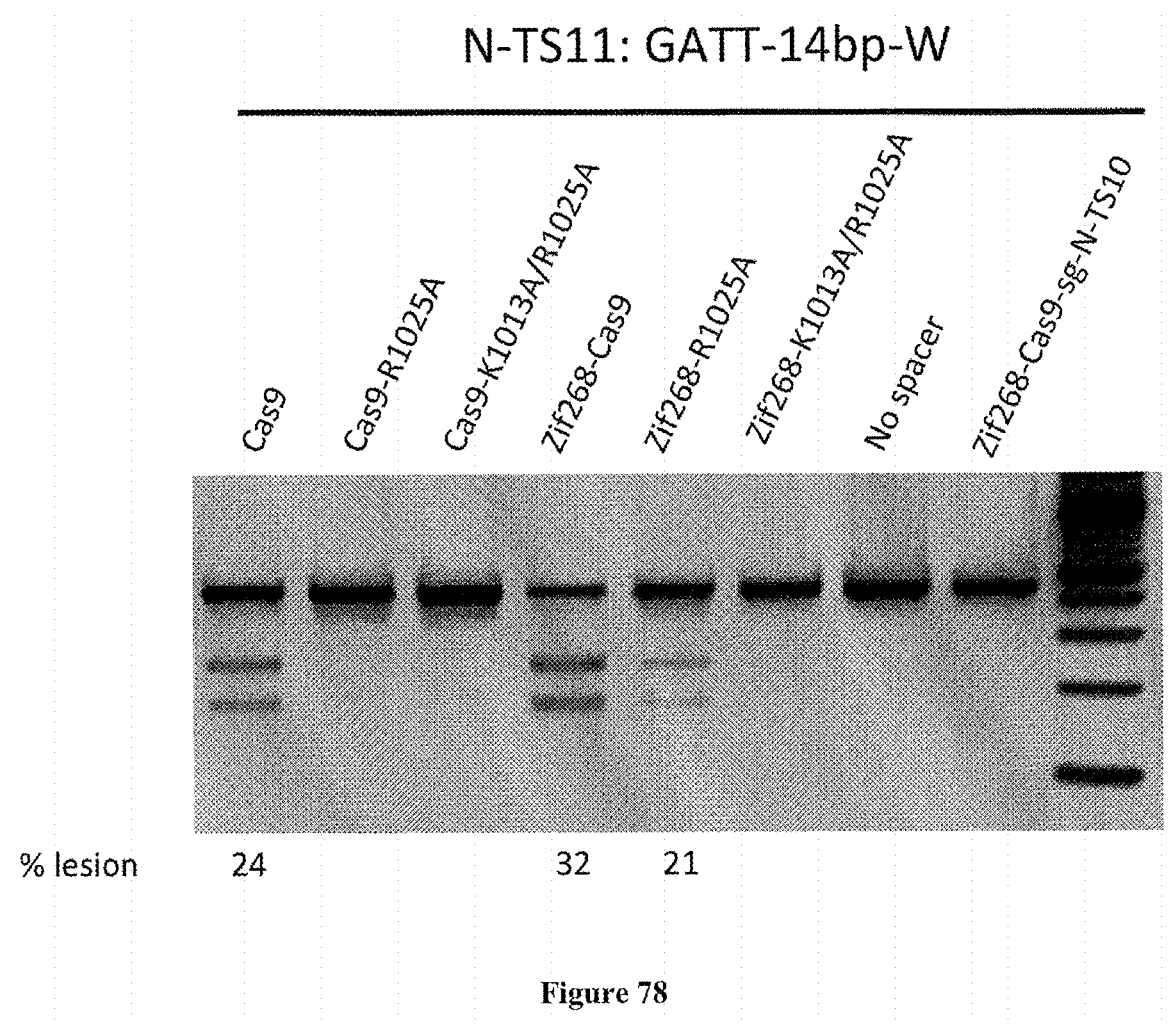
FIG. 78 presents exemplary data demonstrating that a ZFP fusion can restore activity of the single NmCas9 mutant at a chromosomal target site that has a GATT PAM with an 14 bp spacing and Watson (W) orientation of the ZFP binding site. Experiment performed as in FIG. 73, except that a different chromosomal target (N-TS11) site was tested.
Figure 80:
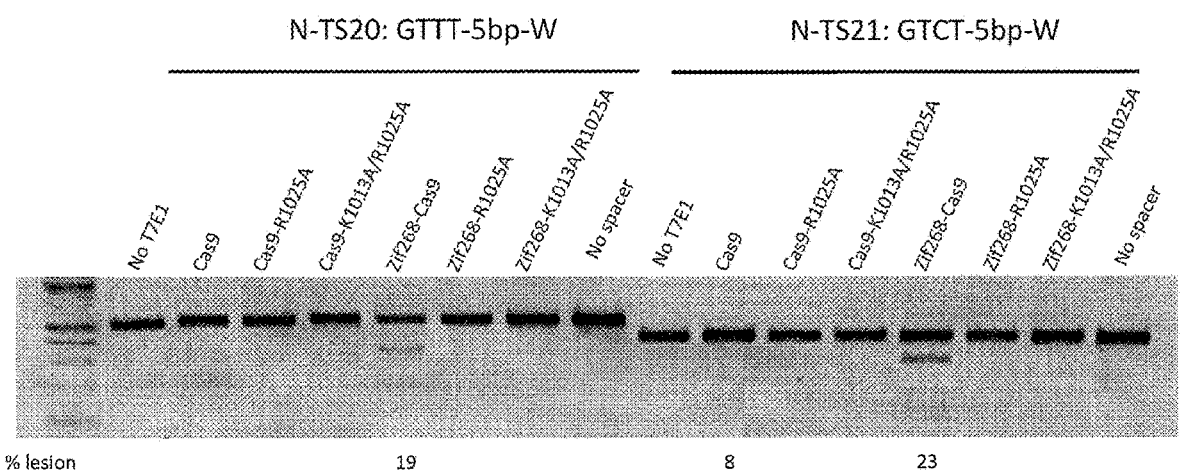
FIG. 80 presents exemplary data demonstrating that a ZFP fusion can enhance activity of NmCas9 at a chromosomal target site that has a GTTT PAM (left panel) or GTCT PAM (right panel) with a 5 bp spacing and Watson (W) orientation of the ZFP binding site. Experiment performed as in FIG. 73, except that a different chromosomal targets (N-TS20, left panel; N-TS21, right panel) sites were tested.
Figure 81:
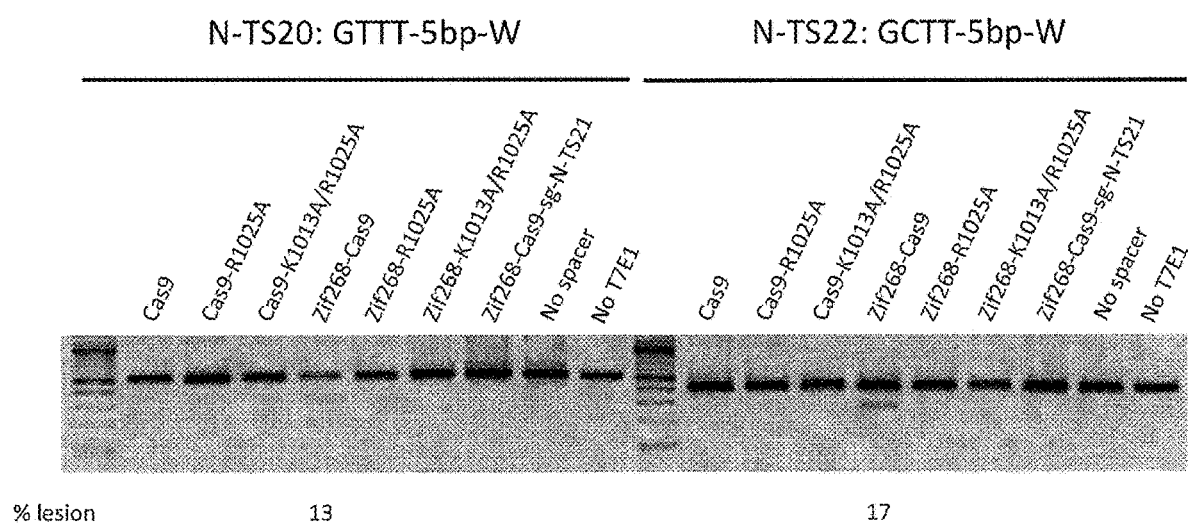
FIG. 81 presents exemplary data demonstrating that a ZFP fusion can enhance activity of NmCas9 at a chromosomal target site that has a GTTT PAM (left panel) or GCTT PAM (right panel) with a 5 bp spacing and Watson (W) orientation of the ZFP binding site. Experiment performed as in FIG. 73, except that a different chromosomal targets (N-TS20, left panel; N-TS22, right panel) sites were tested.
Figure 82:
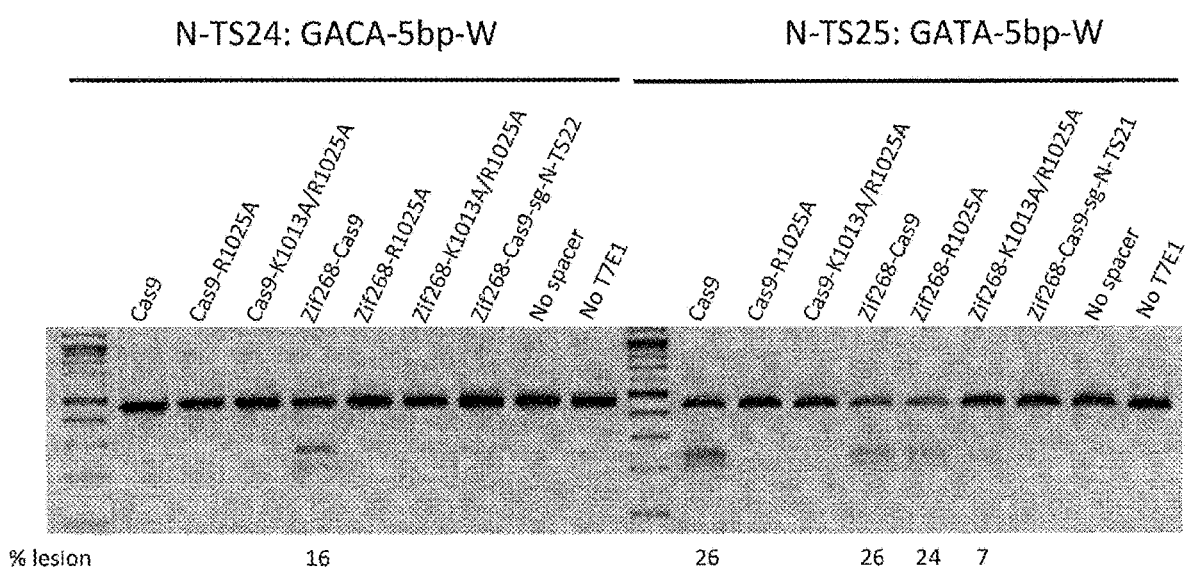
FIG. 82 presents exemplary data demonstrating that a ZFP fusion can permit activity of NmCas9 at a chromosomal target site that has a GACA PAM (left panel) or restore activity of a single or double mutant NmCas9 at GATA PAM (right panel) with a 5 bp spacing and Watson (W) orientation of the ZFP binding site. Experiment performed as in FIG. 73, except that different chromosomal targets (N-TS24, left panel; N-TS25, right panel) sites were tested.
Figure 83:
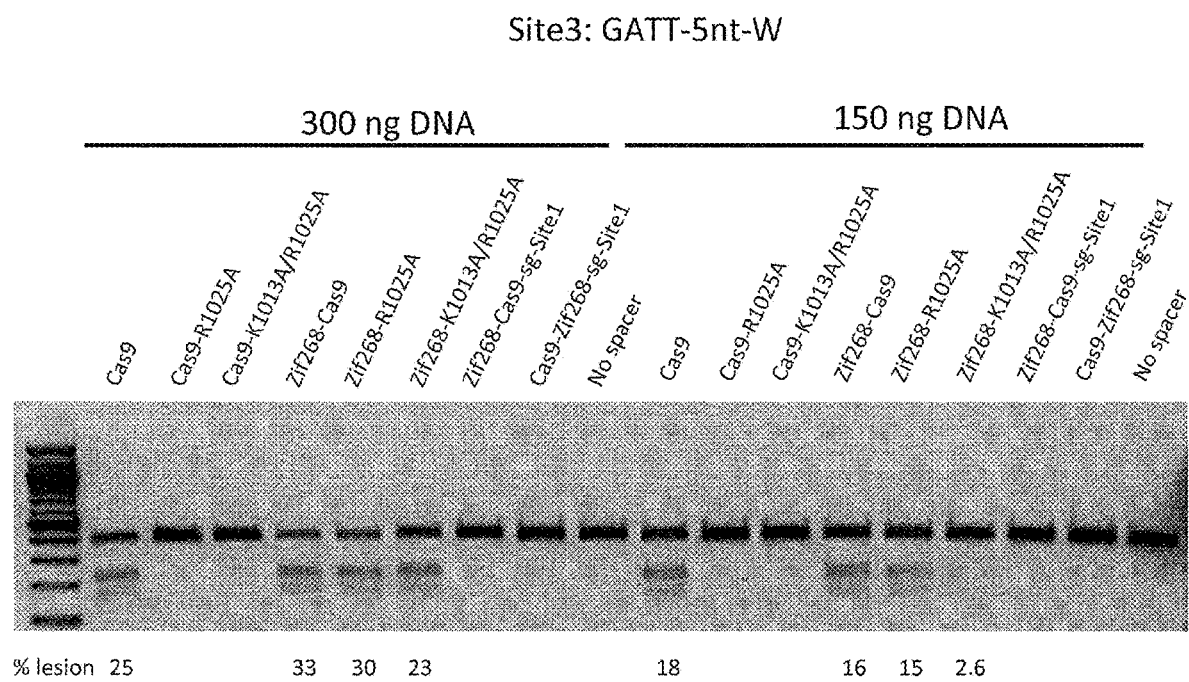
FIG. 83 presents exemplary data demonstrating that a ZFP fusion can restore activity of a single or double mutant NmCas9 at GATT PAM (right panel) with a 5 bp spacing and Watson (W) orientation of the ZFP binding site. Experiment performed as in FIG. 73, except that a different chromosomal target (N-TS3) site was tested at different concentrations of transfected DNA.

In mammalian cells, PAM requirements efficient editing by nmCas9 has been observed with NNNNG(A/C/T)TT PAMs (SEQ ID NO: 17). Hou et al., Efficient genome engineering in human pluripotent stem cells using Cas9 from *Neisseria meningitidis*. Proceedings of the National Academy of Sciences. 2013 Sep. 24; 110(39):15644-9; and Esvelt et al., Orthogonal Cas9 proteins for RNA guided gene regulation and editing. Nature Methods, 2013 November; 10(11):1116-21. An ability of a pDBD fusion to extend the range of targetable PAMs has been examined for NmCas9 as previously shown with SpCas9. On genomic target sites with a ZFP (Zif268) fused to the N-terminus or the C-terminus and where a Zif268 binding site is downstream of the PAM an extension of the range of targetable sequences is observed. These data demonstrate that while wild-type NmCas9 is inactive at these genomic loci, the Zif268 fusion permits robust cleavage (FIGS. 80, and 82; e.g., NNNNGTCT (SEQ ID NO: 18), NNNNGACA (SEQ ID NO: 19)). In addition, at some canonical PAM domains (NNNNGATT (SEQ ID NO: 1), FIGS. 75, 77, 78; NNNNGCTT (SEQ ID NO: 20), FIG. 81; NNNNGTTT (SEQ ID NO: 21), FIG. 80) the ZFP fusion to NmCas9 enhances the activity of the nuclease, in many cases providing activity where unfused NmCas9 is inactive. Thus, a pDBD fusion may provide a method to fully activate Cas9 nucleases even at canonical PAM sites for which they have poor or no activity.

Figure 25:
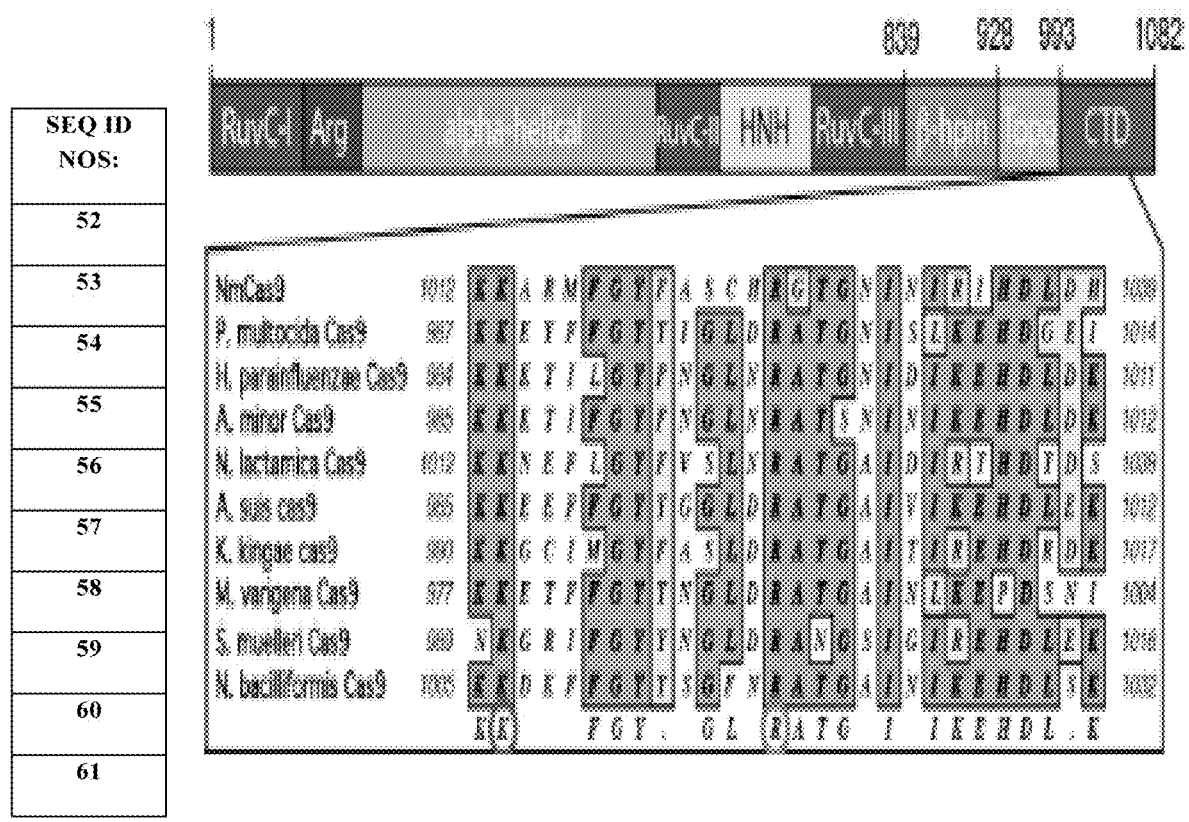
FIG. 25 illustrates one embodiment of a domain organization of NmCas9 based on a structure of a related Type II-C Cas9. Jinek et al., Structures of Cas9 endonucleases reveal RNA mediated conformational activation. Science, 2014 Mar. 14; 343(6176):1247997. The PAM-interacting residues are likely to be found in the Topo or CTD regions based in part on comparison to SpCas9. Anders et al., Structural basis of PAM-dependent target DNA recognition by the Cas9 endonuclease. Nature, 2014 Sep. 25; 513(7519):569-73. Sequence alignment of NmCas9 with 9 related Type II-C orthologs showing conservation of Arg1025 (magenta circle) and Lys1013 (red circle) residues that are candidates for mutagenesis.
Figure 69:
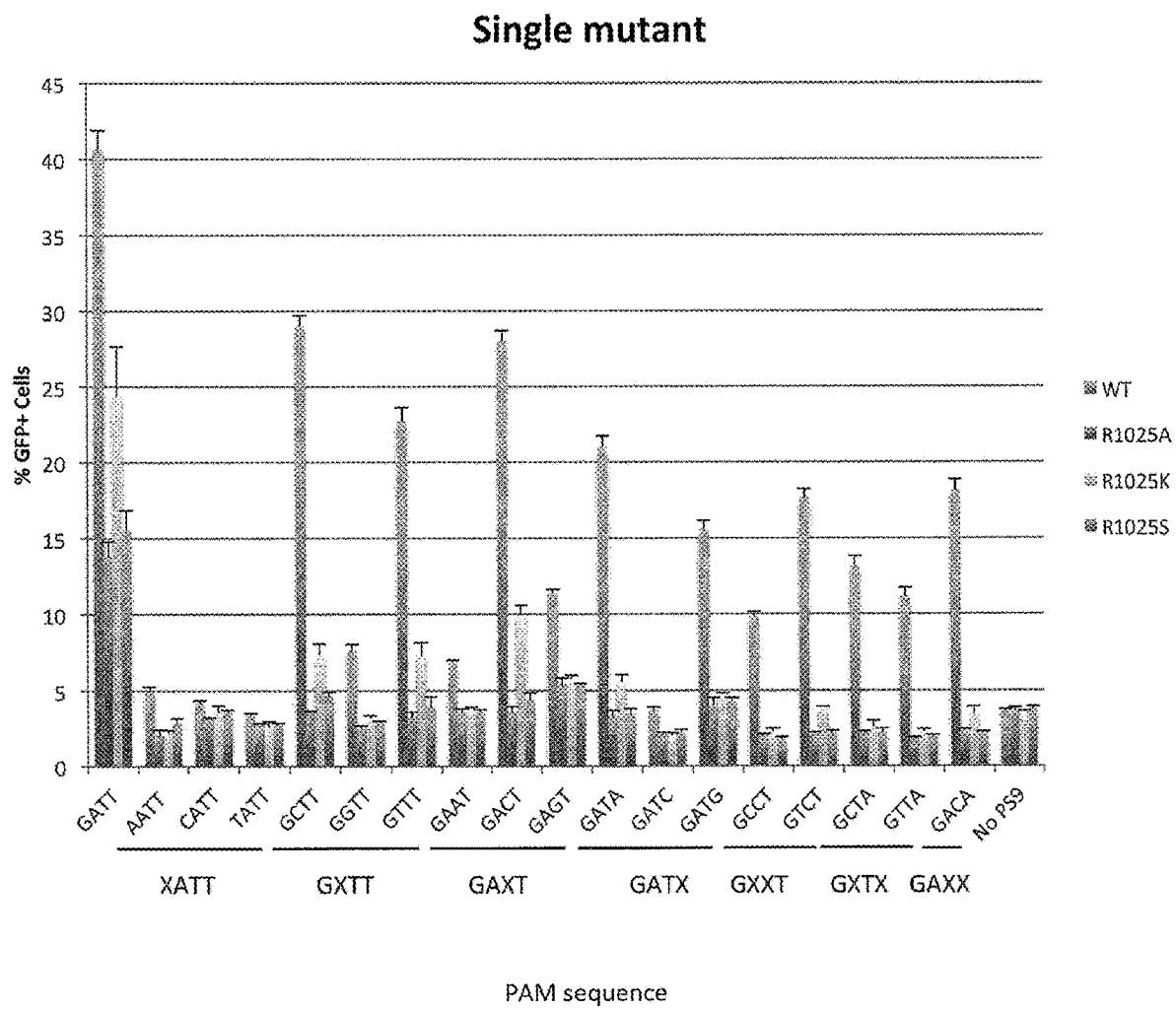
FIG. 69 presents exemplary data for the impact of a single point mutation of a conserved arginine (Arg1025) residue in the PAM interaction domain on NmCas9 activity in a GFP reporter assay. HEK293 cells in 24-well plates were transfected with 100 ng split-GFP reporter (Wilson, K. A., Chateau, M. L. & Porteus, M. H. Design and Development of Artificial Zinc Finger Transcription Factors and Zinc Finger Nucleases to the hTERT Locus. Mol Ther Nucleic Acids 2, e87 (2013)), into which we had cloned a protospacer (with its NNNNGATT PAM) (SEQ ID NO: 1) targeted by the natural *N. meningitidis* 8013 CRISPR spacer 9. Variants carrying PAM mutations (as indicated) were also used. Also included in the transfections were 10 ng of an mCherry-expressing plasmid (as a transfection marker), and 290 ng of a plasmid expressing wt NmCas9 (blue bars) or mutants that change a candidate PAM recognition residue (Arg1025) to Ala, Lys, or Ser (red, green, and purple, respectively). The NmCas9-expressing plasmid also encoded the spacer 9-containing sgRNA. Three identical transfections were done on different days. In each case, after 48 hours post-transfection, cells were harvested and analyzed by flow cytometry to identify the fraction of mCherry-positive cells that were also GFP-positive.
Figure 70:
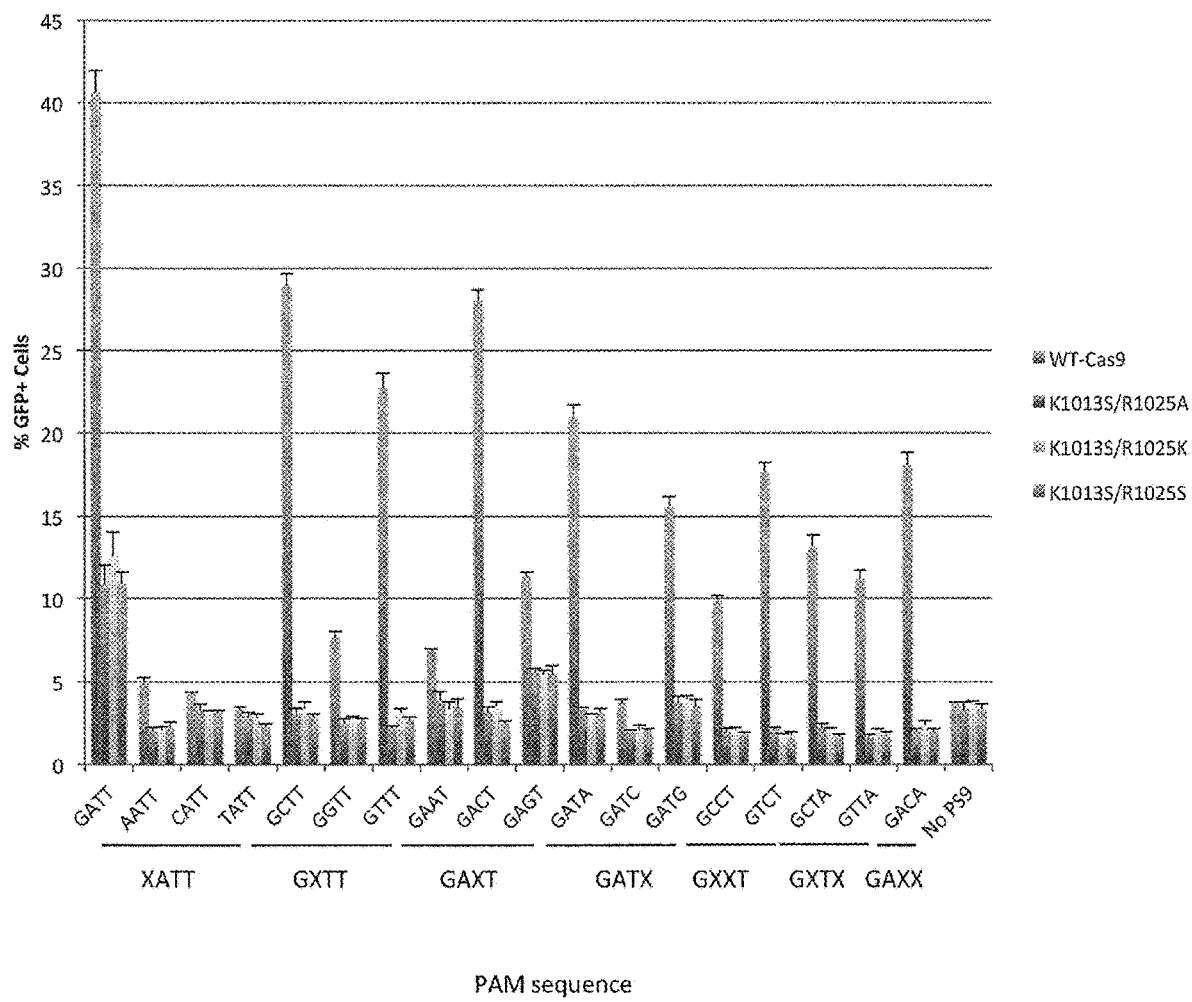
FIG. 70 presents exemplary data for the impact of a double mutation of a conserved arginine (Arg1025) and lysine (Lys1013) residue in the PAM interaction domain on NmCas9 activity in a GFP reporter assay. HEK293 cells in 24-well plates were transfected with 100 ng split-GFP reporter, into which we had cloned a protospacer (with its NNNNGATT PAM) (SEQ ID NO:1) targeted by the natural *N. meningitidis* 8013 CRISPR spacer 9. Variants carrying PAM mutations (as indicated) were also used. Also included in the transfections were 10 ng of an mCherry-expressing plasmid (as a transfection marker), and 290 ng of a plasmid expressing wt NmeCas9 (blue bars) or mutants that change a candidate PAM recognition residue (Arg1025) to Ala, Lys, or Ser (red, green, and purple, respectively), each in combination with a second mutation changing Lys1013 to Ser. The NmeCas9-expressing plasmid also encoded the spacer 9-containing sgRNA. Three identical transfections were done on different days. In each case, after 48 hours post-transfection, cells were harvested and analyzed by flow cytometry to identify the fraction of mCherry-positive cells that were also GFP-positive.
Figure 71:
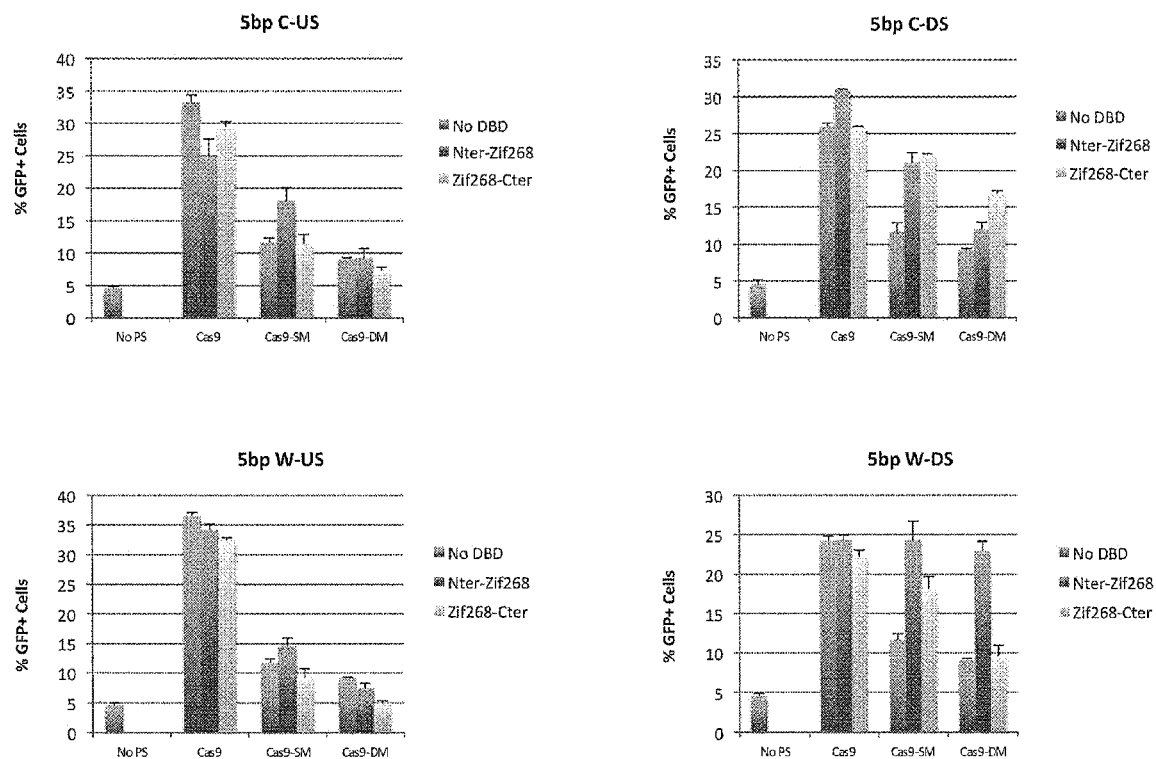
FIG. 71 presents exemplary data examining the ability of an N-terminal C-terminal fusion of Zif268 to NmCas9 to be able to rescue the cleavage activity of attenuated NmCas9 mutants. The split-GFP reporter system was modified to include a Zif268 binding site, either upstream (US) (i.e. on the opposite side of the protospacer to the NNNNGATT PAM) (SEQ ID NO:1) or downstream (DS) (i.e., on the same side as the protospacer as the PAM). In all cases, the Zif268 binding site started 5 bp away from the protospacer (US) or PAM (DS), and was either in the Watson (W) or Crick (C) orientation. The NmCas9-expressing plasmid encoded either WT NmCas9, the R1025A single-mutant NmCas9 (SM), or the K1013A/R1025A double-mutant NmCas9 (DM). In addition, the NmCas9 was fused to no additional domains (blue bars), N-terminal Zif268 (Nter-Zif268, red bars), or C-terminal Zif268 (Zif268-Cter, green bars). HEK293 cells in 24-well plates were transfected with 100 ng split-GFP reporter. Also included in the transfections were 10 ng of an mCherry-expressing plasmid (as a transfection marker), and 290 ng of the plasmid expressing NmeCas9 and the spacer 9-containing sgRNA. Three identical transfections were done on different days. In each case, after 48 hours post-transfection, cells were harvested and analyzed by flow cytometry to identify the fraction of mCherry-positive cells that were also GFP-positive.
Figure 73:
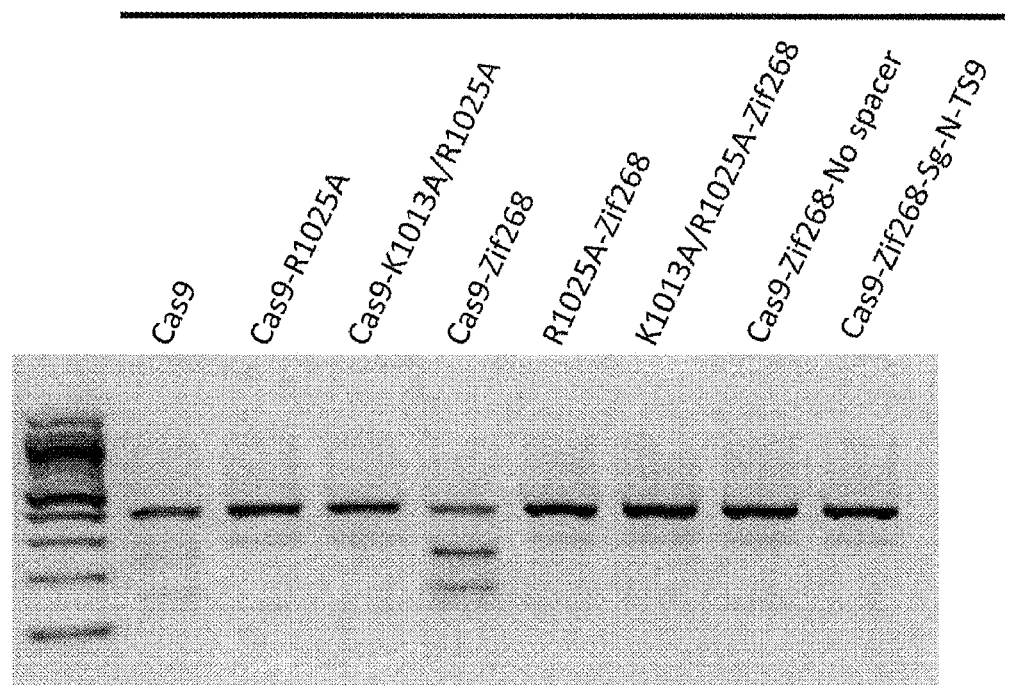
FIG. 73 presents exemplary data demonstrating the ability of a ZFP fusion (Zif268) to enhance the activity of NmCas9 at a preferred GATT PAM genomic target with a 5 bp spacing and Crick (C) orientation of the ZFP binding site. T7EI assay to detect NmCas9-catalyzed genome editing of a chromosomal target site (N-TS5) that has a GATT PAM adjacent to a naturally occurring Zif268-binding DNA sequence. HEK293 cells in 24-well format were transfected with 300 ng of a plasmid expressing NmCas9, or of NmCas9 derivatives as indicated. The plasmid also expressed an NmCas9 sgRNA with a guide sequence complementary to the chromosomal target site. 72 hours after transfection, genomic DNA was prepared from the cells and subjected to T7EI analysis according to standard protocols. The percent editing for Cas9 and Cas9-Zif268 is given underneath the corresponding lanes. The right-most two lanes are negative controls with NmCas9-Zif268, in which the sgRNA construct included no cloned spacer ("Cas9-Zif268-No spacer") or a non-cognate spacer (Cas9-Zif268-Sg-N-TS9). The results show that a ZFP domain fusion to the C-terminus of NmeCas9 can improve editing efficiency of a chromosomal target site that has a GATT PAM.
Figure 74:
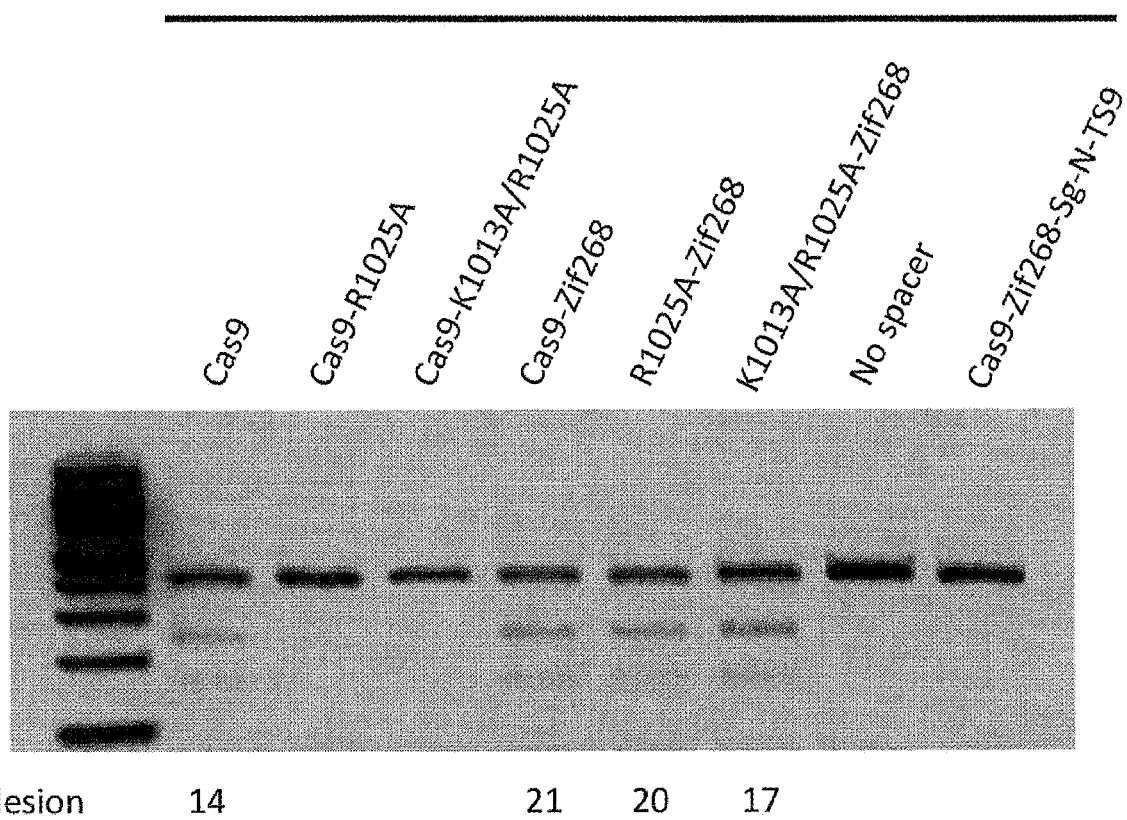
FIG. 74 presents exemplary data demonstrating that a ZFP fusion can restore activity of the single and double NmCas9 mutants at a chromosomal target site that has a GATT PAM with a 9 bp spacing and Crick (C) orientation of the ZFP binding site. Experiment performed as in FIG. 73, except that a different chromosomal target (N-TS7) site was tested.

Although the molecular structure of NmCas9 is not known, we have utilized sequence homology with other Type IIC Cas9s from related species to identify residues that are likely involved in PAM recognition or DNA phosphodiester backbone contacts (e.g., K1013 and R1025; FIG. 25). Mutation of arginine 1025 to alanine, serine lysine dramatically reduces activity at targets sites containing a broad range of functional PAMs (FIG. 69). Mutation of arginine 1025 to alanine, serine or lysine in combination with a mutation of lysine 1013 to serine eliminates any activity above background (FIG. 70). The activity of the R1025A single-mutant NmCas9 (SM), or the K1013A/R1025A double-mutant NmCas9 (DM) can be rescued in GFP reporter assays by the fusion of a ZFP to the N-terminus or C-terminus when the binding site for the ZFP is downstream of the PAM (FIG. 71). ZFP-NmCas9$^{SM}$ or ZFP-NmCas9$^{DM}$ constructs are functional with ZFP binding sites at a number of positions relative to the PAM (FIG. 72) or with a number of different PAM variants (FIG. 79). ZFP fusions to NmCas9$^{SM}$ or NmCas9$^{DM}$ constructs can also restore activity at genomic loci based on T7EI analysis (FIGS. 74, 75, 76, 78 and 82). Thus, we have generated a Type IIC Cas9 platform that is attenuated similar to the SpCas9 Type IIA system using the same principles (summary of activity presented in Table 2).

Although it may be not necessary to understand the mechanism of an invention, it is believed that the above improvements in activity and precision realized by a fusion of a DBD to SpCas9 and NmCas9 and the corresponding attenuating mutations are broadly applicable to other Cas9s. Common design principles between Type II-A and Type II-C Cas9-DBD fusions that achieve excellent precision and improvements in activity demonstrate the applicability of the present invention to all Cas9 platforms and all specific genomic targets. These design principles may be applicable to other CRISPR-based single protein nuclease effector systems (e.g., Type V CpfI).

nism of an invention, it is believed that an ability to expand the targeting capabilities of Cas9 would be particularly valuable for targeting genomic sequences that lack a canonical PAM within a local region of interest (mutation requiring correction in gene therapy applications) or for allele-specific targeting taking advantage of SNPs that distinguish the alleles that represent an active and an inactive PAM, allowing one of the two sequences to be cleaved specifically. This could be a powerful approach for the inactivation of dominant-negative disease causing alleles, such as that Huntington's disease or Myotonic Dystrophy.

Conventional SpCas9 sgRNAs (e.g., for example, TS2, TS3 & TS4; all NGG PAMs) are known to have well-defined off-target sites. Fu et al., Improving CRISPR-Cas nuclease specificity using truncated guide RNAs. Nature Biotechnology, 2014 March; 32(3):279-84; Fu, Y., Foden, J. A., Khayter, C., Maeder, M. L., Reyon, D., Joung, J. K., & Sander, J. D. (2013). High-frequency off-target mutagenesis induced by CRISPR-Cas nucleases in human cells. *Nature Biotech-*

TABLE 2 wild-type, attenuated and ZFP fused NmCaz9 editing efficiency at various genomic target sites

| | EDITING EFFICIENCY | | | | | |
|---|---|---|---|---|---|---|
| SITE NAME | Cas9 | Cas9-R1025A | Cas9-K1019A/-R1025A | Zif268-Cas9 | Zif268-R1025A | Zif268-K1013A/R1025A |
| N-TS3(GATT-5bp-W) | 25,39,33,20 | 0 | 0 | 33,34 | 30 40 | 23,16 |
| N-TS5(GATT-5bp-C) | 11,9,20 | 0 | 0 | 42 | 0 | 0 |
| N-TS7(GATT-9bp-C) | 14,24,33 | 0 | 0 | 21 | 20 | 17 |
| N-TS8(GATT-9bp-W) | 10,19,34 | 9 | 1 | 16 | 21 | 19 |
| N-TS9(GATT-11bp-C) | 20,27 | | | | | |
| N-TS10(GATT-12bp-W) | 0 | 0 | 0 | 31 | 0 | 0 |
| N-TS11(GATT-14bp-W) | 24,13,13 | 0 | 0 | 32 | 21 | 0 |
| N-TS20(GATT-5bp-W) | 0 | 0 | 0 | 19,18,12,15,13 | 0 | 0 |
| N-TS21(GATT-5bp-W) | 8,13,3,4,8 | 0 | 0 | 23,23,11,14,23 | 0 | 0 |
| N-TS22(GATT-5bp-W) | 0 | 0 | 0 | 18,16,12,10,17 | 0 | 0 |
| N-TS24(GATT-5bp-W) | 0 | 0 | 0 | 18,14,43,19,15 | 0 | 0 |
| N-TS25(GATT-5bp-W) | 22,32,26,26 | 0 | 0 | 26,30,33,31,26 | 25,25,35,33,24 | 6,8,23,20,7 |

D. Broadened Range of Cas9 Specific Target Sequences

In one embodiment, the present invention contemplates a method comprising differentially controlling functional recognition of a target site and subsequent cleavage by sequence elements within a Cas9 protein. One of the current limitations of Cas9 may be that, although target site recognition sequence can be programmed with a sgRNA, the ability to bind and cleave the target site sequence may be also dictated by a Cas9 PAM recognition sequence. In some Cas9 isoforms, a PAM sequence of NGG may be highly preferred both for binding and for cleavage. Hsu et al., DNA targeting specificity of RNA-guided Cas9 nucleases. Nature Biotechnology 31, 827-832 (201); Wu et al., Genome-wide binding of the CRISPR endonuclease Cas9 in mammalian cells. Nature Biotechnology (2014); and Kuscu et al., Genome-wide analysis reveals characteristics of off-target sites bound by the Cas9 endonuclease. Nature biotechnology (2014). Lower cleavage activity was observed for NAG PAMs, whereas other PAMs have no activity.

The data presented herein shows the activity of SpCas9 or SpCas9-Zif268 with a common sgRNA on target sites that have each of the 16 different PAM sequences with a flanking Zif268 site 5 base pairs away. Remarkably, a SpCas9-Zif268 construct may be highly active at multiple PAMs (i.e., for example, NGG, NAG, NGC and NGA) with a common sgRNA recognition sequence, equivalent activity at non-NGG PAMs has not been previously described. FIG. 5. Although it may be not necessary to understand the mechanology, 31(9), 822-826. doi:10.1038/nbt.2623. On- and off-target cleavage efficiencies at these sites may be evaluated for SpCas9-DBD constructs, where an attached DBD recognizes a sequence near each target site. Further, improved linkers may be combined with improved SpCas9 PAM recognition domain mutants to construct a Cas9 fusion protein most likely to eliminate off-target activity at the previously identified sequences.

Initial assessment of SpCas9-DBD precision may be done via T7EI assays on PCR amplicons from target and predicted off-target sites. For promising constructs, deep-sequencing of these amplicons will be used quantify lesion rates at each site. Gupta et al., Zinc finger protein-dependent and -independent contributions to the in vivo off-target activity of zinc finger nucleases. Nucleic Acids Research. 2011 Jan. 1; 39(1):381-92. To assess nuclease activity at sites throughout a genome, GUIDE-seq analysis can be performed (Tsai, S. Q. et al. GUIDE-seq enables genome-wide profiling of off-target cleavage by CRISPR-Cas nucleases. *Nature biotechnology* 33, 187-197 (2015)). Regions exhibiting significant GUIDE-seq oligonucleotide incorporation may be characterized for off-target cleavage rates in the nuclease-treated cells using the same PCR-based deep sequencing approach described above. Given preliminary results, it may be anticipated that the precision of Cas9$^{mut}$-DBD has vastly improved and superior activity as compared to Cas9.

Figure 20:
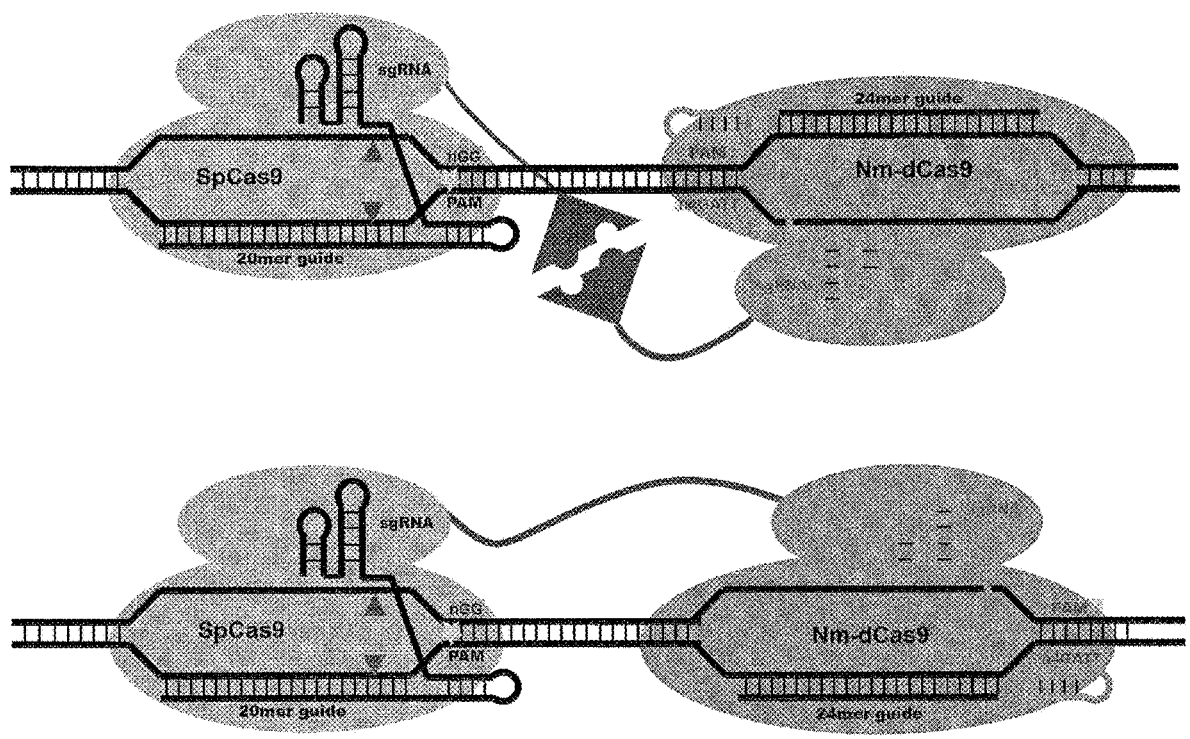
FIG. 20 presents a schematic of SpCas9$^{MT}$ and Nm-dCas9 fusions. (Top) SpCas9$^{MT}$-Nm-dCas9 may be linked through a dimerization domain. (Bottom) SpCas9$^{MT}$-Nm-dCas9 may be fused through peptide linker.
Figure 45:
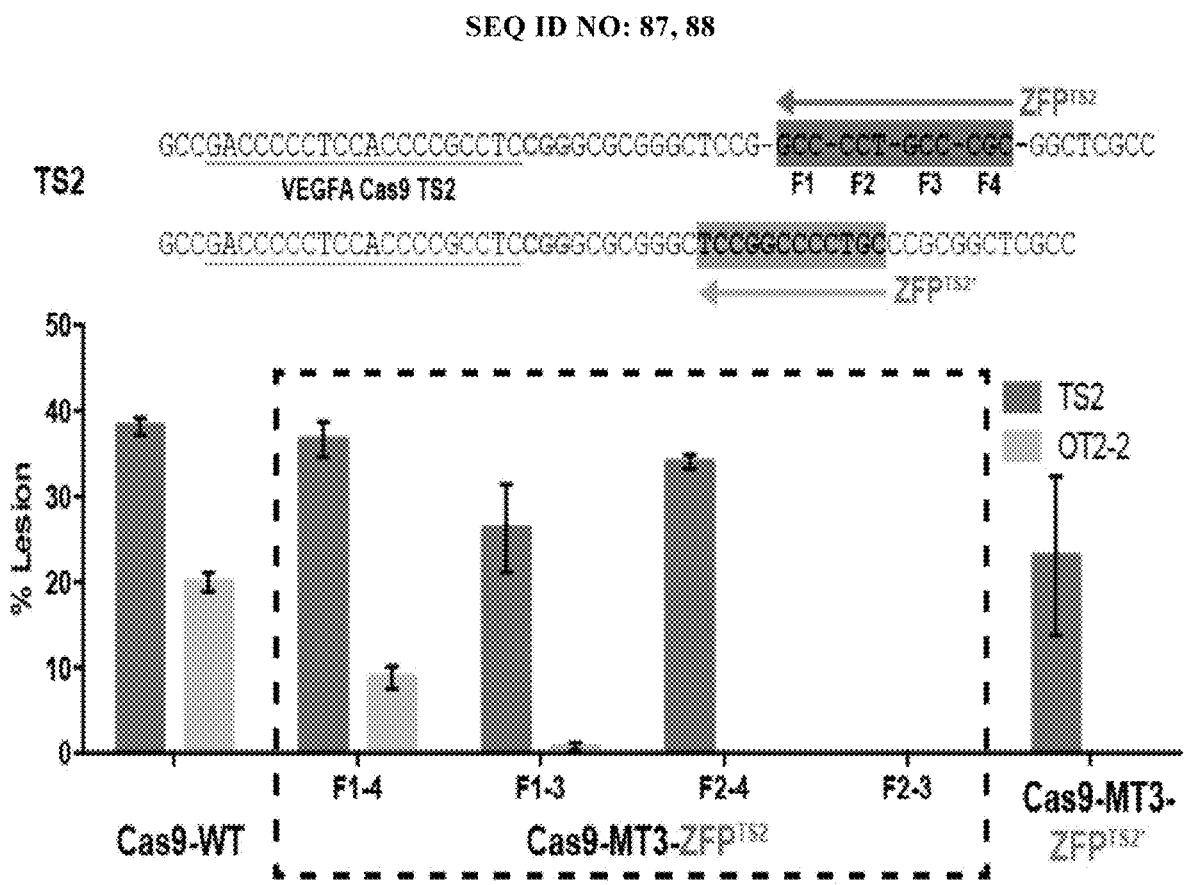
FIG. 45 presents exemplary data comparing lesion rates at TS2 and OT2-2 as determined by T7EI assay for SpCas9$^{WT}$ and SpCas9$^{MT3}$-ZFP$^{TS2}$ variants that alter the number of ZFPs or change them completely (TS2*). The binding site for the TS2*-ZFP is in blue. Removing finger 1 (F2-4) or 4 (F1-3) from the four-finger TS2 ZFP (F1-4) modestly impacts target site activity, but dramatically improves precision. Data are from three independent biological replicates from different days in HEK293T cells. Error bars indicate s.e.m.

TALE or ZFP binding site length may also be varied to provide optimal binding precision. For example, binding site size and affinity of TALEs or ZFPs can be tuned by changing the number of recognition modules that are incorporated into the Cas9 fusion protein (FIG. 45). Bhakta et al., Highly active zinc-finger nucleases by extended modular assembly. Genome Research, 2013 March; 23(3):530-8; Meckler et al., Quantitative analysis of TALE-DNA interactions suggests polarity effects. Nucleic Acids Research. 2013 April; 41(7): 4118-28; and Reyon et al., FLASH assembly of TALENs for high-throughput genome editing. Nature Biotechnology. 2012 May; 30(5):460-5. On-target versus off-target cleavage activity may then be evaluated for different length TALE or ZFP variants to understand how this affects precision. Likewise if a orthogonal Cas9 isoform may be used as the DNA targeting unit the affinity for its target site can potentially be tuned to optimize the on-target versus off-target cleavage rate by truncating its guide RNA (Fu et al., Improving CRISPR-Cas nuclease specificity using truncated guide RNAs. Nature Biotechnology. 2014 March; 32(3):279-84). The association between the two orthogonal Cas9/sgRNAs could be via a direct linkage or a dimerization domain. (FIG. 20)

E. ZFP or TALE Cas9 Fusion Proteins

In one embodiment, the present invention contemplates a method comprising binding a Cas9 fusion protein comprising a ZFP or TALE to a non-standard PAM target site. In one embodiment, a non-standard PAM target site comprises a NAG PAM sequence. Although it may be not necessary to understand the mechanism of an invention, it is believed that a NAG PAM sequence may be weakly cleaved by the standard SpCas9 (e.g., a sub-optimal PAM sequence).

The data presented herein examines spacing and orientation requirements between a DBD target site and a neighboring PAM sequence. For this analysis, a TALE protein was generated that recognized a Zif268 binding site (TAL268). This provided the advantage that the same reporter system to examine the activity of SpCas9, SpCas9-Zif268 and SpCas9-TAL268. The data show that a standard SpCas9/sgRNA may be only functional with a NGG PAM (yellow bar), but not on an NAG PAM (Blue bars). However, SpCas9-Zif268 (red bars) may be active at an NAG PAM on all spacings and orientations of its binding site. A similar broadening of targeting range is observed with ZFP fusions to NmCas9 (Table 2, above). SpCas9-TAL268 (green bars) has a much more restricted spacing and orientation for favorable activity. FIG. 3. Given that TALEs can be programmed to recognize nearly any sequence within the genome (Lamb et al., Directed evolution of the TALE N-terminal domain for recognition of all 5' bases. Nucleic Acids Research. 2013 November; 41(21):9779-85), it should be possible to generate a DBD that may be complementary to almost any desired region of the genome to recruit Cas9 to a desired target site.

F. Cas9-Cas9 Fusion Proteins

In one embodiment, the present invention contemplates a method comprising binding of a Cas9-Cas9 fusion protein (dual Cas9 system) to a composite binding site. This could involve one Cas9 component serving as the nuclease and the other nuclease-dead Cas9 (dCas9) component serving as the targeting domain (analogous to the ZFP or TALE component of the Cas9-ZFP/TALE fusions; FIG. 20). Other embodiments envision the construction of Cas9-Cas9 fusion proteins where both components contain active nuclease domains, where these could be combinations of the fully active nucleases, nuclease-nickase der nickase-nickase combinations, where the nickases could be generated either by inactivation the HNH or the RuvC domains.

A split-GFP reporter assay was employed to demonstrate that SpCas9$^{MT3}$-NmdCas9 and NmdCas9-SpCas9$^{MT3}$ can generate target cleavage with certain arrangements of target sites for NmdCas9 (nuclease-dead) and SpCas9$^{MT3}$ (attenuated). FIGS. 93 and 94. In these constructs the nuclease-dead NmCas9 targets the attenuated SpCas9$^{MT3}$ to the desired target site facilitating cleavage. The SpCas9$^{MT3}$-NmdCas9 construct is capable of targeting genomic sequences, where it efficiently induces lesions (FIG. 95). The presence of some kind of DNA targeting unit is absolutely required, as SpCas9$^{MT3}$ on its own lacks detectable activity. Like SpCas9$^{MT3}$-pDBDs, SpCas9$^{MT3}$-NmdCas9 constructs dramatically increase the precision of SpCas9. SpCas9$^{MT3}$-NmdCas9 was programmed to recognize the TS3 target site that was the focus of some of our SpCas9$^{MT3}$-ZFP studies. The dual Cas9 system efficiently generates lesions at the TS3 target site (FIG. 96). However, at the most active off-target site for wild-type Cas9 (OT3-2) programmed with the TS3 sgRNA, which has lesion rates that are similar to the TS3 target site, the dual Cas9 platform (SpCas9$^{MT3}$-NmdCas9) has no apparent activity (FIG. 97). Thus, like the SpCas9$^{MT3}$-pDBD fusions, the dual Cas9 platform has greatly improved precision. In addition, since it can be programmed simply through the use of orthogonal sgRNAs for Sp and NmCas9, the programming of this nuclease is straightforward.

One of the advantages of the dual Cas9 system over the Cas9-pDBD system is the ability to utilize both nuclease domains to achieve coordinated cleavage at two neighboring positions within the genome. For example, attenuated SpCas9 can be coupled to NmCas9 that is either a nickase or a double-strand nuclease to allow the formation of a single-strand nick neighboring a break or two double-strand breaks together. If a NmCas9 nickase is utilized, the strand that is cleaved can be controlled by the nuclease domain (either HNH or RuvC) that is inactivated. This can in principle be utilized to create extended 5' or 3' overhangs neighboring the blunt double-strand break that is generated by attenuate SpCas9, which are likely to have improved properties for certain types of DNA repair (alternate non-homologous end joining or homology directed repair from an exogenous template). These combinations of dual nuclease-nickase or dual nucleases are functional, and in the case of the dual nucleases provide clear deletions of the intervening sequence (FIG. 98).

G. Drug-Dependent Cas9 pDBD Systems

In one embodiment, the present invention contemplates a method comprising binding of a drug-dependent nuclease system where the attenuated Cas9 and the pDBD (or alternate DTU such as an different Cas9 isoform) where the temporal activity of the nuclease can be controlled by the presence of a small molecule. Small molecule-(Yoshimi K, et. al. Nature Communications, 2014; 5:4240: Spencer D M, et. al. Science, 1993 Nov. 12; 262(5136):1019-24; Hathaway N A, et. al. Cell. Elsevier Inc; 2012 Jun. 22; 149(7):1447-60; Ling F-S, et al. Science Signaling. 2011; 4(164):rs2=rs2) or light-dependent (Konermann S, et al. Nature. 2013 Aug. 22; 500(7463):472-6) dimerization systems have been developed that permit the control of activity of a two-component system. Since SpCas9/sgRNA off-target activity is dose dependent, these systems have been adapted to regulate the association of two fragments of Cas9 (Split-Cas9; Nihongaki Y, et. al. Nature biotechnology. 2015 July; 33(7):755-60; Wright A V, et al. Proceedings of the National Academy of Sciences. 2015 Mar. 10; 112(10):2984-9; Zetsche B, et. al. Nature biotechnology. 2015 February; 33(2):139-42; Davis K M, et. al. Nat Chem Biol. 2015 May; 11(5):316-8).

Figure 47:
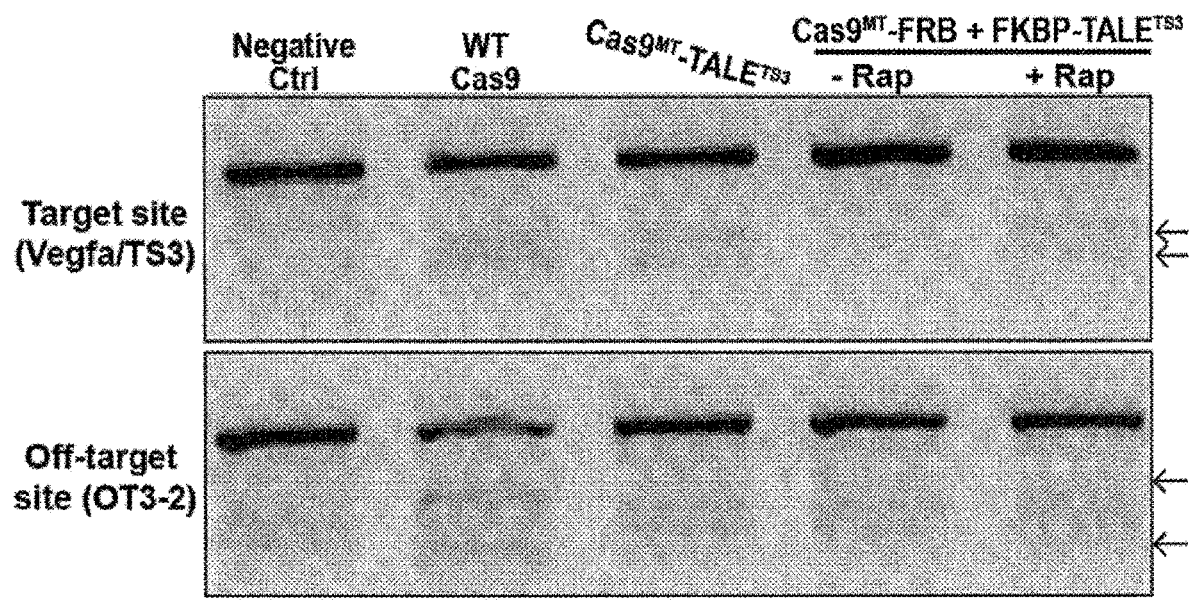
FIG. 47 presents exemplary data showing precise rapamycin-dependent cleavage by Cas9$^{MT}$-FRB and or FKBP-TALE$^{TS3}$ nucleases. T7EI assay on PCR products spanning the TS3 target site (Top) or OT3-2 off-target site (Bottom) genomic loci. Cas9$^{WT}$, Cas9$^{MT}$TALE$^{TS3}$ and Cas9$^{MT}$-FRB FKBP-TALE$^{TS3}$ (+ or −) of 20 nM rapamycin (Rap). Cas9$^{MT}$-FRB FKBP-TALE$^{TS3}$ activity at the target site is Rap-dependent (arrows). At OT3-2, only Cas9$^{WT}$ produces lesions (weak T7EI activity in in all lanes).

However, this framework may not be ideal, as drug-dependent Split-SpCas9 displays reduced target activity and retains modest off-target activity (Zetsche B, et. al. Nature biotechnology. 2015 February; 33(2):139-42). SpCas9-pDBD systems are amenable to the incorporation of a drug- or light-dependent dimerization system that regulates the association of SpCas9 and the pDBD by replacing the covalent linker with a conditional dimerization system (drug or light dependent) (FIG. 2C). A working Rapamycin-dependent prototype was developed for SpCas9-FRB/FKBP-ZFPs and SpCas9-FRB/FKBP-TALEs (FIG. 47). For example, the target activity (with drug) is similar to wild-type SpCas9 without sacrificing the enhanced precision of the SpCas9-pDBD system: wild-type SpCas9 displays activity at the off-target sequence OT3-2, whereas no activity is observed for the drug-dependent system.

Activity and drug-responsiveness of this system has been improved through a number of additional modifications. To increase the turnover of the pDBD in the absence of drug, which can potentially compete with SpCas9-FKBP/FRB-ZFPs complexes if in excess, a destabilized FRB domain has been incorporated (i.e., for example, a PLF triple mutant-FRB*; Stankunas K, et. al. Chembiochem. 2007 Jul. 9; 8(10):1162-9) on the pDBD component. The cellular localization sequences on Cas9 and the pDBD has also been improved. An absence of a nuclear import (NLS) or export (NES) sequence on Cas9 was found to provide the lowest background levels of cleavage while providing the largest drug-dependent activity. For the pDBD the presence of a combination of 2×NLS and 2×NES, which is believed to cause constant cycling between the nucleus and cytoplasm, thereby resulting in improved activity (FIG. 99). The organization of these domains (e.g. FRB* on the N- or C-terminus) also influences activity. These modifications of the system play a role in the generation of the highest levels of performance. This type of regulation should be possible with other small molecule- or light-dependent dimerization systems, and thereby should provide tighter control over activity for gene therapy based uses (gene correction, gene replacement or cell-based therapeutics).

Regulated nuclease activity can be obtained by breaking the Cas9 protein into two independent components (e.g., termed herein "split-Cas9"), where assembly can be controlled. Switching into an active state can be driven through the delivery of a small molecule (Zetsche B, et. al. Nature biotechnology, 2015 February; 33(2):139-42. Davis K M, et. al. Nat Chem Biol. 2015 May; 11(5):316-8) or light of a suitable wavelength (Nihongaki Y, et al. Nature biotechnology. 2015 July; 33(7):755-60). Most of these platforms display lower activity at the target site and off-target sites when compared with standard Cas9. Fusion of a pDBD to one of the Split-SpCas9 components has been demonstrated that dramatically increases its activity at alternate PAM sequences (e.g NAG, FIG. 100).

Activity and drug-responsiveness of the Split-Cas9-ZFP system has also been improved through a number of additional modifications. Using, for example, the cellular localization sequences on the N-terminal and C-terminal components of Split-Cas9. Inclusion or absence of a nuclear import (NLS) or export (NES) sequence on these segments was found to influence the background and drug-dependent cleavage rates of these constructs (FIG. 101).

To generate a more precise system, MT3 attenuating mutations were introduced into the split-SpCas9 system. Using this system tethered to a ZFP that recognizes a neighboring sequence within the TS2 genomic region (split-SpCas9$^{MT3}$-ZFP$^{TS2}$ and a TS3 sgRNA) drug-dependent cleavage of the TS2 target site was achieved. To demonstrate the improvements in precision achieved through drug-dependent systems GUIDE-seq was employed (Tsai, S. Q. et al. *Nature biotechnology* 33, 187-197 (2015).) For this analysis, the precision of wild-type Cas9 was compared to ae drug-dependent Split-Cas9 system. (Zetsche B, et. al. Nature biotechnology, 2015 February; 33(2):139-42); a drug-dependent SpCas9-FKBP/ZFP-FRB* and a drug-dependent split-SpCas9$^{MT3}$-ZFP$^{TS2}$ through Illumina sequencing of genomic regions that have incorporated GUIDE-seq oligonucleotides. The number of reads that are associated with a locus are indicative of the nuclease cleavage activity. When the nuclease activity of these constructs are assayed with a sgRNA (and ZFP) programmed to recognize the TS2 locus, all of these constructs have high activity at the TS2 target site (FIG. 102). The precision of these constructs is quite different as assessed at one of the most active off-target site (OTG2-1). Here both wild-type Cas9 and the Zhang Split-Cas9 display robust activity, whereas an attenuated SpCas9-FKBP/ZFP-FRB* and a drug-dependent split-SpCas9$^{MT3}$-ZFP$^{TS3}$ display no apparent activity. Thus nuclease attenuated drug-dependent systems as disclosed herein display dramatic improvements in precision.

H. Increased sgRNA Activity

Truncated sgRNAs (i.e. less than 20 bases of complementarity) have been utilized to increase precision of Cas9/sgRNA complexes by reducing the degree of potential complementarity with off-target sequences. Fu et al., Improving CRISPR-Cas nuclease specificity using truncated guide RNAs. Nature Biotechnology (2014). Cleavage activity of truncated sgRNA was compared between SpCas9 and SpCas9-Zif268. The data demonstrate that SpCas9-Zif268 displays a higher cleavage activity than SpCas9 where both comprise an identical sgRNA, whether the sgRNA may be a full length sequence or a truncated sequence. FIG. 6. This phenomenon was also observed for NmCas9 fusions to ZFPs at endogenous targets for some canonical PAM domains (NNNNGATT (SEQ ID NO: 1), FIGS. 75, 77, 78; NNNNGCTT (SEQ ID NO: 20), FIG. 81; NNNNGTTT (SEQ ID NO: 21), FIG. 80) the ZFP fusion to NmCas9 enhances the activity of the nuclease, in many cases providing activity where unfused NmCas9 is inactive. Thus, a pDBD fusion may provide a method to fully activate Cas9 nucleases even at canonical PAM sites for which they have poor or no activity. Although it may be not necessary to understand the mechanism of an invention, it is believed that this improved activity represents an additional advantage over the standard nuclease frameworks when using genomic targets.

I. Cas9 PAM Recognition Sequence Mutations

The PAM interaction domain (P1) has been defined based on structural information on the Cas9/sgRNA/target complex and domain substitution studies. Jinek et al., Structures of Cas9 Endonucleases Reveal RNA-Mediated Conformational Activation. Science (2014); Nishimasu et al., Crystal Structure of Cas9 in Complex with Guide RNA and Target DNA. Cell 1-23 (2014); PMID 25079318. Based on the reported crystal structures, there is evidence that for a conservation of residues within the PI domain between Cas9 isoforms from different species share a common PAM recognition sequence. Fonfara et al., Phylogeny of Cas9 determines functional exchangeability of dual-RNA and Cas9 among orthologous type II CRISPR-Cas systems. Nucleic Acids Research 42, 2577-2590 (2014).

In some embodiments, the present invention contemplates a SpCas9 protein comprising two arginine residues at positions 1333 and 1335 (i.e., a RKR motif) that may be a NGG PAM recognition domain. In one embodiment, the present invention contemplates a mutated Cas9 protein (Cas9$^{MT\,\#}$) comprising an $^{1333}$R→$^{1333}$K mutation or an $^{1335}$R→$^{1335}$S mutation. The activity of a Cas9$^{MT\,\#}$ or a Cas9$^{MT\,\#}$-Zif268 were tested using a target site that contains NGG, NAG or NCG PAMs with a neighboring Zif268 site. The data show that Cas9$^{MT\,\#}$ may be inactivated by a single mutation, only modestly effect Cas9$^{MT\,\#}$-Zif268 activity, with the exception of the $^{1335}$R→$^{1335}$S mutation (#4) where activity may be abrogated. The $^{1333}$R→$^{1333}$K mutant (#1) displays similar activity to the wild type (WT) Cas9-Zif268 fusion. FIG. 9. These data suggest that a mutant version of Cas9 that may not be competent for cleavage on its own, but requires an associated DNA-binding domain for function, while still retaining the specificity of the sgRNA and PAM recognition site sequence. This coordination should dramatically improve Cas9 nuclease function precision. It may also be possible to select alternate residues at these positions that allow the PAM specificity of Cas9 to be reprogrammed.

As disclosed herein, a SpCas9-DBD fusion protein displays an improved activity and precision, especially when combined with a mutated PAM recognition sequence that attenuates intrinsic DNA binding affinity. While the presently disclosed mutations weaken native cleavage activity, it may be likely that further attenuation of the DNA-binding affinity of SpCas9 may increase absolute DBD dependence. For example, mutagenizing at least two regions of Cas9 may be expected to reduce its intrinsic activity; 1) the PAM recognition residues, and 2) apparent phosphate-contacting residues near the PAM binding site.

In one embodiment, the present invention contemplates mutations to the PAM recognition residues comprising arginines (e.g., R$^{1333}$ & R$^{1335}$) that participate in base-specific binding. In one embodiment, the mutation may be a substitution. In one embodiment, the mutation may be a combination mutation (e.g., a R1333K and a R1335K). In one embodiment, the mutations that abrogate the independent binding of the Cas9 nuclease to its target site are in phosphodiester backbone contacting residues that reduce the affinity of Cas9 for the DNA. A GFP reporter assay may be used with the array of 16 PAM target sites to monitor nuclease activity of each mutant with and without the DBD.

In one embodiment, the present invention contemplates mutations to Cas9 comprising arginine or lysine residues that participate in DNA phosphate binding. Neutralization of phosphate contacts within DBDs may be a demonstrated method to modulate their binding affinities. Khalil et al., A synthetic biology framework for programming eukaryotic transcription functions. Cell. 2012 Aug. 3; 150(3):647-58. Lysines that are well-positioned to make non-specific contacts with the DNA downstream of the PAM contacting residues. Anders et al., Structural basis of PAM-dependent target DNA recognition by the Cas9 endonuclease. Nature. 2014 Sep. 25; 513(7519):569-73; and FIG. 22. These lysine residues are distal from an sgRNA-DNA interaction site, and so it would not be expected to affect the efficiency of R-loop formation or the precision of DNA cleavage. Szezelkun et al., Direct observation of R-loop formation by single RNA-guided Cas9 and Cascade effector complexes. Proc Natl Acad Sci USA. 2014 May 27; and Sternberg et al., DNA interrogation by the CRISPR RNA guided endonuclease Cas9. Nature. 2014 Mar. 6; 507(7490):62-7. These lysines may be mutated to alanine individually, or in combination, and then nuclease activity of these mutants are compared with or without an attached DBD on genomic targets by using, for example, a T7EI assay. Promising lysine mutants may be combined with PAM mutants identified above to further attenuate Cas9 DNA-binding affinity.

Mutations may be identified in a PAM interaction domain and non-specific phosphate contacts that completely inactivate Cas9 activity independent of an attached DBD. Further characterization of promising constructs may be performed using PCR amplification of a genomic target and deep sequencing to quantify SpCas9$^{MT}$ activity with and without the DBD. PAM recognition domains serve not only as an initial DNA-binding toehold for Cas9, but the binding energy may be also used to provide local DNA unwinding in preparation for (or coupled to) R-loop nucleation, and perhaps allosteric nuclease activation. Thus, accumulated mutations could compromise DNA unwinding and activation so much that a defect cannot be overcome by an appended DBD.

In one embodiment, the present invention contemplates an SpCas9$^{MT\,\#}$-DBD fusion protein comprising a truncated sgRNA (tru-gRNA). Although it may be not necessary to understand the mechanism of an invention, it is believed that tru-gRNAs (i.e., for example, TS1, TS2, TS3 & TS4) improve, but do not eliminate, off-target activity, tru-gRNA (TS1) tested in a GFP reporter assay was found to display similar, or even slightly improved, on-target activity when used with a Cas9-DBD fusion protein relative to Cas9 alone. FIG. 6. Similar improvements may be expected in precision with tru-gRNA/SpCas9$^{MT}$-DBD combinations on endogenous targets. Should residual off-target effects persist even when a SpCas9$^{MT}$-DBD fusion protein may be combined with a tru-gRNA, dual Cas9 nickases (nCas9) or dual FokI-dCas9 nucleases in the context of two different DBDs may help target each monomer to a neighboring target site. In one embodiment, a dual Cas9-DBD fusion protein may comprise orthogonal Cas9 systems (e.g. nSpCas9-DBD nNmCas9-DBD).

In one embodiment, the present invention contemplates an SpCas9 comprising refined PAM specificity wherein genome editing may be improved. In one embodiment, the present invention contemplates a plurality of SpCas9$^{MT}$ variants that can target essentially any sequence within the genome with maximal precision, and that may be capable of allele-specific targeting. Selection strategies that generate SpCas9 variants having altered PAM specificity (SpCas9-PAM$^{MT}$) have been discussed herein in the context of an altered SpCas9-DBD fusion protein. The precision of these SpCas9$^{MT}$-DBD variants may be characterized within a genome and tested for allele-specific targeting, using PAM SNPs as discriminators.

For example, SpCas9-PAM specificity may be refined through mutagenesis of PAM recognition residues. A GFP reporter assay testing PAM recognition mutants demonstrated attenuation of intrinsic nuclease activity (e.g., for example, R$^{1333}$ & R$^{1335}$). FIG. 9. To assess the potential breadth of PAM specificities that can be achieved with SpCas9, the impact of additional mutations may tested using amino acids including, but not limited to, K$^{1107}$, S$^{1136}$, E$^{1219}$, R$^{1333}$ & R$^{1335}$ that make direct or indirect contact with a PAM. Anders et al., Structural basis of PAM-dependent target DNA recognition by the Cas9 endonuclease. Nature, 2014 Sep. 25; 513(7519): 569-73; and FIG. 9.

Figures 23A, 23B:
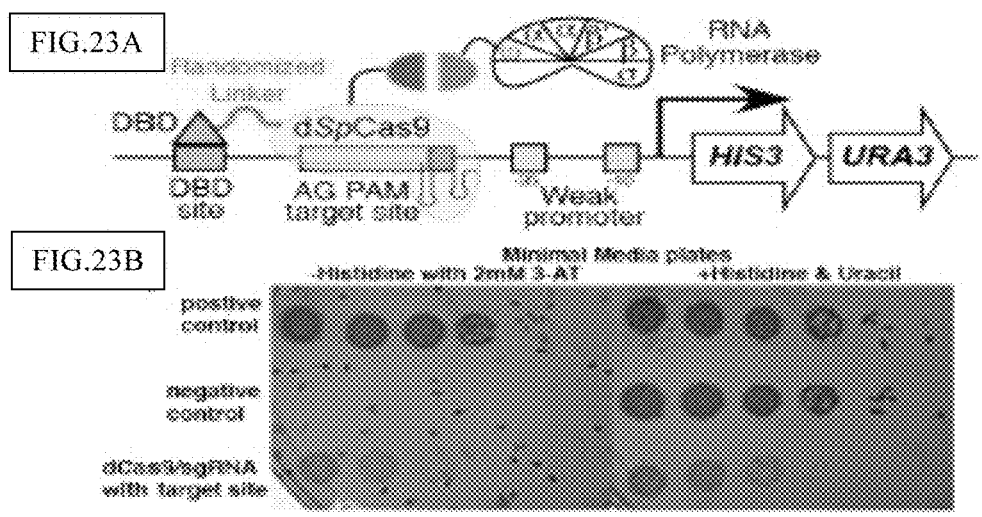
FIG. 23A-B presents.
Figure 24:
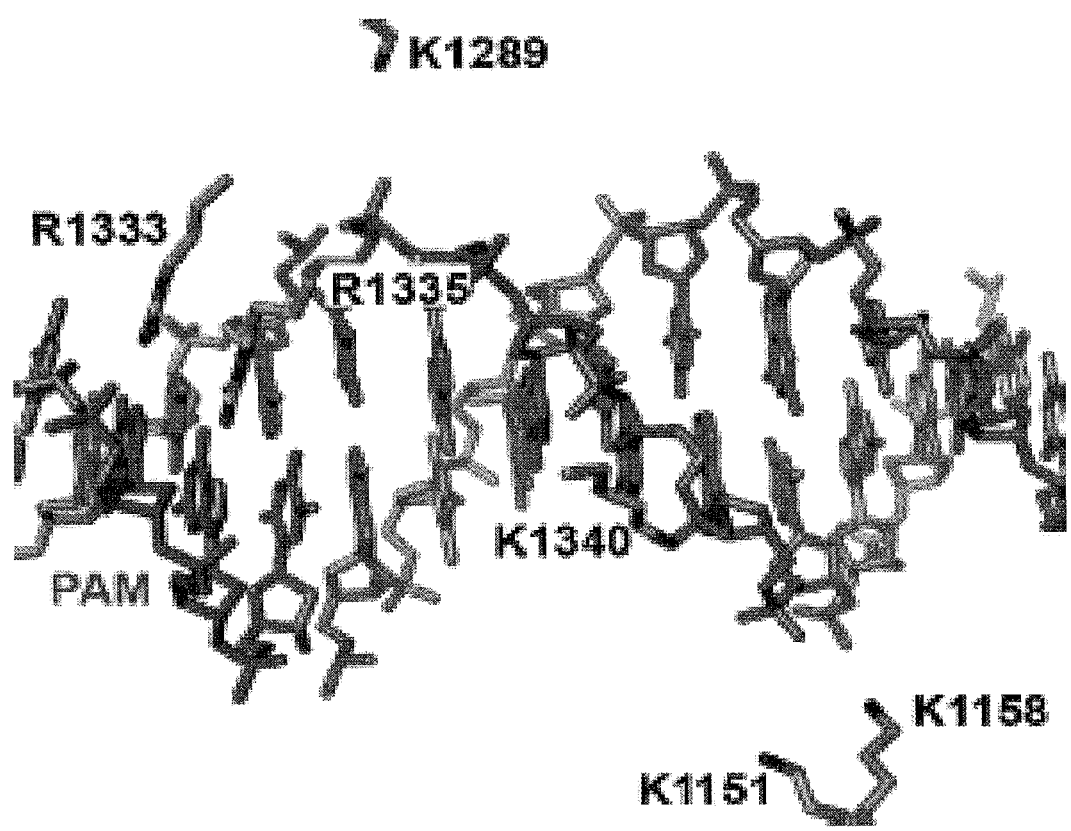
FIG. 24 presents one embodiment of a structural model of potential DNA phosphate contacts in SpCas9. A B-DNA model was constructed using (PMID 18600227) and appended 3' to the PAM (magenta) in a SpCas9 structure. Lysines in proximity to the DNA backbone are shown (no arginines are nearby with the exception of the PAM recognition residues (shown)). These phosphate contacting residues are examples of potential mutagenesis positions to attenuate the independent DNA binding affinity of Cas9 to increase its dependence on the attached DTU.

Using a B2H system, libraries may be searched of sufficient complexity (~$10^8$) to cover all possible amino acid combinations for possible PAM recognition mutants (FIG. 23). Meng et al., A bacterial one-hybrid system for determining the DNA-binding specificity of transcription factors. Nature Biotechnology. 2005 August; 23(8):988-94; and Noyes et al., A systematic characterization of factors that regulate *Drosophila* segmentation via a bacterial one-hybrid system. Nucleic Acids Research. 2008 May; 36(8):2547-60. Randomized libraries can be assembled by known PCR methods and cloned into a B2H dCas9-DBD/sgRNA expression plasmid. Although it may be not necessary to understand the mechanism of an invention, it is believed that these selections affect binding, not nuclease activity, and therefore may be performed in a nuclease-dead (dCas9) fusion protein. These libraries can then be screened as dCas9-DBD/sgRNA combinations on HIS3/URA3 reporter vectors that contain each of the 16 different PAMs (with NGG as a positive control) to select combinations that permit recognition of each PAM. A dCas9-DBD library with each PAM target site may be plated on various concentrations of 3-AT to define a selection stringency where only a few hundred clones survive. These clones may be pooled and deep-sequenced to identify a consensus at the randomized positions. Chu et al., Exploring the DNA-recognition potential of homeodomains. Genome Research. 2012 October; 22(10):1889-98. The specificity of SpCas9$^{MT}$ clones, similar to the consensus sequence for each PAM selection, can be evaluated on all 16 PAMs in the GFP reporter assay and subsequently within a genome by T7EI assay. Cas9 mutant dependence on an attached DBD for nuclease function can be attenuated as necessary by mutation of residues that contact the DNA phosphates.

A negative selection protocol may be used to identify functional nucleases at alternate PAMs. For example, a bacterial 5-FOA/URA3 counter-selection system was reported that may be suitable for the identification of Cas9-DBD variants with mutated PAM sequences. Meng et al., Counter-selectable marker for bacterial-based interaction trap systems. Biotechniques, 2006 February; 40(2):179-84. For example, a low-copy, IPTG-inducible URA3 plasmid (pSC101 origin, kanR-marked) containing a Cas9-DBD target site may be introduced with a mutated PAM sequence into a uracil auxotroph strain (ΔpyrF). Meng et al., A bacterial one-hybrid system for determining the DNA-binding specificity of transcription factors. Nature Biotechnology. 2005 August; 23(8):988-94; and Lutz et al., Independent and tight regulation of transcriptional units in *Escherichia coli* via the LacR/O, the TetR/O and AraC/I1-I2 regulatory elements. Nucleic Acids Research. 1997 Mar. 15; 25(6):1203-10. After transformant selection (KanR), these cells may be electroporated with a Cas9-DBD/sgRNA plasmid library (marked with ampR), and plated on YM media with ampicillin, IPTG (to induce URA) and 5-FOA. Functional Cas9-DBDs variants can cleave and eliminate the URA3 plasmid, permitting survival; cells with nonfunctional Cas9-DBDs retain the plasmid and die via 5-FOA counter-selection. Surviving clones may be pooled and deep-sequenced to identify a consensus at the randomized positions. Chu et al., Exploring the DNA-recognition potential of homeodomains. Genome Research. 2012 October; 22(10):1889-98. The specificity of individual SpCas9$^{MT}$ clones similar to the consensus sequence for each PAM selection can then be evaluated as described above using, for example, a B2H selection approach.

Alternatively, a library depletion strategy may be employed that may be analogous to RNAi-based strategies in mammalian cells to identify essential genes in a particular pathway. Murugaesu et al., High-throughput RNA interference screening using pooled shRNA libraries and next generation sequencing. Genome Biol. 2011; 12(10):R104; Moffat et al., A lentiviral RNAi library for human and mouse genes applied to an arrayed viral high-content screen. Cell. 2006 Mar. 24; 124(6):1283-98; and Root et al., Genome-scale loss-of-function screening with a lentiviral RNAi library. Nature Methods. 2006 September; 3(9):715-9. In these screens, shRNA clones that target essential genes in a pathway of interest are depleted from the initial library because they are lost from the population.

Deep sequencing may be used to compare the distribution of clones in the initial library and in the survivors to identify shRNAs that are lost, which are then retested individually to assess their activity. Similarly, a depletion strategy may be used to identify barcoded clones of the above library that are active in bacteria at a desired PAM site within a kanR-marked plasmid. Based on a protocol for RNAi-based screens, an approximate ~1000-fold oversampling of a library may observe reliable depletion of active Cas9-DBD clones. Thus, a smaller library (~$10^5$ clones) may be used to retain sufficient depth in a lane of HiSeq2000 sequencing (~$2 \times 10^8$ reads/lane) to effectively employ this approach. Clones may be recovered that define a primary consensus sequence useful for bootstrapping through a second library construction (with fixed residues at positions of consensus from clones recovered from the first selection) and a deeper search of neighboring sequence space to identify the most active sequences. The specificity of each of these selected SpCas9-PAM$^{MT}$ clones may then be evaluated using a B2H selection technique as described above.

In one embodiment, the present invention contemplates a method for determining precision of SpCas9$^{MT}$ clones using a genome wide survey. For example, precision of an SpCas9$^{MT}$ clone at a specific genomic target site and predicted off-target genomic sites can be determined by comparing new target sites for each SpCas9$^{MT}$ clone that have an appropriate PAM sequence (i.e., for example, a specific non-NGG PAM). An appropriate DBD can be constructed to target each sequence to create an SpCas9$^{MT}$-DBD fusion protein. The most favorable off-target sites can then be predicted for these sgRNAs using, for example, a CRISPRseek algorithm. Zhu et al., CRISPRseek: A Bio-conductor Package to Identify Target-Specific Guide RNAs for CRISPR-Cas9 Genome-Editing Systems. PLoS ONE. 2014; 9(9):e108424. In addition, GUIDE-seq analysis can be performed (Tsai, S. Q. et al. GUIDE-seq enables genome-wide profiling of off-target cleavage by CRISPR-Cas nucleases. *Nature biotechnology* 33, 187-197 (2015)). Regions exhibiting significant GUIDE-seq oligonucleotide incorporation may be characterized for off target cleavage rates in the nuclease-treated cells using PCR-based deep sequencing. Gupta et al., Zinc finger protein-dependent and -independent contributions to the in vivo off-target activity of zinc finger nucleases. Nucleic Acids Research. 2011 Jan. 1; 39(1):381-92.

In one embodiment, the present invention contemplates a SpCas9$^{MT}$-DBD fusion protein comprising mutated PAM sequences comprising unexpected and superior specific genomic target binding precision. Although it may be not necessary to understand the mechanism of an invention, it is believed that a Cas9$^{MT}$-DBD fusion protein allows a precise cleavage of nearly any sequence within the genome and can provide allele-specific targeting through the use of SNPs that distinguish between alleles. For example, the inactivation of specific dominant-negative alleles could have great utility for gene therapy. In one embodiment, the method contemplates an SNP for siRNA-mediated silencing of Huntington alleles that contain CAG repeat expansions. Pfister et al., Five siRNAs targeting three SNPs may provide therapy for three-quarters of Huntington's disease patients. Curr Biol. 2009 May 12; 19(9):774-8. In principle, Cas9s with allele-specific activity could provide an alternate therapeutic strategy to disable specific harmful alleles in patients.

In one embodiment, the present invention contemplates a method of stringently discriminating between single alleles by targeting a particular heterozygous SNP within a PAM. The data presented herein demonstrates that Cas9 and various PAM recognition mutants already generated could utilize a Cas9-DBD fusion protein to edit single alleles that are distinguished by functional vs. non-functional PAMs.

A database may be used to define cell lines with SNPs that could be used to test the allele-specific discrimination of a Cas9-DBD fusion protein. Forbes et al., COSMIC: mining complete cancer genomes in the Catalogue of Somatic Mutations in Cancer. Nucleic Acids Research. 2011 January; 39 (Database issue):D945-50. The Forbes et al. database contains sequences from >100 cell lines, each with a searchable table of validated SNPs (e.g., 26 heterozygous SNPs in U2OS cells). Potentially distinguishable SNPs and sequence candidate loci in cell lines can be identified from this database to confirm heterozygosity. For validated SNPs, SpCas9$^{MT}$-DBD/sgRNA combinations may be designed to target a single allele. The allelic targeting ratios (relative to negative controls lacking the cognate sgRNA or the appended DBD) can be determined by deep-sequencing PCR amplicons from treated cells.

PAM mutations can also be defined that attenuate NmCas9 activity to achieve dependence on an attached DBD for nuclease activity (FIG. 49). Similar to SpCas9 platforms, two different approaches may be taken to weaken intrinsic DNA binding by NmCas9: 1) attenuation of PAM recognition, and 2) neutralization of arginine and lysine contacts to DNA phosphates. Although the exact structure of NmCas9 has not been reported, a structure of a related Type II-C Cas9 from *A. naeslundii* may be available. Jinek et al., Structures of Cas9 endonucleases reveal RNA mediated conformational activation. Science, 2014 Mar. 14; 343 (6176):1247997. The *A. naesulndii* Cas9 structure confirms that a core nuclease domain organization may be similar between the Type II-A (SpCas9) and Type II-C (NmCas9) families, though peripheral domains differ. Consequently, a C-terminal region (e.g., positions 928 to 1082) may provide the best candidates for PAM- and phosphate-contacting residues to optimize NmCas9 fusion proteins. As with SpCas9 fusion proteins two complementary approaches may identify these residues: 1) protein-DNA photo-crosslinking and 2) sequence conservation in highly related orthologs.

A preferred PAM of NmCas9 (i.e., for example, NNNNGATT (SEQ ID NO: 1)), wherein a T may be well-tolerated in place of the A, may be suited for protein-DNA photo-crosslinking using a commercially available, photoactivatible crosslinker 5-iododeoxyuridine (5IdU), which may be isosteric with T90. Each of the three individual T-to-5IdU substitutions within the NNNNGTTT PAM (SEQ ID NO: 21) of an oligonucleotide duplex may be bound to a purified, nuclease-dead NmCas9 (i.e., for example, a D16A/H588A double mutant, already expressed and purified) in the presence of a complementary sgRNA.

A single T can also be substituted on an opposite strand of the same duplex that carries a NNNNGATT PAM (SEQ ID NO: 1). Photo-crosslinking efficiency for each radiolabeled, 5IdU-substituted target duplex (following irradiation at 308 nm) can also be determined by SDS-PAGE. Wolfe et al., Unusual Rel-like architecture in the DNA-binding domain of the transcription factor Fact. Nature. 1997 Jan. 9; 385(6612):172-6; and Liu et al., Evidence for a non-alpha-helical DNA-binding motif in the Rel homology region. Proc Natl Acad Sci USA. 1994 Feb. 1; 91(3):908-12. Mutant PAMs with inactivating mutations on the non-5IdU-substituted strand can serve as specificity controls. Photo-crosslinking reactions for 5IdU positions displaying efficient, specific crosslinking may be scaled up for mass-spectrometric analysis of trypsin- and S1 nuclease/phosphatase-digested peptide fragments.

DNA contact residues identified by photo crosslinking, as well as nearby arginine, lysine and glutamine residues, may be mutated and activity of each NmCas9$^{MT\,\#}$ relative to wild-type NmCas9 evaluated in a GFP reporter assay. Luscombe et al., Amino acid-base interactions: a three-dimensional analysis of protein-DNA interactions at an atomic level. Nucleic Acids Research, Oxford University Press; 2001 Jul. 1; 29(13):2860-74. NmCas9$^{MT\,\#}$ clones with attenuated activity may then be fused to DBDs to test for recovery of nuclease activity. PAM specificities can be evaluated in a GFP reporter assay, where initially all PAM variants can be evaluated that have three of the four bases in the NNNNGATT (SEQ ID NO: 1) consensus sequence preserved (e.g., 12 combinations).

The above discussed identification of SpCas9 PAM recognition residues, $R^{1333}$ & $R^{1335}$, was made before any reported structure of these interactions. This discovery was facilitated both by available SpCas9 structural models and sequence alignments of closely related Cas9 orthologs, with the expectation that Cas9-DNA contacts are likely to be conserved. In protein-DNA complexes, guanine contacts (GATT PAM) and DNA phosphate contacts are likely to be mediated by either arginine or lysine residues. Luscombe et al., Amino acid-base interactions: a three-dimensional analysis of protein-DNA interactions at an atomic level. Nucleic Acids Research. Oxford University Press; 2001 Jul. 1; 29(13):2860-74. Consequently, mutations of conserved NmCas9 arginine or lysine residues to an alanine are most likely to affect cleavage activity. FIG. 25. Attenuated clones can then be tested as NmCas9$^{MT}$-DBD fusions to confirm recovery of nuclease activity. Some of these mutations successfully attenuate NmCas9 activity (K1013A and R1025A), which can be restored by an attached DBD (FIG. 49)

Based on the above data demonstrating attenuation of SpCas9$^{MT\,\#}$ nuclease activity, it can be expected that, as a result of Cas9 PAM amino acid conservation, NmCas9$^{MT}$ would also demonstrate attenuated nuclease activity. The analysis of relevant residues may be aided by photo-crosslinking data, which should help to clarify DNA-proximal regions. Alterations in PAM specificity for these mutants can be evaluated in the GFP reporter assay. Genome editing activity of favorable NmCas9$^{MT}$ clones can be evaluated on genomic targets in HEK293T cells fused to DBDs programmed to bind neighboring sites. Differences in activity between each NmCas9$^{MT}$ versus NmCas9$^{MT}$-DBD can be examined by T7EI assay. As with SpCas9, further characterization may be performed using PCR amplification of the genomic targets and deep sequencing to quantify editing frequencies at each target site with and without the DBD. Improvements in precision can also be further validated using the above described genome-wide analysis.

For example, a genome-wide assay may be used to define optimal NmCas9$^{MT\,\#}$-DBD fusion proteins for precise target cleavage in human cell lines. Precision of the most promising NmCas9$^{MT\,\#}$-DBD clones can be evaluated at target sites and predicted off-target sites within the genome. Appropriate DBDs can be created to facilitate targeting of each genomic sequence with an NmCas9$^{MT\,\#}$-DBD fusion protein. A set of the most favorable off-target sites can be predicted for these sgRNAs considering both the similarity of the sgRNA genomic sequences and possible alternate PAMs that could be functional for each NmCas9$^{MT\ \#}$ clone based on an evaluation in a GFP reporter assay and predictions developed using the CRISPRseek algorithm. Zhu et al., CRISPRseek: A Bioconductor Package to Identify Target-Specific Guide RNAs for CRISPR-Cas9 Genome-Editing Systems. PLoS ONE. 2014; 9(9):e108424. In addition, GUIDE-seq analysis can be performed (Tsai, S. Q. et al. GUIDE-seq enables genome-wide profiling of off-target cleavage by CRISPR-Cas nucleases. *Nature biotechnology* 33, 187-197 (2015)). Regions exhibiting significant GUIDE-seq oligonucleotide incorporation may be characterized for off-target cleavage rates in the nuclease-treated cells using PCR-based deep sequencing.

J. Improved Cas9 Linkers

In one embodiment, the present invention contemplates a Cas9-DBD construct comprising a linker. In one embodiment, the linker comprises approximately sixty (60) amino acids. Although it may be not necessary to understand the mechanism of an invention, it is believed that such a linker improves the precision of specific genomic target binding. It has been observed that if a DBD binding site is merely repositioned or reoriented relative to the specific genomic target little improvement in precision results. These data indicate that linker flexibility reduces precision via off-target binding due to a large number of sgRNA/DBD binding site permutations that can potentially be cleaved. GFP reporters may be constructed containing alternate spacing and orientation of a DBD binding site relative to a Cas9 target site with a suboptimal NAG PAM. This configuration may also include finer intervals around the most active positions, as well as positions further removed from the Cas9 target site, to better define the distance dependence.

Fusion proteins such as SpCas9-Zif268 or SpCas9-TAL268 may contain a series of shorter linkers to define a minimal length that retains maximum activity at one (or more) binding site positions, but may place further restrictions on activity at other binding site positions. In one embodiment, the present invention contemplates a Cas9-TALE fusion protein or a Cas9-ZFP fusion protein comprising an optimized linker that can recognize virtually any target site. Cermak et al., Efficient design and assembly of custom TALEN and other TAL effector-based constructs for DNA targeting. Nucleic Acids Research. 2011 July; 39(12):e82-2; Lamb et al., Directed evolution of the TALE N-terminal domain for recognition of all 5' bases. Nucleic Acids Research. 2013 November; 41(21):9779-85; Kim et al., A library of TAL effector nucleases spanning the human genome. Nature Biotechnology. 2013 March; 31(3):251-8; and Briggs et al., iterative capped assembly: rapid and scalable synthesis of repeat-module DNA such as TAL effectors from individual monomers. Nucleic Acids Research. 2012 Jun. 26.

Figure 21:
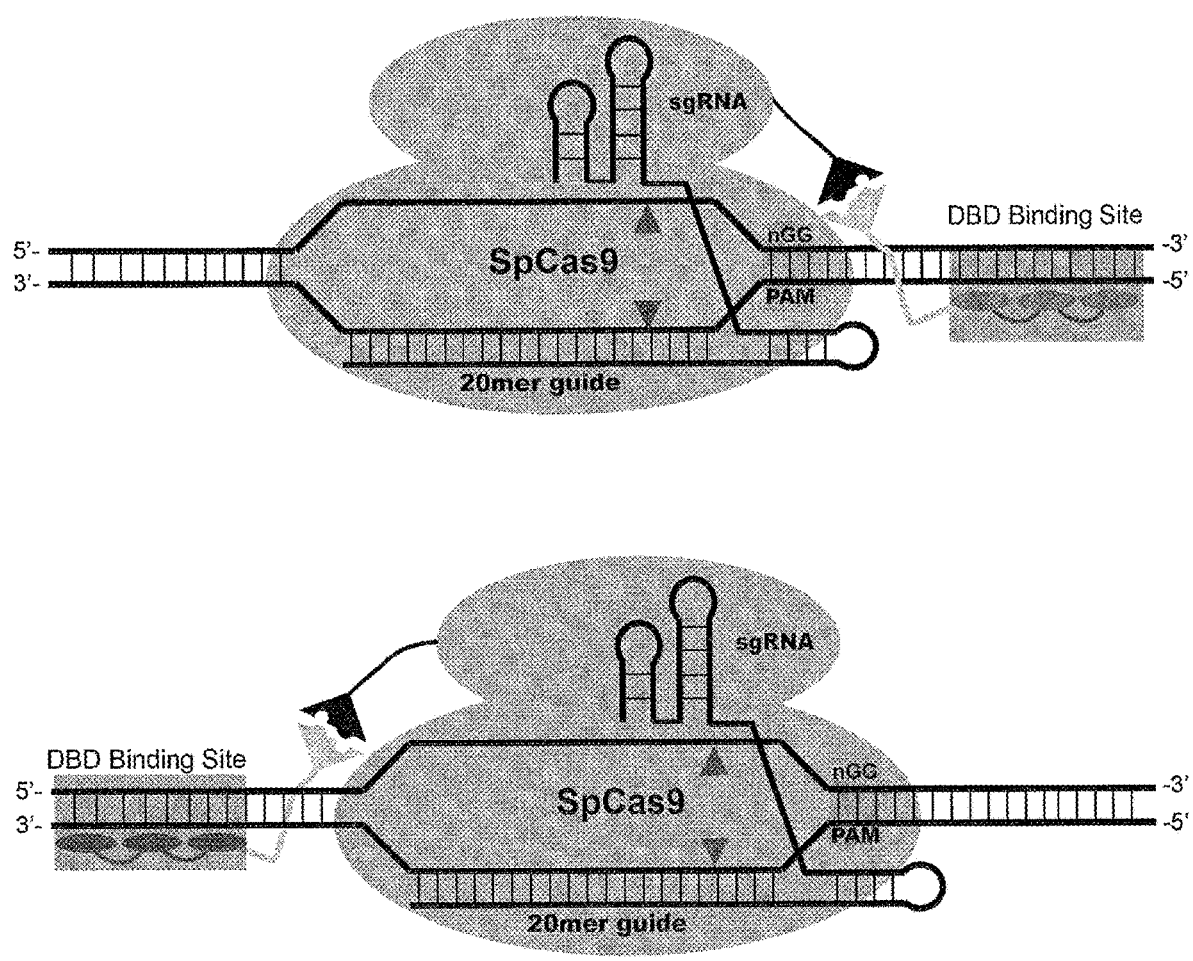
FIG. 21 presents a schematic of coupling SpCas9 to a programmable DBD via dimerization domain.

Using a GFP system SpCas9-DBD fusion proteins may be constructed with short linkers (e.g., less than sixty amino acids) that display both high activity and more selectivity in the particular arrangement of the Cas9 and DBD binding sites. Although it may be not necessary to understand the mechanism of an invention, it is believed that a maximum improvement in linker length and/or binding site position/orientation for a DBD relative to a Cas9 nuclease will differ between ZFPs and TALEs due to their respective structural folds and docking with the DNA. Mak et al., The crystal structure of TAL effector PthXo1 bound to its DNA target. Science. 2012 Feb. 10; 335(6069):716-9; and Deng et al., Structural basis for sequence-specific recognition of DNA by TAL effectors. Science. 2012 Feb. 10; 335(6069):720-3; and Pavletich et al., Zinc finger-DNA recognition: crystal structure of a Zif268-DNA complex at 2.1 A. Science. 1991 May 10; 252(5007):809-17. This linkage will also need to be optimized for any Cas9-nuclease fusion to an orthogonal Cas9 used as the DTU (FIG. 20). Likewise if dimerization domains are employed to associate the Cas9 nuclease with the DTU, it may be likely that a linker between a dimerization domain and a Cas9 nuclease or a dimerization domain and a DTU will need to be improved. (FIGS. 20 & 21).

A functional B2H selection system was established that may be sensitive to the binding of nuclease-dead SpCas9 (dSpCas9) to a target site upstream of a pair of selectable reporter genes. FIG. 23. This B2H selection strain may be a histidine and uracil auxotroph, so survival on minimal media lacking histidine and uracil requires expression of HIS3 and URA3 genes from a reporter vector containing a very weak core promoter. Meng et al., A bacterial one-hybrid system for determining the DNA-binding specificity of transcription factors. Nature Biotechnology. 2005 August; 23(8):988-94; Noyes et al., A systematic characterization of factors that regulate *Drosophila* segmentation via a bacterial one-hybrid system. Nucleic Acids Research. 2008 May; 36(8):2547-60; and Meng et al., Counter-selectable marker for bacterial-based interaction trap systems. Biotechniques. 2006 February; 40(2):179-84. Transcriptional activity of these reporter genes may be increased dramatically by recruiting RNA polymerase via a two-hybrid interaction. A dCas9/sgRNA complex has been established that can activate these reporter genes in the context of a two-hybrid interaction system. FIG. 23. Improved linker lengths for either TALE or ZFP DBD domains may be defined by a GFP reporter analysis. Combinatorial randomization of a conventional linker library and/or randomization of amino acid positions that are most proximal to Cas9 and a DBD are likely to provide linkers that have improvements at junction points. For example, an improved ZFP-homeodomain linker selection was identified with specific residues (e.g., for example, proline) at positions neighboring each DBD. A dCas9 that targets a suboptimal NAG PAM may be combined with an optimally positioned ZFP or TALE binding site to select dCas9-ZFP or dCas9-TALE constructs with improved activity in the selection system. Clones with improved binding activity (and thus improved linkers) may be recovered by plating the cells on increasing concentrations of 3-aminotriazole (3-AT, a competitive inhibitor of His3) until only a few clones survive. Selected linkers for Cas9-ZFPs or Cas9-TALEs can be validated as nucleases on genomic targets in HEK293T cells.

Linkages for NmCas9-DBD fusion proteins may also improve precision and activity using a similar procedure to that described above for SpCas9. In particular, an improvement protocol finds a fusion point (N- or C-terminal) and approximate linker length capable of creating a functional fusion between NmCas9 and a DBD (e.g., TALE or ZFP). PAM specificities have been interrogated for NmCas9 and may be believed to involve a consensus NNNNGATT (SEQ ID NO: 1) sequence. To evaluate NmCas9-DBD fusion activities a suboptimal PAM (i.e., for example, NNNN-GAAT (SEQ ID NO: 22)) may be used to assess improvements in activity that are imparted by a fused DBD.

As discussed above in the context of SpCas9, experiments can be carried out in two steps to validate a functional NmCas9 fusion: 1) using a GFP reporter assay to define an optimal linker length; and 2); a bacterial (e.g., *E. coli*) two hybrid selection of the linker sequence. Esvelt et al., Orthogonal Cas9 proteins for RNA guided gene regulation and editing. Nature Methods, 2013 November; 10(11):1116-

21. The ability to utilize a NmCas9 system with a bacterial selection system has been widely reported. Hou et al., Efficient genome engineering in human pluripotent stem cells using Cas9 from *Neisseria meningitidis*. Proceedings of the National Academy of Sciences. 2013 Sep. 24; 110 (39):15644-9; Zhang et al., Processing-independent CRISPR RNAs limit natural transformation in *Neisseria meningitidis*. Molecular Cell. 2013 May 23; 50(4):488-503; Zhu et al., Using defined finger-finger interfaces as units of assembly for constructing zinc-finger nucleases. Nucleic Acids Research. 2013 Feb. 1; 41(4):2455-65; Gupta et al., An optimized two-finger archive for ZFN-mediated gene targeting. Nature Methods. 2012 Apr. 29; 9(6):588-90; Meng et al., A bacterial one-hybrid system for determining the DNA-binding specificity of transcription factors. Nature Biotechnology. 2005 August; 23(8):988-94; Noyes et al., A systematic characterization of factors that regulate *Drosophila* segmentation via a bacterial one-hybrid system. Nucleic Acids Research. 2008 May; 36(8):2547-60; Noyes et al., Analysis of homeodomain specificities allows the family-wide prediction of preferred recognition sites. Cell. 2008 Jun. 27; 133(7):1277-89; and Enuameh et al., Global analysis of *Drosophila* $Cys_2$-$His_2$ zinc finger proteins reveals a multitude of novel recognition motifs and binding determinants. Genome Research, 2013 June; 23(6):928-40.

Functionality of the NmCas9-DBDs may be verified through assays on genomic target sites with DBDs that are programmed to recognize neighboring sequences, where activity can be assessed by T7EI assay. In these genomic assessments, activity on properly spaced/oriented binding sites and the absence of activity on improperly spaced/oriented sites can be determined.

III. Improved Precision Using Mutant pDBDs

In some embodiments, the present invention contemplates a chimeric Cas9 system that dramatically improves the precision and targeting range of the Cas9 nuclease. In one embodiment, precision and targeting range is improved by augmention of its specificity with an attached pDBD. In one embodiment, the Cas9-pDBD precision is tunable. In one embodiment, the tunable precision includes, but is not limited to, specificity and/or affinity of the associated pDBD. Although it is not necessary to understand the mechanism of an invention, it is believed that therapeutic genome editing, where cleavage precision is of paramount importance, utilizing customized Cas9-pDBDs will play a role in clinical development process.

A. Improved Precision with Mutant Cas9 pDBD Fusions

Figure 60A:
FIG. 60A-D presents exemplary data demonstrating improved precision of SpCas9$^{MT}$-ZFP chimeras.
Figure 60B:
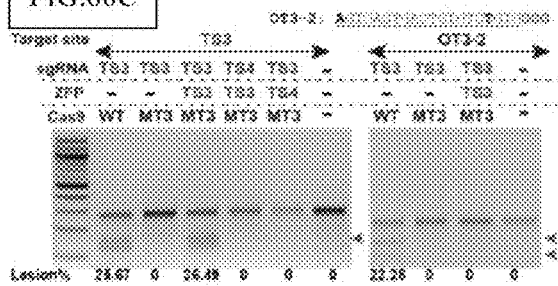
Figure 60C:
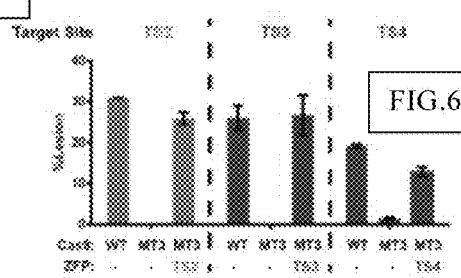

The data presented herein evaluates an improved precision of a $SpCas9^{MT}$ #-pDBD framework at SpCas9 target sites (e.g., for example, TS2, TS3 & TS4; all with NGG PAMs). SgRNAs that recognize these sites have defined on- and off-target activities, which provide a known benchmark to assess improvements in precision. A ZFP was constructed to recognize a sequence near each target site and compared the editing activities of sgRNA programmed SpCas9, $SpCas9^{MT3}$ and $SpCas9^{MT3}$-$ZFP^{TS\,\#}$. FIG. 44A. It was confirmed that $SpCas9^{MT3}$ was nearly inactive at all target sites, where this activity was restored by the presence of a cognate ZFP fusion. FIG. 44B. However, the activity was not rescued with a non-cognate sgRNA or ZFP (FIG. 13 & FIG. 60C). To assess improvements in precision at previously defined off-target sites, PCR products spanning these loci were deep sequenced for $sgRNA^{TS2/TS3/TS4}$. The nuclease activity of SpCas9, and $SpCas9^{MT3}$-$ZFP^{TS2/TS3/TS4}$ was then compared at these target and off-target sites. It was found that $SpCas9^{MT3}$-$ZFP^{TS2/TS3/TS4}$ dramatically increased the precision of target site cleavage. FIG. 44C. In most cases, utilizing $SpCas9^{MT3}$-$ZFP^{TS2/TS3/TS4}$ reduced lesion rates at off-target sites to background levels resulting in improvements in specificity of up to 150-fold. Only one off-target site (OT2-2), which has a neighboring sequence that is similar to the expected ZFPTS2 recognition sequence (data not shown), still displays high lesion rates. One other site (OT2-6), displays some residual activity both for $SpCas9^{MT3}$ and $SpCas9^{MT3}$-$ZFP^{TS2}$ that is above the background error rate within the sequencing data. These data demonstrate a dramatic overall enhancement of the precision of $SpCas9^{MT4}$-ZFPs relative to standard SpCas9.

To discover new off-target sites of $SpCas9^{MT3}$-ZFPs, a GUIDE-seq analysis was performed on SpCas9 and $SpCas9^{MT3}$-$ZFP^{TS\,\#}$. These data are consistent with the focused deep sequencing data of known off target sites: there is a dramatic improvement in precision for the $SpCas9^{MT3}$-$ZFP^{TS\,\#}$. In addition, ESAT peak picking analysis (garberlab.umassmed.edu/software/esat) of the $SpCas9^{MT3}$-$ZFP^{TS\,\#}$ GUIDE-seq data reveal that there is a dramatic reduction in $SpCas9^{MT3}$-$ZFP^{TS\,\#}$ off-target activity genome-wide. FIG. 44D. A small number of weak peaks (less than 5 reads, likely noise) are unique to the $SpCas9^{MT3}$-$ZFP^{TS\,\#}$ (relative to SpCas9 programmed with the same sgRNA), but none appear to be valid off-target sites based on the absence of guide complementary sequence with 6 or fewer mismatches. Thus, $SpCas9^{MT}$ nuclease activity is muzzled, but can be reactivated at specific genomic regions through fusion of a pDBD recognizing a neighboring sequence.

Figure 61:
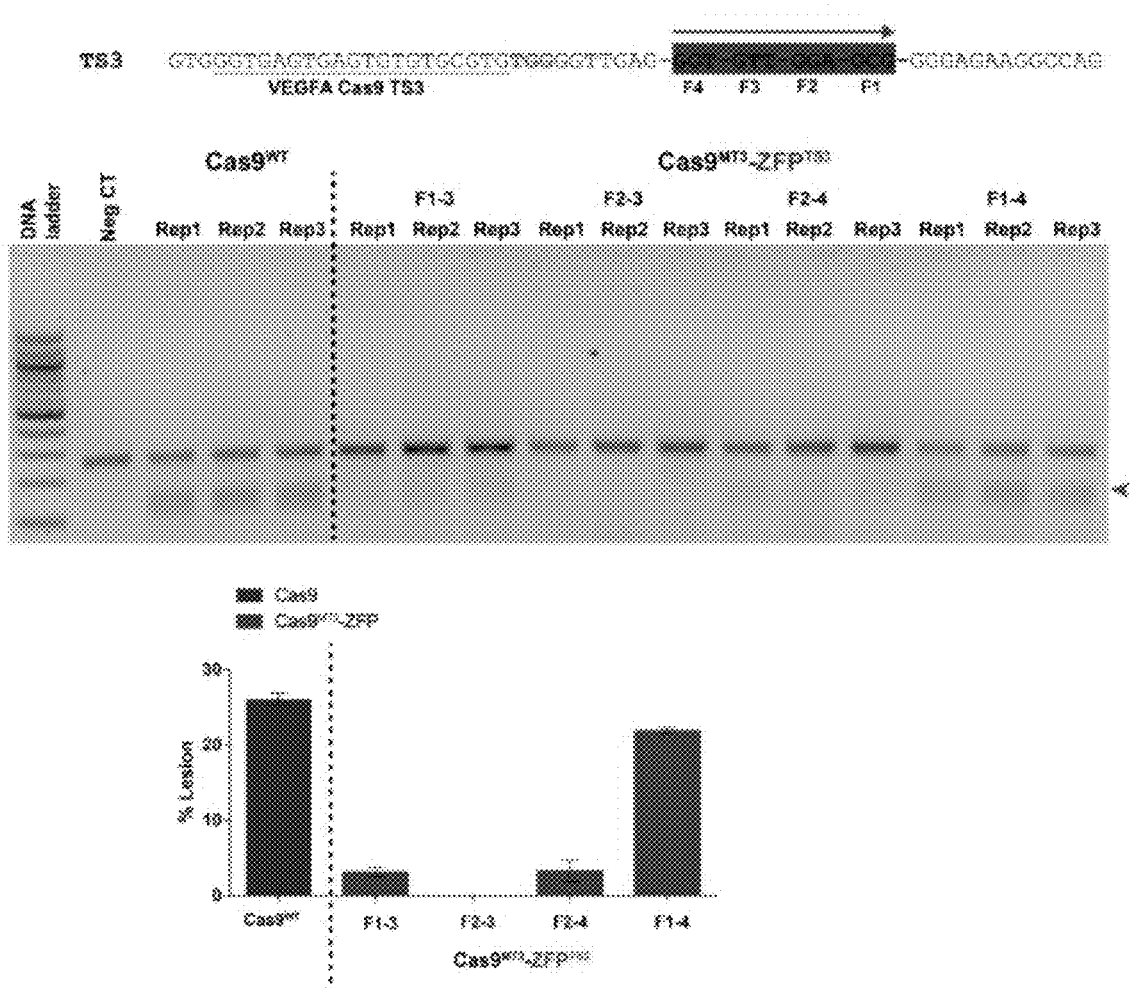
FIG. 61 presents exemplary data of a T7EI activity profile of SpCas9$^{MT3}$-ZFP$^{TS3}$ at the TS3 genomic locus as a function of the number of incorporated fingers. Both Cas9$^{WT}$ and SpCas9$^{MT3}$-ZFP$^{TS3}$ with four fingers (F1-4) achieve efficient target cleavage. Removing a single finger from either end of the zinc finger array (F1-3 or F2-4) dramatically reduces the activity of the SpCas9$^{MT3}$-ZFP chimera. Cleaved products are indicated by magenta arrowheads. The bar graph displays the mean lesion rate in three independent biological replicates (Rep1, Rep2, Rep3) performed on different days in HEK293T cells. Error bars indicate standard error of the mean.

The precision of SpCas9-ZFPs to SpCas9 was compared using sgRNAs with previously defined off-target sites[14,25]. Three different four-finger ZFPs were constructed to recognize 12 base pair sequences neighboring the TS2, TS3 or TS4 sgRNA target sites for use as $SpCas9^{MT3}$-ZFP fusions. FIG. 60A. The activity of SpCas9, $SpCas9^{MT3}$ and $SpCas9^{MT3}$-$ZFP^{TS2/TS3/TS4}$ with a corresponding sgRNA was compared at each target site. In all cases $SpCas9^{MT3}$ dramatically decreased cleavage efficiencies, which were restored by a cognate ZFP fusion. FIG. 60B. The activity of $SpCas9^{MT3}$-ZFP was dependent on the presence of both a cognate sgRNA and ZFP. FIG. 60C. Consistent with the dependence on ZFP binding, truncation of one zinc finger from either end of $ZFP^{TS3}$ reduced the activity of $SpCas9^{MT3}$-$ZFP^{TS3}$ at the TS3 target site, and the removal of two zinc fingers abrogated activity. FIG. 61. The introduction of a third stage of target site licensing supplied by the pDBD dramatically increased the precision of $SpCas9^{MT3}$-$ZFP^{TS3}$ relative to wild type SpCas9 ($SpCas9^{WT}$); lesion rates at the most active off-target site (OT3-2) for $sgRNA^{TS3}$ were 22% by T7EI assay with wild type Cas9, but were undetectable with $SpCas9^{MT3}$-$ZFP^{TS3}$. FIG. 60C.

Figure 60D:
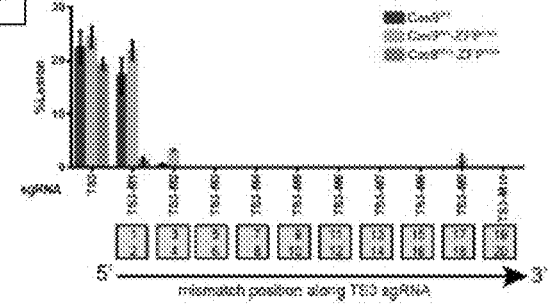

Two TALE arrays were also programmed to target $SpCas9^{MT3}$ to TS3 and TS4 (TALE-TS3 and TALE-TS4). Nuclease activity at the TS3 site but not TS4 can be restored by the related $SpCas9^{MT3}$-TALE fusion. FIG. 62. To examine the catalytic tolerance of the $SpCas9^{MT3}$-$ZFP^{TS3}$/sgRNA complex to mismatches between the guide and a target sequence, a set of guides was used that progressively shift blocks of 2 base mismatches from the 5' to the 3' end of the guide sequence. $SpCas9^{MT3}$-$ZFP^{TS3}$ has a lower tolerance for mismatches between the guide and target site relative to $SpCas9^{WT}$, whereas $SpCas9^{WT}$-$ZFP^{TS3}$ appears to modestly increase the tolerance for mismatches. FIG. 60D and Table 3.

TABLE 3

Average nuclease activity (% Lesion) values of TS3 sgRNA mismatches

| SEQ ID NO: | sgRNA Name | sgRNA sequence | Cas9$^{WT}$ | Cas9$^{WT}$-ZFP$^{TS3}$ | Cas9$^{MT3}$-ZFP$^{TS3}$ |
|---|---|---|---|---|---|
| 23 | TS3 | GGTGAGTGAGTGTGTGCGTG | 22.44 | 24.39 | 19.34 |
| 24 | TS3-M1 | gCCTGAGTGAGTGTGTGCGTG | 17.17 | 21.9 | 1.08 |
| 25 | TS3-M2 | GGCAAGTGAGTGTGTGCGTG | 0.41 | 3.24 | N.D |
| 26 | TS3-M3 | GGTGCTTGAGTGTGTGCGTG | N.D | N.D | N.D |
| 27 | TS3-M4 | GGTGAGGAAGTGTGTGCGTG | N.D | N.D | N.D |
| 28 | TS3-M5 | GGTGAGTGCTTGTGTGCGTG | N.D | N.D | N.D |
| 29 | TS3-M6 | GGTGAGTGAGCATGTGCGTG | N.D | N.D | N.D |
| 30 | TS3-M7 | GGTGAGTGAGTGCATGCGTG | N.D | N.D | N.D |
| 31 | TS3-M8 | GGTGAGTGAGTGTGGTCGTG | N.D | N.D | N.D |
| 32 | TS3-M9 | GGTGAGTGAGTGTGTGTATG | N.D | N.D | N.D |
| 33 | TS3-M10 | GGTGAGTGAGTGTGTGCGCA | N.D | N.D | N.D |

N.D: Not Detected

Figure 46:
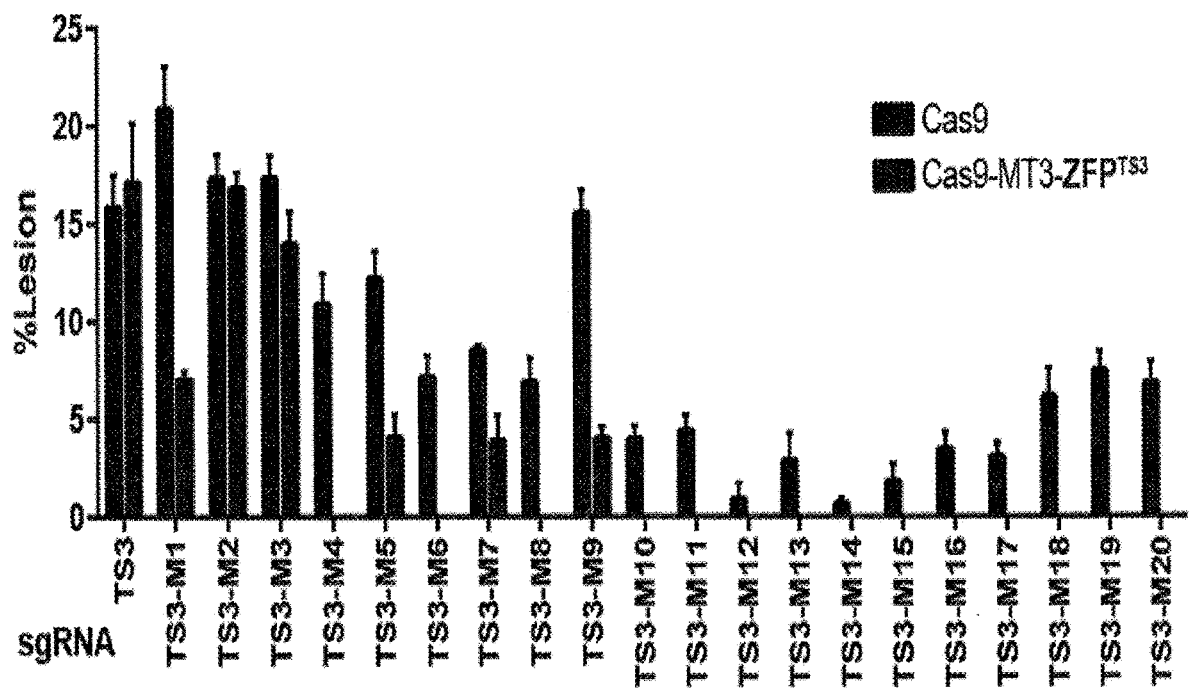
FIG. 46 presents exemplary data showing an activity profile of SpCas9 (blue) and SpCas9$^{MT3}$-ZFP$^{TS3}$ (red) at TS3 target site with guides containing single-base mismatches at the 20 positions (M1-M20) across the target site. Both nucleases have similar activity at the TS3 target site with a fully cognate guide (leftmost bars), but SpCas9$^{MT3}$-ZFP$^{TS3}$ has dramatically enhanced sensitivity to mismatches between the guide and target site. Data are from T7EI assays on amplicons spanning the genomic target site from three independent biological replicates performed on different days in HEK293T cells. Error bars indicate s.e.m.

Consistent with an increased sensitivity to disruptions in sgRNA-target interactions, SpCas9$^{MT3}$-ZFPs exhibit reduced activity with truncated sgRNAs[25], confirming that a higher degree of guide-target site complementarity is required for efficient cleavage with our chimeras. FIG. 63. In addition a series of single base mutations with the sgRNA shifted across the TS3 target site indicates that SpCas9$^{MT3}$-ZFP has superior discrimination to wild-type Cas9 (FIG. 46).

B. Cas9-pDBD System Tunability

One advantage of a SpCas9-pDBD system over other Cas9 platforms is the ability to rapidly tune the affinity and specificity of the attached pDBD to improve its precision. In one embodiment, improved precision of SpCas9$^{MT3}$-ZFP$^{TS2}$ was achieved by truncating the four zinc finger array to reduce its affinity for off-target site OT2-2. High activity at the TS2 target site was maintained despite removal of either of the terminal zinc fingers from SpCas9$^{MT3}$-ZFP$^{TS2}$. However, these truncations reduced or eliminated activity at OT2-2, reflecting a profound improvement in the precision of SpCas9$^{MT3}$-ZFP$^{TS2}$. Similarly, utilization of a ZFP$^{TS2*}$ that recognizes an alternate sequence neighboring the TS2 guide target site also abolishes off-target activity at OT2-2. FIG. 45.

Given the improvements in precision realized by these selective alterations in the composition of a ZFP, it should be possible to achieve even greater enhancements in precision via more focused modification of a ZFP composition and a linker connecting it to SpCas9. These data demonstrate the functionality SpCas9-pDBD chimeras, their broader targeting range and improved precision when compared to standard SpCas9.

C. Increased SpCas9 Precision through Direct and Drug-Dependent pDBD Fusions

In one embodiment, the present invention establishes a framework to facilitate use of the SpCas9-pDBD system to efficiently design, assay and permute this platform to achieve single-site precision for editing the human genome. There are a number of parameters that remain to be optimized in the SpCas9-pDBD system. For example, an initial four-finger SpCas9-ZFPs still retains a low level of off-target activity. FIG. 44. Some of this is residual activity present in the SpCas9$^{MT3}$ (R1335K) mutant that is independent of a pDBD. In addition, linker length/composition as well as improved pDBD affinity and specificity also contribute to improved precision and efficiency.

I. Improved Precision Using SpCas9-pDBD Frameworks

In some embodiments, the present invention contemplates a method utilizing different parameters regulating precision and activity of a SpCas9-pDBD framework to define a framework for highly active and extremely precise nucleases.

a. The Cas9-pDBD Linker

In one embodiment, a SpCas9$^{MT3}$-pDBD construct is connected by a 60-aa linker and displays improvements in precision. FIG. 2B. Although it is not necessary to understand the mechanism of an invention, it is believed that an improved linker length provides additional precision improvements by reducing the number of alternate (e.g., off-target) sgRNA/pDBD binding site permutations.

For example, a GFP reporter assay is used herein to identify improved linker lengths joining SpCas9 to either ZFPs or TALEs that increase their fidelity of target site cleavage. In one embodiment, the GFP reporter assay defines a minimal linker length for SpCas9-Zif268 and SpCas9-TAL268 constructs that retains maximum activity at one (or more) binding site positions, but places further restrictions on the activity at other positions. Improved linkers may be tested for both activity and precision in the context of SpCas9$^{MT3}$-pDBDs designed for TS2/TS3/TS4 genomic sites. FIG. 44. Initial activity and precision may be assessed by T7EI assays. FIGS. 44 and 45.

The most promising linkers can be further evaluated by GUIDE-seq to assess genome-wide off-target activity. GUIDE-seq results may be verified by targeted deep sequencing of PCR products spanning these loci. FIG. 44. The GFP reporter assay and subsequent validation at the TS2/TS3/TS4 genomic targets via GUIDE-seq can identify linkers that display both high activity and more selectivity in the particular arrangement of SpCas9 and pDBD binding sites. The improved linker length and improved binding site position/orientation may differ between ZFPs and TALES due to their differing mechanisms of DNA recognition.

b. Improved Precision Using DNA Recognition Modules (ZFP or TALE)

The data herein has shown that the precision of SpCas9-ZFPs is dependent on the number of ZFP recognition modules, where excessive affinity reduces precision. FIG. 45. Alternatively, in some embodiments binding site size and affinity of TALEs or ZFPs can be tuned by changing the number of incorporated recognition modules. For example, ZFPs may be modified by altering the number of fingers, the type inter-finger linkage and/or the number of DNA phosphate contacts. Alternatively TALEs may be modified by altering the number of modules and/or the use of non-canonical RVD recognition residues. As described above, the TS2/TS3/TS4 genomic sites can be utilized to assay activity and precision, first by T7EI assays, followed by evaluation of the most promising SpCas9$^{MT3}$-pDBDs by GUIDE-seq and targeted deep sequencing. Although it is not necessary to understand the mechanisms of an invention, it is believed that while an optimal number of fingers/modules within a pDBD may vary from site to site, a range of fingers/modules may be defined that is likely to be more favorable with regards to both target activity and precision.

c. SpCas9 Modifications for pDBD Functional Dependence

As shown above, PAM-attenuated SpCas9$^{MT3}$ displays residual nuclease activity at TS2/TS3/TS4 in the absence of the pDBD. Further, attenuation of SpCas9 DNA-binding affinity increases absolute pDBD dependence and thus its precision. In one embodiment, the present invention contemplates at least one mutation in at least two regions of SpCas9 to reduce its intrinsic activity including, but not limited to; i) PAM recognition residues, and ii) phosphate-contacting residues near the PAM binding site.

In one embodiment, the present invention contemplates a Cas9 complex comprising PAM recognition residue mutations. In one embodiment, the mutations are located at arginine residues (e.g., for example, R1333 & R1335) that make base-specific PAM contacts. In one embodiment, the mutations are a combination mutations (e.g. combining R1333K, & R1335K). Such combination mutations are believed to further attenuate independent SpCas9 activity but retain activity in the presence of a fused pDBD. The double-strand break (DSB) formation rate in the absence and presence of the pDBD may be estimated by qPCR-based quantification of the rate of capture of GUIDE-seq oligos at each target site (TS2/TS3/TS4) as a proxy for deep sequencing.

In one embodiment, the present invention contemplates arginine or lysine residue mutations that contact DNA phosphates. Although it is not necessary to understand the mechanism of an invention, it is believed that neutralization of phosphate contacts within pDBDs can modulate their binding affinities. In one embodiment, SpCas9 is mutated at lysine or arginine residues that are positioned to make non-specific contacts with the DNA downstream of the PAM-contacting residues, and so should not affect the efficiency of R-loop formation or the precision of DNA cleavage. The activity of these mutants may be assayed as described for the PAM recognition mutants.

Mutations can be identified that render SpCas9 completely dependent on an attached pDBD. Since the capture of GUIDE-seq oligos is not be a perfect surrogate for the rate of DSB formation, lesion rates may be assessed for the most promising mutants by deep sequencing. Alternatively, lysine or arginine mutants can be combined with PAM mutants for further attenuation of SpCas9 DNA-binding affinity. Although it is not necessary to understand the mechanism of an invention, it is believed that the improved precision of the presently disclosed SpCas9$^{MT}$-pDBDs for TS2/TS3/TS4 are vastly superior to those previously reported. To confirm that superiority, the precision should be shown to be cell line-independent via deep-sequencing and GUIDE-seq analysis.

2. Allele-Specific Targeting Using Single Nucleotide Polymorphisms

The ability to selectively inactivate specific dominant-negative alleles could have great utility. For example, single nucleotide polymorphisms (SNPs) have been proposed as discriminators for siRNA-mediated silencing of Huntingtin alleles that contain CAG repeat expansions. Cas9s with allele-specific activity could provide a therapeutic strategy to disable specific harmful alleles. SpCas9 has been used to achieve incomplete discrimination using a SNP within the guide recognition sequence. Analysis of the presently disclosed Cas9$^{MT3}$-ZFP framework has revealed dramatically improved discrimination for single-base changes within a target sequence. FIG. 46. This increased sensitivity is consistent with improved precision. The feasibility of using SNPs within a guide recognition sequence or a PAM as discriminators are examined herein.

For example, a COSMIC database may be used comprising a list of validated cell line SNPs to test the feasibility of this approach (e.g., identifying twenty-six heterozygous SNPs is U2OS cells). Candidate loci may then be sequenced to confirm the reported SNP heterozygosity and then design SpCas9$^{MT}$-pDBD/sgRNA combinations to target a single allele. Allelic targeting ratios (relative to negative controls lacking the cognate sgRNA or the appended pDBD) may be determined by a frequency that each allele captures GUIDE-seq oligos (via deep sequencing). If DSBs are restricted to a single allele, then only the targeted SNP should be found neighboring the GUIDE-seq oligo sequence. As SpCas9 mutants are identified that have improved attenuation, single base change discrimination can then be examined. Although it is not necessary to understand the mechanism of an invention, it is believed that SpCas9$^{MT}$-pDBDs have great potential for allele-specific targeting but should be subjected empirical verification. If necessary, discrimination can be tested using paralogous sequences that differ by a single base within the genome (e.g. CCR2 and CCR5, which contain many >30 bp regions that differ by a single nucleotide). Relative editing efficiencies on one paralog or the other can be assessed by the PCR/deep sequencing approach described above.

3. Drug- or Photo-Dependent spCas9-pDBD Nuclease Regulation

Small molecule- or photo-dependent dimerization systems have been developed that permit the control of activity of a two-component system. Since SpCas9/sgRNA off-target activity is dose dependent, these systems have been adapted to regulate the association of two fragments of Cas9 (e.g., Split-Cas9).

In one embodiment, the presently disclosed SpCas9-pDBD system comprises a drug- or photo-dependent dimerization system that regulates the association of SpCas9 and the pDBD. In one embodiment, the present invention contemplates a rapamycin-dependent Cas9 complex comprising a SpCas9-FRB/FKBP-ZFP and/or a SpCas9-FRB/FKBP-TALE and/or Split-SpCas9$^{MT}$-pDBD. FIGS. 47, 99, 100, 101 and 102. The data show that the target activity (with drug) is similar to SpCas9$^{WT}$ without sacrificing of the enhanced precision of the SpCas9-pDBD system. In addition, swapping the drug-dependent dimerization domains (e.g. SpCas9-FKBP/FRB-ZFP) and changing the relative order of these domains (e.g. SpCas9-FKBP/ZFP-FRB) can improve the activity and precision of these constructs (FIGS. 99 & 101). This type of improvement of components (fusion partners and their relative position) can be attained for any combination of dimerization domains in principle.

4. SpCas9-FKBP/pDBD-FRB System Improvements a. SpCas9-FKBP/pDBD-FRB Linkers

In one embodiment, the present invention contemplates a GFP reporter system comprising genomic targets to identify a optimal linker length joining Cas9 to a dimerization domain and the pDBD to a dimerization domain that maximizes activity and restricts the relative spacing and orientation of the active binding sites. In one embodiment, the linker joins an SpCas9-FKBP domain and an pDBD-FRB domain.

b. ZFP or TALE DNA Recognition Modules

In one embodiment, the present invention contemplates DNA recognition modules that improve SpCas9-FKBP/pDBD-FRB precision at sites including, but not limited to, TS2, TS3 and TS4 sites. Although it is not necessary to understand the mechanism of an invention it is believed that the optimal number and composition of recognition modules in the pDBD may differ when compared to a Cas9-pDBD covalent system, since greater cooperativity in the binding is likely to occur in the covalent system.

c. Nm-dCas9 as pDBDs

In one embodiment, the present invention contemplates a nuclease-dead NmCas9 as a pDBD for an association through dimerization (FIG. 20). In one embodiment, a mutated nuclease (e.g., SpCas9$^{MT}$) and Nm-dCas9 are programmed through orthogonal sgRNAs to recognize neighboring sequences. Although it is not necessary to understand the mechanism of an invention, it is believed that for this type of dimerization system (e.g. SpCas9$^{MT}$-FKBP/Nm-dCas9-FRB) fusion partners for each dimerization domain and their position on the nuclease are empirically determined. In principle other Cas9 isoforms could be substituted for SpCas9 or Nm-dCas9.)

d. Nuclear Export Sequences

Photo-dependent TALE regulators or drug-dependent Split-SpCas9 fusions have been reported to decrease off-target activity by fusing a nuclear export sequence (NES) instead of a Nuclear Localization Sequence (NLS) to one component. It is believed that an Cas9-NES fusion protein is restricted to the cytoplasm until the inducer is present (light/drug), at which point an NLS-tagged partner can drive nuclear import. In one embodiment, an NES-SpCas9$^{MT}$-FRB fusion protein may be excluded from the nucleus in the absence of rapamycin. In one embodiment, a combination of an NLS with NES-SpCas9$^{MT}$-FRB fusion protein facilitates a transit between the nucleus and cytoplasm in the presence of rapamycin allowing more efficient import of the partner that is located in the cytoplasm (e.g. FIG. 99).

Assessments of activity and precision for constructs of particular interest may occur at an TS2/TS3/TS4 loci initially by T7EI assays such that dose and duration of rapamycin exposure on activity and precision can be examined. The precision of the most promising constructs may be evaluated by GUIDE-seq followed by targeted deep sequencing (e.g. FIG. 102).

e. The Abscisic Acid Regulatory System

A drug-based dimerization system has been previously described based on a plant hormone (i.e., for example, abscisic acid) and its protein partners (ABI & PYL; Liang, F.-S., Ho, W. Q. & Crabtree, G. R. Engineering the ABA plant stress pathway for regulation of induced proximity. *Science Signaling* 4, rs2-rs2 (2011).) Abscisic acid is believed to be bioavailable, and the plant-derived components should have minimal crosstalk with endogenous factors (unlike a rapamycin system). Consequently, a SpCas9$^{MT}$-ABI/PYL-pDBD system may be useful for drug-dependent regulation.

Photo-dependent (e.g., for example, visible light or non-visible light) regulation of TALE-effector and Split-SpCas9 nuclease function have been described. In one embodiment, the present invention contemplates a light-inducible dimerization domain comprising nMag/pMag CRY2/CIB1 (Nihongaki, Y., Kawano, F., Nakajima, & Sato, M. Photo-activatable CRISPR-Cas9 for optogenetic genome editing. *Nature biotechnology* 33, 755-760 (2015)).

D. Improved Precision with NmCas9-pDBD and SpCas9-pDBD Frameworks

Development of a SpCas9-pDBD system (supra) has benefited from extensive data on the 1368-aa SpCas9 protein. However, full realization of genome editing goals involves the development of additional Cas9 orthologs to provide additional PAM specificities and simultaneous deployment of Cas9s with orthogonal guides. In addition, for clinical deployment, the physical size of SpCas9's limits in vivo deliverability to platforms such as AAV vectors and synthetic mRNAs. Alternatively, most Type II-C Cas9s (e.g. *N. meninigitidis;* 1082 residues) and a few Type II-A Cas9s (e.g. *S. aureus;* 1053 residues) are considerably smaller than SpCas9 and may have clinical delivery advantages over SpCas9 platforms.

For example, a compact Cas9 (i.e., for example, NmCas9) was recently validated for genome editing. Alternatively, an SaCas9 platform was also characterized, and its utility for editing in an all-in-one (Cas9+sgRNA) AAV format was documented. Because Cas9s is believed to have some propensity for promiscuous cleavage, compact orthologs should be modified to provide an enhanced precision to tap their clinical potential. In one embodiment, the present invention contemplates NmCas9- and SaCas9-based editing platforms with single-genomic-site accuracy.

Figure 48:
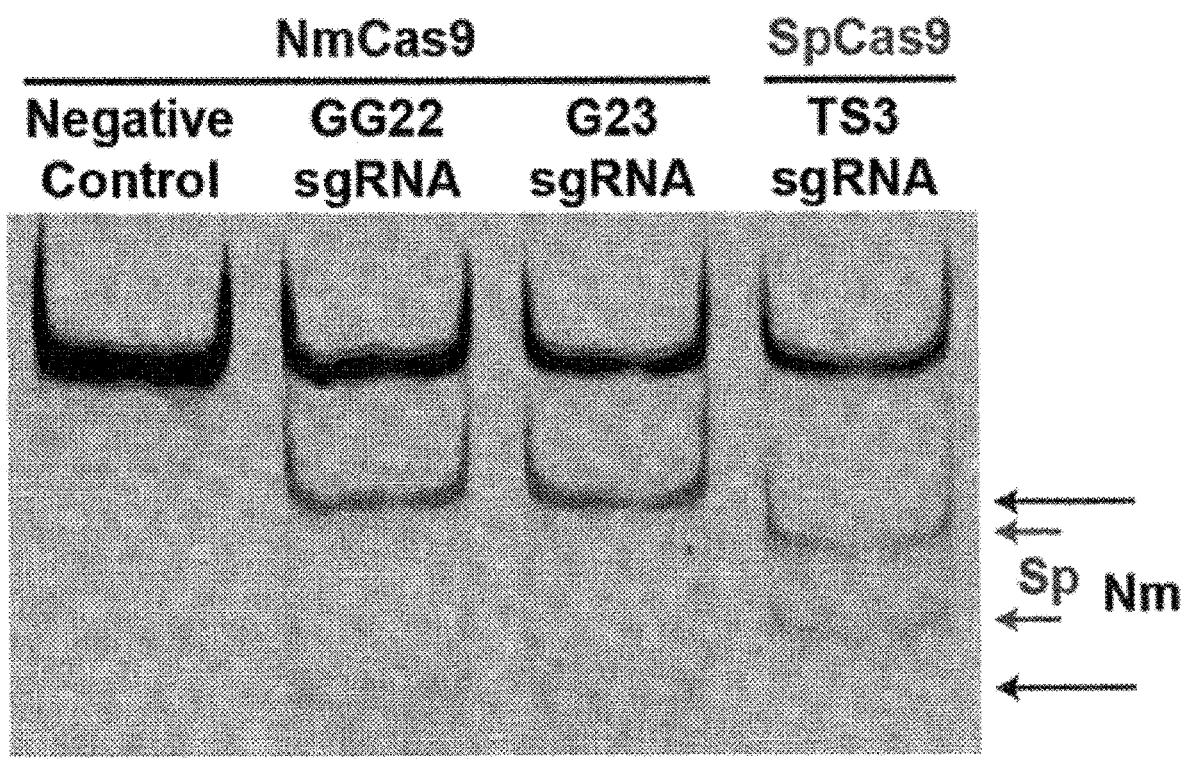
FIG. 48 presents exemplary data showing T7 EI analysis reveals efficient NmCas9 editing of a site adjacent to a GATT PAM within the Vegfa/TS3 amplicon. 24-nt NmCas9 guides with either one (G23) or two (GG22) G residues at the 5' end edit the target as efficiently as the canonical SpCas9/TS3 sgRNA combination.

Preliminary data using NmCas9 demonstrate that a PAM consensus is 5'-N4GATT-3', with considerable variation allowed during bacterial interference (data not shown). However, PAM requirements are more stringent in mammalian cells, and efficient editing has only been documented at N4G(A/C/T)TT, N4GAC(A/T), N4GATA, and N4GTCT PAMs. FIG. 48. It has been reported that mammalian genome editing by NmCas9 also requires strong sgRNA/target seed-sequence complementarity. NmCas9 guide sequences are naturally 24 nts long, though 22- to 26-nt lengths are functional (not shown). As shown above, when using a GFP assay in HEK293 cells, Zif268 fusion to NmCas9 (in conjunction with a Zif268 binding site downstream of the PAM) allows targets with otherwise non-functional PAMs to be cleaved. See, FIG. 49A. This demonstrates that an appended DBD can facilitate cleavage at non-canonical NmCas9/PAM interactions, as with SpCas9 (supra).

Figure 49A:
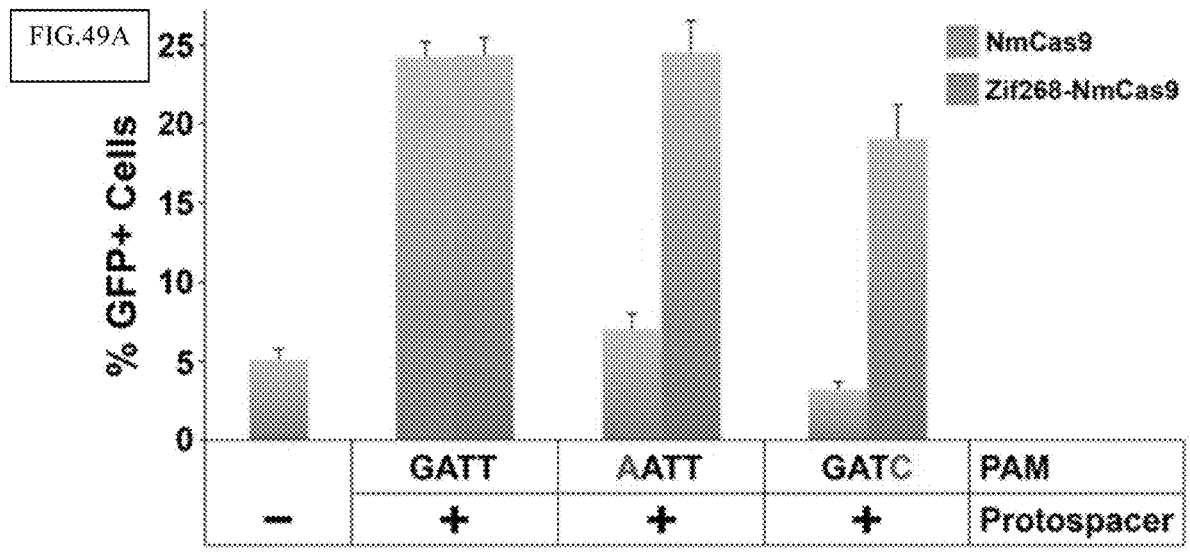
FIG. 49A-B presents exemplary data showing that attenuated NmCas9-PAM interactions can be rescued by a fused DBD. Data are from three independent replicates on different days in HEK293 cells. Error bars indicate s.e.m.
Figure 49B:
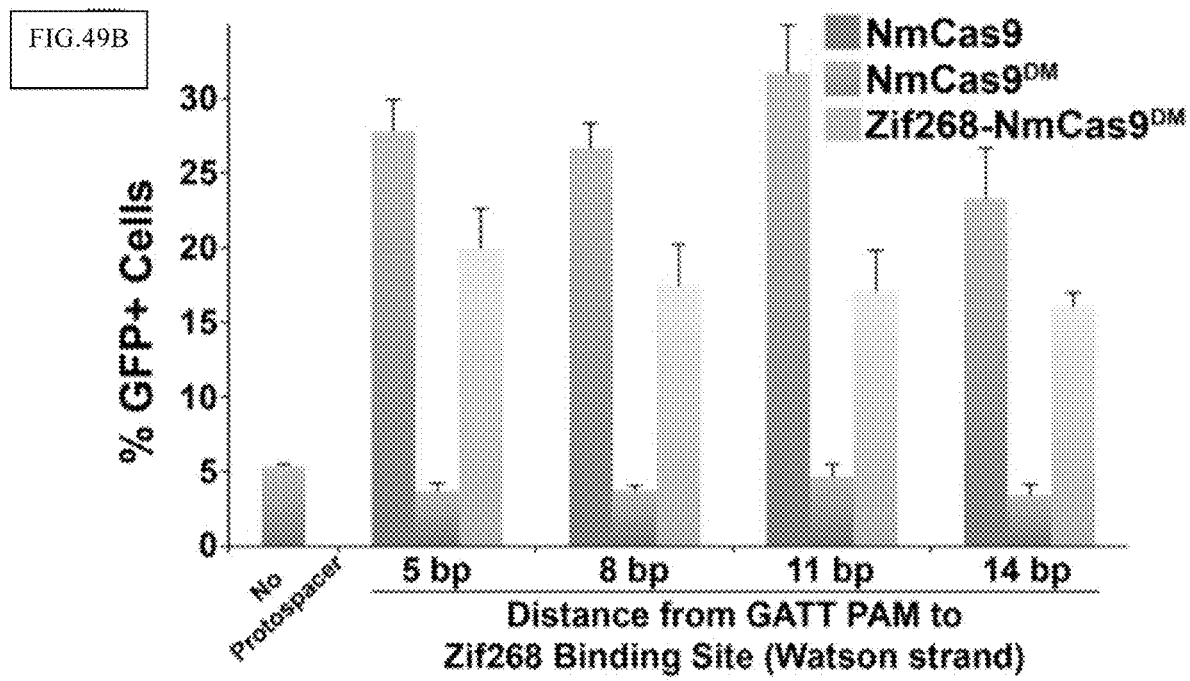

The structure of NmCas9 is not known, nor are associated PAM-recognition residues defined. Nonetheless, some information can be discerned from an *A. naeslundii* Type II-C Cas9 structure (AnCas9). For example, two positively charged NmCas9 residues (e.g., Lys1013 and Arg1025) are particularly well-conserved in Type II-C Cas9 alignments, and the corresponding AnCas9 residues map to a candidate PAM interaction region. The activity of the NmCas9 K1013A/R1025A double mutant (hereafter NmCas9$^{DM1}$) is severely attenuated in the GFP assay in HEK293 cells, but can be rescued by an appended Zif268 pDBD (with a Zif268 binding site downstream of the PAM). FIG. 49B. Although it is not necessary to understand the mechanism of an invention, it is believed that these observations, along with the mutant PAM rescue, strongly suggest that the PAM attenuation/pDBD fusion is a feasible strategy to create more precise compact Cas9 orthologs. Furthermore, recent reports have also provided information on SaCas9, including its functional PAM sequence (5'-NNGRR-3') (SEQ ID NO: 34) and spacer lengths (21-23 nts) thereby facilitating this strategy's extension into a compact Type II-A system.

1. PAM Attenuation/pDBD Fusion Parameters for Enhanced-Precision NmCas9 and SaCas9 a. NmCas9$^{MT}$-pDBD and SaCas9$^{MT}$-pDBD Frameworks

The data presented herein demonstrates that a fused pDBD (either N- or C-terminal, with a 60-aa linker) allows editing of targets with nonfunctional PAMs having a pDBD binding site 5 bp from the PAM. FIG. 49A. Alternative embodiments include, but are not limited to, other NmCas9-pDBD spacings and orientations for SpCas9 and/or NmCas9 fusions to TAL268. For example, one SaCas9 embodiment comprises using a PAM variant (e.g., for example, NN(A/C/T)RR) (SEQ ID NO: 35) that is known to be nonfunctional. Alternatively, alanine and/or serine mutations, either individually or pair-wise, may be introduced that are within an ~25-aa window around a putative PAM-interacting domain of SaCas9, based on Type II-A Cas9 sequence alignments. It can then be determined which of those mutations attenuate SaCas9 function and can be re-activated by Zif268 fusion. FIG. 49B. Initially, a GFP assay in HEK293 cells can be performed, and the most promising set of spacings, orientations, and Zif268-suppressible SaCas9-attenuating mutants may then be validated at corresponding genomic loci by T7EI assay. Several custom-designed ZFP and TALE modules can also be tested on other chromosomal targets with both $Cas9^{MT}$ systems. Finally, NmCas9- and SaCas9-linker length improvements are determined as described above.

b. NmCas9 and SaCas9 Accuracy

In one embodiment, the present invention contemplates a GUIDE-seq assay to compare the editing precision of $Cas9^{WT}$ orthologs and the $Cas9^{MT}$-pDBD variants. In one embodiment, the GUIDE-seq assay identifies Indel frequencies at off-target sites. In one embodiment, the Indel frequencies are quantified by deep-sequencing PCR-amplified loci. In one embodiment, mismatch tolerance at chromosomal editing sites measure the effects of PAM attenuation and pDBD fusion. In one embodiment, off-target propensities of the on- vs. off-target lesion rate ratios identify successful pDBD tenability by varying the number of ZFPs or TALE modules.

2. NmCas9 and SaCas9 Drug-Inducible Dimerization Systems

One disadvantage with AAV delivery of active Cas9/guideRNA combinations is that Cas9 activity (both on and off-target) may persist indefinitely. Accordingly, by successfully implementing drug-inducible $Cas9^{MT}$-pDBD association in the context of one or both compact Cas9s, the system's accuracy enhancements are further improved, and by preventing on-going off-target lesions once the drug is withdrawn and after editing is complete. In one embodiment, the present invention contemplates a NmCas9 and/or a SaCas9 drug-inducible dimerization system.

For example, DNA-binding modules (e.g., ZFP and TALE) attached to NmCas9 or SaCas9 could both be RNA-guided. NmCas9 and its guideRNAs are orthogonal to all Type II-A Cas9s and sgRNAs tested to date, and SaCas9's expected orthogonality and its sgRNAs can be easily confirmed as well. Drug-inducible dimerization modules (e.g., for example, FRB/FKBP or ABI/PYL, and all pair-wise combinations) can be fused to a PAM-attenuated but catalytically active version of a compact Cas9, and the nuclease-dead version of the other. Whether dCas9 can fulfill the same precision-enhancing function provided by the pDBD may then be tested. Initially, a GFP reporter system is used to improve PAM/target orientation and spacing, and then tested using actual chromosomal loci. If this framework can edit its chromosomal loci target sites efficiently, as judged by T7EI assay, an unbiased assay can define the precision of this system relative to the drug-induced pDBD dimerization system.

3. Functional AAV $NmCas9^{MT}$-pDBD and $SaCas9^{MT}$-pDBD Constructs

It is believed that native NmCas9 and SaCas9 ORFs are ~3.25 and 3.16 kb, respectively, so even with added NLSs and minimal expression/processing signals, they are well under the ~4.5 kb packaging limit of current AAV vectors. For example, a four-finger ZFP with a 60-aa linker would increase the ORF size by an additional 0.6 kb, still well within the AAV vector size limit. As explained herein, some embodiments of the present invention minimize linker length to further reduce an AAV Cas9-pDBD packaging size. In some embodiments, the present invention contemplates the delivery of $NmCas9^{MT}$-ZFPs and $SaCas9^{MT}$-ZFPs via AAV into cultured cells. In one embodiment, the AAV comprises a liver specific promoter. In one embodiment, the AAV is an AAV8 serotype. In one embodiment, the AAV8 serotype is hepatocyte-tropic. In one embodiment, the cultured cells comprise HepG2 cells. In one embodiment, the genome of the HepG2 cells comprise Pcsk9 as an editing (NHEJ) target. In one embodiment, the AAV expression constructs is a transfection plasmid.

E. Cas9-pDBD Mediated Gene Correction of Defective CYBB in CGD

Chronic granulomatous disease (CGD), a disorder of phagocytic function, generally presents early in life with severe recurrent infections. The estimated incidence per live birth is 1/200,000 in the US. Conventional clinical management allows many patients to reach adulthood, but CGD patients have only 50% cumulative survival at age 50, and the only curative therapy is hematopoietic stem and progenitor cell (HSPC) transplantation. The molecular defects causing CGD affect the phagocyte NADPH oxidase responsible for the generation of microbicidal reactive oxygen species. About 60% of cases are X-linked (X-CGD) due to mutations in CYBB, an Xp21.1 gene that encodes gp91phox, the glycoprotein subunit of the oxidase.

CGD has long been considered a prime target for gene therapy. Clinical improvement should occur with replacement of a low level of oxidase activity, as CGD patients with as little as 3% normal activity show a much milder phenotype. A normal phenotype could be achieved with high-level correction of only 5-10% of phagocytes, as occurs in asymptomatic XCGD carriers with a skewed Lyon distribution of X-inactivation. As all phagocytes are bone marrow-derived, gene therapy approaches have aimed to replace the defective gene ex vivo in blood or bone marrow HSPCs, and then engraft the autologous cells in the patient. For example, one such trial, using an SFFV-based retroviral vector, showed initial correction of the CGD phenotype in 2 of 3 subjects, but gene expression was eventually diminished or silenced. Further, peripheral blood myeloid cells showed expansion of clones containing insertions at loci associated with immortalization or leukemia. All patients eventually died or underwent HSPC transplantation.

Current CGD gene therapy approaches are focused on gene replacement in CD34+ HSPCs through insertion via self-inactivating lentivirus or knock-in at a safe-harbor locus (AAVS1) via ZFNs. A current trial employs a self-inactivating lentiviral vector encoding a chimeric myeloid promoter to drive CYBB expression. However, achieving near wild-type gp91phox expression requires 8 or more integrations per cell. Because lentivirus generates insertions throughout the genome there is also danger of viral integration causing disruption or dysregulation of nearby genes.

Targeted insertion in the AAVS1 locus limits random integration, but suffers from the challenge of finding a myeloid-specific promoter that can drive high level gp91phox expression with only one integration site. Ideally, gene repair at the defective locus would harness endogenous regulatory elements to drive appropriate gene expression. As inactivating mutations in CYBB are broadly distributed throughout the coding sequence, tailoring a gene correction cassette to each patient's specific mutation is impractical.

Figure 50:
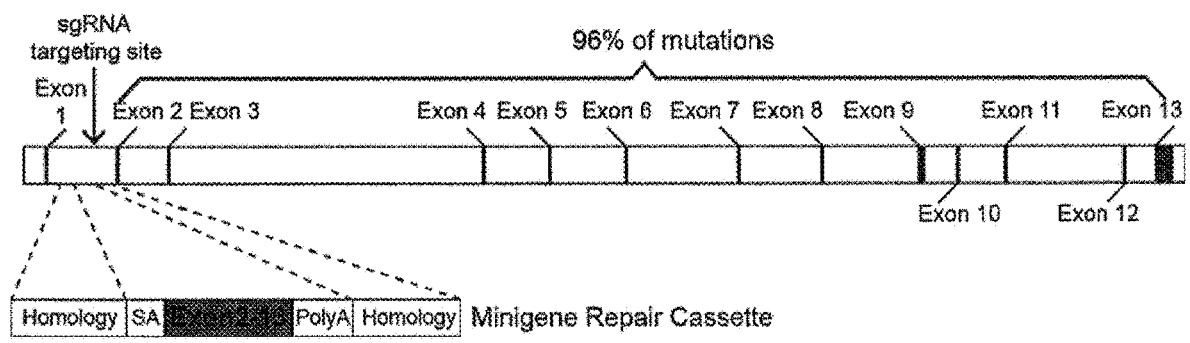
FIG. 50 presents an illustrative overview of a gene-correction strategy via minigene knock-in into an early intron of CYBB. For example, Cas9-pDBDs can be programmed to cleave intron 1 (or 2) in the context of a repair cassette that contains exons 2-13 (or 3-13) flanked by a strong splice acceptor (SA, human β-globin) and a polyA sequence (BGH polyA). These elements may be flanked by homology arms to facilitate HDR-based insertion of the repair cassette.

In one embodiment, the present invention contemplates a minigene cassette flanked by a splice acceptor and polyadenylation site, for insertion into an early intron to capture transcription from the locus and correct any downstream mutations. FIG. 50. This approach has been successfully utilized with ZFNs for factor IX gene correction. At the CYBB locus, a repair cassette introduced into intron 2 would correct 87% of previously described mutations.

To define neutral sites for repair cassette insertion, the CYBB regulatory landscape in three myeloid cell lines was analyzed using ENCODE H3K4Mel Chip-seq data and 3C analysis. These data revealed a complex regulatory landscape that extends to CYBB introns 1-3. In one embodiment, the present invention contemplates a gene correction strategy comprising high efficiency and precision, as well as a minimal impact of minigene insertion on gene expression levels, as some insertion sites may disrupt regulatory elements. For example, a $Cas9^{MT}$-pDBD nuclease may be used for correction of CYBB defects in CD34+ HSPCs from XCGD patients through a systematic optimization including, but not limited to: i) pilot experiments in XCGD-PLB-985 cells, a human myeloid cell line with a disruption in exon 3 of CYBB9; ii) optimization of gene correction in normal CD34+ HSPCs; and iii) assessment of efficacy in HSPCs from XCGD carriers. Although it is not necessary to understand the mechanism of an invention, it is believed that these preliminary data identifies improved nuclease precision and efficiency to provide a clinically effective platform for CGD gene therapy.

1. $SpCas9^{MT}$-pDBD Nuclease and Donor Constructs

Figure 51:
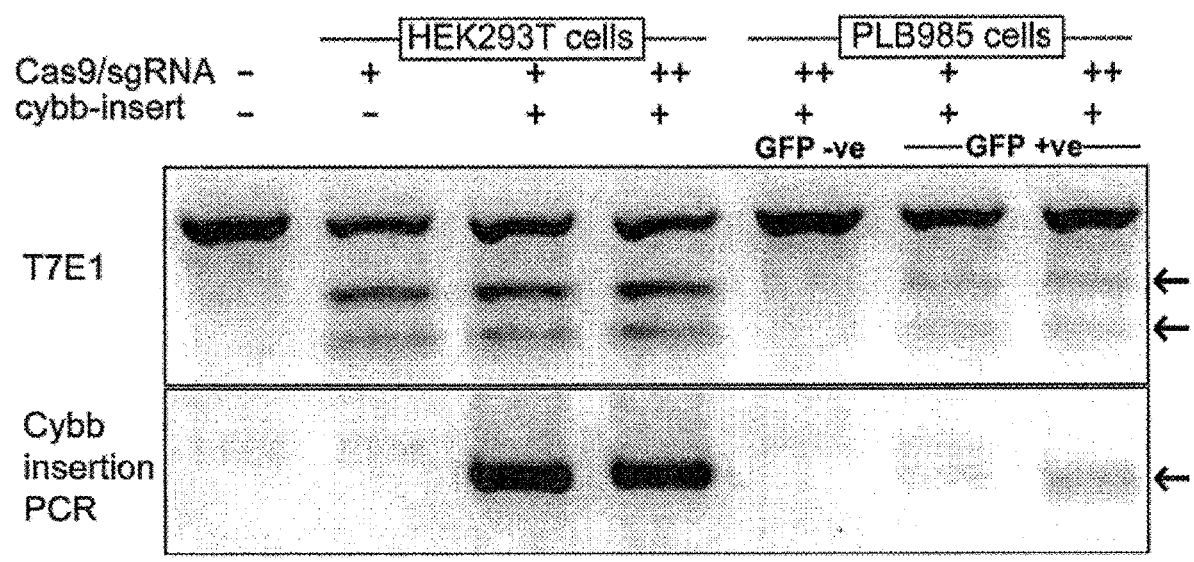
FIG. 51 presents exemplary data showing T7EI activity of SpCas9/sgRNAs in intron 2 of CYBB in HEK293T and PLB985 cells (top panel), and a PCR assay showing CYBB minigene cassette insertion by NHEJ mediated ligation (bottom panel).

In one embodiment, the present invention contemplates assessing nuclease activity and precision in HEK293T cells. Preliminary data show that CYBB introns 1 & 2 are compatible with sgRNAs having NGG PAMs and are predicted to be highly active based on the latest genome wide sgRNA analyses. These sgRNAs have few predicted off-target matches by CRISPRseek analysis and avoid potential regulatory regions identified in ENCODE data. SpCas9 nuclease activity mediated by sgRNAs of interest may be used to determine and identify active guides. FIG. 51.

In one embodiment, the present invention contemplates a construct comprising $Cas9^{MT}$-pDBDs for active sgRNAs. Nuclease activity may be confirmed by T7EI, and then GUIDE-seq followed by focused deep sequencing to determine off-target profiles. In one embodiment, active nuclease pDBDs can be tuned and precision improved to eliminate residual off-target activity. One advantage of the presently disclosed embodiments in contrast to conventional methods is the achievement of precise editing with off-target events that are undetectable by Illumina short-read sequencing. In one embodiment the construct comprises single-stranded oligonucleotide (ssODN) donors with homology arms to the target site that encode a unique restriction enzyme (RE) site within the region. HDR efficiency may be assayed by PCR amplification and RE digestion.

2. Gene Correction Efficiency

XCGD-PLB-985 cells provide a model for gene correction of CYBB due to the presence of a single defective allele. In one embodiment, nucleofection conditions are improved for XCGD-PLB-985s to maximize the rate of nuclease-based HDR insertion of the validated ssODN compared to that of indel formation (e.g., using a T7EI assay). HDR efficiency and precision level obtained for each nuclease may then be confirmed using GUIDE-seq.

XCGD-PLB-985 cells were nucleofected with SpCas9-sgRNA, a Cybb-minigene cassette, and GFP (as a marker for nucleofection) and then flow-sorted for GFP expression. GFP(+) and (−) cells were assessed for SpCas9-induced lesions by T7EI assay, and for NHEJ-mediated minigene insertion by PCR amplification of a newly-formed junction. FIG. 51. GFP(+) cells demonstrated a functional correction of a CGD phenotype, with 5 cells per 1000 showing oxidase activity as NBT dye reduction at the higher dose of SpCas9/sgRNA, 2/1000 at the lower dose, and none in GFP(−) controls. FIG. 51. This data demonstrates a CYBB gene correction with the presently disclosed minigene cassette.

Although it is not necessary to understand the mechanism of an invention, it is believed that the present methods result in dramatic improvements in rescue frequency in comparison to conventionally available assays. Alternatively, the present invention contemplates a knock-in of a human codon-optimized minigene rescue construct comprising sequence features distinct from an endogenous locus. FIG. 50. For example, improvements in precision may include, but are not limited to, parameters comprising: i) homology arm length; ii) donor DNA source, including but not limited to plasmids, minicircles, or AAVs.

Donor DNA insertion efficiency can be evaluated by qPCR, and the integrity of donor integration assessed by PacBio SMRT sequencing to define the donor cassette insertion rate and fidelity. The rate of spurious donor integration can be determined by LAM-PCR sequencing. To increase rates of HDR, alternate DNA repair pathways can be inhibited. Differentiation of XCGD-PLB-985 cells containing targeted minigene insertions into neutrophils can assess the functional effects of gene correction. The rate of splice donor capture by an integrated minigene can be determined by qRT-PCR. XCGD-PLB-985-derived neutrophils can be determined by flow cytometric assays of mAb7D5 binding for gp91phox protein expression, dihydrorhodamine (DHR) fluorescence for NADPH oxidase activity, and/or loss of microbial propidium iodide staining for microbicidal activity. Although it is not necessary to understand the mechanism of an invention, it is believed that the above embodiments are able to define minigene insertion sites that permit an efficient correction of CYBB defects in XCGD-PLB-985 cells by optimizing a splice acceptor sequence of a repair cassette for efficient gene capture. Functional assays should allow correlation with correction of the CGD phenotype.

F. Gene Correction Efficiency and Precision in CD34+ HSPCs

It is generally believed that achieving high levels of donor DNA integration via nuclease-mediated HDR is more challenging in primary HSPCs than in transformed cell lines. To overcome this disadvantage of conventional methods, due to a limited availability of XCGD patient-derived CD34+ cells, the presently disclosed nuclease-based knock-in strategy may be fine-tuned using CD34+ HSPCs from healthy male donors. It has been reported that SpCas9/sgRNA gene inactivation has been performed through the delivery of plasmid-encoded components, but efficient rates of donor DNA integration and cell viability in another study required delivery of nucleases as mRNAs.

In one embodiment, the present invention contemplates a method comparing the efficiency of gene editing and cell viability for $SpCas9^{MT}$-DBDs/sgRNA delivered by plasmid vs. mRNA/sgRNA nucleofection. For example, target site lesion rates can be assessed by T7EI assay[19], and cell viability by Annexin V and 7-Aminoactinomycin D FACS analyses. Further, the efficiency of HDR can be examined using different donor DNAs encoding the required repair cassette. Due to potential plasmid toxicity in CD34+ cells, assays may be performed in both plasmid-based, minicircle-based and/or viral DNA donors (IDLV, Adenoviral and AAV, respectively), particularly AAV6, which efficiently transduces CD34+ HSPCs and has proven to be an efficient non-integrating donor for nuclease-mediated HDR. In some embodiments, the timing of the donor and nuclease delivery can be varied to maximize the efficiency of HDR. In other embodiments, small molecules that support progenitor maintenance during expansion may be used. The precision of the nucleases and the integrity and specificity of donor integration can be assessed as described above.

XCGD-like CD34+ HSPCs have recently been created by transducing normal CD34+ cells with a Cerulean-marked lentivirus encoding shRNAs targeting CYBB transcripts. This system can be utilized to assess the efficiency of CYBB gene correction mediated by the optimal nuclease and donor DNA, with a recoded minigene that is not targeted by the shRNAs, to determine the fraction of macrophages and neutrophils differentiated from marked CD34+ cells with restored NADPH oxidase activity and function. Although it is not necessary to understand the mechanism of an invention, it is believed that with the presently disclosed improved nucleases, alternate donor DNA platforms and supporting culture conditions, are able to achieve high levels of targeted gene correction in CD34+ HSPCs, that equal or exceed the 5-10% level needed for a functional CGD cure.

G. Efficient Gene Correction in XCGD CD34+ HSPCs

In one embodiment, the present invention contemplates a nuclease-mediated CYBB correction in SCGD patient CD34+ HSPCs. In one embodiment, the nuclease comprises a minigene repair cassette having mutations. In one embodiment, improved targeted gene correction conditions (e.g., for example, nucleases, donors, cultures) that are shown to improve efficiency. In one embodiment, the method determines the fraction of functionally corrected macrophages and neutrophils differentiated from these cells.

RNA levels can also be assessed for a minigene donor cassette and the fraction of correctly spliced RNAs between the endogenous exon and the minigene cassette. In other embodiments, an in vivo engraftment potential and function of nuclease-manipulated HSPCs. Preferably, NSG-3GS mice can be evaluated, which unlike NSG mice, produce functional human phagocytes. Although it is not necessary to understand the mechanism of an invention, it is believed that the presently disclosed method achieves a frequency of appropriate RNA splicing with a repair cassette sufficient to generate gp91phox in patient-derived XCGD cells comprising endogenous locus regulatory elements.

H. Excision or Inactivation of HIV Proviral DNA in Reservoir Cells

Highly active antiretroviral therapy (HAART) has dramatically changed the prognosis for individuals infected with HIV-1. Yet, even when HIV-I viremia has been well controlled by these drugs for years, termination of HAART results in viral rebound, most likely coming from latent provirus in long-lived memory CD4$^+$ T cells. So long as latent HIV-1 provirus persists—probably for the life of the infected individual—HAART will be required. Most efforts to eradicate latent HIV-1 proviruses have focused on reactivation of proviral transcription to potentiate the elimination of cells bearing HIV-1 provirus. To date, though, such reactivation efforts have largely been unsuccessful. Alternative approaches for the effective elimination of latent HIV-1 provirus are therefore needed.

Recent advances in the development of targeted gene editing tools provide a potential method for direct inactivation or excision of latent HIV-1 provirus. Specifically, the Cas9/CRISPR programmable nuclease system, a versatile platform for the generation of targeted double-strand breaks within the genome, has been shown to excise HIV-1 provirus in cell lines. However, the activity and precision of the Cas9/CRISP system is suboptimal for clinical application. SpCas9$^{MT3}$-ZFPs have been developed that specifically target the HIV LTR with higher precision than wild-type SpCas9.

Three different SpCas9$^{MT3}$-ZFPs were generated that target different regions of the HIV LTR (T5, T6 and Z1; FIG. 107). Lesion rates of wild-type SpCas9 or SpCas9$^{MT3}$-ZFP were compared with T5, T6 and Z1 sgRNA and these nucleases have similar activity in the T7EI assay measuring nuclease-induced lesion rates (FIG. 107). The SpCas9$^{MT3}$-ZFPs have higher precision. Comparison of lesion rates at one computationally predicted off-target sites for the T5 sgRNAs with either wild-type SpCas9 or SpCas9$^{MT3}$-ZFP$^{T5}$ reveals weak activity for the wild-type nuclease but no activity for SpCas9$^{MT3}$-ZFP$^{T5}$ (FIG. 108). Further improvement of these SpCas9$^{MT3}$-ZFPs or the development of nucleases related to platforms described herein should allow the creation of an efficient, precise nuclease system for the inactivation/excision of HIV-1 provirus from reservoir cells of HIV infected individuals.

IV. Deep Sequencing Analysis of Off-Target Activity

To more broadly assess improvements in Cas9-pDBD precision, PCR products were deep sequenced spanning previously defined off-target sites for sgRNA$^{TS2/TS3/TS4:\ 14,25}$, as well as several additional genomic loci that have favorable ZFP$^{TS2/TS3/TS4}$ recognition and were predicted using CRISPRseek[21,22] to have some complementarity to the TS2/TS3/TS4 guide sequences. Nuclease activity was compared between SpCas9, SpCas9$^{MT3}$, SpCas9$^{WT}$-ZFP$^{TS2/TS3/TS4}$ and SpCas9$^{MT3}$-ZFP$^{TS2/TS3/TS4}$ at these target and off-target sites, and found that SpCas9$^{MT3}$-ZFP$^{TS2/TS3/TS4}$ dramatically increased the precision of target site cleavage. FIG. 64A. In most cases, utilizing SpCas9$^{MT3}$-ZFP$^{TS2/TS3/TS4}$ reduced lesion rates at off-target sites to background levels resulting in improvements in the Specificity Ratio of up to 150-fold. FIG. 64B. Only one off-target site (OT2-2), which has a neighboring sequence that is similar to the expected ZFP$^{TS2}$ recognition sequence and still display high lesion rates. FIG. 65. One other site (OT2-6), displays some residual activity both for SpCas9$^{MT3}$ and SpCas9$^{MT3}$-ZFP$^{TS2}$ that is above the background error rate within our sequencing data. Overall, these data demonstrate a dramatic enhancement in precision for SpCas9$^{MT}$-ZFPs relative to standard SpCas9 at previously defined active off-target sites.

V. Clinical Applications and Insights

Figure 68:
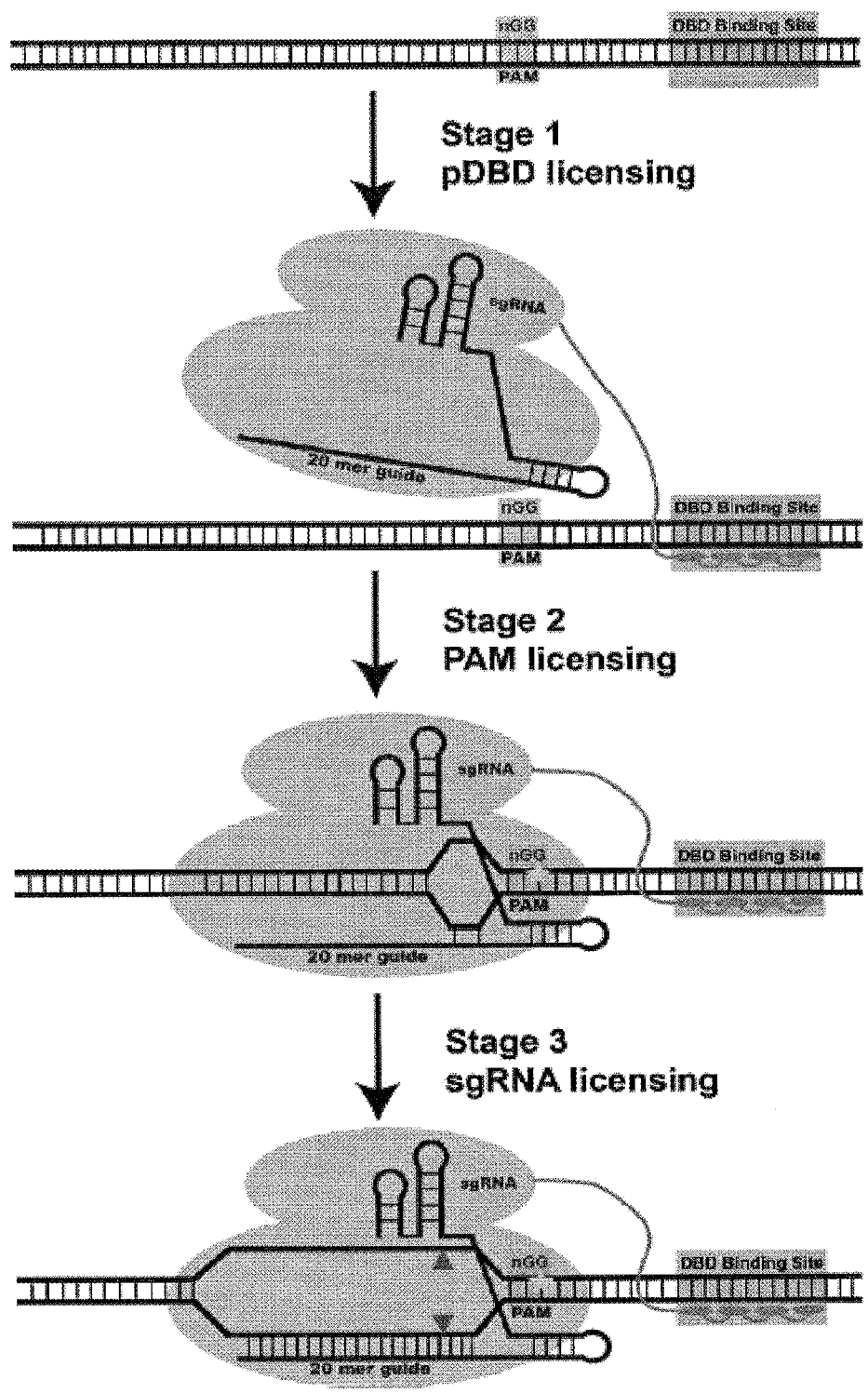
FIG. 68 provides an illustrative model of the three stages of target site licensing that may play a role in the ability of SpCas9$^{MT3}$-pDBD to cleave DNA. Due to the attenuation of SpCas9 DNA-binding affinity (mutation indicated by yellow star), the efficient engagement of a sequence for PAM recognition or guide RNA complementarity requires the presence of a neighboring DNA sequence that can be bound by the attached pDBD. This requirement for pDBD binding adds a third stage of target site licensing for efficient cleavage.

Some embodiments of the present invention encompass of the activity of SpCas9-pDBD chimeric activity that provide new insights into a mechanism of target site licensing by SpCas9 and the methods by which this mechanism can be exploited to improve precision. FIG. 68. Fusion of a pDBD to SpCas9 allows efficient utilization of a broader repertoire of PAM sequences by SpCas9, but even for SpCas9-pDBDs there remains a dichotomy between functional and inactive PAMs. The broader targeting range of SpCas9-pDBDs likely reflects the bypass of a kinetic barrier to R-loop formation that follows PAM recognition, as proposed by Seidel and colleagues[6]. pDBD tethering of SpCas9 may achieve activity at a target site containing a sub-optimal PAM by increasing the effective concentration of SpCas9 around the target site and hence, stabilizing the SpCas9-PAM interaction. For wild type SpCas9, only high affinity (nGG) PAM sites consistently have sufficient residence time to facilitate efficient progression to R-loop formation, but pDBD tethering increases the likelihood that SpCas9/sgRNA can overcome this barrier at sub-optimal PAMs. The data presented herein also support an allosteric licensing mechanism, as described by Doudna and colleagues[5], which likely restricts Cas9 nuclease activity for the majority of sequence combinations in the PAM element even with the increased local concentration afforded by pDBD tethering. The enhanced sensitivity to guide-target site heteroduplex stability observed for the presently disclosed SpCas9$^{MT3}$-ZFP$^{TS3}$ chimera further supports an interplay between PAM recognition and guide complementarity in the licensing of nuclease activity.

Mutations to the SpCas9 PAM interacting domain may introduce a third stage of licensing (pDBD site recognition) for efficient target site cleavage within the SpCas9$^{MT}$-pDBD system. The weakened interaction between mutant Cas9 and the PAM sequence now necessitates increased effective concentration for nuclease function that is achieved by the high affinity interaction of the tethered pDBD with its target site. This dramatically improves precision as assessed using targeted deep sequencing and GUIDE-seq analysis. Compared with previous GUIDE-seq analysis of TS2, TS3 and TS4 targets for SpCas9, five, three and three of the top 5 off-target sites, respectively, were found that were previously described[17]. The discrepancy between these studies could be due to our lower sequencing depth, the use of an alternate cell line, or different delivery methods. Nonetheless, the present analysis excludes the presence of a new class of highly active off-target sites that are generated by the fusion of the ZFP to Cas9. This system has advantages over other previously described Cas9 variant systems that improve precision[10,25,30]. The presently disclosed SpCas9$^{MT}$-pDBD system increases the targeting range of the nuclease by expanding the repertoire of highly active PAM sequences. This is in contrast to dimeric systems (e.g., for example, dual nickases or FokI-dCas9 nucleases) that have a more restricted targeting range due to the requirement for a pair of compatible target sequences. Moreover, the presently disclosed chimeric system may be compatible with either of these dimeric nuclease variants, providing a further potential increase in precision while also expanding the number of compatible target sites for these platforms. In addition, the affinity and the specificity of the pDBD component can also be easily tuned to achieve the desired level of nuclease activity and precision for demanding gene therapy applications.

SpCas9-ZFP's targeting TS2/TS3/TS4 were programmed with four-finger ZFPs, as it was believed that these would have an optimal balance of specificity and affinity, for example, SpCas9$^{MT3}$-ZFP$^{TS3}$. However, SpCas9$^{MT3}$-ZFP$^{TS2}$ resulted in improved precision by utilizing a three finger ZFP demonstrating pDBD flexibility. In addition to tuning a pDBD, further improvements by adjusting linker lengths and its composition should realize improvements in precision (and potentially activity) by further restricting the relative orientation and spacing of the SpCas9 and pDBD. Finally, it should be possible to generate Cas9-pDBD fusions for Cas9 orthologs from other species that have superior characteristics for gene therapy applications (e.g. more compact Type IIC Cas9 nucleases[49,50] for viral delivery). Ultimately, for gene therapy applications where precision, activity and target site location are of paramount importance, the expanded targeting range and precision achieved by the Cas9-pDBD framework provides a potent platform for the optimization of nuclease-based reagents that cleave a single target site in the human genome.

VI. Kits

In another embodiment, the present invention contemplates kits for the practice of the methods of this invention. The kits preferably include one or more containers containing a Cas9 nuclease—DNA targeting unit fusion protein to practice a method of this invention. The kit can optionally contain a Cas9 nuclease fused to a dimerization, domain and a DNA-targeting unit fused to a complementary dimerization domain. The kit can optionally include a zinc finger protein. The kit can optionally include a transcription activator-like effector protein. The kit can optionally include a homeodomain protein. The kit can optionally include a orthogonal Cas9 protein serving as the DNA targeting unit. The kit can optionally include a Cas9 fusion protein comprising a mutated PAM recognition domain. The kit can optionally include a single guide RNA molecule or gene, complementary to a specific genomic target. The kit can optionally include a second single guide RNA molecule or gene, complementary to a specific genomic target for the orthogonal Cas9 protein serving as the DNA-targeting unit. The kit can optionally include a truncated single guide RNA molecule or gene, completely complementary to a desired specific genomic target. The kit can optionally include enzymes capable of performing PCR (i.e., for example, DNA polymerase, Taq polymerase and/or restriction enzymes). The kit can optionally include a pharmaceutically acceptable excipient and/or a delivery vehicle (e.g., a liposome). The reagents may be provided suspended in the excipient and/or delivery vehicle or may be provided as a separate component which can be later combined with the excipient and/or delivery vehicle. The kit may optionally contain additional therapeutics to be co-administered with the nuclease to drive the desired type of DNA repair (e.g. Non-homologous end joining or homology directed repair). The kit may include a small molecule to drive drug-dependent dimerization of the Cas9-nuclease and the DNA targeting unit. The kit may include an exogenous donor DNA (either single stranded or duplex) that can be used as a donor for introducing tailor-made changes to the DNA sequence. The kit may include a small molecule to drive a change in subcellular localization for the Cas9 nuclease or the DNA-targeting unit to control the kinetics of its activity. The kit may include a small molecule to stabilize the Cas9 nuclease-DTU by attenuating degradation due to an attached destabilization domain.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in the editing and/or deletion of a specific genomic target. While the instructional materials typically comprise written or printed materials they are not limited to such. Any medium capable of storing such instructions and communicating them to an end user may be contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials or assistance in the design and implementation of the Cas9 nuclease—DTU for specific genomic targets.

EXPERIMENTAL

Example I

Plasmid Constructs

For Cas9-DBD experiments an sgRNA expression plasmid pLKO1-puro was used as described previously. Stewart et al., Lentivirus-delivered stable gene silencing by RNAi in primary cells. RNA. 2003 April; 9(4):493-501. SpCas9 and SpCas9-DBD fusions are expressed from pCS2-Dest gateway plasmid under chicken beta globin promoter. Villefranc et al., Gateway compatible vectors for analysis of gene function in the zebrafish. Dev Dyn. 2007 November; 236 (11):3077-87. For SSA directed nuclease activity assay, an M427 plasmid was used as previously reported. Wilson et al., Design and Development of Artificial Zinc Finger Transcription Factors and Zinc Finger Nucleases to the hTERT Locus. Mol Ther Nucleic Acids. 2013 Apr. 23; 2:e87.

Cas9-DBD target sites are cloned into SbfI digested backbone in ligation-independently. The SbfI digested M427 vector backbone may be treated with T4 DNA polymerase to recess the ends. Small double stranded oligonucleotides with flanking ends compatible to the recessed ends of vector are hybridized with the vector backbone in a thermocycler and directly transformed into bacteria.

ZFPs were assembled as gBlocks (integrated DNA Technologies) from finger modules based on previously described recognition preferences. ZFPs were cloned into a pCS2-Dest-SpCas9 plasmid backbone cloned thorough BspEI and XhoI sites.

TALEs were assembled via golden gate assembly[55] into JDS TALE plasmids[56]. Assembled TALEs were cloned into BbsI digested pCS2-Dest-SpCas9-TALEntry backbone through Ace65I and BamHI sites.

Sequences of the SpCas9-pDBDs are presented herein and these plasmids are deposited at addgene for distribution to the community. Plasmid reporter assays of nuclease activity utilized the restoration of GFP activity through SSA-mediated repair of an inactive GFP construct using the M427 plasmid[46]. SpCas9 target sites were cloned into plasmid M427 via ligation independent methods following SbfI digestion. Mutations in the PAM interacting domain of SpCas9 were generated by cassette mutagenesis.

Example II

Cell Culture and Transfection

Human Embryonic Kidney (HEK293T) cells were cultured in high glucose DMEM with 10% FBS and 1% Penicillin/Streptomycin (Gibco) at 37° C. incubator with 5% $CO_2$. For transient transfection, early to mid-passage cells (passage number 5-25) were used. Approximately $1.6 \times 10^5$ cells were transfected with 50 ng SpCas9/DBD expressing plasmid, 50 ng sgRNA expressing plasmid, 100 ng mCherry plasmid via Polyfect transfection reagent (Qiagen) in 24-well format according to manufacturer suggested protocol. For SSA-reporter assay, 150 ng M427 SSA-reporter plasmid may be also supplemented to the co-transfection mix.

Example III

Western Blot Analysis

HEK293T cells are transfected with 500 ng Cas9 and 500 ng sgRNA expressing plasmid in a 6-well plate by Lipofectamine 3000 transfection reagent (Invitrogen) according to manufacturer's suggested protocol. 48 hours after transfection, cells are harvested and lysed with 100 ul RIPA buffer. 8 μl of cell lysate is used for electrophoresis and blotting. The blots are probed with anti-HA (Sigma #H9658) and anti alpha-tubilin (Sigma #T6074) primary antibodies; then HRP conjugated anti-mouse IgG (Abeam #ab6808) and anti-rabbit IgG secondary antibodies, respectively. Visualization employed Immobilon Western Chemiluminescent HRP substrate (EMD Millipore #WBKLS0100).

Example IV

Flow Cytometry Reporter Assay 48 hours post transfection; cells were trypsinized and harvested into a microcentrifuge tube. Cells were centrifuged at 500×g for 2 minutes, washed once with 1×PBS and resuspended in 1×PBS for flow cytometry (Becton Dickonson FACScan). For FACS analysis, 10000 events are counted from each sample. To minimize effect of transfection variations among samples, first cells were gated for mCherry expression, and the percentage of EGFP expressing cells were quantified within mCherry positive cells. All the experiment replicates were performed in triplicate on different days and mean values and standard error of the mean may be calculated.

Example V

Genomic 72 hours post transfection; cells were harvested and genomic DNA was extracted via DNeasy Blood and Tissue kit (Qiagen) according to manufacturer suggested protocol. 50 ng input DNA was PCR amplified with Phusion High Fidelity DNA Polymerase (New England Biolabs): 98° C., 15 s; 67° C. 25 s; 72° C. 18 s)×30 cycles, 10 ul of a PCR product was hybridized and treated with 0.5 μl T7 Endonuclease I in 1×NEB Buffer2 for 45 minutes[57]. The samples were run on 2.5% agarose gel and quantified with ImageJ software (PMID 22930834). Indel percentages were calculated as previously described (PMID 23478401). All the experiment replicates were performed in triplicate on different days and mean values and standard error of the mean may be calculated.

Example VI

Targeted Deep-Sequencing

For each generation of each amplicon, a two-step PCR amplification approach was used to first amplify the genomic segments and then installed with barcodes and indexes.

In a first step, "locus-specific primers" were used bearing common overhangs with complementary tails to the TruSeq adaptor sequences. 50 ng input DNA was PCR amplified with Phusion High Fidelity DNA Polymerase (New England Biolabs): (98° C., 15 s; 67° C. 2.5 s; 72° C. 18 s)×30 cycles. 5 μl of each PCR reaction was gel-quantified by ImageJ against a reference ladder and equal amounts from each genomic locus PCR were pooled for each treatment group (15 different treatment groups). The pooled PCR products from each group were run on a 2% agarose gel and the DNA from the expected product size (between 100 and 200 bp) was extracted and purified via QIAquick Gel Extraction Kit (Qiagen).

In a second step, the purified pool from each treatment group was amplified with a "universal forward primer and an indexed reverse primer" to reconstitute the TruSeq adaptors. 2 ng of input DNA was PCR amplified with Phusion High Fidelity DNA Polymerase (New England Biolabs) (98° C., 15 s; 61° C., 25 s; 72° C., 18 s)×9 cycles. 5 µl of each PCR reaction was gel-quantified by ImageJ, and then equal amounts of the products from each treatment group were mixed and run on a 2% agarose gel. Full-size products (~250 bp in length) were gel-extracted and purified via QIAquick Gel Extraction Kit (Qiagen). The purified library was deep sequenced using a paired-end 150 bp Miseq run. Sequences from each genomic locus within a specific index were identified based on a perfect match to the final 11 bp of the proximal genomic primer used for locus amplification.

Insertions or deletions in a SpCas9 target region were defined based on the distance between a "prefix" sequence at the 5' end of each off-target site (typically 10 bp) and a "suffix" sequence at the 3' end of each off-target site (typically 10 bp)[59], where there were typically 33 bp between these elements in the unmodified locus.

Distances that were greater than expected were binned as "insertions (I)", and distances that were shorter were binned as "deletions (D)". Reads that did not contain the suffix sequence were marked as undefined (U). For some loci the background sequencing error rate was high. For example for OT2-1 homopolymer sequence in the guide region leads to a high error rate. All statistical analyses were performed using R, a system for statistical computation and graphics[60].

Log odd ratios of lesion were calculated for the on-target and off-target sites of each individual Cas9 treatment group vs. the untreated control for each of the three independent experiments. T-test was applied to assess whether the log odd ratio was significantly different from 0. i.e., whether there was a significant difference in lesion odds between each individual Cas9 treatment group and the untreated control for the on-target and off-target sites. Odds ratios and their 99% confidence intervals were obtained by taking exponent of the estimated log odds ratios and their 99% confidence intervals. These analyses were also applied to the sum of the lesion rates across all three replicates (combined).

To adjust for multiple comparisons, p-values were adjusted using the Benjamini-Hochberg (BH) method[61]. Only loci that have significant BH-adjusted p-values in the combined data for the treatment group relative to the control were considered significant. GUIDE-Seq off-target analysis for SpCas9-pDBDs. GUIDE-Seq was performed with some modifications to the original protocol[17]. The following primer sets were used for the positive (+) and negative (−) strands to get successful library amplification:

Nuclease_off_+_GSP1
(SEQ ID NO: 36)
GGATCTCGACGCTCTCCCTGTTTAATTGAGTTGTCATATGTTAATAAC +

Nuelease_off_-_GSP1
(SEQ ID NO: 37)
GGATCTCGACGCTCTCCCTATACCGTTATTAACATATGACA -

Nuclease_off_+_TGSP2
(SEQ ID NO: 38)
CTCTCTATGGGCAGTCGGTGATTTGAGTTGTCATATGTTAATAACGGTA +

-continued

Nuclease_off_-_GSP2
(SEQ ID NO: 39)
CCTCTCTATGGGCAGTCGGTGATACATATGACAACTCAATTAAAC -

In addition, this protocol differed from a previously published protocol[17] in the following manner: In a 24-well format, HEK293T cells were transfected with 250 ng Cas9, 150 ng sgRNA, 50 ng GFP, and 10 pmol of annealed GUIDE-Seq oligonucleotide using Lipofectamine 3000 transfection reagent (Invitrogen) according to manufacturer's suggested protocol. 48 hours post-transfection, genomic DNA was extracted via DNeasy Blood and Tissue kit (Qiagen) according to the manufacturer's suggested protocol. Library preparations were done with original adaptors according to protocols described by the Joung laboratory[17], where each library was barcoded for pooled sequencing. The barcoded, purified libraries were deep sequenced as a pool using two paired-end 150 bp MiSeq runs.

Reads containing the identical molecular index and identical starting 8 bp elements on the Read1 were pooled into one unique read. The initial 30 bp and the final 50 bp of the unique Read2 sequences were clipped for removal of the adaptor sequence and low quality sequences and then mapped to the human genome (hg19) using Bowtie[2]. Peaks containing mapped unique reads were identified using a pile-up program ESAT (garberlab.umassmed.edu/software/esat/) using a window of 25 bp with a 15 bp overlap. Neighboring windows that were on different strands of the genome and less than 50 bp apart were merged using Bioconductor package ChIPpeakAnno[62,63]. Peaks that were present with multiple different guides (hotspots[17]) or do not contain unique reads for both sense and anti-sense libraries[17] were discarded. The remaining peaks were searched for sequence elements that were complementary to the nuclease target site using CRISPRseek[21]. Only peaks that harbor a sequence with less than 7 mismatches to the target site were considered potential off-target sites. The number of reads from these regions of the sense and the anti-sense libraries were combined into the final read number.

Example VII

CRISPRseek Analysis

Human hg19 exon and promoter sequences were fetched using Bioconductor packages ChIPpeakAnno[62,63] and TxDb.*Hsapiens*.UCSC.hg19.knownGene. A subset of 16500 exons and 192 promoter sequences of 2 kb each were selected for sgRNA searching and genome-wide off target analysis was using Bioconductor package CRISPRseek[21,22] using the default settings (both nGG and nAG PAMs were allowed) except BSgenomeName=BSgenome.*Hsapiens*.UCSC.hg19, annotateExon=FALSE, outputUniqueREs=FALSE, exportAllgRNAs="fasta" and fetchSequence=FALSE.

After excluding sgRNAs with on-target or/and off-targets in the haplotype blocks, there were 124793 unique sgRNAs from exon sequences and 55687 unique gRNA from promoter sequences included in the analysis. Each guide was binned based on either the off-target site with the fewest number of mismatches to the guide sequence or the sum of the off-target scores for the top 10 off-target sites. The fraction of guides in each bin for exons or promoters was displayed as a pie chart.

Example VIII

Cas9-ZFP Fusions

In principle, Zinc Finger Protein (ZFPs) containing from three to six fingers can be designed for the construction of Cas9-ZFPs, which bind 9 bp to 18 bp target sites respectively (e.g., approximately 3 bp per finger). Based on the data presented herein with the Cas9-ZFP$^{TS2/TS3/TS4}$ system, construction of a four-finger ZFP is preferable for initial testing of Cas9-ZFPs at a particular target site.

For Cas9-ZFPs containing a 58 aa linker the target site can be 5 to 14 bp downstream of the last base pair of the PAM triplet and can be on either the Watson or the Crick strand. If longer ZFPs are desired (5 or 6 fingers), one or more TGSQKP linkers are preferable to break an array into 2 or 3 finger module sets[1]. Other modified linkers can be utilized to skip a base between pairs of zinc finger modules to achieve more favorable recognition by neighboring arrays if desired. For the commercial design of zinc fingers, Sangamo Biosciences' proprietary zinc finger module archive has a design density likely less than every 10 bp[4], combined with the flexibility of the spacing and orientation, multiple ZFPs can be designed and tested around almost any Cas9 target site. These ZFPs can be purchased from Sigma Aldrich.

In addition, a number of open-source systems have been described for selecting or assembling ZFPs. Highly specific ZFPs can be selected from randomized finger libraries using phage or bacterial selections, but this process is labor intensive and may be accessible to only few laboratories. By contrast, modular assembly[6,7,16-20] wherein pre-characterized single zinc finger modules that recognize 3-base-pair (bp) subsites are joined into arrays, rapidly yields ZFPs that bind desired target sites, and has proven to be an effective method for the creation of active Cas9-ZFPs. For modular assembly, a number of zinc finger archives have been described focusing on single-finger (1F)[5,17,19,21] and two-finger (2F) modules[6,7,16,18,22].

Using phage-based selections, Barbas lab identified 1F-modules that target 49 of the 64 triplets[11-14,17]. The Kim lab has reported 1F-modules recognizing 38 of the 64 triplets[19]. A curated archive of 1F-modules that bind 27 of 64 triplets has been published[21].

Recently, using bacterial-one-hybrid based selections Noyes lab defined zinc finger modules that can recognize each of the 64 DNA triplets allowing targeting virtually any DNA sequence[5]. In addition, two-finger archives have been published that take into account finger-finger interface and therefore can yield ZFPs with higher specificity but the targeting range of these 2F archives is more limited[6,7,16,18]. The 1F and 2F archives described herein can be used to design a ZFP roughly every 10 bp, whereas some of the other finger archives can achieve even higher design densities. With the number of finger archives now available, it is possible to design a ZFPA targeting almost every DNA sequence.

Moreover, there are a number of tools available to help users to identify the best target site and design a ZFP. A web-based tool has been designed for the identification of Cas9-ZFP target sites for which ZFPs can be designed from our zinc finger archive, mccb.umassmed.edu/Cas9-pDBD_search. This site provides a simple scoring function for the evaluation of ZFPs with higher activity based on the number of arginine-guanine contacts that are present. Tools from other laboratories are available for the construction of ZFPAs. The "Zinc Finger Tools" published by Barbas lab can identify target sites for single ZFPs and design ZFPs using their archive of 49 1F-modules[23]. scripps.edu/barbas/zfdesign/zfdesignhome.php. The young laboratory has developed a suite of tools "ZiFiT" that allows the design of ZFPAs for a particular target sequence[24]. zifit.partners.org/ZiFiT/. In addition, a zinc finger tool developed by Noyes laboratory can be used to design zinc finger arrays one finger at a time for a desired target sites[5]. zf.princeton.edu/b1h/dna.html. This tool provides multiple zinc finger(s) for every DNA triplet but does not identify the best zinc finger site in a given target sequence.

Example IX

Cas9-TALE Fusions

When designing TALE-arrays for Cas9-TALE fusion, a minimum of a 10 bp target site is preferred (excluding the 5' T) located approximately 10-14 bp downstream and on the Watson strand relative to the NGG PAM site. Alternatively, a target site may comprise a 5' T[25]. Multiple programs are available that allow design of single TAL-arrays including TALE-NT[26] (tale-nt.cac.cornell.edu/) and SAPTA TAL Targeter Tool[27].bao.rice.edu/Research/BioinformaticTools/TAL_targeter.html.

REFERENCES

1. Doudna, J. A. & Charpentier, E. Genome editing. The new frontier of genome engineering with CRISPR-Cas9. Science 346, 1258096-1258096 (2014).
2. Sander, J. D. & Joung, J. K. CRISPR-Cas systems for editing, regulating, and targeting genomes. Nature biotechnology 32, 347-355 (2014).
3. Hsu, P. D., Lander, E. S. & Zhang, F. Development and Applications of CRISPRCas9 for Genome Engineering. Cell 157, 1262-1278 (2014).
4. Jinek, M. et al. A programmable dual-RNA-guided DNA endonuclease in adaptive bacterial immunity. Science 337, 816-821 (2012).
5. Sternberg, S. H., Redding, S., Jinek, M., Greene, E. C. & Doudna, J. A. DNA interrogation by the CRISPR RNA-guided endonuclease Cas9. Nature 507, 62-67 (2014).
6. Szezelkun, M. D. et al. Direct observation of R-loop formation by single RNA guided Cas9 and Cascade effector complexes. Proceedings of the National Academy of Sciences 111, 9798-9803 (2014).
7. Anders, C., Niewoehner, O., Duerst, A. & Jinek, M. Structural basis of PAM dependent target DNA recognition by the Cas9 endonuclease. Nature 513, 569-573 (2014).
8. Jiang, F., Zhou, K., Ma, L., Gressel, S. & Doudna, J. A. STRUCTURAL BIOLOGY. A Cas9-guide RNA complex preorganized for target DNA recognition. Science 348, 1477-1481 (2015).
9. Hsu, P. D. et al. DNA targeting specificity of RNA-guided Cas9 nucleases. Nature biotechnology 31, 827-832 (2013).
10. Tsai, S. Q. et al. Dimeric CRISPR RNA-guided FokI nucleases for highly specific genome editing. Nature biotechnology 32, 569-576 (2014).
11. Zhang, Y. et al. Comparison of non-canonical PAMs for CRISPR/Cas9-mediated DNA cleavage in human cells. Sci Rep 4, 5405 (2014).
12. Gabriel, R., Kalle, von, C. & Schmidt, M. Mapping the precision of genome editing. Nature biotechnology 33, 150-152 (2015).
13. Ledford, H. CRISPR, the disruptor. Nature 522, 20-24 (2015).
14. Fu, Y. et al. High-frequency off-target mutagenesis induced by CRISPR-Cas nucleases in human cells. Nature biotechnology 31, 822-826 (2013).

15. Lin, Y. et al. CRISPR/Cas9 systems have off-target activity with insertions or deletions between target DNA and guide RNA sequences. Nucleic Acids Research 42, 7473-7485 (2014).
16. Pattanayak, V. et al. High-throughput profiling of off-target DNA cleavage reveals RNA-programmed Cas9 nuclease specificity. Nature biotechnology 31, 839-843 (2013).
17. Tsai, S. Q. et al. GUIDE-seq enables genome wide profiling of off-target cleavage by CRISPR-Cas nucleases. Nature biotechnology 33, 187-197 (2015).
18. Frock, R. L. et al. Genome-wide detection of DNA double-stranded breaks induced by engineered nucleases. Nature biotechnology 33, 179-186 (2015).
19. Kim, D. et al. Digenome-seq: genome-wide profiling of CRISPR-Cas9 off-target effects in human cells. Nature Methods 12, 237-243 (2015).
20. Wang, X. et al. Unbiased detection of off-target cleavage by CRISPR-Cas9 and TALENs using integrase-defective lentiviral vectors. Nature biotechnology (2015).
21. Zhu, L. J., Holmes, B. R., Aronin, N. & Brodsky, M. H. CRISPRseek: A Bioconductor Package to Identify Target-Specific Guide RNAs for CRISPR-Cas9 Genome-Editing Systems. PLoS ONE 9, e108424 (2014).
22. Zhu, L. J. Overview of guide RNA design tools for CRISPR-Cas9 genome editing technology. Frontiers in Biology (2015).
23. Brunet, E. et al. Chromosomal translocations induced at specified loci in human stem cells. Proceedings of the National Academy of Sciences 106, 10620-10625 (2009).
24. Lee, H. J., Kim, E. & Kim, J.-S. Targeted chromosomal deletions in human cells using zinc finger nucleases. Genome Research 20, 81-89 (2010).
25. Fu, Y., Sander, J. D., Reyon, D., Cascio, V. M. & Joung. J. K. Improving CRISPRCas nuclease specificity using truncated guide RNAs. Nature biotechnology 32, 279-284 (2014).
26. Cho, S. W. et al. Analysis of off-target effects of CRISPR/Cas-derived RNA guided endonucleases and nickases. Genome Research 24, 132-141 (2014).
27. Ran, F. A. et al. Double Nicking by RNA-Guided CRISPR Cas9 for Enhanced Genome Editing Specificity. Cell 154, 1380-1389 (2013).
28. Mali, P. et al. CAS9 transcriptional activators for target specificity screening and paired nickases for cooperative genome engineering. Nature biotechnology 31, 833-838 (2013).
29. Guilinger, J. P., Thompson, D. B. & Liu, D. R. Fusion of catalytically inactive Cas9 to FokI nuclease improves the specificity of genome modification. Nature biotechnology 32, 577-582 (2014).
30. Zetsche, B., Volz, S. E. & Zhang, F. A split-Cas9 architecture for inducible genome editing and transcription modulation. Nature biotechnology 33, 139-142 (2015).
31. Nihongaki, Y., Kawano, F., Nakajima, T. & Sato, M. Photoactivatable CRISPRCas9 for optogenetic genome editing. Nature biotechnology (2015).
32. Wright, A. V. et al. Rational design of a split-Cas9 enzyme complex. Proceedings of the National Academy of Sciences 112, 2984-2989 (2015).
33. Davis, K. M., Pattanayak, V., Thompson, D. B., Zuris, J. A. & Liu, D. R. Small molecule-triggered Cas9 protein with improved genome-editing specificity. Nat Chem Biol (2015). doi:10.1038/nchembio.1793
34. Kleinstiver, B. P. et al. Engineered CRISPR-Cas9 nucleases with altered PAM specificities. Nature (2015).
35. Kim, S., Kim, D., Cho, S. W., Kim, J. & Kim, J.-S. Highly efficient RNA-guided genome editing in human cells via delivery of purified Cas9 ribonucleoproteins. Genome Research 24, 1012-1019 (2014).
36. Ramakrishna, S. et al. Gene disruption by cell-penetrating peptide-mediated delivery of Cas9 protein and guide RNA. Genome Research 24, 1020-1027 (2014).
37. Zuris, J. A. et al. Cationic lipid-mediated delivery of proteins enables efficient protein-based genome editing in vitro and in vivo. Nature biotechnology 33, 73-80 (2015).
38. Tsai, S. Q. & Joung, J. K. What's changed with genome editing? Cell Stem Cell 15, 3-4 (2014).
39. Umov, F. D., Rebar, E. J., Holmes, M. C., Zhang, H. S. & Gregory, P. D. Genome editing with engineered zinc finger nucleases. Nat Rev Genet 11, 636-646 (2010).
40. Joung, J. K. & Sander, J. D. TALENs: a widely applicable technology for targeted genome editing. Nat. Rev. Mol. Cell Biol. 14, 49-55 (2013).
41. Persikov, A. V. et al. A systematic survey of the Cys2His2 zinc finger DNA-binding landscape. Nucleic Acids Research 43, 1965-1984 (2015).
42. Lamb, B. M., Mercer, A. C. & Barbas, C. F. Directed evolution of the TALE N terminal domain for recognition of all 5' bases. Nucleic Acids Research 41, 9779-9785 (2013).
43. Boissel, S. et al. megaTALs: as rare-cleaving nuclease architecture for therapeutic genome engineering. Nucleic Acids Research 42, 2591-2601 (2014).
44. Khalil, A. S. et al. A synthetic biology framework for programming eukaryotic transcription functions. Cell 150, 647-658 (2013).
45. Meckler, J. F. et al. Quantitative analysis of TALE-DNA interactions suggests polarity effects. Nucleic Acids Research 41, 4118-4128 (2013).
46. Wilson, K. A., Chateau, M. L. & Porteus, M. H. Design and Development of Artificial Zinc Finger Transcription Factors and Zinc Finger Nucleases to the hTERT Locus. Mol Ther Nucleic Acids 2, e87 (2013).
47. Atkinson, H. & Chalmers, R. Delivering the goods: viral and non-viral gene therapy systems and the inherent limits on cargo DNA and internal sequences. Genetica 138, 485-498 (2010).
48. Klemm, J. D. & Pabo, C. O. Oct-1 POU domain-DNA interactions: cooperative binding of isolated subdomains and effects of covalent linkage. Genes & Development 10, 27-36 (1996).
49. Chylinski, K., Makarova, K. S., Charpentier, E. & Koonin, E. V. Classification and evolution of type II CRISPR-Cas systems. Nucleic Acids Research 42, 6091-6105 (2014).
50. Hou, Z. et al. Efficient genome engineering in human pluripotent stem cells using Cas9 from *Neisseria meningitidis*. Proceedings of the National Academy of Sciences 110, 15644-15649 (2013).
51. Kearns, N. A. et al. Cas9 effector-mediated regulation of transcription and differentiation in human pluripotent stem cells. Development 141, 219-223 (2014).
52. Villefranc, J. A., Amigo, J. & Lawson, N. D. Gateway compatible vectors for analysis of gene function in the zebrafish. Dev Dyn 236, 3077-3087 (2007).
53. Gupta, A. et al. An optimized two-finger archive for ZFN-mediated gene targeting. Nature Methods 9, 588-590 (2012).
54. Zhu, C. et al. Using defined finger-finger interfaces as units of assembly for constructing zinc-finger nucleases. Nucleic Acids Research 41, 2455-2465 (2013).

55. Cermak, T. et al. Efficient design and assembly of custom TALEN and other TAL effector-based constructs for DNA targeting. Nucleic Acids Research 39, e82-e82 (2011).
56. Kok, F. O., Gupta, A., Lawson, N. D. & Wolfe, S. A. Construction and application of site-specific artificial nucleases for targeted gene editing. Methods Mol Biol 1101, 267-303 (2014).
57. Gupta, A. et al. Targeted chromosomal deletions and inversions in zebrafish. Genome Research 23, 1008-1017 (2013).
58. Schneider, C. A., Rasband, W. S. &. Eliceiri, K. W. NIH Image to ImageJ: 25 years of image analysis. Nature Methods 9, 671-675 (2012).
59. Gupta, A., Meng, X., Zhu, L. J., Lawson, N. D. & Wolfe, S. A. Zinc finger protein dependent and -independent contributions to the in vivo off-target activity of zinc finger nucleases. Nucleic Acids Research 39, 381-392 (2011).
60. Ihaka, R. & Gentleman, R. R: A Language for Data Analysis and Graphics. Journal of Computational and Graphical Statistics 5, 299-314 (1996).
61. Benjamini, Y. & Hochberg, Y. Controlling the false discovery rate: a practical and powerful approach to multiple testing. Journal of the Royal Statistical Society Series B 57, 289-300 (1995).
62. Zhu, L. J. et al. ChIPpeakAnno: a Bioconductor package to annotate ChIP-seq and ChIP-chip data. BMC Bioinformatics 11, 237 (2010).
63. Zhu, L. J. in Methods in Molecular Biology (eds. Lee, T.-L. & Shui Luk, A. C.) 1067, 105-124 (Humana Press, 2013).

SUPPLEMENTARY REFERENCES

Li, H. et al. In vivo genome editing restores haemostasis in a mouse model of haemophilia. Nature 475, 217-221 (2011)
Yusa, K. et al. Targeted gene correction of α1-antitrypsin deficiency in induced pluripotent stem cells. Nature 478, 391-394 (2011).
Mahiny, A. J. et al. In vivo genome editing using nuclease-encoding mRNA corrects SP-B deficiency. Nature biotechnology (2015).
Gupta, R. M. & Musunuru, K. Expanding the genetic editing tool kit: ZFNs, TALENs, and CRISPR-Cas9, J Clin Invest 124, 4154-4161 (2014).
Persikov, A. V. et al. A systematic survey of the Cys2His2 zinc finger DNA binding landscape. Nucleic Acids Research 43, 1965-1984 (2015).
Zhu, C. et al. Using defined finger-finger interfaces as units of assembly for constructing zinc-finger nucleases. Nucleic Acids Research 41, 2455-2465 (2013).
Gupta, A. et al. An optimized two-finger archive for ZFN-mediated gene targeting. Nature Methods 9, 588-590 (2012).
Maeder, M. L., Thibodeau-Beganny, S., Sander, J. D., Voytas, D. F. & Joung, J. K. Oligomerized pool engineering (OPEN): an 'open-source' protocol for making customized zinc-finger arrays. Nat Protoc 4, 1471-1501 (2009).
Maeder, M. et al. Rapid '"Open-Source"' Engineering of Customized Zinc-Finger Nucleases for Highly Efficient Gene Modification. Molecular Cell 31, 294-301 (2008).
Meng, X., Noyes, M. B., Zhu, L. J., Lawson, N. D. & Wolfe, S. A. Targeted gene inactivation in zebrafish using engineered zinc-finger nucleases. Nature biotechnology 26, 695-701 (2008).
Dreier, B. et al. Development of zinc finger domains for recognition of the 5'-CNN-3' family DNA sequences and their use in the construction of artificial transcription factors. J Biol Chem 280, 35588-35597 (2005).
Dreier, B., Beerli, R., Segal, D., Flippin, J. & Barbas, C. Development of zinc finger domains for recognition of the 5'-ANN-3' family of DNA sequences and their use in the construction of artificial transcription factors. Journal of Biological Chemistry 276, 29466 (2001).
Dreier, B., Segal, D. J. & Barbas, C. F. Insights into the molecular recognition of the 5'-GNN-3' family of DNA sequences by zinc finger domains. J Mol Biol 303, 489-502 (2000).
Segal, D. J., Dreier, B., Beerli, R. R. & Barbas, C. F. Toward controlling gene expression at will: selection and design of zinc finger domains recognizing each of the 5'-GNN-3' DNA target sequences. Proc Natl Acad Sci USA 96, 2758-2763 (1999).
Greisman, H. A. & Pabo, C. O. A general strategy for selecting high-affinity zinc finger proteins for diverse DNA target sites. Science 275, 657-661 (1997).
Sander, J. D. et al. Selection-free zinc-finger-nuclease engineering by context-dependent assembly (CoDA). Nature Methods 8, 67-69 (2011).
Carroll, D., Morton, J. J., Beumer, K. J. & Segal, D. J. Design, construction and in vitro testing of zinc finger nucleases. Nat Protoc 1, 1329-1341 (2006).
Kim, S., Lee, M. J., Kim, H., Kang, M. & Kim, J.-S. Preassembled zinc finger arrays for rapid construction of ZFNs. Nature Methods 8, 7 (2011).
Kim, H. J., Lee, H. J., Kim, H., Cho, S. W. & Kim, J. S. Targeted genome editing in human cells with zinc finger nucleases constructed via modular assembly. Genome Research 19, 1279-1288 (2009).
Bhakta, M. S. et al. Highly active zinc-finger nucleases by extended modular assembly. Genome Research 23, 530-538 (2013).
Zhu, C. et al. Evaluation and application of modularly assembled zinc finger nucleases in zebrafish. Development 138, 4555-4564 (2011).
Doyon, Y. et al. Heritable targeted gene disruption in zebrafish using designed zinc-finger nucleases. Nature biotechnology 26, 702-708 (2008).
Mandell, J. G. & Barbas, C. F. Zinc Finger Tools: custom DNA-binding domains for transcription factors and nucleases. Nucleic Acids Research 34, W516-W523 (2006).
Sander, J. D. et al. ZiFiT (Zinc Finger Targeter): an updated zinc finger engineering tool. Nucleic Acids Research 38, W462-W468 (2010).
Miller, J. C. et al. Improved specificity of TALE-based genome editing using an expanded RVD repertoire. Nature Methods (2015).
Doyle, E. L. et al. TAL Effector-Nucleotide Targeter (TALE-NT) 2.0: tools for TAL effector design and target prediction. Nucleic Acids Research 40, W117-22 (2012).
Lin, Y. et al. SAPTA: a new design tool for improving TALE nuclease activity. Nucleic Acids Research gkt1363 (2014).
Zhu, L. J., Holmes, B. R., Aronin, N. & Brodsky, M. H. CRISPRseek: A Bioconductor Package to Identify Target-Specific Guide RNAs for CRISPRCas9 Genome-Editing Systems. PLoS ONE 9, e108424 (2014).
Lin, Y. et al. CRISPR/Cas9 systems have off-target activity with insertions or deletions between target DNA and guide RNA sequences. Nucleic Acids Research 42, 7473-7485 (2014).

Anders, C., Niewoehner, O., Duerst, A. & Jinek, M. Structural basis of PAM-dependent target DNA recognition by the Cas9 endonuclease. Nature 513, 569-573 (2014).

Elrod-Erickson, M., Rould, M. A., Nekludova, L. & Pabo, C. O. Zif268 protein-DNA complex refined at 1.6 A: a model system for understanding zinc finger-DNA interactions. Structure 4, 1171-1180 (1996).

Lu, X.-J. & Olson, W. K. 3DNA: a versatile, integrated software system for the analysis, rebuilding and visualization of three-dimensional nucleic-acid structures. Nat Protoc 3, 1213-1227 (2008).

Wilson, K. A., Chateau, M. L. & Porteus, M. H. Design and Development of Artificial Zinc Finger Transcription Factors and Zinc Finger Nucleases to the hTERT Locus. Mol Ther Nucleic Acids 2, e87 (2013).

Fu, Y., Sander, J. D., Reyon, D., Cascio, V. M. & Joung, J. K. Improving CRISPR-Cas nuclease specificity using truncated guide RNAs. Nature biotechnology 32, 279-284 (2014).

Gupta, A. et al. An improved predictive recognition model for Cys(2)-His(2)zinc finger proteins. Nucleic Acids Research 42, 4800-4812 (2014).

We claim:

1. A fusion protein comprising a first Cas9 nuclease, said first nuclease comprising a protospacer adjacent motif recognition domain having a lysine-substituted, alanine-substituted or serine-substituted arginine residue and a second Cas9 nuclease.

2. The fusion protein of claim 1, wherein said first and second Cas9 nucleases are selected from the group consisting of *Streptococcus pyogenes* Cas9 (SpCas9), *Staphylococcus aureus* Cas9 (SaCas9), *Neisseria meningitidis* Cas9 (NmCas9) and *Actinomyces naeslundii* Cas9 (AnCas9).

3. The fusion protein of claim 1, wherein said substituted arginine protospacer adjacent motif (PAM) recognition residue participates in a base-specific binding or contacts a phosphodiester backbone.

4. The fusion protein of claim 3, wherein said substituted arginine PAM recognition residue participates in a base-specific binding.

5. The fusion protein of claim 3, wherein said substituted arginine PAM recognition residue contacts a phosphodiester backbone residue.

6. The fusion protein of claim 4, wherein the first Cas9 nuclease has a single point mutation.

7. The fusion protein of claim 5, wherein the first Cas9 nuclease has a double mutation.

8. The fusion protein of claim 1, wherein said first Cas9 nuclease is selected from the group consisting of $SpCas9^{R1333K}$, $SpCas9^{R1333S}$, $SpCas9R^{1335K}$, $NmCas9^{R1025A}$ and $NmCas9^{K1013A/R1025A}$.

9. The fusion protein of claim 1, wherein said second Cas9 nuclease is selected from the group consisting of a Cas9 nickase and a nuclease-dead Cas9 (dCas9).

10. The fusion protein of claim 1, wherein said second Cas9 nuclease is selected from the group consisting of nuclease-dead NmCas9 (NmdCas9), NmCas9 nuclease, NmCas9 HNH nickase, and NmCas9 RuvC nickase.

11. The fusion protein of claim 1, wherein said first and second Cas9 nucleases are bound to a guide RNA comprising a guide sequence element.

12. The fusion protein of claim 11, wherein said guide sequence element is truncated.

13. The fusion protein of claim 12, wherein said truncated guide sequence element is less than twenty nucleotides.

* * * * *

SEQUENCE LISTING

```
<160> NUMBER OF SEQ ID NOS: 153

<210> SEQ ID NO 1
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 1 nnnngatt                                                                  8

<210> SEQ ID NO 2
<211> LENGTH: 4
<212> TYPE: DNA
<213> ORGANISM: Artificial sequence
<220> FEATURE:
<223> OTHER INFORMATION: Synthetic

<400> SEQUENCE: 2 aatc                                                                      4

<210> SEQ ID NO 3
<211> LENGTH: 9
<212> TYPE: DNA
<213> ORGANISM: Artificial sequence
<220> FEATURE:
<223> OTHER INFORMATION: Synthetic

<400> SEQUENCE: 3 gcgtgggcg                                                                 9

<210> SEQ ID NO 4
<211> LENGTH: 12
<212> TYPE: DNA
<213> ORGANISM: Artificial sequence
<220> FEATURE:
<223> OTHER INFORMATION: Synthetic

<400> SEQUENCE: 4
gcgggcaggg gc                                                            12

<210> SEQ ID NO 5
<211> LENGTH: 12
<212> TYPE: DNA
<213> ORGANISM: Artificial sequence
<220> FEATURE:
<223> OTHER INFORMATION: Synthetic

<400> SEQUENCE: 5
```
gcaggggccg ga                                                              12

<210> SEQ ID NO 6
<211> LENGTH: 12
<212> TYPE: DNA
<213> ORGANISM: Artificial sequence
<220> FEATURE:
<223> OTHER INFORMATION: Synthetic

<400> SEQUENCE: 6
ggcgttggag cg                                                              12

<210> SEQ ID NO 7
<211> LENGTH: 12
<212> TYPE: DNA
<213> ORGANISM: Artificial sequence
<220> FEATURE:
<223> OTHER INFORMATION: Synthetic

<400> SEQUENCE: 7
ccggttgatg tg                                                              12

<210> SEQ ID NO 8
<211> LENGTH: 9
<212> TYPE: DNA
<213> ORGANISM: Artificial sequence
<220> FEATURE:
<223> OTHER INFORMATION: Synthetic

<400> SEQUENCE: 8 gcgtgggcg                                                                   9

<210> SEQ ID NO 9
<211> LENGTH: 12
<212> TYPE: DNA
<213> ORGANISM: Artificial sequence
<220> FEATURE:
<223> OTHER INFORMATION: Synthetic

<400> SEQUENCE: 9
gaaacgggat cg                                                              12

<210> SEQ ID NO 10
<211> LENGTH: 15
<212> TYPE: DNA
<213> ORGANISM: Artificial sequence
<220> FEATURE:
<223> OTHER INFORMATION: Synthetic

<400> SEQUENCE: 10
acacagtacc tggca                                                           15

<210> SEQ ID NO 11
<211> LENGTH: 12
<212> TYPE: DNA
<213> ORGANISM: Artificial sequence
<220> FEATURE:
<223> OTHER INFORMATION: Synthetic

<400> SEQUENCE: 11
gaaaagtatc aa                                                              12

<210> SEQ ID NO 12
<211> LENGTH: 10
<212> TYPE: DNA
<213> ORGANISM: Artificial sequence

```
<220> FEATURE:
<223> OTHER INFORMATION: Synthetic

<400> SEQUENCE: 12
tgcgtgggcg                                                                 10

<210> SEQ ID NO 13
<211> LENGTH: 11
<212> TYPE: DNA
<213> ORGANISM: Artificial sequence
<220> FEATURE:
<223> OTHER INFORMATION: Synthetic

<400> SEQUENCE: 13
ttggagcggg g                                                               11

<210> SEQ ID NO 14
<211> LENGTH: 17
<212> TYPE: DNA
<213> ORGANISM: Artificial sequence
<220> FEATURE:
<223> OTHER INFORMATION: Synthetic

<400> SEQUENCE: 14
ttggagcggg gagaagg                                                         17

<210> SEQ ID NO 15
<211> LENGTH: 11
<212> TYPE: DNA
<213> ORGANISM: Artificial sequence
<220> FEATURE:
<223> OTHER INFORMATION: Synthetic

<400> SEQUENCE: 15
tcaaccggtg g                                                               11

<210> SEQ ID NO 16
<211> LENGTH: 17
<212> TYPE: DNA
<213> ORGANISM: Artificial sequence
<220> FEATURE:
<223> OTHER INFORMATION: Synthetic

<400> SEQUENCE: 16
tcaaccggtg gcgcatt                                                         17

<210> SEQ ID NO 17
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(6)
<223> OTHER INFORMATION: The residue in this position can be either A, C
      or T

<400> SEQUENCE: 17 nnnngntt                                                                   8

<210> SEQ ID NO 18
<211> LENGTH: 8
```

```
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 18 nnnngtct                                                                   8

<210> SEQ ID NO 19
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 19 nnnngaca                                                                   8

<210> SEQ ID NO 20
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 20 nnnngctt                                                                   8

<210> SEQ ID NO 21
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 21 nnnngttt                                                                   8

<210> SEQ ID NO 22
<211> LENGTH: 8
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 22 nnnngaat                                                                   8

<210> SEQ ID NO 23
```

```
<211> LENGTH: 20
<212> TYPE: DNA
<213> ORGANISM: Artificial sequence
<220> FEATURE:
<223> OTHER INFORMATION: Synthetic

<400> SEQUENCE: 23
ggtgagtgag tgtgtgcgtg                                              20

<210> SEQ ID NO 24
<211> LENGTH: 21
<212> TYPE: DNA
<213> ORGANISM: Artificial sequence
<220> FEATURE:
<223> OTHER INFORMATION: Synthetic

<400> SEQUENCE: 24
gcctgagtga gtgtgtgcgt g                                            21

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
ggcaagtgag tgtgtgcgtg                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic

<400> SEQUENCE: 26
ggtgcttgag tgtgtgcgtg                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
ggtgaggaag tgtgtgcgtg                                              20

<210> SEQ ID NO 28
<211> LENGTH: 20
<212> TYPE: DNA
<213> ORGANISM: Artificial sequence
<220> FEATURE:
<223> OTHER INFORMATION: Synthetic

<400> SEQUENCE: 28
ggtgagtgct tgtgtgcgtg                                              20

<210> SEQ ID NO 29
<211> LENGTH: 20
<212> TYPE: DNA
<213> ORGANISM: Artificial sequence
<220> FEATURE:
<223> OTHER INFORMATION: Synthetic

<400> SEQUENCE: 29
```

```
ggtgagtgag catgtgcgtg                                          20

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
ggtgagtgag tgcatgcgtg                                          20

<210> SEQ ID NO 31
<211> LENGTH: 20
<212> TYPE: DNA
<213> ORGANISM: Artificial sequence
<220> FEATURE:
<223> OTHER INFORMATION: Synthetic

<400> SEQUENCE: 31
ggtgagtgag tgtggtcgtg                                          20

<210> SEQ ID NO 32
<211> LENGTH: 20
<212> TYPE: DNA
<213> ORGANISM: Artificial sequence
<220> FEATURE:
<223> OTHER INFORMATION: Synthetic

<400> SEQUENCE: 32
ggtgagtgag tgtgtgtatg                                          20

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
ggtgagtgag tgtgtgcgca                                          20

<210> SEQ ID NO 34
<211> LENGTH: 5
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: misc_feature
<222> LOCATION: (4)..(4)
<223> OTHER INFORMATION: wherein n = A or G
<220> FEATURE:
<221> NAME/KEY: misc_feature
<222> LOCATION: (5)..(5)
<223> OTHER INFORMATION: wherein n = A or G

<400> SEQUENCE: 34 nngnn                                                           5

<210> SEQ ID NO 35
<211> LENGTH: 5
<212> TYPE: DNA
```

<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: misc_feature
<222> LOCATION: (3)..(3)
<223> OTHER INFORMATION: The residue in this position could be either A, C or T.
<220> FEATURE:
<221> NAME/KEY: misc_feature
<222> LOCATION: (4)..(4)
<223> OTHER INFORMATION: The residue in this position could be either A or G.
<220> FEATURE:
<221> NAME/KEY: misc_feature
<222> LOCATION: (5)..(5)
<223> OTHER INFORMATION: The residue in this position could be either A or G.

<400> SEQUENCE: 35 nnnnn                                                              5

<210> SEQ ID NO 36
<211> LENGTH: 48
<212> TYPE: DNA
<213> ORGANISM: Artificial sequence
<220> FEATURE:
<223> OTHER INFORMATION: Synthetic

<400> SEQUENCE: 36
ggatctcgac gctctccctg tttaattgag ttgtcatatg ttaataac              48

<210> SEQ ID NO 37
<211> LENGTH: 41
<212> TYPE: DNA
<213> ORGANISM: Artificial sequence
<220> FEATURE:
<223> OTHER INFORMATION: Synthetic

<400> SEQUENCE: 37
ggatctcgac gctctcccta taccgttatt aacatatgac a                     41

<210> SEQ ID NO 38
<211> LENGTH: 49
<212> TYPE: DNA
<213> ORGANISM: Artificial sequence
<220> FEATURE:
<223> OTHER INFORMATION: Synthetic

<400> SEQUENCE: 38
ctctctatgg gcagtcggtg atttgagttg tcatatgtta ataacggta             49

<210> SEQ ID NO 39
<211> LENGTH: 45
<212> TYPE: DNA
<213> ORGANISM: Artificial sequence
<220> FEATURE:
<223> OTHER INFORMATION: Synthetic

<400> SEQUENCE: 39
cctctctatg ggcagtcggt gatacatatg acaactcaat taaac                 45

<210> SEQ ID NO 40
<211> LENGTH: 43
<212> TYPE: DNA

```
<213> ORGANISM: Artificial sequence
<220> FEATURE:
<223> OTHER INFORMATION: Synthetic

<400> SEQUENCE: 40
gggcccaacc tagggcatgg aggcggctgc tggtgcgtgg gcg                    43

<210> SEQ ID NO 41
<211> LENGTH: 43
<212> TYPE: DNA
<213> ORGANISM: Artificial sequence
<220> FEATURE:
<223> OTHER INFORMATION: Synthetic

<400> SEQUENCE: 41
gcatgggtga tgtcaatgcc aaggccagtc aggtgcgtgg gcg                    43

<210> SEQ ID NO 42
<211> LENGTH: 43
<212> TYPE: DNA
<213> ORGANISM: Artificial sequence
<220> FEATURE:
<223> OTHER INFORMATION: Synthetic

<400> SEQUENCE: 42
cctggaccca acgccccagg agaagagcga aggtgcgtgg gcg                    43

<210> SEQ ID NO 43
<211> LENGTH: 43
<212> TYPE: DNA
<213> ORGANISM: Artificial sequence
<220> FEATURE:
<223> OTHER INFORMATION: Synthetic

<400> SEQUENCE: 43
gctggcggaa gacagagtgc tgctattcac ctctgcgtgg gcg                    43

<210> SEQ ID NO 44
<211> LENGTH: 36
<212> TYPE: DNA
<213> ORGANISM: Artificial sequence
<220> FEATURE:
<223> OTHER INFORMATION: Synthetic

<400> SEQUENCE: 44
ttcgacacca ccatagacag aaagcggtac acctct                            36

<210> SEQ ID NO 45
<211> LENGTH: 36
<212> TYPE: DNA
<213> ORGANISM: Artificial sequence
<220> FEATURE:
<223> OTHER INFORMATION: Synthetic

<400> SEQUENCE: 45
ttcgacacca ccatagacaa aaagcggtac acctct                            36

<210> SEQ ID NO 46
<211> LENGTH: 36
<212> TYPE: DNA
<213> ORGANISM: Artificial sequence
<220> FEATURE:
<223> OTHER INFORMATION: Synthetic

<400> SEQUENCE: 46
ttcgacacca ccatagacag caagcggtac acctct                            36
```

<210> SEQ ID NO 47
<211> LENGTH: 36
<212> TYPE: DNA
<213> ORGANISM: Artificial sequence
<220> FEATURE:
<223> OTHER INFORMATION: Synthetic

<400> SEQUENCE: 47
ttcgacacca ccatagacag aaagaagtac acctct         36

<210> SEQ ID NO 48
<211> LENGTH: 36
<212> TYPE: DNA
<213> ORGANISM: Artificial sequence
<220> FEATURE:
<223> OTHER INFORMATION: Synthetic

<400> SEQUENCE: 48
ttcgacacca ccatagacag aaagagctac acctct         36

<210> SEQ ID NO 49
<211> LENGTH: 48
<212> TYPE: DNA
<213> ORGANISM: Artificial sequence
<220> FEATURE:
<223> OTHER INFORMATION: Synthetic

<400> SEQUENCE: 49
gtgggtgagt gagtgtgtgc gtgtggggtt gagggcgttg gagcgggg         48

<210> SEQ ID NO 50
<211> LENGTH: 53
<212> TYPE: DNA
<213> ORGANISM: Artificial sequence
<220> FEATURE:
<223> OTHER INFORMATION: Synthetic

<400> SEQUENCE: 50
cccgaccccc tccaccccgc ctccgggcgc gggctccggc ccctgcccgc ggc         53

<210> SEQ ID NO 51
<211> LENGTH: 48
<212> TYPE: DNA
<213> ORGANISM: Artificial sequence
<220> FEATURE:
<223> OTHER INFORMATION: Synthetic

<400> SEQUENCE: 51
cctgagtccg agcagaagaa gaagggctcc catcacatca accggtgg         48

<210> SEQ ID NO 52
<211> LENGTH: 28
<212> TYPE: PRT
<213> ORGANISM: Neisseria meningitidis

<400> SEQUENCE: 52

Lys Lys Ala Arg Met Phe Gly Tyr Phe Ala Ser Cys His Arg Gly Thr
1               5                   10                  15

Gly Asn Ile Asn Ile Lys Ile Asn Asp Leu Asp Asn
            20                  25

<210> SEQ ID NO 53
<211> LENGTH: 28
<212> TYPE: PRT

```
<213> ORGANISM: Pasteurella multocida

<400> SEQUENCE: 53

Lys Lys Glu Tyr Phe Phe Gly Tyr Tyr Ile Gly Leu Asp Arg Ala Thr
1               5                   10                  15

Gly Asn Ile Ser Leu Lys Glu His Asp Gly Glu Ile
            20                  25

<210> SEQ ID NO 54
<211> LENGTH: 28
<212> TYPE: PRT
<213> ORGANISM: Haemophilus parainfluenzae

<400> SEQUENCE: 54

Lys Lys Lys Thr Ile Leu Gly Tyr Phe Asn Gly Leu Asn Arg Ala Thr
1               5                   10                  15

Gly Asn Ile Asp Ile Lys Glu His Asp Leu Asp Lys
            20                  25

<210> SEQ ID NO 55
<211> LENGTH: 28
<212> TYPE: PRT
<213> ORGANISM: Actinobacillus minor

<400> SEQUENCE: 55

Lys Lys Lys Thr Ile Phe Gly Tyr Phe Asn Gly Leu Asn Arg Ala Thr
1               5                   10                  15

Ser Asn Ile Asn Ile Lys Glu His Asp Leu Asp Lys
            20                  25

<210> SEQ ID NO 56
<211> LENGTH: 28
<212> TYPE: PRT
<213> ORGANISM: Neisseria lactamica

<400> SEQUENCE: 56

Lys Lys Asn Glu Phe Leu Gly Tyr Gly Val Ser Leu Asn Arg Ala Thr
1               5                   10                  15

Gly Ala Ile Asp Ile Arg Thr His Asp Thr Asp Ser
            20                  25

<210> SEQ ID NO 57
<211> LENGTH: 28
<212> TYPE: PRT
<213> ORGANISM: Actinobacillus suis

<400> SEQUENCE: 57

Lys Lys Glu Glu Phe Phe Gly Tyr Tyr Gly Gly Leu Asp Arg Ala Thr
1               5                   10                  15

Gly Ala Ile Val Ile Lys Glu His Asp Leu Glu Lys
            20                  25

<210> SEQ ID NO 58
<211> LENGTH: 28
<212> TYPE: PRT
<213> ORGANISM: Kingella kingae

<400> SEQUENCE: 58

Lys Lys Gly Cys Ile Met Gly Tyr Phe Ala Ser Leu Asp Arg Ala Thr
1               5                   10                  15

Gly Ala Ile Thr Ile Arg Glu His Asp Arg Asp Lys
            20                  25
```

<210> SEQ ID NO 59
<211> LENGTH: 28
<212> TYPE: PRT
<213> ORGANISM: Mannheimia varigena

<400> SEQUENCE: 59

Lys Lys Glu Thr Phe Phe Gly Tyr Tyr Asn Gly Leu Asp Arg Ala Thr
1               5                   10                  15

Gly Ala Ile Asn Leu Lys Glu Pro Asp Ser Asn Ile
            20                  25

<210> SEQ ID NO 60
<211> LENGTH: 28
<212> TYPE: PRT
<213> ORGANISM: Simonsiella muelleri

<400> SEQUENCE: 60

Asn Lys Gly Arg Ile Phe Gly Tyr Tyr Asn Gly Leu Asp Arg Ala Asn
1               5                   10                  15

Gly Ser Ile Gly Ile Arg Glu His Asp Leu Glu Lys
            20                  25

<210> SEQ ID NO 61
<211> LENGTH: 28
<212> TYPE: PRT
<213> ORGANISM: Neisseria bacilliformis

<400> SEQUENCE: 61

Lys Lys Asp Lys Phe Phe Gly Tyr Tyr Ser Gly Phe Asn Arg Ala Thr
1               5                   10                  15

Gly Ala Ile Asn Ile Lys Glu His Asp Leu Ser Lys
            20                  25

<210> SEQ ID NO 62
<211> LENGTH: 160
<212> TYPE: DNA
<213> ORGANISM: Streptococcus pyogenes

<400> SEQUENCE: 62
ggcgcgcctg cagccttcaa gtacttcgac accaccatag acagaaagcg gtacacctct    60
acaaaggagg tcctggacgc cacactgatt catcagtcaa ttacggggct ctatgaaaca   120
agaatcgacc tctctcagct cggtggagac ggcaccggcg                         160

<210> SEQ ID NO 63
<211> LENGTH: 160
<212> TYPE: DNA
<213> ORGANISM: Artificial sequence
<220> FEATURE:
<223> OTHER INFORMATION: Synthetic

<400> SEQUENCE: 63
ggcgcgcctg cagccttcaa gtacttcgac accaccatag acaaaaagcg gtacacctct    60
acaaaggagg tcctggacgc cacactgatt catcagtcaa ttacggggct ctatgaaaca   120
agaatcgacc tctctcagct cggtggagac ggcaccggcg                         160

<210> SEQ ID NO 64
<211> LENGTH: 160
<212> TYPE: DNA
<213> ORGANISM: Artificial sequence
<220> FEATURE:

<223> OTHER INFORMATION: Synthetic

<400> SEQUENCE: 64

| ggcgcgcctg cagccttcaa gtacttcgac accaccatag acagcaagcg gtacacctct | 60 |
| acaaaggagg tcctggacgc cacactgatt catcagtcaa ttacggggct ctatgaaaca | 120 |
| agaatcgacc tctctcagct cggtggagac ggcaccggcg | 160 |

<210> SEQ ID NO 65
<211> LENGTH: 160
<212> TYPE: DNA
<213> ORGANISM: Artificial sequence
<220> FEATURE:
<223> OTHER INFORMATION: Synthetic

<400> SEQUENCE: 65

| ggcgcgcctg cagccttcaa gtacttcgac accaccatag acagaaagaa gtacacctct | 60 |
| acaaaggagg tcctggacgc cacactgatt catcagtcaa ttacggggct ctatgaaaca | 120 |
| agaatcgacc tctctcagct cggtggagac ggcaccggcg | 160 |

<210> SEQ ID NO 66
<211> LENGTH: 160
<212> TYPE: DNA
<213> ORGANISM: Artificial sequence
<220> FEATURE:
<223> OTHER INFORMATION: Synthetic

<400> SEQUENCE: 66

| ggcgcgcctg cagccttcaa gtacttcgac accaccatag acagaaagag ctacacctct | 60 |
| acaaaggagg tcctggacgc cacactgatt catcagtcaa ttacggggct ctatgaaaca | 120 |
| agaatcgacc tctctcagct cggtggagac ggcaccggcg | 160 |

<210> SEQ ID NO 67
<211> LENGTH: 8729
<212> TYPE: DNA
<213> ORGANISM: Artificial sequence
<220> FEATURE:
<223> OTHER INFORMATION: Synthetic

<400> SEQUENCE: 67

| accgccattc tgcctgggga cgtcggagca agcttgattt aggtgacact atagaataca | 60 |
| agctacttgt tctttttgca ggatcccatc gattcgaatt caaggatcaa caagtttgta | 120 |
| caaaaaagca ggctggcgcc accatggaca gaagtactc cattgggctc gatatcggta | 180 |
| ccaacagcgt cggctgggcc gtcattacgg acgagtacaa ggtgccgagc aaaaaattca | 240 |
| aagttctggg caataccgat cgccacagca taaagaagaa cctcattgga gccctcctgt | 300 |
| tcgactccgg ggagacggcc gaagccacgc ggctcaaaag aacagcacgg cgcagatata | 360 |
| cccgcagaaa gaatcggatc tgctacctgc aggagatctt tagtaatgag atggctaagg | 420 |
| tggatgactc tttcttccat aggctggagg agtccttttt ggtggaggag gataaaaagc | 480 |
| acgagcgcca cccaatcttt ggcaatatcg tggacgaggt ggcgtaccat gaaaagtacc | 540 |
| caaccatata tcatctgagg aagaagctgg tagacagtac tgataaggct gacttgcggt | 600 |
| tgatctatct cgcgctggcg cacatgatca aatttcgggg acacttcctc atcgaggggg | 660 |
| acctgaaccc agacaacagc gatgtcgaca aactctttat ccaactggtt cagacttaca | 720 |
| atcagctttt cgaggagaac ccgatcaacg catccgcgct tgacgccaaa gcaatcctga | 780 |
| gcgctaggct gtccaaatcc cggcggctcg aaaacctcat cgcacagctc cctggggaga | 840 |

-continued

```
agaagaacgg cctgtttggt aatcttatcg ccctgtcact cgggctgacc cccaacttta    900
aatctaactt cgacctggcc gaagatgcca agctgcaact gagcaaagac acctacgatg    960
atgatctcga caatctgctg gcccagatcg gcgaccagta cgcagacctt tttttggcgg   1020
caaagaacct gtcagacgcc attctgctga gtgatattct gcgagtgaac acggagatca   1080
ccaaagctcc gctgagcgct agtatgatca agcgctatga tgagcaccac caagacttga   1140 cttgctgaa ggcccttgtc agacagcaac tgcctgagaa gtacaaggaa attttcttcg   1200
atcagtctaa aaatggctac gccggataca ttgacggcgg agcaagccag gaggaatttt   1260
acaaatttat taagcccatc ttggaaaaaa tggacgcac cgaggagctg ctggtaaagc   1320
tgaacagaga agatctgttg cgcaaacagc gcactttcga caatggaagc atcccccacc   1380
agattcacct gggcgaactg cacgctatcc tcaggcggca agaggatttc tacccctttt   1440
tgaaagataa cagggaaaag attgagaaaa tcctcacatt tcggataccc tactatgtag   1500 gcccctcgc tcggggaaat tccagattcg cgtggatgac tcgcaaatca gaagagacca   1560
tcactccctg gaacttcgag gaagtcgtgg ataagggggc ctctgcccag tccttcatcg   1620
aaaggatgac taactttgat aaaaatctgc ctaacgaaaa ggtgcttcct aaacactctc   1680
tgctgtacga gtacttcaca gtttataacg agctcaccaa ggtcaaatac gtcacagaag   1740
ggatgagaaa gccagcattc ctgtctggag agcagaagaa agctatcgtg gacctcctct   1800
tcaagacgaa ccggaaagtt accgtgaaac agctcaaaga agactatttc aaaaagattg   1860
aatgtttcga ctctgttgaa atcagcggag tggaggatcg cttcaacgca tccctgggaa   1920
cgtatcacga tctcctgaaa atcattaaag acaaggactt cctggacaat gaggagaacg   1980
aggacattct tgaggacatt gtcctcaccc ttacgttgtt tgaagatagg gagatgattg   2040
aagaacgctt gaaaacttac gctcatctct tcgacgacaa agtcatgaaa cagctcaaga   2100
gacgccgata tacaggatgg gggcggctgt caagaaaaac tgatcaatggc atccgagaca   2160 agcagagtgg aaagacaatc ctggattttc ttaagtccga tggatttgcc aaccggaact   2220
tcatgcagtt gatccatgat gactctctca cctttaagga ggacatccag aaagcacaag   2280
tttctggcca gggggacagt cttcacgagc acatcgctaa tcttgcaggt agcccagcta   2340
tcaaaaaggg aatactgcag accgttaagg tcgtggatga actcgtcaaa gtaatgggaa   2400
ggcataagcc cgagaatatc gttatcgaga tggcccgaga gaaccaaact acccagaagg   2460
gacagaagaa cagtagggaa aggatgaaga ggattgaaga gggtataaaa gaactggggt   2520
cccaaatcct taaggaacac ccagttgaaa cacccagct tcagaatgag aagctctacc   2580
tgtactacct gcagaacggc agggacatgt acgtggatca ggaactggac atcaaccggt   2640
tgtccgacta cgacgtggat catatcgtgc cccaaagctt tctcaaagat gattctattg   2700
ataataaagt gttgacaaga tccgataaaa atagagggaa gagtgataac gtcccctcag   2760
aagaagttgt caagaaaatg aaaaattatt ggcggcagct gctgaacgcc aaactgatca   2820
cacaacggaa gttcgataat ctgactaagg ctgaacgagg tggcctgtct gagttggata   2880
aagccggctt catcaaaagg cagcttgttg agacacgcca gatcaccaag cacgtggccc   2940
aaattctcga ttcacgcatg aacaccagt acgatgaaaa tgcaaactg attcgagagg   3000 tgaaagttat tactctgaag tctaagctgg tctcagattt cagaaaggac tttcagtttt   3060
ataaggtgag agagatcaac aattaccacc atgcgcatga tgcctacctg aatgcagtgg   3120
taggcactgc acttatcaaa aaatatccca agctggaatc tgaatttgtt tacgagact   3180
```

```
ataaagtgta cgatgttagg aaaatgatcg caaagtctga gcaggaaata ggcaaggcca    3240
ccgctaagta cttctttac agcaatatta tgaattttt caagaccgag attacactgg     3300
ccaatggaga gattcggaag cgaccactta tcgaaacaaa cggagaaaca ggagaaatcg    3360
tgtgggacaa gggtagggat ttcgcgacag tccgcaaggt cctgtccatg ccgcaggtga   3420
acatcgttaa aaagaccgaa gtacagaccg gaggcttctc caaggaaagt atcctcccga   3480
aaaggaacag cgacaagctg atcgcacgca aaaagattg ggaccccaag aaatacggcg    3540
gattcgattc tcctacagtc gcttacagtg tactggttgt ggccaaagtg gagaaaggga   3600
agtctaaaaa actcaaaagc gtcaaggaac tgctgggcat cacaatcatg gagcgatcca   3660
gcttcgagaa aaaccccatc gactttctcg aagcgaaagg atataaagag gtcaaaaaag   3720
acctcatcat taagctgccc aagtactctc tctttgagct tgaaaacggc cggaaacgaa   3780
tgctcgctag tgcgggcgag ctgcagaaag gtaacgagct ggcactgccc tctaaatacg   3840
ttaatttctt gtatctggcc agccactatg aaaagctcaa agggtctccc gaagataatg   3900
agcagaagca gctgttcgtg aacaacaca aacactacct tgatgagatc atcgagcaaa    3960
taagcgagtt ctccaaaaga gtgatcctcg ccgacgctaa cctcgataag gtgctttctg   4020
cttacaataa gcacagggat aagcccatca gggagcaggc agaaaacatt atccacttgt   4080
ttactctgac caacttgggc gcgcctgcag ccttcaagta cttcgacacc accatagaca   4140
gaaagcggta cacctctaca aaggaggtcc tggacgccac actgattcat cagtcaatta   4200
cggggctcta tgaaacaaga atcgacctct ctcagctcgg tggagacggc accggcgggc   4260
ccaagaagaa gaggaaggta tacccatacg atgttcctga ctatgcgggc tatccctatg   4320
acgtcccgga ctatgcagga tcgtatcctt atgacgttcc agattacgct ggatccgccg   4380
ctccggcagc taagaaaaag aaactggatt tcgaatccgg acgcccatat gcttgccctg   4440
tcgagtcctg cgatcgccgc ttttctcgct cggatgagct tacccgccat atccgcatcc   4500
ataccggtca gaagcccttc cagtgtcgaa tctgcatgcg taacttcagt cgtagtgacc   4560
accttaccac ccacatccgc acccacacag gcgagaagcc ttttgcctgt gacatttgtg   4620
ggaggaagtt tgccaggagt gatgaacgca agaggcatac caaaatccat ttaagacaga   4680
aggactaagc ggccgcctcg agatatctag acccagcttt cttgtacaaa gtggttgatc   4740
ctctcgagcc tctagaacta tagtgagtcg tattacgtag atccagacat gataagatac   4800
attgatgagt ttggacaaac cacaactaga atgcagtgaa aaaatgctt tatttgtgaa    4860 atttgtgatg ctattgcttt atttgtaacc attataagct gcaataaaca agttaacaac   4920
aacaattgca ttcattttat gtttcaggtt caggggagg tgtgggaggt ttttaattc     4980 gcggccgcgg cgccaatgca tttgggccgg tacccagctt ttgttccctt tagtgagggt   5040
taattgcgcg cttggcgtaa tcatggtcat agctgtttcc tgtgtgaaat tgttatccgc   5100
tcacaattcc acacaacata cgagccgaa gcataaagtg taaagcctgg ggtgcctaat    5160
gagtgagcta actcacatta attgcgttgc gctcactgcc cgctttccag tcgggaaacc   5220
tgtcgtgcca gctgcattaa tgaatcggcc aacgcgcggg gagaggcggt ttgcgtattg   5280
ggcgctcttc cgcttcctcg ctcactgact cgctgcgctc ggtcgttcgg ctgcggcgag   5340
cggtatcagc tcactcaaag gcggtaatac ggttatccac agaatcaggg gataacgcag   5400
gaaagaacat gtgagcaaaa ggccagcaaa aggccaggaa ccgtaaaaag gccgcgttgc   5460
tggcgttttt ccataggctc cgcccccctg acgagcatca caaaaatcga cgctcaagtc   5520
agaggtggcg aaacccgaca ggactataaa gataccaggc gtttccccct ggaagctccc   5580
```

```
tcgtgcgctc tcctgttccg accctgccgc ttaccggata cctgtccgcc tttctccctt    5640
cgggaagcgt ggcgctttct catagctcac gctgtaggta tctcagttcg gtgtaggtcg    5700
ttcgctccaa gctgggctgt gtgcacgaac cccccgttca gcccgaccgc tgcgccttat    5760
ccggtaacta tcgtcttgag tccaacccgg taagacacga cttatcgcca ctggcagcag    5820
ccactggtaa caggattagc agagcgaggt atgtaggcgg tgctacagag ttcttgaagt    5880
ggtggcctaa ctacggctac actagaagga cagtatttgg tatctgcgct ctgctgaagc    5940
cagttacctt cggaaaaaga gttggtagct cttgatccgg caaacaaacc accgctggta    6000
gcggtggttt ttttgtttgc aagcagcaga ttacgcgcag aaaaaaagga tctcaagaag    6060
atcctttgat cttttctacg gggtctgacg ctcagtggaa cgaaaactca cgttaaggga    6120
ttttggtcat gagattatca aaaggatct cacctagat cctttaaat taaaatgaa    6180 gttttaaatc aatctaaagt atatatgagt aaacttggtc tgacagttac caatgcttaa    6240
tcagtgaggc acctatctca gcgatctgtc tatttcgttc atccatagtt gcctgactcc    6300
ccgtcgtgta gataactacg atacgggagg gcttaccatc tggccccagt gctgcaatga    6360
taccgcgaga cccacgctca ccggctccag atttatcagc aataaaccag ccagccggaa    6420
gggccgagcg cagaagtggt cctgcaactt tatccgcctc catccagtct attaattgtt    6480
gccgggaagc tagagtaagt agttcgccag ttaatagttt cgcaacgtt gttgccattg    6540 ctacaggcat cgtggtgtca cgctcgtcgt ttggtatggc ttcattcagc tccggttccc    6600
aacgatcaag gcgagttaca tgatcccca tgttgtgcaa aaaagcggtt agctccttcg    6660
gtcctccgat cgttgtcaga agtaagttgg ccgcagtgtt atcactcatg gttatggcag    6720
cactgcataa ttctcttact gtcatgccat ccgtaagatg cttttctgtg actggtgagt    6780
actcaaccaa gtcattctga gaatagtgta tgcggcgacc gagttgctct tgcccggcgt    6840
caatacggga taataccgcg ccacatagca gaactttaaa agtgctcatc attggaaaac    6900
gttcttcggg gcgaaaactc tcaaggatct taccgctgtt gagatccagt tcgatgtaac    6960
ccactcgtgc acccaactga tcttcagcat cttttacttt caccagcgtt tctgggtgag    7020
caaaaacagg aaggcaaaat gccgcaaaaa agggaataag ggcgacacgg aaatgttgaa    7080
tactcatact cttcctttt caatattatt gaagcattta tcagggttat tgtctcatga    7140
gcggatacat atttgaatgt atttagaaaa ataaacaaat aggggttccg cgcacatttc    7200
cccgaaaagt gccacctaaa ttgtaagcgt taatattttg ttaaaattcg cgttaaattt    7260
ttgttaaatc agctcatttt ttaaccaata ggccgaaatc ggcaaaatcc cttataaatc    7320
aaaagaatag accgagatag ggttgagtgt tgttccagtt tggaacaaga gtccactatt    7380
aaagaacgtg gactccaacg tcaaagggcg aaaaaccgtc tatcagggcg atggcccact    7440
acgtgaacca tcaccctaat caagtttttt ggggtcgagg tgccgtaaag cactaaatcg    7500
gaaccctaaa gggagccccc gatttagagc ttgacgggga agccggcgaa cgtggcgag    7560 aaaggaaggg aagaaagcga aaggagcggg cgctagggcg ctggcaagtg tagcggtcac    7620
gctgcgcgta accaccacac ccgccgcgct taatgcgccg ctacagggcg cgtcccattc    7680
gccattcagg ctgcgcaact gttgggaagg gcgatcggtg cgggcctctt cgctattacg    7740
ccagtcgacc atagccaatt caatatggcg tatatggact catgccaatt caatatggtg    7800 gatctgacc tgtgccaatt caatatggcg tatatggact cgtgccaatt caatatggtg    7860
gatctggacc ccagccaatt caatatggcg gacttggcac catgccaatt caatatggcg    7920
```

```
gacttggcac tgtgccaact ggggaggggt ctacttggca cggtgccaag tttgaggagg    7980
ggtcttggcc ctgtgccaag tccgccatat tgaattggca tggtgccaat aatggcggcc    8040
atattggcta tatgccagga tcaatatata ggcaatatcc aatatggccc tatgccaata    8100
tggctattgg ccaggttcaa tactatgtat tggccctatg ccatatagta ttccatatat    8160
gggttttcct attgacgtag atagcccctc ccaatgggcg gtcccatata ccatatatgg    8220
ggcttcctaa taccgccat agccactccc ccattgacgt caatggtctc tatatatggt    8280
ctttcctatt gacgtcatat gggcggtcct attgacgtat atggcgcctc ccccattgac    8340
gtcaattacg gtaaatggcc cgcctggctc aatgcccatt gacgtcaata ggaccaccca    8400
ccattgacgt caatgggatg gctcattgcc cattcatatc cgttctcacg cccctattg    8460 acgtcaatga cggtaaatgg cccacttggc agtacatcaa tatctattaa tagtaacttg    8520
gcaagtacat tactattgga aggacgccag ggtacattgg cagtactccc attgacgtca    8580
atggcggtaa atggcccgcg atggctgcca agtacatccc cattgacgtc aatggggagg    8640
ggcaatgacg caaatgggcg ttccattgac gtaaatgggc ggtaggcgtg cctaatggga    8700
ggtctatata agcaatgctc gtttaggga                                     8729
```

<210> SEQ ID NO 68
<211> LENGTH: 8831
<212> TYPE: DNA
<213> ORGANISM: Artificial sequence
<220> FEATURE:
<223> OTHER INFORMATION: Synthetic

<400> SEQUENCE: 68

```
accgccattc tgcctggga cgtcggagca agcttgattt aggtgacact atagaataca      60
agctacttgt tcttttttgca ggatcccatc gattcgaatt caaggatcaa caagtttgta    120
caaaaaagca ggctggcgcc accatgggta gagccgcgcc ggcagctaag aaaaagaaac    180
tggatcaatt gcgcccatat gcttgccctg tcgagtcctg cgatcgccgc ttttctcgct    240
cggatgagct tacccgccat atccgcatcc ataccggtca gaagcccttc cagtgtcgaa    300
tctgcatgcg taacttcagt cgtagtgacc accttaccac ccacatccgc acccacacag    360
gcgagaagcc ttttgcctgt gacatttgtg ggaggaagtt tgccaggagt gatgaacgca    420
agaggcatac caaaatccat ttaagacaga aggaccccgg gtctggaggt agcggctcaa    480
gtggccgtac ggcagctcct gcggcaaaaa agaaaaagtt ggactctgaa ttcggaagcg    540
acaagaagta ctccattggg ctcgatatcg gtaccaacag cgtcggctgg gccgtcatta    600
cggacgagta caaggtgccg agcaaaaaaat tcaaagttct gggcaatacc gatcgccaca    660
gcataaagaa gaacctcatt ggagccctcc tgttcgactc cggggagacg gccgaagcca    720
cgcggctcaa aagaacagca cggcgcagat atacccgcag aaagaatcgg atctgctacc    780
tgcaggagat ctttagtaat gagatggcta aggtggatga ctctttcttc cataggctgg    840
aggagtcctt tttggtggag gaggataaaa agcacgagc ccacccaatc tttggcaata    900
tcgtggacga ggtggcgtac catgaaaagt acccaaccat atatcatctg aggaagaagc    960
tggtagacag tactgataag gctgacttgc ggttgatcta tctcgcgctg gcgcacatga    1020
tcaaatttcg gggacacttc ctcatcgagg gggacctgaa cccagacaac agcgatgtcg    1080
acaaactctt tatccaactg gttcagactt acaatcagct tttcgaggag aacccgatca    1140
acgcatccgg cgttgacgcc aaagcaatcc tgagcgctag gctgtccaaa tcccggcggc    1200
tcgaaaacct catcgcacag ctccctgggg agaagaagaa cggcctgttt ggtaatctta    1260
```

```
tcgccctgtc actcgggctg accccaact  ttaaatctaa cttcgacctg gccgaagatg   1320
ccaagctgca actgagcaaa gacacctacg atgatgatct cgacaatctg ctggcccaga   1380
tcggcgacca gtacgcagac ctttttttgg cggcaaagaa cctgtcagac gccattctgc   1440
tgagtgatat tctgcgagtg aacacggaga tcaccaaagc tccgctgagc gctagtatga   1500
tcaagcgcta tgatgagcac caccaagact tgactttgct gaaggccctt gtcagacagc   1560
aactgcctga agtacaag gaaattttct cgatcagtc taaaaatggc tacgccggat     1620
acattgacgg cggagcaagc caggaggaat tttacaaatt tattaagccc atcttggaaa   1680
aaatggacgg caccgaggag ctgctggtaa agctgaacag agaagatctg ttgcgcaaac   1740
agcgcacttt cgacaatgga agcatccccc accagattca cctgggcgaa ctgcacgcta   1800
tcctcaggcg gcaagaggat ttctacccct ttttgaaaga taacagggaa aagattgaga   1860
aaatcctcac atttcggata ccctactatg taggccccct cgctcgggga aattccagat   1920
tcgcgtggat gactcgcaaa tcagaagaga ccatcactcc ctggaacttc gaggaagtcg   1980
tggataaggg ggcctctgcc cagtccttca tcgaaaggat gactaacttt gataaaaatc   2040
tgcctaacga aaaggtgctt cctaaacact ctctgctgta cgagtacttc acagtttata   2100
acgagctcac caaggtcaaa tacgtcacag aagggatgag aaagccagca ttcctgtctg   2160
gagagcagaa gaaagctatc gtggacctcc tcttcaagac gaaccggaaa gttaccgtga   2220
aacagctcaa agaagactat ttcaaaaaga ttgaatgttt cgactctgtt gaaatcagcg   2280
gagtggagga tcgcttcaac gcatcccctgg gaacgtatca cgatctcctg aaaatcatta   2340
aagacaagga cttcctggac aatgaggaga acgaggacat tcttgaggac attgtcctca   2400
cccttacgtt gtttgaagat agggagatga ttgaagaacg cttgaaaact tacgctcatc   2460
tcttcgacga caaagtcatg aaacagctca agagacgccg atatacagga tgggggcggc   2520
tgtcaagaaa actgatcaat ggcatccgag acaagcagag tggaaagaca atcctggatt   2580
ttcttaagtc cgatggattt gccaaccgga acttcatgca gttgatccat gatgactctc   2640
tcacctttaa ggaggacatc cagaaagcac aagtttctgg ccaggggac agtcttcacg    2700
agcacatcgc taatcttgca ggtagcccag ctatcaaaaa gggaatactg cagaccgtta   2760
aggtcgtgga tgaactcgtc aaagtaatgg gaaggcataa gcccgagaat atcgttatcg   2820
agatggcccg agagaaccaa actacccaga agggacagaa gaacagtagg gaaaggatga   2880
agaggattga agagggtata aaagaactgg ggtcccaaat ccttaaggaa cacccagttg   2940
aaaacaccca gcttcagaat gagaagctct acctgtacta cctgcagaac ggcagggaca   3000
tgtacgtgga tcaggaactg gacatcaacc ggttgtccga ctacgacgtg gatcatatcg   3060
tgccccaaag ctttctcaaa gatgattcta ttgataataa agtgttgaca agatccgata   3120
aaaatagagg gaagagtgat aacgtcccct cagaagaagt tgtcaagaaa atgaaaaatt   3180
attggcggca gctgctgaac gccaaactga tcacacaacg gaagttcgat aatctgacta   3240
aggctgaacg aggtggcctg tctgagttgg ataaagccgg cttcatcaaa aggcagcttg   3300
ttgagacacg ccagatcacc aagcacgtgg cccaaattct cgattcacgc atgaacacca   3360
agtacgatga aaatgacaaa ctgattcgag aggtgaaagt tattactctg aagtctaagc   3420
tggtctcaga tttcagaaag actttcagt tttataaggt gagagagatc aacaattacc    3480
accatgcgca tgatgcctac ctgaatgcag tggtaggcac tgcacttatc aaaaaatatc   3540
ccaagctgga atctgaattt gtttacggag actataaagt gtacgatgtt aggaaaatga   3600
```

```
tcgcaaagtc tgagcaggaa ataggcaagg ccaccgctaa gtacttcttt tacagcaata    3660
ttatgaattt tttcaagacc gagattacac tggccaatgg agagattcgg aagcgaccac    3720
ttatcgaaac aaacggagaa acaggagaaa tcgtgtggga caagggtagg gatttcgcga    3780
cagtccgcaa ggtcctgtcc atgccgcagg tgaacatcgt taaaaagacc gaagtacaga    3840
ccggaggctt ctccaaggaa agtatcctcc cgaaaaggaa cagcgacaag ctgatcgcac    3900
gcaaaaaaga ttgggacccc aagaaatacg gcggattcga ttctcctaca gtcgcttaca    3960
gtgtactggt tgtggccaaa gtggagaaag ggaagtctaa aaaactcaaa agcgtcaagg    4020
aactgctggg catcacaatc atggagcgat ccagcttcga gaaaaacccc atcgactttc    4080
tcgaagcgaa aggatataaa gaggtcaaaa aagacctcat cattaagctg cccaagtact    4140
ctctctttga gcttgaaaac ggccggaaac gaatgctcgc tagtgcgggc gagctgcaga    4200
aaggtaacga gctggcactg ccctctaaat acgttaattt cttgtatctg gccagccact    4260
atgaaaagct caaagggtct cccgaagata tgagcagaa gcagctgttc gtggaacaac    4320
acaaacacta ccttgatgag atcatcgagc aaataagcga gttctccaaa agagtgatcc    4380
tcgccgacgc taacctcgat aaggtgcttt ctgcttacaa taagcacagg ataagccca    4440 tcagggagca ggcagaaaac attatccact tgtttactct gaccaacttg ggcgcgcctg    4500
cagccttcaa gtacttcgac accaccatag acagaaagcg gtacacctct acaaaggagg    4560
tcctggacgc cacactgatt catcagtcaa ttacggggct ctatgaaaca gaatcgacc    4620 tctctcagct cggtggagac ggcaccggcg ggcccaagaa gaagaggaag gtatacccat    4680
acgatgttcc tgactatgcg ggctatccct atgacgtccc ggactatgca ggatcgtatc    4740
cttatgacgt tccagattac gctggatcct aatgattcga atccggataa gcggccgcct    4800
cgagatatct agacccagct ttcttgtaca agtggttga tcctctcgag cctctagaac    4860
tatagtgagt cgtattacgt agatccagac atgataagat acattgatga gtttggacaa    4920
accacaacta gaatgcagtg aaaaaaatgc tttatttgtg aaatttgtga tgctattgct    4980
ttatttgtaa ccattataag ctgcaataaa caagttaaca acaacaattg cattcatttt    5040
atgtttcagg ttcaggggga ggtgtgggag gttttttaat tcgcggccgc ggcgccaatg    5100
cattgggccc ggtacccagc ttttgttccc tttagtgagg gttaattgcg cgcttggcgt    5160
aatcatggtc atagctgttt cctgtgtgaa attgttatcc gctcacaatt ccacacaaca    5220
tacgagccgg aagcataaag tgtaaagcct ggggtgccta atgagtgagc taactcacat    5280
taattgcgtt gcgctcactg cccgctttcc agtcgggaaa cctgtcgtgc cagctgcatt    5340
aatgaatcgg ccaacgcgcg gggagaggcg gtttgcgtat tgggcgctct tccgcttcct    5400
cgctcactga ctcgctgcgc tcggtcgttc ggctgcggcg agcggtatca gctcactcaa    5460
aggcggtaat acggttatcc acagaatcag gggataacgc aggaaagaac atgtgagcaa    5520
aaggccagca aaaggccagg aaccgtaaaa aggccgcgtt gctggcgttt ttccataggc    5580
tccgcccccc tgacgagcat cacaaaaatc gacgctcaag tcagaggtgg cgaaacccga    5640
caggactata agataccag gcgtttcccc ctggaagctc cctcgtgcgc tctcctgttc    5700
cgaccctgcc gcttaccgga tacctgtccg cctttctccc ttcgggaagc gtggcgcttt    5760
ctcatagctc acgctgtagg tatctcagtt cggtgtaggt cgttcgctcc aagctgggct    5820
gtgtgcacga accccccgtt cagcccgacc gctgcgcctt atccggtaac tatcgtcttg    5880
agtccaaccc ggtaagacac gacttatcgc cactggcagc agccactggt aacaggatta    5940
gcagagcgag gtatgtaggc ggtgctacag agttcttgaa gtggtggcct aactacggct    6000
```

```
acactagaag gacagtattt ggtatctgcg ctctgctgaa gccagttacc ttcggaaaaa    6060
gagttggtag ctcttgatcc ggcaaacaaa ccaccgctgg tagcggtggt ttttttgttt    6120
gcaagcagca gattacgcgc agaaaaaaag gatctcaaga agatcctttg atcttttcta    6180
cggggtctga cgctcagtgg aacgaaaact cacgttaagg gattttggtc atgagattat    6240
caaaaaggat cttcacctag atccttttaa attaaaaatg aagttttaaa tcaatctaaa    6300
gtatatatga gtaaacttgg tctgacagtt accaatgctt aatcagtgag gcacctatct    6360
cagcgatctg tctatttcgt tcatccatag ttgcctgact ccccgtcgtg tagataacta    6420
cgatacggga gggcttacca tctggcccca gtgctgcaat gataccgcga gacccacgct    6480
caccggctcc agatttatca gcaataaacc agccagccgg aagggccgag cgcagaagtg    6540
gtcctgcaac tttatccgcc tccatccagt ctattaattg ttgccgggaa gctagagtaa    6600
gtagttcgcc agttaatagt ttgcgcaacg ttgttgccat tgctacaggc atcgtggtgt    6660
cacgctcgtc gtttggtatg gcttcattca gctccggttc ccaacgatca aggcgagtta    6720
catgatcccc catgttgtgc aaaaaagcgg ttagctcctt cggtcctccg atcgttgtca    6780
gaagtaagtt ggccgcagtg ttatcactca tggttatggc agcactgcat aattctctta    6840
ctgtcatgcc atccgtaaga tgcttttctg tgactggtga gtactcaacc aagtcattct    6900
gagaatagtg tatgcggcga ccgagttgct cttgcccggc gtcaatacgg gataataccg    6960
cgccacatag cagaacttta aaagtgctca tcattggaaa acgttcttcg ggcgaaaac    7020 tctcaaggat cttaccgctg ttgagatcca gttcgatgta acccactcgt gcacccaact    7080
gatcttcagc atcttttact ttcaccagcg tttctgggtg agcaaaaaca ggaaggcaaa    7140
atgccgcaaa aaagggaata agggcgacac ggaaatgttg aatactcata ctcttccttt    7200
ttcaatatta ttgaagcatt tatcagggtt attgtctcat gagcggatac atatttgaat    7260
gtatttagaa aaataaacaa ataggggttc cgcgcacatt tccccgaaaa gtgccaccta    7320
aattgtaagc gttaatattt tgttaaaatt cgcgttaaat ttttgttaaa tcagctcatt    7380
ttttaaccaa taggccgaaa tcggcaaaat cccttataaa tcaaaagaat agaccgagat    7440
agggttgagt gttgttccag tttggaacaa gagtccacta ttaaagaacg tggactccaa    7500
cgtcaaaggg cgaaaaaccg tctatcaggg cgatggccca ctacgtgaac catcaccta    7560 atcaagtttt tggggtcga ggtgccgtaa agcactaaat cggaacccta agggagccc    7620 ccgatttaga gcttgacggg gaaagccggc gaacgtggcg agaaaggaag ggaagaaagc    7680
gaaaggagcg ggcgctaggg cgctggcaag tgtagcggtc acgctgcgcg taaccaccac    7740
acccgccgcg cttaatgcgc cgctacaggg cgcgtcccat tcgccattca ggctgcgcaa    7800
ctgttgggaa gggcgatcgg tgcgggcctc ttcgctatta cgccagtcga ccatagccaa    7860
ttcaatatgg cgtatatgga ctcatgccaa ttcaatatgg tggatctgga cctgtgccaa    7920
ttcaatatgg cgtatatgga ctcgtgccaa ttcaatatgg tggatctgga ccccagccaa    7980
ttcaatatgg cggacttggc accatgccaa ttcaatatgg cggacttggc actgtgccaa    8040
ctggggaggg gtctacttgg cacggtgcca agtttgagga ggggtcttgg ccctgtgcca    8100
agtccgccat attgaattgg catggtgcca ataatggcgg ccatattggc tatatgccag    8160
gatcaatata taggcaatat ccaatatggc cctatgccaa tatggctatt ggccaggttc    8220
aatactatgt attggcccta tgccatatag tattccatat atgggttttc ctattgacgt    8280
agatagcccc tcccaatggg cggtcccata taccatatat ggggcttcct aataccgccc    8340
```

| | |
|---|---:|
| atagccactc ccccattgac gtcaatggtc tctatatatg gtctttccta ttgacgtcat | 8400 |
| atgggcggtc ctattgacgt atatggcgcc tcccccattg acgtcaatta cggtaaatgg | 8460 |
| cccgcctggc tcaatgccca ttgacgtcaa taggaccacc caccattgac gtcaatggga | 8520 |
| tggctcattg cccattcata tccgttctca cgccccctat tgacgtcaat gacggtaaat | 8580 |
| ggcccacttg gcagtacatc aatatctatt aatagtaact tggcaagtac attactattg | 8640 |
| gaaggacgcc agggtacatt ggcagtactc ccattgacgt caatggcggt aaatggcccg | 8700 |
| cgatggctgc caagtacatc cccattgacg tcaatgggga ggggcaatga cgcaaatggg | 8760 |
| cgttccattg acgtaaatgg gcggtaggcg tgcctaatgg gaggtctata taagcaatgc | 8820 |
| tcgtttaggg a | 8831 |

<210> SEQ ID NO 69
<211> LENGTH: 10061
<212> TYPE: DNA
<213> ORGANISM: Artificial sequence
<220> FEATURE:
<223> OTHER INFORMATION: Synthetic

<400> SEQUENCE: 69

| | |
|---|---:|
| accgccattc tgcctgggga cgtcggagca agcttgattt aggtgacact atagaataca | 60 |
| agctacttgt tcttttttgca ggatcccatc gattcgaatt caaggatcaa caagtttgta | 120 |
| caaaaaagca ggctggcgcc accatggaca gaagtactc cattgggctc gatatcggta | 180 |
| ccaacagcgt cggctgggcc gtcattacgg acgagtacaa ggtgccgagc aaaaaattca | 240 |
| aagttctggg caataccgat cgccacagca taaagaagaa cctcattgga gccctcctgt | 300 |
| tcgactccgg ggagacggcc gaagccacgc ggctcaaaag aacagcacgg cgcagatata | 360 |
| cccgcagaaa gaatcggatc tgctacctgc aggagatctt tagtaatgag atggctaagg | 420 |
| tggatgactc tttcttccat aggctggagg agtcctttt ggtggaggag ataaaaagc | 480 |
| acgagcgcca cccaatcttt ggcaatatcg tggacgaggt ggcgtaccat gaaaagtacc | 540 |
| caaccatata tcatctgagg aagaagctgg tagacagtac tgataaggct gacttgcggt | 600 |
| tgatctatct cgcgctggcg cacatgatca aatttcgggg acacttcctc atcgaggggg | 660 |
| acctgaaccc agacaacagc gatgtcgaca aactctttat ccaactggtt cagacttaca | 720 |
| atcagctttt cgaggagaac ccgatcaacg catccgcgt tgacgccaaa gcaatcctga | 780 |
| gcgctaggct gtccaaatcc cggcggctcg aaaacctcat cgcacagctc cctggggaga | 840 |
| agaagaacgg cctgtttggt aatcttatcg ccctgtcact cggctgacc cccaacttta | 900 |
| aatctaactt cgacctggcc gaagatgcca agctgcaact gagcaaagac acctacgatg | 960 |
| atgatctcga caatctgctg gcccagatcg gcgaccagta cgcagacctt tttttggcgg | 1020 |
| caaagaacct gtcagacgcc attctgctga gtgatattct gcgagtgaac acggagatca | 1080 |
| ccaaagctcc gctgagcgct agtatgatca agcgctatga tgagcaccac caagacttga | 1140 |
| ctttgctgaa ggcccttgtc agacagcaac tgcctgagaa gtacaaggaa atttttcttcg | 1200 |
| atcagtctaa aaatggctac gccggataca ttgacggcgg agcaagccag gaggaatttt | 1260 |
| acaaatttat taagcccatc ttggaaaaaa tggacggcac cgaggagctg ctggtaaagc | 1320 |
| tgaacagaga agatctgttg cgcaaacagc gcactttcga caatggaagc atcccccacc | 1380 |
| agattcacct gggcgaactg cacgctatcc tcaggcggca agaggatttc taccccttt | 1440 |
| tgaaagataa cagggaaaag attgagaaaa tcctcacatt tcggatacc tactatgtag | 1500 |
| gccccctcgc tcggggaaat tccagattcg cgtggatgac tcgcaaatca gaagagacca | 1560 |

```
tcactccctg gaacttcgag gaagtcgtgg ataaggggc ctctgcccag tccttcatcg    1620
aaaggatgac taactttgat aaaaatctgc ctaacgaaaa ggtgcttcct aaacactctc    1680
tgctgtacga gtacttcaca gtttataacg agctcaccaa ggtcaaatac gtcacagaag    1740
ggatgagaaa gccagcattc ctgtctggag agcagaagaa agctatcgtg gacctcctct    1800
tcaagacgaa ccggaaagtt accgtgaaac agctcaaaga agactatttc aaaaagattg    1860
aatgtttcga ctctgttgaa atcagcggag tggaggatcg cttcaacgca tccctgggaa    1920
cgtatcacga tctcctgaaa atcattaaag acaaggactt cctggacaat gaggagaacg    1980
aggacattct tgaggacatt gtcctcaccc ttacgttgtt tgaagatagg gagatgattg    2040
aagaacgctt gaaaacttac gctcatctct tcgacgacaa agtcatgaaa cagctcaaga    2100
gacgccgata tacaggatgg gggcggctgt caagaaaact gatcaatggc atccgagaca    2160
agcagagtgg aaagacaatc ctggattttc ttaagtccga tggatttgcc aaccggaact    2220
tcatgcagtt gatccatgat gactctctca cctttaagga ggacatccag aaagcacaag    2280
tttctggcca gggggacagt cttcacgagc acatcgctaa tcttgcaggt agcccagcta    2340
tcaaaaaggg aatactgcag accgttaagg tcgtggatga actcgtcaaa gtaatgggaa    2400
ggcataagcc cgagaatatc gttatcgaga tggcccgaga gaaccaaact acccagaagg    2460
gacagaagaa cagtagggaa aggatgaaga ggattgaaga gggtataaaa gaactggggt    2520
cccaaatcct taaggaacac ccagttgaaa cacccagct tcagaatgag aagctctacc    2580
tgtactacct gcagaacggc agggacatgt acgtggatca ggaactggac atcaaccggt    2640
tgtccgacta cgacgtggat catatcgtgc cccaaagctt tctcaaagat gattctattg    2700
ataataaagt gttgacaaga tccgataaaa atagagggaa gagtgataac gtcccctcag    2760
aagaagttgt caagaaaatg aaaaattatt ggcggcagct gctgaacgcc aaactgatca    2820
cacaacggaa gttcgataat ctgactaagg ctgaacgagg tggcctgtct gagttggata    2880
aagccggctt catcaaaagg cagcttgttg agacacgcca gatcaccaag cacgtggccc    2940
aaattctcga ttcacgcatg aacaccaagt acgatgaaaa tgacaaactg attcgagagg    3000
tgaaagttat tactctgaag tctaagctgg tctcagattt cagaaaggac tttcagtttt    3060
ataaggtgag agagatcaac aattaccacc atgcgcatga tgcctacctg aatgcagtgg    3120
taggcactgc acttatcaaa aaatatccca agctggaatc tgaatttgtt tacgagact    3180 ataaagtgta cgatgttagg aaaatgatcg caaagtctga gcaggaaata ggcaaggcca    3240
ccgctaagta cttcttttac agcaatatta tgaattttt caagaccgag attacactgg    3300
ccaatggaga gattcggaag cgaccactta tcgaaacaaa cggagaaaca ggagaaatcg    3360
tgtgggacaa gggtagggat ttcgcgacag tccgcaaggt cctgtccatg ccgcaggtga    3420
acatcgttaa aaagaccgaa gtacagaccg gaggcttctc caaggaaagt atcctcccga    3480
aaaggaacag cgacaagctg atcgcacgca aaaaagattg gaccccaag aaatacggcg    3540 gattcgattc tcctacagtc gcttacagtg tactggttgt ggccaaagtg gagaaaggga    3600
agtctaaaaa actcaaaagc gtcaaggaac tgctgggcat cacaatcatg gagcgatcca    3660
gcttcgagaa aaacccatc gactttctcg aagcgaaagg atataaagag gtcaaaaaag    3720
acctcatcat taagctgccc aagtactctc tctttgagct tgaaaacggc cggaaacgaa    3780
tgctcgctag tgcgggcgag ctgcagaaag gtaacgagct ggcactgccc tctaaatacg    3840
ttaatttctt gtatctggcc agccactatg aaaagctcaa agggtctccc gaagataatg    3900
```

```
agcagaagca gctgttcgtg gaacaacaca aacactacct tgatgagatc atcgagcaaa      3960
taagcgagtt ctccaaaaga gtgatcctcg ccgacgctaa cctcgataag gtgctttctg      4020
cttacaataa gcacagggat aagcccatca gggagcaggc agaaaacatt atccacttgt      4080
ttactctgac caacttgggc gcgcctgcag ccttcaagta cttcgacacc accatagaca      4140
gaaagcggta cacctctaca aaggaggtcc tggacgccac actgattcat cagtcaatta      4200
cggggctcta tgaaacaaga atcgacctct ctcagctcgg tggagacggc accggcgggc      4260
ccaagaagaa gaggaaggta tacccatacg atgttcctga ctatgcgggc tatccctatg      4320
acgtcccgga ctatgcagga tcgtatcctt atgacgttcc agattacgct ggatccgccg      4380
ctccggcagc taagaaaaag aaactggatt tcgaatccgg agtacctatg gtggacttga      4440
ggacactcgg ttattcgcaa cagcaacagg agaaaatcaa gcctaaggtc aggagcaccg      4500
tcgcgcaaca ccacgaggcg cttgtggggc atggcttcac tcatgcgcat attgtcgcgc      4560
tttcacagca ccctgcggcg cttgggacgg tggctgtcaa ataccaagat atgattgcgg      4620
ccctgcccga agccacgcac gaggcaattg taggggtcgg taaacagtgg tcggagcgc       4680 gagcacttga ggcgctgctg actgtggcgg gtgagcttag ggggcctccg ctccagctcg      4740
acaccgggca gctgctgaag atcgcgaaga gaggggggagt aacagcggta gaggcagtgc     4800
acgcctggcg caatgcgctc accggggccc ccttgcccct gaacctgacc ccggaccaag      4860
tggtggctat cgccagcaac aatggcggca agcaagcgct cgaaacgtg cagcggctgt       4920 tgccggtgct gtgccaggac catggcctga ctccggacca agtggtggct atcgccagcc      4980 acgatgcgg caagcaagcg ctcgaaacg tgcagcggct gttgccggtg ctgtgccagg         5040
accatggcct gaccccggac caagtggtgg ctatcgccag caacaatggc ggcaagcaag      5100
cgctcgaaac ggtgcagcgg ctgttgccgg tgctgtgcca ggaccatggc ctgaccccgg      5160
accaagtggt ggctatcgcc agcaacggtg cggcaagca agcgctcgaa acggtgcagc        5220
ggctgttgcc ggtgctgtgc caggaccatg gcctgacccc ggaccaagtg gtggctatcg      5280
ccagcaacaa tggcggcaag caagcgctcg aaacggtgca gcggctgttg ccggtgctgt      5340
gccaggacca tggcctgacc ccggaccaag tggtggctat cgccagcaac aatggcggca      5400
agcaagcgct cgaaacggtg cagcggctgt tgccggtgct gtgccaggac catggcctga      5460
ccccggacca agtggtggct atcgccagca acaatggcgg caagcaagcg ctcgaaacgg      5520
tgcagcggct gttgccggtg ctgtgccagg accatggcct gactccggac caagtggtgg      5580
ctatcgccag ccacgatgcg gcaagcaag cgctcgaaac ggtgcagcgg ctgttgccgg        5640
tgctgtgcca ggaccatggc ctgaccccgg accaagtggt ggctatcgcc agcaacaatg      5700
gcggcaagca agcgctcgaa acggtgcagc ggctgttgcc ggtgctgtgc caggaccatg      5760
gcctgacccc ggaccaagtg gtggctatcg ctaataataa cggaggacgg ccagccttgg      5820
agtccatcgt agcccaattg tccaggcccg atcccgcgtt ggctgcgtta acgaatgacc      5880
atctggtggc gttggcatgt cttggtggac gacccgcgct cgatgcagtc aaaaagggtc      5940
tgcctcatgc tcccgcattg atcaaaagaa ccaaccggcg gattcccgag agaacttccc      6000
atcgagtcgc gggatcttaa gcggccgcct cgagatatct agacccagct tcttgtaca       6060 aagtggttga tcctctcgag cctctagaac tatagtgagt cgtattacgt agatccagac      6120
atgataagat acattgatga gtttggacaa accacaacta gaatgcagtg aaaaaaatgc      6180
tttatttgtg aaatttgtga tgctattgct ttatttgtaa ccattataag ctgcaataaa      6240
caagttaaca acaacaattg cattcatttt atgtttcagg ttcaggggga ggtgtgggag      6300
```

```
gtttttttaat tcgcggccgc ggcgccaatg cattgggccc ggtacccagc ttttgttccc    6360
tttagtgagg gttaattgcg cgcttggcgt aatcatggtc atagctgttt cctgtgtgaa    6420
attgttatcc gctcacaatt ccacacaaca tacgagccgg aagcataaag tgtaaagcct    6480
ggggtgccta atgagtgagc taactcacat taattgcgtt gcgctcactg cccgctttcc    6540
agtcgggaaa cctgtcgtgc cagctgcatt aatgaatcgg ccaacgcgcg gggagaggcg    6600
gtttgcgtat tgggcgctct tccgcttcct cgctcactga ctcgctgcgc tcggtcgttc    6660
ggctgcggcg agcggtatca gctcactcaa aggcggtaat acggttatcc acagaatcag    6720
gggataacgc aggaaagaac atgtgagcaa aaggccagca aaaggccagg aaccgtaaaa    6780
aggccgcgtt gctggcgttt ttccataggc tccgcccccc tgacgagcat cacaaaaatc    6840
gacgctcaag tcagaggtgg cgaaacccga caggactata agataccag gcgtttcccc    6900 ctggaagctc cctcgtgcgc tctcctgttc cgaccctgcc gcttaccgga tacctgtccg    6960
cctttctccc ttcggaagc gtggcgcttt ctcatagctc acgctgtagg tatctcagtt    7020
cggtgtaggt cgttcgctcc aagctgggct gtgtgcacga accccccgtt cagcccgacc    7080
gctgcgcctt atccggtaac tatcgtcttg agtccaaccc ggtaagacac gacttatcgc    7140
cactggcagc agccactggt aacaggatta gcagagcgag gtatgtaggc ggtgctacag    7200
agttcttgaa gtggtggcct aactacggct acactagaag gacagtattt ggtatctgcg    7260
ctctgctgaa gccagttacc ttcggaaaaa gagttggtag ctcttgatcc ggcaaacaaa    7320
ccaccgctgg tagcggtggt ttttttgttt gcaagcagca gattacgcgc agaaaaaaag    7380
gatctcaaga agatcctttg atcttttcta cggggtctga cgctcagtgg aacgaaaact    7440
cacgttaagg gattttggtc atgagattat caaaaaggat cttcacctag atccttttaa    7500
attaaaaatg aagttttaaa tcaatctaaa gtatatatga gtaaacttgg tctgacagtt    7560
accaatgctt aatcagtgag gcacctatct cagcgatctg tctatttcgt tcatccatag    7620
ttgcctgact ccccgtcgtg tagataacta cgatacggga gggcttacca tctggcccca    7680
gtgctgcaat gataccgcga gacccacgct caccggctcc agatttatca gcaataaacc    7740
agccagccgg aagggccgag cgcagaagtg gtcctgcaac tttatccgcc tccatccagt    7800
ctattaattg ttgccgggaa gctagagtaa gtagttcgcc agttaatagt ttgcgcaacg    7860
ttgttgccat tgctacaggc atcgtggtgt cacgctcgtc gtttggtatg gcttcattca    7920
gctccggttc ccaacgatca aggcgagtta catgatcccc catgttgtgc aaaaaagcgg    7980
ttagctcctt cggtcctccg atcgttgtca gaagtaagtt ggccgcagtg ttatcactca    8040
tggttatggc agcactgcat aattctctta ctgtcatgcc atccgtaaga tgcttttctg    8100
tgactggtga gtactcaacc aagtcattct gagaatagtg tatgcggcga ccgagttgct    8160
cttgcccggc gtcaatacgg gataataccg cgccacatag cagaacttta aaagtgctca    8220
tcattggaaa acgttcttcg gggcgaaaac tctcaaggat cttaccgctg ttgagatcca    8280
gttcgatgta acccactcgt gcacccaact gatcttcagc atcttttact ttcaccagcg    8340
tttctgggtg agcaaaaaca ggaaggcaaa atgccgcaaa aaagggaata agggcgacac    8400
ggaaatgttg aatactcata ctcttccttt ttcaatatta ttgaagcatt tatcagggtt    8460
attgtctcat gagcggatac atatttgaat gtatttagaa aaataaacaa ataggggttc    8520
cgcgcacatt tccccgaaaa gtgccaccta aattgtaagc gttaatattt tgttaaaatt    8580
cgcgttaaat ttttgttaaa tcagctcatt ttttaaccaa taggccgaaa tcggcaaaat    8640
```

| | |
|---|---|
| cccttataaa tcaaaagaat agaccgagat agggttgagt gttgttccag tttgaacaa | 8700 |
| gagtccacta ttaaagaacg tggactccaa cgtcaaaggg cgaaaaaccg tctatcaggg | 8760 |
| cgatggccca ctacgtgaac catcacccta atcaagtttt ttggggtcga ggtgccgtaa | 8820 |
| agcactaaat cggaacccta aagggagccc ccgatttaga gcttgacggg gaaagccggc | 8880 |
| gaacgtggcg agaaaggaag ggaagaaagc gaaaggagcg ggcgctaggg cgctggcaag | 8940 |
| tgtagcggtc acgctgcgcg taaccaccac acccgccgcg cttaatgcgc cgctacaggg | 9000 |
| cgcgtcccat tcgccattca ggctgcgcaa ctgttgggaa gggcgatcgg tgcgggcctc | 9060 |
| ttcgctatta cgccagtcga ccatagccaa ttcaatatgg cgtatatgga ctcatgccaa | 9120 |
| ttcaatatgg tggatctgga cctgtgccaa ttcaatatgg cgtatatgga ctcgtgccaa | 9180 |
| ttcaatatgg tggatctgga ccccagccaa ttcaatatgg cggacttggc accatgccaa | 9240 |
| ttcaatatgg cggacttggc actgtgccaa ctggggaggg gtctacttgg cacggtgcca | 9300 |
| agtttgagga ggggtcttgg ccctgtgcca agtccgccat attgaattgg catggtgcca | 9360 |
| ataatggcgg ccatattggc tatatgccag gatcaatata taggcaatat ccaatatggc | 9420 |
| cctatgccaa tatggctatt ggccaggttc aatactatgt attggcccta tgccatatag | 9480 |
| tattccatat atgggttttc ctattgacgt agatagcccc tcccaatggg cggtcccata | 9540 |
| taccatatat ggggcttcct aataccgccc atagccactc ccccattgac gtcaatggtc | 9600 |
| tctatatatg gtctttccta ttgacgtcat atgggcggtc ctattgacgt atatggcgcc | 9660 |
| tcccccattg acgtcaatta cggtaaatgg cccgcctggc tcaatgccca ttgacgtcaa | 9720 |
| taggaccacc caccattgac gtcaatggga tggctcattg cccattcata tccgttctca | 9780 |
| cgccccctat tgacgtcaat gacggtaaat ggcccacttg gcagtacatc aatatctatt | 9840 |
| aatagtaact tggcaagtac attactattg gaaggacgcc agggtacatt ggcagtactc | 9900 |
| ccattgacgt caatggcggt aaatggcccg cgatggctgc caagtacatc cccattgacg | 9960 |
| tcaatgggga ggggcaatga cgcaaatggg cgttccattg acgtaaatgg gcggtaggcg | 10020 |
| tgcctaatgg gaggtctata taagcaatgc tcgtttaggg a | 10061 |

<210> SEQ ID NO 70
<211> LENGTH: 10163
<212> TYPE: DNA
<213> ORGANISM: Artificial sequence
<220> FEATURE:
<223> OTHER INFORMATION: Synthetic

<400> SEQUENCE: 70

| | |
|---|---|
| accgccattc tgcctgggga cgtcggagca agcttgattt aggtgacact atagaataca | 60 |
| agctacttgt tctttttgca ggatcccatc gattcgaatt caaggatcaa caagtttgta | 120 |
| caaaaaagca ggctggcgcc accatgggta gagccgcgcc ggcagctaag aaaaagaaac | 180 |
| tggatcaatt ggtacctatg gtggacttga ggacactcgg ttattcgcaa cagcaacagg | 240 |
| agaaaatcaa gcctaaggtc aggagcaccg tcgcgcaaca ccacgaggcg cttgtggggc | 300 |
| atggcttcac tcatgcgcat attgtcgcgc tttcacagca ccctgcggcg cttgggacgg | 360 |
| tggctgtcaa ataccaagat atgattgcgg ccctgcccga agccacgcac gaggcaattg | 420 |
| taggggtcgg taaacagtgg tcgggagcgc gagcacttga ggcgctgctg actgtggcgg | 480 |
| gtgagcttag ggggcctccg ctccagctcg acaccgggca gctgctgaag atcgcgaaga | 540 |
| gaggggggagt aacagcggta gaggcagtgc acgcctggcg caatgcgctc accgggccc | 600 |
| ccttgccccct gaacctgacc ccggaccaag tggtggctat cgccagcaac aatggcggca | 660 |

```
agcaagcgct cgaaacggtg cagcggctgt tgccggtgct gtgccaggac catggcctga    720
ctccggacca agtggtggct atcgccagcc acgatggcgg caagcaagcg ctcgaaacgg    780
tgcagcggct gttgccggtg ctgtgccagg accatggcct gaccccggac caagtggtgg    840
ctatcgccag caacaatggc ggcaagcaag cgctcgaaac ggtgcagcgg ctgttgccgg    900
tgctgtgcca ggaccatggc ctgaccccgg accaagtggt ggctatcgcc agcaacggtg    960
gcggcaagca agcgctcgaa acggtgcagc ggctgttgcc ggtgctgtgc caggaccatg   1020
gcctgacccc ggaccaagtg gtggctatcg ccagcaacaa tggcggcaag caagcgctcg   1080
aaacggtgca gcggctgttg ccggtgctgt gccaggacca tggcctgacc ccggaccaag   1140
tggtggctat cgccagcaac aatggcggca agcaagcgct cgaaacggtg cagcggctgt   1200
tgccggtgct gtgccaggac catggcctga ccccggacca agtggtggct atcgccagca   1260
acaatggcgg caagcaagcg ctcgaaacgg tgcagcggct gttgccggtg ctgtgccagg   1320
accatggcct gactccggac caagtggtgg ctatcgccag ccacgatggc ggcaagcaag   1380
cgctcgaaac ggtgcagcgg ctgttgccgg tgctgtgcca ggaccatggc ctgaccccgg   1440
accaagtggt ggctatcgcc agcaacaatg gcggcaagca agcgctcgaa acggtgcagc   1500
ggctgttgcc ggtgctgtgc caggaccatg gcctgacccc ggaccaagtg gtggctatcg   1560
ctaataataa cggaggacgg ccagccttgg agtccatcgt agcccaattg tccaggcccg   1620
atcccgcgtt ggctgcgtta acgaatgacc atctggtggc gttggcatgt cttggtggac   1680
gacccgcgct cgatgcagtc aaaaagggtc tgcctcatgc tcccgcattg atcaaaagaa   1740
ccaaccggcg gattcccgag agaacttccc atcgagtcgc gggatctccc gggtctggag   1800
gtagcggctc aagtggccgt acggcagctc ctgcggcaaa aagaaaaag ttggactctg   1860 aattcggaag cgacaagaag tactccattg ggctcgatat cggtaccaac agcgtcggct   1920
gggccgtcat tacggacgag tacaaggtgc cgagcaaaaa attcaaagtt ctgggcaata   1980
ccgatcgcca cagcataaag aagaacctca ttggagcact cctgttcgac tccggggaga   2040
cggccgaagc cacgcggctc aaaagaacag cacggcgcag atatacccgc agaaagaatc   2100
ggatctgcta cctgcaggag atctttagta atgagatggc taaggtggat gactctttct   2160
tccataggct ggaggagtcc ttttggtgg aggaggataa aaagcacgag cgccacccaa   2220
tctttggcaa tatcgtggac gaggtggcgt accatgaaaa gtacccaacc atatatcatc   2280
tgaggaagaa gctggtagac agtactgata aggctgactt gcggttgatc tatctcgcgc   2340
tggcgcacat gatcaaattt cggggacact tcctcatcga gggggacctg aacccagaca   2400
acagcgatgt cgacaaactc tttatccaac tggttcagac ttacaatcag cttttcgagg   2460
agaacccgat caacgcatcc ggcgttgacg ccaaagcaat cctgagcgct aggctgtcca   2520
aatcccggcg gctcgaaaac ctcatcgcac agctccctgg ggagaagaag aacggcctgt   2580
ttggtaatct tatcgccctg tcactcgggc tgacccccaa cttaaatct aacttcgacc   2640 tggccgaaga tgccaagctg caactgagca agacaccta cgatgatgat ctcgacaatc   2700
tgctggccca gatcggcgac cagtacgcag acctttttt ggcggcaaag aacctgtcag   2760
acgccattct gctgagtgat attctgcgag tgaacacgga gatcaccaaa gctccgctga   2820
gcgctagtat gatcaagcgc tatgatgagc accaccaaga cttgactttg ctgaaggccc   2880
ttgtcagaca gcaactgcct gagaagtaca aggaaatttt cttcgatcag tctaaaaatg   2940
gctacgccgg atacattgac ggcggagcaa gccaggagga attttacaaa tttattaagc   3000
```

```
ccatcttgga aaaaatggac ggcaccgagg agctgctggt aaagctgaac agagaagatc   3060
tgttgcgcaa acagcgcact ttcgacaatg aagcatccc ccaccagatt cacctgggcg    3120
aactgcacgc tatcctcagg cggcaagagg atttctaccc cttttttgaaa gataacaggg   3180 aaaagattga gaaatcctc acatttcgga taccctacta tgtaggcccc ctcgctcggg     3240
gaaattccag attcgcgtgg atgactcgca aatcagaaga gaccatcact ccctggaact   3300
tcgaggaagt cgtggataag ggggcctctg cccagtcctt catcgaaagg atgactaact   3360
ttgataaaaa tctgcctaac gaaaaggtgc ttcctaaaca ctctctgctg tacgagtact   3420
tcacagttta taacgagctc accaaggtca aatacgtcac agaagggatg agaaagccag   3480
cattcctgtc tggagagcag aagaaagcta tcgtggacct cctcttcaag acgaaccgga   3540
aagttaccgt gaaacagctc aaagaagact atttcaaaaa gattgaatgt ttcgactctg   3600
ttgaaatcag cggagtggag gatcgcttca acgcatccct gggaacgtat cacgatctcc   3660
tgaaaatcat taaagacaag gacttcctgg acaatgagga gaacgaggac attcttgagg   3720
acattgtcct caccccttacg ttgtttgaag atagggagat gattgaagaa cgcttgaaaaa   3780 cttacgctca tctcttcgac gacaaagtca tgaaacagct caagagacgc cgatatacag   3840 gatggggcg gctgtcaaga aaactgatca atggcatccg agacaagcag agtggaaaga   3900
caatcctgga ttttcttaag tccgatggat ttgccaaccg gaacttcatg cagttgatcc   3960
atgatgactc tctcaccttt aaggaggaca tccagaaagc acaagtttct ggccagggg   4020 acagtcttca cgagcacatc gctaatcttg caggtagccc agctatcaaa aagggaatac   4080
tgcagaccgt taaggtcgtg gatgaactcg tcaaagtaat gggaaggcat aagcccgaga   4140
atatcgttat cgagatggcc cgagagaacc aaactaccca gaagggacag aagaacagta   4200
gggaaaggat gaagaggatt gaagagggta taaaagaact ggggtcccaa atccttaagg   4260
aacacccagt tgaaaacacc cagcttcaga atgagaagct ctacctgtac tacctgcaga   4320
acggcaggga catgtacgtg gatcaggaac tggacatcaa ccggttgtcc gactacgacg   4380
tggatcatat cgtgccccaa agctttctca agatgattc tattgataat aaagtgttga   4440
caagatccga taaaaataga gggaagagtg ataacgtccc ctcagaagaa gttgtcaaga   4500
aaatgaaaaa ttattggcgg cagctgctga acgccaaact gatcacacaa cggaagttcg   4560
ataatctgac taaggctgaa cgaggtggcc tgtctgagtt ggataaagcc ggcttcatca   4620
aaaggcagct tgttgagaca cgccagatca ccaagcacgt ggcccaaatt ctcgattcac   4680
gcatgaacac caagtacgat gaaaatgaca aactgattcg agaggtgaaa gttattactc   4740
tgaagtctaa gctggtctca gatttcagaa aggactttca gttttataag gtgagagaga   4800
tcaacaatta ccaccatgcg catgatgcct acctgaatgc agtggtaggc actgcactta   4860
tcaaaaaata tcccaagctg gaatctgaat tgtttacgg agactataaa gtgtacgatg   4920
ttaggaaaat gatcgcaaag tctgagcagg aaataggcaa ggccaccgct aagtacttct   4980
tttacagcaa tattatgaat ttttttcaaga ccgagattac actggccaat ggagagattc   5040
ggaagcgacc acttatcgaa acaaacggag aaacaggaga aatcgtgtgg gacaagggta   5100
gggatttcgc gacagtccgc aaggtcctgt ccatgccgca ggtgaacatc gttaaaaaga   5160
ccgaagtaca gaccggaggc ttctccaagg aaagtatcct cccgaaaagg aacagcgaca   5220
agctgatcgc acgcaaaaaa gattgggacc ccaagaaata cggcggattc gattctccta   5280
cagtcgctta cagtgtactg gttgtggcca agtggagaa agggagtct aaaaaactca   5340 aaagcgtcaa ggaactgctg ggcatcacaa tcatggagcg atccagcttc gagaaaaacc   5400
```

```
ccatcgactt tctcgaagcg aaaggatata agagggtcaa aaagacctc atcattaagc    5460 tgcccaagta ctctctcttt gagcttgaaa acggccggaa acgaatgctc gctagtgcgg    5520
gcgagctgca gaaaggtaac gagctggcac tgccctctaa atacgttaat ttcttgtatc    5580
tggccagcca ctatgaaaag ctcaaagggt ctcccgaaga taatgagcag aagcagctgt    5640
tcgtggaaca acacaaacac taccttgatg agatcatcga gcaaataagc gagttctcca    5700
aaagagtgat cctcgccgac gctaacctcg ataaggtgct ttctgcttac aataagcaca    5760
gggataagcc catcagggag caggcagaaa acattatcca cttgtttact ctgaccaact    5820
tgggcgcgcc tgcagccttc aagtacttcg acaccaccat agacagaaag cggtacacct    5880
ctacaaagga ggtcctggac gccacactga ttcatcagtc aattacgggg ctctatgaaa    5940
caagaatcga cctctctcag ctcggtggag acggcaccgg cgggcccaag aagaagagga    6000
aggtataccc atacgatgtt cctgactatg cgggctatcc ctatgacgtc ccggactatg    6060
caggatcgta tccttatgac gttccagatt acgctggatc ctaatgattc gaatccggat    6120
aagcggccgc ctcgagatat ctagacccag ctttcttgta caaagtggtt gatcctctcg    6180
agcctctaga actatagtga gtcgtattac gtagatccag acatgataag atacattgat    6240
gagtttggac aaaccacaac tagaatgcag tgaaaaaaat gctttatttg tgaaatttgt    6300
gatgctattg cttatttgt aaccattata agctgcaata acaagttaa caacaacaat    6360 tgcattcatt ttatgtttca ggttcagggg gaggtgtggg aggtttttta attcgcggcc    6420
gcggcgccaa tgcattgggc ccggtaccca gcttttgttc cctttagtga gggttaattg    6480
cgcgcttggc gtaatcatgg tcatagctgt ttcctgtgtg aaattgttat ccgctcacaa    6540
ttccacacaa catacgagcc ggaagcataa agtgtaaagc ctggggtgcc taatgagtga    6600
gctaactcac attaattgcg ttgcgctcac tgcccgcttt ccagtcggga aacctgtcgt    6660
gccagctgca ttaatgaatc ggccaacgcg cggggagagg cggtttgcgt attgggcgct    6720
cttccgcttc ctcgctcact gactcgctgc gctcggtcgt tcggctgcgg cgagcggtat    6780
cagctcactc aaaggcggta atacggttat ccacagaatc aggggataac gcaggaaaga    6840
acatgtgagc aaaaggccag caaaaggcca ggaaccgtaa aaaggccgcg ttgctggcgt    6900
ttttccatag gctccgcccc cctgacgagc atcacaaaaa tcgacgctca agtcagaggt    6960
ggcgaaaccc gacaggacta taaagatacc aggcgtttcc ccctggaagc tccctcgtgc    7020
gctctcctgt tccgaccctg ccgcttaccg gatacctgtc cgcctttctc ccttcgggaa    7080
gcgtggcgct ttctcatagc tcacgctgta ggtatctcag ttcggtgtag tcgttcgct    7140 ccaagctggg ctgtgtgcac gaaccccccg ttcagcccga ccgctgcgcc ttatccggta    7200
actatcgtct tgagtccaac ccggtaagac acgacttatc gccactggca gcagccactg    7260
gtaacaggat tagcagagcg aggtatgtag gcggtgctac agagttcttg aagtggtggc    7320
ctaactacgg ctacactaga aggacagtat ttggtatctg cgctctgctg aagccagtta    7380
ccttcggaaa aagagttggt agctcttgat ccggcaaaca aaccaccgct ggtagcggtg    7440
gtttttttgt ttgcaagcag cagattacgc gcagaaaaaa aggatctcaa gaagatcctt    7500
tgatcttttc tacggggtct gacgctcagt ggaacgaaaa ctcacgttaa gggattttgg    7560
tcatgagatt atcaaaaagg atcttcacct agatcctttt aaattaaaaa tgaagtttta    7620
aatcaatcta agtatatat gagtaaactt ggtctgacag ttaccaatgc ttaatcagtg    7680
aggcacctat ctcagcgatc tgtctatttc gttcatccat agttgcctga ctccccgtcg    7740
```

```
tgtagataac tacgatacgg gagggcttac catctggccc cagtgctgca atgataccgc    7800
gagacccacg ctcaccggct ccagatttat cagcaataaa ccagccagcc ggaagggccg    7860
agcgcagaag tggtcctgca actttatccg cctccatcca gtctattaat tgttgccggg    7920
aagctagagt aagtagttcg ccagttaata gtttgcgcaa cgttgttgcc attgctacag    7980
gcatcgtggt gtcacgctcg tcgtttggta tggcttcatt cagctccggt tcccaacgat    8040
caaggcgagt tacatgatcc cccatgttgt gcaaaaaagc ggttagctcc ttcggtcctc    8100
cgatcgttgt cagaagtaag ttggccgcag tgttatcact catggttatg gcagcactgc    8160
ataattctct tactgtcatg ccatccgtaa gatgcttttc tgtgactggt gagtactcaa    8220
ccaagtcatt ctgagaatag tgtatgcggc gaccgagttg ctcttgcccg cgtcaatac    8280
gggataatac cgcgccacat agcagaactt taaaagtgct catcattgga aaacgttctt    8340
cggggcgaaa actctcaagg atcttaccgc tgttgagatc cagttcgatg taacccactc    8400
gtgcacccaa ctgatcttca gcatctttta ctttcaccag cgtttctggg tgagcaaaaa    8460
caggaaggca aaatgccgca aaaaagggaa taagggcgac acggaaatgt tgaatactca    8520
tactcttcct ttttcaatat tattgaagca tttatcaggg ttattgtctc atgagcggat    8580
acatatttga atgtatttag aaaaataaac aaataggggg tccgcgcaca tttccccgaa    8640
aagtgccacc taaattgtaa gcgttaatat tttgttaaaa ttcgcgttaa attttgtta    8700
aatcagctca tttttaacc aataggccga atcggcaaa atcccttata aatcaaaaga    8760
atagaccgag atagggttga gtgttgttcc agtttggaac aagagtccac tattaaagaa    8820
cgtggactcc aacgtcaaag ggcgaaaaac cgtctatcag ggcgatggcc cactacgtga    8880
accatcaccc taatcaagtt tttttggggtc gaggtgccgt aaagcactaa atcggaaccc    8940
taaagggagc cccgatttta gagcttgacg gggaaagccg cgaacgtgg cgagaaagga    9000
agggaagaaa gcgaaaggag cgggcgctag ggcgctggca agtgtagcgg tcacgctgcg    9060
cgtaaccacc acaccgccg cgcttaatgc gccgctacag ggcgcgtccc attcgccatt    9120
caggctgcgc aactgttggg aagggcgatc ggtgcgggcc tcttcgctat tacgccagtc    9180
gaccatagcc aattcaatat ggcgtatatg gactcatgcc aattcaatat ggtggatctg    9240
gacctgtgcc aattcaatat ggcgtatatg gactcgtgcc aattcaatat ggtggatctg    9300
gaccccagcc aattcaatat ggcggacttg gcaccatgcc aattcaatat ggcggacttg    9360
gcactgtgcc aactggggag gggtctactt ggcacggtgc caagtttgag gagggtctt    9420
ggccctgtgc caagtccgcc atattgaatt ggcatggtgc caataatggc ggccatattg    9480
gctatatgcc aggatcaata tataggcaat atccaatatg gccctatgcc aatatggcta    9540
ttggccaggt tcaatactat gtattggccc tatgccatat agtattccat atatgggttt    9600
tcctattgac gtagatagcc cctcccaatg ggcggtccca tataccatat atgggcttc    9660
ctaataccgc ccatagccac tcccccattg acgtcaatgg tctctatata tggtctttcc    9720
tattgacgtc atatgggcgg tcctattgac gtatatggcg cctcccccat tgacgtcaat    9780
tacggtaaat ggcccgcctg gctcaatgcc cattgacgtc aataggacca cccaccattg    9840
acgtcaatgg gatggctcat tgcccattca tatccgttct cacgcccct attgacgtca    9900
atgacggtaa atgcccact tggcagtaca tcaatatcta ttaatagtaa cttggcaagt    9960
acattactat tggaaggacg ccagggtaca ttggcagtac tcccattgac gtcaatggcg   10020
gtaaatggcc cgcgatggct gccaagtaca tccccattga cgtcaatggg gaggggcaat   10080
gacgcaaatg ggcgttccat tgacgtaaat gggcggtagg cgtgcctaat gggaggtcta   10140
```

<210> SEQ ID NO 71
<211> LENGTH: 8768
<212> TYPE: DNA
<213> ORGANISM: Artificial sequence
<220> FEATURE:
<223> OTHER INFORMATION: Synthetic

<400> SEQUENCE: 71

| | | | | | |
|---|---|---|---|---|---|
| accgccattc | tgcctgggga | cgtcggagca | agcttgattt | aggtgacact | atagaataca | 60 |
| agctacttgt | tcttttttgca | ggatcccatc | gattcgaatt | caaggatcaa | caagtttgta | 120 |
| caaaaaagca | ggctggcgcc | accatggaca | agaagtactc | cattgggctc | gatatcggta | 180 |
| ccaacagcgt | cggctgggcc | gtcattacgg | acgagtacaa | ggtgccgagc | aaaaaattca | 240 |
| aagttctggg | caataccgat | cgccacagca | taaagaagaa | cctcattgga | gccctcctgt | 300 |
| tcgactccgg | ggagacggcc | gaagccacgc | ggctcaaaag | aacagcacgg | cgcagatata | 360 |
| cccgcagaaa | gaatcggatc | tgctacctgc | aggagatctt | tagtaatgag | atggctaagg | 420 |
| tggatgactc | tttcttccat | aggctggagg | agtcctttt  | ggtggaggag | ataaaaagc  | 480 |
| acgagcgcca | cccaatcttt | ggcaatatcg | tggacgaggt | ggcgtaccat | gaaaagtacc | 540 |
| caaccatata | tcatctgagg | aagaagctgg | tagacagtac | tgataaggct | gacttgcgt  | 600 |
| tgatctatct | cgcgctggcg | cacatgatca | aatttcgggg | acacttcctc | atcgaggggg | 660 |
| acctgaaccc | agacaacagc | gatgtcgaca | aactctttat | ccaactggtt | cagacttaca | 720 |
| atcagctttt | cgaggagaac | ccgatcaacg | catccggcgt | tgacgccaaa | gcaatcctga | 780 |
| gcgctaggct | gtccaaatcc | cggcggctcg | aaaacctcat | cgcacagctc | cctggggaga | 840 |
| agaagaacgg | cctgtttggt | aatcttatcg | ccctgtcact | cgggctgacc | cccaacttta | 900 |
| aatctaactt | cgacctggcc | gaagatgcca | agctgcaact | gagcaaagac | acctacgatg | 960 |
| atgatctcga | caatctgctg | gcccagatcg | gcgaccagta | cgcagaccttt | ttttggcgg  | 1020 |
| caaagaacct | gtcagacgcc | attctgctga | gtgatattct | gcgagtgaac | acggagatca | 1080 |
| ccaaagctcc | gctgagcgct | agtatgatca | agcgctatga | tgagcaccac | caagacttga | 1140 |
| ctttgctgaa | ggcccttgtc | agacagcaac | tgcctgagaa | gtacaaggaa | atttctctcg | 1200 |
| atcagtctaa | aaatggctac | gccggataca | ttgacggcgg | agcaagccag | gaggaattt  | 1260 |
| acaaatttat | taagcccatc | ttggaaaaaa | tggacggcac | cgaggagctg | ctggtaaagc | 1320 |
| tgaacagaga | agatctgttg | cgcaaacagc | gcactttcga | caatggaagc | atcccccacc | 1380 |
| agattcacct | gggcgaactg | cacgctatcc | tcaggcggca | agaggatttc | taccccttt  | 1440 |
| tgaaagataa | cagggaaaag | attgagaaaa | tcctcacatt | tcggataccc | tactatgtag | 1500 |
| gccccctcgc | tcggggaaat | tccagattcg | cgtggatgac | tcgcaaatca | gaagagacca | 1560 |
| tcactccctg | gaacttcgag | gaagtcgtgg | ataagggggc | tctgcccag  | tccttcatcg | 1620 |
| aaaggatgac | taactttgat | aaaaatctgc | ctaacgaaaa | ggtgcttcct | aaacactctc | 1680 |
| tgctgtacga | gtacttcaca | gtttataacg | agctcaccaa | ggtcaaatac | gtcacagaag | 1740 |
| ggatgagaaa | gccagcattc | ctgtctggag | agcagaagaa | agctatcgtg | gacctcctct | 1800 |
| tcaagacgaa | ccggaaagtt | accgtgaaac | agctcaaaga | agactatttc | aaaaagattg | 1860 |
| aatgtttcga | ctctgttgaa | atcagcggag | tggaggatcg | cttcaacgca | tccctgggaa | 1920 |
| cgtatcacga | tctcctgaaa | atcattaaag | acaaggactt | cctggacaat | gaggagaacg | 1980 |

```
aggacattct tgaggacatt gtcctcaccc ttacgttgtt tgaagatagg gagatgattg    2040
aagaacgctt gaaaacttac gctcatctct tcgacgacaa agtcatgaaa cagctcaaga    2100
gacgccgata tacaggatgg gggcggctgt caagaaaact gatcaatggc atccgagaca    2160
agcagagtgg aaagacaatc ctggattttc ttaagtccga tggatttgcc aaccggaact    2220
tcatgcagtt gatccatgat gactctctca cctttaagga ggacatccag aaagcacaag    2280
tttctggcca gggggacagt cttcacgagc acatcgctaa tcttgcaggt agcccagcta    2340
tcaaaaaggg aatactgcag accgttaagg tcgtggatga actcgtcaaa gtaatgggaa    2400
ggcataagcc cgagaatatc gttatcgaga tggcccgaga gaaccaaact acccagaagg    2460
gacagaagaa cagtagggaa aggatgaaga ggattgaaga gggtataaaa gaactggggt    2520
cccaaatcct taaggaacac ccagttgaaa cacccagct tcagaatgag aagctctacc     2580
tgtactacct gcagaacggc agggacatgt acgtggatca ggaactggac atcaaccggt    2640
tgtccgacta cgacgtggat catatcgtgc cccaaagctt tctcaaagat gattctattg    2700
ataataaagt gttgacaaga tccgataaaa atagagggaa gagtgataac gtcccctcag    2760
aagaagttgt caagaaaatg aaaaattatt ggcggcagct gctgaacgcc aaactgatca    2820
cacaacggaa gttcgataat ctgactaagg ctgaacgagg tggcctgtct gagttggata    2880
aagccggctt catcaaaagg cagcttgttg agacacgcca gatcaccaag cacgtggccc    2940
aaattctcga ttcacgcatg aacaccaagt acgatgaaaa tgacaaactg attcgagagg    3000
tgaaagttat tactctgaag tctaagctgg tctcagattt cagaaaggac tttcagtttt    3060
ataaggtgag agagatcaac aattaccacc atgcgcatga tgcctacctg aatgcagtgg    3120
taggcactgc acttatcaaa aaatatccca agctggaatc tgaatttgtt tacggagact    3180
ataaagtgta cgatgttagg aaaatgatcg caaagtctga gcaggaaata ggcaaggcca    3240
ccgctaagta cttcttttac agcaatatta tgaattttt caagaccgag attacactgg     3300
ccaatggaga gattcggaag cgaccactta tcgaaacaaa cggagaaaca ggagaaatcg    3360
tgtgggacaa gggtagggat ttcgcgacag tccgcaaggt cctgtccatg ccgcaggtga    3420
acatcgttaa aaagaccgaa gtacagaccg gaggcttctc caaggaaagt atcctcccga    3480
aaaggaacag cgacaagctg atcgcacgca aaaaagattg gaccccaag aaatacggcg     3540 gattcgattc tcctacagtc gcttacagtg tactggttgt ggccaaagtg agaaaggga    3600 agtctaaaaa actcaaaagc gtcaaggaac tgctgggcat cacaatcatg gagcgatcca    3660
gcttcgagaa aaaccccatc gactttctcg aagcgaaagg atataaagag gtcaaaaaag    3720
acctcatcat taagctgccc aagtactctc tctttgagct tgaaaacggc cggaaacgaa    3780
tgctcgctag tgcgggcgag ctgcagaaag gtaacgagct ggcactgccc tctaaatacg    3840
ttaatttctt gtatctggcc agccactatg aaaagctcaa agggtctccc gaagataatg    3900
agcagaagca gctgttcgtg gaacaacaca aacactacct tgatgagatc atcgagcaaa    3960
taagcgagtt ctccaaaaga gtgatcctcg ccgacgctaa cctcgataag gtgctttctg    4020
cttacaataa gcacagggat aagcccatca gggagcaggc agaaaacatt atccacttgt    4080
ttactctgac caacttgggc gcgcctgcag ccttcaagta cttcgacacc accatagaca    4140
gaaagcggta cacctctaca aaggaggtcc tggacgccac actgattcat cagtcaatta    4200
cggggctcta tgaaacaaga atcgacctct ctcagctcgg tggagacggc accggcgggc    4260
ccaagaagaa gaggaaggta tacccatacg atgttcctga ctatgcgggc tatccctatg    4320
acgtcccgga ctatgcagga tcgtatcctt atgacgttcc agattacgct ggatccgccg    4380
```

```
ctccggcagc taagaaaaag aaactggatt tcgaatccgg aaagccctat aaatgtcctg    4440
aatgtggcaa gtccttctcg gagaagagcc acctgacacg gcaccaacgc acgcacactg    4500
gtgagaagcc atacgcgtgt cctgtcgagt cctgtgaccg ccgcttcagt cggagcgacc    4560
acctgacaca gcacatccgc attcacacag ggcaaaaacc gtttcaatgc cgcatctgca    4620
tgaggaactt cagcgacaag ggccacctga cccggcacat ccgcacccac acaggagaaa    4680
agcccttcgc ctgtgacatc tgcggcagga agttcgcgcg gagcgacgac ctgacacggc    4740
acaccaagat ccacctccgt cagaaagacc ccgggtaatg actcgagcct ctagaactat    4800
agtgagtcgt attacgtaga tccagacatg ataagataca ttgatgagtt tggacaaacc    4860
acaactagaa tgcagtgaaa aaatgctttt atttgtgaaa tttgtgatgc tattgcttta    4920
tttgtaacca ttataagctg caataaacaa gttaacaaca acaattgcat tcattttatg    4980
tttcaggttc aggggggagt gtgggaggtt ttttaattcg cggccgcggc gccaatgcat    5040
tgggcccggt acccagcttt tgttcccttt agtgagggtt aattgcgcgc ttggcgtaat    5100
catggtcata gctgtttcct gtgtgaaatt gttatccgct cacaattcca cacaacatac    5160
gagccggaag cataaagtgt aaagcctggg gtgcctaatg agtgagctaa ctcacattaa    5220
ttgcgttgcg ctcactgccc gctttccagt cgggaaacct gtcgtgccag ctgcattaat    5280
gaatcggcca acgcgcgggg agaggcggtt tgcgtattgg gcgctcttcc gcttcctcgc    5340
tcactgactc gctgcgctcg tcgttcggc tgcggcgagc ggtatcagct cactcaaagg    5400
cggtaatacg gttatccaca gaatcagggg ataacgcagg aaagaacatg tgagcaaaag    5460
gccagcaaaa ggccaggaac cgtaaaaagg ccgcgttgct ggcgtttttc cataggctcc    5520
gcccccctga cgagcatcac aaaaatcgac gctcaagtca gaggtggcga acccgacag    5580 gactataaag ataccaggcg tttccccctg gaagctccct cgtgcgctct cctgttccga    5640
ccctgccgct taccggatac ctgtccgcct ttctcccttc gggaagcgtg gcgctttctc    5700
atagctcacg ctgtaggtat ctcagttcgg tgtaggtcgt tcgctccaag ctgggctgtg    5760
tgcacgaacc ccccgttcag cccgaccgct gcgccttatc cggtaactat cgtcttgagt    5820
ccaacccggt aagacacgac ttatcgccac tggcagcagc cactggtaac aggattagca    5880
gagcgaggta tgtaggcggt gctacagagt tcttgaagtg gtggcctaac tacggctaca    5940
ctagaaggac agtatttggt atctgcgctc tgctgaagcc agttaccttc ggaaaaagag    6000
ttggtagctc ttgatccggc aaacaaacca ccgctggtag cggtggtttt tttgtttgca    6060
agcagcagat tacgcgcaga aaaaaggat ctcaagaaga tcctttgatc ttttctacgg    6120
ggtctgacgc tcagtggaac gaaaactcac gttaagggat tttggtcatg agattatcaa    6180
aaaggatctt cacctagatc cttttaaatt aaaaatgaag ttttaaatca atctaaagta    6240
tatatgagta aacttggtct gacagttacc aatgcttaat cagtgaggca cctatctcag    6300
cgatctgtct atttcgttca tccatagttg cctgactccc cgtcgtgtag ataactacga    6360
tacgggaggg cttaccatct ggccccagtg ctgcaatgat accgcgagac ccacgctcac    6420
cggctccaga tttatcagca ataaaccagc cagccggaag ggccgagcgc agaagtggtc    6480
ctgcaacttt atccgcctcc atccagtcta ttaattgttg ccgggaagct agagtaagta    6540
gttcgccagt taatagtttg cgcaacgttg ttgccattgc tacaggcatc gtggtgtcac    6600
gctcgtcgtt tggtatggct tcattcagct ccggttccca acgatcaagg cgagttacat    6660
gatcccccat gttgtgcaaa aaagcggtta gctccttcgg tcctccgatc gttgtcagaa    6720
```

```
gtaagttggc cgcagtgtta tcactcatgg ttatggcagc actgcataat tctcttactg   6780
tcatgccatc cgtaagatgc ttttctgtga ctggtgagta ctcaaccaag tcattctgag   6840
aatagtgtat gcggcgaccg agttgctctt gcccggcgtc aatacgggat aataccgcgc   6900
cacatagcag aactttaaaa gtgctcatca ttggaaaacg ttcttcgggg cgaaaactct   6960
caaggatctt accgctgttg agatccagtt cgatgtaacc cactcgtgca cccaactgat   7020
cttcagcatc ttttactttc accagcgttt ctgggtgagc aaaaacagga aggcaaaatg   7080
ccgcaaaaaa gggaataagg gcgacacgga aatgttgaat actcatactc ttcctttttc   7140
aatattattg aagcatttat cagggttatt gtctcatgag cggatacata tttgaatgta   7200
tttagaaaaa taaacaaata ggggttccgc gcacatttcc ccgaaaagtg ccacctaaat   7260
tgtaagcgtt aatattttgt taaaattcgc gttaaatttt tgttaaatca gctcattttt   7320
taaccaatag gccgaaatcg gcaaaatccc ttataaatca aagaataga ccgagatagg   7380 gttgagtgtt gttccagttt ggaacaagag tccactatta agaacgtgg actccaacgt   7440 caaagggcga aaaccgtct atcagggcga tgggcccacta cgtgaaccat caccctaatc   7500
aagttttttg gggtcgaggt gccgtaaagc actaaatcgg aaccctaaag ggagcccccg   7560
atttagagct tgacggggaa agccggcgaa cgtggcgaga aggaaggga agaaagcgaa   7620 aggagcgggc gctagggcgc tggcaagtgt agcggtcacg ctgcgcgtaa ccaccacacc   7680
cgccgcgctt aatgcgccgc tacagggcgc gtcccattcg ccattcaggc tgcgcaactg   7740
ttgggaaggg cgatcggtgc gggcctcttc gctattacgc cagtcgacca tagccaattc   7800
aatatggcgt atatggactc atgccaattc aatatggtgg atctggacct gtgccaattc   7860
aatatggcgt atatggactc gtgccaattc aatatggtgg atctggaccc cagccaattc   7920
aatatggcgc acttggcacc atgccaattc aatatggcgg acttggcact gtgccaactg   7980
gggaggggtc tacttggcac ggtgccaagt ttgaggaggg gtcttggccc tgtgccaagt   8040 ccgcccatatt gaattggcat ggtgccaata atggcggcca tattggctat atgccaggat   8100
caatatatag gcaatatcca atatggcccct atgccaatat ggctattggc caggttcaat   8160
actatgtatt ggccctatgc catatagtat tccatatatg ggttttccta ttgacgtaga   8220
tagcccctcc caatgggcgg tcccatatac catatatggg gcttcctaat accgcccata   8280
gccactcccc cattgacgtc aatggtctct atatatggtc tttcctattg acgtcatatg   8340
ggcggtccta ttgacgtata tggcgcctcc cccattgacg tcaattacgg taaatggccc   8400
gcctggctca atgcccattg acgtcaatag gaccacccac cattgacgtc aatgggatgg   8460
ctcattgccc attcatatcc gttctcacgc ccctattga cgtcaatgac ggtaaatggc   8520
ccacttggca gtacatcaat atctattaat agtaacttgg caagtacatt actattggaa   8580
ggacgccagg gtacattggc agtactccca ttgacgtcaa tggcggtaaa tggcccgcga   8640
tggctgccaa gtacatcccc attgacgtca atggggaggg gcaatgacgc aaatgggcgt   8700
tccattgacg taaatgggcg gtaggcgtgc ctaatgggag gtctatataa gcaatgctcg   8760
tttaggga                                                          8768
```

<210> SEQ ID NO 72
<211> LENGTH: 8768
<212> TYPE: DNA
<213> ORGANISM: Artificial sequence
<220> FEATURE:
<223> OTHER INFORMATION: Synthetic

<400> SEQUENCE: 72

-continued

```
accgccattc tgcctgggga cgtcggagca agcttgattt aggtgacact atagaataca    60
agctacttgt tcttttgca ggatcccatc gattcgaatt caaggatcaa caagtttgta    120
caaaaaagca ggctggcgcc accatggaca agaagtactc cattgggctc gatatcggta   180
ccaacagcgt cggctgggcc gtcattacgg acgagtacaa ggtgccgagc aaaaaattca   240
aagttctggg caataccgat cgccacagca taaagaagaa cctcattgga gccctcctgt   300
tcgactccgg ggagacggcc gaagccacgg ggctcaaaag aacagcacgg cgcagatata   360
cccgcagaaa gaatcggatc tgctacctgc aggagatctt tagtaatgag atggctaagg   420
tggatgactc tttcttccat aggctggagg agtccttttt ggtggaggag gataaaaagc   480
acgagcgcca cccaatcttt ggcaatatcg tggacgaggt ggcgtaccat gaaaagtacc   540
caaccatata tcatctgagg aagaagctgg tagacagtac tgataaggct gacttgcggt   600
tgatctatct cgcgctggcg cacatgatca aatttcgggg acacttcctc atcgagggg   660
acctgaaccc agacaacagc gatgtcgaca aactctttat ccaactggtt cagacttaca   720
atcagctttt cgaggagaac ccgatcaacg catccggcgt tgacgccaaa gcaatcctga   780
gcgctaggct gtccaaatcc cggcggctcg aaaacctcat cgcacagctc ctggggaga    840
agaagaacgg cctgtttggt aatcttatcg ccctgtcact cgggctgacc cccaacttta   900
aatctaactt cgacctggcc gaagatgcca agctgcaact gagcaaagac acctacgatg   960
atgatctcga caatctgctg gcccagatcg gcgaccagta cgcagaccct tttttggcgg  1020
caaagaacct gtcagacgcc attctgctga gtgatattct gcgagtgaac acggagatca  1080
ccaaagctcc gctgagcgct agtatgatca agcgctatga tgagcaccac caagacttga  1140
ctttgctgaa ggcccttgtc agacagcaac tgcctgagaa gtacaaggaa attttcttcg  1200
atcagtctaa aaatggctac gccggataca ttgacggcgg agcaagccag gaggaatttt  1260
acaaatttat taagcccatc ttggaaaaaa tggacggcac cgaggagctg ctggtaaagc  1320
tgaacagaga agatctgttg cgcaaacagc gcactttcga caatggaagc atcccccacc  1380
agattcacct gggcgaactg cacgctatcc tcaggcggca agaggatttc taccccttt   1440
tgaaagataa cagggaaaag attgagaaaa tcctcacatt tcggatacc tactatgtag   1500
gcccctcgc tcggggaaat tccagattcg cgtggatgac tcgcaaatca gaagagacca   1560
tcactccctg gaacttcgag gaagtcgtgg ataaggggc ctctgcccag tccttcatcg   1620
aaaggatgac taactttgat aaaaatctgc ctaacgaaaa ggtgcttcct aaacactctc   1680
tgctgtacga gtacttcaca gtttataacg agctcaccaa ggtcaaatac gtcacagaag   1740
ggatgagaaa gccagcattc ctgtctggag agcagaagaa agctatcgtg gacctcctct   1800
tcaagacgaa ccgaaagtt accgtgaaac agctcaaaga agactatttc aaaaagattg   1860
aatgtttcga ctctgttgaa atcagcggag tggaggatcg cttcaacgca tccctgggaa   1920
cgtatcacga tctcctgaaa atcattaaag acaaggactt cctggacaat gaggagaacg   1980
aggacattct tgaggacatt gtcctcaccc ttacgttgtt tgaagatagg gagatgattg   2040
aagaacgctt gaaaacttac gctcatctct tcgacgacaa agtcatgaaa cagctcaaga   2100
gacgccgata taccaggatgg gggcggctgt caagaaaact gatcaatggc atccgagaca   2160
agcagagtgg aaagacaatc ctggattttc ttaagtccga tggatttgcc aaccggaact   2220
tcatgcagtt gatccatgat gactctctca cctttaagga ggacatccag aaagcacaag   2280
tttctggcca gggggacagt cttcacgagc acatcgctaa tcttgcaggt agcccagcta  2340
```

-continued

```
tcaaaaaggg aatactgcag accgttaagg tcgtggatga actcgtcaaa gtaatgggaa    2400
ggcataagcc cgagaatatc gttatcgaga tggcccgaga gaaccaaact acccagaagg    2460
gacagaagaa cagtagggaa aggatgaaga ggattgaaga gggtataaaa gaactggggt    2520
cccaaatcct taaggaacac ccagttgaaa acacccagct tcagaatgag aagctctacc    2580
tgtactacct gcagaacggc agggacatgt acgtggatca ggaactggac atcaaccggt    2640
tgtccgacta cgacgtggat catatcgtgc cccaaagctt tctcaaagat gattctattg    2700
ataataaagt gttgacaaga tccgataaaa atagagggaa gagtgataac gtcccctcag    2760
aagaagttgt caagaaaatg aaaaattatt ggcggcagct gctgaacgcc aaactgatca    2820
cacaacggaa gttcgataat ctgactaagg ctgaacgagg tggcctgtct gagttggata    2880
aagccggctt catcaaaagg cagcttgttg agacacgcca gatcaccaag cacgtggccc    2940
aaattctcga ttcacgcatg aacaccaagt acgatgaaaa tgacaaactg attcgagagg    3000
tgaaagttat tactctgaag tctaagctgg tctcagattt cagaaaggac tttcagtttt    3060
ataaggtgag agagatcaac aattaccacc atgcgcatga tgcctacctg aatgcagtgg    3120
taggcactgc acttatcaaa aaatatccca agctggaatc tgaatttgtt tacggagact    3180
ataaagtgta cgatgttagg aaaatgatcg caaagtctga gcaggaaata ggcaaggcca    3240
ccgctaagta cttcttttac agcaatatta tgaatttttt caagaccgag attacactgg    3300
ccaatggaga gattcggaag cgaccactta tcgaaacaaa cggagaaaca ggagaaatcg    3360
tgtgggacaa gggtagggat ttcgcgacag tccgcaaggt cctgtccatg ccgcaggtga    3420
acatcgttaa aaagaccgaa gtacagaccg gaggcttctc caaggaaagt atcctcccga    3480
aaaggaacag cgacaagctg atcgcacgca aaaagattg ggaccccaag aaatacggcg    3540
gattcgattc tcctacagtc gcttacagtg tactggttgt ggccaaagtg gagaaaggga    3600
agtctaaaaa actcaaaagc gtcaaggaac tgctgggcat cacaatcatg gagcgatcca    3660
gcttcgagaa aaaccccatc gactttctcg aagcgaaagg atataagag gtcaaaaaag    3720 acctcatcat taagctgccc aagtactctc tctttgagct tgaaaacggc cggaaacgaa    3780
tgctcgctag tgcgggcgag ctgcagaaag gtaacgagct ggcactgccc tctaaatacg    3840
ttaatttctt gtatctggcc agccactatg aaaagctcaa agggtctccc gaagataatg    3900
agcagaagca gctgttcgtg gaacaacaca acactacct tgatgagatc atcgagcaaa    3960
taagcgagtt ctccaaaaga gtgatcctcg ccgacgctaa cctcgataag gtgctttctg    4020
cttacaataa gcacagggat aagcccatca gggagcaggc agaaaacatt atccacttgt    4080
ttactctgac caacttgggc gcgcctgcag ccttcaagta cttcgacacc accatagaca    4140
gaaagaagta cacctctaca aaggaggtcc tggacgccac actgattcat cagtcaatta    4200
cggggctcta tgaaacaaga atcgacctct ctcagctcgg tggagacggc accggcgggc    4260
ccaagaagaa gaggaaggta tacccatacg atgttcctga ctatgcgggc tatccctatg    4320
acgtcccgga ctatgcagga tcgtatcctt atgacgttcc agattacgct ggatccgccg    4380
ctccggcagc taagaaaaag aaactggatt tcgaatccgg aaagccctat aaatgtcctg    4440
aatgtggcaa gtccttctcg gagaagagcc acctgacacg gcaccaacgc acgcacactg    4500
gtgagaagcc atacgcgtgt cctgtcgagt cctgtgaccg ccgcttcagt cggagcgacc    4560
acctgacaca gcacatccgc attcacacag gcaaaaacc gtttcaatgc cgcatctgca    4620
tgaggaactt cagcgacaag ggccacctga cccggcacat ccgcacccac acaggagaaa    4680
agcccttcgc ctgtgacatc tgcggcagga agttcgcgcg gagcgacgac ctgacacggc    4740
```

```
acaccaagat ccacctccgt cagaaagacc ccgggtaatg actcgagcct ctagaactat   4800
agtgagtcgt attacgtaga tccagacatg ataagataca ttgatgagtt tggacaaacc   4860
acaactagaa tgcagtgaaa aaaatgcttt atttgtgaaa tttgtgatgc tattgcttta   4920
tttgtaacca ttataagctg caataaacaa gttaacaaca caattgcat tcattttatg    4980 tttcaggttc aggggaggt gtgggaggtt ttttaattcg cggccgcggc gccaatgcat    5040
tgggcccggt acccagcttt tgttcccttt agtgagggtt aattgcgcgc ttggcgtaat   5100
catggtcata gctgtttcct gtgtgaaatt gttatccgct cacaattcca cacaacatac   5160
gagccggaag cataaagtgt aaagcctggg gtgcctaatg agtgagctaa ctcacattaa   5220
ttgcgttgcg ctcactgccc gctttccagt cgggaaacct gtcgtgccag ctgcattaat   5280
gaatcggcca acgcgcgggg agaggcggtt tgcgtattgg gcgctcttcc gcttcctcgc   5340
tcactgactc gctgcgctcg gtcgttcggc tgcggcgagc ggtatcagct cactcaaagg   5400
cggtaatacg gttatccaca gaatcagggg ataacgcagg aaagaacatg tgagcaaaag   5460
gccagcaaaa ggccaggaac cgtaaaaagg ccgcgttgct ggcgtttttc cataggctcc   5520
gcccccctga cgagcatcac aaaaatcgac gctcaagtca gaggtggcga aacccgacag   5580
gactataaag ataccaggcg tttccccctg gaagctccct cgtgcgctct cctgttccga   5640
ccctgccgct taccggatac ctgtccgcct ttctcccttc gggaagcgtg gcgctttctc   5700
atagctcacg ctgtaggtat ctcagttcgg tgtaggtcgt tcgctccaag ctgggctgtg   5760
tgcacgaacc ccccgttcag cccgaccgct gcgccttatc cggtaactat cgtcttgagt   5820
ccaacccggt aagacacgac ttatcgccac tggcagcagc cactggtaac aggattagca   5880
gagcgaggta tgtaggcggt gctacagagt tcttgaagtg gtggcctaac tacggctaca   5940
ctagaaggac agtatttggt atctgcgctc tgctgaagcc agttaccttc ggaaaaagag   6000
ttggtagctc ttgatccggc aaacaaacca ccgctggtag cggtggtttt tttgtttgca   6060
agcagcagat tacgcgcaga aaaaaaggat ctcaagaaga tcctttgatc ttttctacgg   6120
ggtctgacgc tcagtggaac gaaaactcac gttaagggat tttggtcatg agattatcaa   6180
aaaggatctt cacctagatc cttttaaatt aaaaatgaag ttttaaatca atctaaagta   6240
tatatgagta aacttggtct gacagttacc aatgcttaat cagtgaggca cctatctcag   6300
cgatctgtct atttcgttca tccatagttg cctgactccc cgtcgtgtag ataactacga   6360
tacgggaggg cttaccatct ggccccagtg ctgcaatgat accgcgagac ccacgctcac   6420
cggctccaga tttatcagca ataaaccagc cagccggaag ggccgagcgc agaagtggtc   6480
ctgcaacttt atccgcctcc atccagtcta ttaattgttg ccgggaagct agagtaagta   6540
gttcgccagt taatagtttg cgcaacgttg ttgccattgc tacaggcatc gtggtgtcac   6600
gctcgtcgtt tggtatggct tcattcagct ccggttccca acgatcaagg cgagttacat   6660 gatccccat gttgtgcaaa aaagcggtta gctccttcgg tcctccgatc gttgtcagaa    6720
gtaagttggc cgcagtgtta tcactcatgg ttatggcagc actgcataat tctcttactg   6780
tcatgccatc cgtaagatgc ttttctgtga ctggtgagta ctcaaccaag tcattctgag   6840
aatagtgtat gcggcgaccg agttgctctt gcccggcgtc aatacgggat aataccgcgc   6900
cacatagcag aactttaaaa gtgctcatca ttggaaaacg ttcttcgggg cgaaaactct   6960
caaggatctt accgctgttg agatccagtt cgatgtaacc cactcgtgca cccaactgat   7020
cttcagcatc ttttactttc accagcgttt ctgggtgagc aaaaacagga aggcaaaatg   7080
```

```
ccgcaaaaaa gggaataagg gcgacacgga aatgttgaat actcatactc ttccttttc     7140
aatattattg aagcatttat cagggttatt gtctcatgag cggatacata tttgaatgta    7200
tttagaaaaa taaacaaata ggggttccgc gcacatttcc ccgaaaagtg ccacctaaat    7260
tgtaagcgtt aatattttgt taaaattcgc gttaaatttt tgttaaatca gctcattttt    7320
taaccaatag gccgaaatcg gcaaaatccc ttataaatca aaagaataga ccgagatagg    7380
gttgagtgtt gttccagttt ggaacaagag tccactatta agaacgtggg actccaacgt    7440
caaagggcga aaaccgtct atcagggcga tggcccacta cgtgaaccat caccctaatc     7500
aagttttttg gggtcgaggt gccgtaaagc actaaatcgg aaccctaaag ggagcccccg    7560
atttagagct tgacggggaa agccggcgaa cgtggcgaga aggaaggga agaaagcgaa      7620
aggagcgggc gctagggcgc tggcaagtgt agcggtcacg ctgcgcgtaa ccaccacacc    7680
cgccgcgctt aatgcgccgc tacagggcgc gtcccattcg ccattcaggc tgcgcaactg    7740
ttgggaaggg cgatcggtgc gggcctcttc gctattacgc cagtcgacca tagccaattc    7800
aatatggcgt atatggactc atgccaattc aatatggtgg atctggacct gtgccaattc    7860
aatatggcgt atatggactc gtgccaattc aatatggtgg atctggaccc cagccaattc    7920
aatatggcgg acttggcacc atgccaattc aatatggcgg acttggcact gtgccaactg    7980
gggaggggtc tacttggcac ggtgccaagt ttgaggaggg gtcttggccc tgtgccaagt    8040
ccgccatatt gaattggcat ggtgccaata atggcggcca tattggctat atgccaggat    8100
caatatatag gcaatatcca atatggcccct atgccaatat ggctattggc caggttcaat    8160
actatgtatt ggcccctatgc catatagtat tccatatatg ggttttccta ttgacgtaga    8220
tagcccctcc caatgggcgg tcccatatac catatatggg gcttcctaat accgcccata    8280
gccactcccc cattgacgtc aatggtctct atatatggtc tttcctattg acgtcatatg    8340
ggcggtccta ttgacgtata tggcgcctcc cccattgacg tcaattacgg taaatggccc    8400
gcctggctca atgcccattg acgtcaatag gaccacccac cattgacgtc aatgggatgg    8460
ctcattgccc attcatatcc gttctcacgc cccctattga cgtcaatgac ggtaaatggc    8520
ccacttggca gtacatcaat atctattaat agtaacttgg caagtacatt actattggaa    8580
ggacgccagg gtacattggc agtactccca ttgacgtcaa tggcggtaaa tggcccgcga    8640
tggctgccaa gtacatcccc attgacgtca atggggaggg gcaatgacgc aaatgggcgt    8700
tccattgacg taaatgggcg gtaggcgtgc ctaatgggag gtctatataa gcaatgctcg    8760
tttaggga                                                              8768
```

<210> SEQ ID NO 73  
<211> LENGTH: 8768  
<212> TYPE: DNA  
<213> ORGANISM: Artificial sequence  
<220> FEATURE:  
<223> OTHER INFORMATION: Synthetic

<400> SEQUENCE: 73

```
accgccattc tgcctgggga cgtcggagca agcttgattt aggtgacact atagaataca     60
agctacttgt tctttttgca ggatcccatc gattcgaatt caaggatcaa caagtttgta    120
caaaaaagca ggctggcgcc accatggaca agaagtactc cattgggctc gatatcggta    180
ccaacagcgt cggctgggcc gtcattacgg acgagtacaa ggtgccgagc aaaaaattca    240
aagttctggg caataccgat cgccacagca taaagaagaa cctcattgga gcctcctgt    300
tcgactccgg ggagacggcc gaagccacgc ggctcaaaag aacagcacgg cgcagatata    360
```

```
cccgcagaaa gaatcggatc tgctacctgc aggagatctt tagtaatgag atggctaagg    420
tggatgactc tttcttccat aggctggagg agtcctttt  ggtggaggag ataaaaagc    480 acgagcgcca cccaatcttt ggcaatatcg tggacgaggt ggcgtaccat gaaaagtacc    540
caaccatata tcatctgagg aagaagctgg tagacagtac tgataaggct gacttgcggt    600
tgatctatct cgcgctggcg cacatgatca aatttcgggg acacttcctc atcgaggggg    660
acctgaaccc agacaacagc gatgtcgaca aactctttat ccaactggtt cagacttaca    720
atcagctttt cgaggagaac ccgatcaacg catccggcgt tgacgccaaa gcaatcctga    780
gcgctaggct gtccaaatcc cggcggctcg aaaacctcat cgcacagctc ctggggaga     840 agaagaacgg cctgtttggt aatcttatcg ccctgtcact cgggctgacc cccaacttta    900
aatctaactt cgacctggcc gaagatgcca agctgcaact gagcaaagac acctacgatg    960
atgatctcga caatctgctg gcccagatcg gcgaccagta cgcagacctt tttttggcgg   1020
caaagaacct gtcagacgcc attctgctga gtgatattct gcgagtgaac acggagatca   1080
ccaaagctcc gctgagcgct agtatgatca agcgctatga tgagcaccac caagacttga   1140
ctttgctgaa ggcccttgtc agacagcaac tgcctgagaa gtacaaggaa attttcttcg   1200
atcagtctaa aaatggctac gccggataca ttgacggcgg agcaagccag gaggaatttt   1260
acaaatttat taagcccatc ttggaaaaaa tggacgcac  cgaggagctg ctggtaaagc   1320
tgaacagaga agatctgttg cgcaaacagc gcactttcga caatggaagc atcccccacc   1380
agattcacct gggcgaactg cacgctatcc tcaggcggca agaggatttc tacccctttt   1440
tgaaagataa cagggaaaag attgagaaaa tcctcacatt tcggataccc tactatgtag   1500
gccccctcgc tcggggaaat tccagattcg cgtggatgac tcgcaaatca gaagagacca   1560
tcactccctg gaacttcgag gaagtcgtgg ataaggggc  ctctgcccag tccttcatcg   1620
aaaggatgac taactttgat aaaaatctgc ctaacgaaaa ggtgcttcct aaacactctc   1680
tgctgtacga gtacttcaca gtttataacg agctcaccaa ggtcaaatac gtcacagaag   1740
ggatgagaaa gccagcattc ctgtctggag agcagaagaa agctatcgtg gacctcctct   1800
tcaagacgaa ccggaaagtt accgtgaaac agctcaaaga agactatttc aaaaagattg   1860 aatgttcga  ctctgttgaa atcagcggag tggaggatcg cttcaacgca tccctgggaa   1920
cgtatcacga tctcctgaaa atcattaaag acaaggactt cctggacaat gaggagaacg   1980
aggacattct tgaggacatt gtcctcaccc ttacgttgtt tgaagatagg gagatgattg   2040
aagaacgctt gaaaacttac gctcatctct tcgacgacaa agtcatgaaa cagctcaaga   2100
gacgccgata tacaggatgg gggcggctgt caagaaaact gatcaatggc atccgagaca   2160
agcagagtgg aaagacaatc ctggatttc  ttaagtccga tggatttgcc aaccggaact   2220
tcatgcagtt gatccatgat gactctctca cctttaagga ggacatccag aaagcacaag   2280
tttctggcca gggggacagt cttcacgagc acatcgctaa tcttgcaggt agcccagcta   2340
tcaaaaaggg aatactgcag accgttaagg tcgtggatga actcgtcaaa gtaatgggaa   2400
ggcataagcc cgagaatatc gttatcgaga tggcccgaga gaaccaaact acccagaagg   2460
gacagaagaa cagtagggaa aggatgaaga ggattgaaga gggtataaaa gaactggggt   2520
cccaaatcct taaggaacac ccagttgaaa cacccagct  tcagaatgag aagctctacc   2580
tgtactacct gcagaacggc agggacatgt acgtggatca ggaactggac atcaaccggt   2640
tgtccgacta cgacgtggat catatcgtgc cccaaagctt tctcaaagat gattctattg   2700
```

```
ataataaagt gttgacaaga tccgataaaa atagagggaa gagtgataac gtcccctcag    2760
aagaagttgt caagaaaatg aaaaattatt ggcggcagct gctgaacgcc aaactgatca    2820
cacaacggaa gttcgataat ctgactaagg ctgaacgagg tggcctgtct gagttggata    2880
aagccggctt catcaaaagg cagcttgttg agacacgcca gatcaccaag cacgtggccc    2940
aaattctcga ttcacgcatg aacaccaagt acgatgaaaa tgacaaactg attcgagagg    3000
tgaaagttat tactctgaag tctaagctgg tctcagattt cagaaaggac tttcagtttt    3060
ataaggtgag agagatcaac aattaccacc atgcgcatga tgcctacctg aatgcagtgg    3120
taggcactgc acttatcaaa aaatatccca agctggaatc tgaatttgtt tacggagact    3180
ataaagtgta cgatgttagg aaaatgatcg caaagtctga gcaggaaata ggcaaggcca    3240
ccgctaagta cttcttttac agcaatatta tgaatttttt caagaccgag attacactgg    3300
ccaatggaga gattcggaag cgaccactta tcgaaacaaa cggagaaaca ggagaaatcg    3360
tgtgggacaa gggtagggat ttcgcgacag tccgcaaggt cctgtccatg ccgcaggtga    3420
acatcgttaa aaagaccgaa gtacagaccg gaggcttctc caaggaaagt atcctcccga    3480
aaaggaacag cgacaagctg atcgcacgca aaaagattg ggaccccaag aaatacggcg    3540
gattcgattc tcctacagtc gcttacagtg tactggttgt ggccaaagtg gagaaaggga    3600
agtctaaaaa actcaaaagc gtcaaggaac tgctgggcat cacaatcatg gagcgatcca    3660
gcttcgaaaa aaacccatc gactttctcg aagcgaaagg atataaagag gtcaaaaaag    3720
acctcatcat taagctgccc aagtactctc tctttgagct tgaaaacggc cggaaacgaa    3780
tgctcgctag tgcgggcgag ctgcagaaag gtaacgagct ggcactgccc tctaaatacg    3840
ttaatttctt gtatctggcc agccactatg aaaagctcaa agggtctccc gaagataatg    3900
agcagaagca gctgttcgtg gaacaacaca acactacct tgatgagatc atcgagcaaa    3960
taagcgagtt ctccaaaaga gtgatcctcg ccgacgctaa cctcgataag gtgctttctg    4020
cttacaataa gcacagggat aagcccatca gggagcaggc agaaaacatt atccacttgt    4080
ttactctgac caacttgggc gcgcctgcag ccttcaagta cttcgacacc accatagaca    4140
gaaagcggta cacctctaca aaggaggtcc tggacgccac actgattcat cagtcaatta    4200
cggggctcta tgaaacaaga atcgacctct ctcagctcgg tggagacggc accggcgggc    4260
ccaagaagaa gaggaaggta tacccatacg atgttcctga ctatgcgggc tatcccatg    4320 acgtcccgga ctatgcagga tcgtatcctt atgacgttcc agattacgct ggatccgccg    4380
ctccggcagc taagaaaag aaactggatt tcgaatccgg aaagcccatat aaatgtcctg    4440 aatgtggcaa gtccttctcg cggagcgacg acctgacacg gcaccaacgt acgcacactg    4500
gtgagaagcc atacgcgtgt cctgtcgagt cctgtgaccg ccgcttcagt cagaagggac    4560
acctgacacg gcacatccgc attcacacag gcaaaaacc gtttcaatgc cgcatctgca    4620
tgaggaactt cagcatccgt agcagcctga cacggcacat ccgcacccac acaggagaaa    4680
agcccttcgc ctgtgacatc tgcggcagga agttcgcgct gagccaccac ctgacacggc    4740
acaccaagat ccacctccgt cagaaagacc ccgggtaatg actcgagcct ctagaactat    4800
agtgagtcgt attacgtaga tccagacatg ataagataca ttgatgagtt tggacaaacc    4860
acaactagaa tgcagtgaaa aaaatgcttt atttgtgaaa tttgtgatgc tattgcttta    4920
tttgtaacca ttataagctg caataaacaa gttaacaaca acaattgcat tcattttatg    4980
tttcaggttc agggggaggt gtgggaggtt ttttaattcg cggccgcggc gccaatgcat    5040
tgggcccggt acccagcttt tgttcccttt agtgagggtt aattgcgcgc ttggcgtaat    5100
```

```
catggtcata gctgtttcct gtgtgaaatt gttatccgct cacaattcca cacaacatac      5160
gagccggaag cataaagtgt aaagcctggg gtgcctaatg agtgagctaa ctcacattaa      5220
ttgcgttgcg ctcactgccc gctttccagt cgggaaacct gtcgtgccag ctgcattaat      5280
gaatcggcca acgcgcgggg agaggcggtt tgcgtattgg gcgctcttcc gcttcctcgc      5340
tcactgactc gctgcgctcg gtcgttcggc tgcggcgagc ggtatcagct cactcaaagg      5400
cggtaatacg gttatccaca gaatcagggg ataacgcagg aaagaacatg tgagcaaaag      5460
gccagcaaaa ggccaggaac cgtaaaaagg ccgcgttgct ggcgtttttc cataggctcc      5520
gcccccctga cgagcatcac aaaaatcgac gctcaagtca gaggtggcga acccgacag      5580 gactataaag ataccaggcg tttccccctg gaagctccct cgtgcgctct cctgttccga      5640
ccctgccgct taccggatac ctgtccgcct ttctcccttc gggaagcgtg gcgctttctc      5700
atagctcacg ctgtaggtat ctcagttcgg tgtaggtcgt tcgctccaag ctgggctgtg      5760
tgcacgaacc cccgttcag cccgaccgct gcgccttatc cggtaactat cgtcttgagt       5820
ccaacccggt aagacacgac ttatcgccac tggcagcagc cactggtaac aggattagca     5880
gagcgaggta tgtaggcggt gctacagagt tcttgaagtg gtggcctaac tacggctaca     5940
ctagaaggac agtatttggt atctgcgctc tgctgaagcc agttaccttc ggaaaaagag     6000
ttggtagctc ttgatccggc aaacaaacca ccgctggtag cggtggtttt tttgtttgca     6060
agcagcagat tacgcgcaga aaaaaggat ctcaagaaga tcctttgatc ttttctacgg      6120
ggtctgacgc tcagtggaac gaaaactcac gttaagggat tttggtcatg agattatcaa     6180
aaaggatctt cacctagatc cttttaaatt aaaaatgaag ttttaaatca atctaaagta     6240
tatatgagta aacttggtct gacagttacc aatgcttaat cagtgaggca cctatctcag     6300
cgatctgtct atttcgttca tccatagttg cctgactccc cgtcgtgtag ataactacga     6360
tacgggaggg cttaccatct ggccccagt ctgcaatgat accgcgagac ccacgctcac      6420
cggctccaga tttatcagca ataaaccagc cagccggaag ggccgagcgc agaagtggtc     6480
ctgcaacttt atccgcctcc atccagtcta ttaattgttg ccgggaagct agagtaagta     6540
gttcgccagt taatagtttg cgcaacgttg ttgccattgc tacaggcatc gtggtgtcac     6600
gctcgtcgtt tggtatggct tcattcagct ccggttccca acgatcaagg cgagttacat     6660 gatccccat gttgtgcaaa aaagcggtta gctccttcgg tcctccgatc gttgtcagaa      6720
gtaagttggc cgcagtgtta tcactcatgg ttatggcagc actgcataat tctcttactg     6780
tcatgccatc cgtaagatgc ttttctgtga ctggtgagta ctcaaccaag tcattctgag     6840
aatagtgtat gcggcgaccg agttgctctt gcccggcgtc aatacgggat aataccgcgc     6900
cacatagcag aactttaaaa gtgctcatca ttggaaaacg ttcttcgggg cgaaaactct     6960
caaggatctt accgctgttg agatccagtt cgatgtaacc cactcgtgca cccaactgat     7020
cttcagcatc ttttactttc accagcgttt ctgggtgagc aaaaacagga aggcaaaatg     7080
ccgcaaaaaa gggaataagg gcgacacgga aatgttgaat actcatactc ttcctttttc     7140
aatattattg aagcatttat cagggttatt gtctcatgag cggatacata tttgaatgta     7200
tttagaaaaa taaacaaata ggggttccgc gcacatttcc ccgaaaagtg ccacctaaat     7260
tgtaagcgtt aatattttgt taaaattcgc gttaaatttt tgttaaatca gctcatttt     7320 taaccaatag gccgaaatcg gcaaaatccc ttataaatca aaagaataga ccgagatagg    7380
gttgagtgtt gttccagttt ggaacaagag tccactatta aagaacgtgg actccaacgt   7440
```

| | | | | | |
|---|---|---|---|---|---|
| caaagggcga | aaaaccgtct | atcagggcga | tggcccacta | cgtgaaccat | caccctaatc | 7500 |
| aagttttttg | gggtcgaggt | gccgtaaagc | actaaatcgg | aaccctaaag | ggagcccccg | 7560 |
| atttagagct | tgacggggaa | agccggcgaa | cgtggcgaga | aaggaaggga | agaaagcgaa | 7620 |
| aggagcgggc | gctagggcgc | tggcaagtgt | agcggtcacg | ctgcgcgtaa | ccaccacacc | 7680 |
| cgccgcgctt | aatgcgccgc | tacagggcgc | gtcccattcg | ccattcaggc | tgcgcaactg | 7740 |
| ttgggaaggg | cgatcggtgc | gggcctcttc | gctattacgc | cagtcgacca | tagccaattc | 7800 |
| aatatggcgt | atatggactc | atgccaattc | aaatggtgg | atctggacct | gtgccaattc | 7860 |
| aatatggcgt | atatggactc | gtgccaattc | aaatggtgg | atctggaccc | cagccaattc | 7920 |
| aatatggcgg | acttggcacc | atgccaattc | aaatggcgg | acttggcact | gtgccaactg | 7980 |
| gggaggggtc | tacttggcac | ggtgccaagt | ttgaggaggg | gtcttggccc | tgtgccaagt | 8040 |
| ccgccatatt | gaattggcat | ggtgccaata | atggcggcca | tattggctat | atgccaggat | 8100 |
| caatatatag | gcaatatcca | atatggccct | atgccaatat | ggctattggc | caggttcaat | 8160 |
| actatgtatt | ggccctatgc | catatagtat | tccatatatg | ggttttccta | ttgacgtaga | 8220 |
| tagcccctcc | caatgggcgg | tcccatatac | catatatggg | gcttcctaat | accgcccata | 8280 |
| gccactcccc | cattgacgtc | aatggtctct | atatatggtc | tttcctattg | acgtcatatg | 8340 |
| ggcggtccta | ttgacgtata | tggcgcctcc | cccattgacg | tcaattacgg | taaatggccc | 8400 |
| gcctggctca | atgcccattg | acgtcaatag | gaccacccac | cattgacgtc | aatgggatgg | 8460 |
| ctcattgccc | attcatatcc | gttctcacgc | cccctattga | cgtcaatgac | ggtaaatggc | 8520 |
| ccacttggca | gtacatcaat | atctattaat | agtaacttgg | caagtacatt | actattggaa | 8580 |
| ggacgccagg | gtacattggc | agtactccca | ttgacgtcaa | tggcggtaaa | tggcccgcga | 8640 |
| tggctgccaa | gtacatcccc | attgacgtca | atggggaggg | gcaatgacgc | aaatgggcgt | 8700 |
| tccattgacg | taaatgggcg | gtaggcgtgc | ctaatgggag | gtctatataa | gcaatgctcg | 8760 |
| tttaggga | | | | | 8768 |

<210> SEQ ID NO 74
<211> LENGTH: 8768
<212> TYPE: DNA
<213> ORGANISM: Artificial sequence
<220> FEATURE:
<223> OTHER INFORMATION: Synthetic

<400> SEQUENCE: 74

| | | | | | |
|---|---|---|---|---|---|
| accgccattc | tgcctgggga | cgtcggagca | agcttgattt | aggtgacact | atagaataca | 60 |
| agctacttgt | tcttttttgca | ggatcccatc | gattcgaatt | caaggatcaa | caagtttgta | 120 |
| caaaaaagca | ggctggcgcc | accatggaca | agaagtactc | cattgggctc | gatatcggta | 180 |
| ccaacagcgt | cggctgggcc | gtcattacgg | acgagtacaa | ggtgccgagc | aaaaaattca | 240 |
| aagttctggg | caataccgat | cgccacagca | taaagaagaa | cctcattgga | gcctcctgt | 300 |
| tcgactccgg | ggagacggcc | gaagccacgc | ggctcaaaag | aacagcacgg | cgcagatata | 360 |
| cccgcagaaa | gaatcggatc | tgctacctgc | aggagatctt | tagtaatgag | atggctaagg | 420 |
| tggatgactc | tttcttccat | aggctggagg | agtcctttt | ggtggaggag | gataaaaagc | 480 |
| acgagcgcca | cccaatcttt | ggcaatatcg | tggacgaggt | ggcgtaccat | gaaaagtacc | 540 |
| caaccatata | tcatctgagg | aagaagctgg | tagacagtac | tgataaggct | gacttgcggt | 600 |
| tgatctatct | cgcgctggcg | cacatgatca | aatttcgggg | acacttcctc | atcgaggggg | 660 |
| acctgaaccc | agacaacagc | gatgtcgaca | aactctttat | ccaactggtt | cagacttaca | 720 |

```
atcagctttt cgaggagaac ccgatcaacg catccggcgt tgacgccaaa gcaatcctga    780
gcgctaggct gtccaaatcc cggcggctcg aaaacctcat cgcacagctc cctggggaga    840
agaagaacgg cctgtttggt aatcttatcg ccctgtcact cgggctgacc cccaacttta    900
aatctaactt cgacctggcc gaagatgcca agctgcaact gagcaaagac acctacgatg    960
atgatctcga caatctgctg gcccagatcg gcgaccagta cgcagacctt tttttggcgg   1020
caaagaacct gtcagacgcc attctgctga gtgatattct gcgagtgaac acggagatca   1080
ccaaagctcc gctgagcgct agtatgatca gcgctatga tgagcaccac caagacttga   1140
ctttgctgaa ggcccttgtc agacagcaac tgcctgagaa gtacaaggaa attttcttcg   1200
atcagtctaa aaatggctac gccggataca ttgacggcgg agcaagccag gaggaattt   1260 acaaatttat taagcccatc ttggaaaaaa tggacggcac cgaggagctg ctggtaaagc   1320
tgaacagaga agatctgttg cgcaaacagc gcactttcga caatggaagc atcccccacc   1380
agattcacct gggcgaactg cacgctatcc tcaggcggca agaggatttc taccccttt   1440 tgaaagataa cagggaaaag attgagaaaa tcctcacatt tcggataccc tactatgtag   1500
gccccctcgc tcggggaaat tccagattcg cgtggatgac tcgcaaatca gaagagacca   1560
tcactccctg gaacttcgag gaagtcgtgg ataaggggc ctctgcccag tccttcatcg   1620
aaaggatgac taactttgat aaaaatctgc taacgaaaa ggtgcttcct aaacactctc   1680
tgctgtacga gtacttcaca gtttataacg agctcaccaa ggtcaaatac gtcacagaag   1740
ggatgagaaa gccagcattc ctgtctggag agcagaagaa agctatcgtg gacctcctct   1800
tcaagacgaa ccggaaagtt accgtgaaac agctcaaaga agactatttc aaaaagattg   1860
aatgtttcga ctctgttgaa atcagcggag tggaggatcg cttcaacgca tccctgggaa   1920
cgtatcacga tctcctgaaa atcattaaag acaaggactt cctggacaat gaggagaacg   1980
aggacattct tgaggacatt gtcctcaccc ttacgttgtt tgaagatagg gagatgattg   2040
aagaacgctt gaaaacttac gctcatctct tcgacgacaa agtcatgaaa cagctcaaga   2100
gacgccgata tacaggatgg gggcggctgt caagaaaaact gatcaatggc atccgagaca   2160
agcagagtgg aaagacaatc ctggatttc ttaagtccga tggatttgcc aaccggaact   2220
tcatgcagtt gatccatgat gactctctca cctttaagga ggacatccag aaagcacaag   2280
tttctggcca gggggacagt cttcacgagc acatcgctaa tcttgcaggt agcccagcta   2340
tcaaaaaggg aatactgcag accgttaagg tcgtggatga actcgtcaaa gtaatgggaa   2400
ggcataagcc cgagaatatc gttatcgaga tggcccgaga gaaccaaact acccagaagg   2460
gacagaagaa cagtagggaa aggatgaaga ggattgaaga gggtataaaa gaactggggt   2520
cccaaatcct taaggaacac ccagttgaaa cacccagctc tcagaatgag aagctctacc   2580
tgtactacct gcagaacggc agggacatgt acgtggatca ggaactggac atcaaccggt   2640
tgtccgacta cgacgtggat catatcgtgc cccaaagctt tctcaaagat gattctattg   2700
ataataaagt gttgacaaga tccgataaaa atagagggaa gagtgataac gtcccctcag   2760
aagaagttgt caagaaaatg aaaaattatt ggcggcagct gctgaacgcc aaactgatca   2820
cacaacggaa gttcgataat ctgactaagg ctgaacgagg tggcctgtct gagttggata   2880
aagccggctt catcaaaagg cagcttgttg agacacgcca gatcaccaag cacgtggccc   2940
aaattctcga ttcacgcatg aacaccaagt acgatgaaaa tgacaaactg attcgagagg   3000
tgaaagttat tactctgaag tctaagctgg tctcagattt cagaaaggac tttcagtttt   3060
```

```
ataaggtgag agagatcaac aattaccacc atgcgcatga tgcctacctg aatgcagtgg    3120
taggcactgc acttatcaaa aaatatccca agctggaatc tgaatttgtt tacggagact    3180
ataaagtgta cgatgttagg aaaatgatcg caaagtctga gcaggaaata ggcaaggcca    3240
ccgctaagta cttcttttac agcaatatta tgaattttt caagaccgag attacactgg     3300
ccaatggaga gattcggaag cgaccactta tcgaaacaaa cggagaaaca ggagaaatcg    3360
tgtgggacaa gggtagggat ttcgcgacag tccgcaaggt cctgtccatg ccgcaggtga    3420
acatcgttaa aaagaccgaa gtacagaccg gaggcttctc caaggaaagt atcctcccga    3480
aaaggaacag cgacaagctg atcgcacgca aaaaagattg gaccccaag aaatacggcg     3540 gattcgattc tcctacagtc gcttacagtg tactggttgt ggccaaagtg gagaagggga    3600
agtctaaaaa actcaaaagc gtcaaggaac tgctgggcat cacaatcatg gagcgatcca    3660
gcttcgagaa aaacccatc gactttctcg aagcgaaagg atataaagag gtcaaaaaag     3720
acctcatcat taagctgccc aagtactctc tctttgagct tgaaaacggc cggaaacgaa    3780
tgctcgctag tgcgggcgag ctgcagaaag gtaacgagct ggcactgccc tctaaatacg    3840
ttaatttctt gtatctggcc agccactatg aaaagctcaa agggtctccc gaagataatg    3900
agcagaagca gctgttcgtg gaacaacaca acactacct tgatgagatc atcgagcaaa     3960
taagcgagtt ctccaaaaga gtgatcctcg ccgacgctaa cctcgataag gtgctttctg    4020
cttacaataa gcacagggat aagcccatca gggagcaggc agaaaacatt atccacttgt    4080
ttactctgac caacttgggc gcgcctgcag ccttcaagta cttcgacacc accatagaca    4140
gaaagaagta cacctctaca aaggaggtcc tggacgccac actgattcat cagtcaatta    4200
cggggctcta tgaaacaaga atcgacctct ctcagctcgg tggagacggc accggcgggc    4260
ccaagaagaa gaggaaggta tacccatacg atgttcctga ctatgcgggc tatccctatg    4320
acgtcccgga ctatgcagga tcgtatcctt atgacgttcc agattacgct ggatccgccg    4380
ctccggcagc taagaaaaag aaactggatt tcgaatccgg aaagccctat aaatgtcctg    4440
aatgtggcaa gtccttctcg cggagcgacg acctgacacg gcaccaacgt acgcacactg    4500
gtgagaagcc atacgcgtgt cctgtcgagt cctgtgaccg ccgcttcagt cagaagggac    4560
acctgacacg gcacatccgc attcacacag gcaaaaacc gtttcaatgc cgcatctgca    4620
tgaggaactt cagcatccgt agcagcctga cacggcacat ccgcacccac acaggagaaa    4680
agcccttcgc ctgtgacatc tgcggcagga agttcgcgct gagccaccac ctgacacggc    4740
acaccaagat ccacctccgt cagaaagacc ccgggtaatg actcgagcct ctagaactat    4800
agtgagtcgt attacgtaga tccagacatg ataagataca ttgatgagtt tggacaaacc    4860
acaactagaa tgcagtgaaa aaaatgcttt atttgtgaaa tttgtgatgc tattgcttta    4920
tttgtaacca ttataagctg caataaacaa gttaacaaca caattgcat tcattttatg     4980 tttcaggttc agggggaggt gtgggaggtt ttttaattcg cggccgcggc gccaatgcat    5040
tgggcccggt acccagcttt tgttcccttt agtgagggtt aattgcgcgc ttggcgtaat    5100
catggtcata gctgtttcct gtgtgaaatt gttatccgct cacaattcca cacaacatac    5160
gagccggaag cataaagtgt aaagcctggg gtgcctaatg agtgagctaa ctcacattaa    5220
ttgcgttgcg ctcactgccc gctttccagt cgggaaacct gtcgtgccag ctgcattaat    5280
gaatcggcca acgcgcgggg agaggcggtt tgcgtattgg cgctcttccg cttcctcgc     5340 tcactgactc gctgcgctcg gtcgttcggc tgcggcgagc ggtatcagct cactcaaagg    5400
cggtaatacg gttatccaca gaatcagggg ataacgcagg aaagaacatg tgagcaaaag    5460
```

```
gccagcaaaa ggccaggaac cgtaaaaagg ccgcgttgct ggcgttttc cataggctcc    5520 gccccctga cgagcatcac aaaaatcgac gctcaagtca gaggtggcga acccgacag    5580 gactataaag ataccaggcg ttcccctg gaagctccct cgtgcgctct cctgttccga    5640
ccctgccgct taccggatac ctgtccgcct ttctcccttc gggaagcgtg gcgctttctc    5700
atagctcacg ctgtaggtat ctcagttcgg tgtaggtcgt tcgctccaag ctgggctgtg    5760
tgcacgaacc ccccgttcag cccgaccgct gcgccttatc cggtaactat cgtcttgagt    5820
ccaacccggt aagacacgac ttatcgccac tggcagcagc cactggtaac aggattagca    5880
gagcgaggta tgtaggcggt gctacagagt tcttgaagtg gtggcctaac tacggctaca    5940
ctagaaggac agtatttggt atctgcgctc tgctgaagcc agttaccttc ggaaaaagag    6000
ttggtagctc ttgatccggc aaacaaacca ccgctggtag cggtggtttt tttgtttgca    6060
agcagcagat tacgcgcaga aaaaaggat ctcaagaaga tcctttgatc ttttctacgg    6120
ggtctgacgc tcagtggaac gaaaactcac gttaagggat tttggtcatg agattatcaa    6180
aaaggatctt cacctagatc cttttaaatt aaaaatgaag ttttaaatca atctaaagta    6240
tatatgagta aacttggtct gacagttacc aatgcttaat cagtgaggca cctatctcag    6300
cgatctgtct atttcgttca tccatagttg cctgactccc cgtcgtgtag ataactacga    6360
tacgggaggg cttaccatct ggccccagtg ctgcaatgat accgcgagac ccacgctcac    6420
cggctccaga tttatcagca ataaaccagc cagccggaag ggccgagcgc agaagtggtc    6480
ctgcaacttt atccgcctcc atccagtcta ttaattgttg ccgggaagct agagtaagta    6540
gttcgccagt taatagtttg cgcaacgttg ttgccattgc tacaggcatc gtggtgtcac    6600
gctcgtcgtt tggtatggct tcattcagct ccggttccca acgatcaagg cgagttacat    6660 gatccccat gttgtgcaaa aaagcggtta gctccttcgg tcctccgatc gttgtcagaa    6720
gtaagttggc cgcagtgtta tcactcatgg ttatggcagc actgcataat tctcttactg    6780
tcatgccatc cgtaagatgc ttttctgtga ctggtgagta ctcaaccaag tcattctgag    6840
aatagtgtat gcggcgaccg agttgctctt gcccggcgtc aatacgggat aataccgcgc    6900
cacatagcag aactttaaaa gtgctcatca ttggaaaacg ttcttcgggg cgaaaactct    6960
caaggatctt accgctgttg agatccagtt cgatgtaacc cactcgtgca cccaactgat    7020
cttcagcatc ttttactttc accagcgttt ctgggtgagc aaaaacagga aggcaaaatg    7080
ccgcaaaaaa gggaataagg gcgacacgga aatgttgaat actcatactc ttcctttttc    7140
aatattattg aagcatttat cagggttatt gtctcatgag cggatacata tttgaatgta    7200
tttagaaaaa taaacaaata ggggttccgc gcacatttcc ccgaaaagtg ccacctaaat    7260
tgtaagcgtt aatattttgt taaaattcgc gttaaatttt tgttaaatca gctcattttt    7320
taaccaatag gccgaaatcg gcaaaatccc ttataaatca aagaataga ccgagatagg    7380 gttgagtgtt gttccagttt ggaacaagag tccactatta agaacgtgg actccaacgt    7440 caaagggcga aaaccgtct atcagggcga tggcccacta cgtgaaccat caccctaatc    7500 aagtttttg gggtcgaggt gccgtaaagc actaaatcgg aaccctaaag ggagcccccg    7560
atttagagct tgacggggaa agccggcgaa cgtggcgaga aggaaggga agaaagcgaa    7620 aggagcgggc gctagggcgc tggcaagtgt agcggtcacg ctgcgcgtaa ccaccacacc    7680
cgccgcgctt aatgcgccgc tacagggcgc gtcccattcg ccattcaggc tgcgcaactg    7740
ttgggaaggg cgatcggtgc gggcctcttc gctattacgc cagtcgacca tagccaattc    7800
```

| | |
|---|---:|
| aatatggcgt atatggactc atgccaattc aatatggtgg atctggacct gtgccaattc | 7860 |
| aatatggcgt atatggactc gtgccaattc aatatggtgg atctggaccc cagccaattc | 7920 |
| aatatggcgg acttggcacc atgccaattc aatatggcgg acttggcact gtgccaactg | 7980 |
| gggaggggtc tacttggcac ggtgccaagt ttgaggaggg gtcttggccc tgtgccaagt | 8040 |
| ccgccatatt gaattggcat ggtgccaata atggcggcca tattggctat atgccaggat | 8100 |
| caatatatag gcaatatcca atatggcect atgccaatat ggctattggc caggttcaat | 8160 |
| actatgtatt ggccctatgc catatagtat tccatatatg ggttttccta ttgacgtaga | 8220 |
| tagcccctcc caatgggcgg tcccatatac catatatggg gcttcctaat accgcccata | 8280 |
| gccactcccc cattgacgtc aatggtctct atatatggtc tttcctattg acgtcatatg | 8340 |
| ggcggtccta ttgacgtata tggcgcctcc cccattgacg tcaattacgg taaatggccc | 8400 |
| gcctggctca atgcccattg acgtcaatag gaccacccac cattgacgtc aatgggatgg | 8460 |
| ctcattgccc attcatatcc gttctcacgc cccctattga cgtcaatgac ggtaaatggc | 8520 |
| ccacttggca gtacatcaat atctattaat agtaacttgg caagtacatt actattggaa | 8580 |
| ggacgccagg gtacattggc agtactccca ttgacgtcaa tggcggtaaa tgcccgcga | 8640 |
| tggctgccaa gtacatcccc attgacgtca atggggaggg gcaatgacgc aaatgggcgt | 8700 |
| tccattgacg taaatgggcg gtaggcgtgc ctaatgggag gtctatataa gcaatgctcg | 8760 |
| tttaggga | 8768 |

<210> SEQ ID NO 75
<211> LENGTH: 8768
<212> TYPE: DNA
<213> ORGANISM: Artificial sequence
<220> FEATURE:
<223> OTHER INFORMATION: Synthetic

<400> SEQUENCE: 75

| | |
|---|---:|
| accgccattc tgcctgggga cgtcggagca agcttgattt aggtgacact atagaataca | 60 |
| agctacttgt tcttttttgca ggatcccatc gattcgaatt caaggatcaa caagtttgta | 120 |
| caaaaaagca ggctggcgcc accatggaca agaagtactc cattgggctc gatatcggta | 180 |
| ccaacagcgt cggctgggcc gtcattacgg acgagtacaa ggtgccgagc aaaaaattca | 240 |
| aagttctggg caataccgat cgccacagca taaagaagaa cctcattgga gccctcctgt | 300 |
| tcgactccgg ggagacggcc gaagccacgc ggctcaaaag aacagcacgg cgcagatata | 360 |
| cccgcagaaa gaatcggatc tgctacctgc aggagatctt tagtaatgag atggctaagg | 420 |
| tggatgactc tttcttccat aggctggagg agtcctttt ggtggaggag gataaaaagc | 480 |
| acgagcgcca cccaatcttt ggcaatatcg tggacgaggt ggcgtaccat gaaaagtacc | 540 |
| caaccatata tcatctgagg aagaagctgg tagacagtac tgataaggct gacttgcggt | 600 |
| tgatctatct cgcgctggcg cacatgatca aatttcgggg acacttcctc atcgaggggg | 660 |
| acctgaaccc agacaacagc gatgtcgaca aactctttat ccaactggtt cagacttaca | 720 |
| atcagctttt cgaggagaac ccgatcaacg catccggcgt tgacgccaaa gcaatcctga | 780 |
| gcgctaggct gtccaaatcc cggcggctcg aaaacctcat cgcacagctc ctggggaga | 840 |
| agaagaacgg cctgtttggt aatctatcg ccctgtcact cgggctgacc cccaacttta | 900 |
| aatctaactt cgacctggcc gaagatgcca agctgcaact gagcaaagac acctacgatg | 960 |
| atgatctcga caatctgctg gcccagatcg gcgaccagta cgcagacctt tttttggcgg | 1020 |
| caaagaacct gtcagacgcc attctgctga gtgatattct gcgagtgaac acggagatca | 1080 |

```
ccaaagctcc gctgagcgct agtatgatca agcgctatga tgagcaccac caagacttga   1140
ctttgctgaa ggcccttgtc agacagcaac tgcctgagaa gtacaaggaa attttcttcg   1200
atcagtctaa aaatggctac gccggataca ttgacggcgg agcaagccag gaggaatttt   1260
acaaatttat taagcccatc ttggaaaaaa tggacggcac cgaggagctg ctggtaaagc   1320
tgaacagaga agatctgttg cgcaaacagc gcactttcga caatggaagc atcccccacc   1380
agattcacct gggcgaactg cacgctatcc tcaggcggca agaggatttc tacccctttt   1440
tgaaagataa cagggaaaag attgagaaaa tcctcacatt tcggataccc tactatgtag   1500
gccccctcgc tcggggaaat tccagattcg cgtggatgac tcgcaaatca gaagagacca   1560
tcactccctg gaacttcgag gaagtcgtgg ataagggggc tctgcccag tccttcatcg   1620 aaaggatgac taactttgat aaaaatctgc ctaacgaaaa ggtgcttcct aaacactctc   1680
tgctgtacga gtacttcaca gtttataacg agctcaccaa ggtcaaatac gtcacagaag   1740
ggatgagaaa gccagcattc ctgtctggag agcagaagaa agctatcgtg gacctcctct   1800
tcaagacgaa ccggaaagtt accgtgaaac agctcaaaga agactatttc aaaaagattg   1860
aatgtttcga ctctgttgaa atcagcggag tggaggatcg cttcaacgca tccctgggaa   1920
cgtatcacga tctcctgaaa atcattaaag acaaggactt cctggacaat gaggagaacg   1980
aggacattct tgaggacatt gtcctcaccc ttacgttgtt tgaagatagg gagatgattg   2040
aagaacgctt gaaaacttac gctcatctct tcgacgacaa agtcatgaaa cagctcaaga   2100
gacgccgata tacaggatgg gggcggctgt caagaaaact gatcaatggc atccgagaca   2160
agcagagtgg aaagacaatc ctggattttc ttaagtccga tggatttgcc aaccggaact   2220
tcatgcagtt gatccatgat gactctctca ccttttaagga ggacatccag aaagcacaag   2280
tttctggcca gggggacagt cttcacgagc acatcgctaa tcttgcaggt agcccagcta   2340
tcaaaaaggg aatactgcag accgttaagg tcgtggatga actcgtcaaa gtaatgggaa   2400
ggcataagcc cgagaatatc gttatcgaga tggcccgaga gaaccaaact acccagaagg   2460
gacagaagaa cagtagggaa aggatgaaga ggattgaaga gggtataaaa gaactggggt   2520
cccaaatcct taaggaacac ccagttgaaa acacccagct tcagaatgag aagctctacc   2580
tgtactacct gcagaacggc agggacatgt acgtggatca ggaactggac atcaaccggt   2640
tgtccgacta cgacgtggat catatcgtgc cccaaagctt tctcaaagat gattctattg   2700
ataataaagt gttgacaaga tccgataaaa atagagggaa gagtgataac gtcccctcag   2760
aagaagttgt caagaaaatg aaaaattatt ggcggcagct gctgaacgcc aaactgatca   2820
cacaacggaa gttcgataat ctgactaagg ctgaacgagg tggcctgtct gagttggata   2880
aagccggctt catcaaaagg cagcttgttg agacacgcca gatcaccaag cacgtggccc   2940
aaattctcga ttcacgcatg aacaccaagt acgatgaaaa tgacaaactg attcgagagg   3000
tgaaagttat tactctgaag tctaagctgg tctcagattt cagaaaggac ttcagttttt   3060
ataaggtgag agagatcaac aattaccacc atgcgcatga tgcctacctg aatgcagtgg   3120
taggcactgc acttatcaaa aaatatccca agctggaatc tgaatttgtt tacgagagact   3180 ataaagtgta cgatgttagg aaaatgatcg caaagtctga gcaggaaata ggcaaggcca   3240
ccgctaagta cttcttttac agcaatatta tgaatttttt caagaccgag attacactgg   3300
ccaatggaga gattcggaag cgaccactta tcgaaacaaa cggagaaaca ggagaaatcg   3360
tgtgggacaa gggtagggat ttcgcgacag tccgcaaggt cctgtccatg ccgcaggtga   3420
```

```
acatcgttaa aaagaccgaa gtacagaccg gaggcttctc caaggaaagt atcctcccga    3480
aaaggaacag cgacaagctg atcgcacgca aaaaagattg ggaccccaag aaatacggcg    3540
gattcgattc tcctacagtc gcttacagtg tactggttgt ggccaaagtg gagaaaggga    3600
agtctaaaaa actcaaaagc gtcaaggaac tgctgggcat cacaatcatg gagcgatcca    3660
gcttcgagaa aaaccccatc gactttctcg aagcgaaagg atataaagag gtcaaaaaag    3720
acctcatcat taagctgccc aagtactctc tctttgagct tgaaaacggc cggaaacgaa    3780
tgctcgctag tgcgggcgag ctgcagaaag gtaacgagct ggcactgccc tctaaatacg    3840
ttaatttctt gtatctggcc agccactatg aaaagctcaa agggtctccc gaagataatg    3900
agcagaagca gctgttcgtg gaacaacaca acactacct tgatgagatc atcgagcaaa    3960
taagcgagtt ctccaaaaga gtgatcctcg ccgacgctaa cctcgataag gtgcttcctg    4020
cttacaataa gcacagggat aagcccatca gggagcaggc agaaaacatt atccacttgt    4080
ttactctgac caacttgggc gcgcctgcag ccttcaagta cttcgacacc accatagaca    4140
gaaagcggta cacctctaca aaggaggtcc tggacgccac actgattcat cagtcaatta    4200
cggggctcta tgaaacaaga atcgacctct ctcagctcgg tggagacggc accggcgggc    4260
ccaagaagaa gaggaaggta tacccatacg atgttcctga ctatgcgggc tatccctatg    4320
acgtcccgga ctatgcagga tcgtatcctt atgacgttcc agattacgct ggatccgccg    4380
ctccggcagc taagaaaaag aaactggatt tcgaatccgg aaagccctat aaatgtcctg    4440
aatgtggcaa gtccttctcg cagagcggag acctgacacg gcaccaacgt acgcacactg    4500
gtgagaagcc atacgcgtgt cctgtcgagt cctgtgaccg ccgcttcagt gagaagagcc    4560
acctgacacg gcacatccgc attcacacag ggcaaaaacc gtttcaatgc cgcatctgca    4620
tgaggaactt cagctgtgcc caccacctga cacggcacat ccgcacccac acaggagaaa    4680
agcccttcgc ctgtgacatc tgcggcagga agttcgcgga ccggagcacc ctgacacagc    4740
acaccaagat ccacctccgt cagaaagacc ccgggtaatg actcgagcct ctagaactat    4800
agtgagtcgt attacgtaga tccagacatg ataagataca ttgatgagtt tggacaaacc    4860
acaactagaa tgcagtgaaa aaaatgcttt atttgtgaaa tttgtgatgc tattgcttta    4920
tttgtaacca ttataagctg caataaacaa gttaacaaca caattgcat tcattttatg    4980
tttcaggttc agggggaggt gtgggaggtt ttttaattcg cggccgcggc gccaatgcat    5040
tgggcccggt acccagcttt tgttcccttt agtgagggtt aattgcgcgc ttggcgtaat    5100
catggtcata gctgtttcct gtgtgaaatt gttatccgct cacaattcca cacaacatac    5160
gagccggaag cataaagtgt aaagcctggg gtgcctaatg agtgagctaa ctcacattaa    5220
ttgcgttgcg ctcactgccc gctttccagt cgggaaacct gtcgtgccag ctgcattaat    5280
gaatcggcca acgcgcgggg agaggcggtt tgcgtattgg gcgctcttcc gcttcctcgc    5340
tcactgactc gctgcgctcg gtcgttcggc tgcggcgagc ggtatcagct cactcaaagg    5400
cggtaatacg gttatccaca gaatcagggg ataacgcagg aaagaacatg tgagcaaaag    5460
gccagcaaaa ggccaggaac cgtaaaaagg ccgcgttgct ggcgtttttc cataggctcc    5520
gcccccctga cgagcatcac aaaaatcgac gctcaagtca gaggtggcga aacccgacag    5580
gactataaag ataccaggcg tttccccctg gaagctccct cgtgcgctct cctgttccga    5640
ccctgccgct taccggatac ctgtccgcct ttctcccttc gggaagcgtg gcgctttctc    5700
atagctcacg ctgtaggtat ctcagttcgg tgtaggtcgt tcgctccaag ctgggctgtg    5760
tgcacgaacc ccccgttcag cccgaccgct gcgccttatc cggtaactat cgtcttgagt    5820
```

```
ccaacccggt aagacacgac ttatcgccac tggcagcagc cactggtaac aggattagca    5880
gagcgaggta tgtaggcggt gctacagagt tcttgaagtg gtggcctaac tacggctaca    5940
ctagaaggac agtatttggt atctgcgctc tgctgaagcc agttaccttc ggaaaaagag    6000
ttggtagctc ttgatccggc aaacaaacca ccgctggtag cggtggtttt tttgtttgca    6060
agcagcagat tacgcgcaga aaaaaggat ctcaagaaga tcctttgatc ttttctacgg     6120
ggtctgacgc tcagtggaac gaaaactcac gttaagggat tttggtcatg agattatcaa    6180
aaaggatctt cacctagatc cttttaaatt aaaaatgaag ttttaaatca atctaaagta    6240
tatatgagta aacttggtct gacagttacc aatgcttaat cagtgaggca cctatctcag    6300
cgatctgtct atttcgttca tccatagttg cctgactccc cgtcgtgtag ataactacga    6360
tacgggaggg cttaccatct ggccccagtg ctgcaatgat accgcgagac ccacgctcac    6420
cggctccaga tttatcagca ataaaccagc cagccggaag ggccgagcgc agaagtggtc    6480
ctgcaacttt atccgcctcc atccagtcta ttaattgttg ccgggaagct agagtaagta    6540
gttcgccagt taatagtttg cgcaacgttg ttgccattgc tacaggcatc gtggtgtcac    6600
gctcgtcgtt tggtatggct tcattcagct ccggttccca acgatcaagg cgagttacat    6660 gatccccat gttgtgcaaa aaagcggtta gctccttcgg tcctccgatc gttgtcagaa     6720
gtaagttggc cgcagtgtta tcactcatgg ttatggcagc actgcataat tctcttactg    6780
tcatgccatc cgtaagatgc ttttctgtga ctggtgagta ctcaaccaag tcattctgag    6840
aatagtgtat gcggcgaccg agttgctctt gcccggcgtc aatacgggat aataccgcgc    6900
cacatagcag aactttaaaa gtgctcatca ttggaaaacg ttcttcgggg cgaaaactct    6960
caaggatctt accgctgttg agatccagtt cgatgtaacc cactcgtgca cccaactgat    7020
cttcagcatc ttttactttc accagcgttt ctgggtgagc aaaaacagga aggcaaaatg    7080
ccgcaaaaaa gggaataagg gcgacacgga aatgttgaat actcatactc ttcctttttc    7140
aatattattg aagcatttat cagggttatt gtctcatgag cggatacata tttgaatgta    7200
tttagaaaaa taaacaaata ggggttccgc gcacatttcc ccgaaaagtg ccacctaaat    7260
tgtaagcgtt aatattttgt taaaattcgc gttaaatttt tgttaaatca gctcattttt    7320
taaccaatag gccgaaatcg gcaaaatccc ttataaatca aaagaataga ccgagatagg    7380
gttgagtgtt gttccagttt ggaacaagag tccactatta agaacgtgg actccaacgt     7440 caaagggcga aaaccgtct atcagggcga tggcccacta cgtgaaccat caccctaatc     7500
aagttttttg gggtcgaggt gccgtaaagc actaaatcgg aaccctaaag ggagcccccg    7560
atttagagct tgacggggaa agccggcgaa cgtggcgaga aggaaggga agaaagcgaa     7620 aggagcgggc gctagggcgc tggcaagtgt agcggtcacg ctgcgcgtaa ccaccacacc    7680
cgccgcgctt aatgcgccgc tacagggcgc gtcccattcg ccattcaggc tgcgcaactg    7740
ttgggaaggg cgatcggtgc gggcctcttc gctattacgc cagtcgacca tagccaattc    7800
aatatggcgt atatggactc atgccaattc aatatggtgg atctggacct gtgccaattc    7860 aatatgcgt atatggactc gtgccaattc aatatggtgg atctggaccc agccaattc     7920 aatatggcgg acttggcacc atgccaattc aatatgcgg acttggcact gtgccaactg     7980
gggaggggtc tacttggcac ggtgccaagt tgaggaggg gtcttggccc tgtgccaagt     8040
ccgccatatt gaattggcat ggtgccaata atggcggcca tattggctat atgccaggat    8100
caatatatag gcaatatcca atatggccct atgccaatat ggctattggc caggttcaat    8160
```

-continued

| | | |
|---|---|---|
| actatgtatt ggccctatgc catatagtat tccatatatg ggttttccta ttgacgtaga | 8220 | |
| tagcccctcc caatgggcgg tcccatatac catatatggg gcttcctaat accgcccata | 8280 | |
| gccactcccc cattgacgtc aatggtctct atatatggtc tttcctattg acgtcatatg | 8340 | |
| ggcggtccta ttgacgtata tggcgcctcc cccattgacg tcaattacgg taaatggccc | 8400 | |
| gcctggctca atgcccattg acgtcaatag gaccacccac cattgacgtc aatgggatgg | 8460 | |
| ctcattgccc attcatatcc gttctcacgc cccctattga cgtcaatgac ggtaaatggc | 8520 | |
| ccacttggca gtacatcaat atctattaat agtaacttgg caagtacatt actattggaa | 8580 | |
| ggacgccagg gtacattggc agtactccca ttgacgtcaa tggcggtaaa tgccccgcga | 8640 | |
| tggctgccaa gtacatcccc attgacgtca atggggaggg gcaatgacgc aaatgggcgt | 8700 | |
| tccattgacg taaatgggcg gtaggcgtgc ctaatgggag gtctatataa gcaatgctcg | 8760 | |
| tttaggga | 8768 | |

<210> SEQ ID NO 76
<211> LENGTH: 8768
<212> TYPE: DNA
<213> ORGANISM: Artificial sequence
<220> FEATURE:
<223> OTHER INFORMATION: Synthetic

<400> SEQUENCE: 76

| | | |
|---|---|---|
| accgccattc tgcctgggga cgtcggagca agcttgattt aggtgacact atagaataca | 60 | |
| agctacttgt tcttttttgca ggatcccatc gattcgaatt caaggatcaa caagtttgta | 120 | |
| caaaaaagca ggctggcgcc accatggaca agaagtactc cattgggctc gatatcggta | 180 | |
| ccaacagcgt cggctgggcc gtcattacgg acgagtacaa ggtgccgagc aaaaaattca | 240 | |
| aagttctggg caataccgat cgccacagca taaagaagaa cctcattgga gccctcctgt | 300 | |
| tcgactccgg ggagacggcc gaagccacgc ggctcaaaag aacagcacgg cgcagatata | 360 | |
| cccgcagaaa gaatcggatc tgctacctgc aggagatctt tagtaatgag atggctaagg | 420 | |
| tggatgactc tttcttccat aggctggagg agtcctttttt ggtggaggag gataaaaagc | 480 | |
| acgagcgcca cccaatcttt ggcaatatcg tggacgaggt ggcgtaccat gaaaagtacc | 540 | |
| caaccatata tcatctgagg aagaagctgg tagacagtac tgataaggct gacttgcggt | 600 | |
| tgatctatct cgcgctggcg cacatgatca aatttcgggg acacttcctc atcgaggggg | 660 | |
| acctgaaccc agacaacagc gatgtcgaca aactctttat ccaactggtt cagacttaca | 720 | |
| atcagctttt cgaggagaac ccgatcaacg catccggcgt tgacgccaaa gcaatcctga | 780 | |
| gcgctaggct gtccaaatcc cggcggctcg aaaacctcat cgcacagctc cctggggaga | 840 | |
| agaagaacgg cctgtttggt aatcttatcg ccctgtcact cggctgacc cccaacttta | 900 | |
| aatctaactt cgacctggcc gaagatgcca agctgcaact gagcaaagac acctacgatg | 960 | |
| atgatctcga caatctgctg gcccagatcg gcgaccagta cgcagacctt tttttggcgg | 1020 | |
| caaagaacct gtcagacgcc attctgctga gtgatattct gcgagtgaac acggagatca | 1080 | |
| ccaaagctcc gctgagcgct agtatgatca gcgctatga tgagcaccac caagacttga | 1140 | |
| ctttgctgaa ggcccttgtc agacagcaac tgcctgagaa gtacaaggaa attttcttcg | 1200 | |
| atcagtctaa aaatggctac gccggataca ttgacggcgg agcaagccag gaggaatttt | 1260 | |
| acaaatttat taagcccatc ttggaaaaaa tggacggcac cgaggagctg ctggtaaagc | 1320 | |
| tgaacagaga agatctgttg cgcaaacagc gcacttttcga caatggaagc atccccccacc | 1380 | |
| agattcacct gggcgaactg cacgctatcc tcaggcggca agaggatttc taccccttt | 1440 | |

```
tgaaagataa cagggaaaag attgagaaaa tcctcacatt tcggataccc tactatgtag   1500 gcccctcgc tcggggaaat tccagattcg cgtggatgac tcgcaaatca gaagagacca   1560
tcactccctg gaacttcgag gaagtcgtgg ataaggggc ctctgcccag tccttcatcg   1620
aaaggatgac taactttgat aaaaatctgc ctaacgaaaa ggtgcttcct aaacactctc   1680
tgctgtacga gtacttcaca gtttataacg agctcaccaa ggtcaaatac gtcacagaag   1740
ggatgagaaa gccagcattc ctgtctggag agcagaagaa agctatcgtg gacctcctct   1800
tcaagacgaa ccggaaagtt accgtgaaac agctcaaaga agactatttc aaaaagattg   1860
aatgtttcga ctctgttgaa atcagcgag tggaggatcg cttcaacgca tccctgggaa   1920
cgtatcacga tctcctgaaa atcattaaag acaaggactt cctggacaat gaggagaacg   1980
aggacattct tgaggacatt gtcctcaccc ttacgttgtt tgaagatagg gagatgattg   2040
aagaacgctt gaaaacttac gctcatctct tcgacgacaa agtcatgaaa cagctcaaga   2100
gacgccgata tacaggatgg gggcggctgt caagaaaact gatcaatggc atccgagaca   2160
agcagagtgg aaagacaatc ctggattttc ttaagtccga tggatttgcc aaccggaact   2220
tcatgcagtt gatccatgat gactctctca cctttaagga ggacatccag aaagcacaag   2280
tttctggcca gggggacagt cttcacgagc acatcgctaa tcttgcaggt agcccagcta   2340
tcaaaaaggg aatactgcag accgttaagg tcgtggatga actcgtcaaa gtaatgggaa   2400
ggcataagcc cgagaatatc gttatcgaga tggcccgaga gaaccaaact acccagaagg   2460
gacagaagaa cagtagggaa aggatgaaga ggattgaaga gggtataaaa gaactggggt   2520
cccaaatcct taaggaacac ccagttgaaa acacccagct tcagaatgag aagctctacc   2580
tgtactacct gcagaacggc agggacatgt acgtggatca ggaactggac atcaaccggt   2640
tgtccgacta cgacgtggat catatcgtgc cccaaagctt tctcaaagat gattctattg   2700
ataataaagt gttgacaaga tccgataaaa atagagggaa gagtgataac gtcccctcag   2760
aagaagttgt caagaaaatg aaaaattatt ggcggcagct gctgaacgcc aaactgatca   2820
cacaacggaa gttcgataat ctgactaagg ctgaacgagg tggcctgtct gagttggata   2880
aagccggctt catcaaaagg cagcttgttg agacacgcca gatcaccaag cacgtggccc   2940
aaattctcga ttcacgcatg aacaccaagt acgatgaaaa tgacaaactg attcgagagg   3000
tgaaagttat tactctgaag tctaagctgg tctcagattt cagaaaggac tttcagtttt   3060
ataaggtgag agagatcaac aattaccacc atgcgcatga tgcctacctg aatgcagtgg   3120
taggcactgc acttatcaaa aaatatccca agctggaatc tgaatttgtt tacgagact   3180 ataaagtgta cgatgttagg aaaatgatcg caaagtctga gcaggaaata ggcaaggcca   3240
ccgctaagta cttcttttac agcaatatta tgaattttt caagaccgag attacactgg   3300
ccaatggaga gattcggaag cgaccactta tcgaaacaaa cggagaaaca ggagaaatcg   3360
tgtgggacaa gggtagggat ttcgcgacag tccgcaaggt cctgtccatg ccgcaggtga   3420
acatcgttaa aaagaccgaa gtacagaccg gaggcttctc caaggaaagt atcctcccga   3480
aaaggaacag cgacaagctg atcgcacgca aaaagattg ggaccccaag aaatacggcg   3540
gattcgattc tcctacagtc gcttacagtg tactggttgt ggccaaagtg gagaaaggga   3600
agtctaaaaa actcaaaagc gtcaaggaac tgctgggcat cacaatcatg gagcgatcca   3660
gcttcgagaa aaaccccatc gactttctcg aagcgaaagg atataaagag gtcaaaaag   3720 acctcatcat taagctgccc aagtactctc tctttgagct tgaaaacggc cggaaacgaa   3780
```

```
tgctcgctag tgcgggcgag ctgcagaaag gtaacgagct ggcactgccc tctaaatacg    3840
ttaatttctt gtatctggcc agccactatg aaaagctcaa agggtctccc gaagataatg    3900
agcagaagca gctgttcgtg gaacaacaca acactacct  tgatgagatc atcgagcaaa    3960
taagcgagtt ctccaaaaga gtgatcctcg ccgacgctaa cctcgataag gtgctttctg    4020
cttacaataa gcacagggat aagcccatca gggagcaggc agaaaacatt atccacttgt    4080
ttactctgac caacttgggc gcgcctgcag ccttcaagta cttcgacacc accatagaca    4140
gaaagaagta cacctctaca aaggaggtcc tggacgccac actgattcat cagtcaatta    4200
cggggctcta tgaaacaaga atcgacctct ctcagctcgg tggagacggc accggcgggc    4260
ccaagaagaa gaggaaggta tacccatacg atgttcctga ctatgcgggc tatccctatg    4320
acgtcccgga ctatgcagga tcgtatcctt atgacgttcc agattacgct ggatccgccg    4380
ctccggcagc taagaaaaag aaactggatt tcgaatccgg aaagccctat aaatgtcctg    4440
aatgtggcaa gtccttctcg cagagcggag acctgacacg gcaccaacgt acgcacactg    4500
gtgagaagcc atacgcgtgt cctgtcgagt cctgtgaccg ccgcttcagt gagaagagcc    4560
acctgacacg gcacatccgc attcacacag ggcaaaaacc gtttcaatgc cgcatctgca    4620
tgaggaactt cagctgtgcc caccacctga cacggcacat ccgcacccac acaggagaaa    4680
agcccttcgc ctgtgacatc tgcggcagga agttcgcgga ccggagcacc ctgacacagc    4740
acaccaagat ccacctccgt cagaaagacc ccgggtaatg actcgagcct ctagaactat    4800
agtgagtcgt attacgtaga tccagacatg ataagataca ttgatgagtt tggacaaacc    4860
acaactagaa tgcagtgaaa aaaatgcttt atttgtgaaa tttgtgatgc tattgcttta    4920
tttgtaacca ttataagctg caataaacaa gttaacaaca acaattgcat tcattttatg    4980
tttcaggttc agggggaggt gtgggaggtt ttttaattcg cggccgcggc gccaatgcat    5040
tgggcccggt acccagcttt tgttcccttt agtgagggtt aattgcgcgc ttggcgtaat    5100
catggtcata gctgtttcct gtgtgaaatt gttatccgct cacaattcca cacaacatac    5160
gagccggaag cataaagtgt aaagcctggg gtgcctaatg agtgagctaa ctcacattaa    5220
ttgcgttgcg ctcactgccc gctttccagt cgggaaacct gtcgtgccag ctgcattaat    5280
gaatcggcca acgcgcgggg agaggcggtt tgcgtattgg gcgctcttcc gcttcctcgc    5340
tcactgactc gctgcgctcg gtcgttcggc tgcggcgagc ggtatcagct cactcaaagg    5400
cggtaatacg gttatccaca gaatcagggg ataacgcagg aaagaacatg tgagcaaaag    5460
gccagcaaaa ggccaggaac cgtaaaaagg ccgcgttgct ggcgtttttc cataggctcc    5520
gcccccctga cgagcatcac aaaaatcgac gctcaagtca gaggtggcga aacccgacag    5580
gactataaag ataccaggcg tttccccctg gaagctccct cgtgcgctct cctgttccga    5640
ccctgccgct taccggatac ctgtccgcct ttctcccttc gggaagcgtg gcgctttctc    5700
atagctcacg ctgtaggtat ctcagttcgg tgtaggtcgt tcgctccaag ctgggctgtg    5760
tgcacgaacc ccccgttcag cccgaccgct gcgccttatc cggtaactat cgtcttgagt    5820
ccaacccggt aagacacgac ttatcgccac tggcagcagc cactggtaac aggattagca    5880
gagcgaggta tgtaggcggt gctacagagt tcttgaagtg gtggcctaac tacggctaca    5940
ctagaaggac agtatttggt atctgcgctc tgctgaagcc agttaccttc ggaaaaagag    6000
ttggtagctc ttgatccggc aaacaaacca ccgctggtag cggtggtttt tttgtttgca    6060
agcagcagat tacgcgcaga aaaaaaggat ctcaagaaga tcctttgatc ttttctacgg    6120
ggtctgacgc tcagtggaac gaaaactcac gttaagggat tttggtcatg agattatcaa    6180
```

```
aaaggatctt cacctagatc cttttaaatt aaaaatgaag ttttaaatca atctaaagta    6240
tatatgagta aacttggtct gacagttacc aatgcttaat cagtgaggca cctatctcag    6300
cgatctgtct atttcgttca tccatagttg cctgactccc cgtcgtgtag ataactacga    6360
tacgggaggg cttaccatct ggccccagtg ctgcaatgat accgcgagac ccacgctcac    6420
cggctccaga tttatcagca ataaaccagc cagccggaag ggccgagcgc agaagtggtc    6480
ctgcaacttt atccgcctcc atccagtcta ttaattgttg ccgggaagct agagtaagta    6540
gttcgccagt taatagtttg cgcaacgttg ttgccattgc tacaggcatc gtggtgtcac    6600
gctcgtcgtt tggtatggct tcattcagct ccggttccca acgatcaagg cgagttacat    6660 gatccccat gttgtgcaaa aaagcggtta gctccttcgg tcctccgatc gttgtcagaa    6720
gtaagttggc cgcagtgtta tcactcatgg ttatggcagc actgcataat tctcttactg    6780
tcatgccatc cgtaagatgc ttttctgtga ctggtgagta ctcaaccaag tcattctgag    6840
aatagtgtat gcggcgaccg agttgctctt gcccggcgtc aatacgggat aataccgcgc    6900
cacatagcag aactttaaaa gtgctcatca ttggaaaacg ttcttcgggg cgaaaactct    6960
caaggatctt accgctgttg agatccagtt cgatgtaacc cactcgtgca cccaactgat    7020
cttcagcatc ttttactttc accagcgttt ctgggtgagc aaaaacagga aggcaaaatg    7080
ccgcaaaaaa gggaataagg gcgacacgga aatgttgaat actcatactc ttcctttttc    7140
aatattattg aagcatttat cagggttatt gtctcatgag cggatacata tttgaatgta    7200
tttagaaaaa taaacaaata ggggttccgc gcacatttcc ccgaaaagtg ccacctaaat    7260
tgtaagcgtt aatattttgt taaaattcgc gttaaatttt tgttaaatca gctcattttt    7320
taaccaatag gccgaaatcg gcaaaatccc ttataaatca aaagaataga ccgagatagg    7380
gttgagtgtt gttccagttt ggaacaagag tccactatta agaacgtgg actccaacgt    7440 caaagggcga aaaccgtct atcagggcga tggcccacta cgtgaaccat caccctaatc    7500
aagttttttg gggtcgaggt gccgtaaagc actaaatcgg aaccctaaag ggagccccg    7560 atttagagct tgacggggaa agccggcgaa cgtggcgaga aggaaggga agaaagcgaa    7620 aggagcgggc gctagggcgc tggcaagtgt agcggtcacg ctgcgcgtaa ccaccacacc    7680
cgccgcgctt aatgcgccgc tacagggcgc gtcccattcg ccattcaggc tgcgcaactg    7740
ttgggaaggg cgatcggtgc gggcctcttc gctattacgc cagtcgacca tagccaattc    7800
aatatggcgt atatggactc atgccaattc aatatggtgg atctggacct gtgccaattc    7860
aatatggcgt atatggactc gtgccaattc aatatggtgg atctggaccc cagccaattc    7920
aatatggcgg acttggcacc atgccaattc aatatggcgg acttggcact gtgccaactg    7980
gggaggggtc tacttggcac ggtgccaagt ttgaggaggg gtcttggccc tgtgccaagt    8040
ccgccatatt gaattggcat ggtgccaata atggcggcca tattggctat atgccaggat    8100
caatatatag gcaatatcca atatggccct atgccaatat ggctattggc caggttcaat    8160
actatgtatt ggccctatgc catatagtat tccatatatg ggttttccta ttgacgtaga    8220
tagcccctcc caatgggcgg tcccatatac catatatggg cttcctaat accgcccata    8280 gccactcccc cattgacgtc aatggtctct atatatggtt tttcctattg acgtcatatg    8340
ggcggtccta ttgacgtata tggcgcctcc cccattgacg tcaattacgg taaatggccc    8400
gcctggctca atgccattg acgtcaatag gaccacccac cattgacgtc aatgggatgg    8460
ctcattgccc attcatatcc gttctcacgc cccctattga cgtcaatgac ggtaaatggc    8520
```

```
ccacttggca gtacatcaat atctattaat agtaacttgg caagtacatt actattggaa      8580
ggacgccagg gtacattggc agtactccca ttgacgtcaa tggcggtaaa tggcccgcga      8640
tggctgccaa gtacatcccc attgacgtca atggggaggg gcaatgacgc aaatgggcgt      8700
tccattgacg taaatgggcg gtaggcgtgc ctaatgggag gtctatataa gcaatgctcg      8760
tttaggga                                                               8768

<210> SEQ ID NO 77
<211> LENGTH: 1510
<212> TYPE: PRT
<213> ORGANISM: Artificial sequence
<220> FEATURE:
<223> OTHER INFORMATION: Synthetic

<400> SEQUENCE: 77

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn Gln
            180                 185                 190

Leu Phe Glu Glu Asn Pro Ile Asn Ala Ser Gly Val Asp Ala Lys Ala
        195                 200                 205

Ile Leu Ser Ala Arg Leu Ser Lys Ser Arg Arg Leu Glu Asn Leu Ile
    210                 215                 220

Ala Gln Leu Pro Gly Glu Lys Lys Asn Gly Leu Phe Gly Asn Leu Ile
225                 230                 235                 240

Ala Leu Ser Leu Gly Leu Thr Pro Asn Phe Lys Ser Asn Phe Asp Leu
                245                 250                 255

Ala Glu Asp Ala Lys Leu Gln Leu Ser Lys Asp Thr Tyr Asp Asp Asp
            260                 265                 270

Leu Asp Asn Leu Leu Ala Gln Ile Gly Asp Gln Tyr Ala Asp Leu Phe
        275                 280                 285

Leu Ala Ala Lys Asn Leu Ser Asp Ala Ile Leu Leu Ser Asp Ile Leu
    290                 295                 300

Arg Val Asn Thr Glu Ile Thr Lys Ala Pro Leu Ser Ala Ser Met Ile
305                 310                 315                 320
```

```
Lys Arg Tyr Asp Glu His His Gln Asp Leu Thr Leu Leu Lys Ala Leu
                325                 330                 335

Val Arg Gln Gln Leu Pro Glu Lys Tyr Lys Glu Ile Phe Phe Asp Gln
            340                 345                 350

Ser Lys Asn Gly Tyr Ala Gly Tyr Ile Asp Gly Gly Ala Ser Gln Glu
        355                 360                 365

Glu Phe Tyr Lys Phe Ile Lys Pro Ile Leu Glu Lys Met Asp Gly Thr
    370                 375                 380

Glu Glu Leu Leu Val Lys Leu Asn Arg Glu Asp Leu Leu Arg Lys Gln
385                 390                 395                 400

Arg Thr Phe Asp Asn Gly Ser Ile Pro His Gln Ile His Leu Gly Glu
                405                 410                 415

Leu His Ala Ile Leu Arg Arg Gln Glu Asp Phe Tyr Pro Phe Leu Lys
            420                 425                 430

Asp Asn Arg Glu Lys Ile Glu Lys Ile Leu Thr Phe Arg Ile Pro Tyr
        435                 440                 445

Tyr Val Gly Pro Leu Ala Arg Gly Asn Ser Arg Phe Ala Trp Met Thr
    450                 455                 460

Arg Lys Ser Glu Glu Thr Ile Thr Pro Trp Asn Phe Glu Glu Val Val
465                 470                 475                 480

Asp Lys Gly Ala Ser Ala Gln Ser Phe Ile Glu Arg Met Thr Asn Phe
                485                 490                 495

Asp Lys Asn Leu Pro Asn Glu Lys Val Leu Pro Lys His Ser Leu Leu
            500                 505                 510

Tyr Glu Tyr Phe Thr Val Tyr Asn Glu Leu Thr Lys Val Lys Tyr Val
        515                 520                 525

Thr Glu Gly Met Arg Lys Pro Ala Phe Leu Ser Gly Glu Gln Lys Lys
    530                 535                 540

Ala Ile Val Asp Leu Leu Phe Lys Thr Asn Arg Lys Val Thr Val Lys
545                 550                 555                 560

Gln Leu Lys Glu Asp Tyr Phe Lys Lys Ile Glu Cys Phe Asp Ser Val
                565                 570                 575

Glu Ile Ser Gly Val Glu Asp Phe Asn Ala Ser Leu Gly Thr Tyr His
            580                 585                 590

Asp Leu Leu Lys Ile Ile Lys Asp Lys Asp Phe Leu Asp Asn Glu Glu
        595                 600                 605

Asn Glu Asp Ile Leu Glu Asp Ile Val Leu Thr Leu Thr Leu Phe Glu
    610                 615                 620

Asp Arg Glu Met Ile Glu Glu Arg Leu Lys Thr Tyr Ala His Leu Phe
625                 630                 635                 640

Asp Asp Lys Val Met Lys Gln Leu Lys Arg Arg Arg Tyr Thr Gly Trp
                645                 650                 655

Gly Arg Leu Ser Arg Lys Leu Ile Asn Gly Thr Arg Asp Lys Gln Ser
            660                 665                 670

Gly Lys Thr Ile Leu Asp Phe Leu Lys Ser Asp Gly Phe Ala Asn Arg
        675                 680                 685

Asn Phe Met Gln Leu Ile His Asp Asp Ser Leu Thr Phe Lys Glu Asp
    690                 695                 700

Ile Gln Lys Ala Gln Val Ser Gly Gln Gly Asp Ser Leu His Glu His
705                 710                 715                 720

Ile Ala Asn Leu Ala Gly Ser Pro Ala Ile Lys Lys Gly Ile Leu Gln
                725                 730                 735
```

```
Thr Val Lys Val Val Asp Glu Leu Val Lys Val Met Gly Arg His Lys
            740                 745                 750

Pro Glu Asn Ile Val Ile Glu Met Ala Arg Asn Gln Thr Thr Gln Lys
            755                 760                 765

Gly Gln Lys Asn Ser Arg Glu Arg Met Lys Arg Ile Glu Glu Gly Ile
        770                 775                 780

Lys Glu Leu Gly Ser Gln Ile Leu Lys Glu His Pro Val Glu Asn Thr
785                 790                 795                 800

Gln Leu Gln Asn Glu Lys Leu Tyr Leu Tyr Tyr Leu Gln Asn Gly Arg
                805                 810                 815

Asp Met Tyr Val Asp Gln Glu Leu Asp Ile Asn Arg Leu Ser Asp Tyr
            820                 825                 830

Asp Val Asp His Ile Val Pro Gln Ser Phe Leu Lys Asp Asp Ser Ile
            835                 840                 845

Asp Asn Lys Val Leu Thr Arg Ser Asp Lys Asn Arg Gly Lys Ser Asp
        850                 855                 860

Asn Val Pro Ser Glu Glu Val Val Lys Lys Met Lys Asn Tyr Trp Arg
865                 870                 875                 880

Gln Leu Leu Asn Ala Lys Leu Ile Thr Gln Arg Lys Phe Asp Asn Leu
                885                 890                 895

Thr Lys Ala Glu Arg Gly Gly Leu Ser Glu Leu Asp Lys Ala Gly Phe
            900                 905                 910

Ile Lys Arg Gln Leu Val Glu Thr Arg Gln Ile Thr Lys His Val Ala
            915                 920                 925

Gln Ile Leu Asp Ser Arg Met Asn Thr Lys Tyr Asp Glu Asn Asp Lys
        930                 935                 940

Leu Ile Arg Glu Val Lys Val Ile Thr Leu Lys Ser Lys Leu Val Ser
945                 950                 955                 960

Asp Phe Arg Lys Asp Phe Gln Phe Tyr Lys Val Arg Glu Ile Asn Asn
                965                 970                 975

Tyr His His Ala His Asp Ala Tyr Leu Asn Ala Val Val Gly Thr Ala
            980                 985                 990

Leu Ile Lys Lys Tyr Pro Lys Leu  Glu Ser Glu Phe Val  Tyr Gly Asp
            995                 1000                 1005

Tyr Lys Val Tyr Asp Val Arg  Lys Met Ile Ala Lys  Ser Glu Gln
     1010                 1015                 1020

Glu Ile Gly Lys Ala Thr Ala  Lys Tyr Phe Phe Tyr  Ser Asn Ile
     1025                 1030                 1035

Met Asn Phe Phe Lys Thr Glu  Ile Thr Leu Ala Asn  Gly Glu Ile
     1040                 1045                 1050

Arg Lys Arg Pro Leu Ile Glu  Thr Asn Gly Glu Thr  Gly Glu Ile
     1055                 1060                 1065

Val Trp Asp Lys Gly Arg Asp  Ala Phe Thr Val Arg  Lys Val Leu
     1070                 1075                 1080

Ser Met Pro Gln Val Asn Ile  Val Lys Lys Thr Glu  Val Gln Thr
     1085                 1090                 1095

Gly Gly Phe Ser Lys Glu Ser  Ile Leu Pro Lys Arg  Asn Ser Asp
     1100                 1105                 1110

Lys Leu Ile Ala Arg Lys Lys  Asp Trp Asp Pro Lys  Lys Tyr Gly
     1115                 1120                 1125

Gly Phe Asp Ser Pro Thr Val  Ala Tyr Ser Val Leu  Val Val Ala
     1130                 1135                 1140

Lys Val Glu Lys Gly Lys Ser  Lys Lys Leu Lys Ser  Val Lys Glu
```

```
                1145                1150                1155

Leu Leu Gly Ile Thr Ile Met Glu Arg Ser Ser Phe Glu Lys Asn
    1160                1165                1170

Pro Ile Asp Phe Leu Glu Ala Lys Gly Tyr Lys Glu Val Lys Lys
    1175                1180                1185

Asp Leu Ile Ile Lys Leu Pro Lys Tyr Ser Leu Phe Glu Leu Glu
    1190                1195                1200

Asn Gly Arg Lys Arg Met Leu Ala Ser Ala Gly Glu Leu Gln Gly
    1205                1210                1215

Asn Glu Leu Ala Leu Pro Ser Lys Tyr Val Asn Phe Leu Tyr Leu
    1220                1225                1230

Ala Ser His Tyr Glu Lys Leu Lys Gly Ser Pro Glu Asp Asn Glu
    1235                1240                1245

Gln Lys Gln Leu Phe Val Glu Gln His Lys His Tyr Leu Asp Glu
    1250                1255                1260

Ile Ile Glu Gln Ile Ser Glu Phe Ser Lys Arg Val Ile Leu Ala
    1265                1270                1275

Asp Ala Asn Leu Asp Lys Val Leu Ser Ala Tyr Asn Lys His Arg
    1280                1285                1290

Asp Lys Pro Ile Arg Glu Gln Ala Glu Asn Ile Ile His Leu Phe
    1295                1300                1305

Thr Leu Thr Asn Leu Gly Ala Pro Ala Ala Phe Lys Tyr Phe Asp
    1310                1315                1320

Thr Thr Ile Asp Arg Lys Arg Tyr Thr Ser Thr Lys Glu Val Leu
    1325                1330                1335

Asp Ala Thr Leu Thr Ile His Gln Ser Ile Thr Gly Leu Tyr Glu
    1340                1345                1350

Thr Arg Ile Asp Leu Ser Gln Leu Gly Gly Asp Gly Thr Gly Gly
    1355                1360                1365

Pro Lys Lys Lys Arg Lys Val Tyr Pro Tyr Asp Val Pro Asp Tyr
    1370                1375                1380

Ala Gly Tyr Pro Tyr Asp Val Pro Asp Tyr Ala Gly Ser Tyr Pro
    1385                1390                1395

Tyr Asp Val Pro Asp Tyr Ala Gly Ser Ala Ala Pro Ala Ala Lys
    1400                1405                1410

Lys Lys Lys Leu Asp Phe Glu Ser Gly Arg Pro Tyr Ala Cys Pro
    1415                1420                1425

Val Glu Ser Cys Asp Arg Arg Phe Ser Arg Ser Asp Glu Leu Thr
    1430                1435                1440

Arg His Ile Arg Ile His Thr Gly Gln Lys Pro Phe Gln Cys Arg
    1445                1450                1455

Ile Cys Met Arg Asn Phe Ser Arg Ser Asp His Leu Thr Thr His
    1460                1465                1470

Ile Arg Thr His Thr Gly Glu Lys Pro Phe Ala Cys Asp Ile Cys
    1475                1480                1485

Gly Arg Lys Phe Ala Arg Ser Asp Glu Arg Lys Arg His Thr Lys
    1490                1495                1500

Ile His Leu Arg Gln Lys Asp
    1505                1510

<210> SEQ ID NO 78
<211> LENGTH: 1542
<212> TYPE: PRT
<213> ORGANISM: Artificial sequence
```

<220> FEATURE:
<223> OTHER INFORMATION: Synthetic

<400> SEQUENCE: 78

Met Gly Arg Ala Ala Pro Ala Ala Lys Lys Lys Leu Asp Gln Leu
1               5                   10                  15

Arg Pro Tyr Ala Cys Pro Val Glu Ser Cys Asp Arg Arg Phe Ser Arg
            20                  25                  30

Ser Asp Glu Leu Thr Arg His Ile Arg Ile His Thr Gly Gln Lys Pro
        35                  40                  45

Phe Gln Cys Arg Ile Cys Met Arg Asn Phe Ser Arg Ser Asp His Leu
    50                  55                  60

Thr Thr His Ile Arg Thr His Thr Gly Glu Lys Pro Phe Ala Cys Asp
65                  70                  75                  80

Ile Cys Gly Arg Lys Phe Ala Arg Ser Asp Glu Arg Lys Arg His Thr
                85                  90                  95

Lys Ile His Leu Arg Gln Lys Asp Pro Gly Ser Gly Gly Ser Gly Ser
            100                 105                 110

Ser Gly Arg Thr Ala Ala Pro Ala Ala Lys Lys Lys Leu Asp Ser
        115                 120                 125

Glu Phe Gly Ser Asp Lys Lys Tyr Ser Ile Gly Leu Asp Ile Gly Thr
    130                 135                 140

Asn Ser Val Gly Trp Ala Val Ile Thr Asp Glu Tyr Lys Val Pro Ser
145                 150                 155                 160

Lys Lys Phe Lys Val Leu Gly Asn Thr Asp Arg His Ser Ile Lys Lys
                165                 170                 175

Asn Leu Ile Gly Ala Leu Leu Phe Asp Ser Gly Glu Thr Ala Glu Ala
            180                 185                 190

Thr Arg Leu Lys Arg Thr Ala Arg Arg Arg Tyr Thr Arg Arg Lys Asn
    195                 200                 205

Arg Ile Cys Tyr Leu Gln Glu Ile Phe Ser Asn Glu Met Ala Lys Val
        210                 215                 220

Asp Asp Ser Phe Phe His Arg Leu Glu Glu Ser Phe Leu Val Glu Glu
225                 230                 235                 240

Asp Lys Lys His Glu Arg His Pro Ile Phe Gly Asn Ile Val Asp Glu
                245                 250                 255

Val Ala Tyr His Glu Lys Tyr Pro Thr Ile Tyr His Leu Arg Lys Lys
            260                 265                 270

Leu Val Asp Ser Thr Asp Lys Ala Asp Leu Arg Leu Ile Tyr Leu Ala
    275                 280                 285

Leu Ala His Met Ile Lys Phe Arg Gly His Phe Leu Ile Glu Gly Asp
        290                 295                 300

Leu Asn Pro Asp Asn Ser Asp Val Asp Lys Leu Phe Ile Gln Leu Val
305                 310                 315                 320

Gln Thr Tyr Asn Gln Leu Phe Glu Glu Asn Pro Ile Asn Ala Ser Gly
                325                 330                 335

Val Asp Ala Lys Ala Ile Leu Ser Ala Arg Leu Ser Lys Ser Arg Arg
            340                 345                 350

Leu Glu Asn Leu Ile Ala Gln Leu Pro Gly Lys Lys Asn Gly Leu
    355                 360                 365

Phe Gly Asn Leu Ile Ala Leu Ser Leu Gly Leu Thr Pro Asn Phe Lys
        370                 375                 380

Ser Asn Phe Asp Leu Ala Glu Asp Ala Lys Leu Gln Leu Ser Lys Asp
385                 390                 395                 400

```
Thr Tyr Asp Asp Asp Leu Asp Asn Leu Leu Ala Gln Ile Gly Asp Gln
                405                 410                 415

Tyr Ala Asp Leu Phe Leu Ala Ala Lys Asn Leu Ser Asp Ala Ile Leu
            420                 425                 430

Leu Ser Asp Ile Leu Arg Val Asn Thr Glu Ile Thr Lys Ala Pro Leu
        435                 440                 445

Ser Ala Ser Met Ile Lys Arg Tyr Asp Glu His His Gln Asp Leu Thr
    450                 455                 460

Leu Leu Lys Ala Leu Val Arg Gln Gln Leu Pro Glu Lys Tyr Lys Glu
465                 470                 475                 480

Ile Phe Phe Asp Gln Ser Lys Asn Gly Tyr Ala Gly Tyr Ile Asp Gly
                485                 490                 495

Gly Ala Ser Gln Glu Glu Phe Tyr Lys Phe Ile Lys Pro Ile Leu Glu
            500                 505                 510

Lys Met Asp Gly Thr Glu Glu Leu Leu Val Lys Leu Asn Arg Glu Asp
        515                 520                 525

Leu Leu Arg Lys Gln Arg Thr Phe Asp Asn Gly Ser Ile Pro His Gln
    530                 535                 540

Ile His Leu Gly Glu Leu His Ala Ile Leu Arg Arg Gln Glu Asp Phe
545                 550                 555                 560

Tyr Pro Phe Leu Lys Asp Asn Arg Glu Lys Ile Glu Lys Ile Leu Thr
                565                 570                 575

Phe Arg Ile Pro Tyr Tyr Val Gly Pro Leu Ala Arg Gly Asn Ser Arg
            580                 585                 590

Phe Ala Trp Met Thr Arg Lys Ser Glu Glu Thr Ile Thr Pro Trp Asn
        595                 600                 605

Phe Glu Glu Val Val Asp Lys Gly Ala Ser Ala Gln Ser Phe Ile Glu
    610                 615                 620

Arg Met Thr Asn Phe Asp Lys Asn Leu Pro Asn Glu Lys Val Leu Pro
625                 630                 635                 640

Lys His Ser Leu Leu Tyr Glu Tyr Phe Thr Val Tyr Asn Glu Leu Thr
                645                 650                 655

Lys Val Lys Tyr Val Thr Glu Gly Met Arg Lys Pro Ala Phe Leu Ser
            660                 665                 670

Gly Glu Gln Lys Lys Ala Ile Val Asp Leu Leu Phe Lys Thr Asn Arg
        675                 680                 685

Lys Val Thr Val Lys Gln Leu Lys Glu Asp Tyr Phe Lys Lys Ile Glu
    690                 695                 700

Cys Phe Asp Ser Val Glu Ile Ser Gly Val Glu Asp Arg Phe Asn Ala
705                 710                 715                 720

Ser Leu Gly Thr Tyr His Asp Leu Leu Lys Ile Ile Lys Asp Lys Asp
                725                 730                 735

Phe Leu Asp Asn Glu Glu Asn Glu Asp Ile Leu Glu Asp Ile Val Leu
            740                 745                 750

Thr Leu Thr Leu Phe Glu Asp Arg Glu Met Ile Glu Glu Arg Leu Lys
        755                 760                 765

Thr Tyr Ala His Leu Phe Asp Asp Lys Val Met Lys Gln Leu Lys Arg
    770                 775                 780

Arg Arg Tyr Thr Gly Trp Gly Arg Leu Ser Arg Lys Leu Ile Asn Gly
785                 790                 795                 800

Ile Arg Asp Lys Gln Ser Gly Lys Thr Ile Leu Asp Phe Leu Lys Ser
                805                 810                 815
```

```
Asp Gly Phe Ala Asn Arg Asn Phe Met Gln Leu Ile His Asp Ser
            820                 825                 830

Leu Thr Phe Lys Glu Asp Ile Gln Lys Ala Gln Val Ser Gly Gln Gly
        835                 840                 845

Asp Ser Leu His Glu His Ile Ala Asn Leu Ala Gly Ser Pro Ala Ile
            850                 855                 860

Lys Lys Gly Ile Leu Gln Thr Val Lys Val Val Asp Glu Leu Val Lys
865                 870                 875                 880

Val Met Gly Arg His Lys Pro Glu Asn Ile Val Ile Glu Met Ala Arg
                885                 890                 895

Glu Asn Gln Thr Thr Gln Lys Gly Gln Lys Asn Ser Arg Glu Arg Met
            900                 905                 910

Lys Arg Ile Glu Glu Gly Ile Lys Glu Leu Gly Ser Gln Ile Leu Lys
        915                 920                 925

Glu His Pro Val Glu Asn Thr Gln Leu Gln Asn Glu Lys Leu Tyr Leu
    930                 935                 940

Tyr Tyr Leu Gln Asn Gly Arg Asp Met Tyr Val Asp Gln Glu Leu Asp
945                 950                 955                 960

Ile Asn Arg Leu Ser Asp Tyr Asp Val Asp His Ile Val Pro Gln Ser
                965                 970                 975

Phe Leu Lys Asp Asp Ser Ile Asp Asn Lys Val Leu Thr Arg Ser Asp
            980                 985                 990

Lys Asn Arg Gly Lys Ser Asp Asn  Val Pro Ser Glu Glu  Val Val Lys
        995                 1000                1005

Lys Met Lys Asn Tyr Trp Arg Gln Leu Leu Asn Ala Lys Leu Ile
    1010                1015                1020

Thr Gln Arg Lys Phe Asp Asn Leu Thr Lys Ala Glu Arg Gly Gly
    1025                1030                1035

Leu Ser Glu Leu Asp Lys Ala Gly Phe Ile Lys Arg Gln Leu Val
    1040                1045                1050

Glu Thr Arg Gln Ile Thr Lys His Val Ala Gln Ile Leu Asp Ser
    1055                1060                1065

Arg Met Asn Thr Lys Tyr Asp Glu Asn Asp Lys Leu Ile Arg Glu
    1070                1075                1080

Val Lys Val Ile Thr Leu Lys Ser Lys Leu Val Ser Asp Phe Arg
    1085                1090                1095

Lys Asp Phe Gln Phe Tyr Lys Val Arg Glu Ile Asn Asn Tyr His
    1100                1105                1110

His Ala His Asp Ala Tyr Leu Asn Ala Val Val Gly Thr Ala Leu
    1115                1120                1125

Ile Lys Lys Tyr Pro Lys Leu Glu Ser Glu Phe Val Tyr Gly Asp
    1130                1135                1140

Tyr Lys Val Tyr Asp Val Arg Lys Met Ile Ala Lys Ser Glu Gln
    1145                1150                1155

Glu Ile Gly Lys Ala Thr Ala Lys Tyr Phe Phe Tyr Ser Asn Ile
    1160                1165                1170

Met Asn Phe Phe Lys Thr Glu Ile Thr Leu Ala Asn Gly Glu Ile
    1175                1180                1185

Arg Lys Arg Pro Leu Ile Glu Thr Asn Gly Glu Thr Gly Glu Ile
    1190                1195                1200

Val Trp Asp Lys Gly Arg Asp Phe Ala Thr Val Arg Lys Val Leu
    1205                1210                1215

Ser Met Pro Gln Val Asn Ile Val Lys Lys Thr Glu Val Gln Thr
```

```
              1220                1225                1230

Gly Gly Phe Ser Lys Glu Ser Ile Leu Pro Lys Arg Asn Ser Asp
        1235                1240                1245

Lys Leu Ile Ala Arg Lys Lys Asp Trp Asp Pro Lys Lys Tyr Gly
        1250                1255                1260

Gly Phe Asp Ser Pro Thr Val Ala Tyr Ser Val Leu Val Val Ala
        1265                1270                1275

Lys Val Glu Lys Gly Lys Ser Lys Lys Leu Lys Ser Val Lys Glu
        1280                1285                1290

Leu Leu Gly Ile Thr Ile Met Glu Arg Ser Ser Phe Glu Lys Asn
        1295                1300                1305

Pro Ile Asp Phe Leu Glu Ala Lys Gly Tyr Lys Glu Val Lys Lys
        1310                1315                1320

Asp Leu Ile Ile Lys Leu Pro Lys Tyr Ser Leu Phe Glu Leu Glu
        1325                1330                1335

Asn Gly Arg Lys Arg Met Leu Ala Ser Ala Gly Glu Leu Gln Lys
        1340                1345                1350

Gly Asn Glu Leu Ala Leu Pro Ser Lys Tyr Val Asn Phe Leu Tyr
        1355                1360                1365

Leu Ala Ser His Tyr Glu Lys Leu Lys Gly Ser Pro Glu Asp Asn
        1370                1375                1380

Glu Gln Lys Gln Leu Phe Val Glu Gln His Lys His Tyr Leu Asp
        1385                1390                1395

Glu Ile Ile Glu Gln Ile Ser Glu Phe Ser Lys Arg Val Ile Leu
        1400                1405                1410

Ala Asp Ala Asn Leu Asp Lys Val Leu Ser Ala Tyr Asn Lys His
        1415                1420                1425

Arg Asp Lys Pro Ile Arg Glu Gln Ala Glu Asn Ile Ile His Leu
        1430                1435                1440

Phe Thr Leu Thr Asn Leu Gly Ala Pro Ala Ala Phe Lys Tyr Phe
        1445                1450                1455

Asp Thr Thr Ile Asp Arg Lys Arg Tyr Thr Ser Thr Lys Glu Val
        1460                1465                1470

Leu Asp Ala Thr Leu Ile His Gln Ser Ile Thr Gly Leu Tyr Glu
        1475                1480                1485

Thr Arg Ile Asp Leu Ser Gln Leu Gly Gly Asp Gly Thr Gly Gly
        1490                1495                1500

Pro Lys Lys Lys Arg Lys Val Tyr Pro Tyr Asp Val Pro Asp Tyr
        1505                1510                1515

Ala Gly Tyr Pro Tyr Asp Val Pro Asp Tyr Ala Gly Ser Tyr Pro
        1520                1525                1530

Tyr Asp Val Pro Asp Tyr Ala Gly Ser
        1535                1540

<210> SEQ ID NO 79
<211> LENGTH: 2008
<212> TYPE: PRT
<213> ORGANISM: Artificial sequence
<220> FEATURE:
<223> OTHER INFORMATION: Synthetic

<400> SEQUENCE: 79

Met Gly Arg Ala Ala Pro Ala Ala Lys Lys Lys Lys Leu Asp Gln Leu
1               5                   10                  15

Gly Ala Ser Gly Ser Pro Gly Ser Gly Gly Ser Gly Ser Ser Gly Arg
```

```
            20                  25                  30
Thr Ala Ala Pro Ala Ala Lys Lys Lys Lys Leu Asp Ser Glu Phe Gly
             35                  40                  45
Ser Gly Ser Asp Lys Lys Tyr Ser Ile Gly Leu Asp Ile Gly Thr Asn
 50                  55                  60
Ser Val Gly Trp Ala Val Ile Thr Asp Glu Tyr Lys Val Pro Ser Lys
 65                  70                  75                  80
Lys Phe Lys Val Leu Gly Asn Thr Asp Arg His Ser Ile Lys Lys Asn
                 85                  90                  95
Leu Ile Gly Ala Leu Leu Phe Asp Ser Gly Glu Thr Ala Glu Ala Thr
                100                 105                 110
Arg Leu Lys Arg Thr Ala Arg Arg Tyr Thr Arg Arg Lys Asn Arg
            115                 120                 125
Ile Cys Tyr Leu Gln Glu Ile Phe Ser Asn Glu Met Ala Lys Val Asp
            130                 135                 140
Asp Ser Phe Phe His Arg Leu Glu Glu Ser Phe Leu Val Glu Glu Asp
145                 150                 155                 160
Lys Lys His Glu Arg His Pro Ile Phe Gly Asn Ile Val Asp Glu Val
                165                 170                 175
Ala Tyr His Glu Lys Tyr Pro Thr Ile Tyr His Leu Arg Lys Lys Leu
            180                 185                 190
Val Asp Ser Thr Asp Lys Ala Asp Leu Arg Leu Ile Tyr Leu Ala Leu
            195                 200                 205
Ala His Met Ile Lys Phe Arg Gly His Phe Leu Ile Glu Gly Asp Leu
            210                 215                 220
Asn Pro Asp Asn Ser Asp Val Asp Lys Leu Phe Ile Gln Leu Val Gln
225                 230                 235                 240
Thr Tyr Asn Gln Leu Phe Glu Glu Asn Pro Ile Asn Ala Ser Gly Val
                245                 250                 255
Asp Ala Lys Ala Ile Leu Ser Ala Arg Leu Ser Lys Ser Arg Arg Leu
            260                 265                 270
Glu Asn Leu Ile Ala Gln Leu Pro Gly Glu Lys Lys Asn Gly Leu Phe
            275                 280                 285
Gly Asn Leu Ile Ala Leu Ser Leu Gly Leu Thr Pro Asn Phe Lys Ser
            290                 295                 300
Asn Phe Asp Leu Ala Glu Asp Ala Lys Leu Gln Leu Ser Lys Asp Thr
305                 310                 315                 320
Tyr Asp Asp Asp Leu Asp Asn Leu Leu Ala Gln Ile Gly Asp Gln Tyr
                325                 330                 335
Ala Asp Leu Phe Leu Ala Ala Lys Asn Leu Ser Asp Ala Ile Leu Leu
            340                 345                 350
Ser Asp Ile Leu Arg Val Asn Thr Glu Ile Thr Lys Ala Pro Leu Ser
            355                 360                 365
Ala Ser Met Ile Lys Arg Tyr Asp Glu His His Gln Asp Leu Thr Leu
            370                 375                 380
Leu Lys Ala Leu Val Arg Gln Gln Leu Pro Glu Lys Tyr Lys Glu Ile
385                 390                 395                 400
Phe Phe Asp Gln Ser Lys Asn Gly Tyr Ala Gly Tyr Ile Asp Gly Gly
                405                 410                 415
Ala Ser Gln Glu Glu Phe Tyr Lys Phe Ile Lys Pro Ile Leu Glu Lys
            420                 425                 430
Met Asp Gly Thr Glu Glu Leu Leu Val Lys Leu Asn Arg Glu Asp Leu
            435                 440                 445
```

```
Leu Arg Lys Gln Arg Thr Phe Asp Asn Gly Ser Ile Pro His Gln Ile
    450                 455                 460

His Leu Gly Glu Leu His Ala Ile Leu Arg Arg Gln Glu Asp Phe Tyr
465                 470                 475                 480

Pro Phe Leu Lys Asp Asn Arg Glu Lys Ile Glu Lys Ile Leu Thr Phe
                485                 490                 495

Arg Ile Pro Tyr Tyr Val Gly Pro Leu Ala Arg Gly Asn Ser Arg Phe
            500                 505                 510

Ala Trp Met Thr Arg Lys Ser Glu Glu Thr Ile Thr Pro Trp Asn Phe
        515                 520                 525

Glu Glu Val Val Asp Lys Gly Ala Ser Ala Gln Ser Phe Ile Glu Arg
530                 535                 540

Met Thr Asn Phe Asp Lys Asn Leu Pro Asn Glu Lys Val Leu Pro Lys
545                 550                 555                 560

His Ser Leu Leu Tyr Glu Tyr Phe Thr Val Tyr Asn Glu Leu Thr Lys
                565                 570                 575

Val Lys Tyr Val Thr Glu Gly Met Arg Lys Pro Ala Phe Leu Ser Gly
            580                 585                 590

Glu Gln Lys Lys Ala Ile Val Asp Leu Leu Phe Lys Thr Asn Arg Lys
        595                 600                 605

Val Thr Val Lys Gln Leu Lys Glu Asp Tyr Phe Lys Lys Ile Glu Cys
610                 615                 620

Phe Asp Ser Val Glu Ile Ser Gly Val Glu Asp Arg Phe Asn Ala Ser
625                 630                 635                 640

Leu Gly Thr Tyr His Asp Leu Leu Lys Ile Ile Lys Asp Lys Asp Phe
                645                 650                 655

Leu Asp Asn Glu Glu Asn Glu Asp Ile Leu Glu Asp Ile Val Leu Thr
            660                 665                 670

Leu Thr Leu Phe Glu Asp Arg Glu Met Ile Glu Glu Arg Leu Lys Thr
        675                 680                 685

Tyr Ala His Leu Phe Asp Asp Lys Val Met Lys Gln Leu Lys Arg Arg
690                 695                 700

Arg Tyr Thr Gly Trp Gly Arg Leu Ser Arg Lys Leu Ile Asn Gly Ile
705                 710                 715                 720

Arg Asp Lys Gln Ser Gly Lys Thr Ile Leu Asp Phe Leu Lys Ser Asp
                725                 730                 735

Gly Phe Ala Asn Arg Asn Phe Met Gln Leu Ile His Asp Asp Ser Leu
            740                 745                 750

Thr Phe Lys Glu Asp Ile Gln Lys Ala Gln Val Ser Gly Gln Gly Asp
        755                 760                 765

Ser Leu His Glu His Ile Ala Asn Leu Ala Gly Ser Pro Ala Ile Lys
770                 775                 780

Lys Gly Ile Leu Gln Thr Val Lys Val Val Asp Glu Leu Val Lys Val
785                 790                 795                 800

Met Gly Arg His Lys Pro Glu Asn Ile Val Ile Glu Met Ala Arg Glu
                805                 810                 815

Asn Gln Thr Thr Gln Lys Gly Gln Lys Asn Ser Arg Glu Arg Met Lys
            820                 825                 830

Arg Ile Glu Glu Gly Ile Lys Glu Leu Gly Ser Gln Ile Leu Lys Glu
        835                 840                 845

His Pro Val Glu Asn Thr Gln Leu Gln Asn Glu Lys Leu Tyr Leu Tyr
850                 855                 860
```

```
Tyr Leu Gln Asn Gly Arg Asp Met Tyr Val Asp Gln Glu Leu Asp Ile
865                 870                 875                 880

Asn Arg Leu Ser Asp Tyr Asp Val Asp His Ile Val Pro Gln Ser Phe
            885                 890                 895

Leu Lys Asp Asp Ser Ile Asp Asn Lys Val Leu Thr Arg Ser Asp Lys
        900                 905                 910

Asn Arg Gly Lys Ser Asp Asn Val Pro Ser Glu Glu Val Val Lys Lys
        915                 920                 925

Met Lys Asn Tyr Trp Arg Gln Leu Leu Asn Ala Lys Leu Ile Thr Gln
        930                 935                 940

Arg Lys Phe Asp Asn Leu Thr Lys Ala Glu Arg Gly Gly Leu Ser Glu
945                 950                 955                 960

Leu Asp Lys Ala Gly Phe Ile Lys Arg Gln Leu Val Glu Thr Arg Gln
            965                 970                 975

Ile Thr Lys His Val Ala Gln Ile Leu Asp Ser Arg Met Asn Thr Lys
        980                 985                 990

Tyr Asp Glu Asn Asp Lys Leu Ile Arg Glu Val Lys Val Ile Thr Leu
        995                 1000                1005

Lys Ser Lys Leu Val Ser Asp Phe Arg Lys Asp Phe Gln Phe Tyr
1010                1015                1020

Lys Val Arg Glu Ile Asn Asn Tyr His His Ala His Asp Ala Tyr
1025                1030                1035

Leu Asn Ala Val Val Gly Thr Ala Leu Ile Lys Lys Tyr Pro Lys
1040                1045                1050

Leu Glu Ser Glu Phe Val Tyr Gly Asp Tyr Lys Val Tyr Asp Val
1055                1060                1065

Arg Lys Met Ile Ala Lys Ser Glu Gln Glu Ile Gly Lys Ala Thr
1070                1075                1080

Ala Lys Tyr Phe Phe Tyr Ser Asn Ile Met Asn Phe Phe Lys Thr
1085                1090                1095

Glu Ile Thr Leu Ala Asn Gly Glu Ile Arg Lys Arg Pro Leu Ile
1100                1105                1110

Glu Thr Asn Gly Glu Thr Gly Glu Ile Val Trp Asp Lys Gly Arg
1115                1120                1125

Asp Phe Ala Thr Val Arg Lys Val Leu Ser Met Pro Gln Val Asn
1130                1135                1140

Ile Val Lys Lys Thr Glu Val Gln Thr Gly Gly Phe Ser Lys Glu
1145                1150                1155

Ser Ile Leu Pro Lys Arg Asn Ser Asp Lys Leu Ile Ala Arg Lys
1160                1165                1170

Lys Asp Trp Asp Pro Lys Lys Tyr Gly Gly Phe Asp Ser Pro Thr
1175                1180                1185

Val Ala Tyr Ser Val Leu Val Val Ala Lys Val Glu Lys Gly Lys
1190                1195                1200

Ser Lys Lys Leu Lys Ser Val Lys Glu Leu Leu Gly Ile Thr Ile
1205                1210                1215

Met Glu Arg Ser Ser Phe Glu Lys Asn Pro Ile Asp Phe Leu Glu
1220                1225                1230

Ala Lys Gly Tyr Lys Glu Val Lys Lys Asp Leu Ile Ile Lys Leu
1235                1240                1245

Pro Lys Tyr Ser Leu Phe Glu Leu Glu Asn Gly Arg Lys Arg Met
1250                1255                1260

Leu Ala Ser Ala Gly Glu Leu Gln Lys Gly Asn Glu Leu Ala Leu
```

-continued

```
              1265                1270                1275
Pro Ser Lys Tyr Val Asn Phe Leu Tyr Leu Ala Ser His Tyr Glu
        1280                1285                1290
Lys Leu Lys Gly Ser Pro Glu Asp Asn Glu Gln Lys Gln Leu Phe
        1295                1300                1305
Val Glu Gln His Lys His Tyr Leu Asp Glu Ile Ile Glu Gln Ile
        1310                1315                1320
Ser Glu Phe Ser Lys Arg Val Ile Leu Ala Asp Ala Asn Leu Asp
        1325                1330                1335
Lys Val Leu Ser Ala Tyr Asn Lys His Arg Asp Lys Pro Ile Arg
        1340                1345                1350
Glu Gln Ala Glu Asn Ile Ile His Leu Phe Thr Leu Thr Asn Leu
        1355                1360                1365
Gly Ala Pro Ala Ala Phe Lys Tyr Phe Asp Thr Thr Ile Asp Arg
        1370                1375                1380
Lys Arg Tyr Thr Ser Thr Lys Glu Val Leu Asp Ala Thr Leu Ile
        1385                1390                1395
His Gln Ser Ile Thr Gly Leu Tyr Glu Thr Arg Ile Asp Leu Ser
        1400                1405                1410
Gln Leu Gly Gly Asp Gly Thr Gly Gly Pro Lys Lys Lys Arg Lys
        1415                1420                1425
Val Tyr Pro Tyr Asp Val Pro Asp Tyr Ala Gly Tyr Pro Tyr Asp
        1430                1435                1440
Val Pro Asp Tyr Ala Gly Ser Tyr Pro Tyr Asp Val Pro Asp Tyr
        1445                1450                1455
Ala Gly Ser Ala Ala Pro Ala Lys Lys Lys Leu Asp Phe
        1460                1465                1470
Glu Ser Gly Val Pro Met Val Asp Leu Arg Thr Leu Gly Tyr Ser
        1475                1480                1485
Gln Gln Gln Gln Glu Lys Ile Lys Pro Lys Val Arg Ser Thr Val
        1490                1495                1500
Ala Gln His His Glu Ala Leu Val Gly His Gly Phe Thr His Ala
        1505                1510                1515
His Ile Val Ala Leu Ser Gln His Pro Ala Ala Leu Gly Thr Val
        1520                1525                1530
Ala Val Lys Tyr Gln Asp Met Ile Ala Ala Leu Pro Glu Ala Thr
        1535                1540                1545
His Glu Ala Ile Val Gly Val Gly Lys Gln Trp Ser Gly Ala Arg
        1550                1555                1560
Ala Leu Glu Ala Leu Leu Thr Val Ala Gly Glu Leu Arg Gly Pro
        1565                1570                1575
Pro Leu Gln Leu Asp Thr Gly Gln Leu Leu Lys Ile Ala Lys Arg
        1580                1585                1590
Gly Gly Val Thr Ala Val Glu Ala Val His Ala Trp Arg Asn Ala
        1595                1600                1605
Leu Thr Gly Ala Pro Leu Pro Leu Asn Leu Thr Pro Asp Gln Val
        1610                1615                1620
Val Ala Ile Ala Ser Asn Asn Gly Gly Lys Gln Ala Leu Glu Thr
        1625                1630                1635
Val Gln Arg Leu Leu Pro Val Leu Cys Gln Asp His Gly Leu Thr
        1640                1645                1650
Pro Asp Gln Val Val Ala Ile Ala Ser His Asp Gly Gly Lys Gln
        1655                1660                1665
```

Ala Leu Glu Thr Val Gln Arg Leu Leu Pro Val Leu Cys Gln Asp
1670                1675                1680

His Gly Leu Thr Pro Asp Gln Val Val Ala Ile Ala Ser Asn Asn
    1685                1690                1695

Gly Gly Lys Gln Ala Leu Glu Thr Val Gln Arg Leu Leu Pro Val
1700                1705                1710

Leu Cys Gln Asp His Gly Leu Thr Pro Asp Gln Val Val Ala Ile
    1715                1720                1725

Ala Ser Asn Gly Gly Lys Gln Ala Leu Glu Thr Val Gln Arg
1730                1735                1740

Leu Leu Pro Val Leu Cys Gln Asp His Gly Leu Thr Pro Asp Gln
    1745                1750                1755

Val Val Ala Ile Ala Ser Asn Asn Gly Gly Lys Gln Ala Leu Glu
1760                1765                1770

Thr Val Gln Arg Leu Leu Pro Val Leu Cys Gln Asp His Gly Leu
    1775                1780                1785

Thr Pro Asp Gln Val Val Ala Ile Ala Ser Asn Asn Gly Gly Lys
1790                1795                1800

Gln Ala Leu Glu Thr Val Gln Arg Leu Leu Pro Val Leu Cys Gln
    1805                1810                1815

Asp His Gly Leu Thr Pro Asp Gln Val Val Ala Ile Ala Ser Asn
1820                1825                1830

Asn Gly Gly Lys Gln Ala Leu Glu Thr Val Gln Arg Leu Leu Pro
    1835                1840                1845

Val Leu Cys Gln Asp His Gly Leu Thr Pro Asp Gln Val Val Ala
1850                1855                1860

Ile Ala Ser His Asp Gly Gly Lys Gln Ala Leu Glu Thr Val Gln
    1865                1870                1875

Arg Leu Leu Pro Val Leu Cys Gln Asp His Gly Leu Thr Pro Asp
1880                1885                1890

Gln Val Val Ala Ile Ala Ser Asn Asn Gly Gly Lys Gln Ala Leu
    1895                1900                1905

Glu Thr Val Gln Arg Leu Leu Pro Val Leu Cys Gln Asp His Gly
1910                1915                1920

Leu Thr Pro Asp Gln Val Val Ala Ile Ala Asn Asn Gly Gly
    1925                1930                1935

Arg Pro Ala Leu Glu Ser Ile Val Ala Gln Leu Ser Arg Pro Asp
1940                1945                1950

Pro Ala Leu Ala Ala Leu Thr Asn Asp His Leu Val Ala Leu Ala
    1955                1960                1965

Cys Leu Gly Gly Arg Pro Ala Leu Asp Ala Val Lys Lys Gly Leu
1970                1975                1980

Pro His Ala Pro Ala Leu Ile Lys Arg Thr Asn Arg Arg Ile Pro
    1985                1990                1995

Glu Arg Thr Ser His Arg Val Ala Gly Ser
2000                2005

<210> SEQ ID NO 80
<211> LENGTH: 1986
<212> TYPE: PRT
<213> ORGANISM: Artificial sequence
<220> FEATURE:
<223> OTHER INFORMATION: Synthetic

<400> SEQUENCE: 80

```
Met Gly Arg Ala Ala Pro Ala Ala Lys Lys Lys Leu Asp Gln Leu
1               5                   10                  15

Val Pro Met Val Asp Leu Arg Thr Leu Gly Tyr Ser Gln Gln Gln
            20                  25                  30

Glu Lys Ile Lys Pro Lys Val Arg Ser Thr Val Ala Gln His His Glu
        35                  40                  45

Ala Leu Val Gly His Gly Phe Thr His Ala His Ile Val Ala Leu Ser
    50                  55                  60

Gln His Pro Ala Ala Leu Gly Thr Val Ala Val Lys Tyr Gln Asp Met
65                  70                  75                  80

Ile Ala Ala Leu Pro Glu Ala Thr His Glu Ala Ile Val Gly Val Gly
                85                  90                  95

Lys Gln Trp Ser Gly Ala Arg Ala Leu Glu Ala Leu Leu Thr Val Ala
                100                 105                 110

Gly Glu Leu Arg Gly Pro Leu Gln Leu Asp Thr Gly Gln Leu Leu
            115                 120                 125

Lys Ile Ala Lys Arg Gly Gly Val Thr Ala Val Glu Ala Val His Ala
    130                 135                 140

Trp Arg Asn Ala Leu Thr Gly Ala Pro Leu Pro Leu Asn Leu Thr Pro
145                 150                 155                 160

Asp Gln Val Val Ala Ile Ala Ser Asn Asn Gly Gly Lys Gln Ala Leu
                165                 170                 175

Glu Thr Val Gln Arg Leu Leu Pro Val Leu Cys Gln Asp His Gly Leu
            180                 185                 190

Thr Pro Asp Gln Val Val Ala Ile Ala Ser His Asp Gly Gly Lys Gln
            195                 200                 205

Ala Leu Glu Thr Val Gln Arg Leu Leu Pro Val Leu Cys Gln Asp His
    210                 215                 220

Gly Leu Thr Pro Asp Gln Val Val Ala Ile Ala Ser Asn Asn Gly Gly
225                 230                 235                 240

Lys Gln Ala Leu Glu Thr Val Gln Arg Leu Leu Pro Val Leu Cys Gln
                245                 250                 255

Asp His Gly Leu Thr Pro Asp Gln Val Val Ala Ile Ala Ser Asn Gly
            260                 265                 270

Gly Gly Lys Gln Ala Leu Glu Thr Val Gln Arg Leu Leu Pro Val Leu
    275                 280                 285

Cys Gln Asp His Gly Leu Thr Pro Asp Gln Val Val Ala Ile Ala Ser
    290                 295                 300

Asn Asn Gly Gly Lys Gln Ala Leu Glu Thr Val Gln Arg Leu Leu Pro
305                 310                 315                 320

Val Leu Cys Gln Asp His Gly Leu Thr Pro Asp Gln Val Val Ala Ile
            325                 330                 335

Ala Ser Asn Asn Gly Gly Lys Gln Ala Leu Glu Thr Val Gln Arg Leu
            340                 345                 350

Leu Pro Val Leu Cys Gln Asp His Gly Leu Thr Pro Asp Gln Val Val
            355                 360                 365

Ala Ile Ala Ser Asn Asn Gly Gly Lys Gln Ala Leu Glu Thr Val Gln
    370                 375                 380

Arg Leu Leu Pro Val Leu Cys Gln Asp His Gly Leu Thr Pro Asp Gln
385                 390                 395                 400

Val Val Ala Ile Ala Ser His Asp Gly Gly Lys Gln Ala Leu Glu Thr
                405                 410                 415
```

```
Val Gln Arg Leu Leu Pro Val Leu Cys Gln Asp His Gly Leu Thr Pro
            420                 425                 430

Asp Gln Val Val Ala Ile Ala Ser Asn Asn Gly Gly Lys Gln Ala Leu
            435                 440                 445

Glu Thr Val Gln Arg Leu Leu Pro Val Leu Cys Gln Asp His Gly Leu
            450                 455                 460

Thr Pro Asp Gln Val Val Ala Ile Ala Asn Asn Asn Gly Gly Arg Pro
465                 470                 475                 480

Ala Leu Glu Ser Ile Val Ala Gln Leu Ser Arg Pro Asp Pro Ala Leu
            485                 490                 495

Ala Ala Leu Thr Asn Asp His Leu Val Ala Leu Ala Cys Leu Gly Gly
            500                 505                 510

Arg Pro Ala Leu Asp Ala Val Lys Lys Gly Leu Pro His Ala Pro Ala
            515                 520                 525

Leu Ile Lys Arg Thr Asn Arg Arg Ile Pro Glu Arg Thr Ser His Arg
            530                 535                 540

Val Ala Gly Ser Pro Gly Ser Gly Gly Ser Gly Ser Ser Gly Arg Thr
545                 550                 555                 560

Ala Ala Pro Ala Ala Lys Lys Lys Lys Leu Asp Ser Glu Phe Gly Ser
            565                 570                 575

Asp Lys Lys Tyr Ser Ile Gly Leu Asp Ile Gly Thr Asn Ser Val Gly
            580                 585                 590

Trp Ala Val Ile Thr Asp Glu Tyr Lys Val Pro Ser Lys Lys Phe Lys
            595                 600                 605

Val Leu Gly Asn Thr Asp Arg His Ser Ile Lys Lys Asn Leu Ile Gly
            610                 615                 620

Ala Leu Leu Phe Asp Ser Gly Glu Thr Ala Glu Ala Thr Arg Leu Lys
625                 630                 635                 640

Arg Thr Ala Arg Arg Arg Tyr Thr Arg Arg Lys Asn Arg Ile Cys Tyr
            645                 650                 655

Leu Gln Glu Ile Phe Ser Asn Glu Met Ala Lys Val Asp Asp Ser Phe
            660                 665                 670

Phe His Arg Leu Glu Glu Ser Phe Leu Val Glu Glu Asp Lys Lys His
            675                 680                 685

Glu Arg His Pro Ile Phe Gly Asn Ile Val Asp Glu Val Ala Tyr His
            690                 695                 700

Glu Lys Tyr Pro Thr Ile Tyr His Leu Arg Lys Lys Leu Val Asp Ser
705                 710                 715                 720

Thr Asp Lys Ala Asp Leu Arg Leu Ile Tyr Leu Ala Leu Ala His Met
            725                 730                 735

Ile Lys Phe Arg Gly His Phe Leu Ile Glu Gly Asp Leu Asn Pro Asp
            740                 745                 750

Asn Ser Asp Val Asp Lys Leu Phe Ile Gln Leu Val Gln Thr Tyr Asn
            755                 760                 765

Gln Leu Phe Glu Glu Asn Pro Ile Asn Ala Ser Gly Val Asp Ala Lys
            770                 775                 780

Ala Ile Leu Ser Ala Arg Leu Ser Lys Ser Arg Arg Leu Glu Asn Leu
785                 790                 795                 800

Ile Ala Gln Leu Pro Gly Glu Lys Lys Asn Gly Leu Phe Gly Asn Leu
            805                 810                 815

Ile Ala Leu Ser Leu Gly Leu Thr Pro Asn Phe Lys Ser Asn Phe Asp
            820                 825                 830

Leu Ala Glu Asp Ala Lys Leu Gln Leu Ser Lys Asp Thr Tyr Asp Asp
```

```
                835                 840                 845
Asp Leu Asp Asn Leu Leu Ala Gln Ile Gly Asp Gln Tyr Ala Asp Leu
850                 855                 860

Phe Leu Ala Ala Lys Asn Leu Ser Asp Ala Ile Leu Leu Ser Asp Ile
865                 870                 875                 880

Leu Arg Val Asn Thr Glu Ile Thr Lys Ala Pro Leu Ser Ala Ser Met
                885                 890                 895

Ile Lys Arg Tyr Asp Glu His His Gln Asp Leu Thr Leu Leu Lys Ala
                900                 905                 910

Leu Val Arg Gln Gln Leu Pro Glu Lys Tyr Lys Glu Ile Phe Phe Asp
                915                 920                 925

Gln Ser Lys Asn Gly Tyr Ala Gly Tyr Ile Asp Gly Gly Ala Ser Gln
930                 935                 940

Glu Glu Phe Tyr Lys Phe Ile Lys Pro Ile Leu Glu Lys Met Asp Gly
945                 950                 955                 960

Thr Glu Glu Leu Leu Val Lys Leu Asn Arg Glu Asp Leu Leu Arg Lys
                965                 970                 975

Gln Arg Thr Phe Asp Asn Gly Ser Ile Pro His Gln Ile His Leu Gly
                980                 985                 990

Glu Leu His Ala Ile Leu Arg Arg  Gln Glu Asp Phe Tyr  Pro Phe Leu
                995                 1000                1005

Lys Asp Asn Arg Glu Lys Ile  Glu Lys Ile Leu Thr  Phe Arg Ile
1010                1015                1020

Pro Tyr Tyr Val Gly Pro Leu  Ala Arg Gly Asn Ser  Arg Phe Ala
1025                1030                1035

Trp Met Thr Arg Lys Ser Glu  Glu Thr Ile Thr Pro  Trp Asn Phe
1040                1045                1050

Glu Glu Val Val Asp Lys Gly  Ala Ser Ala Gln Ser  Phe Ile Glu
1055                1060                1065

Arg Met Thr Asn Phe Asp Lys  Asn Leu Pro Asn Glu  Lys Val Leu
1070                1075                1080

Pro Lys His Ser Leu Leu Tyr  Glu Tyr Phe Thr Val  Tyr Asn Glu
1085                1090                1095

Leu Thr Lys Val Lys Tyr Val  Thr Glu Gly Met Arg  Lys Pro Ala
1100                1105                1110

Phe Leu Ser Gly Glu Gln Lys  Lys Ala Ile Val Asp  Leu Leu Phe
1115                1120                1125

Lys Thr Asn Arg Lys Val Thr  Val Lys Gln Leu Lys  Glu Asp Tyr
1130                1135                1140

Phe Lys Lys Ile Glu Cys Phe  Asp Ser Val Glu Ile  Ser Gly Val
1145                1150                1155

Glu Asp Arg Phe Asn Ala Ser  Leu Gly Thr Tyr His  Asp Leu Leu
1160                1165                1170

Lys Ile Ile Lys Asp Lys Asp  Phe Leu Asp Asn Glu  Glu Asn Glu
1175                1180                1185

Asp Ile Leu Glu Asp Ile Val  Leu Thr Leu Thr Leu  Phe Glu Asp
1190                1195                1200

Arg Glu Met Ile Glu Glu Arg  Leu Lys Thr Tyr Ala  His Leu Phe
1205                1210                1215

Asp Asp Lys Val Met Lys Gln  Leu Lys Arg Arg Arg  Tyr Thr Gly
1220                1225                1230

Trp Gly Arg Leu Ser Arg Lys  Leu Ile Asn Gly Ile  Arg Asp Lys
1235                1240                1245
```

```
Gln Ser Gly Lys Thr Ile Leu Asp Phe Leu Lys Ser Asp Gly Phe
    1250                1255                1260

Ala Asn Arg Asn Phe Met Gln Leu Ile His Asp Asp Ser Leu Thr
    1265                1270                1275

Phe Lys Glu Asp Ile Gln Lys Ala Gln Val Ser Gly Gln Gly Asp
    1280                1285                1290

Ser Leu His Glu His Ile Ala Asn Leu Ala Gly Ser Pro Ala Ile
    1295                1300                1305

Lys Lys Gly Ile Leu Gln Thr Val Lys Val Val Asp Glu Leu Val
    1310                1315                1320

Lys Val Met Gly Arg His Lys Pro Glu Asn Ile Val Ile Glu Met
    1325                1330                1335

Ala Arg Glu Asn Gln Thr Thr Gln Lys Gly Gln Lys Asn Ser Arg
    1340                1345                1350

Glu Arg Met Lys Arg Ile Glu Glu Gly Ile Lys Glu Leu Gly Ser
    1355                1360                1365

Gln Ile Leu Lys Glu His Pro Val Glu Asn Thr Gln Leu Gln Asn
    1370                1375                1380

Glu Lys Leu Tyr Leu Tyr Tyr Leu Gln Asn Gly Arg Asp Met Tyr
    1385                1390                1395

Val Asp Gln Glu Leu Asp Ile Asn Arg Leu Ser Asp Tyr Asp Val
    1400                1405                1410

Asp His Ile Val Pro Gln Ser Phe Leu Lys Asp Asp Ser Ile Asp
    1415                1420                1425

Asn Lys Val Leu Thr Arg Ser Asp Lys Asn Arg Gly Lys Ser Asp
    1430                1435                1440

Asn Val Pro Ser Glu Glu Val Val Lys Lys Met Lys Asn Tyr Trp
    1445                1450                1455

Arg Gln Leu Leu Asn Ala Lys Leu Ile Thr Gln Arg Lys Phe Asp
    1460                1465                1470

Asn Leu Thr Lys Ala Glu Arg Gly Gly Leu Ser Glu Leu Asp Lys
    1475                1480                1485

Ala Gly Phe Ile Lys Arg Gln Leu Val Glu Thr Arg Gln Ile Thr
    1490                1495                1500

Lys His Val Ala Gln Ile Leu Asp Ser Arg Met Asn Thr Lys Tyr
    1505                1510                1515

Asp Glu Asn Asp Lys Leu Ile Arg Glu Val Lys Val Ile Thr Leu
    1520                1525                1530

Lys Ser Lys Leu Val Ser Asp Phe Arg Lys Asp Phe Gln Phe Tyr
    1535                1540                1545

Lys Val Arg Glu Ile Asn Asn Tyr His His Ala His Asp Ala Tyr
    1550                1555                1560

Leu Asn Ala Val Val Gly Thr Ala Leu Ile Lys Lys Tyr Pro Lys
    1565                1570                1575

Leu Glu Ser Glu Phe Val Tyr Gly Asp Tyr Lys Val Tyr Asp Val
    1580                1585                1590

Arg Lys Met Ile Ala Lys Ser Glu Gln Glu Ile Gly Lys Ala Thr
    1595                1600                1605

Ala Lys Tyr Phe Phe Tyr Ser Asn Ile Met Asn Phe Phe Lys Thr
    1610                1615                1620

Glu Ile Thr Leu Ala Asn Gly Glu Ile Arg Lys Arg Pro Leu Ile
    1625                1630                1635
```

Glu Thr Asn Gly Glu Thr Gly Glu Ile Val Trp Asp Lys Gly Arg
    1640                1645                1650

Asp Phe Ala Thr Val Arg Lys Val Leu Ser Met Pro Gln Val Asn
    1655                1660                1665

Ile Val Lys Lys Thr Glu Val Gln Thr Gly Gly Phe Ser Lys Glu
    1670                1675                1680

Ser Ile Leu Pro Lys Arg Asn Ser Asp Lys Leu Ile Ala Arg Lys
    1685                1690                1695

Lys Asp Trp Asp Pro Lys Lys Tyr Gly Gly Phe Asp Ser Pro Thr
    1700                1705                1710

Val Ala Tyr Ser Val Leu Val Ala Lys Val Glu Lys Gly Lys
    1715                1720                1725

Ser Lys Lys Leu Lys Ser Val Lys Glu Leu Leu Gly Ile Thr Ile
    1730                1735                1740

Met Glu Arg Ser Ser Phe Glu Lys Asn Pro Ile Asp Phe Leu Glu
    1745                1750                1755

Ala Lys Gly Tyr Lys Glu Val Lys Lys Asp Leu Ile Ile Lys Leu
    1760                1765                1770

Pro Lys Tyr Ser Leu Phe Glu Leu Glu Asn Gly Arg Lys Arg Met
    1775                1780                1785

Leu Ala Ser Ala Gly Glu Leu Gln Lys Gly Asn Glu Leu Ala Leu
    1790                1795                1800

Pro Ser Lys Tyr Val Asn Phe Leu Tyr Leu Ala Ser His Tyr Glu
    1805                1810                1815

Lys Leu Lys Gly Ser Pro Glu Asp Asn Glu Gln Lys Gln Leu Phe
    1820                1825                1830

Val Glu Gln His Lys His Tyr Leu Asp Glu Ile Ile Glu Gln Ile
    1835                1840                1845

Ser Glu Phe Ser Lys Arg Val Ile Leu Ala Asp Ala Asn Leu Asp
    1850                1855                1860

Lys Val Leu Ser Ala Tyr Asn Lys His Arg Asp Lys Pro Ile Arg
    1865                1870                1875

Glu Gln Ala Glu Asn Ile Ile His Leu Phe Thr Leu Thr Asn Leu
    1880                1885                1890

Gly Ala Pro Ala Ala Phe Lys Tyr Phe Asp Thr Thr Ile Asp Arg
    1895                1900                1905

Lys Arg Tyr Thr Ser Thr Lys Glu Val Leu Asp Ala Thr Leu Ile
    1910                1915                1920

His Gln Ser Ile Thr Gly Leu Tyr Glu Thr Arg Ile Asp Leu Ser
    1925                1930                1935

Gln Leu Gly Gly Asp Gly Thr Gly Gly Pro Lys Lys Lys Arg Lys
    1940                1945                1950

Val Tyr Pro Tyr Asp Val Pro Asp Tyr Ala Gly Tyr Pro Tyr Asp
    1955                1960                1965

Val Pro Asp Tyr Ala Gly Ser Tyr Pro Tyr Asp Val Pro Asp Tyr
    1970                1975                1980

Ala Gly Ser
    1985

<210> SEQ ID NO 81
<211> LENGTH: 1544
<212> TYPE: PRT
<213> ORGANISM: Artificial sequence
<220> FEATURE:
<223> OTHER INFORMATION: Synthetic

<400> SEQUENCE: 81

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
```

```
            405                 410                 415
Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830
```

```
Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230
```

Asn Phe Leu Tyr Leu Ala Ser His Tyr Glu Lys Leu Lys Gly Ser
1235                 1240                1245

Pro Glu Asp Asn Glu Gln Lys Gln Leu Phe Val Glu Gln His Lys
1250                 1255                1260

His Tyr Leu Asp Glu Ile Ile Glu Gln Ile Ser Glu Phe Ser Lys
1265                 1270                1275

Arg Val Ile Leu Ala Asp Ala Asn Leu Asp Lys Val Leu Ser Ala
1280                 1285                1290

Tyr Asn Lys His Arg Asp Lys Pro Ile Arg Glu Gln Ala Glu Asn
1295                 1300                1305

Ile Ile His Leu Phe Thr Leu Thr Asn Leu Gly Ala Pro Ala Ala
1310                 1315                1320

Phe Lys Tyr Phe Asp Thr Thr Ile Asp Arg Lys Arg Tyr Thr Ser
1325                 1330                1335

Thr Lys Glu Val Leu Asp Ala Thr Leu Ile His Gln Ser Ile Thr
1340                 1345                1350

Gly Leu Tyr Glu Thr Arg Ile Asp Leu Ser Gln Leu Gly Gly Asp
1355                 1360                1365

Gly Thr Gly Gly Pro Lys Lys Lys Arg Lys Val Tyr Pro Tyr Asp
1370                 1375                1380

Val Pro Asp Tyr Ala Gly Tyr Pro Tyr Asp Val Pro Asp Tyr Ala
1385                 1390                1395

Gly Ser Tyr Pro Tyr Asp Val Pro Asp Tyr Ala Gly Ser Ala Ala
1400                 1405                1410

Pro Ala Ala Lys Lys Lys Lys Leu Asp Phe Glu Ser Gly Lys Pro
1415                 1420                1425

Tyr Lys Cys Pro Glu Cys Gly Lys Ser Phe Ser Gln Ser Gly Asp
1430                 1435                1440

Leu Thr Arg His Gln Arg Thr His Thr Gly Glu Lys Pro Tyr Ala
1445                 1450                1455

Cys Pro Val Glu Ser Cys Asp Arg Arg Phe Ser Glu Lys Ser His
1460                 1465                1470

Leu Thr Arg His Ile Arg Ile His Thr Gly Gln Lys Pro Phe Gln
1475                 1480                1485

Cys Arg Ile Cys Met Arg Asn Phe Ser Cys Ala His His Leu Thr
1490                 1495                1500

Arg His Ile Arg Thr His Thr Gly Glu Lys Pro Phe Ala Cys Asp
1505                 1510                1515

Ile Cys Gly Arg Lys Phe Ala Asp Arg Ser Thr Leu Thr Gln His
1520                 1525                1530

Thr Lys Ile His Leu Arg Gln Lys Asp Pro Gly
1535                 1540

<210> SEQ ID NO 82
<211> LENGTH: 1544
<212> TYPE: PRT
<213> ORGANISM: Artificial sequence
<220> FEATURE:
<223> OTHER INFORMATION: Synthetic

<400> SEQUENCE: 82

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

-continued

```
Lys Val Leu Gly Asn Thr Asp Arg His Ser Ile Lys Lys Asn Leu Ile
             35                  40                  45
Gly Ala Leu Leu Phe Asp Ser Gly Glu Thr Ala Glu Ala Thr Arg Leu
 50                  55                  60
Lys Arg Thr Ala Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
            130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
            210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
            405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
```

```
            450                 455                 460
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880
```

```
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
         1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
```

```
Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Thr Gly Gly Pro Lys Lys Lys Arg Lys Val Tyr Pro Tyr Asp
    1370                1375                1380

Val Pro Asp Tyr Ala Gly Tyr Pro Tyr Asp Val Pro Asp Tyr Ala
    1385                1390                1395

Gly Ser Tyr Pro Tyr Asp Val Pro Asp Tyr Ala Gly Ser Ala Ala
    1400                1405                1410

Pro Ala Ala Lys Lys Lys Lys Leu Asp Phe Glu Ser Gly Lys Pro
    1415                1420                1425

Tyr Lys Cys Pro Glu Cys Gly Lys Ser Phe Ser Gln Lys Gly His
    1430                1435                1440

Leu Thr Arg His Gln Arg Thr His Thr Gly Glu Lys Pro Tyr Ala
    1445                1450                1455

Cys Pro Val Glu Ser Cys Asp Arg Arg Phe Ser Asp Arg Ser Asp
    1460                1465                1470

Leu Thr Arg His Ile Arg Ile His Thr Gly Gln Lys Pro Phe Gln
    1475                1480                1485

Cys Arg Ile Cys Met Arg Asn Phe Ser Arg Ser Asp His Leu Thr
    1490                1495                1500

Arg His Ile Arg Thr His Thr Gly Glu Lys Pro Phe Ala Cys Asp
    1505                1510                1515

Ile Cys Gly Arg Lys Phe Ala Gln Ser Gly Asp Leu Thr Arg His
    1520                1525                1530

Thr Lys Ile His Leu Arg Gln Lys Asp Pro Gly
    1535                1540

<210> SEQ ID NO 83
<211> LENGTH: 1544
<212> TYPE: PRT
<213> ORGANISM: Artificial sequence
<220> FEATURE:
<223> OTHER INFORMATION: Synthetic

<400> SEQUENCE: 83

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
```

```
              500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
                690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
                850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
```

```
Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                    980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320
```

```
Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Gly Thr Gly Gly Pro Lys Lys Lys Arg Lys Val Tyr Pro Tyr Asp
1370                1375                1380

Val Pro Asp Tyr Ala Gly Tyr Pro Tyr Asp Val Pro Asp Tyr Ala
1385                1390                1395

Gly Ser Tyr Pro Tyr Asp Val Pro Asp Tyr Ala Gly Ser Ala Ala
1400                1405                1410

Pro Ala Ala Lys Lys Lys Lys Leu Asp Phe Glu Ser Gly Lys Pro
1415                1420                1425

Tyr Lys Cys Pro Glu Cys Gly Lys Ser Phe Ser Arg Ser Asp Asp
1430                1435                1440

Leu Thr Arg His Gln Arg Thr His Thr Gly Glu Lys Pro Tyr Ala
1445                1450                1455

Cys Pro Val Glu Ser Cys Asp Arg Arg Phe Ser Gln Lys Gly His
1460                1465                1470

Leu Thr Arg His Ile Arg Ile His Thr Gly Gln Lys Pro Phe Gln
1475                1480                1485

Cys Arg Ile Cys Met Arg Asn Phe Ser Ile Arg Ser Ser Leu Thr
1490                1495                1500

Arg His Ile Arg Thr His Thr Gly Glu Lys Pro Phe Ala Cys Asp
1505                1510                1515

Ile Cys Gly Arg Lys Phe Ala Leu Ser His His Leu Thr Arg His
1520                1525                1530

Thr Lys Ile His Leu Arg Gln Lys Asp Pro Gly
1535                1540
```

<210> SEQ ID NO 84
<211> LENGTH: 47
<212> TYPE: DNA
<213> ORGANISM: Artificial sequence
<220> FEATURE:
<223> OTHER INFORMATION: Synthetic

<400> SEQUENCE: 84 gacccccctcc accccgcctc cgggcgcggg ctccggcccc tgcccgc         47

<210> SEQ ID NO 85
<211> LENGTH: 47
<212> TYPE: DNA
<213> ORGANISM: Artificial sequence
<220> FEATURE:
<223> OTHER INFORMATION: Synthetic

<400> SEQUENCE: 85
ggtgagtgag tgtgtgcgtg tggggttgag ggtgttggag cggggag         47

<210> SEQ ID NO 86
<211> LENGTH: 47
<212> TYPE: DNA
<213> ORGANISM: Artificial sequence
<220> FEATURE:
<223> OTHER INFORMATION: Synthetic

<400> SEQUENCE: 86
gagtccgagc agaagaagaa gggctcccat cacatcaacc ggtggcg    47

<210> SEQ ID NO 87
<211> LENGTH: 58
<212> TYPE: DNA
<213> ORGANISM: Artificial sequence
<220> FEATURE:
<223> OTHER INFORMATION: Synthetic

<400> SEQUENCE: 87 gccgacccc tccaccccgc ctccgggcgc gggctccggc ccctgcccgc ggctcgcc    58

<210> SEQ ID NO 88
<211> LENGTH: 58
<212> TYPE: DNA
<213> ORGANISM: Artificial sequence
<220> FEATURE:
<223> OTHER INFORMATION: Synthetic

<400> SEQUENCE: 88 gccgacccc tccaccccgc ctccgggcgc gggctccggc ccctgcccgc ggctcgcc    58

<210> SEQ ID NO 89
<211> LENGTH: 43
<212> TYPE: DNA
<213> ORGANISM: Artificial sequence
<220> FEATURE:
<223> OTHER INFORMATION: Synthetic

<400> SEQUENCE: 89
gggcccaacc tagggcatgg aggcggctgc tggtgcgtgg gcg    43

<210> SEQ ID NO 90
<211> LENGTH: 43
<212> TYPE: DNA
<213> ORGANISM: Artificial sequence
<220> FEATURE:
<223> OTHER INFORMATION: Synthetic

<400> SEQUENCE: 90
gcatgggtga tgtcaatgcc aaggccagtc aggtgcgtgg gcg    43

<210> SEQ ID NO 91
<211> LENGTH: 43
<212> TYPE: DNA
<213> ORGANISM: Artificial sequence
<220> FEATURE:
<223> OTHER INFORMATION: Synthetic

<400> SEQUENCE: 91
cctggaccca acgccccagg agaagagcga aggtgcgtgg gcg    43

<210> SEQ ID NO 92
<211> LENGTH: 43
<212> TYPE: DNA
<213> ORGANISM: Artificial sequence
<220> FEATURE:
<223> OTHER INFORMATION: Synthetic

<400> SEQUENCE: 92
gctggcggaa gacagagtgc tgctattcac ctctgcgtgg gcg    43

<210> SEQ ID NO 93
<211> LENGTH: 43
<212> TYPE: PRT
<213> ORGANISM: Artificial sequence
<220> FEATURE:
<223> OTHER INFORMATION: Synthetic

<400> SEQUENCE: 93

Gly Gly Gly Cys Cys Cys Ala Ala Cys Cys Thr Ala Gly Gly Gly Cys
1               5                   10                  15

Ala Thr Gly Gly Ala Gly Gly Cys Gly Gly Cys Thr Gly Cys Thr Gly
            20                  25                  30

Gly Thr Gly Cys Gly Thr Gly Gly Cys Gly
            35                  40

<210> SEQ ID NO 94
<211> LENGTH: 43
<212> TYPE: DNA
<213> ORGANISM: Artificial sequence
<220> FEATURE:
<223> OTHER INFORMATION: Synthetic

<400> SEQUENCE: 94
gggcccaacc tagggcatgg aggcggctgc tggtgcgtgg gcg                43

<210> SEQ ID NO 95
<211> LENGTH: 49
<212> TYPE: DNA
<213> ORGANISM: Artificial sequence
<220> FEATURE:
<223> OTHER INFORMATION: Synthetic

<400> SEQUENCE: 95
atggacccct aggtctccgg aggctacacg tgttccccga tcccgtttc          49

<210> SEQ ID NO 96
<211> LENGTH: 47
<212> TYPE: DNA
<213> ORGANISM: Artificial sequence
<220> FEATURE:
<223> OTHER INFORMATION: Synthetic

<400> SEQUENCE: 96
tgtttggtgg gtactcaccc agggctaaga gctgccaggt actgtgt            47

<210> SEQ ID NO 97
<211> LENGTH: 47
<212> TYPE: DNA
<213> ORGANISM: Artificial sequence
<220> FEATURE:
<223> OTHER INFORMATION: Synthetic

<400> SEQUENCE: 97
gaccccctcc acccgcctc cgggcgcggg ctccggcccc tgcccgc             47

<210> SEQ ID NO 98
<211> LENGTH: 47
<212> TYPE: DNA
<213> ORGANISM: Artificial sequence
<220> FEATURE:
<223> OTHER INFORMATION: Synthetic

<400> SEQUENCE: 98
ggtgagtgag tgtgtgcgtg tggggttgag ggtgttggag cggggag            47

<210> SEQ ID NO 99
<211> LENGTH: 47
<212> TYPE: DNA
<213> ORGANISM: Artificial sequence

```
<220> FEATURE:
<223> OTHER INFORMATION: Synthetic

<400> SEQUENCE: 99
gagtccgagc agaagaagaa gggctcccat cacatcaacc ggtggcg                47

<210> SEQ ID NO 100
<211> LENGTH: 58
<212> TYPE: DNA
<213> ORGANISM: Artificial sequence
<220> FEATURE:
<223> OTHER INFORMATION: Synthetic

<400> SEQUENCE: 100
gtgggtgagt gagtgtgtgc gtgtgggtt gagggtgttg gagccgggag aaggccag     58

<210> SEQ ID NO 101
<211> LENGTH: 58
<212> TYPE: DNA
<213> ORGANISM: Artificial sequence
<220> FEATURE:
<223> OTHER INFORMATION: Synthetic

<400> SEQUENCE: 101
gtgggtgagt gagtgtgtgc gtgtgggtt gagggtgttg gagcggggag aaggccag     58

<210> SEQ ID NO 102
<211> LENGTH: 58
<212> TYPE: DNA
<213> ORGANISM: Artificial sequence
<220> FEATURE:
<223> OTHER INFORMATION: Synthetic

<400> SEQUENCE: 102
cctgagtccg agcagaagaa gaagggctcc catcacatca accggtggcg cattgcca    58

<210> SEQ ID NO 103
<211> LENGTH: 58
<212> TYPE: DNA
<213> ORGANISM: Artificial sequence
<220> FEATURE:
<223> OTHER INFORMATION: Synthetic

<400> SEQUENCE: 103
gtgggtgagt gagtgtgtgc gtgtgggtt gagggtgttg gagcggggag aaggccag     58

<210> SEQ ID NO 104
<211> LENGTH: 58
<212> TYPE: DNA
<213> ORGANISM: Artificial sequence
<220> FEATURE:
<223> OTHER INFORMATION: Synthetic

<400> SEQUENCE: 104
cctgagtccg agcagaagaa gaagggctcc catcacatca accggtggcg cattgcca    58

<210> SEQ ID NO 105
<211> LENGTH: 20
<212> TYPE: DNA
<213> ORGANISM: Artificial sequence
<220> FEATURE:
<223> OTHER INFORMATION: Synthetic

<400> SEQUENCE: 105
gagtgagtgt gtgcgtgtgg                                              20
```

```
<210> SEQ ID NO 106
<211> LENGTH: 21
<212> TYPE: DNA
<213> ORGANISM: Artificial sequence
<220> FEATURE:
<223> OTHER INFORMATION: Synthetic

<400> SEQUENCE: 106
gtccgagcag aagaagaagg g                                              21

<210> SEQ ID NO 107
<211> LENGTH: 58
<212> TYPE: DNA
<213> ORGANISM: Artificial sequence
<220> FEATURE:
<223> OTHER INFORMATION: Synthetic

<400> SEQUENCE: 107 gccgacccc tccaccccgc ctccgggcgc gggctccggc ccctgcccgc ggctcgcc      58

<210> SEQ ID NO 108
<211> LENGTH: 58
<212> TYPE: DNA
<213> ORGANISM: Artificial sequence
<220> FEATURE:
<223> OTHER INFORMATION: Synthetic

<400> SEQUENCE: 108 gccgacccc tccaccccgc ctccgggcgc gggctccggc ccctgcccgc ggctcgcc      58

<210> SEQ ID NO 109
<211> LENGTH: 45
<212> TYPE: DNA
<213> ORGANISM: Artificial sequence
<220> FEATURE:
<223> OTHER INFORMATION: Synthetic

<400> SEQUENCE: 109
gggcccctcc accccgcctc tggccaagtt ttgaggatag ggagg                    45

<210> SEQ ID NO 110
<211> LENGTH: 12
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, t or u

<400> SEQUENCE: 110
gcggryargg rn                                                        12

<210> SEQ ID NO 111
<211> LENGTH: 58
<212> TYPE: DNA
<213> ORGANISM: Artificial sequence
<220> FEATURE:
<223> OTHER INFORMATION: Synthetic

<400> SEQUENCE: 111 gccgacccc tccaccccgc ctccgggcgc gggctccggc ccctgcccgc ggctcgcc      58

<210> SEQ ID NO 112
<211> LENGTH: 58
```

```
<212> TYPE: DNA
<213> ORGANISM: Artificial sequence
<220> FEATURE:
<223> OTHER INFORMATION: Synthetic

<400> SEQUENCE: 112
gccgaccccc tccaccccgc ctccgggcgc gggctccggc ccctgcccgc ggctcgcc    58

<210> SEQ ID NO 113
<211> LENGTH: 58
<212> TYPE: DNA
<213> ORGANISM: Artificial sequence
<220> FEATURE:
<223> OTHER INFORMATION: Synthetic

<400> SEQUENCE: 113
tagggccccc tccaccccgc ctctggccaa gttttgagga tagggaggtg ggtagccc    58

<210> SEQ ID NO 114
<211> LENGTH: 1110
<212> TYPE: PRT
<213> ORGANISM: Neisseria meningitidis

<400> SEQUENCE: 114
```

Met Val Pro Lys Lys Arg Lys Val Ala Ala Phe Lys Pro Asn Ser
1               5                   10                  15

Ile Asn Tyr Ile Leu Gly Leu Asp Ile Gly Ile Ala Ser Val Gly Trp
20 25 30

Ala Met Val Glu Ile Asp Glu Glu Glu Asn Pro Ile Arg Leu Ile Asp
35 40 45

Leu Gly Val Arg Val Phe Glu Arg Ala Glu Val Pro Lys Thr Gly Asp
50 55 60

Ser Leu Ala Met Ala Arg Arg Leu Ala Arg Ser Val Arg Arg Leu Thr
65 70 75 80

Arg Arg Arg Ala His Arg Leu Leu Arg Thr Arg Arg Leu Leu Lys Arg
85 90 95

Glu Gly Val Leu Gln Ala Ala Asn Phe Asp Glu Asn Gly Leu Ile Lys
100 105 110

Ser Leu Pro Asn Thr Pro Trp Gln Leu Arg Ala Ala Ala Leu Asp Arg
115 120 125

Lys Leu Thr Pro Leu Glu Trp Ser Ala Val Leu Leu His Leu Ile Lys
130 135 140

His Arg Gly Tyr Leu Ser Gln Arg Lys Asn Glu Gly Glu Thr Ala Asp
145 150 155 160

Lys Glu Leu Gly Ala Leu Leu Lys Gly Val Ala Gly Asn Ala His Ala
165 170 175

Leu Gln Thr Gly Asp Phe Arg Thr Pro Ala Glu Leu Ala Leu Asn Lys
180 185 190

Phe Glu Lys Glu Ser Gly His Ile Arg Asn Gln Arg Ser Asp Tyr Ser
195 200 205

His Thr Phe Ser Arg Lys Asp Leu Gln Ala Glu Leu Ile Leu Leu Phe
210 215 220

Glu Lys Gln Lys Glu Phe Gly Asn Pro His Val Ser Gly Gly Leu Lys
225 230 235 240

Glu Gly Ile Glu Thr Leu Leu Met Thr Gln Arg Pro Ala Leu Ser Gly
245 250 255

Asp Ala Val Gln Lys Met Leu Gly His Cys Thr Phe Glu Pro Ala Glu
260 265 270

```
Pro Lys Ala Ala Lys Asn Thr Tyr Thr Ala Glu Arg Phe Ile Trp Leu
        275                 280                 285
Thr Lys Leu Asn Asn Leu Arg Ile Leu Glu Gln Gly Ser Glu Arg Pro
290                 295                 300
Leu Thr Asp Thr Glu Arg Ala Thr Leu Met Asp Glu Pro Tyr Arg Lys
305                 310                 315                 320
Ser Lys Leu Thr Tyr Ala Gln Ala Arg Lys Leu Leu Gly Leu Glu Asp
                325                 330                 335
Thr Ala Phe Phe Lys Gly Leu Arg Tyr Gly Lys Asp Asn Ala Glu Ala
                340                 345                 350
Ser Thr Leu Met Glu Met Lys Ala Tyr His Ala Ile Ser Arg Ala Leu
            355                 360                 365
Glu Lys Glu Gly Leu Lys Asp Lys Lys Ser Pro Leu Asn Leu Ser Pro
        370                 375                 380
Glu Leu Gln Asp Glu Ile Gly Thr Ala Phe Ser Leu Phe Lys Thr Asp
385                 390                 395                 400
Glu Asp Ile Thr Gly Arg Leu Lys Asp Arg Ile Gln Pro Glu Ile Leu
                405                 410                 415
Glu Ala Leu Leu Lys His Ile Ser Phe Asp Lys Phe Val Gln Ile Ser
                420                 425                 430
Leu Lys Ala Leu Arg Arg Ile Val Pro Leu Met Glu Gln Gly Lys Arg
            435                 440                 445
Tyr Asp Glu Ala Cys Ala Glu Ile Tyr Gly Asp His Tyr Gly Lys Lys
    450                 455                 460
Asn Thr Glu Glu Lys Ile Tyr Leu Pro Pro Ile Pro Ala Asp Glu Ile
465                 470                 475                 480
Arg Asn Pro Val Val Leu Arg Ala Leu Ser Gln Ala Arg Lys Val Ile
                485                 490                 495
Asn Gly Val Val Arg Arg Tyr Gly Ser Pro Ala Arg Ile His Ile Glu
            500                 505                 510
Thr Ala Arg Glu Val Gly Lys Ser Phe Lys Asp Arg Lys Glu Ile Glu
        515                 520                 525
Lys Arg Gln Glu Glu Asn Arg Lys Asp Arg Glu Lys Ala Ala Ala Lys
        530                 535                 540
Phe Arg Glu Tyr Phe Pro Asn Phe Val Gly Glu Pro Lys Ser Lys Asp
545                 550                 555                 560
Ile Leu Lys Leu Arg Leu Tyr Glu Gln Gln His Gly Lys Cys Leu Tyr
                565                 570                 575
Ser Gly Lys Glu Ile Asn Leu Gly Arg Leu Asn Glu Lys Gly Tyr Val
            580                 585                 590
Glu Ile Asp His Ala Leu Pro Phe Ser Arg Thr Trp Asp Asp Ser Phe
        595                 600                 605
Asn Asn Lys Val Leu Val Leu Gly Ser Glu Asn Gln Asn Lys Gly Asn
610                 615                 620
Gln Thr Pro Tyr Glu Tyr Phe Asn Gly Lys Asp Asn Ser Arg Glu Trp
625                 630                 635                 640
Gln Glu Phe Lys Ala Arg Val Glu Thr Ser Arg Phe Pro Arg Ser Lys
                645                 650                 655
Lys Gln Arg Ile Leu Leu Gln Lys Phe Asp Glu Asp Gly Phe Lys Glu
                660                 665                 670
Arg Asn Leu Asn Asp Thr Arg Tyr Val Asn Arg Phe Leu Cys Gln Phe
            675                 680                 685
```

```
Val Ala Asp Arg Met Arg Leu Thr Gly Lys Gly Lys Lys Arg Val Phe
690                 695                 700

Ala Ser Asn Gly Gln Ile Thr Asn Leu Leu Arg Gly Phe Trp Gly Leu
705                 710                 715                 720

Arg Lys Val Arg Ala Glu Asn Asp Arg His His Ala Leu Asp Ala Val
            725                 730                 735

Val Val Ala Cys Ser Thr Val Ala Met Gln Gln Lys Ile Thr Arg Phe
                740                 745                 750

Val Arg Tyr Lys Glu Met Asn Ala Phe Asp Gly Lys Thr Ile Asp Lys
            755                 760                 765

Glu Thr Gly Glu Val Leu His Gln Lys Thr His Phe Pro Gln Pro Trp
770                 775                 780

Glu Phe Phe Ala Gln Glu Val Met Ile Arg Val Phe Gly Lys Pro Asp
785                 790                 795                 800

Gly Lys Pro Glu Phe Glu Ala Asp Thr Leu Glu Lys Leu Arg Thr
                805                 810                 815

Leu Leu Ala Glu Lys Leu Ser Ser Arg Pro Glu Ala Val His Glu Tyr
                820                 825                 830

Val Thr Pro Leu Phe Val Ser Arg Ala Pro Asn Arg Lys Met Ser Gly
                835                 840                 845

Gln Gly His Met Glu Thr Val Lys Ser Ala Lys Arg Leu Asp Glu Gly
850                 855                 860

Val Ser Val Leu Arg Val Pro Leu Thr Gln Leu Lys Leu Lys Asp Leu
865                 870                 875                 880

Glu Lys Met Val Asn Arg Glu Arg Glu Pro Lys Leu Tyr Glu Ala Leu
                885                 890                 895

Lys Ala Arg Leu Glu Ala His Lys Asp Asp Pro Ala Lys Ala Phe Ala
            900                 905                 910

Glu Pro Phe Tyr Lys Tyr Asp Lys Ala Gly Asn Arg Thr Gln Gln Val
            915                 920                 925

Lys Ala Val Arg Val Glu Gln Val Gln Lys Thr Gly Val Trp Val Arg
            930                 935                 940

Asn His Asn Gly Ile Ala Asp Asn Ala Thr Met Val Arg Val Asp Val
945                 950                 955                 960

Phe Glu Lys Gly Asp Lys Tyr Tyr Leu Val Pro Ile Tyr Ser Trp Gln
            965                 970                 975

Val Ala Lys Gly Ile Leu Pro Asp Arg Ala Val Val Gln Gly Lys Asp
            980                 985                 990

Glu Glu Asp Trp Gln Leu Ile Asp  Asp Ser Phe Asn Phe  Lys Phe Ser
            995                 1000                1005

Leu His  Pro Asn Asp Leu Val  Glu Val Ile Thr Lys  Lys Ala Arg
    1010                1015                1020

Met Phe  Gly Tyr Phe Ala Ser  Cys His Arg Gly Thr  Gly Asn Ile
    1025                1030                1035

Asn Ile  Arg Ile His Asp Leu  Asp His Lys Ile Gly  Lys Asn Gly
    1040                1045                1050

Ile Leu  Glu Gly Ile Gly Val  Lys Thr Ala Leu Ser  Phe Gln Lys
    1055                1060                1065

Tyr Gln  Ile Asp Glu Leu Gly  Lys Glu Ile Arg Pro  Cys Arg Leu
    1070                1075                1080

Lys Lys  Arg Pro Pro Val Arg  Tyr Pro Tyr Asp Val  Pro Asp Tyr
    1085                1090                1095

Ala Ala  Ala Pro Ala Ala Lys  Lys Lys Lys Leu Asp
```

<210> SEQ ID NO 115
<211> LENGTH: 1110
<212> TYPE: PRT
<213> ORGANISM: Artificial sequence
<220> FEATURE:
<223> OTHER INFORMATION: Synthetic

<400> SEQUENCE: 115

Met Val Pro Lys Lys Arg Lys Val Ala Ala Phe Lys Pro Asn Ser
1               5                   10                  15

Ile Asn Tyr Ile Leu Gly Leu Asp Ile Gly Ile Ala Ser Val Gly Trp
            20                  25                  30

Ala Met Val Glu Ile Asp Glu Glu Asn Pro Ile Arg Leu Ile Asp
                35                  40                  45

Leu Gly Val Arg Val Phe Glu Arg Ala Glu Val Pro Lys Thr Gly Asp
    50                  55                  60

Ser Leu Ala Met Ala Arg Arg Leu Ala Arg Ser Val Arg Arg Leu Thr
65                  70                  75                  80

Arg Arg Arg Ala His Arg Leu Leu Arg Thr Arg Arg Leu Leu Lys Arg
                85                  90                  95

Glu Gly Val Leu Gln Ala Ala Asn Phe Asp Glu Asn Gly Leu Ile Lys
                100                 105                 110

Ser Leu Pro Asn Thr Pro Trp Gln Leu Arg Ala Ala Leu Asp Arg
                115                 120                 125

Lys Leu Thr Pro Leu Glu Trp Ser Ala Val Leu Leu His Leu Ile Lys
130                 135                 140

His Arg Gly Tyr Leu Ser Gln Arg Lys Asn Glu Gly Glu Thr Ala Asp
145                 150                 155                 160

Lys Glu Leu Gly Ala Leu Leu Lys Gly Val Ala Gly Asn Ala His Ala
                165                 170                 175

Leu Gln Thr Gly Asp Phe Arg Thr Pro Ala Glu Leu Ala Leu Asn Lys
                180                 185                 190

Phe Glu Lys Glu Ser Gly His Ile Arg Asn Gln Arg Ser Asp Tyr Ser
                195                 200                 205

His Thr Phe Ser Arg Lys Asp Leu Gln Ala Glu Leu Ile Leu Leu Phe
210                 215                 220

Glu Lys Gln Lys Glu Phe Gly Asn Pro His Val Ser Gly Gly Leu Lys
225                 230                 235                 240

Glu Gly Ile Glu Thr Leu Leu Met Thr Gln Arg Pro Ala Leu Ser Gly
                245                 250                 255

Asp Ala Val Gln Lys Met Leu Gly His Cys Thr Phe Glu Pro Ala Glu
                260                 265                 270

Pro Lys Ala Ala Lys Asn Thr Tyr Thr Ala Glu Arg Phe Ile Trp Leu
            275                 280                 285

Thr Lys Leu Asn Asn Leu Arg Ile Leu Glu Gln Gly Ser Glu Arg Pro
290                 295                 300

Leu Thr Asp Thr Glu Arg Ala Thr Leu Met Asp Glu Pro Tyr Arg Lys
305                 310                 315                 320

Ser Lys Leu Thr Tyr Ala Gln Ala Arg Lys Leu Leu Gly Leu Glu Asp
                325                 330                 335

Thr Ala Phe Phe Lys Gly Leu Arg Tyr Gly Lys Asp Asn Ala Glu Ala
                340                 345                 350

Ser Thr Leu Met Glu Met Lys Ala Tyr His Ala Ile Ser Arg Ala Leu

```
              355                 360                 365
Glu Lys Glu Gly Leu Lys Asp Lys Ser Pro Leu Asn Leu Ser Pro
370                 375                 380

Glu Leu Gln Asp Glu Ile Gly Thr Ala Phe Ser Leu Phe Lys Thr Asp
385                 390                 395                 400

Glu Asp Ile Thr Gly Arg Leu Lys Asp Arg Ile Gln Pro Glu Ile Leu
                405                 410                 415

Glu Ala Leu Leu Lys His Ile Ser Phe Asp Lys Phe Val Gln Ile Ser
                420                 425                 430

Leu Lys Ala Leu Arg Arg Ile Val Pro Leu Met Glu Gln Gly Lys Arg
            435                 440                 445

Tyr Asp Glu Ala Cys Ala Glu Ile Tyr Gly Asp His Tyr Gly Lys Lys
            450                 455                 460

Asn Thr Glu Glu Lys Ile Tyr Leu Pro Pro Ile Pro Ala Asp Glu Ile
465                 470                 475                 480

Arg Asn Pro Val Val Leu Arg Ala Leu Ser Gln Ala Arg Lys Val Ile
                485                 490                 495

Asn Gly Val Val Arg Arg Tyr Gly Ser Pro Ala Arg Ile His Ile Glu
            500                 505                 510

Thr Ala Arg Glu Val Gly Lys Ser Phe Lys Asp Arg Lys Glu Ile Glu
            515                 520                 525

Lys Arg Gln Glu Glu Asn Arg Lys Asp Arg Glu Lys Ala Ala Ala Lys
530                 535                 540

Phe Arg Glu Tyr Phe Pro Asn Phe Val Gly Glu Pro Lys Ser Lys Asp
545                 550                 555                 560

Ile Leu Lys Leu Arg Leu Tyr Glu Gln Gln His Gly Lys Cys Leu Tyr
                565                 570                 575

Ser Gly Lys Glu Ile Asn Leu Gly Arg Leu Asn Glu Lys Gly Tyr Val
            580                 585                 590

Glu Ile Asp His Ala Leu Pro Phe Ser Arg Thr Trp Asp Asp Ser Phe
            595                 600                 605

Asn Asn Lys Val Leu Val Leu Gly Ser Glu Asn Gln Asn Lys Gly Asn
610                 615                 620

Gln Thr Pro Tyr Glu Tyr Phe Asn Gly Lys Asp Asn Ser Arg Glu Trp
625                 630                 635                 640

Gln Glu Phe Lys Ala Arg Val Glu Thr Ser Arg Phe Pro Arg Ser Lys
                645                 650                 655

Lys Gln Arg Ile Leu Leu Gln Lys Phe Asp Glu Asp Gly Phe Lys Glu
            660                 665                 670

Arg Asn Leu Asn Asp Thr Arg Tyr Val Asn Arg Phe Leu Cys Gln Phe
            675                 680                 685

Val Ala Asp Arg Met Arg Leu Thr Gly Lys Gly Lys Lys Arg Val Phe
690                 695                 700

Ala Ser Asn Gly Gln Ile Thr Asn Leu Leu Arg Gly Phe Trp Gly Leu
705                 710                 715                 720

Arg Lys Val Arg Ala Glu Asn Asp Arg His His Ala Leu Asp Ala Val
                725                 730                 735

Val Val Ala Cys Ser Thr Val Ala Met Gln Gln Lys Ile Thr Arg Phe
            740                 745                 750

Val Arg Tyr Lys Glu Met Asn Ala Phe Asp Gly Lys Thr Ile Asp Lys
            755                 760                 765

Glu Thr Gly Glu Val Leu His Gln Lys Thr His Phe Pro Gln Pro Trp
770                 775                 780
```

```
Glu Phe Phe Ala Gln Glu Val Met Ile Arg Val Phe Gly Lys Pro Asp
785                 790                 795                 800

Gly Lys Pro Glu Phe Glu Ala Asp Thr Leu Glu Lys Leu Arg Thr
            805                 810                 815

Leu Leu Ala Glu Lys Leu Ser Ser Arg Pro Glu Ala Val His Glu Tyr
        820                 825                 830

Val Thr Pro Leu Phe Val Ser Arg Ala Pro Asn Arg Lys Met Ser Gly
            835                 840                 845

Gln Gly His Met Glu Thr Val Lys Ser Ala Lys Arg Leu Asp Glu Gly
        850                 855                 860

Val Ser Val Leu Arg Val Pro Leu Thr Gln Leu Lys Leu Lys Asp Leu
865                 870                 875                 880

Glu Lys Met Val Asn Arg Glu Arg Glu Pro Lys Leu Tyr Glu Ala Leu
                885                 890                 895

Lys Ala Arg Leu Glu Ala His Lys Asp Asp Pro Ala Lys Ala Phe Ala
            900                 905                 910

Glu Pro Phe Tyr Lys Tyr Asp Lys Ala Gly Asn Arg Thr Gln Gln Val
        915                 920                 925

Lys Ala Val Arg Val Glu Gln Val Gln Lys Thr Gly Val Trp Val Arg
    930                 935                 940

Asn His Asn Gly Ile Ala Asp Asn Ala Thr Met Val Arg Val Asp Val
945                 950                 955                 960

Phe Glu Lys Gly Asp Lys Tyr Tyr Leu Val Pro Ile Tyr Ser Trp Gln
                965                 970                 975

Val Ala Lys Gly Ile Leu Pro Asp Arg Ala Val Val Gln Gly Lys Asp
            980                 985                 990

Glu Glu Asp Trp Gln Leu Ile Asp Asp Ser Phe Asn Phe Lys Phe Ser
        995                 1000                1005

Leu His Pro Asn Asp Leu Val Glu Val Ile Thr Lys Lys Ala Arg
    1010                1015                1020

Met Phe Gly Tyr Phe Ala Ser Cys His Ala Gly Thr Gly Asn Ile
    1025                1030                1035

Asn Ile Arg Ile His Asp Leu Asp His Lys Ile Gly Lys Asn Gly
    1040                1045                1050

Ile Leu Glu Gly Ile Gly Val Lys Thr Ala Leu Ser Phe Gln Lys
    1055                1060                1065

Tyr Gln Ile Asp Glu Leu Gly Lys Glu Ile Arg Pro Cys Arg Leu
    1070                1075                1080

Lys Lys Arg Pro Pro Val Arg Tyr Pro Tyr Asp Val Pro Asp Tyr
    1085                1090                1095

Ala Ala Ala Pro Ala Ala Lys Lys Lys Lys Leu Asp
    1100                1105                1110

<210> SEQ ID NO 116
<211> LENGTH: 1110
<212> TYPE: PRT
<213> ORGANISM: Artificial sequence
<220> FEATURE:
<223> OTHER INFORMATION: Synthetic

<400> SEQUENCE: 116

Met Val Pro Lys Lys Lys Arg Lys Val Ala Ala Phe Lys Pro Asn Ser
1               5                   10                  15

Ile Asn Tyr Ile Leu Gly Leu Asp Ile Gly Ile Ala Ser Val Gly Trp
            20                  25                  30
```

```
Ala Met Val Glu Ile Asp Glu Glu Asn Pro Ile Arg Leu Ile Asp
            35                  40                  45
Leu Gly Val Arg Val Phe Glu Arg Ala Glu Val Pro Lys Thr Gly Asp
 50                  55                  60
Ser Leu Ala Met Ala Arg Arg Leu Ala Arg Ser Val Arg Arg Leu Thr
 65                  70                  75                  80
Arg Arg Arg Ala His Arg Leu Leu Arg Thr Arg Arg Leu Leu Lys Arg
                 85                  90                  95
Glu Gly Val Leu Gln Ala Ala Asn Phe Asp Glu Asn Gly Leu Ile Lys
                100                 105                 110
Ser Leu Pro Asn Thr Pro Trp Gln Leu Arg Ala Ala Leu Asp Arg
            115                 120                 125
Lys Leu Thr Pro Leu Glu Trp Ser Ala Val Leu Leu His Leu Ile Lys
            130                 135                 140
His Arg Gly Tyr Leu Ser Gln Arg Lys Asn Glu Gly Glu Thr Ala Asp
145                 150                 155                 160
Lys Glu Leu Gly Ala Leu Leu Lys Gly Val Ala Gly Asn Ala His Ala
                165                 170                 175
Leu Gln Thr Gly Asp Phe Arg Thr Pro Ala Glu Leu Ala Leu Asn Lys
            180                 185                 190
Phe Glu Lys Glu Ser Gly His Ile Arg Asn Gln Arg Ser Asp Tyr Ser
            195                 200                 205
His Thr Phe Ser Arg Lys Asp Leu Gln Ala Glu Leu Ile Leu Leu Phe
210                 215                 220
Glu Lys Gln Lys Glu Phe Gly Asn Pro His Val Ser Gly Gly Leu Lys
225                 230                 235                 240
Glu Gly Ile Glu Thr Leu Leu Met Thr Gln Arg Pro Ala Leu Ser Gly
                245                 250                 255
Asp Ala Val Gln Lys Met Leu Gly His Cys Thr Phe Glu Pro Ala Glu
                260                 265                 270
Pro Lys Ala Ala Lys Asn Thr Tyr Thr Ala Glu Arg Phe Ile Trp Leu
            275                 280                 285
Thr Lys Leu Asn Asn Leu Arg Ile Leu Glu Gln Gly Ser Glu Arg Pro
            290                 295                 300
Leu Thr Asp Thr Glu Arg Ala Thr Leu Met Asp Glu Pro Tyr Arg Lys
305                 310                 315                 320
Ser Lys Leu Thr Tyr Ala Gln Ala Arg Lys Leu Leu Gly Leu Glu Asp
                325                 330                 335
Thr Ala Phe Phe Lys Gly Leu Arg Tyr Gly Lys Asp Asn Ala Glu Ala
                340                 345                 350
Ser Thr Leu Met Glu Met Lys Ala Tyr His Ala Ile Ser Arg Ala Leu
            355                 360                 365
Glu Lys Glu Gly Leu Lys Asp Lys Lys Ser Pro Leu Asn Leu Ser Pro
            370                 375                 380
Glu Leu Gln Asp Glu Ile Gly Thr Ala Phe Ser Leu Phe Lys Thr Asp
385                 390                 395                 400
Glu Asp Ile Thr Gly Arg Leu Lys Asp Arg Ile Gln Pro Glu Ile Leu
                405                 410                 415
Glu Ala Leu Leu Lys His Ile Ser Phe Asp Lys Phe Val Gln Ile Ser
                420                 425                 430
Leu Lys Ala Leu Arg Arg Ile Val Pro Leu Met Glu Gln Gly Lys Arg
            435                 440                 445
```

-continued

```
Tyr Asp Glu Ala Cys Ala Glu Ile Tyr Gly Asp His Tyr Gly Lys Lys
450                 455                 460
Asn Thr Glu Glu Lys Ile Tyr Leu Pro Pro Ile Pro Ala Asp Glu Ile
465                 470                 475                 480
Arg Asn Pro Val Val Leu Arg Ala Leu Ser Gln Ala Arg Lys Val Ile
            485                 490                 495
Asn Gly Val Val Arg Arg Tyr Gly Ser Pro Ala Arg Ile His Ile Glu
            500                 505                 510
Thr Ala Arg Glu Val Gly Lys Ser Phe Lys Asp Arg Lys Glu Ile Glu
            515                 520                 525
Lys Arg Gln Glu Glu Asn Arg Lys Asp Arg Glu Lys Ala Ala Ala Lys
530                 535                 540
Phe Arg Glu Tyr Phe Pro Asn Phe Val Gly Glu Pro Lys Ser Lys Asp
545                 550                 555                 560
Ile Leu Lys Leu Arg Leu Tyr Glu Gln Gln His Gly Lys Cys Leu Tyr
            565                 570                 575
Ser Gly Lys Glu Ile Asn Leu Gly Arg Leu Asn Glu Lys Gly Tyr Val
            580                 585                 590
Glu Ile Asp His Ala Leu Pro Phe Ser Arg Thr Trp Asp Asp Ser Phe
            595                 600                 605
Asn Asn Lys Val Leu Val Leu Gly Ser Glu Asn Gln Asn Lys Gly Asn
610                 615                 620
Gln Thr Pro Tyr Glu Tyr Phe Asn Gly Lys Asp Asn Ser Arg Glu Trp
625                 630                 635                 640
Gln Glu Phe Lys Ala Arg Val Glu Thr Ser Arg Phe Pro Arg Ser Lys
            645                 650                 655
Lys Gln Arg Ile Leu Leu Gln Lys Phe Asp Glu Asp Gly Phe Lys Glu
            660                 665                 670
Arg Asn Leu Asn Asp Thr Arg Tyr Val Asn Arg Phe Leu Cys Gln Phe
            675                 680                 685
Val Ala Asp Arg Met Arg Leu Thr Gly Lys Gly Lys Lys Arg Val Phe
690                 695                 700
Ala Ser Asn Gly Gln Ile Thr Asn Leu Leu Arg Gly Phe Trp Gly Leu
705                 710                 715                 720
Arg Lys Val Arg Ala Glu Asn Asp Arg His His Ala Leu Asp Ala Val
            725                 730                 735
Val Val Ala Cys Ser Thr Val Ala Met Gln Gln Lys Ile Thr Arg Phe
            740                 745                 750
Val Arg Tyr Lys Glu Met Asn Ala Phe Asp Gly Lys Thr Ile Asp Lys
            755                 760                 765
Glu Thr Gly Glu Val Leu His Gln Lys Thr His Phe Pro Gln Pro Trp
770                 775                 780
Glu Phe Phe Ala Gln Glu Val Met Ile Arg Val Phe Gly Lys Pro Asp
785                 790                 795                 800
Gly Lys Pro Glu Phe Glu Glu Ala Asp Thr Leu Glu Lys Leu Arg Thr
            805                 810                 815
Leu Leu Ala Glu Lys Leu Ser Ser Arg Pro Glu Ala Val His Glu Tyr
            820                 825                 830
Val Thr Pro Leu Phe Val Ser Arg Ala Pro Asn Arg Lys Met Ser Gly
            835                 840                 845
Gln Gly His Met Glu Thr Val Lys Ser Ala Lys Arg Leu Asp Glu Gly
850                 855                 860
Val Ser Val Leu Arg Val Pro Leu Thr Gln Leu Lys Leu Lys Asp Leu
```

|  |  |  |  | 865 |  |  |  |  | 870 |  |  |  |  | 875 |  |  |  |  | 880 |

Glu Lys Met Val Asn Arg Glu Arg Pro Lys Leu Tyr Glu Ala Leu
                885                 890                 895

Lys Ala Arg Leu Glu Ala His Lys Asp Pro Ala Lys Ala Phe Ala
            900                 905                 910

Glu Pro Phe Tyr Lys Tyr Asp Lys Ala Gly Asn Arg Thr Gln Gln Val
            915                 920                 925

Lys Ala Val Arg Val Glu Gln Val Gln Lys Thr Gly Val Trp Val Arg
            930                 935                 940

Asn His Asn Gly Ile Ala Asp Asn Ala Thr Met Val Arg Val Asp Val
945                 950                 955                 960

Phe Glu Lys Gly Asp Lys Tyr Tyr Leu Val Pro Ile Tyr Ser Trp Gln
                965                 970                 975

Val Ala Lys Gly Ile Leu Pro Asp Arg Ala Val Val Gln Gly Lys Asp
            980                 985                 990

Glu Glu Asp Trp Gln Leu Ile Asp Asp Ser Phe Asn Phe Lys Phe Ser
            995                 1000                1005

Leu His Pro Asn Asp Leu Val Glu Val Ile Thr Lys Ala Ala Arg
    1010                1015                1020

Met Phe Gly Tyr Phe Ala Ser Cys His Ala Gly Thr Gly Asn Ile
    1025                1030                1035

Asn Ile Arg Ile His Asp Leu Asp His Lys Ile Gly Lys Asn Gly
    1040                1045                1050

Ile Leu Glu Gly Ile Gly Val Lys Thr Ala Leu Ser Phe Gln Lys
    1055                1060                1065

Tyr Gln Ile Asp Glu Leu Gly Lys Glu Ile Arg Pro Cys Arg Leu
    1070                1075                1080

Lys Lys Arg Pro Pro Val Arg Tyr Pro Tyr Asp Val Pro Asp Tyr
    1085                1090                1095

Ala Ala Ala Pro Ala Ala Lys Lys Lys Lys Leu Asp
    1100                1105                1110

<210> SEQ ID NO 117
<211> LENGTH: 1240
<212> TYPE: PRT
<213> ORGANISM: Artificial sequence
<220> FEATURE:
<223> OTHER INFORMATION: Synthetic

<400> SEQUENCE: 117

Met Gly Arg Ala Ala Pro Ala Ala Lys Lys Lys Leu Asp Gln Leu
1               5                   10                  15

Arg Pro Tyr Ala Cys Pro Val Glu Ser Cys Asp Arg Arg Phe Ser Arg
                20                  25                  30

Ser Asp Glu Leu Thr Arg His Ile Arg Ile His Thr Gly Gln Lys Pro
            35                  40                  45

Phe Gln Cys Arg Ile Cys Met Arg Asn Phe Ser Arg Ser Asp His Leu
        50                  55                  60

Thr Thr His Ile Arg Thr His Thr Gly Glu Lys Pro Phe Ala Cys Asp
65                  70                  75                  80

Ile Cys Gly Arg Lys Phe Ala Arg Ser Asp Glu Arg Lys Arg His Thr
                85                  90                  95

Lys Ile His Leu Arg Gln Lys Asp Pro Gly Ser Gly Gly Ser Gly Ser
            100                 105                 110

Ser Gly Arg Thr Ala Ala Pro Ala Ala Lys Lys Lys Lys Leu Asp Ile

-continued

```
            115                 120                 125
Arg Lys Leu Val Pro Lys Lys Arg Lys Val Ala Ala Phe Lys Pro
130                 135                 140
Asn Ser Ile Asn Tyr Ile Leu Gly Leu Asp Ile Gly Ile Ala Ser Val
145                 150                 155                 160
Gly Trp Ala Met Val Glu Ile Asp Glu Glu Asn Pro Ile Arg Leu
                165                 170                 175
Ile Asp Leu Gly Val Arg Val Phe Glu Arg Ala Glu Val Pro Lys Thr
                180                 185                 190
Gly Asp Ser Leu Ala Met Ala Arg Arg Leu Ala Arg Ser Val Arg Arg
                195                 200                 205
Leu Thr Arg Arg Arg Ala His Arg Leu Leu Arg Thr Arg Arg Leu Leu
210                 215                 220
Lys Arg Glu Gly Val Leu Gln Ala Ala Asn Phe Asp Glu Asn Gly Leu
225                 230                 235                 240
Ile Lys Ser Leu Pro Asn Thr Pro Trp Gln Leu Arg Ala Ala Ala Leu
                245                 250                 255
Asp Arg Lys Leu Thr Pro Leu Glu Trp Ser Ala Val Leu Leu His Leu
                260                 265                 270
Ile Lys His Arg Gly Tyr Leu Ser Gln Arg Lys Asn Glu Gly Glu Thr
                275                 280                 285
Ala Asp Lys Glu Leu Gly Ala Leu Leu Lys Gly Val Ala Gly Asn Ala
290                 295                 300
His Ala Leu Gln Thr Gly Asp Phe Arg Thr Pro Ala Glu Leu Ala Leu
305                 310                 315                 320
Asn Lys Phe Glu Lys Glu Ser Gly His Ile Arg Asn Gln Arg Ser Asp
                325                 330                 335
Tyr Ser His Thr Phe Ser Arg Lys Asp Leu Gln Ala Glu Leu Ile Leu
                340                 345                 350
Leu Phe Glu Lys Gln Lys Glu Phe Gly Asn Pro His Val Ser Gly Gly
                355                 360                 365
Leu Lys Glu Gly Ile Glu Thr Leu Leu Met Thr Gln Arg Pro Ala Leu
                370                 375                 380
Ser Gly Asp Ala Val Gln Lys Met Leu Gly His Cys Thr Phe Glu Pro
385                 390                 395                 400
Ala Glu Pro Lys Ala Ala Lys Asn Thr Tyr Thr Ala Glu Arg Phe Ile
                405                 410                 415
Trp Leu Thr Lys Leu Asn Asn Leu Arg Ile Leu Glu Gln Gly Ser Glu
                420                 425                 430
Arg Pro Leu Thr Asp Thr Glu Arg Ala Thr Leu Met Asp Glu Pro Tyr
                435                 440                 445
Arg Lys Ser Lys Leu Thr Tyr Ala Gln Ala Arg Lys Leu Leu Gly Leu
                450                 455                 460
Glu Asp Thr Ala Phe Phe Lys Gly Leu Arg Tyr Gly Lys Asp Asn Ala
465                 470                 475                 480
Glu Ala Ser Thr Leu Met Glu Met Lys Ala Tyr His Ala Ile Ser Arg
                485                 490                 495
Ala Leu Glu Lys Glu Gly Leu Lys Asp Lys Lys Ser Pro Leu Asn Leu
                500                 505                 510
Ser Pro Glu Leu Gln Asp Glu Ile Gly Thr Ala Phe Ser Leu Phe Lys
                515                 520                 525
Thr Asp Glu Asp Ile Thr Gly Arg Leu Lys Asp Arg Ile Gln Pro Glu
                530                 535                 540
```

-continued

```
Ile Leu Glu Ala Leu Leu Lys His Ile Ser Phe Asp Lys Phe Val Gln
545                 550                 555                 560

Ile Ser Leu Lys Ala Leu Arg Arg Ile Val Pro Leu Met Glu Gln Gly
                565                 570                 575

Lys Arg Tyr Asp Glu Ala Cys Ala Glu Ile Tyr Gly Asp His Tyr Gly
            580                 585                 590

Lys Lys Asn Thr Glu Glu Lys Ile Tyr Leu Pro Pro Ile Pro Ala Asp
        595                 600                 605

Glu Ile Arg Asn Pro Val Val Leu Arg Ala Leu Ser Gln Ala Arg Lys
610                 615                 620

Val Ile Asn Gly Val Val Arg Arg Tyr Gly Ser Pro Ala Arg Ile His
625                 630                 635                 640

Ile Glu Thr Ala Arg Glu Val Gly Lys Ser Phe Lys Asp Arg Lys Glu
                645                 650                 655

Ile Glu Lys Arg Gln Glu Glu Asn Arg Lys Asp Arg Glu Lys Ala Ala
            660                 665                 670

Ala Lys Phe Arg Glu Tyr Phe Pro Asn Phe Val Gly Glu Pro Lys Ser
        675                 680                 685

Lys Asp Ile Leu Lys Leu Arg Leu Tyr Glu Gln Gln His Gly Lys Cys
690                 695                 700

Leu Tyr Ser Gly Lys Glu Ile Asn Leu Gly Arg Leu Asn Glu Lys Gly
705                 710                 715                 720

Tyr Val Glu Ile Asp His Ala Leu Pro Phe Ser Arg Thr Trp Asp Asp
                725                 730                 735

Ser Phe Asn Asn Lys Val Leu Val Leu Gly Ser Glu Asn Gln Asn Lys
            740                 745                 750

Gly Asn Gln Thr Pro Tyr Glu Tyr Phe Asn Gly Lys Asp Asn Ser Arg
        755                 760                 765

Glu Trp Gln Glu Phe Lys Ala Arg Val Glu Thr Ser Arg Phe Pro Arg
770                 775                 780

Ser Lys Lys Gln Arg Ile Leu Leu Gln Lys Phe Asp Glu Asp Gly Phe
785                 790                 795                 800

Lys Glu Arg Asn Leu Asn Asp Thr Arg Tyr Val Asn Arg Phe Leu Cys
                805                 810                 815

Gln Phe Val Ala Asp Arg Met Arg Leu Thr Gly Lys Gly Lys Lys Arg
            820                 825                 830

Val Phe Ala Ser Asn Gly Gln Ile Thr Asn Leu Leu Arg Gly Phe Trp
        835                 840                 845

Gly Leu Arg Lys Val Arg Ala Glu Asn Asp Arg His His Ala Leu Asp
850                 855                 860

Ala Val Val Val Ala Cys Ser Thr Val Ala Met Gln Gln Lys Ile Thr
865                 870                 875                 880

Arg Phe Val Arg Tyr Lys Glu Met Asn Ala Phe Asp Gly Lys Thr Ile
                885                 890                 895

Asp Lys Glu Thr Gly Glu Val Leu His Gln Lys Thr His Phe Pro Gln
            900                 905                 910

Pro Trp Glu Phe Phe Ala Gln Glu Val Met Ile Arg Val Phe Gly Lys
        915                 920                 925

Pro Asp Gly Lys Pro Glu Phe Glu Glu Ala Asp Thr Leu Glu Lys Leu
930                 935                 940

Arg Thr Leu Leu Ala Glu Lys Leu Ser Ser Arg Pro Glu Ala Val His
945                 950                 955                 960
```

Glu Tyr Val Thr Pro Leu Phe Val Ser Arg Ala Pro Asn Arg Lys Met
                965                 970                 975

Ser Gly Gln Gly His Met Glu Thr Val Lys Ser Ala Lys Arg Leu Asp
        980                 985                 990

Glu Gly Val Ser Val Leu Arg Val Pro Leu Thr Gln Leu Lys Leu Lys
            995                 1000                1005

Asp Leu Glu Lys Met Val Asn Arg Glu Arg Glu Pro Lys Leu Tyr
    1010                1015                1020

Glu Ala Leu Lys Ala Arg Leu Glu Ala His Lys Asp Asp Pro Ala
    1025                1030                1035

Lys Ala Phe Ala Glu Pro Phe Tyr Lys Tyr Asp Lys Ala Gly Asn
    1040                1045                1050

Arg Thr Gln Gln Val Lys Ala Val Arg Val Glu Gln Val Gln Lys
    1055                1060                1065

Thr Gly Val Trp Val Arg Asn His Asn Gly Ile Ala Asp Asn Ala
    1070                1075                1080

Thr Met Val Arg Val Asp Val Phe Glu Lys Gly Asp Lys Tyr Tyr
    1085                1090                1095

Leu Val Pro Ile Tyr Ser Trp Gln Val Ala Lys Gly Ile Leu Pro
    1100                1105                1110

Asp Arg Ala Val Val Gln Gly Lys Asp Glu Asp Trp Gln Leu
    1115                1120                1125

Ile Asp Asp Ser Phe Asn Phe Lys Phe Ser Leu His Pro Asn Asp
    1130                1135                1140

Leu Val Glu Val Ile Thr Lys Lys Ala Arg Met Phe Gly Tyr Phe
    1145                1150                1155

Ala Ser Cys His Arg Gly Thr Gly Asn Ile Asn Ile Arg Ile His
    1160                1165                1170

Asp Leu Asp His Lys Ile Gly Lys Asn Gly Ile Leu Glu Gly Ile
    1175                1180                1185

Gly Val Lys Thr Ala Leu Ser Phe Gln Lys Tyr Gln Ile Asp Glu
    1190                1195                1200

Leu Gly Lys Glu Ile Arg Pro Cys Arg Leu Lys Lys Arg Pro Pro
    1205                1210                1215

Val Arg Tyr Pro Tyr Asp Val Pro Asp Tyr Ala Ala Ala Pro Ala
    1220                1225                1230

Ala Lys Lys Lys Lys Leu Asp
    1235                1240

<210> SEQ ID NO 118
<211> LENGTH: 1246
<212> TYPE: PRT
<213> ORGANISM: Artificial sequence
<220> FEATURE:
<223> OTHER INFORMATION: Synthetic

<400> SEQUENCE: 118

Met Val Pro Lys Lys Lys Arg Lys Val Ala Ala Phe Lys Pro Asn Ser
1               5                   10                  15

Ile Asn Tyr Ile Leu Gly Leu Asp Ile Gly Ile Ala Ser Val Gly Trp
            20                  25                  30

Ala Met Val Glu Ile Asp Glu Glu Asn Pro Ile Arg Leu Ile Asp
        35                  40                  45

Leu Gly Val Arg Val Phe Glu Arg Ala Glu Val Pro Lys Thr Gly Asp
    50                  55                  60

```
Ser Leu Ala Met Ala Arg Arg Leu Ala Arg Ser Val Arg Arg Leu Thr
 65                  70                  75                  80

Arg Arg Arg Ala His Arg Leu Leu Arg Thr Arg Arg Leu Leu Lys Arg
                 85                  90                  95

Glu Gly Val Leu Gln Ala Ala Asn Phe Asp Glu Asn Gly Leu Ile Lys
            100                 105                 110

Ser Leu Pro Asn Thr Pro Trp Gln Leu Arg Ala Ala Leu Asp Arg
            115                 120                 125

Lys Leu Thr Pro Leu Glu Trp Ser Ala Val Leu Leu His Leu Ile Lys
            130                 135                 140

His Arg Gly Tyr Leu Ser Gln Arg Lys Asn Glu Gly Glu Thr Ala Asp
145                 150                 155                 160

Lys Glu Leu Gly Ala Leu Leu Lys Gly Val Ala Gly Asn Ala His Ala
                165                 170                 175

Leu Gln Thr Gly Asp Phe Arg Thr Pro Ala Glu Leu Ala Leu Asn Lys
            180                 185                 190

Phe Glu Lys Glu Ser Gly His Ile Arg Asn Gln Arg Ser Asp Tyr Ser
            195                 200                 205

His Thr Phe Ser Arg Lys Asp Leu Gln Ala Glu Leu Ile Leu Leu Phe
210                 215                 220

Glu Lys Gln Lys Glu Phe Gly Asn Pro His Val Ser Gly Gly Leu Lys
225                 230                 235                 240

Glu Gly Ile Glu Thr Leu Leu Met Thr Gln Arg Pro Ala Leu Ser Gly
                245                 250                 255

Asp Ala Val Gln Lys Met Leu Gly His Cys Thr Phe Glu Pro Ala Glu
            260                 265                 270

Pro Lys Ala Ala Lys Asn Thr Tyr Thr Ala Glu Arg Phe Ile Trp Leu
            275                 280                 285

Thr Lys Leu Asn Asn Leu Arg Ile Leu Glu Gln Gly Ser Glu Arg Pro
            290                 295                 300

Leu Thr Asp Thr Glu Arg Ala Thr Leu Met Asp Glu Pro Tyr Arg Lys
305                 310                 315                 320

Ser Lys Leu Thr Tyr Ala Gln Ala Arg Lys Leu Leu Gly Leu Glu Asp
                325                 330                 335

Thr Ala Phe Phe Lys Gly Leu Arg Tyr Gly Lys Asp Asn Ala Glu Ala
            340                 345                 350

Ser Thr Leu Met Glu Met Lys Ala Tyr His Ala Ile Ser Arg Ala Leu
            355                 360                 365

Glu Lys Glu Gly Leu Lys Asp Lys Lys Ser Pro Leu Asn Leu Ser Pro
            370                 375                 380

Glu Leu Gln Asp Glu Ile Gly Thr Ala Phe Ser Leu Phe Lys Thr Asp
385                 390                 395                 400

Glu Asp Ile Thr Gly Arg Leu Lys Asp Arg Ile Gln Pro Glu Ile Leu
                405                 410                 415

Glu Ala Leu Leu Lys His Ile Ser Phe Asp Lys Phe Val Gln Ile Ser
            420                 425                 430

Leu Lys Ala Leu Arg Arg Ile Val Pro Leu Met Glu Gln Gly Lys Arg
            435                 440                 445

Tyr Asp Glu Ala Cys Ala Glu Ile Tyr Gly Asp His Tyr Gly Lys Lys
            450                 455                 460

Asn Thr Glu Glu Lys Ile Tyr Leu Pro Pro Ile Pro Ala Asp Glu Ile
465                 470                 475                 480

Arg Asn Pro Val Val Leu Arg Ala Leu Ser Gln Ala Arg Lys Val Ile
```

```
                485             490             495
Asn Gly Val Val Arg Arg Tyr Gly Ser Pro Ala Arg Ile His Ile Glu
            500                 505                 510

Thr Ala Arg Glu Val Gly Lys Ser Phe Lys Asp Arg Lys Glu Ile Glu
            515                 520                 525

Lys Arg Gln Glu Glu Asn Arg Lys Asp Arg Glu Lys Ala Ala Ala Lys
            530                 535                 540

Phe Arg Glu Tyr Phe Pro Asn Phe Val Gly Glu Pro Lys Ser Lys Asp
545                 550                 555                 560

Ile Leu Lys Leu Arg Leu Tyr Glu Gln Gln His Gly Lys Cys Leu Tyr
                565                 570                 575

Ser Gly Lys Glu Ile Asn Leu Gly Arg Leu Asn Glu Lys Gly Tyr Val
            580                 585                 590

Glu Ile Asp His Ala Leu Pro Phe Ser Arg Thr Trp Asp Asp Ser Phe
            595                 600                 605

Asn Asn Lys Val Leu Val Leu Gly Ser Glu Asn Gln Asn Lys Gly Asn
            610                 615                 620

Gln Thr Pro Tyr Glu Tyr Phe Asn Gly Lys Asp Asn Ser Arg Glu Trp
625                 630                 635                 640

Gln Glu Phe Lys Ala Arg Val Glu Thr Ser Arg Phe Pro Arg Ser Lys
                645                 650                 655

Lys Gln Arg Ile Leu Leu Gln Lys Phe Asp Glu Asp Gly Phe Lys Glu
            660                 665                 670

Arg Asn Leu Asn Asp Thr Arg Tyr Val Asn Arg Phe Leu Cys Gln Phe
            675                 680                 685

Val Ala Asp Arg Met Arg Leu Thr Gly Lys Gly Lys Lys Arg Val Phe
690                 695                 700

Ala Ser Asn Gly Gln Ile Thr Asn Leu Leu Arg Gly Phe Trp Gly Leu
705                 710                 715                 720

Arg Lys Val Arg Ala Glu Asn Asp Arg His His Ala Leu Asp Ala Val
                725                 730                 735

Val Val Ala Cys Ser Thr Val Ala Met Gln Gln Lys Ile Thr Arg Phe
            740                 745                 750

Val Arg Tyr Lys Glu Met Asn Ala Phe Asp Gly Lys Thr Ile Asp Lys
            755                 760                 765

Glu Thr Gly Glu Val Leu His Gln Lys Thr His Phe Pro Gln Pro Trp
            770                 775                 780

Glu Phe Phe Ala Gln Glu Val Met Ile Arg Val Phe Gly Lys Pro Asp
785                 790                 795                 800

Gly Lys Pro Glu Phe Glu Glu Ala Asp Thr Leu Glu Lys Leu Arg Thr
                805                 810                 815

Leu Leu Ala Glu Lys Leu Ser Ser Arg Pro Glu Ala Val His Glu Tyr
            820                 825                 830

Val Thr Pro Leu Phe Val Ser Arg Ala Pro Asn Arg Lys Met Ser Gly
            835                 840                 845

Gln Gly His Met Glu Thr Val Lys Ser Ala Lys Arg Leu Asp Glu Gly
            850                 855                 860

Val Ser Val Leu Arg Val Pro Leu Thr Gln Leu Lys Leu Lys Asp Leu
865                 870                 875                 880

Glu Lys Met Val Asn Arg Glu Arg Glu Pro Lys Leu Tyr Glu Ala Leu
                885                 890                 895

Lys Ala Arg Leu Glu Ala His Lys Asp Asp Pro Ala Lys Ala Phe Ala
            900                 905                 910
```

Glu Pro Phe Tyr Lys Tyr Asp Lys Ala Gly Asn Arg Thr Gln Gln Val
            915                 920                 925

Lys Ala Val Arg Val Glu Gln Val Gln Lys Thr Gly Val Trp Val Arg
    930                 935                 940

Asn His Asn Gly Ile Ala Asp Asn Ala Thr Met Val Arg Val Asp Val
945                 950                 955                 960

Phe Glu Lys Gly Asp Lys Tyr Tyr Leu Val Pro Ile Tyr Ser Trp Gln
                965                 970                 975

Val Ala Lys Gly Ile Leu Pro Asp Arg Ala Val Val Gln Gly Lys Asp
                980                 985                 990

Glu Glu Asp Trp Gln Leu Ile Asp Asp Ser Phe Asn Phe Lys Phe Ser
            995                 1000                1005

Leu His Pro Asn Asp Leu Val Glu Val Ile Thr Lys Lys Ala Arg
        1010                1015                1020

Met Phe Gly Tyr Phe Ala Ser Cys His Arg Gly Thr Gly Asn Ile
        1025                1030                1035

Asn Ile Arg Ile His Asp Leu Asp His Lys Ile Gly Lys Asn Gly
        1040                1045                1050

Ile Leu Glu Gly Ile Gly Val Lys Thr Ala Leu Ser Phe Gln Lys
        1055                1060                1065

Tyr Gln Ile Asp Glu Leu Gly Lys Glu Ile Arg Pro Cys Arg Leu
        1070                1075                1080

Lys Lys Arg Pro Pro Val Arg Tyr Pro Tyr Asp Val Pro Asp Tyr
        1085                1090                1095

Ala Ala Gly Thr Gly Gly Pro Lys Lys Lys Arg Lys Val Tyr Pro
        1100                1105                1110

Tyr Asp Val Pro Asp Tyr Ala Gly Tyr Pro Tyr Asp Val Pro Asp
        1115                1120                1125

Tyr Ala Gly Ser Tyr Pro Tyr Asp Val Pro Asp Tyr Ala Gly Ser
        1130                1135                1140

Ala Ala Pro Ala Ala Lys Lys Lys Lys Leu Asp Phe Glu Ser Gly
        1145                1150                1155

Arg Pro Tyr Ala Cys Pro Val Glu Ser Cys Asp Arg Arg Phe Ser
        1160                1165                1170

Arg Ser Asp Glu Leu Thr Arg His Ile Arg Ile His Thr Gly Gln
        1175                1180                1185

Lys Pro Phe Gln Cys Arg Ile Cys Met Arg Asn Phe Ser Arg Ser
        1190                1195                1200

Asp His Leu Thr Thr His Ile Arg Thr His Thr Gly Glu Lys Pro
        1205                1210                1215

Phe Ala Cys Asp Ile Cys Gly Arg Lys Phe Ala Arg Ser Asp Glu
        1220                1225                1230

Arg Lys Arg His Thr Lys Ile His Leu Arg Gln Lys Asp
        1235                1240

<210> SEQ ID NO 119
<211> LENGTH: 1240
<212> TYPE: PRT
<213> ORGANISM: Artificial sequence
<220> FEATURE:
<223> OTHER INFORMATION: Synthetic

<400> SEQUENCE: 119

Met Gly Arg Ala Ala Pro Ala Ala Lys Lys Lys Lys Leu Asp Gln Leu
1               5                   10                  15

```
Arg Pro Tyr Ala Cys Pro Val Glu Ser Cys Asp Arg Arg Phe Ser Arg
            20                  25                  30

Ser Asp Glu Leu Thr Arg His Ile Arg Ile His Thr Gly Gln Lys Pro
        35                  40                  45

Phe Gln Cys Arg Ile Cys Met Arg Asn Phe Ser Arg Ser Asp His Leu
50                  55                  60

Thr Thr His Ile Arg Thr His Thr Gly Glu Lys Pro Phe Ala Cys Asp
65                  70                  75                  80

Ile Cys Gly Arg Lys Phe Ala Arg Ser Asp Glu Arg Lys Arg His Thr
                85                  90                  95

Lys Ile His Leu Arg Gln Lys Asp Pro Gly Ser Gly Ser Gly Ser
            100                 105                 110

Ser Gly Arg Thr Ala Ala Pro Ala Ala Lys Lys Lys Leu Asp Ile
        115                 120                 125

Arg Lys Leu Val Pro Lys Lys Arg Lys Val Ala Ala Phe Lys Pro
    130                 135                 140

Asn Ser Ile Asn Tyr Ile Leu Gly Leu Asp Ile Gly Ile Ala Ser Val
145                 150                 155                 160

Gly Trp Ala Met Val Glu Ile Asp Glu Glu Asn Pro Ile Arg Leu
                165                 170                 175

Ile Asp Leu Gly Val Arg Val Phe Glu Arg Ala Glu Val Pro Lys Thr
            180                 185                 190

Gly Asp Ser Leu Ala Met Ala Arg Arg Leu Ala Arg Ser Val Arg Arg
        195                 200                 205

Leu Thr Arg Arg Arg Ala His Arg Leu Leu Arg Thr Arg Arg Leu Leu
    210                 215                 220

Lys Arg Glu Gly Val Leu Gln Ala Ala Asn Phe Asp Glu Asn Gly Leu
225                 230                 235                 240

Ile Lys Ser Leu Pro Asn Thr Pro Trp Gln Leu Arg Ala Ala Ala Leu
            245                 250                 255

Asp Arg Lys Leu Thr Pro Leu Glu Trp Ser Ala Val Leu Leu His Leu
        260                 265                 270

Ile Lys His Arg Gly Tyr Leu Ser Gln Arg Lys Asn Glu Gly Glu Thr
    275                 280                 285

Ala Asp Lys Glu Leu Gly Ala Leu Leu Lys Gly Val Ala Gly Asn Ala
290                 295                 300

His Ala Leu Gln Thr Gly Asp Phe Arg Thr Pro Ala Glu Leu Ala Leu
305                 310                 315                 320

Asn Lys Phe Glu Lys Glu Ser Gly His Ile Arg Asn Gln Arg Ser Asp
            325                 330                 335

Tyr Ser His Thr Phe Ser Arg Lys Asp Leu Gln Ala Glu Leu Ile Leu
        340                 345                 350

Leu Phe Glu Lys Gln Lys Glu Phe Gly Asn Pro His Val Ser Gly Gly
    355                 360                 365

Leu Lys Glu Gly Ile Glu Thr Leu Leu Met Thr Gln Arg Pro Ala Leu
370                 375                 380

Ser Gly Asp Ala Val Gln Lys Met Leu Gly His Cys Thr Phe Glu Pro
385                 390                 395                 400

Ala Glu Pro Lys Ala Ala Lys Asn Thr Tyr Thr Ala Glu Arg Phe Ile
            405                 410                 415

Trp Leu Thr Lys Leu Asn Asn Leu Arg Ile Leu Glu Gln Gly Ser Glu
        420                 425                 430
```

```
Arg Pro Leu Thr Asp Thr Glu Arg Ala Thr Leu Met Asp Glu Pro Tyr
            435                 440                 445

Arg Lys Ser Lys Leu Thr Tyr Ala Gln Ala Arg Lys Leu Leu Gly Leu
450                 455                 460

Glu Asp Thr Ala Phe Phe Lys Gly Leu Arg Tyr Gly Lys Asp Asn Ala
465                 470                 475                 480

Glu Ala Ser Thr Leu Met Glu Met Lys Ala Tyr His Ala Ile Ser Arg
                485                 490                 495

Ala Leu Glu Lys Glu Gly Leu Lys Asp Lys Lys Ser Pro Leu Asn Leu
                500                 505                 510

Ser Pro Glu Leu Gln Asp Glu Ile Gly Thr Ala Phe Ser Leu Phe Lys
            515                 520                 525

Thr Asp Glu Asp Ile Thr Gly Arg Leu Lys Asp Arg Ile Gln Pro Glu
530                 535                 540

Ile Leu Glu Ala Leu Leu Lys His Ile Ser Phe Asp Lys Phe Val Gln
545                 550                 555                 560

Ile Ser Leu Lys Ala Leu Arg Arg Ile Val Pro Leu Met Glu Gln Gly
                565                 570                 575

Lys Arg Tyr Asp Glu Ala Cys Ala Glu Ile Tyr Gly Asp His Tyr Gly
            580                 585                 590

Lys Lys Asn Thr Glu Glu Lys Ile Tyr Leu Pro Pro Ile Pro Ala Asp
595                 600                 605

Glu Ile Arg Asn Pro Val Val Leu Arg Ala Leu Ser Gln Ala Arg Lys
            610                 615                 620

Val Ile Asn Gly Val Val Arg Arg Tyr Gly Ser Pro Ala Arg Ile His
625                 630                 635                 640

Ile Glu Thr Ala Arg Glu Val Gly Lys Ser Phe Lys Asp Arg Lys Glu
                645                 650                 655

Ile Glu Lys Arg Gln Glu Glu Asn Arg Lys Asp Arg Glu Lys Ala Ala
            660                 665                 670

Ala Lys Phe Arg Glu Tyr Phe Pro Asn Phe Val Gly Glu Pro Lys Ser
            675                 680                 685

Lys Asp Ile Leu Lys Leu Arg Leu Tyr Glu Gln Gln His Gly Lys Cys
690                 695                 700

Leu Tyr Ser Gly Lys Glu Ile Asn Leu Gly Arg Leu Asn Glu Lys Gly
705                 710                 715                 720

Tyr Val Glu Ile Asp His Ala Leu Pro Phe Ser Arg Thr Trp Asp Asp
                725                 730                 735

Ser Phe Asn Asn Lys Val Leu Val Leu Gly Ser Glu Asn Gln Asn Lys
            740                 745                 750

Gly Asn Gln Thr Pro Tyr Glu Tyr Phe Asn Gly Lys Asp Asn Ser Arg
            755                 760                 765

Glu Trp Gln Glu Phe Lys Ala Arg Val Glu Thr Ser Arg Phe Pro Arg
770                 775                 780

Ser Lys Lys Gln Arg Ile Leu Leu Gln Lys Phe Asp Glu Asp Gly Phe
785                 790                 795                 800

Lys Glu Arg Asn Leu Asn Asp Thr Arg Tyr Val Asn Arg Phe Leu Cys
                805                 810                 815

Gln Phe Val Ala Asp Arg Met Arg Leu Thr Gly Lys Gly Lys Lys Arg
            820                 825                 830

Val Phe Ala Ser Asn Gly Gln Ile Thr Asn Leu Leu Arg Gly Phe Trp
            835                 840                 845

Gly Leu Arg Lys Val Arg Ala Glu Asn Asp Arg His His Ala Leu Asp
```

```
                850                 855                 860
Ala Val Val Ala Cys Ser Thr Val Ala Met Gln Gln Lys Ile Thr
865                 870                 875                 880

Arg Phe Val Arg Tyr Lys Glu Met Asn Ala Phe Asp Gly Lys Thr Ile
                885                 890                 895

Asp Lys Glu Thr Gly Glu Val Leu His Gln Lys Thr His Phe Pro Gln
            900                 905                 910

Pro Trp Glu Phe Phe Ala Gln Glu Val Met Ile Arg Val Phe Gly Lys
        915                 920                 925

Pro Asp Gly Lys Pro Glu Phe Glu Glu Ala Asp Thr Leu Glu Lys Leu
    930                 935                 940

Arg Thr Leu Leu Ala Glu Lys Leu Ser Ser Arg Pro Glu Ala Val His
945                 950                 955                 960

Glu Tyr Val Thr Pro Leu Phe Val Ser Arg Ala Pro Asn Arg Lys Met
                965                 970                 975

Ser Gly Gln Gly His Met Glu Thr Val Lys Ser Ala Lys Arg Leu Asp
            980                 985                 990

Glu Gly Val Ser Val Leu Arg Val Pro Leu Thr Gln Leu Lys Leu Lys
        995                 1000                1005

Asp Leu Glu Lys Met Val Asn Arg Glu Arg Glu Pro Lys Leu Tyr
    1010                1015                1020

Glu Ala Leu Lys Ala Arg Leu Glu Ala His Lys Asp Asp Pro Ala
    1025                1030                1035

Lys Ala Phe Ala Glu Pro Phe Tyr Lys Tyr Asp Lys Ala Gly Asn
    1040                1045                1050

Arg Thr Gln Gln Val Lys Ala Val Arg Val Glu Gln Val Gln Lys
    1055                1060                1065

Thr Gly Val Trp Val Arg Asn His Asn Gly Ile Ala Asp Asn Ala
    1070                1075                1080

Thr Met Val Arg Val Asp Val Phe Glu Lys Gly Asp Lys Tyr Tyr
    1085                1090                1095

Leu Val Pro Ile Tyr Ser Trp Gln Val Ala Lys Gly Ile Leu Pro
    1100                1105                1110

Asp Arg Ala Val Val Gln Gly Lys Asp Glu Glu Asp Trp Gln Leu
    1115                1120                1125

Ile Asp Asp Ser Phe Asn Phe Lys Phe Ser Leu His Pro Asn Asp
    1130                1135                1140

Leu Val Glu Val Ile Thr Lys Lys Ala Arg Met Phe Gly Tyr Phe
    1145                1150                1155

Ala Ser Cys His Ala Gly Thr Gly Asn Ile Asn Ile Arg Ile His
    1160                1165                1170

Asp Leu Asp His Lys Ile Gly Lys Asn Gly Ile Leu Glu Gly Ile
    1175                1180                1185

Gly Val Lys Thr Ala Leu Ser Phe Gln Lys Tyr Gln Ile Asp Glu
    1190                1195                1200

Leu Gly Lys Glu Ile Arg Pro Cys Arg Leu Lys Lys Arg Pro Pro
    1205                1210                1215

Val Arg Tyr Pro Tyr Asp Val Pro Asp Tyr Ala Ala Ala Pro Ala
    1220                1225                1230

Ala Lys Lys Lys Lys Leu Asp
    1235                1240

<210> SEQ ID NO 120
```

```
<211> LENGTH: 1246
<212> TYPE: PRT
<213> ORGANISM: Artificial sequence
<220> FEATURE:
<223> OTHER INFORMATION: Synthetic

<400> SEQUENCE: 120

Met Val Pro Lys Lys Lys Arg Lys Val Ala Ala Phe Lys Pro Asn Ser
1               5                   10                  15

Ile Asn Tyr Ile Leu Gly Leu Asp Ile Gly Ile Ala Ser Val Gly Trp
            20                  25                  30

Ala Met Val Glu Ile Asp Glu Glu Asn Pro Ile Arg Leu Ile Asp
        35                  40                  45

Leu Gly Val Arg Val Phe Glu Arg Ala Glu Val Pro Lys Thr Gly Asp
    50                  55                  60

Ser Leu Ala Met Ala Arg Arg Leu Ala Arg Ser Val Arg Arg Leu Thr
65                  70                  75                  80

Arg Arg Arg Ala His Arg Leu Leu Arg Thr Arg Arg Leu Leu Lys Arg
                85                  90                  95

Glu Gly Val Leu Gln Ala Ala Asn Phe Asp Glu Asn Gly Leu Ile Lys
            100                 105                 110

Ser Leu Pro Asn Thr Pro Trp Gln Leu Arg Ala Ala Ala Leu Asp Arg
        115                 120                 125

Lys Leu Thr Pro Leu Glu Trp Ser Ala Val Leu Leu His Leu Ile Lys
    130                 135                 140

His Arg Gly Tyr Leu Ser Gln Arg Lys Asn Glu Gly Glu Thr Ala Asp
145                 150                 155                 160

Lys Glu Leu Gly Ala Leu Leu Lys Gly Val Ala Gly Asn Ala His Ala
                165                 170                 175

Leu Gln Thr Gly Asp Phe Arg Thr Pro Ala Glu Leu Ala Leu Asn Lys
            180                 185                 190

Phe Glu Lys Glu Ser Gly His Ile Arg Asn Gln Arg Ser Asp Tyr Ser
        195                 200                 205

His Thr Phe Ser Arg Lys Asp Leu Gln Ala Glu Leu Ile Leu Leu Phe
    210                 215                 220

Glu Lys Gln Lys Glu Phe Gly Asn Pro His Val Ser Gly Gly Leu Lys
225                 230                 235                 240

Glu Gly Ile Glu Thr Leu Leu Met Thr Gln Arg Pro Ala Leu Ser Gly
                245                 250                 255

Asp Ala Val Gln Lys Met Leu Gly His Cys Thr Phe Glu Pro Ala Glu
            260                 265                 270

Pro Lys Ala Ala Lys Asn Thr Tyr Thr Ala Glu Arg Phe Ile Trp Leu
        275                 280                 285

Thr Lys Leu Asn Asn Leu Arg Ile Leu Glu Gln Gly Ser Glu Arg Pro
    290                 295                 300

Leu Thr Asp Thr Glu Arg Ala Thr Leu Met Asp Glu Pro Tyr Arg Lys
305                 310                 315                 320

Ser Lys Leu Thr Tyr Ala Gln Ala Arg Lys Leu Leu Gly Leu Glu Asp
                325                 330                 335

Thr Ala Phe Phe Lys Gly Leu Arg Tyr Gly Lys Asp Asn Ala Glu Ala
            340                 345                 350

Ser Thr Leu Met Glu Met Lys Ala Tyr His Ala Ile Ser Arg Ala Leu
        355                 360                 365

Glu Lys Glu Gly Leu Lys Asp Lys Ser Pro Leu Asn Leu Ser Pro
    370                 375                 380
```

```
Glu Leu Gln Asp Glu Ile Gly Thr Ala Phe Ser Leu Phe Lys Thr Asp
385                 390                 395                 400

Glu Asp Ile Thr Gly Arg Leu Lys Asp Arg Ile Gln Pro Glu Ile Leu
            405                 410                 415

Glu Ala Leu Leu Lys His Ile Ser Phe Asp Lys Phe Val Gln Ile Ser
        420                 425                 430

Leu Lys Ala Leu Arg Arg Ile Val Pro Leu Met Glu Gln Gly Lys Arg
    435                 440                 445

Tyr Asp Glu Ala Cys Ala Glu Ile Tyr Gly Asp His Tyr Gly Lys Lys
450                 455                 460

Asn Thr Glu Glu Lys Ile Tyr Leu Pro Pro Ile Pro Ala Asp Glu Ile
465                 470                 475                 480

Arg Asn Pro Val Val Leu Arg Ala Leu Ser Gln Ala Arg Lys Val Ile
            485                 490                 495

Asn Gly Val Val Arg Arg Tyr Gly Ser Pro Ala Arg Ile His Ile Glu
        500                 505                 510

Thr Ala Arg Glu Val Gly Lys Ser Phe Lys Asp Arg Lys Glu Ile Glu
    515                 520                 525

Lys Arg Gln Glu Glu Asn Arg Lys Asp Arg Glu Lys Ala Ala Ala Lys
530                 535                 540

Phe Arg Glu Tyr Phe Pro Asn Phe Val Gly Glu Pro Lys Ser Lys Asp
545                 550                 555                 560

Ile Leu Lys Leu Arg Leu Tyr Glu Gln Gln His Gly Lys Cys Leu Tyr
            565                 570                 575

Ser Gly Lys Glu Ile Asn Leu Gly Arg Leu Asn Glu Lys Gly Tyr Val
        580                 585                 590

Glu Ile Asp His Ala Leu Pro Phe Ser Arg Thr Trp Asp Asp Ser Phe
    595                 600                 605

Asn Asn Lys Val Leu Val Leu Gly Ser Glu Asn Gln Asn Lys Gly Asn
610                 615                 620

Gln Thr Pro Tyr Glu Tyr Phe Asn Gly Lys Asp Asn Ser Arg Glu Trp
625                 630                 635                 640

Gln Glu Phe Lys Ala Arg Val Glu Thr Ser Arg Phe Pro Arg Ser Lys
            645                 650                 655

Lys Gln Arg Ile Leu Leu Gln Lys Phe Asp Glu Asp Gly Phe Lys Glu
        660                 665                 670

Arg Asn Leu Asn Asp Thr Arg Tyr Val Asn Arg Phe Leu Cys Gln Phe
    675                 680                 685

Val Ala Asp Arg Met Arg Leu Thr Gly Lys Gly Lys Lys Arg Val Phe
690                 695                 700

Ala Ser Asn Gly Gln Ile Thr Asn Leu Leu Arg Gly Phe Trp Gly Leu
705                 710                 715                 720

Arg Lys Val Arg Ala Glu Asn Asp Arg His His Ala Leu Asp Ala Val
            725                 730                 735

Val Val Ala Cys Ser Thr Val Ala Met Gln Gln Lys Ile Thr Arg Phe
        740                 745                 750

Val Arg Tyr Lys Glu Met Asn Ala Phe Asp Gly Lys Thr Ile Asp Lys
    755                 760                 765

Glu Thr Gly Glu Val Leu His Gln Lys Thr His Phe Pro Gln Pro Trp
770                 775                 780

Glu Phe Phe Ala Gln Glu Val Met Ile Arg Val Phe Gly Lys Pro Asp
785                 790                 795                 800
```

```
Gly Lys Pro Glu Phe Glu Glu Ala Asp Thr Leu Glu Lys Leu Arg Thr
                805                 810                 815
Leu Leu Ala Glu Lys Leu Ser Ser Arg Pro Glu Ala Val His Glu Tyr
            820                 825                 830
Val Thr Pro Leu Phe Val Ser Arg Ala Pro Asn Arg Lys Met Ser Gly
            835                 840                 845
Gln Gly His Met Glu Thr Val Lys Ser Ala Lys Arg Leu Asp Glu Gly
    850                 855                 860
Val Ser Val Leu Arg Val Pro Leu Thr Gln Leu Lys Leu Lys Asp Leu
865                 870                 875                 880
Glu Lys Met Val Asn Arg Glu Arg Glu Pro Lys Leu Tyr Glu Ala Leu
                885                 890                 895
Lys Ala Arg Leu Glu Ala His Lys Asp Asp Pro Ala Lys Ala Phe Ala
                900                 905                 910
Glu Pro Phe Tyr Lys Tyr Asp Lys Ala Gly Asn Arg Thr Gln Gln Val
            915                 920                 925
Lys Ala Val Arg Val Glu Gln Val Gln Lys Thr Gly Val Trp Val Arg
            930                 935                 940
Asn His Asn Gly Ile Ala Asp Asn Ala Thr Met Val Arg Val Asp Val
945                 950                 955                 960
Phe Glu Lys Gly Asp Lys Tyr Tyr Leu Val Pro Ile Tyr Ser Trp Gln
                965                 970                 975
Val Ala Lys Gly Ile Leu Pro Asp Arg Ala Val Val Gln Gly Lys Asp
            980                 985                 990
Glu Glu Asp Trp Gln Leu Ile Asp  Asp Ser Phe Asn Phe  Lys Phe Ser
    995                 1000                1005
Leu His  Pro Asn Asp Leu Val  Glu Val Ile Thr Lys  Lys Ala Arg
    1010                1015                1020
Met Phe  Gly Tyr Phe Ala Ser  Cys His Ala Gly Thr  Gly Asn Ile
    1025                1030                1035
Asn Ile  Arg Ile His Asp Leu  Asp His Lys Ile Gly  Lys Asn Gly
    1040                1045                1050
Ile Leu  Glu Gly Ile Gly Val  Lys Thr Ala Leu Ser  Phe Gln Lys
    1055                1060                1065
Tyr Gln  Ile Asp Glu Leu Gly  Lys Glu Ile Arg Pro  Cys Arg Leu
    1070                1075                1080
Lys Lys  Arg Pro Pro Val Arg  Tyr Pro Tyr Asp Val  Pro Asp Tyr
    1085                1090                1095
Ala Ala  Gly Thr Gly Gly Pro  Lys Lys Lys Arg Lys  Val Tyr Pro
    1100                1105                1110
Tyr Asp  Val Pro Asp Tyr Ala  Gly Tyr Pro Tyr Asp  Val Pro Asp
    1115                1120                1125
Tyr Ala  Gly Ser Tyr Pro Tyr  Asp Val Pro Asp Tyr  Ala Gly Ser
    1130                1135                1140
Ala Ala  Pro Ala Ala Lys Lys  Lys Lys Leu Asp Phe  Glu Ser Gly
    1145                1150                1155
Arg Pro  Tyr Ala Cys Pro Val  Glu Ser Cys Asp Arg  Arg Phe Ser
    1160                1165                1170
Arg Ser  Asp Glu Leu Thr Arg  His Ile Arg Ile His  Thr Gly Gln
    1175                1180                1185
Lys Pro  Phe Gln Cys Arg Ile  Cys Met Arg Asn Phe  Ser Arg Ser
    1190                1195                1200
Asp His  Leu Thr Thr His Ile  Arg Thr His Thr Gly  Glu Lys Pro
```

```
                    1205                1210                1215

Phe Ala Cys Asp Ile Cys Gly Arg Lys Phe Ala Arg Ser Asp Glu
    1220                1225                1230

Arg Lys Arg His Thr Lys Ile His Leu Arg Gln Lys Asp
    1235                1240                1245

<210> SEQ ID NO 121
<211> LENGTH: 1240
<212> TYPE: PRT
<213> ORGANISM: Artificial sequence
<220> FEATURE:
<223> OTHER INFORMATION: Synthetic

<400> SEQUENCE: 121

Met Gly Arg Ala Ala Pro Ala Ala Lys Lys Lys Lys Leu Asp Gln Leu
1               5                   10                  15

Arg Pro Tyr Ala Cys Pro Val Glu Ser Cys Asp Arg Arg Phe Ser Arg
            20                  25                  30

Ser Asp Glu Leu Thr Arg His Ile Arg Ile His Thr Gly Gln Lys Pro
        35                  40                  45

Phe Gln Cys Arg Ile Cys Met Arg Asn Phe Ser Arg Ser Asp His Leu
    50                  55                  60

Thr Thr His Ile Arg Thr His Thr Gly Glu Lys Pro Phe Ala Cys Asp
65                  70                  75                  80

Ile Cys Gly Arg Lys Phe Ala Arg Ser Asp Glu Arg Lys Arg His Thr
                85                  90                  95

Lys Ile His Leu Arg Gln Lys Asp Pro Gly Ser Gly Gly Ser Gly Ser
            100                 105                 110

Ser Gly Arg Thr Ala Ala Pro Ala Ala Lys Lys Lys Lys Leu Asp Ile
        115                 120                 125

Arg Lys Leu Val Pro Lys Lys Arg Lys Val Ala Ala Phe Lys Pro
    130                 135                 140

Asn Ser Ile Asn Tyr Ile Leu Gly Leu Asp Ile Gly Ile Ala Ser Val
145                 150                 155                 160

Gly Trp Ala Met Val Glu Ile Asp Glu Glu Asn Pro Ile Arg Leu
                165                 170                 175

Ile Asp Leu Gly Val Arg Val Phe Glu Arg Ala Glu Val Pro Lys Thr
            180                 185                 190

Gly Asp Ser Leu Ala Met Ala Arg Arg Leu Ala Arg Ser Val Arg Arg
        195                 200                 205

Leu Thr Arg Arg Arg Ala His Arg Leu Leu Arg Thr Arg Arg Leu Leu
    210                 215                 220

Lys Arg Glu Gly Val Leu Gln Ala Ala Asn Phe Asp Glu Asn Gly Leu
225                 230                 235                 240

Ile Lys Ser Leu Pro Asn Thr Pro Trp Gln Leu Arg Ala Ala Leu
                245                 250                 255

Asp Arg Lys Leu Thr Pro Leu Glu Trp Ser Ala Val Leu Leu His Leu
            260                 265                 270

Ile Lys His Arg Gly Tyr Leu Ser Gln Arg Lys Asn Glu Gly Glu Thr
        275                 280                 285

Ala Asp Lys Glu Leu Gly Ala Leu Leu Lys Gly Val Ala Gly Asn Ala
    290                 295                 300

His Ala Leu Gln Thr Gly Asp Phe Arg Thr Pro Ala Glu Leu Ala Leu
305                 310                 315                 320

Asn Lys Phe Glu Lys Glu Ser Gly His Ile Arg Asn Gln Arg Ser Asp
```

-continued

```
                325                 330                 335
Tyr Ser His Thr Phe Ser Arg Lys Asp Leu Gln Ala Glu Leu Ile Leu
            340                 345                 350
Leu Phe Glu Lys Gln Lys Glu Phe Gly Asn Pro His Val Ser Gly Gly
            355                 360                 365
Leu Lys Glu Gly Ile Glu Thr Leu Leu Met Thr Gln Arg Pro Ala Leu
            370                 375                 380
Ser Gly Asp Ala Val Gln Lys Met Leu Gly His Cys Thr Phe Glu Pro
385                 390                 395                 400
Ala Glu Pro Lys Ala Ala Lys Asn Thr Tyr Thr Ala Glu Arg Phe Ile
                405                 410                 415
Trp Leu Thr Lys Leu Asn Asn Leu Arg Ile Leu Glu Gln Gly Ser Glu
                420                 425                 430
Arg Pro Leu Thr Asp Thr Glu Arg Ala Thr Leu Met Asp Glu Pro Tyr
                435                 440                 445
Arg Lys Ser Lys Leu Thr Tyr Ala Gln Ala Arg Lys Leu Leu Gly Leu
                450                 455                 460
Glu Asp Thr Ala Phe Phe Lys Gly Leu Arg Tyr Gly Lys Asp Asn Ala
465                 470                 475                 480
Glu Ala Ser Thr Leu Met Glu Met Lys Ala Tyr His Ala Ile Ser Arg
                485                 490                 495
Ala Leu Glu Lys Glu Gly Leu Lys Asp Lys Lys Ser Pro Leu Asn Leu
                500                 505                 510
Ser Pro Glu Leu Gln Asp Glu Ile Gly Thr Ala Phe Ser Leu Phe Lys
                515                 520                 525
Thr Asp Glu Asp Ile Thr Gly Arg Leu Lys Asp Arg Ile Gln Pro Glu
                530                 535                 540
Ile Leu Glu Ala Leu Leu Lys His Ile Ser Phe Asp Lys Phe Val Gln
545                 550                 555                 560
Ile Ser Leu Lys Ala Leu Arg Arg Ile Val Pro Leu Met Glu Gln Gly
                565                 570                 575
Lys Arg Tyr Asp Glu Ala Cys Ala Glu Ile Tyr Gly Asp His Tyr Gly
                580                 585                 590
Lys Lys Asn Thr Glu Glu Lys Ile Tyr Leu Pro Pro Ile Pro Ala Asp
                595                 600                 605
Glu Ile Arg Asn Pro Val Val Leu Arg Ala Leu Ser Gln Ala Arg Lys
                610                 615                 620
Val Ile Asn Gly Val Val Arg Arg Tyr Gly Ser Pro Ala Arg Ile His
625                 630                 635                 640
Ile Glu Thr Ala Arg Glu Val Gly Lys Ser Phe Lys Asp Arg Lys Glu
                645                 650                 655
Ile Glu Lys Arg Gln Glu Glu Asn Arg Lys Asp Arg Glu Lys Ala Ala
                660                 665                 670
Ala Lys Phe Arg Glu Tyr Phe Pro Asn Phe Val Gly Glu Pro Lys Ser
                675                 680                 685
Lys Asp Ile Leu Lys Leu Arg Leu Tyr Glu Gln Gln His Gly Lys Cys
                690                 695                 700
Leu Tyr Ser Gly Lys Glu Ile Asn Leu Gly Arg Leu Asn Glu Lys Gly
705                 710                 715                 720
Tyr Val Glu Ile Asp His Ala Leu Pro Phe Ser Arg Thr Trp Asp Asp
                725                 730                 735
Ser Phe Asn Asn Lys Val Leu Val Leu Gly Ser Glu Asn Gln Asn Lys
                740                 745                 750
```

-continued

Gly Asn Gln Thr Pro Tyr Glu Tyr Phe Asn Gly Lys Asp Asn Ser Arg
             755                 760                 765

Glu Trp Gln Glu Phe Lys Ala Arg Val Glu Thr Ser Arg Phe Pro Arg
    770                 775                 780

Ser Lys Lys Gln Arg Ile Leu Leu Gln Lys Phe Asp Glu Asp Gly Phe
785                 790                 795                 800

Lys Glu Arg Asn Leu Asn Asp Thr Arg Tyr Val Asn Arg Phe Leu Cys
                805                 810                 815

Gln Phe Val Ala Asp Arg Met Arg Leu Thr Gly Lys Gly Lys Lys Arg
            820                 825                 830

Val Phe Ala Ser Asn Gly Gln Ile Thr Asn Leu Leu Arg Gly Phe Trp
            835                 840                 845

Gly Leu Arg Lys Val Arg Ala Glu Asn Asp Arg His His Ala Leu Asp
    850                 855                 860

Ala Val Val Val Ala Cys Ser Thr Val Ala Met Gln Gln Lys Ile Thr
865                 870                 875                 880

Arg Phe Val Arg Tyr Lys Glu Met Asn Ala Phe Asp Gly Lys Thr Ile
                885                 890                 895

Asp Lys Glu Thr Gly Glu Val Leu His Gln Lys Thr His Phe Pro Gln
            900                 905                 910

Pro Trp Glu Phe Phe Ala Gln Glu Val Met Ile Arg Val Phe Gly Lys
            915                 920                 925

Pro Asp Gly Lys Pro Glu Phe Glu Glu Ala Asp Thr Leu Glu Lys Leu
    930                 935                 940

Arg Thr Leu Leu Ala Glu Lys Leu Ser Ser Arg Pro Glu Ala Val His
945                 950                 955                 960

Glu Tyr Val Thr Pro Leu Phe Val Ser Arg Ala Pro Asn Arg Lys Met
                965                 970                 975

Ser Gly Gln Gly His Met Glu Thr Val Lys Ser Ala Lys Arg Leu Asp
            980                 985                 990

Glu Gly Val Ser Val Leu Arg Val Pro Leu Thr Gln Leu Lys Leu Lys
    995                 1000                1005

Asp Leu Glu Lys Met Val Asn Arg Glu Arg Glu Pro Lys Leu Tyr
    1010                1015                1020

Glu Ala Leu Lys Ala Arg Leu Glu Ala His Lys Asp Asp Pro Ala
    1025                1030                1035

Lys Ala Phe Ala Glu Pro Phe Tyr Lys Tyr Asp Lys Ala Gly Asn
    1040                1045                1050

Arg Thr Gln Gln Val Lys Ala Val Arg Val Glu Gln Val Gln Lys
    1055                1060                1065

Thr Gly Val Trp Val Arg Asn His Asn Gly Ile Ala Asp Asn Ala
    1070                1075                1080

Thr Met Val Arg Val Asp Val Phe Glu Lys Gly Asp Lys Tyr Tyr
    1085                1090                1095

Leu Val Pro Ile Tyr Ser Trp Gln Val Ala Lys Gly Ile Leu Pro
    1100                1105                1110

Asp Arg Ala Val Val Gln Gly Lys Asp Glu Glu Asp Trp Gln Leu
    1115                1120                1125

Ile Asp Asp Ser Phe Asn Phe Lys Phe Ser Leu His Pro Asn Asp
    1130                1135                1140

Leu Val Glu Val Ile Thr Lys Ala Ala Arg Met Phe Gly Tyr Phe
    1145                1150                1155

-continued

Ala Ser Cys His Ala Gly Thr Gly Asn Ile Asn Ile Arg Ile His
    1160                1165                1170

Asp Leu Asp His Lys Ile Gly Lys Asn Gly Ile Leu Glu Gly Ile
    1175                1180                1185

Gly Val Lys Thr Ala Leu Ser Phe Gln Lys Tyr Gln Ile Asp Glu
    1190                1195                1200

Leu Gly Lys Glu Ile Arg Pro Cys Arg Leu Lys Lys Arg Pro Pro
    1205                1210                1215

Val Arg Tyr Pro Tyr Asp Val Pro Asp Tyr Ala Ala Ala Pro Ala
    1220                1225                1230

Ala Lys Lys Lys Lys Leu Asp
    1235                1240

<210> SEQ ID NO 122
<211> LENGTH: 1246
<212> TYPE: PRT
<213> ORGANISM: Artificial sequence
<220> FEATURE:
<223> OTHER INFORMATION: Synthetic

<400> SEQUENCE: 122

Met Val Pro Lys Lys Arg Lys Val Ala Ala Phe Lys Pro Asn Ser
1               5                   10                  15

Ile Asn Tyr Ile Leu Gly Leu Asp Ile Gly Ile Ala Ser Val Gly Trp
            20                  25                  30

Ala Met Val Glu Ile Asp Glu Glu Asn Pro Ile Arg Leu Ile Asp
            35                  40                  45

Leu Gly Val Arg Val Phe Glu Arg Ala Glu Val Pro Lys Thr Gly Asp
    50                  55                  60

Ser Leu Ala Met Ala Arg Arg Leu Ala Arg Ser Val Arg Arg Leu Thr
65                  70                  75                  80

Arg Arg Arg Ala His Arg Leu Leu Arg Thr Arg Arg Leu Leu Lys Arg
                    85                  90                  95

Glu Gly Val Leu Gln Ala Ala Asn Phe Asp Glu Asn Gly Leu Ile Lys
                100                 105                 110

Ser Leu Pro Asn Thr Pro Trp Gln Leu Arg Ala Ala Ala Leu Asp Arg
            115                 120                 125

Lys Leu Thr Pro Leu Glu Trp Ser Ala Val Leu Leu His Leu Ile Lys
    130                 135                 140

His Arg Gly Tyr Leu Ser Gln Arg Lys Asn Glu Gly Glu Thr Ala Asp
145                 150                 155                 160

Lys Glu Leu Gly Ala Leu Leu Lys Gly Val Ala Gly Asn Ala His Ala
                    165                 170                 175

Leu Gln Thr Gly Asp Phe Arg Thr Pro Ala Glu Leu Ala Leu Asn Lys
                180                 185                 190

Phe Glu Lys Glu Ser Gly His Ile Arg Asn Gln Arg Ser Asp Tyr Ser
            195                 200                 205

His Thr Phe Ser Arg Lys Asp Leu Gln Ala Glu Leu Ile Leu Leu Phe
    210                 215                 220

Glu Lys Gln Lys Glu Phe Gly Asn Pro His Val Ser Gly Gly Leu Lys
225                 230                 235                 240

Glu Gly Ile Glu Thr Leu Leu Met Thr Gln Arg Pro Ala Leu Ser Gly
                    245                 250                 255

Asp Ala Val Gln Lys Met Leu Gly His Cys Thr Phe Glu Pro Ala Glu
                260                 265                 270

```
Pro Lys Ala Ala Lys Asn Thr Tyr Thr Ala Glu Arg Phe Ile Trp Leu
            275                 280                 285
Thr Lys Leu Asn Asn Leu Arg Ile Leu Glu Gln Gly Ser Glu Arg Pro
290                 295                 300
Leu Thr Asp Thr Glu Arg Ala Thr Leu Met Asp Glu Pro Tyr Arg Lys
305                 310                 315                 320
Ser Lys Leu Thr Tyr Ala Gln Ala Arg Lys Leu Leu Gly Leu Glu Asp
                325                 330                 335
Thr Ala Phe Phe Lys Gly Leu Arg Tyr Gly Lys Asp Asn Ala Glu Ala
            340                 345                 350
Ser Thr Leu Met Glu Met Lys Ala Tyr His Ala Ile Ser Arg Ala Leu
        355                 360                 365
Glu Lys Glu Gly Leu Lys Asp Lys Lys Ser Pro Leu Asn Leu Ser Pro
    370                 375                 380
Glu Leu Gln Asp Glu Ile Gly Thr Ala Phe Ser Leu Phe Lys Thr Asp
385                 390                 395                 400
Glu Asp Ile Thr Gly Arg Leu Lys Asp Arg Ile Gln Pro Glu Ile Leu
                405                 410                 415
Glu Ala Leu Leu Lys His Ile Ser Phe Asp Lys Phe Val Gln Ile Ser
            420                 425                 430
Leu Lys Ala Leu Arg Arg Ile Val Pro Leu Met Glu Gln Gly Lys Arg
        435                 440                 445
Tyr Asp Glu Ala Cys Ala Glu Ile Tyr Gly Asp His Tyr Gly Lys Lys
    450                 455                 460
Asn Thr Glu Glu Lys Ile Tyr Leu Pro Pro Ile Pro Ala Asp Glu Ile
465                 470                 475                 480
Arg Asn Pro Val Val Leu Arg Ala Leu Ser Gln Ala Arg Lys Val Ile
                485                 490                 495
Asn Gly Val Val Arg Arg Tyr Gly Ser Pro Ala Arg Ile His Ile Glu
            500                 505                 510
Thr Ala Arg Glu Val Gly Lys Ser Phe Lys Asp Arg Lys Glu Ile Glu
        515                 520                 525
Lys Arg Gln Glu Glu Asn Arg Lys Asp Arg Glu Lys Ala Ala Ala Lys
    530                 535                 540
Phe Arg Glu Tyr Phe Pro Asn Phe Val Gly Glu Pro Lys Ser Lys Asp
545                 550                 555                 560
Ile Leu Lys Leu Arg Leu Tyr Glu Gln Gln His Gly Lys Cys Leu Tyr
                565                 570                 575
Ser Gly Lys Glu Ile Asn Leu Gly Arg Leu Asn Glu Lys Gly Tyr Val
            580                 585                 590
Glu Ile Asp His Ala Leu Pro Phe Ser Arg Thr Trp Asp Asp Ser Phe
        595                 600                 605
Asn Asn Lys Val Leu Val Leu Gly Ser Glu Asn Gln Asn Lys Gly Asn
    610                 615                 620
Gln Thr Pro Tyr Glu Tyr Phe Asn Gly Lys Asp Asn Ser Arg Glu Trp
625                 630                 635                 640
Gln Glu Phe Lys Ala Arg Val Glu Thr Ser Arg Phe Pro Arg Ser Lys
                645                 650                 655
Lys Gln Arg Ile Leu Leu Gln Lys Phe Asp Glu Asp Gly Phe Lys Glu
            660                 665                 670
Arg Asn Leu Asn Asp Thr Arg Tyr Val Asn Arg Phe Leu Cys Gln Phe
        675                 680                 685
Val Ala Asp Arg Met Arg Leu Thr Gly Lys Gly Lys Lys Arg Val Phe
```

```
        690                 695                 700
Ala Ser Asn Gly Gln Ile Thr Asn Leu Leu Arg Gly Phe Trp Gly Leu
705                 710                 715                 720

Arg Lys Val Arg Ala Glu Asn Asp Arg His His Ala Leu Asp Ala Val
                725                 730                 735

Val Val Ala Cys Ser Thr Val Ala Met Gln Gln Lys Ile Thr Arg Phe
                740                 745                 750

Val Arg Tyr Lys Glu Met Asn Ala Phe Asp Gly Lys Thr Ile Asp Lys
                755                 760                 765

Glu Thr Gly Glu Val Leu His Gln Lys Thr His Phe Pro Gln Pro Trp
770                 775                 780

Glu Phe Phe Ala Gln Glu Val Met Ile Arg Val Phe Gly Lys Pro Asp
785                 790                 795                 800

Gly Lys Pro Glu Phe Glu Glu Ala Asp Thr Leu Glu Lys Leu Arg Thr
                805                 810                 815

Leu Leu Ala Glu Lys Leu Ser Ser Arg Pro Glu Ala Val His Glu Tyr
                820                 825                 830

Val Thr Pro Leu Phe Val Ser Arg Ala Pro Asn Arg Lys Met Ser Gly
                835                 840                 845

Gln Gly His Met Glu Thr Val Lys Ser Ala Lys Arg Leu Asp Glu Gly
            850                 855                 860

Val Ser Val Leu Arg Val Pro Leu Thr Gln Leu Lys Leu Lys Asp Leu
865                 870                 875                 880

Glu Lys Met Val Asn Arg Glu Arg Glu Pro Lys Leu Tyr Glu Ala Leu
                885                 890                 895

Lys Ala Arg Leu Glu Ala His Lys Asp Asp Pro Ala Lys Ala Phe Ala
                900                 905                 910

Glu Pro Phe Tyr Lys Tyr Asp Lys Ala Gly Asn Arg Thr Gln Gln Val
                915                 920                 925

Lys Ala Val Arg Val Glu Gln Val Gln Lys Thr Gly Val Trp Val Arg
                930                 935                 940

Asn His Asn Gly Ile Ala Asp Asn Ala Thr Met Val Arg Val Asp Val
945                 950                 955                 960

Phe Glu Lys Gly Asp Lys Tyr Tyr Leu Val Pro Ile Tyr Ser Trp Gln
                965                 970                 975

Val Ala Lys Gly Ile Leu Pro Asp Arg Ala Val Val Gln Gly Lys Asp
                980                 985                 990

Glu Glu Asp Trp Gln Leu Ile Asp Asp Ser Phe Asn Phe Lys Phe Ser
                995                 1000                1005

Leu His Pro Asn Asp Leu Val Glu Val Ile Thr Lys Ala Ala Arg
    1010                1015                1020

Met Phe Gly Tyr Phe Ala Ser Cys His Ala Gly Thr Gly Asn Ile
    1025                1030                1035

Asn Ile Arg Ile His Asp Leu Asp His Lys Ile Gly Lys Asn Gly
    1040                1045                1050

Ile Leu Glu Gly Ile Gly Val Lys Thr Ala Leu Ser Phe Gln Lys
    1055                1060                1065

Tyr Gln Ile Asp Glu Leu Gly Lys Glu Ile Arg Pro Cys Arg Leu
    1070                1075                1080

Lys Lys Arg Pro Pro Val Arg Tyr Pro Tyr Asp Val Pro Asp Tyr
    1085                1090                1095

Ala Ala Gly Thr Gly Gly Pro Lys Lys Lys Arg Lys Val Tyr Pro
    1100                1105                1110
```

```
Tyr Asp Val Pro Asp Tyr Ala Gly Tyr Pro Tyr Asp Val Pro Asp
    1115                1120                1125

Tyr Ala Gly Ser Tyr Pro Tyr Asp Val Pro Asp Tyr Ala Gly Ser
    1130                1135                1140

Ala Ala Pro Ala Ala Lys Lys Lys Leu Asp Phe Glu Ser Gly
    1145                1150                1155

Arg Pro Tyr Ala Cys Pro Val Glu Ser Cys Asp Arg Arg Phe Ser
    1160                1165                1170

Arg Ser Asp Glu Leu Thr Arg His Ile Arg Ile His Thr Gly Gln
    1175                1180                1185

Lys Pro Phe Gln Cys Arg Ile Cys Met Arg Asn Phe Ser Arg Ser
    1190                1195                1200

Asp His Leu Thr Thr His Ile Arg Thr His Thr Gly Glu Lys Pro
    1205                1210                1215

Phe Ala Cys Asp Ile Cys Gly Arg Lys Phe Ala Arg Ser Asp Glu
    1220                1225                1230

Arg Lys Arg His Thr Lys Ile His Leu Arg Gln Lys Asp
    1235                1240                1245

<210> SEQ ID NO 123
<211> LENGTH: 59
<212> TYPE: DNA
<213> ORGANISM: Artificial sequence
<220> FEATURE:
<223> OTHER INFORMATION: Synthetic

<400> SEQUENCE: 123
tccccggcat cctagcgcgc tgggctagca atcgcctccg cgtcccttcc aacagtacc      59

<210> SEQ ID NO 124
<211> LENGTH: 59
<212> TYPE: DNA
<213> ORGANISM: Artificial sequence
<220> FEATURE:
<223> OTHER INFORMATION: Synthetic

<400> SEQUENCE: 124
tccccggcat cctagcgcgc tgggctagcg gtactgttgg aagggacgcg gaggcgatt      59

<210> SEQ ID NO 125
<211> LENGTH: 59
<212> TYPE: DNA
<213> ORGANISM: Artificial sequence
<220> FEATURE:
<223> OTHER INFORMATION: Synthetic

<400> SEQUENCE: 125
ggtactgttg aagggacgc ggaggcgatt gctagctccc cggcatccta gcgcgctgg       59

<210> SEQ ID NO 126
<211> LENGTH: 59
<212> TYPE: DNA
<213> ORGANISM: Artificial sequence
<220> FEATURE:
<223> OTHER INFORMATION: Synthetic

<400> SEQUENCE: 126
aatcgcctcc gcgtcccttc caacagtacc gctagctccc cggcatccta gcgcgctgg      59

<210> SEQ ID NO 127
<211> LENGTH: 59
```

<212> TYPE: DNA
<213> ORGANISM: Artificial sequence
<220> FEATURE:
<223> OTHER INFORMATION: Synthetic

<400> SEQUENCE: 127
tccccggcat cctagcgcgc tgggctagca atcgcctccg cgtcccttcc aacagtacc    59

<210> SEQ ID NO 128
<211> LENGTH: 59
<212> TYPE: DNA
<213> ORGANISM: Artificial sequence
<220> FEATURE:
<223> OTHER INFORMATION: Synthetic

<400> SEQUENCE: 128
tccccggcat cctagcgcgc tgggctagcg gtactgttgg aagggacgcg gaggcgatt    59

<210> SEQ ID NO 129
<211> LENGTH: 59
<212> TYPE: DNA
<213> ORGANISM: Artificial sequence
<220> FEATURE:
<223> OTHER INFORMATION: Synthetic

<400> SEQUENCE: 129
ggtactgttg aagggacgc ggaggcgatt gctagctccc cggcatccta gcgcgctgg     59

<210> SEQ ID NO 130
<211> LENGTH: 59
<212> TYPE: DNA
<213> ORGANISM: Artificial sequence
<220> FEATURE:
<223> OTHER INFORMATION: Synthetic

<400> SEQUENCE: 130
aatcgcctcc gcgtcccttc caacagtacc gctagctccc cggcatccta gcgcgctgg    59

<210> SEQ ID NO 131
<211> LENGTH: 71
<212> TYPE: DNA
<213> ORGANISM: Artificial sequence
<220> FEATURE:
<223> OTHER INFORMATION: Synthetic

<400> SEQUENCE: 131
ggtgagtgag tgtgtgcgtg tggggttgag ggcgttggag cggggagaag gccaggggtc    60
actccaggat t                                                         71

<210> SEQ ID NO 132
<211> LENGTH: 23
<212> TYPE: DNA
<213> ORGANISM: Artificial sequence
<220> FEATURE:
<223> OTHER INFORMATION: Synthetic

<400> SEQUENCE: 132
gaccccctcc accccgcctc cgg                                            23

<210> SEQ ID NO 133
<211> LENGTH: 23
<212> TYPE: DNA
<213> ORGANISM: Artificial sequence
<220> FEATURE:
<223> OTHER INFORMATION: Synthetic

<400> SEQUENCE: 133 ctgcccccccc accccgccac tgg 23

<210> SEQ ID NO 134
<211> LENGTH: 1544
<212> TYPE: PRT
<213> ORGANISM: Artificial sequence
<220> FEATURE:
<223> OTHER INFORMATION: Synthetic

<400> SEQUENCE: 134

```
Met Gly Arg Ala Ala Pro Ala Ala Lys Lys Lys Lys Leu Asp Gln Leu
1               5                   10                  15

Gly Ala Ser Gly Ser Pro Gly Ser Gly Ser Gly Ser Ser Gly Arg
            20                  25                  30

Thr Ala Ala Pro Ala Ala Lys Lys Lys Lys Leu Asp Ser Glu Phe Gly
            35                  40                  45

Ser Gly Ser Asp Lys Lys Tyr Ser Ile Gly Leu Asp Ile Gly Thr Asn
50                  55                  60

Ser Val Gly Trp Ala Val Ile Thr Asp Glu Tyr Lys Val Pro Ser Lys
65                  70                  75                  80

Lys Phe Lys Val Leu Gly Asn Thr Asp Arg His Ser Ile Lys Lys Asn
                85                  90                  95

Leu Ile Gly Ala Leu Leu Phe Asp Ser Gly Glu Thr Ala Glu Ala Thr
            100                 105                 110

Arg Leu Lys Arg Thr Ala Arg Arg Tyr Thr Arg Arg Lys Asn Arg
            115                 120                 125

Ile Cys Tyr Leu Gln Glu Ile Phe Ser Asn Glu Met Ala Lys Val Asp
130                 135                 140

Asp Ser Phe Phe His Arg Leu Glu Glu Ser Phe Leu Val Glu Glu Asp
145                 150                 155                 160

Lys Lys His Glu Arg His Pro Ile Phe Gly Asn Ile Val Asp Glu Val
                165                 170                 175

Ala Tyr His Glu Lys Tyr Pro Thr Ile Tyr His Leu Arg Lys Lys Leu
            180                 185                 190

Val Asp Ser Thr Asp Lys Ala Asp Leu Arg Leu Ile Tyr Leu Ala Leu
            195                 200                 205

Ala His Met Ile Lys Phe Arg Gly His Phe Leu Ile Glu Gly Asp Leu
210                 215                 220

Asn Pro Asp Asn Ser Asp Val Asp Lys Leu Phe Ile Gln Leu Val Gln
225                 230                 235                 240

Thr Tyr Asn Gln Leu Phe Glu Glu Asn Pro Ile Asn Ala Ser Gly Val
                245                 250                 255

Asp Ala Lys Ala Ile Leu Ser Ala Arg Leu Ser Lys Ser Arg Arg Leu
            260                 265                 270

Glu Asn Leu Ile Ala Gln Leu Pro Gly Glu Lys Lys Asn Gly Leu Phe
            275                 280                 285

Gly Asn Leu Ile Ala Leu Ser Leu Gly Leu Thr Pro Asn Phe Lys Ser
290                 295                 300

Asn Phe Asp Leu Ala Glu Asp Ala Lys Leu Gln Leu Ser Lys Asp Thr
305                 310                 315                 320

Tyr Asp Asp Asp Leu Asp Asn Leu Leu Ala Gln Ile Gly Asp Gln Tyr
                325                 330                 335

Ala Asp Leu Phe Leu Ala Ala Lys Asn Leu Ser Asp Ala Ile Leu Leu
            340                 345                 350
```

-continued

Ser Asp Ile Leu Arg Val Asn Thr Glu Ile Thr Lys Ala Pro Leu Ser
            355                 360                 365

Ala Ser Met Ile Lys Arg Tyr Asp Glu His His Gln Asp Leu Thr Leu
370                 375                 380

Leu Lys Ala Leu Val Arg Gln Gln Leu Pro Glu Lys Tyr Lys Glu Ile
385                 390                 395                 400

Phe Phe Asp Gln Ser Lys Asn Gly Tyr Ala Gly Tyr Ile Asp Gly Gly
                405                 410                 415

Ala Ser Gln Glu Glu Phe Tyr Lys Phe Ile Lys Pro Ile Leu Glu Lys
            420                 425                 430

Met Asp Gly Thr Glu Glu Leu Leu Val Lys Leu Asn Arg Glu Asp Leu
            435                 440                 445

Leu Arg Lys Gln Arg Thr Phe Asp Asn Gly Ser Ile Pro His Gln Ile
450                 455                 460

His Leu Gly Glu Leu His Ala Ile Leu Arg Arg Gln Glu Asp Phe Tyr
465                 470                 475                 480

Pro Phe Leu Lys Asp Asn Arg Glu Lys Ile Glu Lys Ile Leu Thr Phe
                485                 490                 495

Arg Ile Pro Tyr Tyr Val Gly Pro Leu Ala Arg Gly Asn Ser Arg Phe
            500                 505                 510

Ala Trp Met Thr Arg Lys Ser Glu Glu Thr Ile Thr Pro Trp Asn Phe
            515                 520                 525

Glu Glu Val Val Asp Lys Gly Ala Ser Ala Gln Ser Phe Ile Glu Arg
530                 535                 540

Met Thr Asn Phe Asp Lys Asn Leu Pro Asn Glu Lys Val Leu Pro Lys
545                 550                 555                 560

His Ser Leu Leu Tyr Glu Tyr Phe Thr Val Tyr Asn Glu Leu Thr Lys
                565                 570                 575

Val Lys Tyr Val Thr Glu Gly Met Arg Lys Pro Ala Phe Leu Ser Gly
            580                 585                 590

Glu Gln Lys Lys Ala Ile Val Asp Leu Leu Phe Lys Thr Asn Arg Lys
            595                 600                 605

Val Thr Val Lys Gln Leu Lys Glu Asp Tyr Phe Lys Lys Ile Glu Cys
610                 615                 620

Phe Asp Ser Val Glu Ile Ser Gly Val Glu Asp Arg Phe Asn Ala Ser
625                 630                 635                 640

Leu Gly Thr Tyr His Asp Leu Leu Lys Ile Ile Lys Asp Lys Asp Phe
                645                 650                 655

Leu Asp Asn Glu Glu Asn Glu Asp Ile Leu Glu Asp Ile Val Leu Thr
            660                 665                 670

Leu Thr Leu Phe Glu Asp Arg Glu Met Ile Glu Glu Arg Leu Lys Thr
            675                 680                 685

Tyr Ala His Leu Phe Asp Asp Lys Val Met Lys Gln Leu Lys Arg Arg
690                 695                 700

Arg Tyr Thr Gly Trp Gly Arg Leu Ser Arg Lys Leu Ile Asn Gly Ile
705                 710                 715                 720

Arg Asp Lys Gln Ser Gly Lys Thr Ile Leu Asp Phe Leu Lys Ser Asp
                725                 730                 735

Gly Phe Ala Asn Arg Asn Phe Met Gln Leu Ile His Asp Asp Ser Leu
            740                 745                 750

Thr Phe Lys Glu Asp Ile Gln Lys Ala Gln Val Ser Gly Gln Gly Asp
            755                 760                 765

-continued

```
Ser Leu His Glu His Ile Ala Asn Leu Ala Gly Ser Pro Ala Ile Lys
770                 775                 780

Lys Gly Ile Leu Gln Thr Val Lys Val Val Asp Glu Leu Val Lys Val
785                 790                 795                 800

Met Gly Arg His Lys Pro Glu Asn Ile Val Ile Glu Met Ala Arg Glu
                805                 810                 815

Asn Gln Thr Thr Gln Lys Gly Gln Lys Asn Ser Arg Glu Arg Met Lys
                820                 825                 830

Arg Ile Glu Glu Gly Ile Lys Glu Leu Gly Ser Gln Ile Leu Lys Glu
                835                 840                 845

His Pro Val Glu Asn Thr Gln Leu Gln Asn Glu Lys Leu Tyr Leu Tyr
850                 855                 860

Tyr Leu Gln Asn Gly Arg Asp Met Tyr Val Asp Gln Glu Leu Asp Ile
865                 870                 875                 880

Asn Arg Leu Ser Asp Tyr Asp Val Asp His Ile Val Pro Gln Ser Phe
                885                 890                 895

Leu Lys Asp Asp Ser Ile Asp Asn Lys Val Leu Thr Arg Ser Asp Lys
                900                 905                 910

Asn Arg Gly Lys Ser Asp Asn Val Pro Ser Glu Glu Val Val Lys Lys
                915                 920                 925

Met Lys Asn Tyr Trp Arg Gln Leu Leu Asn Ala Lys Leu Ile Thr Gln
930                 935                 940

Arg Lys Phe Asp Asn Leu Thr Lys Ala Glu Arg Gly Gly Leu Ser Glu
945                 950                 955                 960

Leu Asp Lys Ala Gly Phe Ile Lys Arg Gln Leu Val Glu Thr Arg Gln
                965                 970                 975

Ile Thr Lys His Val Ala Gln Ile Leu Asp Ser Arg Met Asn Thr Lys
                980                 985                 990

Tyr Asp Glu Asn Asp Lys Leu Ile Arg Glu Val Lys Val Ile Thr Leu
                995                 1000                1005

Lys Ser Lys Leu Val Ser Asp Phe Arg Lys Asp Phe Gln Phe Tyr
   1010            1015                1020

Lys Val Arg Glu Ile Asn Asn Tyr His His Ala His Asp Ala Tyr
   1025            1030                1035

Leu Asn Ala Val Val Gly Thr Ala Leu Ile Lys Lys Tyr Pro Lys
   1040            1045                1050

Leu Glu Ser Glu Phe Val Tyr Gly Asp Tyr Lys Val Tyr Asp Val
   1055            1060                1065

Arg Lys Met Ile Ala Lys Ser Glu Gln Glu Ile Gly Lys Ala Thr
   1070            1075                1080

Ala Lys Tyr Phe Phe Tyr Ser Asn Ile Met Asn Phe Phe Lys Thr
   1085            1090                1095

Glu Ile Thr Leu Ala Asn Gly Glu Ile Arg Lys Arg Pro Leu Ile
   1100            1105                1110

Glu Thr Asn Gly Glu Thr Gly Glu Ile Val Trp Asp Lys Gly Arg
   1115            1120                1125

Asp Phe Ala Thr Val Arg Lys Val Leu Ser Met Pro Gln Val Asn
   1130            1135                1140

Ile Val Lys Lys Thr Glu Val Gln Thr Gly Gly Phe Ser Lys Glu
   1145            1150                1155

Ser Ile Leu Pro Lys Arg Asn Ser Asp Lys Leu Ile Ala Arg Lys
   1160            1165                1170

Lys Asp Trp Asp Pro Lys Lys Tyr Gly Gly Phe Asp Ser Pro Thr
```

-continued

```
            1175                1180                1185

Val Ala Tyr Ser Val Leu Val Ala Lys Val Glu Lys Gly Lys
    1190                1195                1200

Ser Lys Lys Leu Lys Ser Val Lys Glu Leu Leu Gly Ile Thr Ile
    1205                1210                1215

Met Glu Arg Ser Ser Phe Glu Lys Asn Pro Ile Asp Phe Leu Glu
    1220                1225                1230

Ala Lys Gly Tyr Lys Glu Val Lys Lys Asp Leu Ile Ile Lys Leu
    1235                1240                1245

Pro Lys Tyr Ser Leu Phe Glu Leu Glu Asn Gly Arg Lys Arg Met
    1250                1255                1260

Leu Ala Ser Ala Gly Glu Leu Gln Lys Gly Asn Glu Leu Ala Leu
    1265                1270                1275

Pro Ser Lys Tyr Val Asn Phe Leu Tyr Leu Ala Ser His Tyr Glu
    1280                1285                1290

Lys Leu Lys Gly Ser Pro Glu Asp Asn Glu Gln Lys Gln Leu Phe
    1295                1300                1305

Val Glu Gln His Lys His Tyr Leu Asp Glu Ile Ile Glu Gln Ile
    1310                1315                1320

Ser Glu Phe Ser Lys Arg Val Ile Leu Ala Asp Ala Asn Leu Asp
    1325                1330                1335

Lys Val Leu Ser Ala Tyr Asn Lys His Arg Asp Lys Pro Ile Arg
    1340                1345                1350

Glu Gln Ala Glu Asn Ile Ile His Leu Phe Thr Leu Thr Asn Leu
    1355                1360                1365

Gly Ala Pro Ala Ala Phe Lys Tyr Phe Asp Thr Thr Ile Asp Arg
    1370                1375                1380

Lys Lys Tyr Thr Ser Thr Lys Glu Val Leu Asp Ala Thr Leu Ile
    1385                1390                1395

His Gln Ser Ile Thr Gly Leu Tyr Glu Thr Arg Ile Asp Leu Ser
    1400                1405                1410

Gln Leu Gly Gly Asp Gly Thr Gly Gly Pro Lys Lys Lys Arg Lys
    1415                1420                1425

Val Ile Gly Ser Ser Gly Met Gly Val Gln Val Glu Thr Ile Ser
    1430                1435                1440

Pro Gly Asp Gly Arg Thr Phe Pro Lys Arg Gly Gln Thr Cys Val
    1445                1450                1455

Val His Tyr Thr Gly Met Leu Glu Asp Gly Lys Lys Phe Asp Ser
    1460                1465                1470

Ser Arg Asp Arg Asn Lys Pro Phe Lys Phe Met Leu Gly Lys Gln
    1475                1480                1485

Glu Val Ile Arg Gly Trp Glu Glu Gly Val Ala Gln Met Ser Val
    1490                1495                1500

Gly Gln Arg Ala Lys Leu Thr Ile Ser Pro Asp Tyr Ala Tyr Gly
    1505                1510                1515

Ala Thr Gly His Pro Gly Ile Ile Pro Pro His Ala Thr Leu Val
    1520                1525                1530

Phe Asp Val Glu Leu Leu Lys Leu Glu Leu Glu
    1535                1540

<210> SEQ ID NO 135
<211> LENGTH: 341
<212> TYPE: PRT
<213> ORGANISM: Artificial sequence
```

<220> FEATURE:
<223> OTHER INFORMATION: Synthetic

<400> SEQUENCE: 135

Met Gly Arg Gly Ser Leu Gln Ala Ala Pro Ala Ala Lys Lys Lys
1               5                   10                  15

Leu Asp Gln Leu Ala Ser Gly Gly Gly Ser Gly Ala Ala Pro Lys
            20                  25                  30

Lys Lys Arg Lys Val Ser Glu Leu Gly Gly Gly Ser Asp Tyr Lys
        35                  40                  45

Asp His Asp Gly Asp Tyr Lys Asp His Asp Ile Asp Tyr Lys Asp
    50                  55                  60

Asp Asp Lys Leu Glu Gly Gly Gly Ser Gly Leu Asp Leu Ala Ser
65                  70                  75                  80

Leu Ile Leu Gly Asn Pro Gly Ser Leu Asp Leu Ala Ser Leu Ile Leu
                85                  90                  95

Pro Arg Gly Gly Gly Ser Gly Ala Gly Gly Val Pro Ser Gly
            100                 105                 110

Lys Pro Tyr Lys Cys Pro Glu Cys Gly Lys Ser Phe Ser Glu Lys Ser
            115                 120                 125

His Leu Thr Arg His Gln Arg Thr His Thr Gly Glu Lys Pro Tyr Ala
130                 135                 140

Cys Pro Val Glu Ser Cys Asp Arg Arg Phe Ser Arg Ser Asp His Leu
145                 150                 155                 160

Thr Gln His Ile Arg Ile His Thr Gly Gln Lys Pro Phe Gln Cys Arg
                165                 170                 175

Ile Cys Met Arg Asn Phe Ser Asp Lys Gly His Leu Thr Arg His Ile
            180                 185                 190

Arg Thr His Thr Gly Glu Lys Pro Phe Ala Cys Asp Ile Cys Gly Arg
        195                 200                 205

Lys Phe Ala Arg Ser Asp Asp Leu Thr Arg His Thr Lys Ile His Leu
210                 215                 220

Arg Gln Lys Asp Pro Gly Gly Ser Gly Ser Gly Gly Gly Ser Gly
225                 230                 235                 240

Gly Gly Gly Ser Arg Thr Ile Leu Trp His Glu Met Trp His Glu Gly
                245                 250                 255

Leu Glu Glu Ala Ser Arg Leu Tyr Phe Gly Glu Arg Asn Val Lys Gly
            260                 265                 270

Met Phe Glu Val Leu Glu Pro Leu His Ala Met Met Glu Arg Gly Pro
        275                 280                 285

Gln Thr Leu Lys Glu Thr Ser Phe Asn Gln Ala Tyr Gly Arg Asp Leu
    290                 295                 300

Met Glu Ala Gln Glu Trp Cys Arg Lys Tyr Met Lys Ser Gly Asn Val
305                 310                 315                 320

Pro Asp Leu Leu Gln Ala Phe Asp Leu Tyr Tyr His Val Phe Arg Arg
                325                 330                 335

Ile Ser Lys Glu Phe
            340

<210> SEQ ID NO 136
<211> LENGTH: 707
<212> TYPE: PRT
<213> ORGANISM: Artificial sequence
<220> FEATURE:
<223> OTHER INFORMATION: Synthetic

<400> SEQUENCE: 136

```
Met Gly Arg Ala Ala Pro Ala Ala Lys Lys Lys Leu Asp Gln Leu
1               5                   10                  15

Gly Ala Ser Gly Ser Pro Gly Ser Asp Lys Lys Tyr Ser Ile Gly Leu
            20                  25                  30

Asp Ile Gly Thr Asn Ser Val Gly Trp Ala Val Ile Thr Asp Glu Tyr
                35                  40                  45

Lys Val Pro Ser Lys Lys Phe Lys Val Leu Gly Asn Thr Asp Arg His
    50                  55                      60

Ser Ile Lys Lys Asn Leu Ile Gly Ala Leu Leu Phe Asp Ser Gly Glu
65                  70                  75                  80

Thr Ala Glu Ala Thr Arg Leu Lys Arg Thr Ala Arg Arg Tyr Thr
                85                  90                  95

Arg Arg Lys Asn Arg Ile Cys Tyr Leu Gln Glu Ile Phe Ser Asn Glu
                100                 105                 110

Met Ala Lys Val Asp Asp Ser Phe Phe His Arg Leu Glu Glu Ser Phe
            115                 120                 125

Leu Val Glu Glu Asp Lys Lys His Glu Arg His Pro Ile Phe Gly Asn
    130                 135                 140

Ile Val Asp Glu Val Ala Tyr His Glu Lys Tyr Pro Thr Ile Tyr His
145                 150                 155                 160

Leu Arg Lys Lys Leu Val Asp Ser Thr Asp Lys Ala Asp Leu Arg Leu
                165                 170                 175

Ile Tyr Leu Ala Leu Ala His Met Ile Lys Phe Arg Gly His Phe Leu
                180                 185                 190

Ile Glu Gly Asp Leu Asn Pro Asp Asn Ser Asp Val Asp Lys Leu Phe
            195                 200                 205

Ile Gln Leu Val Gln Thr Tyr Asn Gln Leu Phe Glu Glu Asn Pro Ile
    210                 215                 220

Asn Ala Ser Gly Val Asp Ala Lys Ala Ile Leu Ser Ala Arg Leu Ser
225                 230                 235                 240

Lys Ser Arg Arg Leu Glu Asn Leu Ile Ala Gln Leu Pro Gly Glu Lys
                245                 250                 255

Lys Asn Gly Leu Phe Gly Asn Leu Ile Ala Leu Ser Leu Gly Leu Thr
            260                 265                 270

Pro Asn Phe Lys Ser Asn Phe Asp Leu Ala Glu Asp Ala Lys Leu Gln
        275                 280                 285

Leu Ser Lys Asp Thr Tyr Asp Asp Asp Leu Asp Asn Leu Leu Ala Gln
    290                 295                 300

Ile Gly Asp Gln Tyr Ala Asp Leu Phe Leu Ala Ala Lys Asn Leu Ser
305                 310                 315                 320

Asp Ala Ile Leu Leu Ser Asp Ile Leu Arg Val Asn Thr Glu Ile Thr
                325                 330                 335

Lys Ala Pro Leu Ser Ala Ser Met Ile Lys Arg Tyr Asp Glu His His
            340                 345                 350

Gln Asp Leu Thr Leu Leu Lys Ala Leu Val Arg Gln Gln Leu Pro Glu
        355                 360                 365

Lys Tyr Lys Glu Ile Phe Phe Asp Gln Ser Lys Asn Gly Tyr Ala Gly
    370                 375                 380

Tyr Ile Asp Gly Gly Ala Ser Gln Glu Glu Phe Tyr Lys Phe Ile Lys
385                 390                 395                 400

Pro Ile Leu Glu Lys Met Asp Gly Thr Glu Glu Leu Leu Val Lys Leu
                405                 410                 415
```

```
Asn Arg Glu Asp Leu Leu Arg Lys Gln Arg Thr Phe Asp Asn Gly Ser
            420                 425                 430

Ile Pro His Gln Ile His Leu Gly Glu Leu His Ala Ile Leu Arg Arg
        435                 440                 445

Gln Glu Asp Phe Tyr Pro Phe Leu Lys Asp Asn Arg Glu Lys Ile Glu
    450                 455                 460

Lys Ile Leu Thr Phe Arg Ile Pro Tyr Val Gly Pro Leu Ala Arg
465                 470                 475                 480

Gly Asn Ser Arg Phe Ala Trp Met Thr Arg Lys Ser Glu Glu Thr Ile
                485                 490                 495

Thr Pro Trp Asn Phe Glu Glu Val Val Asp Lys Gly Ala Ser Ala Gln
            500                 505                 510

Ser Phe Ile Glu Arg Met Thr Asn Phe Asp Lys Asn Leu Pro Asn Glu
        515                 520                 525

Lys Val Leu Pro Lys His Ser Leu Leu Tyr Glu Tyr Phe Thr Val Tyr
    530                 535                 540

Asn Glu Leu Thr Lys Val Lys Tyr Val Thr Glu Gly Met Arg Lys Pro
545                 550                 555                 560

Ala Phe Leu Ser Gly Glu Gln Lys Lys Ala Ile Val Asp Leu Leu Phe
                565                 570                 575

Lys Thr Asn Arg Lys Val Thr Val Lys Gln Leu Lys Glu Asp Tyr Phe
            580                 585                 590

Lys Lys Ile Glu Gly Thr Gly Gly Pro Lys Lys Arg Lys Val Ile
    595                 600                 605

Gly Ser Ser Gly Ile Leu Trp His Glu Met Trp His Glu Gly Leu Glu
    610                 615                 620

Glu Ala Ser Arg Leu Tyr Phe Gly Glu Arg Asn Val Lys Gly Met Phe
625                 630                 635                 640

Glu Val Leu Glu Pro Leu His Ala Met Met Glu Arg Gly Pro Gln Thr
                645                 650                 655

Leu Lys Glu Thr Ser Phe Asn Gln Ala Tyr Gly Arg Asp Leu Met Glu
            660                 665                 670

Ala Gln Glu Trp Cys Arg Lys Tyr Met Lys Ser Gly Asn Val Lys Asp
    675                 680                 685

Leu Thr Gln Ala Trp Asp Leu Tyr Tyr His Val Phe Arg Arg Ile Ser
690                 695                 700

Lys Leu Glu
705

<210> SEQ ID NO 137
<211> LENGTH: 1157
<212> TYPE: PRT
<213> ORGANISM: Artificial sequence
<220> FEATURE:
<223> OTHER INFORMATION: Synthetic

<400> SEQUENCE: 137

Met Gly Val Gln Val Glu Thr Ile Ser Pro Gly Asp Gly Arg Thr Phe
1               5                   10                  15

Pro Lys Arg Gly Gln Thr Cys Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60
```

```
Ala Gln Met Ser Val Gly Gln Arg Ala Lys Leu Thr Ile Ser Pro Asp
 65                  70                  75                  80

Tyr Ala Tyr Gly Ala Thr Gly His Pro Gly Ile Ile Pro Pro His Ala
                 85                  90                  95

Thr Leu Val Phe Asp Val Glu Leu Leu Lys Leu Glu Gly Ala Gly Gly
            100                 105                 110

Cys Phe Asp Ser Val Glu Ile Ser Gly Val Glu Asp Arg Phe Asn Ala
        115                 120                 125

Ser Leu Gly Thr Tyr His Asp Leu Leu Lys Ile Ile Lys Asp Lys Asp
    130                 135                 140

Phe Leu Asp Asn Glu Asn Glu Asp Ile Leu Glu Asp Ile Val Leu
145                 150                 155                 160

Thr Leu Thr Leu Phe Glu Asp Arg Glu Met Ile Glu Glu Arg Leu Lys
                165                 170                 175

Thr Tyr Ala His Leu Phe Asp Asp Lys Val Met Lys Gln Leu Lys Arg
            180                 185                 190

Arg Arg Tyr Thr Gly Trp Gly Arg Leu Ser Arg Lys Leu Ile Asn Gly
        195                 200                 205

Ile Arg Asp Lys Gln Ser Gly Lys Thr Ile Leu Asp Phe Leu Lys Ser
    210                 215                 220

Asp Gly Phe Ala Asn Arg Asn Phe Met Gln Leu Ile His Asp Asp Ser
225                 230                 235                 240

Leu Thr Phe Lys Glu Asp Ile Gln Lys Ala Gln Val Ser Gly Gln Gly
                245                 250                 255

Asp Ser Leu His Glu His Ile Ala Asn Leu Ala Gly Ser Pro Ala Ile
            260                 265                 270

Lys Lys Gly Ile Leu Gln Thr Val Lys Val Val Asp Glu Leu Val Lys
        275                 280                 285

Val Met Gly Arg His Lys Pro Glu Asn Ile Val Ile Glu Met Ala Arg
    290                 295                 300

Glu Asn Gln Thr Thr Gln Lys Gly Gln Lys Asn Ser Arg Glu Arg Met
305                 310                 315                 320

Lys Arg Ile Glu Glu Gly Ile Lys Glu Leu Gly Ser Gln Ile Leu Lys
                325                 330                 335

Glu His Pro Val Glu Asn Thr Gln Leu Gln Asn Glu Lys Leu Tyr Leu
            340                 345                 350

Tyr Tyr Leu Gln Asn Gly Arg Asp Met Tyr Val Asp Gln Glu Leu Asp
        355                 360                 365

Ile Asn Arg Leu Ser Asp Tyr Asp Val Asp His Ile Val Pro Gln Ser
    370                 375                 380

Phe Leu Lys Asp Asp Ser Ile Asp Asn Lys Val Leu Thr Arg Ser Asp
385                 390                 395                 400

Lys Asn Arg Gly Lys Ser Asp Asn Val Pro Ser Glu Glu Val Val Lys
                405                 410                 415

Lys Met Lys Asn Tyr Trp Arg Gln Leu Leu Asn Ala Lys Leu Ile Thr
            420                 425                 430

Gln Arg Lys Phe Asp Asn Leu Thr Lys Ala Glu Arg Gly Gly Leu Ser
        435                 440                 445

Glu Leu Asp Lys Ala Gly Phe Ile Lys Arg Gln Leu Val Glu Thr Arg
    450                 455                 460

Gln Ile Thr Lys His Val Ala Gln Ile Leu Asp Ser Arg Met Asn Thr
465                 470                 475                 480
```

-continued

```
Lys Tyr Asp Glu Asn Asp Lys Leu Ile Arg Glu Val Lys Val Ile Thr
                485                 490                 495
Leu Lys Ser Lys Leu Val Ser Asp Phe Arg Lys Asp Phe Gln Phe Tyr
            500                 505                 510
Lys Val Arg Glu Ile Asn Asn Tyr His His Ala His Asp Ala Tyr Leu
        515                 520                 525
Asn Ala Val Val Gly Thr Ala Leu Ile Lys Lys Tyr Pro Lys Leu Glu
    530                 535                 540
Ser Glu Phe Val Tyr Gly Asp Tyr Lys Val Tyr Asp Val Arg Lys Met
545                 550                 555                 560
Ile Ala Lys Ser Glu Gln Glu Ile Gly Lys Ala Thr Ala Lys Tyr Phe
                565                 570                 575
Phe Tyr Ser Asn Ile Met Asn Phe Phe Lys Thr Glu Ile Thr Leu Ala
            580                 585                 590
Asn Gly Glu Ile Arg Lys Arg Pro Leu Ile Glu Thr Asn Gly Glu Thr
        595                 600                 605
Gly Glu Ile Val Trp Asp Lys Gly Arg Asp Phe Ala Thr Val Arg Lys
    610                 615                 620
Val Leu Ser Met Pro Gln Val Asn Ile Val Lys Lys Thr Glu Val Gln
625                 630                 635                 640
Thr Gly Gly Phe Ser Lys Glu Ser Ile Leu Pro Lys Arg Asn Ser Asp
                645                 650                 655
Lys Leu Ile Ala Arg Lys Lys Asp Trp Asp Pro Lys Lys Tyr Gly Gly
            660                 665                 670
Phe Asp Ser Pro Thr Val Ala Tyr Ser Val Leu Val Val Ala Lys Val
        675                 680                 685
Glu Lys Gly Lys Ser Lys Lys Leu Lys Ser Val Lys Glu Leu Leu Gly
    690                 695                 700
Ile Thr Ile Met Glu Arg Ser Ser Phe Glu Lys Asn Pro Ile Asp Phe
705                 710                 715                 720
Leu Glu Ala Lys Gly Tyr Lys Glu Val Lys Lys Asp Leu Ile Ile Lys
                725                 730                 735
Leu Pro Lys Tyr Ser Leu Phe Glu Leu Glu Asn Gly Arg Lys Arg Met
            740                 745                 750
Leu Ala Ser Ala Gly Glu Leu Gln Lys Gly Asn Glu Leu Ala Leu Pro
        755                 760                 765
Ser Lys Tyr Val Asn Phe Leu Tyr Leu Ala Ser His Tyr Glu Lys Leu
    770                 775                 780
Lys Gly Ser Pro Glu Asp Asn Glu Gln Lys Gln Leu Phe Val Glu Gln
785                 790                 795                 800
His Lys His Tyr Leu Asp Glu Ile Ile Glu Gln Ile Ser Glu Phe Ser
                805                 810                 815
Lys Arg Val Ile Leu Ala Asp Ala Asn Leu Asp Lys Val Leu Ser Ala
            820                 825                 830
Tyr Asn Lys His Arg Asp Lys Pro Ile Arg Glu Gln Ala Glu Asn Ile
        835                 840                 845
Ile His Leu Phe Thr Leu Thr Asn Leu Gly Ala Pro Ala Ala Phe Lys
    850                 855                 860
Tyr Phe Asp Thr Thr Ile Asp Arg Lys Lys Tyr Thr Ser Thr Lys Glu
865                 870                 875                 880
Val Leu Asp Ala Thr Leu Ile His Gln Ser Ile Thr Gly Leu Tyr Glu
                885                 890                 895
Thr Arg Ile Asp Leu Ser Gln Leu Gly Gly Asp Gly Thr Gly Gly Pro
```

```
                    900             905             910
Lys Lys Lys Arg Lys Val Tyr Pro Tyr Asp Val Pro Asp Tyr Ala Gly
                915             920             925

Tyr Pro Tyr Asp Val Pro Asp Tyr Ala Gly Ser Tyr Pro Tyr Asp Val
            930             935             940

Pro Asp Tyr Ala Gly Ser Ala Ala Pro Ala Ala Lys Lys Lys Lys Leu
945             950             955             960

Asp Phe Glu Ser Gly Lys Pro Tyr Lys Cys Pro Glu Cys Gly Lys Ser
                965             970             975

Phe Ser Arg Ser Asp Asp Leu Thr Arg His Gln Arg Thr His Thr Gly
            980             985             990

Glu Lys Pro Tyr Ala Cys Pro Val Glu Ser Cys Asp Arg Arg Phe Ser
                995            1000            1005

Gln Lys Gly His Leu Thr Arg His Ile Arg Ile His Thr Gly Gln
        1010            1015            1020

Lys Pro Phe Gln Cys Arg Ile Cys Met Arg Asn Phe Ser Ile Arg
        1025            1030            1035

Ser Ser Leu Thr Arg His Ile Arg Thr His Thr Gly Glu Lys Pro
        1040            1045            1050

Phe Ala Cys Asp Ile Cys Gly Arg Lys Phe Ala Leu Ser His His
        1055            1060            1065

Leu Thr Arg His Thr Lys Ile His Leu Arg Gln Lys Asp Pro Gly
        1070            1075            1080

Gly Ser Gly Ser Leu Glu Gly Asp Tyr Lys Asp His Asp Gly Asp
        1085            1090            1095

Tyr Lys Asp His Asp Ile Asp Tyr Lys Asp Asp Asp Lys Gln
        1100            1105            1110

Gly Ser Glu Leu Gly Ser Gly Arg Ala Ala Pro Ala Ala Lys Lys
        1115            1120            1125

Lys Lys Leu Asp Gln Leu Gly Ala Ser Gly Ser Gly Gly Ser
        1130            1135            1140

Ser Gly Ala Ala Pro Lys Lys Arg Lys Val Ser Glu Phe
        1145            1150            1155

<210> SEQ ID NO 138
<211> LENGTH: 42
<212> TYPE: DNA
<213> ORGANISM: Artificial sequence
<220> FEATURE:
<223> OTHER INFORMATION: Synthetic

<400> SEQUENCE: 138
gggagctctc tggctaacta gggaacccac tgcttaagcc tc                  42

<210> SEQ ID NO 139
<211> LENGTH: 46
<212> TYPE: DNA
<213> ORGANISM: Artificial sequence
<220> FEATURE:
<223> OTHER INFORMATION: Synthetic

<400> SEQUENCE: 139
cctccctgga aagtccccag cggaaagtcc cttgtagaaa gctcga              46

<210> SEQ ID NO 140
<211> LENGTH: 47
<212> TYPE: DNA
<213> ORGANISM: Artificial sequence
```

<220> FEATURE:
<223> OTHER INFORMATION: Synthetic

<400> SEQUENCE: 140
ccgctgggga ctttccaggg aggtgtggcc tgggcgggac tggggag          47

<210> SEQ ID NO 141
<211> LENGTH: 1575
<212> TYPE: PRT
<213> ORGANISM: Artificial sequence
<220> FEATURE:
<223> OTHER INFORMATION: Synthetic

<400> SEQUENCE: 141

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

```
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
```

-continued

```
Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
            995                 1000                1005

Val Tyr  Gly Asp Tyr Lys Val  Tyr Asp Val Arg Lys  Met Ile Ala
1010                1015                1020

Lys Ser  Glu Gln Glu Ile Gly  Lys Ala Thr Ala Lys  Tyr Phe Phe
1025                1030                1035

Tyr Ser  Asn Ile Met Asn Phe  Phe Lys Thr Glu Ile  Thr Leu Ala
1040                1045                1050

Asn Gly  Glu Ile Arg Lys Arg  Pro Leu Ile Glu Thr  Asn Gly Glu
1055                1060                1065

Thr Gly  Glu Ile Val Trp Asp  Lys Gly Arg Asp Phe  Ala Thr Val
1070                1075                1080

Arg Lys  Val Leu Ser Met Pro  Gln Val Asn Ile Val  Lys Lys Thr
1085                1090                1095

Glu Val  Gln Thr Gly Gly Phe  Ser Lys Glu Ser Ile  Leu Pro Lys
1100                1105                1110

Arg Asn  Ser Asp Lys Leu Ile  Ala Arg Lys Lys Asp  Trp Asp Pro
1115                1120                1125

Lys Lys  Tyr Gly Gly Phe Asp  Ser Pro Thr Val Ala  Tyr Ser Val
1130                1135                1140

Leu Val  Val Ala Lys Val Glu  Lys Gly Lys Ser Lys  Lys Leu Lys
1145                1150                1155

Ser Val  Lys Glu Leu Leu Gly  Ile Thr Ile Met Glu  Arg Ser Ser
```

-continued

```
         1160                1165                1170

Phe Glu Lys Asn Pro Ile Asp Phe Leu Glu Ala Lys Gly Tyr Lys
         1175                1180                1185

Glu Val Lys Lys Asp Leu Ile Ile Lys Leu Pro Lys Tyr Ser Leu
         1190                1195                1200

Phe Glu Leu Glu Asn Gly Arg Lys Arg Met Leu Ala Ser Ala Gly
         1205                1210                1215

Glu Leu Gln Lys Gly Asn Glu Leu Ala Leu Pro Ser Lys Tyr Val
         1220                1225                1230

Asn Phe Leu Tyr Leu Ala Ser His Tyr Glu Lys Leu Lys Gly Ser
         1235                1240                1245

Pro Glu Asp Asn Glu Gln Lys Gln Leu Phe Val Glu Gln His Lys
         1250                1255                1260

His Tyr Leu Asp Glu Ile Ile Glu Gln Ile Ser Glu Phe Ser Lys
         1265                1270                1275

Arg Val Ile Leu Ala Asp Ala Asn Leu Asp Lys Val Leu Ser Ala
         1280                1285                1290

Tyr Asn Lys His Arg Asp Lys Pro Ile Arg Glu Gln Ala Glu Asn
         1295                1300                1305

Ile Ile His Leu Phe Thr Leu Thr Asn Leu Gly Ala Pro Ala Ala
         1310                1315                1320

Phe Lys Tyr Phe Asp Thr Thr Ile Asp Arg Lys Lys Tyr Thr Ser
         1325                1330                1335

Thr Lys Glu Val Leu Asp Ala Thr Leu Ile His Gln Ser Ile Thr
         1340                1345                1350

Gly Leu Tyr Glu Thr Arg Ile Asp Leu Ser Gln Leu Gly Gly Asp
         1355                1360                1365

Gly Thr Gly Gly Pro Lys Lys Lys Arg Lys Val Tyr Pro Tyr Asp
         1370                1375                1380

Val Pro Asp Tyr Ala Gly Tyr Pro Tyr Asp Val Pro Asp Tyr Ala
         1385                1390                1395

Gly Ser Tyr Pro Tyr Asp Val Pro Asp Tyr Ala Gly Ser Ala Ala
         1400                1405                1410

Pro Ala Ala Lys Lys Lys Lys Leu Asp Phe Glu Ser Gly Arg Pro
         1415                1420                1425

Phe Ala Cys Asp Ile Cys Gly Lys Lys Phe Ala Arg Ser Asp His
         1430                1435                1440

Leu Thr Thr His Thr Lys Ile His Thr Gly Gln Lys Pro Phe Gln
         1445                1450                1455

Cys Arg Ile Cys Met Arg Asn Phe Ser Arg Ser Asp Asn Leu Lys
         1460                1465                1470

Gln His Ile Arg Thr His Thr Gly Glu Lys Pro Phe Ala Cys Asp
         1475                1480                1485

Ile Cys Gly Lys Lys Phe Ala Arg Asn Ser Asn Leu Thr Gln His
         1490                1495                1500

Thr Lys Ile His Thr His Pro Arg Ala Pro Ile Pro Lys Pro Phe
         1505                1510                1515

Gln Cys Arg Ile Cys Met Arg Asn Phe Ser Gln Ser Ser Asp Leu
         1520                1525                1530

Thr Arg His Ile Arg Thr His Thr Gly Glu Lys Pro Phe Ala Cys
         1535                1540                1545

Asp Ile Cys Gly Arg Lys Phe Ala Arg Ser Asp Asn Leu Thr Arg
         1550                1555                1560
```

His Thr Lys Ile His Leu Arg Asp Lys Gln Pro Gly
    1565            1570            1575

<210> SEQ ID NO 142
<211> LENGTH: 1547
<212> TYPE: PRT
<213> ORGANISM: Artificial sequence
<220> FEATURE:
<223> OTHER INFORMATION: Synthetic

<400> SEQUENCE: 142

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765
```

Thr Thr Gln Lys Gly Gln Lys Asn Ser Arg Glu Arg Met Lys Arg Ile
770             775                 780

Glu Glu Gly Ile Lys Glu Leu Gly Ser Gln Ile Leu Lys Glu His Pro
785             790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995             1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys

```
            1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Lys Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

Gly Thr Gly Gly Pro Lys Lys Lys Arg Lys Val Tyr Pro Tyr Asp
        1370                1375                1380

Val Pro Asp Tyr Ala Gly Tyr Pro Tyr Asp Val Pro Asp Tyr Ala
        1385                1390                1395

Gly Ser Tyr Pro Tyr Asp Val Pro Asp Tyr Ala Gly Ser Ala Ala
        1400                1405                1410

Pro Ala Ala Lys Lys Lys Leu Asp Phe Glu Ser Gly Arg Pro
        1415                1420                1425

Phe Gln Cys Arg Ile Cys Met Arg Asn Phe Ser Gln Ser Gly His
        1430                1435                1440

Leu Lys Ser His Ile Arg Thr His Thr Gly Glu Lys Pro Phe Ala
        1445                1450                1455

Cys Asp Ile Cys Gly Lys Lys Phe Ala Gln Ser Ser Asp Leu Thr
        1460                1465                1470

Arg His Thr Lys Ile His Thr His Pro Arg Ala Pro Ile Pro Lys
        1475                1480                1485

Pro Phe Gln Cys Arg Ile Cys Met Arg Asn Phe Ser Gln Ser Gly
        1490                1495                1500

Asn Leu Thr Arg His Ile Arg Thr His Thr Gly Glu Lys Pro Phe
        1505                1510                1515

Ala Cys Asp Ile Cys Gly Arg Lys Phe Ala Gln Ser Gly Ala Leu
        1520                1525                1530

Thr Arg His Thr Lys Ile His Leu Arg Asp Lys Gln Pro Gly
        1535                1540                1545

<210> SEQ ID NO 143
<211> LENGTH: 1547
<212> TYPE: PRT
<213> ORGANISM: Artificial sequence
```

```
<220> FEATURE:
<223> OTHER INFORMATION: Synthetic

<400> SEQUENCE: 143

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145             150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225             230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305             310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385             390                 395                 400
```

```
Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815
```

-continued

Gln Asn Gly Arg Asp Met Tyr Val Asp Glu Leu Asp Ile Asn Arg
            820                 825                 830

Leu Ser Asp Tyr Asp Val Asp His Ile Val Pro Gln Ser Phe Leu Lys
            835                 840             845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

Asn Gly Glu Ile Arg Lys Arg Pro Leu Ile Glu Thr Asn Gly Glu
            1055                1060                1065

Thr Gly Glu Ile Val Trp Asp Lys Gly Arg Asp Phe Ala Thr Val
            1070                1075                1080

Arg Lys Val Leu Ser Met Pro Gln Val Asn Ile Val Lys Lys Thr
            1085                1090                1095

Glu Val Gln Thr Gly Gly Phe Ser Lys Glu Ser Ile Leu Pro Lys
            1100                1105                1110

Arg Asn Ser Asp Lys Leu Ile Ala Arg Lys Lys Asp Trp Asp Pro
            1115                1120                1125

Lys Lys Tyr Gly Gly Phe Asp Ser Pro Thr Val Ala Tyr Ser Val
            1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val

```
                 1220             1225                  1230

Asn  Phe  Leu  Tyr  Leu  Ala  Ser  His  Tyr  Glu  Lys  Leu  Lys  Gly  Ser
     1235                 1240                 1245

Pro  Glu  Asp  Asn  Glu  Gln  Lys  Gln  Leu  Phe  Val  Glu  Gln  His  Lys
     1250                 1255                 1260

His  Tyr  Leu  Asp  Glu  Ile  Ile  Glu  Gln  Ile  Ser  Glu  Phe  Ser  Lys
     1265                 1270                 1275

Arg  Val  Ile  Leu  Ala  Asp  Ala  Asn  Leu  Asp  Lys  Val  Leu  Ser  Ala
     1280                 1285                 1290

Tyr  Asn  Lys  His  Arg  Asp  Lys  Pro  Ile  Arg  Glu  Gln  Ala  Glu  Asn
     1295                 1300                 1305

Ile  Ile  His  Leu  Phe  Thr  Leu  Thr  Asn  Leu  Gly  Ala  Pro  Ala  Ala
     1310                 1315                 1320

Phe  Lys  Tyr  Phe  Asp  Thr  Thr  Ile  Asp  Arg  Lys  Lys  Tyr  Thr  Ser
     1325                 1330                 1335

Thr  Lys  Glu  Val  Leu  Asp  Ala  Thr  Leu  Ile  His  Gln  Ser  Ile  Thr
     1340                 1345                 1350

Gly  Leu  Tyr  Glu  Thr  Arg  Ile  Asp  Leu  Ser  Gln  Leu  Gly  Gly  Asp
     1355                 1360                 1365

Gly  Thr  Gly  Gly  Pro  Lys  Lys  Lys  Arg  Lys  Val  Tyr  Pro  Tyr  Asp
     1370                 1375                 1380

Val  Pro  Asp  Tyr  Ala  Gly  Tyr  Pro  Tyr  Asp  Val  Pro  Asp  Tyr  Ala
     1385                 1390                 1395

Gly  Ser  Tyr  Pro  Tyr  Asp  Val  Pro  Asp  Tyr  Ala  Gly  Ser  Ala  Ala
     1400                 1405                 1410

Pro  Ala  Ala  Lys  Lys  Lys  Lys  Leu  Asp  Phe  Glu  Ser  Gly  Arg  Pro
     1415                 1420                 1425

Phe  Gln  Cys  Arg  Ile  Cys  Met  Arg  Asn  Phe  Ser  Arg  Ser  Asp  Asn
     1430                 1435                 1440

Leu  Thr  Arg  His  Ile  Arg  Thr  His  Thr  Gly  Glu  Lys  Pro  Phe  Ala
     1445                 1450                 1455

Cys  Asp  Ile  Cys  Gly  Lys  Lys  Phe  Ala  Arg  Ser  Asp  His  Leu  Thr
     1460                 1465                 1470

Arg  His  Thr  Lys  Ile  His  Thr  His  Pro  Arg  Ala  Pro  Ile  Pro  Lys
     1475                 1480                 1485

Pro  Phe  Gln  Cys  Arg  Ile  Cys  Met  Arg  Asn  Phe  Ser  Leu  Lys  Gly
     1490                 1495                 1500

Asn  Leu  Thr  Arg  His  Ile  Arg  Thr  His  Thr  Gly  Glu  Lys  Pro  Phe
     1505                 1510                 1515

Ala  Cys  Asp  Ile  Cys  Gly  Arg  Lys  Phe  Ala  Arg  Ser  Asp  His  Leu
     1520                 1525                 1530

Ser  Asp  His  Thr  Lys  Ile  His  Leu  Arg  Asp  Lys  Gln  Pro  Gly
     1535                 1540                 1545
```

<210> SEQ ID NO 144
<211> LENGTH: 103
<212> TYPE: DNA
<213> ORGANISM: Artificial sequence
<220> FEATURE:
<223> OTHER INFORMATION: Synthetic

<400> SEQUENCE: 144
gaccccctcc accccgcctc gttttagagc tagaaatagc aagttaaaat aaggctagtc    60
cgttatcaac ttgaaaaagt ggcaccgagt cggtgctttt ttt                      103

<210> SEQ ID NO 145
<211> LENGTH: 103
<212> TYPE: DNA
<213> ORGANISM: Artificial sequence
<220> FEATURE:
<223> OTHER INFORMATION: Synthetic

<400> SEQUENCE: 145
ggtgagtgag tgtgtgcgtg gttttagagc tagaaatagc aagttaaaat aaggctagtc    60
cgttatcaac ttgaaaaagt ggcaccgagt cggtgctttt ttt                      103

<210> SEQ ID NO 146
<211> LENGTH: 103
<212> TYPE: DNA
<213> ORGANISM: Artificial sequence
<220> FEATURE:
<223> OTHER INFORMATION: Synthetic

<400> SEQUENCE: 146
gagtccgagc agaagaagaa gttttagagc tagaaatagc aagttaaaat aaggctagtc    60
cgttatcaac ttgaaaaagt ggcaccgagt cggtgctttt ttt                      103

<210> SEQ ID NO 147
<211> LENGTH: 103
<212> TYPE: DNA
<213> ORGANISM: Artificial sequence
<220> FEATURE:
<223> OTHER INFORMATION: Synthetic

<400> SEQUENCE: 147
tacttccggg cacagtccac gttttagagc tagaaatagc aagttaaaat aaggctagtc    60
cgttatcaac ttgaaaaagt ggcaccgagt cggtgctttt ttt                      103

<210> SEQ ID NO 148
<211> LENGTH: 150
<212> TYPE: DNA
<213> ORGANISM: Artificial sequence
<220> FEATURE:
<223> OTHER INFORMATION: Synthetic

<400> SEQUENCE: 148
ggggagaagg ccaggggtca ctgttgtagc tcccttctc atttcggaaa cgaaatgaga     60
accgttgcta caataaggcc gtctgaaaag atgtgccgca acgctctgcc ccttaaagct   120
tctgctttaa ggggcatcgt ttattttttt                                    150

<210> SEQ ID NO 149
<211> LENGTH: 2546
<212> TYPE: PRT
<213> ORGANISM: Artificial sequence
<220> FEATURE:
<223> OTHER INFORMATION: Synthetic

<400> SEQUENCE: 149

Met Pro Lys Lys Lys Arg Lys Val Ala Ala Phe Lys Pro Asn Pro Ile
1               5                   10                  15

Asn Tyr Ile Leu Gly Leu Ala Ile Gly Ile Ala Ser Val Gly Trp Ala
                20                  25                  30

Met Val Glu Ile Asp Glu Asp Glu Asn Pro Ile Cys Leu Ile Asp Leu
            35                  40                  45

Gly Val Arg Val Phe Glu Arg Ala Glu Val Pro Lys Thr Gly Asp Ser
        50                  55                  60

Leu Ala Met Ala Arg Arg Leu Ala Arg Ser Val Arg Leu Thr Arg
65                  70                  75                  80

Arg Arg Ala His Arg Leu Leu Arg Ala Arg Arg Leu Leu Lys Arg Glu
            85                  90                  95

Gly Val Leu Gln Ala Ala Asp Phe Asp Glu Asn Gly Leu Ile Lys Ser
            100                 105                 110

Leu Pro Asn Thr Pro Trp Gln Leu Arg Ala Ala Leu Asp Arg Lys
            115                 120                 125

Leu Thr Pro Leu Glu Trp Ser Ala Val Leu Leu His Leu Ile Lys His
130                 135                 140

Arg Gly Tyr Leu Ser Gln Arg Lys Asn Glu Gly Glu Thr Ala Asp Lys
145                 150                 155                 160

Glu Leu Gly Ala Leu Leu Lys Gly Val Ala Asp Asn Ala His Ala Leu
            165                 170                 175

Gln Thr Gly Asp Phe Arg Thr Pro Ala Glu Leu Ala Leu Asn Lys Phe
            180                 185                 190

Glu Lys Glu Ser Gly His Ile Arg Asn Gln Arg Gly Asp Tyr Ser His
            195                 200                 205

Thr Phe Ser Arg Lys Asp Leu Gln Ala Glu Leu Ile Leu Leu Phe Glu
210                 215                 220

Lys Gln Lys Glu Phe Gly Asn Pro His Val Ser Gly Leu Lys Glu
225                 230                 235                 240

Gly Ile Glu Thr Leu Leu Met Thr Gln Arg Pro Ala Leu Ser Gly Asp
            245                 250                 255

Ala Val Gln Lys Met Leu Gly His Cys Thr Phe Glu Pro Ala Glu Pro
            260                 265                 270

Lys Ala Ala Lys Asn Thr Tyr Thr Ala Glu Arg Phe Ile Trp Leu Thr
            275                 280                 285

Lys Leu Asn Asn Leu Arg Ile Leu Glu Gln Gly Ser Glu Arg Pro Leu
            290                 295                 300

Thr Asp Thr Glu Arg Ala Thr Leu Met Asp Glu Pro Tyr Arg Lys Ser
305                 310                 315                 320

Lys Leu Thr Tyr Ala Gln Ala Arg Lys Leu Leu Gly Leu Glu Asp Thr
            325                 330                 335

Ala Phe Phe Lys Gly Leu Arg Tyr Gly Lys Asp Asn Ala Glu Ala Ser
            340                 345                 350

Thr Leu Met Glu Met Lys Ala Tyr His Ala Ile Ser Arg Ala Leu Glu
            355                 360                 365

Lys Glu Gly Leu Lys Asp Lys Ser Pro Leu Asn Leu Ser Pro Glu
            370                 375                 380

Leu Gln Asp Glu Ile Gly Thr Ala Phe Ser Leu Phe Lys Thr Asp Glu
385                 390                 395                 400

Asp Ile Thr Gly Arg Leu Lys Asp Arg Ile Gln Pro Glu Ile Leu Glu
            405                 410                 415

Ala Leu Leu Lys His Ile Ser Phe Asp Lys Phe Val Gln Ile Ser Leu
            420                 425                 430

Lys Ala Leu Arg Arg Ile Val Pro Leu Met Glu Gln Gly Lys Arg Tyr
            435                 440                 445

Asp Glu Ala Cys Ala Glu Ile Tyr Gly Asp His Tyr Gly Lys Lys Asn
            450                 455                 460

Thr Glu Glu Lys Ile Tyr Leu Pro Pro Ile Pro Ala Asp Glu Ile Arg
465                 470                 475                 480

```
Asn Pro Val Val Leu Arg Ala Leu Ser Gln Ala Arg Lys Val Ile Asn
                485                 490                 495
Gly Val Val Arg Arg Tyr Gly Ser Pro Ala Arg Ile His Ile Glu Thr
            500                 505                 510
Ala Arg Glu Val Gly Lys Ser Phe Lys Asp Arg Lys Glu Ile Glu Lys
        515                 520                 525
Arg Gln Glu Glu Asn Arg Lys Asp Arg Glu Lys Ala Ala Lys Phe
    530                 535                 540
Arg Glu Tyr Phe Pro Asn Phe Val Gly Glu Pro Lys Ser Lys Asp Ile
545                 550                 555                 560
Leu Lys Leu Arg Leu Tyr Glu Gln Gln His Gly Lys Cys Leu Tyr Ser
                565                 570                 575
Gly Lys Glu Ile Asn Leu Gly Arg Leu Asn Glu Lys Gly Tyr Val Glu
            580                 585                 590
Ile Ala Ala Ala Leu Pro Phe Ser Arg Thr Trp Asp Asp Ser Phe Asn
        595                 600                 605
Asn Lys Val Leu Val Leu Gly Ser Glu Ala Gln Asn Lys Gly Asn Gln
    610                 615                 620
Thr Pro Tyr Glu Tyr Phe Asn Gly Lys Asp Asn Ser Arg Glu Trp Gln
625                 630                 635                 640
Glu Phe Lys Ala Arg Val Glu Thr Ser Arg Phe Pro Arg Ser Lys Lys
                645                 650                 655
Gln Arg Ile Leu Leu Gln Lys Phe Glu Asp Gly Phe Lys Glu Arg
            660                 665                 670
Asn Leu Asn Asp Thr Arg Tyr Val Asn Arg Phe Leu Cys Gln Phe Val
        675                 680                 685
Ala Asp Arg Met Arg Leu Thr Gly Lys Gly Lys Lys Arg Val Phe Ala
    690                 695                 700
Ser Asn Gly Gln Ile Thr Asn Leu Leu Arg Gly Phe Trp Gly Leu Arg
705                 710                 715                 720
Lys Val Arg Ala Glu Asn Asp Arg His His Ala Leu Asp Ala Val Val
                725                 730                 735
Val Ala Cys Ser Thr Val Ala Met Gln Gln Lys Ile Thr Arg Phe Val
            740                 745                 750
Arg Tyr Lys Glu Met Asn Ala Phe Asp Gly Lys Thr Ile Asp Lys Glu
        755                 760                 765
Thr Gly Glu Val Leu His Gln Lys Thr His Phe Pro Gln Pro Trp Glu
    770                 775                 780
Phe Phe Ala Gln Glu Val Met Ile Arg Val Phe Gly Lys Pro Asp Gly
785                 790                 795                 800
Lys Pro Glu Phe Glu Glu Ala Asp Thr Pro Glu Lys Leu Arg Thr Leu
                805                 810                 815
Leu Ala Glu Lys Leu Ser Ser Arg Pro Glu Ala Val His Glu Tyr Val
            820                 825                 830
Thr Pro Leu Phe Val Ser Arg Ala Pro Asn Arg Lys Met Ser Gly Gln
        835                 840                 845
Gly His Met Glu Thr Val Lys Ser Ala Lys Arg Leu Asp Glu Gly Val
    850                 855                 860
Ser Val Leu Arg Val Pro Leu Thr Gln Leu Lys Leu Lys Asp Leu Glu
865                 870                 875                 880
Lys Met Val Asn Arg Glu Arg Glu Pro Lys Leu Tyr Glu Ala Leu Lys
                885                 890                 895
Ala Arg Leu Glu Ala His Lys Asp Asp Pro Ala Lys Ala Phe Ala Glu
```

```
              900             905             910
Pro Phe Tyr Lys Tyr Asp Lys Ala Gly Asn Arg Thr Gln Gln Val Lys
            915             920             925
Ala Val Arg Val Glu Gln Val Gln Lys Thr Gly Val Trp Val Arg Asn
            930             935             940
His Asn Gly Ile Ala Asp Asn Ala Thr Met Val Arg Val Asp Val Phe
945             950             955             960
Glu Lys Gly Asp Lys Tyr Tyr Leu Val Pro Ile Tyr Ser Trp Gln Val
            965             970             975
Ala Lys Gly Ile Leu Pro Asp Arg Ala Val Val Gln Gly Lys Asp Glu
            980             985             990
Glu Asp Trp Gln Leu Ile Asp Asp Ser Phe Asn Phe Lys Phe Ser Leu
            995             1000            1005
His Pro Asn Asp Leu Val Glu Val Ile Thr Lys Lys Ala Arg Met
            1010            1015            1020
Phe Gly Tyr Phe Ala Ser Cys His Arg Gly Thr Gly Asn Ile Asn
            1025            1030            1035
Ile Arg Ile His Asp Leu Asp His Lys Ile Gly Lys Asn Gly Ile
            1040            1045            1050
Leu Glu Gly Ile Gly Val Lys Thr Ala Leu Ser Phe Gln Lys Tyr
            1055            1060            1065
Gln Ile Asp Glu Leu Gly Lys Glu Ile Arg Pro Cys Arg Leu Lys
            1070            1075            1080
Lys Arg Pro Pro Val Arg Ser Arg Ala Asp Pro Lys Lys Lys Arg
            1085            1090            1095
Lys Val Glu Ala Ser Asp Tyr Lys Asp His Asp Gly Asp Tyr Lys
            1100            1105            1110
Asp His Asp Ile Asp Tyr Lys Asp Asp Asp Asp Lys Thr Ser Gly
            1115            1120            1125
Gly Gly Ser Gly Gly Ser Arg Thr Ala Ala Pro Ala Ala Lys
            1130            1135            1140
Lys Lys Lys Leu Asp Ser Glu Phe Gly Ser Gly Ser Asp Lys Lys
            1145            1150            1155
Tyr Ser Ile Gly Leu Asp Ile Gly Thr Asn Ser Val Gly Trp Ala
            1160            1165            1170
Val Ile Thr Asp Glu Tyr Lys Val Pro Ser Lys Lys Phe Lys Val
            1175            1180            1185
Leu Gly Asn Thr Asp Arg His Ser Ile Lys Lys Asn Leu Ile Gly
            1190            1195            1200
Ala Leu Leu Phe Asp Ser Gly Glu Thr Ala Glu Ala Thr Arg Leu
            1205            1210            1215
Lys Arg Thr Ala Arg Arg Arg Tyr Thr Arg Arg Lys Asn Arg Ile
            1220            1225            1230
Cys Tyr Leu Gln Glu Ile Phe Ser Asn Glu Met Ala Lys Val Asp
            1235            1240            1245
Asp Ser Phe Phe His Arg Leu Glu Glu Ser Phe Leu Val Glu Glu
            1250            1255            1260
Asp Lys Lys His Glu Arg His Pro Ile Phe Gly Asn Ile Val Asp
            1265            1270            1275
Glu Val Ala Tyr His Glu Lys Tyr Pro Thr Ile Tyr His Leu Arg
            1280            1285            1290
Lys Lys Leu Val Asp Ser Thr Asp Lys Ala Asp Leu Arg Leu Ile
            1295            1300            1305
```

-continued

Tyr Leu Ala Leu Ala His Met Ile Lys Phe Arg Gly His Phe Leu
    1310            1315            1320

Ile Glu Gly Asp Leu Asn Pro Asp Asn Ser Asp Val Asp Lys Leu
    1325            1330            1335

Phe Ile Gln Leu Val Gln Thr Tyr Asn Gln Leu Phe Glu Glu Asn
    1340            1345            1350

Pro Ile Asn Ala Ser Gly Val Asp Ala Lys Ala Ile Leu Ser Ala
    1355            1360            1365

Arg Leu Ser Lys Ser Arg Arg Leu Glu Asn Leu Ile Ala Gln Leu
    1370            1375            1380

Pro Gly Glu Lys Lys Asn Gly Leu Phe Gly Asn Leu Ile Ala Leu
    1385            1390            1395

Ser Leu Gly Leu Thr Pro Asn Phe Lys Ser Asn Phe Asp Leu Ala
    1400            1405            1410

Glu Asp Ala Lys Leu Gln Leu Ser Lys Asp Thr Tyr Asp Asp Asp
    1415            1420            1425

Leu Asp Asn Leu Leu Ala Gln Ile Gly Asp Gln Tyr Ala Asp Leu
    1430            1435            1440

Phe Leu Ala Ala Lys Asn Leu Ser Asp Ala Ile Leu Leu Ser Asp
    1445            1450            1455

Ile Leu Arg Val Asn Thr Glu Ile Thr Lys Ala Pro Leu Ser Ala
    1460            1465            1470

Ser Met Ile Lys Arg Tyr Asp Glu His His Gln Asp Leu Thr Leu
    1475            1480            1485

Leu Lys Ala Leu Val Arg Gln Gln Leu Pro Glu Lys Tyr Lys Glu
    1490            1495            1500

Ile Phe Phe Asp Gln Ser Lys Asn Gly Tyr Ala Gly Tyr Ile Asp
    1505            1510            1515

Gly Gly Ala Ser Gln Glu Glu Phe Tyr Lys Phe Ile Lys Pro Ile
    1520            1525            1530

Leu Glu Lys Met Asp Gly Thr Glu Glu Leu Leu Val Lys Leu Asn
    1535            1540            1545

Arg Glu Asp Leu Leu Arg Lys Gln Arg Thr Phe Asp Asn Gly Ser
    1550            1555            1560

Ile Pro His Gln Ile His Leu Gly Glu Leu His Ala Ile Leu Arg
    1565            1570            1575

Arg Gln Glu Asp Phe Tyr Pro Phe Leu Lys Asp Asn Arg Glu Lys
    1580            1585            1590

Ile Glu Lys Ile Leu Thr Phe Arg Ile Pro Tyr Tyr Val Gly Pro
    1595            1600            1605

Leu Ala Arg Gly Asn Ser Arg Phe Ala Trp Met Thr Arg Lys Ser
    1610            1615            1620

Glu Glu Thr Ile Thr Pro Trp Asn Phe Glu Glu Val Val Asp Lys
    1625            1630            1635

Gly Ala Ser Ala Gln Ser Phe Ile Glu Arg Met Thr Asn Phe Asp
    1640            1645            1650

Lys Asn Leu Pro Asn Glu Lys Val Leu Pro Lys His Ser Leu Leu
    1655            1660            1665

Tyr Glu Tyr Phe Thr Val Tyr Asn Glu Leu Thr Lys Val Lys Tyr
    1670            1675            1680

Val Thr Glu Gly Met Arg Lys Pro Ala Phe Leu Ser Gly Glu Gln
    1685            1690            1695

-continued

```
Lys Lys Ala Ile Val Asp Leu Leu Phe Lys Thr Asn Arg Lys Val
    1700                1705                1710

Thr Val Lys Gln Leu Lys Glu Asp Tyr Phe Lys Lys Ile Glu Cys
    1715                1720                1725

Phe Asp Ser Val Glu Ile Ser Gly Val Glu Asp Arg Phe Asn Ala
    1730                1735                1740

Ser Leu Gly Thr Tyr His Asp Leu Leu Lys Ile Lys Asp Lys
    1745                1750                1755

Asp Phe Leu Asp Asn Glu Glu Asn Glu Asp Ile Leu Glu Asp Ile
    1760                1765                1770

Val Leu Thr Leu Thr Leu Phe Glu Asp Arg Glu Met Ile Glu Glu
    1775                1780                1785

Arg Leu Lys Thr Tyr Ala His Leu Phe Asp Asp Lys Val Met Lys
    1790                1795                1800

Gln Leu Lys Arg Arg Arg Tyr Thr Gly Trp Gly Arg Leu Ser Arg
    1805                1810                1815

Lys Leu Ile Asn Gly Ile Arg Asp Lys Gln Ser Gly Lys Thr Ile
    1820                1825                1830

Leu Asp Phe Leu Lys Ser Asp Gly Phe Ala Asn Arg Asn Phe Met
    1835                1840                1845

Gln Leu Ile His Asp Asp Ser Leu Thr Phe Lys Glu Asp Ile Gln
    1850                1855                1860

Lys Ala Gln Val Ser Gly Gln Gly Asp Ser Leu His Glu His Ile
    1865                1870                1875

Ala Asn Leu Ala Gly Ser Pro Ala Ile Lys Lys Gly Ile Leu Gln
    1880                1885                1890

Thr Val Lys Val Val Asp Glu Leu Val Lys Val Met Gly Arg His
    1895                1900                1905

Lys Pro Glu Asn Ile Val Ile Glu Met Ala Arg Glu Asn Gln Thr
    1910                1915                1920

Thr Gln Lys Gly Gln Lys Asn Ser Arg Glu Arg Met Lys Arg Ile
    1925                1930                1935

Glu Glu Gly Ile Lys Glu Leu Gly Ser Gln Ile Leu Lys Glu His
    1940                1945                1950

Pro Val Glu Asn Thr Gln Leu Gln Asn Glu Lys Leu Tyr Leu Tyr
    1955                1960                1965

Tyr Leu Gln Asn Gly Arg Asp Met Tyr Val Asp Gln Glu Leu Asp
    1970                1975                1980

Ile Asn Arg Leu Ser Asp Tyr Asp Val Asp His Ile Val Pro Gln
    1985                1990                1995

Ser Phe Leu Lys Asp Asp Ser Ile Asp Asn Lys Val Leu Thr Arg
    2000                2005                2010

Ser Asp Lys Asn Arg Gly Lys Ser Asp Asn Val Pro Ser Glu Glu
    2015                2020                2025

Val Val Lys Lys Met Lys Asn Tyr Trp Arg Gln Leu Leu Asn Ala
    2030                2035                2040

Lys Leu Ile Thr Gln Arg Lys Phe Asp Asn Leu Thr Lys Ala Glu
    2045                2050                2055

Arg Gly Gly Leu Ser Glu Leu Asp Lys Ala Gly Phe Ile Lys Arg
    2060                2065                2070

Gln Leu Val Glu Thr Arg Gln Ile Thr Lys His Val Ala Gln Ile
    2075                2080                2085

Leu Asp Ser Arg Met Asn Thr Lys Tyr Asp Glu Asn Asp Lys Leu
```

-continued

```
              2090                2095                2100
Ile Arg Glu Val Lys Val Ile Thr Leu Lys Ser Lys Leu Val Ser
    2105                2110                2115
Asp Phe Arg Lys Asp Phe Gln Phe Tyr Lys Val Arg Glu Ile Asn
    2120                2125                2130
Asn Tyr His His Ala His Asp Ala Tyr Leu Asn Ala Val Val Gly
    2135                2140                2145
Thr Ala Leu Ile Lys Lys Tyr Pro Lys Leu Glu Ser Glu Phe Val
    2150                2155                2160
Tyr Gly Asp Tyr Lys Val Tyr Asp Val Arg Lys Met Ile Ala Lys
    2165                2170                2175
Ser Glu Gln Glu Ile Gly Lys Ala Thr Ala Lys Tyr Phe Phe Tyr
    2180                2185                2190
Ser Asn Ile Met Asn Phe Phe Lys Thr Glu Ile Thr Leu Ala Asn
    2195                2200                2205
Gly Glu Ile Arg Lys Arg Pro Leu Ile Glu Thr Asn Gly Glu Thr
    2210                2215                2220
Gly Glu Ile Val Trp Asp Lys Gly Arg Asp Phe Ala Thr Val Arg
    2225                2230                2235
Lys Val Leu Ser Met Pro Gln Val Asn Ile Val Lys Lys Thr Glu
    2240                2245                2250
Val Gln Thr Gly Gly Phe Ser Lys Glu Ser Ile Leu Pro Lys Arg
    2255                2260                2265
Asn Ser Asp Lys Leu Ile Ala Arg Lys Lys Asp Trp Asp Pro Lys
    2270                2275                2280
Lys Tyr Gly Gly Phe Asp Ser Pro Thr Val Ala Tyr Ser Val Leu
    2285                2290                2295
Val Val Ala Lys Val Glu Lys Gly Lys Ser Lys Lys Leu Lys Ser
    2300                2305                2310
Val Lys Glu Leu Leu Gly Ile Thr Ile Met Glu Arg Ser Ser Phe
    2315                2320                2325
Glu Lys Asn Pro Ile Asp Phe Leu Glu Ala Lys Gly Tyr Lys Glu
    2330                2335                2340
Val Lys Lys Asp Leu Ile Ile Lys Leu Pro Lys Tyr Ser Leu Phe
    2345                2350                2355
Glu Leu Glu Asn Gly Arg Lys Arg Met Leu Ala Ser Ala Gly Glu
    2360                2365                2370
Leu Gln Lys Gly Asn Glu Leu Ala Leu Pro Ser Lys Tyr Val Asn
    2375                2380                2385
Phe Leu Tyr Leu Ala Ser His Tyr Glu Lys Leu Lys Gly Ser Pro
    2390                2395                2400
Glu Asp Asn Glu Gln Lys Gln Leu Phe Val Glu Gln His Lys His
    2405                2410                2415
Tyr Leu Asp Glu Ile Ile Glu Gln Ile Ser Glu Phe Ser Lys Arg
    2420                2425                2430
Val Ile Leu Ala Asp Ala Asn Leu Asp Lys Val Leu Ser Ala Tyr
    2435                2440                2445
Asn Lys His Arg Asp Lys Pro Ile Arg Glu Gln Ala Glu Asn Ile
    2450                2455                2460
Ile His Leu Phe Thr Leu Thr Asn Leu Gly Ala Pro Ala Ala Phe
    2465                2470                2475
Lys Tyr Phe Asp Thr Thr Ile Asp Arg Lys Lys Tyr Thr Ser Thr
    2480                2485                2490
```

-continued

```
Lys Glu Val Leu Asp Ala Thr Leu Ile His Gln Ser Ile Thr Gly
    2495                2500                2505

Leu Tyr Glu Thr Arg Ile Asp Leu Ser Gln Leu Gly Gly Asp Gly
    2510                2515                2520

Thr Gly Gly Pro Lys Lys Arg Lys Val Ile Gly Ser Ser Gly
    2525                2530                2535

Ser Gly Gly Ser Gly Ser Leu Glu
    2540                2545

<210> SEQ ID NO 150
<211> LENGTH: 2551
<212> TYPE: PRT
<213> ORGANISM: Artificial sequence
<220> FEATURE:
<223> OTHER INFORMATION: Synthetic

<400> SEQUENCE: 150

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720
```

```
His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
        740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
```

```
                1130              1135              1140
Leu Val Val Ala Lys Val Glu Lys Gly Lys Ser Lys Lys Leu Lys
    1145              1150              1155
Ser Val Lys Glu Leu Leu Gly Ile Thr Ile Met Glu Arg Ser Ser
    1160              1165              1170
Phe Glu Lys Asn Pro Ile Asp Phe Leu Glu Ala Lys Gly Tyr Lys
    1175              1180              1185
Glu Val Lys Lys Asp Leu Ile Ile Lys Leu Pro Lys Tyr Ser Leu
    1190              1195              1200
Phe Glu Leu Glu Asn Gly Arg Lys Arg Met Leu Ala Ser Ala Gly
    1205              1210              1215
Glu Leu Gln Lys Gly Asn Glu Leu Ala Leu Pro Ser Lys Tyr Val
    1220              1225              1230
Asn Phe Leu Tyr Leu Ala Ser His Tyr Glu Lys Leu Lys Gly Ser
    1235              1240              1245
Pro Glu Asp Asn Glu Gln Lys Gln Leu Phe Val Glu Gln His Lys
    1250              1255              1260
His Tyr Leu Asp Glu Ile Ile Glu Gln Ile Ser Glu Phe Ser Lys
    1265              1270              1275
Arg Val Ile Leu Ala Asp Ala Asn Leu Asp Lys Val Leu Ser Ala
    1280              1285              1290
Tyr Asn Lys His Arg Asp Lys Pro Ile Arg Glu Gln Ala Glu Asn
    1295              1300              1305
Ile Ile His Leu Phe Thr Leu Thr Asn Leu Gly Ala Pro Ala Ala
    1310              1315              1320
Phe Lys Tyr Phe Asp Thr Thr Ile Asp Arg Lys Lys Tyr Thr Ser
    1325              1330              1335
Thr Lys Glu Val Leu Asp Ala Thr Leu Ile His Gln Ser Ile Thr
    1340              1345              1350
Gly Leu Tyr Glu Thr Arg Ile Asp Leu Ser Gln Leu Gly Gly Asp
    1355              1360              1365
Gly Thr Gly Gly Pro Lys Lys Arg Lys Val Tyr Pro Tyr Asp
    1370              1375              1380
Val Pro Asp Tyr Ala Gly Tyr Pro Tyr Asp Val Pro Asp Tyr Ala
    1385              1390              1395
Gly Ser Tyr Pro Tyr Asp Val Pro Asp Tyr Ala Gly Ser Ala Ala
    1400              1405              1410
Pro Ala Ala Lys Lys Lys Lys Leu Asp Phe Glu Ser Gly Met Pro
    1415              1420              1425
Lys Lys Lys Arg Lys Val Ala Ala Phe Lys Pro Asn Pro Ile Asn
    1430              1435              1440
Tyr Ile Leu Gly Leu Ala Ile Gly Ile Ala Ser Val Gly Trp Ala
    1445              1450              1455
Met Val Glu Ile Asp Glu Asp Glu Asn Pro Ile Cys Leu Ile Asp
    1460              1465              1470
Leu Gly Val Arg Val Phe Glu Arg Ala Glu Val Pro Lys Thr Gly
    1475              1480              1485
Asp Ser Leu Ala Met Ala Arg Arg Leu Ala Arg Ser Val Arg Arg
    1490              1495              1500
Leu Thr Arg Arg Arg Ala His Arg Leu Leu Arg Ala Arg Arg Leu
    1505              1510              1515
Leu Lys Arg Glu Gly Val Leu Gln Ala Ala Asp Phe Asp Glu Asn
    1520              1525              1530
```

-continued

Gly Leu Ile Lys Ser Leu Pro Asn Thr Pro Trp Gln Leu Arg Ala
1535            1540                1545

Ala Ala Leu Asp Arg Lys Leu Thr Pro Leu Glu Trp Ser Ala Val
1550            1555                1560

Leu Leu His Leu Ile Lys His Arg Gly Tyr Leu Ser Gln Arg Lys
1565            1570                1575

Asn Glu Gly Glu Thr Ala Asp Lys Glu Leu Gly Ala Leu Leu Lys
1580            1585                1590

Gly Val Ala Asp Asn Ala His Ala Leu Gln Thr Gly Asp Phe Arg
1595            1600                1605

Thr Pro Ala Glu Leu Ala Leu Asn Lys Phe Glu Lys Glu Ser Gly
1610            1615                1620

His Ile Arg Asn Gln Arg Gly Asp Tyr Ser His Thr Phe Ser Arg
1625            1630                1635

Lys Asp Leu Gln Ala Glu Leu Ile Leu Leu Phe Glu Lys Gln Lys
1640            1645                1650

Glu Phe Gly Asn Pro His Val Ser Gly Gly Leu Lys Glu Gly Ile
1655            1660                1665

Glu Thr Leu Leu Met Thr Gln Arg Pro Ala Leu Ser Gly Asp Ala
1670            1675                1680

Val Gln Lys Met Leu Gly His Cys Thr Phe Glu Pro Ala Glu Pro
1685            1690                1695

Lys Ala Ala Lys Asn Thr Tyr Thr Ala Glu Arg Phe Ile Trp Leu
1700            1705                1710

Thr Lys Leu Asn Asn Leu Arg Ile Leu Glu Gln Gly Ser Glu Arg
1715            1720                1725

Pro Leu Thr Asp Thr Glu Arg Ala Thr Leu Met Asp Glu Pro Tyr
1730            1735                1740

Arg Lys Ser Lys Leu Thr Tyr Ala Gln Ala Arg Lys Leu Leu Gly
1745            1750                1755

Leu Glu Asp Thr Ala Phe Phe Lys Gly Leu Arg Tyr Gly Lys Asp
1760            1765                1770

Asn Ala Glu Ala Ser Thr Leu Met Glu Met Lys Ala Tyr His Ala
1775            1780                1785

Ile Ser Arg Ala Leu Glu Lys Glu Gly Leu Lys Asp Lys Lys Ser
1790            1795                1800

Pro Leu Asn Leu Ser Pro Glu Leu Gln Asp Glu Ile Gly Thr Ala
1805            1810                1815

Phe Ser Leu Phe Lys Thr Asp Glu Asp Ile Thr Gly Arg Leu Lys
1820            1825                1830

Asp Arg Ile Gln Pro Glu Ile Leu Glu Ala Leu Leu Lys His Ile
1835            1840                1845

Ser Phe Asp Lys Phe Val Gln Ile Ser Leu Lys Ala Leu Arg Arg
1850            1855                1860

Ile Val Pro Leu Met Glu Gln Gly Lys Arg Tyr Asp Glu Ala Cys
1865            1870                1875

Ala Glu Ile Tyr Gly Asp His Tyr Gly Lys Lys Asn Thr Glu Glu
1880            1885                1890

Lys Ile Tyr Leu Pro Pro Ile Pro Ala Asp Glu Ile Arg Asn Pro
1895            1900                1905

Val Val Leu Arg Ala Leu Ser Gln Ala Arg Lys Val Ile Asn Gly
1910            1915                1920

```
Val Val Arg Arg Tyr Gly Ser Pro Ala Arg Ile His Ile Glu Thr
1925                1930                1935

Ala Arg Glu Val Gly Lys Ser Phe Lys Asp Arg Lys Glu Ile Glu
1940                1945                1950

Lys Arg Gln Glu Glu Asn Arg Lys Asp Arg Glu Lys Ala Ala Ala
1955                1960                1965

Lys Phe Arg Glu Tyr Phe Pro Asn Phe Val Gly Glu Pro Lys Ser
1970                1975                1980

Lys Asp Ile Leu Lys Leu Arg Leu Tyr Glu Gln Gln His Gly Lys
1985                1990                1995

Cys Leu Tyr Ser Gly Lys Glu Ile Asn Leu Gly Arg Leu Asn Glu
2000                2005                2010

Lys Gly Tyr Val Glu Ile Ala Ala Ala Leu Pro Phe Ser Arg Thr
2015                2020                2025

Trp Asp Asp Ser Phe Asn Asn Lys Val Leu Val Leu Gly Ser Glu
2030                2035                2040

Ala Gln Asn Lys Gly Asn Gln Thr Pro Tyr Glu Tyr Phe Asn Gly
2045                2050                2055

Lys Asp Asn Ser Arg Glu Trp Gln Glu Phe Lys Ala Arg Val Glu
2060                2065                2070

Thr Ser Arg Phe Pro Arg Ser Lys Lys Gln Arg Ile Leu Leu Gln
2075                2080                2085

Lys Phe Asp Glu Asp Gly Phe Lys Glu Arg Asn Leu Asn Asp Thr
2090                2095                2100

Arg Tyr Val Asn Arg Phe Leu Cys Gln Phe Val Ala Asp Arg Met
2105                2110                2115

Arg Leu Thr Gly Lys Gly Lys Lys Arg Val Phe Ala Ser Asn Gly
2120                2125                2130

Gln Ile Thr Asn Leu Leu Arg Gly Phe Trp Gly Leu Arg Lys Val
2135                2140                2145

Arg Ala Glu Asn Asp Arg His His Ala Leu Asp Ala Val Val Val
2150                2155                2160

Ala Cys Ser Thr Val Ala Met Gln Gln Lys Ile Thr Arg Phe Val
2165                2170                2175

Arg Tyr Lys Glu Met Asn Ala Phe Asp Gly Lys Thr Ile Asp Lys
2180                2185                2190

Glu Thr Gly Glu Val Leu His Gln Lys Thr His Phe Pro Gln Pro
2195                2200                2205

Trp Glu Phe Phe Ala Gln Glu Val Met Ile Arg Val Phe Gly Lys
2210                2215                2220

Pro Asp Gly Lys Pro Glu Phe Glu Glu Ala Asp Thr Pro Glu Lys
2225                2230                2235

Leu Arg Thr Leu Leu Ala Glu Lys Leu Ser Ser Arg Pro Glu Ala
2240                2245                2250

Val His Glu Tyr Val Thr Pro Leu Phe Val Ser Arg Ala Pro Asn
2255                2260                2265

Arg Lys Met Ser Gly Gln Gly His Met Glu Thr Val Lys Ser Ala
2270                2275                2280

Lys Arg Leu Asp Glu Gly Val Ser Val Leu Arg Val Pro Leu Thr
2285                2290                2295

Gln Leu Lys Leu Lys Asp Leu Glu Lys Met Val Asn Arg Glu Arg
2300                2305                2310

Glu Pro Lys Leu Tyr Glu Ala Leu Lys Ala Arg Leu Glu Ala His
```

-continued

```
             2315                2320                2325

Lys Asp Asp Pro Ala Lys Ala Phe Ala Glu Pro Phe Tyr Lys Tyr
         2330                2335                2340

Asp Lys Ala Gly Asn Arg Thr Gln Gln Val Lys Ala Val Arg Val
         2345                2350                2355

Glu Gln Val Gln Lys Thr Gly Val Trp Val Arg Asn His Asn Gly
         2360                2365                2370

Ile Ala Asp Asn Ala Thr Met Val Arg Val Asp Val Phe Glu Lys
         2375                2380                2385

Gly Asp Lys Tyr Tyr Leu Val Pro Ile Tyr Ser Trp Gln Val Ala
         2390                2395                2400

Lys Gly Ile Leu Pro Asp Arg Ala Val Val Gln Gly Lys Asp Glu
         2405                2410                2415

Glu Asp Trp Gln Leu Ile Asp Asp Ser Phe Asn Phe Lys Phe Ser
         2420                2425                2430

Leu His Pro Asn Asp Leu Val Glu Val Ile Thr Lys Lys Ala Arg
         2435                2440                2445

Met Phe Gly Tyr Phe Ala Ser Cys His Arg Gly Thr Gly Asn Ile
         2450                2455                2460

Asn Ile Arg Ile His Asp Leu Asp His Lys Ile Gly Lys Asn Gly
         2465                2470                2475

Ile Leu Glu Gly Ile Gly Val Lys Thr Ala Leu Ser Phe Gln Lys
         2480                2485                2490

Tyr Gln Ile Asp Glu Leu Gly Lys Glu Ile Arg Pro Cys Arg Leu
         2495                2500                2505

Lys Lys Arg Pro Pro Val Arg Ser Arg Ala Asp Pro Lys Lys Lys
         2510                2515                2520

Arg Lys Val Glu Ala Ser Asp Tyr Lys Asp His Asp Gly Asp Tyr
         2525                2530                2535

Lys Asp His Asp Ile Asp Tyr Lys Asp Asp Asp Lys
         2540                2545                2550
```

<210> SEQ ID NO 151
<211> LENGTH: 2551
<212> TYPE: PRT
<213> ORGANISM: Artificial sequence
<220> FEATURE:
<223> OTHER INFORMATION: Synthetic

<400> SEQUENCE: 151

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
```

```
            115                 120                 125
His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540
```

-continued

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

-continued

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Lys Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp

```
          1355                1360                1365

Gly  Thr  Gly  Gly  Pro  Lys  Lys  Arg  Lys  Val  Tyr  Pro  Tyr  Asp
          1370                1375                1380

Val  Pro  Asp  Tyr  Ala  Gly  Tyr  Pro  Tyr  Asp  Val  Pro  Asp  Tyr  Ala
          1385                1390                1395

Gly  Ser  Tyr  Pro  Tyr  Asp  Val  Pro  Asp  Tyr  Ala  Gly  Ser  Ala  Ala
          1400                1405                1410

Pro  Ala  Ala  Lys  Lys  Lys  Leu  Asp  Phe  Glu  Ser  Gly  Met  Pro
          1415                1420                1425

Lys  Lys  Lys  Arg  Lys  Val  Ala  Ala  Phe  Lys  Pro  Asn  Pro  Ile  Asn
          1430                1435                1440

Tyr  Ile  Leu  Gly  Leu  Asp  Ile  Gly  Ile  Ala  Ser  Val  Gly  Trp  Ala
          1445                1450                1455

Met  Val  Glu  Ile  Asp  Glu  Asp  Glu  Asn  Pro  Ile  Cys  Leu  Ile  Asp
          1460                1465                1470

Leu  Gly  Val  Arg  Val  Phe  Glu  Arg  Ala  Glu  Val  Pro  Lys  Thr  Gly
          1475                1480                1485

Asp  Ser  Leu  Ala  Met  Ala  Arg  Arg  Leu  Ala  Arg  Ser  Val  Arg  Arg
          1490                1495                1500

Leu  Thr  Arg  Arg  Arg  Ala  His  Arg  Leu  Leu  Arg  Ala  Arg  Arg  Leu
          1505                1510                1515

Leu  Lys  Arg  Glu  Gly  Val  Leu  Gln  Ala  Ala  Asp  Phe  Asp  Glu  Asn
          1520                1525                1530

Gly  Leu  Ile  Lys  Ser  Leu  Pro  Asn  Thr  Pro  Trp  Gln  Leu  Arg  Ala
          1535                1540                1545

Ala  Ala  Leu  Asp  Arg  Lys  Leu  Thr  Pro  Leu  Glu  Trp  Ser  Ala  Val
          1550                1555                1560

Leu  Leu  His  Leu  Ile  Lys  His  Arg  Gly  Tyr  Leu  Ser  Gln  Arg  Lys
          1565                1570                1575

Asn  Glu  Gly  Glu  Thr  Ala  Asp  Lys  Glu  Leu  Gly  Ala  Leu  Leu  Lys
          1580                1585                1590

Gly  Val  Ala  Asp  Asn  Ala  His  Ala  Leu  Gln  Thr  Gly  Asp  Phe  Arg
          1595                1600                1605

Thr  Pro  Ala  Glu  Leu  Ala  Leu  Asn  Lys  Phe  Glu  Lys  Glu  Ser  Gly
          1610                1615                1620

His  Ile  Arg  Asn  Gln  Arg  Gly  Asp  Tyr  Ser  His  Thr  Phe  Ser  Arg
          1625                1630                1635

Lys  Asp  Leu  Gln  Ala  Glu  Leu  Ile  Leu  Leu  Phe  Glu  Lys  Gln  Lys
          1640                1645                1650

Glu  Phe  Gly  Asn  Pro  His  Val  Ser  Gly  Gly  Leu  Lys  Glu  Gly  Ile
          1655                1660                1665

Glu  Thr  Leu  Leu  Met  Thr  Gln  Arg  Pro  Ala  Leu  Ser  Gly  Asp  Ala
          1670                1675                1680

Val  Gln  Lys  Met  Leu  Gly  His  Cys  Thr  Phe  Glu  Pro  Ala  Glu  Pro
          1685                1690                1695

Lys  Ala  Ala  Lys  Asn  Thr  Tyr  Thr  Ala  Glu  Arg  Phe  Ile  Trp  Leu
          1700                1705                1710

Thr  Lys  Leu  Asn  Asn  Leu  Arg  Ile  Leu  Glu  Gln  Gly  Ser  Glu  Arg
          1715                1720                1725

Pro  Leu  Thr  Asp  Thr  Glu  Arg  Ala  Thr  Leu  Met  Asp  Glu  Pro  Tyr
          1730                1735                1740

Arg  Lys  Ser  Lys  Leu  Thr  Tyr  Ala  Gln  Ala  Arg  Lys  Leu  Leu  Gly
          1745                1750                1755
```

Leu Glu Asp Thr Ala Phe Phe Lys Gly Leu Arg Tyr Gly Lys Asp
1760                1765                1770

Asn Ala Glu Ala Ser Thr Leu Met Glu Met Lys Ala Tyr His Ala
1775                1780                1785

Ile Ser Arg Ala Leu Glu Lys Glu Gly Leu Lys Asp Lys Lys Ser
1790                1795                1800

Pro Leu Asn Leu Ser Pro Glu Leu Gln Asp Glu Ile Gly Thr Ala
1805                1810                1815

Phe Ser Leu Phe Lys Thr Asp Glu Asp Ile Thr Gly Arg Leu Lys
1820                1825                1830

Asp Arg Ile Gln Pro Glu Ile Leu Glu Ala Leu Leu Lys His Ile
1835                1840                1845

Ser Phe Asp Lys Phe Val Gln Ile Ser Leu Lys Ala Leu Arg Arg
1850                1855                1860

Ile Val Pro Leu Met Glu Gln Gly Lys Arg Tyr Asp Glu Ala Cys
1865                1870                1875

Ala Glu Ile Tyr Gly Asp His Tyr Gly Lys Lys Asn Thr Glu Glu
1880                1885                1890

Lys Ile Tyr Leu Pro Pro Ile Pro Ala Asp Glu Ile Arg Asn Pro
1895                1900                1905

Val Val Leu Arg Ala Leu Ser Gln Ala Arg Lys Val Ile Asn Gly
1910                1915                1920

Val Val Arg Arg Tyr Gly Ser Pro Ala Arg Ile His Ile Glu Thr
1925                1930                1935

Ala Arg Glu Val Gly Lys Ser Phe Lys Asp Arg Lys Glu Ile Glu
1940                1945                1950

Lys Arg Gln Glu Glu Asn Arg Lys Asp Arg Glu Lys Ala Ala Ala
1955                1960                1965

Lys Phe Arg Glu Tyr Phe Pro Asn Phe Val Gly Glu Pro Lys Ser
1970                1975                1980

Lys Asp Ile Leu Lys Leu Arg Leu Tyr Glu Gln Gln His Gly Lys
1985                1990                1995

Cys Leu Tyr Ser Gly Lys Glu Ile Asn Leu Gly Arg Leu Asn Glu
2000                2005                2010

Lys Gly Tyr Val Glu Ile Ala Ala Ala Leu Pro Phe Ser Arg Thr
2015                2020                2025

Trp Asp Asp Ser Phe Asn Asn Lys Val Leu Val Leu Gly Ser Glu
2030                2035                2040

Ala Gln Asn Lys Gly Asn Gln Thr Pro Tyr Glu Tyr Phe Asn Gly
2045                2050                2055

Lys Asp Asn Ser Arg Glu Trp Gln Glu Phe Lys Ala Arg Val Glu
2060                2065                2070

Thr Ser Arg Phe Pro Arg Ser Lys Lys Gln Arg Ile Leu Leu Gln
2075                2080                2085

Lys Phe Asp Glu Asp Gly Phe Lys Glu Arg Asn Leu Asn Asp Thr
2090                2095                2100

Arg Tyr Val Asn Arg Phe Leu Cys Gln Phe Val Ala Asp Arg Met
2105                2110                2115

Arg Leu Thr Gly Lys Gly Lys Lys Arg Val Phe Ala Ser Asn Gly
2120                2125                2130

Gln Ile Thr Asn Leu Leu Arg Gly Phe Trp Gly Leu Arg Lys Val
2135                2140                2145

```
Arg Ala Glu Asn Asp Arg His His Ala Leu Asp Ala Val Val Val
2150            2155            2160

Ala Cys Ser Thr Val Ala Met Gln Gln Lys Ile Thr Arg Phe Val
2165            2170            2175

Arg Tyr Lys Glu Met Asn Ala Phe Asp Gly Lys Thr Ile Asp Lys
2180            2185            2190

Glu Thr Gly Glu Val Leu His Gln Lys Thr His Phe Pro Gln Pro
2195            2200            2205

Trp Glu Phe Phe Ala Gln Glu Val Met Ile Arg Val Phe Gly Lys
2210            2215            2220

Pro Asp Gly Lys Pro Glu Phe Glu Glu Ala Asp Thr Pro Glu Lys
2225            2230            2235

Leu Arg Thr Leu Leu Ala Glu Lys Leu Ser Ser Arg Pro Glu Ala
2240            2245            2250

Val His Glu Tyr Val Thr Pro Leu Phe Val Ser Arg Ala Pro Asn
2255            2260            2265

Arg Lys Met Ser Gly Gln Gly His Met Glu Thr Val Lys Ser Ala
2270            2275            2280

Lys Arg Leu Asp Glu Gly Val Ser Val Leu Arg Val Pro Leu Thr
2285            2290            2295

Gln Leu Lys Leu Lys Asp Leu Glu Lys Met Val Asn Arg Glu Arg
2300            2305            2310

Glu Pro Lys Leu Tyr Glu Ala Leu Lys Ala Arg Leu Glu Ala His
2315            2320            2325

Lys Asp Asp Pro Ala Lys Ala Phe Ala Glu Pro Phe Tyr Lys Tyr
2330            2335            2340

Asp Lys Ala Gly Asn Arg Thr Gln Gln Val Lys Ala Val Arg Val
2345            2350            2355

Glu Gln Val Gln Lys Thr Gly Val Trp Val Arg Asn His Asn Gly
2360            2365            2370

Ile Ala Asp Asn Ala Thr Met Val Arg Val Asp Val Phe Glu Lys
2375            2380            2385

Gly Asp Lys Tyr Tyr Leu Val Pro Ile Tyr Ser Trp Gln Val Ala
2390            2395            2400

Lys Gly Ile Leu Pro Asp Arg Ala Val Val Gln Gly Lys Asp Glu
2405            2410            2415

Glu Asp Trp Gln Leu Ile Asp Asp Ser Phe Asn Phe Lys Phe Ser
2420            2425            2430

Leu His Pro Asn Asp Leu Val Glu Val Ile Thr Lys Lys Ala Arg
2435            2440            2445

Met Phe Gly Tyr Phe Ala Ser Cys His Arg Gly Thr Gly Asn Ile
2450            2455            2460

Asn Ile Arg Ile His Asp Leu Asp His Lys Ile Gly Lys Asn Gly
2465            2470            2475

Ile Leu Glu Gly Ile Gly Val Lys Thr Ala Leu Ser Phe Gln Lys
2480            2485            2490

Tyr Gln Ile Asp Glu Leu Gly Lys Glu Ile Arg Pro Cys Arg Leu
2495            2500            2505

Lys Lys Arg Pro Pro Val Arg Ser Arg Ala Asp Pro Lys Lys Lys
2510            2515            2520

Arg Lys Val Glu Ala Ser Asp Tyr Lys Asp His Asp Gly Asp Tyr
2525            2530            2535

Lys Asp His Asp Ile Asp Tyr Lys Asp Asp Asp Asp Lys
```

```
                      2540              2545              2550

<210> SEQ ID NO 152
<211> LENGTH: 2551
<212> TYPE: PRT
<213> ORGANISM: Artificial sequence
<220> FEATURE:
<223> OTHER INFORMATION: Synthetic

<400> SEQUENCE: 152

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
```

-continued

```
            355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
        610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
        770                 775                 780
```

-continued

```
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185
```

```
Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Lys Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Thr Gly Gly Pro Lys Lys Lys Arg Lys Val Tyr Pro Tyr Asp
    1370                1375                1380

Val Pro Asp Tyr Ala Gly Tyr Pro Tyr Asp Val Pro Asp Tyr Ala
    1385                1390                1395

Gly Ser Tyr Pro Tyr Asp Val Pro Asp Tyr Ala Gly Ser Ala Ala
    1400                1405                1410

Pro Ala Ala Lys Lys Lys Lys Leu Asp Phe Glu Ser Gly Met Pro
    1415                1420                1425

Lys Lys Lys Arg Lys Val Ala Ala Phe Lys Pro Asn Pro Ile Asn
    1430                1435                1440

Tyr Ile Leu Gly Leu Ala Ile Gly Ile Ala Ser Val Gly Trp Ala
    1445                1450                1455

Met Val Glu Ile Asp Glu Asp Glu Asn Pro Ile Cys Leu Ile Asp
    1460                1465                1470

Leu Gly Val Arg Val Phe Glu Arg Ala Glu Val Pro Lys Thr Gly
    1475                1480                1485

Asp Ser Leu Ala Met Ala Arg Arg Leu Ala Arg Ser Val Arg Arg
    1490                1495                1500

Leu Thr Arg Arg Arg Ala His Arg Leu Leu Arg Ala Arg Arg Leu
    1505                1510                1515

Leu Lys Arg Glu Gly Val Leu Gln Ala Ala Asp Phe Asp Glu Asn
    1520                1525                1530

Gly Leu Ile Lys Ser Leu Pro Asn Thr Pro Trp Gln Leu Arg Ala
    1535                1540                1545

Ala Ala Leu Asp Arg Lys Leu Thr Pro Leu Glu Trp Ser Ala Val
    1550                1555                1560

Leu Leu His Leu Ile Lys His Arg Gly Tyr Leu Ser Gln Arg Lys
    1565                1570                1575

Asn Glu Gly Glu Thr Ala Asp Lys Glu Leu Gly Ala Leu Leu Lys
```

```
            1580                1585                1590
Gly Val Ala Asp Asn Ala His Ala Leu Gln Thr Gly Asp Phe Arg
    1595                1600                1605
Thr Pro Ala Glu Leu Ala Leu Asn Lys Phe Glu Lys Glu Ser Gly
    1610                1615                1620
His Ile Arg Asn Gln Arg Gly Asp Tyr Ser His Thr Phe Ser Arg
    1625                1630                1635
Lys Asp Leu Gln Ala Glu Leu Ile Leu Leu Phe Glu Lys Gln Lys
    1640                1645                1650
Glu Phe Gly Asn Pro His Val Ser Gly Gly Leu Lys Glu Gly Ile
    1655                1660                1665
Glu Thr Leu Leu Met Thr Gln Arg Pro Ala Leu Ser Gly Asp Ala
    1670                1675                1680
Val Gln Lys Met Leu Gly His Cys Thr Phe Glu Pro Ala Glu Pro
    1685                1690                1695
Lys Ala Ala Lys Asn Thr Tyr Thr Ala Glu Arg Phe Ile Trp Leu
    1700                1705                1710
Thr Lys Leu Asn Asn Leu Arg Ile Leu Glu Gln Gly Ser Glu Arg
    1715                1720                1725
Pro Leu Thr Asp Thr Glu Arg Ala Thr Leu Met Asp Glu Pro Tyr
    1730                1735                1740
Arg Lys Ser Lys Leu Thr Tyr Ala Gln Ala Arg Lys Leu Leu Gly
    1745                1750                1755
Leu Glu Asp Thr Ala Phe Phe Lys Gly Leu Arg Tyr Gly Lys Asp
    1760                1765                1770
Asn Ala Glu Ala Ser Thr Leu Met Glu Met Lys Ala Tyr His Ala
    1775                1780                1785
Ile Ser Arg Ala Leu Glu Lys Glu Gly Leu Lys Asp Lys Lys Ser
    1790                1795                1800
Pro Leu Asn Leu Ser Pro Glu Leu Gln Asp Glu Ile Gly Thr Ala
    1805                1810                1815
Phe Ser Leu Phe Lys Thr Asp Glu Asp Ile Thr Gly Arg Leu Lys
    1820                1825                1830
Asp Arg Ile Gln Pro Glu Ile Leu Glu Ala Leu Leu Lys His Ile
    1835                1840                1845
Ser Phe Asp Lys Phe Val Gln Ile Ser Leu Lys Ala Leu Arg Arg
    1850                1855                1860
Ile Val Pro Leu Met Glu Gln Gly Lys Arg Tyr Asp Glu Ala Cys
    1865                1870                1875
Ala Glu Ile Tyr Gly Asp His Tyr Gly Lys Lys Asn Thr Glu Glu
    1880                1885                1890
Lys Ile Tyr Leu Pro Pro Ile Pro Ala Asp Glu Ile Arg Asn Pro
    1895                1900                1905
Val Val Leu Arg Ala Leu Ser Gln Ala Arg Lys Val Ile Asn Gly
    1910                1915                1920
Val Val Arg Arg Tyr Gly Ser Pro Ala Arg Ile His Ile Glu Thr
    1925                1930                1935
Ala Arg Glu Val Gly Lys Ser Phe Lys Asp Arg Lys Glu Ile Glu
    1940                1945                1950
Lys Arg Gln Glu Glu Asn Arg Lys Asp Arg Glu Lys Ala Ala Ala
    1955                1960                1965
Lys Phe Arg Glu Tyr Phe Pro Asn Phe Val Gly Glu Pro Lys Ser
    1970                1975                1980
```

```
Lys Asp Ile Leu Lys Leu Arg Leu Tyr Glu Gln Gln His Gly Lys
    1985            1990                1995

Cys Leu Tyr Ser Gly Lys Glu Ile Asn Leu Gly Arg Leu Asn Glu
    2000            2005                2010

Lys Gly Tyr Val Glu Ile Asp His Ala Leu Pro Phe Ser Arg Thr
    2015            2020                2025

Trp Asp Asp Ser Phe Asn Asn Lys Val Leu Val Leu Gly Ser Glu
    2030            2035                2040

Asn Gln Asn Lys Gly Asn Gln Thr Pro Tyr Glu Tyr Phe Asn Gly
    2045            2050                2055

Lys Asp Asn Ser Arg Glu Trp Gln Glu Phe Lys Ala Arg Val Glu
    2060            2065                2070

Thr Ser Arg Phe Pro Arg Ser Lys Lys Gln Arg Ile Leu Leu Gln
    2075            2080                2085

Lys Phe Asp Glu Asp Gly Phe Lys Glu Arg Asn Leu Asn Asp Thr
    2090            2095                2100

Arg Tyr Val Asn Arg Phe Leu Cys Gln Phe Val Ala Asp Arg Met
    2105            2110                2115

Arg Leu Thr Gly Lys Gly Lys Lys Arg Val Phe Ala Ser Asn Gly
    2120            2125                2130

Gln Ile Thr Asn Leu Leu Arg Gly Phe Trp Gly Leu Arg Lys Val
    2135            2140                2145

Arg Ala Glu Asn Asp Arg His His Ala Leu Asp Ala Val Val Val
    2150            2155                2160

Ala Cys Ser Thr Val Ala Met Gln Gln Lys Ile Thr Arg Phe Val
    2165            2170                2175

Arg Tyr Lys Glu Met Asn Ala Phe Asp Gly Lys Thr Ile Asp Lys
    2180            2185                2190

Glu Thr Gly Glu Val Leu His Gln Lys Thr His Phe Pro Gln Pro
    2195            2200                2205

Trp Glu Phe Phe Ala Gln Glu Val Met Ile Arg Val Phe Gly Lys
    2210            2215                2220

Pro Asp Gly Lys Pro Glu Phe Glu Glu Ala Asp Thr Pro Glu Lys
    2225            2230                2235

Leu Arg Thr Leu Leu Ala Glu Lys Leu Ser Ser Arg Pro Glu Ala
    2240            2245                2250

Val His Glu Tyr Val Thr Pro Leu Phe Val Ser Arg Ala Pro Asn
    2255            2260                2265

Arg Lys Met Ser Gly Gln Gly His Met Glu Thr Val Lys Ser Ala
    2270            2275                2280

Lys Arg Leu Asp Glu Gly Val Ser Val Leu Arg Val Pro Leu Thr
    2285            2290                2295

Gln Leu Lys Leu Lys Asp Leu Glu Lys Met Val Asn Arg Glu Arg
    2300            2305                2310

Glu Pro Lys Leu Tyr Glu Ala Leu Lys Ala Arg Leu Glu Ala His
    2315            2320                2325

Lys Asp Asp Pro Ala Lys Ala Phe Ala Glu Pro Phe Tyr Lys Tyr
    2330            2335                2340

Asp Lys Ala Gly Asn Arg Thr Gln Gln Val Lys Ala Val Arg Val
    2345            2350                2355

Glu Gln Val Gln Lys Thr Gly Val Trp Val Arg Asn His Asn Gly
    2360            2365                2370
```

```
Ile Ala Asp Asn Ala Thr Met Val Arg Val Asp Val Phe Glu Lys
2375                    2380                2385

Gly Asp Lys Tyr Tyr Leu Val Pro Ile Tyr Ser Trp Gln Val Ala
2390                    2395                2400

Lys Gly Ile Leu Pro Asp Arg Ala Val Val Gln Gly Lys Asp Glu
2405                    2410                2415

Glu Asp Trp Gln Leu Ile Asp Asp Ser Phe Asn Phe Lys Phe Ser
2420                    2425                2430

Leu His Pro Asn Asp Leu Val Glu Val Ile Thr Lys Lys Ala Arg
2435                    2440                2445

Met Phe Gly Tyr Phe Ala Ser Cys His Arg Gly Thr Gly Asn Ile
2450                    2455                2460

Asn Ile Arg Ile His Asp Leu Asp His Lys Ile Gly Lys Asn Gly
2465                    2470                2475

Ile Leu Glu Gly Ile Gly Val Lys Thr Ala Leu Ser Phe Gln Lys
2480                    2485                2490

Tyr Gln Ile Asp Glu Leu Gly Lys Glu Ile Arg Pro Cys Arg Leu
2495                    2500                2505

Lys Lys Arg Pro Pro Val Arg Ser Arg Ala Asp Pro Lys Lys Lys
2510                    2515                2520

Arg Lys Val Glu Ala Ser Asp Tyr Lys Asp His Asp Gly Asp Tyr
2525                    2530                2535

Lys Asp His Asp Ile Asp Tyr Lys Asp Asp Asp Lys
2540                    2545                2550
```

<210> SEQ ID NO 153
<211> LENGTH: 2551
<212> TYPE: PRT
<213> ORGANISM: Artificial sequence
<220> FEATURE:
<223> OTHER INFORMATION: Synthetic
<400> SEQUENCE: 153

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
        260                 265                 270

Asp Asp Leu Asp Asn Leu Leu Ala Gln Ile Gly Asp Gln Tyr Ala Asp
    275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
        340                 345                 350

Asp Gln Ser Lys Asn Gly Tyr Ala Gly Tyr Ile Asp Gly Gly Ala Ser
    355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
    435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
    515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
```

```
                595                 600                 605
   Asn Glu Glu Asn Glu Asp Ile Leu Glu Asp Ile Val Leu Thr Leu Thr
   610                 615                 620

Leu Phe Glu Asp Arg Glu Met Ile Glu Glu Arg Leu Lys Thr Tyr Ala
   625                 630                 635                 640

His Leu Phe Asp Asp Lys Val Met Lys Gln Leu Lys Arg Arg Arg Tyr
                       645                 650                 655

Thr Gly Trp Gly Arg Leu Ser Arg Lys Leu Ile Asn Gly Ile Arg Asp
                       660                 665                 670

Lys Gln Ser Gly Lys Thr Ile Leu Asp Phe Leu Lys Ser Asp Gly Phe
                       675                 680                 685

Ala Asn Arg Asn Phe Met Gln Leu Ile His Asp Asp Ser Leu Thr Phe
   690                 695                 700

Lys Glu Asp Ile Gln Lys Ala Gln Val Ser Gly Gln Gly Asp Ser Leu
   705                 710                 715                 720

His Glu His Ile Ala Asn Leu Ala Gly Ser Pro Ala Ile Lys Lys Gly
                       725                 730                 735

Ile Leu Gln Thr Val Lys Val Val Asp Glu Leu Val Lys Val Met Gly
                       740                 745                 750

Arg His Lys Pro Glu Asn Ile Val Ile Glu Met Ala Arg Glu Asn Gln
                       755                 760                 765

Thr Thr Gln Lys Gly Gln Lys Asn Ser Arg Glu Arg Met Lys Arg Ile
   770                 775                 780

Glu Glu Gly Ile Lys Glu Leu Gly Ser Gln Ile Leu Lys Glu His Pro
   785                 790                 795                 800

Val Glu Asn Thr Gln Leu Gln Asn Glu Lys Leu Tyr Leu Tyr Tyr Leu
                       805                 810                 815

Gln Asn Gly Arg Asp Met Tyr Val Asp Gln Glu Leu Asp Ile Asn Arg
                       820                 825                 830

Leu Ser Asp Tyr Asp Val Asp His Ile Val Pro Gln Ser Phe Leu Lys
                       835                 840                 845

Asp Asp Ser Ile Asp Asn Lys Val Leu Thr Arg Ser Asp Lys Asn Arg
   850                 855                 860

Gly Lys Ser Asp Asn Val Pro Ser Glu Glu Val Val Lys Lys Met Lys
   865                 870                 875                 880

Asn Tyr Trp Arg Gln Leu Leu Asn Ala Lys Leu Ile Thr Gln Arg Lys
                       885                 890                 895

Phe Asp Asn Leu Thr Lys Ala Glu Arg Gly Gly Leu Ser Glu Leu Asp
                       900                 905                 910

Lys Ala Gly Phe Ile Lys Arg Gln Leu Val Glu Thr Arg Gln Ile Thr
                       915                 920                 925

Lys His Val Ala Gln Ile Leu Asp Ser Arg Met Asn Thr Lys Tyr Asp
                       930                 935                 940

Glu Asn Asp Lys Leu Ile Arg Glu Val Lys Val Ile Thr Leu Lys Ser
   945                 950                 955                 960

Lys Leu Val Ser Asp Phe Arg Lys Asp Phe Gln Phe Tyr Lys Val Arg
                       965                 970                 975

Glu Ile Asn Asn Tyr His His Ala His Asp Ala Tyr Leu Asn Ala Val
                       980                 985                 990

Val Gly Thr Ala Leu Ile Lys Lys  Tyr Pro Lys Leu Glu  Ser Glu Phe
                       995                 1000                1005

Val Tyr  Gly Asp Tyr Lys Val  Tyr Asp Val Arg Lys  Met Ile Ala
   1010                1015                1020
```

Lys Ser Glu Gln Glu Ile Gly Lys Ala Thr Ala Lys Tyr Phe Phe
1025           1030                1035

Tyr Ser Asn Ile Met Asn Phe Phe Lys Thr Glu Ile Thr Leu Ala
1040           1045                1050

Asn Gly Glu Ile Arg Lys Arg Pro Leu Ile Glu Thr Asn Gly Glu
1055           1060                1065

Thr Gly Glu Ile Val Trp Asp Lys Gly Arg Asp Phe Ala Thr Val
1070           1075                1080

Arg Lys Val Leu Ser Met Pro Gln Val Asn Ile Val Lys Lys Thr
1085           1090                1095

Glu Val Gln Thr Gly Gly Phe Ser Lys Glu Ser Ile Leu Pro Lys
1100           1105                1110

Arg Asn Ser Asp Lys Leu Ile Ala Arg Lys Lys Asp Trp Asp Pro
1115           1120                1125

Lys Lys Tyr Gly Gly Phe Asp Ser Pro Thr Val Ala Tyr Ser Val
1130           1135                1140

Leu Val Val Ala Lys Val Glu Lys Gly Lys Ser Lys Lys Leu Lys
1145           1150                1155

Ser Val Lys Glu Leu Leu Gly Ile Thr Ile Met Glu Arg Ser Ser
1160           1165                1170

Phe Glu Lys Asn Pro Ile Asp Phe Leu Glu Ala Lys Gly Tyr Lys
1175           1180                1185

Glu Val Lys Lys Asp Leu Ile Ile Lys Leu Pro Lys Tyr Ser Leu
1190           1195                1200

Phe Glu Leu Glu Asn Gly Arg Lys Arg Met Leu Ala Ser Ala Gly
1205           1210                1215

Glu Leu Gln Lys Gly Asn Glu Leu Ala Leu Pro Ser Lys Tyr Val
1220           1225                1230

Asn Phe Leu Tyr Leu Ala Ser His Tyr Glu Lys Leu Lys Gly Ser
1235           1240                1245

Pro Glu Asp Asn Glu Gln Lys Gln Leu Phe Val Glu Gln His Lys
1250           1255                1260

His Tyr Leu Asp Glu Ile Ile Glu Gln Ile Ser Glu Phe Ser Lys
1265           1270                1275

Arg Val Ile Leu Ala Asp Ala Asn Leu Asp Lys Val Leu Ser Ala
1280           1285                1290

Tyr Asn Lys His Arg Asp Lys Pro Ile Arg Glu Gln Ala Glu Asn
1295           1300                1305

Ile Ile His Leu Phe Thr Leu Thr Asn Leu Gly Ala Pro Ala Ala
1310           1315                1320

Phe Lys Tyr Phe Asp Thr Thr Ile Asp Arg Lys Lys Tyr Thr Ser
1325           1330                1335

Thr Lys Glu Val Leu Asp Ala Thr Leu Ile His Gln Ser Ile Thr
1340           1345                1350

Gly Leu Tyr Glu Thr Arg Ile Asp Leu Ser Gln Leu Gly Gly Asp
1355           1360                1365

Gly Thr Gly Gly Pro Lys Lys Lys Arg Lys Val Tyr Pro Tyr Asp
1370           1375                1380

Val Pro Asp Tyr Ala Gly Tyr Pro Tyr Asp Val Pro Asp Tyr Ala
1385           1390                1395

Gly Ser Tyr Pro Tyr Asp Val Pro Asp Tyr Ala Gly Ser Ala Ala
1400           1405                1410

```
Pro Ala Ala Lys Lys Lys Lys Leu Asp Phe Glu Ser Gly Met Pro
    1415                1420                1425
Lys Lys Lys Arg Lys Val Ala Ala Phe Lys Pro Asn Pro Ile Asn
    1430                1435                1440
Tyr Ile Leu Gly Leu Asp Ile Gly Ile Ala Ser Val Gly Trp Ala
    1445                1450                1455
Met Val Glu Ile Asp Glu Asp Glu Asn Pro Ile Cys Leu Ile Asp
    1460                1465                1470
Leu Gly Val Arg Val Phe Glu Arg Ala Glu Val Pro Lys Thr Gly
    1475                1480                1485
Asp Ser Leu Ala Met Ala Arg Arg Leu Ala Arg Ser Val Arg Arg
    1490                1495                1500
Leu Thr Arg Arg Arg Ala His Arg Leu Leu Arg Ala Arg Arg Leu
    1505                1510                1515
Leu Lys Arg Glu Gly Val Leu Gln Ala Ala Asp Phe Asp Glu Asn
    1520                1525                1530
Gly Leu Ile Lys Ser Leu Pro Asn Thr Pro Trp Gln Leu Arg Ala
    1535                1540                1545
Ala Ala Leu Asp Arg Lys Leu Thr Pro Leu Glu Trp Ser Ala Val
    1550                1555                1560
Leu Leu His Leu Ile Lys His Arg Gly Tyr Leu Ser Gln Arg Lys
    1565                1570                1575
Asn Glu Gly Glu Thr Ala Asp Lys Glu Leu Gly Ala Leu Leu Lys
    1580                1585                1590
Gly Val Ala Asp Asn Ala His Ala Leu Gln Thr Gly Asp Phe Arg
    1595                1600                1605
Thr Pro Ala Glu Leu Ala Leu Asn Lys Phe Glu Lys Glu Ser Gly
    1610                1615                1620
His Ile Arg Asn Gln Arg Gly Asp Tyr Ser His Thr Phe Ser Arg
    1625                1630                1635
Lys Asp Leu Gln Ala Glu Leu Ile Leu Leu Phe Glu Lys Gln Lys
    1640                1645                1650
Glu Phe Gly Asn Pro His Val Ser Gly Gly Leu Lys Glu Gly Ile
    1655                1660                1665
Glu Thr Leu Leu Met Thr Gln Arg Pro Ala Leu Ser Gly Asp Ala
    1670                1675                1680
Val Gln Lys Met Leu Gly His Cys Thr Phe Glu Pro Ala Glu Pro
    1685                1690                1695
Lys Ala Ala Lys Asn Thr Tyr Thr Ala Glu Arg Phe Ile Trp Leu
    1700                1705                1710
Thr Lys Leu Asn Asn Leu Arg Ile Leu Glu Gln Gly Ser Glu Arg
    1715                1720                1725
Pro Leu Thr Asp Thr Glu Arg Ala Thr Leu Met Asp Glu Pro Tyr
    1730                1735                1740
Arg Lys Ser Lys Leu Thr Tyr Ala Gln Ala Arg Lys Leu Leu Gly
    1745                1750                1755
Leu Glu Asp Thr Ala Phe Phe Lys Gly Leu Arg Tyr Gly Lys Asp
    1760                1765                1770
Asn Ala Glu Ala Ser Thr Leu Met Glu Met Lys Ala Tyr His Ala
    1775                1780                1785
Ile Ser Arg Ala Leu Glu Lys Glu Gly Leu Lys Asp Lys Lys Ser
    1790                1795                1800
Pro Leu Asn Leu Ser Pro Glu Leu Gln Asp Glu Ile Gly Thr Ala
```

-continued

```
            1805                1810                1815
Phe Ser Leu Phe Lys Thr Asp Glu Asp Ile Thr Gly Arg Leu Lys
            1820                1825                1830
Asp Arg Ile Gln Pro Glu Ile Leu Glu Ala Leu Leu Lys His Ile
            1835                1840                1845
Ser Phe Asp Lys Phe Val Gln Ile Ser Leu Lys Ala Leu Arg Arg
            1850                1855                1860
Ile Val Pro Leu Met Glu Gln Gly Lys Arg Tyr Asp Glu Ala Cys
            1865                1870                1875
Ala Glu Ile Tyr Gly Asp His Tyr Gly Lys Lys Asn Thr Glu Glu
            1880                1885                1890
Lys Ile Tyr Leu Pro Pro Ile Pro Ala Asp Glu Ile Arg Asn Pro
            1895                1900                1905
Val Val Leu Arg Ala Leu Ser Gln Ala Arg Lys Val Ile Asn Gly
            1910                1915                1920
Val Val Arg Arg Tyr Gly Ser Pro Ala Arg Ile His Ile Glu Thr
            1925                1930                1935
Ala Arg Glu Val Gly Lys Ser Phe Lys Asp Arg Lys Glu Ile Glu
            1940                1945                1950
Lys Arg Gln Glu Glu Asn Arg Lys Asp Arg Glu Lys Ala Ala Ala
            1955                1960                1965
Lys Phe Arg Glu Tyr Phe Pro Asn Phe Val Gly Glu Pro Lys Ser
            1970                1975                1980
Lys Asp Ile Leu Lys Leu Arg Leu Tyr Glu Gln Gln His Gly Lys
            1985                1990                1995
Cys Leu Tyr Ser Gly Lys Glu Ile Asn Leu Gly Arg Leu Asn Glu
            2000                2005                2010
Lys Gly Tyr Val Glu Ile Asp His Ala Leu Pro Phe Ser Arg Thr
            2015                2020                2025
Trp Asp Asp Ser Phe Asn Asn Lys Val Leu Val Leu Gly Ser Glu
            2030                2035                2040
Asn Gln Asn Lys Gly Asn Gln Thr Pro Tyr Glu Tyr Phe Asn Gly
            2045                2050                2055
Lys Asp Asn Ser Arg Glu Trp Gln Glu Phe Lys Ala Arg Val Glu
            2060                2065                2070
Thr Ser Arg Phe Pro Arg Ser Lys Lys Gln Arg Ile Leu Leu Gln
            2075                2080                2085
Lys Phe Asp Glu Asp Gly Phe Lys Glu Arg Asn Leu Asn Asp Thr
            2090                2095                2100
Arg Tyr Val Asn Arg Phe Leu Cys Gln Phe Val Ala Asp Arg Met
            2105                2110                2115
Arg Leu Thr Gly Lys Gly Lys Lys Arg Val Phe Ala Ser Asn Gly
            2120                2125                2130
Gln Ile Thr Asn Leu Leu Arg Gly Phe Trp Gly Leu Arg Lys Val
            2135                2140                2145
Arg Ala Glu Asn Asp Arg His His Ala Leu Asp Ala Val Val Val
            2150                2155                2160
Ala Cys Ser Thr Val Ala Met Gln Gln Lys Ile Thr Arg Phe Val
            2165                2170                2175
Arg Tyr Lys Glu Met Asn Ala Phe Asp Gly Lys Thr Ile Asp Lys
            2180                2185                2190
Glu Thr Gly Glu Val Leu His Gln Lys Thr His Phe Pro Gln Pro
            2195                2200                2205
```

```
Trp Glu Phe Phe Ala Gln Glu Val Met Ile Arg Val Phe Gly Lys
2210                2215                    2220

Pro Asp Gly Lys Pro Glu Phe Glu Glu Ala Asp Thr Pro Glu Lys
2225                2230                    2235

Leu Arg Thr Leu Leu Ala Glu Lys Leu Ser Ser Arg Pro Glu Ala
2240                2245                    2250

Val His Glu Tyr Val Thr Pro Leu Phe Val Ser Arg Ala Pro Asn
2255                2260                    2265

Arg Lys Met Ser Gly Gln Gly His Met Glu Thr Val Lys Ser Ala
2270                2275                    2280

Lys Arg Leu Asp Glu Gly Val Ser Val Leu Arg Val Pro Leu Thr
2285                2290                    2295

Gln Leu Lys Leu Lys Asp Leu Glu Lys Met Val Asn Arg Glu Arg
2300                2305                    2310

Glu Pro Lys Leu Tyr Glu Ala Leu Lys Ala Arg Leu Glu Ala His
2315                2320                    2325

Lys Asp Asp Pro Ala Lys Ala Phe Ala Glu Pro Phe Tyr Lys Tyr
2330                2335                    2340

Asp Lys Ala Gly Asn Arg Thr Gln Gln Val Lys Ala Val Arg Val
2345                2350                    2355

Glu Gln Val Gln Lys Thr Gly Val Trp Val Arg Asn His Asn Gly
2360                2365                    2370

Ile Ala Asp Asn Ala Thr Met Val Arg Val Asp Val Phe Glu Lys
2375                2380                    2385

Gly Asp Lys Tyr Tyr Leu Val Pro Ile Tyr Ser Trp Gln Val Ala
2390                2395                    2400

Lys Gly Ile Leu Pro Asp Arg Ala Val Val Gln Gly Lys Asp Glu
2405                2410                    2415

Glu Asp Trp Gln Leu Ile Asp Asp Ser Phe Asn Phe Lys Phe Ser
2420                2425                    2430

Leu His Pro Asn Asp Leu Val Glu Val Ile Thr Lys Lys Ala Arg
2435                2440                    2445

Met Phe Gly Tyr Phe Ala Ser Cys His Arg Gly Thr Gly Asn Ile
2450                2455                    2460

Asn Ile Arg Ile His Asp Leu Asp His Lys Ile Gly Lys Asn Gly
2465                2470                    2475

Ile Leu Glu Gly Ile Gly Val Lys Thr Ala Leu Ser Phe Gln Lys
2480                2485                    2490

Tyr Gln Ile Asp Glu Leu Gly Lys Glu Ile Arg Pro Cys Arg Leu
2495                2500                    2505

Lys Lys Arg Pro Pro Val Arg Ser Arg Ala Asp Pro Lys Lys Lys
2510                2515                    2520

Arg Lys Val Glu Ala Ser Asp Tyr Lys Asp His Asp Gly Asp Tyr
2525                2530                    2535

Lys Asp His Asp Ile Asp Tyr Lys Asp Asp Asp Lys
2540                2545                    2550
```